US008207396B2

(12) United States Patent
Payne et al.

(10) Patent No.: US 8,207,396 B2
(45) Date of Patent: Jun. 26, 2012

(54) GENE DISRUPTIONS, COMPOSITIONS AND METHODS RELATING THERETO

(75) Inventors: Bobby Joe Payne, The Woodlands, TX (US); Mary Jean Sparks, Magnolia, TX (US); Wen Xiong, Tomball, TX (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/031,009

(22) Filed: Feb. 18, 2011

(65) Prior Publication Data

US 2011/0173708 A1 Jul. 14, 2011

Related U.S. Application Data

(63) Continuation of application No. 11/814,549, filed as application No. PCT/US2006/027777 on Jul. 18, 2006, now Pat. No. 7,931,902.

(60) Provisional application No. 60/708,312, filed on Aug. 15, 2005.

(51) Int. Cl.
*G01N 33/00* (2006.01)

(52) U.S. Cl. .......................................................... 800/3

(58) Field of Classification Search ........................ None
See application file for complete search history.

(56) References Cited

U.S. PATENT DOCUMENTS

2003/0194791 A1 10/2003 Baker et al.
2004/0185531 A1 9/2004 Ashkenazi et al.

FOREIGN PATENT DOCUMENTS
WO    WO 2005/058028       6/2005

OTHER PUBLICATIONS

Hirohata et al. (Journal of Biological Chemistry. 2002; 277(14): 12182-12189).*
Tang (International Journal of Biochemistry and Cell Biology. 2011; 33(1): 33-44).*
Abu-Elheiga et al., "Continuous Fatty Acid Oxidation and Reduced Fat Storage in Mice Lacking Acetyl-CoA Carboxylase 2" Science 291(5513): 2613-2616, (2001).
Aggarwal et al., "Acinar Cells of the Pancreas Are a Target of Interleukin-22" Journal of Interferon Cytokine Research 21(12): 1047-1053, (2001).
Ahmed at al., "Characterization of a new full length TMPRSS3 isoform and identification of mutant alleles responsible for nonsyndromic recessive deafness in Newfoundland and Pakistan" BMC Medical Genetics 5(1): 24 (2004).
Angata et al.,"Cloning and Characterization of a Novel Mouse Siglec, mSiglec-F" Journal of Biological Chemistry 276(48): 45128-45136, (2001).
Argraves et al., "Fibulins: Physiological and Disease Perspectives" European Molecular Biology, Organization 4(12): 1127-1131, (2003).

Baldwin et al., "Functional characterization of novel human and mouse equilibrative nucleoside transporters (hENT3 and mENT3) located in intracellular membranes" Journal of Biological Chemistry, 280(16): 15880-15887, (2005).
Barbosa et al., "Identification of the Homologous Beige and Chediak-Higashi Syndrome Genes", Nature, 382: 262-265, (1996).
Ben-Yosef et al., "Claudin 14 Knockout Mice, a Model for Autosomal Recessive Deafness DFNB29, are Deaf due to Cochlear Hair Cell Degeneration", Human Molecular Genetics 12(16): 2049-2061, (2003).
Beyer et al., "Fibroblast Growth Factor 22 and its Potential Role During skin Development and Repair", Experimental Cell Research 287: 228-236, (2003).
Bjarnadpttir et al., "The human and mouse repertoire of the adhesion family of G-protein-coupled receptors" Genomics 84(1): 23-33, (2004).
Boilly et al., "FGF Signals for Cell Proliferation and Migration Through Different Pathways", Cytokine, Growth Factor Rev. 11: 295-302, (2000).
Bork (Genome Res 2000:10;398-400).
Bosserhoff et al., "Expression, Function and Clinical Relevance of MIA (Melanoma Inhibitory Activity)", Histol. Histopathol. 17: 289-300, (2002).
Brakenhoff et al., "The human E48 antigen, highly homologous to the murine Ly-6 antigen ThB, is a GPI-anchored molecule apparently involved in keratinocyte cell-cell adhesion", Journal of Cell Biology, 129(6): 1677-1689, (1995).
Brownbill et al., "Neurokinin B is a Paracrine Vasodilator in the Human Fetal Placental Circulation", Journal of Clinical Endocrinology & Metabolism 88(5): 2164-2170, (2003).
Cao et al., "Pancreatic-Derived Factor (FAM3B), a Novel Islet Cytokine, Induces Apoptosis of Insulin-Secreting (3-Cells" Diabetes 52: 2296-2303, (Sep. 2003).

(Continued)

*Primary Examiner* — Scott Long
(74) *Attorney, Agent, or Firm* — Bonny Yeung; Christopher De Vry; Arnold & Porter LLP

(57) ABSTRACT

The present invention relates to transgenic animals, as well as compositions and methods relating to the characterization of gene function. Specifically, the present invention provides transgenic mice comprising disruptions in PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 genes. Such in vivo studies and characterizations may provide valuable identification and discovery of therapeutics and/or treatments useful in the prevention, amelioration or correction of diseases or dysfunctions associated with gene disruptions such as neurological disorders; cardiovascular, endothelial or angiogenic disorders; eye abnormalities; immunological disorders; oncological disorders; bone metabolic abnormalities or disorders; lipid metabolic disorders; or developmental abnormalities.

5 Claims, 110 Drawing Sheets

OTHER PUBLICATIONS

Cappello et al., "CCL16/LEC Powerfully Triggers Effector and Antigen-presenting of Macrophages and Enhances T Cell Cytotoxicity" Journal of Leukocyte Biology 75: 135-142, (2004).

Cases et al., "Cloning of DGAT2, a Second Mammalian Diacylglycerol Acyltransferase, and Related Family Members" Journal of Biological Chemistry 276(42): 38870-38876, (2001).

Chen et al., "Cloning and Uterus/Oviduct-Specific Expression of a Novel Estrogen-regulated Gene (ERG1)" Journal of Biological Chemistry, 275(7):5248, (2000).

Clark et al., "The secreted protein discovery initiative (SPDI), a large-scale effort to identify novel human secreted and transmembrane proteins: a bioinformatics assessment", Genome Research 13(10):2265-2270, (2003).

Clayton et al., "Antigen-presenting Cell Exosomes are Protected from Complement-Mediated Lysis by Expression of CD55 and CD59" European Journal of Immunology, 33: 522-531, (2003).

Cohen-Salmon et al., "Fdp, a New Fibrocyte-derived Protein Related to MIA/CD-RAP, Has an in Vitro Effect on the Early Differentiation of the Inner Ear Mesenchyme" Journal of Biological Chemistry 275(51): 40036-40041, (Dec. 22, 2000).

Cornish et al., "Characterization of Siglec-5, a Novel Glycoprotein Expressed on Myeloid Cells Related to CD33" Blood 92(6): 2123-2132, (Sep. 15, 1998).

Cosma et al., "Molecular and functional analysis of SUMF1 mutations in multiple sulfatase deficiency", Human Mutation 23(6): 576-581, (2004).

Cosma et al., "The Multiple Sulfatase Deficiency Gene Encodes an Essential and Limiting Factor for the Activity of Sulfatases" Cell 113(4):421-422, (2003).

Coutinho et al., "An Evolving Hierarchical Family Classification for Glycosyltransferases", Journal of Molecular Biology 328(2): 307-317, (Apr. 25, 2003).

Cui et al., "ECRG2, a novel candidate of tumor suppressor gene in the esophageal carcinoma, interacts directly with metallothionein 2A and links to apoptosis" Biochem. & Biophys. Res. Comm. 302(4):904-915, (2003).

Culi and Mann, "Boca, an Endoplasmic Reticulum Protein Required for Wingless Signaling and Trafficking of LDL Receptor Family Members in *Drosophila*" Cell 112(3): 343-354, (2003).

De Cat and David, "Developmental roles of the glypicans". Semin. Cell Dev. Biol. 12(2): 117-125, (2001).

Debets, R., et al., "Two Novel IL-1 Family Members, IL-1b and IL-1E, Function as an Antagonist and Agonist of NF-KB Activation Through the Orphan IL-1 Receptor-Related Protein 21" The Journal of Immunology 167(3): 1440-1446, (2001).

DeLorey et al., "Mice lacking the j3₃ subunit of the GABAA receptor have the epilepsy phenotype and many of the behavorial characteristics of Angelman syndrome" J Neurosci. 18(20): 8505-8514, (1998).

Dierks et al., "Multiple Sultafase Deficiency is Caused by Mutations in the Gene Encoding the Human C-Formylglycine Generating Enzyme" Cell 113:435-444, (May 16, 2003).

Doetschman (Lab. Animal Sci., 1999; 49: 137-143).

Dorsch et al., "Ectopic Expression of Delta4 Impairs Hematopoietic Development and Leads to Lymphoproliferative Disease" Blood 100(6): 2046-2055, (2002).

Duarte et al., "Dosage-sensitive requirement for mouse Dll4 in artery development" Genes and Development 18:2474-2478, (2004).

Eishenhaber et al., "Enzymes and Auxiliary Factors for GPI Lipid Anchor Biosynthesis and Post-Translational Transfer to Proteins" Biocssays 25(4):367-385, (2003).

Erickson-Miller, "Characterization of Siglec-5 (CD170) Expression and Functional Activity of Anti-Siglec-5 Antibodies on Human Phagocytes" Experimental Hematology 31: 382-388, (2003).

Eriksson et al., "Three-dimensional Structure of Human Basic Fibroblast Growth Factor", PNAS, 88: 3441-3445, (Apr. 1991).

Esther et al., "Mice Lacking angiotensin-converting enzyme have low blood pressure, renal pathology, and reduced male fertility" Laboratory Investigation 74(5): 953-965, (1996).

Everett et al (Nat Genetics 1997; 17:411-422).

Filmus, J., "Glypicans in growth control and cancer" Glycobiology 11(3): 19R-23R, (2001).

Fredrikkson at al., "Novel human G protein-coupled receptors with long N-terminals containing GPS domains and Ser/Thr-rich regions" FEBS Letters 531(3): 407-414, (2002).

Gale et al., "Haploinsufficiency of delta-like 4 Ligand Results in Embryonic Lethality due to Major Defects in Arterial and Vascular Development" Proc. Natl Acad Sci USA 101(45):15949-15954, (2004).

Gerlai (Trends Neurosci, 1996; 19: 177-181).

Gonzalez-Mariscal et al., "Tight junction proteins" Prog Biophys Mol Biol. 81(1): 1-44, (2003).

Guiducci et al., "Intralesional Injection of Adenovirus Encoding CC Chemokine Ligand 16 Inhibits Mammary Tumor Growth and Prevents Metastatic-Induced Death after Surgical Removal of the Treated Primary Tumor" Journal of Immunolo. 72(7):4026-4036, (2004).

Guipponi et al., "T e Transmembrane Serine Protease (TMPRSS3) Mutated in Deafness DFNB8/10 Activates the Epithelial Sodium Channel (ENaC) in vitro" Human Molecular Genetics 11(23): 2829-2836, (2002).

Han et al., "Identification of eight genes encoding chemokine-like factor superfamily members 1 8 (CKLFSF1 8) by in silico cloning and experimental validation" Genomics 81:609-617, (2003).

Hauri et al. Biochem. Soc. Symp. 69: 73-82, (2002).

Hedrick et al., "Characterization of a Novel CC Chemokine, HCC-4, Whose Expression is Increased by Interleukin-10" Blood 91(11):4242-4247, (Jun. 1, 1998).

Heiskala at al., "The Roles of Claudin Superfamily Proteins in Paracellular Transport" (2001).

Hellmann et al., "Novel mouse endothelial cell surface marker is suppressed during differentiation of the blood brain barrier" Developmental Dynamics 202(4): 325-332, (1995).

Herz and Marschang, "Coaxing the LDL Receptor Family into the Fold" Cell 112(3): 289-292, (2003).

Hirohata et al., "Punctin, a novel ADAMTS-like molecule, ADAMTSL-1, in extracellular matrix" Journal of Biological Chemistry 277(14): 12182-12189, (Apr. 5, 2002).

Hnasko et al., "Distribution and characterization of plasmalemma vesicle protein-1 in rat endocrine glands" Journal of Endocrinology 175(3):649-661, (2002).

Howard et al., "LEC Induces Chemotaxis and Adhesion by Interacting with CCR1 and CCR8" Blood, 96(3): 840-845, (Aug. 1, 2000).

Hsieh at al., "Mesd Encodes an LRP5/6 Chaperone Essential for Specification of Mouse Embryonic Polarity", Cell 112: 355-367, (Feb. 7, 2003).

Huynh et al., "Induction of U0-44 Gene Expression by Tamoxifen in the Rat Uterus and Ovary" Endocrinology 142(7): 2985-2995, (Jan. 12, 2001).

Tmamura et al., "Protection from Pancreatitis by the Zymogen Granule Membrane Protein Integral Membrane-associated Protein-1" The Journal of Biological Chemistry 277(52):50725-50733, (2002).

Ishibashi et al., "Identification of a new multigene four-transmembrane family (MS4A) related to CD20, HTm4 and subunit of the high-affinity IgE receptor" Gene 264(1): 87-93, (2001).

Itoh et al., "Mouse hepatocyte growth factor activator gene: its expression not only in the liver but also in the gastrointestinal tract" Biochim Biophys Acta. 1491(1-3): 295-302, (2000).

Itoh et al., "Regeneration of Injured Mucosa is Impaired in Hepatocyte Growth Factor Activator—Deficient Mice" Gastroenterology 127(5): 1423-1435, (2004).

Izumikawa et al., "Nematode chondroitin polymerizing factor showing cell-/organ-specific expression is indispensable for chondroitin synthesis and embryonic cell division", Journal of Biological Chemistry 279(51): 53755-53761, (Dec. 17, 2004).

Jacks et al., (Nature, 1992; 359: 295-300).

Jaenisch, (Science, 1988; 240: 1468-1474).

Jeong et al., "Androgen Receptor Corepressor-19 kDa (ARR19), a Leucine-Rich Protein that Represses the Transcriptional Activity of Androgen Receptor through Recruitment of Histone Deacetylase", Molecular Endocrinology 18(1): 13-25, (2004).

Jones et al., "Recognition of Sialylated Meningococcal Lipopolysaccharide by Siglecs Expressed on Myeloid Cells Lead to Enhanced Bacterial Uptake" Molecular Microbiology 49(5): 1213-1225, (2003).

Juriloff et al., "Investigations of the genomic region that contains the clf1 mutation, a causal gene in multifactorial cleft lip and palate in mice" Birth Defects Res. A Clin. Mol. Teratol. 73(2):103-113, (2005).

Kasik et al., "A cDNA Cloned from Pregnant Mouse Uterus Exhibits Temporo-Spatial Expression and Predicts a Novel Protein" Biochemical Journal 330: 947-950, (1998).

Kato et al., "Nucleoside transport at the blood-testis barrier studied with primary-cultured sertoli cells" J Pharmacol Exp Ther. 312(2): 601-608, (2005).

Katoh and Katoh, "IGSFil gene, frequently up-regulated in intestinal-type gastric cancer, encodes adhesion molecule homologous to CXP.DR, FLJ22415 and ESAM" International Journal of Oncology 23(2):525-531, (Aug. 2003).

Katoh et al., "WNT3-WNT14B and WNT3A-WNT14 gene clusters CReview)" International Journal of Molecular Medicine 9(6): 579-584, (2002).

Katsanis et al., "Isolation of a Paralog of the Doyne Honeycomb Retinal Dystrophy Gene from the Multiple Retinopathy Critical Region on 11813" Human Genetics 106: 66-72, (2000).

Kim et al. (Journal of Biological Chemistry; 282(40): 29359-29367, (2007).

Kirikoshi et al., "Molecular cloning and characterization of mouse Wnt14b, clustered with mouse Wnt3 in mouse chromosome 11" International Journal of Molecular Medicine 9(2): 135-139, (2002).

Kirikoshi et al., "Molecular cloning and characterization of WNT14B, a novel member of the WNT gene family", International Journal of Oncology, 19(5): 947-952, (2001).

Kitagawa et al., "Molecular cloning of a chondroitin polymerizing factor that cooperates with chondroitin synthase for chondroitin polymerization" J Biol Chem. 278(26): 23666-23671, (2003).

Kotenko Sergei et al., "Identification of the Functional Interleukin-22 (IL-22) Receptor Complex." J. Bio. Chem. 276(4): 2725-2732, (Jan. 2001).

Krebs et al., "Haploinsufficient Lethality and Formation of Arteriovenous Malformations in Notch Pathway Mutants" Genes and Development 18: 2469-2473, (2004).

Krebs et al., "Notch Signaling is Essential for Vascular Morphogenesis in Mice" Genes Development 14: 1343-1352, (2000).

Kuehn et al., (Nature, 1987; 326: 295-298).

Kumar et al., "Identification and Initial Characterization of Four Novel Members of the Interleukin-1 Family" The Journal of Biological Chemistry 275:10308-10314, (2000).

Laliberte et al., "Neurokinin B causes concentration-dependent relaxation of isolated human placental resistance vessels" Regulatory Peptides 117(2): 123-126, (2004).

Langenbach et al., "Prostaglandin Synthase 1 Gene Disruption in Mice Reduces Arachidonic Acid-Induced Inflammation and Indomethancin-Induced Gastric Ulceration" Cell 83(3): 483-92, (Nov. 3, 1995).

Lauret et al., "Membrane-Bound Delta-4 Notch Ligand Reduces the Proliferative Activity of Primitive Human Hematopoietic CD34+CD38low Cells While Maintaining Their LTC-IC Potential" Leukemia 18: 788-797, (2004).

Lee et al. J. Med. Genet. 40(8): 629-631, (2003).

LeJeune, D., et al., "Interleukin-22 (IL-22) Activates the JAK/STAT, ERK, JNK and p38 MAP Kinase Pathways in a Rat Hepatoma Cell Line" The Journal of Biological Chemistry 277(37): 33676-33682, (2002).

Leong et al., "Molecular Cloning, Characterization and Isolation of Novel Spliced Variants of the Human Ortholog of a Rat Estrogen-Regulated Membrane-Associated Protein, U0-44" Oncogene 23:5707-5718, (2004).

Li et al., "Complete Regression of Experimental Solid Tumors by Combination LEC/chTNT-3 Immunotherapy and CD25+ T-Cell Depletion" Cancer Research 63(23): 8384-8392, (2003).

Liang et al., "Identification of a CD20-, Fc RI-, and HTm4-Related Gene Family: Sixteen New MS4A Family Members Expressed in Human and Mouse" Genomics 72(2): 119-127, (2001).

Liu et al. (Genomics, 2000; 65: 283-292).

Liu et al., "Molecular Cloning and Chromosomal Mapping of a Candidate Cytokine Gene Selectively Expressed in Human CD34+ Cells" Genomics 65(3): 283-292, (2000).

Lu et al. Drug Metab. Dispos. 32(12): 1455-1461, (2004).

Mailhos et al., "Delta4, an Endothelial Specific Notch Ligand Expressed at Sites of Physiological and Tumor Angiogenesis" Differentiation 69: 135-144, (2001).

Marshall at al, "FDC-SP, a novel secreted protein expressed by follicular dendritic cells" J Immunol 169(5):2381-2389, (Sep. 1, 2002).

Matsuo et al., "Identification of a Novel Thioredoxin-related Transmembrane Protein", Journal of Biological Chemistry 276(13): 10032-10038, (Mar. 30, 2001).

Matsuo et al., "TMX, a Human Transmembrane Oxidoreductase of the Thioredoxin Family: the Possible Role in Disulfide-linked Protein Folding in the Endoplasmic Reticulum", Archives of Biochemistry & Biophysics 423: 81-87, (2004).

Meegalla et al., "Concerted elevation of acyl-coenzyme A:diacylglycerol acyltransferase (DGAT) activity through independent stimulation of mRNA expression of DGAT1 and DGAT2 by carbohydrate and insulin" Biochem. & Biophys. Res. Comm. 298(3):317-323, (Nov. 1, 2002).

Meng et al., "Complete Physical Map of the Common Deletion Region in Williams Syndrome and Identification and Characterization of Three Novel Genes" Human Genetics 103:590-599, (1998).

Mitsui et al., "Structure and hair follicle-specific expression of genes encoding the rat high sulfur protein B2 family" Gene 208(2):123-129, (1998).

Miyazawa et al., "Molecular Cloning and Sequence Analysis of the cDNA for a Human Serine Protease Responsible for Activation of Hepatocyte Growth Factor" The Journal of Biological Chemistry 268(14):10024-10028, (1993).

Moens et al., (Development, 1993; 119: 485-499).

Moffatt et al., "Identification of a conserved cluster of skin-specific genes encoding secreted proteins" Gene 334:123-131, (Jun. 9, 2004).

Moog-Lutz et al., "JAML, a Novel Protein with Characteristics of a Junctional Adhesion Molecule, is Induced Differentiation of Myeloid Leukemia Cells" Blood 102(9): 3371-3378, (2003).

Murzin at al., "-Trefoil fold : Patterns of structure and sequence in the Kunitz inhibitors interleukins-1 and 1 and fibroblast growth factors" Journal of Molecular Biology 223(2):531-543, (1992).

Nakatake at al., "Identification of a novel fibroblast growth factor, FGF-22, preferentially expressed in the inner root sheath of the hair follicle" Biochimica et Biophysica Acta 1517(3):460-463, (2001).

Nakayama et al., "Liver-Expressed Chemokine/CC Chemokine Ligand 16 Attracts Eosinophils by Interacting with Histamine H4 Receptor" Journal of Immunology 173:2078-2083, (2004).

Niimi at al. Molecular Cell Biology 21(21): 7380-7390 (2001).

Nishimura at al., "Identification of a novel FGF,FGF-21, preferentially expressed in the liver" Biochimica at Biophysica Acta 1492(1):203-206, (2000).

Nomiyama et al., "Human CC Chemokine Liver-Expressed Chemokine/CCL 16 is a Functional Ligand for CCR1, CCR2 and CCR5, and Constitutively Expressed by Hepatocytes" International Immunology 13(8):1021-1029, (2001).

O'Brien at al., "The CA 125 gene: an extracellular superstructure dominated by repeat sequences" Tumour Biol. 22(6): 348-366, (2001).

O'Brien et al., "The CA 125 gene: a newly discovered extension of the glycosylated N-terminal domain doubles the size of this extracellular superstructure" Tumour Biol. 23(3):154-169, (2002).

Ohishi at al., "PIG-S and PIG-T, Essential for GPI Anchor Attachment to Proteins, form a Complex with GAA1 and GPI8" EMBO Journal 20(15): 4088-4098, (2001).

Ohishi et al., "Two subunits of glycosylphosphatidylinositol transamidase, GPI8 and PIG-T, form a functionally important intermolecular disulfide bridge" The Journal of Biological Chemistry 278(16): 13959-13967, (2003).

Page et al., "Excessive Placental Secretion of Neurokinin B During the Third Trimester Causes Pre-Eclampsia" Nature 405:797-800, (Jun. 15, 2000).

Paine-Saunders at al., "GPC6, a Novel Member of the Glypican Gene Family, Encodes a Product Structurally Related to GPC4 and is Colocalized with GPC5 on Human Chromosome 13" Genomics 57(3):455-458, (1999).

Pao et al., "Major facilitator superfamily" Microbiol Mol Biol Rev. 62(1):1-34 (1998).

Park et al., "Suprabasin, a novel epidermal differentiation marker and potential cornified envelope precursor" Journal of Biological Chemistry 277(47): 45195-45202, (2002).

Patel et al., "OB-BP1/Siglec-6" Journal of Biological Chemistry 274(32): 22729-22738, (1999).

Perez Jurado et al., "TBL2, a novel transducin family member in the WBS deletion: characterization of the complete sequence, genomic structure, transcriptional variants and the mouse ortholog" Cytogenetics, Cell Genetics 86(3-4): 277-284, (1999).

Pinto et al., "mRNA expression of tachykinins and tachykinin receptors in different human tissues", European Journal Pharmacol. 494(2-3): 233-239, (2004).

Preusser-Kunze et al., "Molecular Characterization of the Human Ca-formylglycine-generating Enzyme", Journal of Biological Chemistry 280(15): 14900-14910, (2005).

Puente and Lopez-Otin, "A Genomic Analysis of Rat Proteases and Protease Inhibitors" Genome Research, 14(4): 609-622, (2004).

Pyagay et al., "Collagen triple helix repeat containing 1, a novel secreted protein in injured and diseased arteries, inhibits collagen expression and promotes cell migration" Circulation Research, 96(2):261-268 (Feb. 4, 2005).

Qian et al., "Mouse Wnt9b transforming activity, tissue-specific expression, and evolution" Genomics, 81(1): 34-46, (2003).

Racay, 2002, Bratisl Lek Listy, 103: 121-126.

Radaeva et al., "Interleukin 22 (IL-22) Plays a Protective Role in T Cell-mediated Murine Hepatitis: IL-22 is a Survival Factor for Hepatocytes via STAT3 Activation", Hepatology 39: 1332-1342, (2004).

Ramesh et al., "Melanoma differentiation-associated gene 7/interleukin (IL)-24 is a novel ligand that regulates angiogenesis via the IL-22 receptor" Cancer Research, 63(16): 5105-5113, (2003).

Raschperger et al., "CLMP, a Novel Member of the CTX Family and a New Component of Epithelial Tight Junctions" The Journal of Biological Chemistry 279(1): 796-804, (2004).

Rendtorff et al., "Identification and Characterization of an Inner Ear-Expressed Human Melanoma Inhibitory Activity (MIA)-like Gene (MIAL) with a Frequent Polymorphism That Abolishes Translation", Genomics 71(1):40-52, (2001).

Robertson et al., "A Novel Conserved Cochlear Gene, OTOR: Identification, Expression Analysis, and Chromosomal Mapping" Genomics 66(3): 242-248, (2000).

Rogers et al., "Characterization of a Cluster of Human High/Ultrahigh Sulfur Keratin-associated Protein Genes Embedded in the Type I Keratin Gene Domain on Chromosome 17q12-21" Journal of Biological Chemistry, 276(22): 19440-19451, (2001).

Rui et al., "Molecular Cloning and Characterization of Four Isoforms of mCKLF, Mouse Homologues of Human Chemokine-like Factor" Molecular Breeding 30: 229-237, (2003).

Rump et al., "Binding of Ovarian Cancer Antigen CA125/MUC16 to Mesothelin Mediates Cell Adhesion", Journal of Biological Chemistry 279(10): 9190-9198, (2004).

Sauane et al., "Mda-7/IL-24 induces apoptosis of diverse cancer cell lines through JAK/STAT—independent pathways" Journal of Cellular Physiology 196(2): 334-345, (2003).

Sawasaki et al., "The transmembrane protease serine D variant: a potential Tumour candidate for diagnosis and therapeutic intervention in ovarian cancer.", Biol.25(3): 141-148, (2004).

Schlembach et al., "Neurokinin B Peptide Serum Levels are Higher in Normotensive Pregnant Women than in Preeclamptic Pregnant Women" American journal of obstetrics and gynecology 189(5): 1418-1422, (2003).

Schrag et al., "Lectin control of protein folding and sorting in the secretory pathway", Trends Biochem. Sci. 8(1): 49-57, (2003).

Scott et al, Nat Genetics Apr. 1999; 21:440-443.

Shibuya et al., "A Cluster of 21 Keratin-Associated Protein Genes within Introns of Another Gene on Human Chromosome 21q22.3" Genomics 83(4): 679-693, (2004).

Shimomura et al., "Activation of the Zymogen of Hepatocyte Growth Factor Activator by Thrombin" Journal of Biological Chemistry 268: 22927-22932, (1993).

Shoudai et al., "Isolation of cDNA encoding a novel human CC chemokine NCC-4/LEC" Biochimica et Biophysica Acta 1396(3):273-277, (Mar. 13, 1998).

Shutter et al., "D114, a Novel Notch Ligand Expressed in Arterial Endothelium" Genes & Development 14: 1313-1318, (2000).

Stan et al., "cDNA and Protein Sequence, Genomic Organization, and Analysis of cis Regulatory Elements of Mouse and Human PLVAP Genes" Genomics 72(3): 304-313,(2001).

Stan, Radu V., "Multiple PV1 dimers reside in the same stomatal or fenestral diaphragm", American journal of physiology. Heart and circulatory physiology 286(4): H1347-H1353, (2004).

Stoll et al., "Backbone Dynamics of the Human MIA Protein Studied by 15N NMR Relaxation: Implications for Extended Interactions of SH3 Domains" Protein Sci. 12: 510-519, (2003).

Stone et al., "Lipopenia and Skin Barrier Abnormalities in DGAT2-deficient Mice" Journal of Biological Chemistry 279(12): 11767-11776, (Mar. 19, 2004).

Strasly et al., "CCL16 Activates an Angiogenic Program in Vascular Endothelial Cells" Blood 103(1): 40-49, (2004).

Tachiiri et al., "Genomic structure and inducible expression of the IL-22 receptor chain in mice" Genes and Immunity 4(2): 153-159, (2003).

Tjin et al., "Multiple Myeloma Cells Catalyze Hepatocyte Growth Factor (HGF) Activation by Secreting the Serine Protease HGF-activator" Blood 104(7): 2172-2175, (Oct. 2004).

Tohda et al., "Notch ligands, Delta-1 and Delta-4 suppress the self-renewal capacity and long-term growth of two myeloblastic leukemia cell lines" Int. J. Oncology 22(5): 1073-1079, (2003).

Towne et al., "Interleukin (IL)-1F6, IL-1F8, and IL-1F9 Signal through IL-1Rrp2 and IL-1RAcP to Activate the Pathway Leading to NF-B and MAPKs" Journal of Biological Chemistry 279(14):13677-13688, (2004).

Tsukita et al., "Multifunctional strands in tight junctions" Nat Rev Mol Cell Biol. 2(4): 285-293, (2001).

Umemori et al., "FGF22 and its Close Relatives are Presynaptic Organizing Molecules in the Mammalian Brain" Cell 118: 257-270, (Jul. 23, 2004).

Underwood et al., "Ovarian tumor cells express a novel multi-domain cell surface serine protease", Biochem. Biophys. Acta 1502(3): 337-350, (Nov. 15, 2000).

Vainauskas et al., "Structural requirements for the recruitment of Gaal into a functional glycosylphosphatidylinositol transamidase complex" Journal of Biological Chemistry 277(34): 30535-30542, (2002).

Van Adelsberg, "Activation of Hepatocyte Growth Factor (HGF) by Endogenous HGF Activator is Required for Metanephric Kidney Morphogenesis in Vitro" Journal of Biological Chemistry 276: 15099-15106, (2001).

Veugelers et al., "Glypican-6, a new member of the glypican family of cell surface heparan sulfate proteoglycans" Journal of Biological Chemistry 274(38): 26968-26977, (1999).

Wakimoto et al., "A novel diacylglycerol acyltransferase (DGAT2) is decreased in human psoriatic skin and increased in diabetic mice." Biochem Biophys Res Commun. 310(2): 296-302 (Oct. 17, 2003).

Wallrapp et al., "A novel transmembrane serine protease (TMPRSS3) overexpressed in pancreatic cancer", Cancer Research 60(10): 2602-2606, (May 15, 2000).

Wang et al., "The SPRY domain-containing SOCS box protein 1 (SSB-1) interacts with MET and enhances the hepatocyte growth factor-induced Erk-Elk-1-serum response element pathway" Journal of Biological Chemistry 280(16): 16393-16401, (2005).

Waterman et al., "Activities of overt and latent diacylglycerol acyltransferases (DGATs I and II) in liver microsomes of ob/ob mice" Int J Obes Relat Metab Disord. 26(5): 742-743, (2002).

Wattenhofer et al., "Mutations in the TMPRSS3 Gene are a Rare Cause of Childhood Nonsyndromic Deafness in Caucasian Patients" J. Mol. Med. 80: 124-131, (2002).

Weng et al., "Increased expression of prostate-specific G-protein-coupled receptor in human prostate intraepithelial neoplasia and prostate cancers" Int. J. Cancer 113(5): 811-818, (2005).

Wilcox et al., "Mutations in the Gene Encoding Tight Junction Claudin-14 Cause Autosomal Recessive Deafness DFNB29" Cell 104: 165-172, (Jan. 12, 2001).

Wilkie et al., "Functions of Fibroblast Growth Factors and their Receptors." Curr. Biol. 5(5):500-507, (1995).

Wines et al., "Identification of Mesoderm Development (mesd) Candidate Genes by Comparative Mapping and Genome Sequence Analysis" Genomics 72(1): 88-98, (2001).

Wolk et al., "IL-22 Increases the Innate Immunity of Tissues" Immunity 21(2): 241-254, (2004).

Wong et al., "Characterization of the Oligosaccharides Associated with the Human Ovarian Tumor Marker CA125" The Journal of Biological Chemistry 278(31): 28619-28634, (2003).

Wu et al., "Generation of Committed Erythroid BFU-E and CFU-E Progenitors Does Not Require Erythropoietin or the Erythropoietin Receptor" Cell 83: 59-67, (1995).

Xia et al., "Identification of a prostate-specific G-protein coupled receptor in prostate cancer", Oncogene 20(41): 5903-5907, (2001).

Xia et al., "Overexpression of chemokine-like factor 2 promotes the proliferation and survival of C2C12 skeletal muscle cells" Biochim Biophys Acta 1591: 163-173, (2002).

Xie et al., "Interleukin (IL)-22, a Novel Human Cytokine That Signals through the Interferon Receptor-related Proteins CRF2-4 and IL-22R." J. Bio. Chem. 275(4): 31335-31339, (2000).

Xu et al., "PSGR, a Novel Prostate-Specific Gene with Homogy to a G Protein-Coupled Receptor, is Overexpressed in Prostate Cancer" Cancer Research 60: 6568-6572, (2000).

Yada, "Chondroitin sulfate synthase-2. Molecular cloning and characterization of a novel human glycosyltransferase homologous to chondroitin sulfate glucuronyltransferase, which has dual enzymatic activities" Journal of Biological Chemistry 278(32):30235-30247,(May 20, 2003).

Yerushalmi et al., "ERGL, a novel gene related to ERGIC-53 that is highly expressed in normal and neoplastic prostate and several other tissues" Gene 265(1-2): 55-60, (2001).

Yuan et al., "Cloning and genetic characterization of an evolutionarily conserved human olfactory receptor that is differentially expressed across species" Gene 278(1-2): 41-51, (2001).

Yue et al., "Short Tandem Repeat Polymorphism in a Novel Esophageal Cancer-Related Gene (ECRG2) Implicates Susceptibility to Esophageal Cancer in Chinese Population", International Journal of Cancer 108(2): 232-236, (2004).

Zhang et al., "The LRP5 high-bone-mass G171V mutation disrupts LRP5 interaction with Mesd." Molecular & Cellular Biology 24(11): 4677-4684, (2004).

Zhang et al., "The Murine Inhibitory Receptor MSiglec-E is Expressed Broadly on Cells of the Innate Immune System Whereas mSiglec-F is Restricted to Eosinophils" European Journal of Immunology, 34: 1175-1184, (2004).

Zhu et al., "Cloning, Expression, and Initial Characterization of a Novel Cytokine-like Gene Family", Genomics 80(2): 144-150, (2002).

* cited by examiner

FIGURE 1

CCCAAGCCAGCCGAGCCGCCAGAGCCGCGGGCCGCGGGGGTGTCGCGGGCCCAACCCCAGGATGCTCCCCTGCG
CCTCCTGCCTACCCGGGTCTCTACTGCTCTGGGCGCTGCTACTGTTGCTCTTGGGATCAGCTTCTCCTCAGGAT
TCTGAAGAGCCCGACAGCTACACGGAATGCACAGATGGCTATGAGTGGGACCCAGACAGCCAGCACTGCCGGGA
TGTCAACGAGTGTCTGACCATCCCTGAGGCCTGCAAGGGGGAAATGAAGTGCATCAACCACTACGGGGGCTACT
TGTGCCTGCCCCGCTCCGCTGCCGTCATCAACGACCTACATGGCGAGGGACCCCGCCACCAGTGCCTCCCGCT
CAACACCCCAACCCCTGCCCACCAGGCTATGAGCCCGACGATCAGGACAGCTGTGTGGATGTGGACGAGTGTGC
CCAGGCCCTGCACGACTGTCGCCCCAGCCAGGACTGCCATAACTTGCCTGGCTCCTATCAGTGCACCTGCCCTG
ATGGTTACCGCAAGATCGGGCCCGAGTGTGTGGACATAGACGAGTGCCGCTACCGCTACTGCCAGCACCGCTGC
GTGAACCTGCCTGGCTCCTTCCGCTGCCAGTGCGAGCCGGGCTTCCAGCTGGGGCCTAACAACCGCTCCTGTGT
TGATGTGAACGAGTGTGACATGGGGGCCCCATGCGAGCAGCGCTGCTTCAACTCCTATGGGACCTTCCTGTGTC
GCTGCCACCAGGGCTATGAGCTGCATCGGGATGGCTTCTCCTGCAGTGATATTGATGAGTGTAGCTACTCCAGC
TACCTCTGTCAGTACCGCTGCGTCAACGAGCCAGGCCGTTTCTCCTGCCACTGCCCACAGGGTTACCAGCTGCT
GGCCACACGCCTCTGCCAAGACATTGATGAGTGTGAGTCTGGTGCGCACCAGTGCTCCGAGGCCCAAACCTGTG
TCAACTTCCATGGGGGCTACCGCTGCGTGGACACCAACCGCTGCGTGGAGCCCTACATCCAGGTCTCTGAGAAC
CGCTGTCTCTGCCCGGCCTCCAACCCTCTATGTCGAGAGCAGCCTTCATCCATTGTGCACCGCTACATGACCAT
CACCTCGGAGCGGAGCGTGCCCGCTGACGTGTTCCAGATCCAGGCGACCTCCGTCTACCCGGTGCCTACAATG
CCTTTCAGATCCGTGCTGGAAACTCGCAGGGGGACTTTTACATTAGGCAAATCAACAACGTCAGCGCCATGCTG
GTCCTCGCCCGGCCGGTGACGGGCCCCCGGGAGTACGTGCTGGACCTGGAGATGGTCACCATGAATTCCCTCAT
GAGCTACCGGGCCAGCTCTGTACTGAGGCTCACCGTCTTTGTAGGGGCCTACACCTTCTGAGGAGCAGGAGGGA
GCCACCCTCCCTGCAGCTACCCTAGCTGAGGAGCCTGTTGTGAGGGGCAGAATGAGAAAGGCAATAAAGGGAGA
AAGAAAGTCCTGGTGGCTGAGGTGGGCGGGTCACACTGCAGGAAGCCTCAGGCTGGGGCAGGGTGGCACTTGGG
GGGGCAGGCCAAGTTCACCTAAATGGGGGTCTCTATATGTTCAGGCCCAGGGGCCCCCATTGACAGGAGCTGGG
AGCTCTGCACCACGAGCTTCAGTCACCCCGAGAGGAGAGGAGGTAACGAGGAGGGCGGACTCCAGGCCCCGGCC
CAGAGATTTGGACTTGGCTGGCTTGCAGGGGTCCTAAGAAACTCCACTCTGGACAGCGCCAGGAGGCCCTGGGT
TCCATTCCTAACTCTGCCTCAAACTGTACATTTGGATAAGCCCTAGTAGTTCCCTGGGCCTGTTTTTCTATAAA
ACGAGGCAACTGGAAAAAAAAAAAA

FIGURE 2

```
MLPCASCLPGSLLLWALLLLLLGSASPQDSEEPDSYTECTDGYEWDPDSQHCRDVNECLTI
PEACKGEMKCINHYGGYLCLPRSAAVINDLHGEGPPPPVPPAQHPNPCPPGYEPDDQDSCV
DVDECAQALHDCRPSQDCHNLPGSYQCTCPDGYRKIGPECVDIDECRYRYCQHRCVNLPGS
FRCQCEPGFQLGPNNRSCVDVNECDMGAPCEQRCFNSYGTFLCRCHQGYELHRDGFSCSDI
DECSYSSYLCQYRCVNEPGRFSCHCPQGYQLLATRLCQDIDECESGAHQCSEAQTCVNFHG
GYRCVDTNRCVEPYIQVSENRCLCPASNPLCREQPSSIVHRYMTITSERSVPADVFQIQAT
SVYPGAYNAFQTRAGNSQGDFYTRQTNNVSAMLVLARPVTGPREYVLDLEMVTMNSLMSYR
ASSVLRLTVFVGAYTF
```

Signal sequence:              Amino acids 1-25

N-glycosylation sites:        Amino acids 198-202;394-398

N-myristoylation sites:       Amino acids
                              76-82;145-151;182-188;
                              222-228;290-296;305-311;371-377;
                              381-387

Aspartic acid and asparagine hydroxylation sites:
                              140-152;177-189;217-229;258-270

FIGURE 3

```
CCCACGCGTCCGGCCTTCTCTCTGGACTTTGCATTTCCATTCCTTTTCATTGACAAACTGACTTTTTTTATTTC
TTTTTTTCCATCTCTGGGCCAGCTTGGGATCCTAGGCCGCCCTGGGAAGACATTTGTGTTTTACACACATAAGG
ATCTGTCTTTGGGGTTTCTTCTTCCTCCCCTCACATTGGCATTGCTTAGTGGTTGTGTGGCGACGGAGACCACG
TGGGCTCAGTGCTTGCTTGCACTTATCTGCCTAGGTACATCGAAGTCTTTTGACCTCCATACAGTGATTATGCC
TGTCATCGCTGGTGGTATCCTGGCGGCCTTGCTCCTGCTGATAGTTGTCGTGCTCTGTCTTTACTTCAAAATAC
ACAACGCGCTAAAAGCTGCAAAGGAACCTGAAGCTGTGGCTGTAAAAAATCACAACCCAGACAAGGTGTGGTGG
GCCAAGAACAGCCAGGCCAAAACCATTGCCACGGAGTCTTGTCCTGCCCTGCAGTGCTGTGAAGGATATAGAAT
GTGTGCCAGTTTTGATTCCCTGCCACCTTGCTGTTGCGACATAAATGAGGGCCTCTGAGTTAGGAAAGGCTCCC
TTCTCAAAGCAGAGCCCTGAAGACTTCAATGATGTCAATGAGGCCACCTGTTTGTGATGTGCAGGCACAGAAGA
AAGGCACAGCTCCCCATCAGTTTCATGGAAAATAACTCAGTGCCTGCTGGGAACCAGCTGCTGGAGATCCCTAC
AGAGAGCTTCCACTGGGGGCAACCCTTCCAGGAAGGAGTTGGGGAGAGAGAACCCTCACTGTGGGGAATGCTGA
TAAACCAGTCACACAGCTGCTCTATTCTCACACAAATCTACCCCTTGCGTGGCTGGAACTGACGTTTCCCTGGA
GGTGTCCAGAAAGCTGATGTAACACAGAGCCTATAAAAGCTGTCGGTCCTTAAGGCTGCCCAGCGCCTTGCCAA
AATGGAGCTTGTAAGAAGGCTCATGCCATTGACCCTCTTAATTCTCTCCTGTTTGGCGGAGCTGACAATGGCGG
AGGCTGAAGGCAATGCAAGCTGCACAGTCAGTCTAGGGGGTGCCAATATGGCAGAGACCCACAAAGCCATGATC
CTGCAACTCAATCCCAGTGAGAACTGCACCTGGACAATAGAAAGACCAGAAAACAAAAGCATCAGAATTATCTT
TTCCTATGTCCAGCTTGATCCAGATGGAAGCTGTGAAAGTGAAAACATTAAAGTCTTTGACGGAACCTCCAGCA
ATGGGCCTCTGCTAGGGCAAGTCTGCAGTAAAAACGACTATGTTCCTGTATTTGAATCATCATCCAGTACATTG
ACGTTTCAAATAGTTACTGACTCAGCAAGAATTCAAAGAACTGTCTTTGTCTTCTACTACTTCTTCTCTCCTAA
CATCTCTATTCCAAACTGTGGCGGTTACCTGGATACCTTGGAAGGATCCTTCACCAGCCCCAATTACCCAAAGC
CGCATCCTGAGCTGGCTTATTGTGTGTGGCACATACAAGTGGAGAAAGATTACAAGATAAAACTAAACTTCAAA
GAGATTTTCCTAGAAATAGACAAACAGTGCAAATTTGATTTTCTTGCCATCTATGATGGCCCCTCCACCAACTC
TGGCCTGATTGGACAAGTCTGTGGCCGTGTGACTCCCACCTTCGAATCGTCATCAAACTCTCTGACTGTCGTGT
TGTCTACAGATTATGCCAATTCTTACCGGGATTTTCTGCTTCCTACACCTCAATTTATGCAGAAAACATCAAC
ACTACATCTTTAACTTGCTCTTCTGACAGGATGAGAGTTATTATAAGCAAATCCTACCTAGAGGCTTTTAACTC
TAATGGGAATAACTTGCAACTAAAAGACCCAACTTGCAGACCAAAATTATCAAATGTTGTGGAATTTTCTGTCC
CTCTTAATGGATGTGGTACAATCAGAAAGGTAGAAGATCAGTCAATTACTTACACCAATATAATCACCTTTTCT
GCATCCTCAACTTCTGAAGTGATCACCCGTCAGAAACAACTCCAGATTATTGTGAAGTGTGAAATGGGACATAA
TTCTACAGTGGAGATAATATACATAACAGAAGATGATGTAATACAAAGTCAAAATGCACTGGGCAAATATAACA
CCAGCATGGCTCTTTTTGAATCCAATTCATTTGAAAAGACTATACTTGAATCACCATATTATGTGGATTTGAAC
CAAACTCTTTTTGTTCAAGTTAGTCTGCACACCTCAGATCCAAATTTGGTGGTGTTTCTTGATACCTGTAGAGC
CTCTCCCACCTCTGACTTTGCATCTCCAACCTACGACCTAATCAAGAGTGGATGTAGTCGAGATGAAACTTGTA
AGGTGTATCCCTTATTTGGACACTATGGGAGATTCCAGTTTAATGCCTTTAAATTCTTGAGAAGTATGAGCTCT
GTGTATCTGCAGTGTAAAGTTTTGATATGTGATAGCAGTGACCACCAGTCTCGCTGCAATCAAGGTTGTGTCTC
CAGAAGCAAACGAGACATTTCTTCATATAAATGGAAAACAGATTCCATCATAGGACCCATTCGTCTGAAAAGGG
ATCGAAGTGCAAGTGGCAATTCAGGATTTCAGCATGAAACACATGCGGAAGAAACTCCAAACCAGCCTTTCAAC
AGTGTGCATCTGTTTTCCTTCATGGTTCTAGCTCTGAATGTGGTGACTGTAGCGACAATCACAGTGAGGCATTT
TGTAAATCAACGGGCAGACTACAAATACCAGAAGCTGCAGAACTATTAACTAACAGGTCCAACCCTAAGTGAGA
CATGTTTCTCCAGGATGCCAAAGGAAATGCTACCTCGTGGCTACACATATTTGAATAAATGAGGAAGGGCCTG
AAAGTGACACACAGGCCTGCATGTAAAAAAA
```

FIGURE 4

```
MELVRRLMPLTLLILSCLAELTMAEAEGNASCTVSLGGANMAETHKAMILQLNPSENCTWT
IERPENKSIRIIFSYVQLDPDGSCESENIKVFDGTSSNGPLLGQVCSKNDYVPVFESSSST
LTFQIVTDSARIQRTVFVFYYFFSPNISIPNCGGYLDTLEGSFTSPNYPKPHPELAYCVWH
IQVEKDYKIKLNFKEIFLEIDKQCKFDFLAIYDGPSTNSGLIGQVCGRVTPTFESSSNSLT
VVLSTDYANSYRGFSASYTSIYAENINTTSLTCSSDRMRVIISKSYLEAFNSNGNNLQLKD
PTCRPKLSNVVEFSVPLNGCGTIRKVEDQSITYTNIITFSASSTSEVITRQKQLQIIVKCE
MGHNSTVEIIYITEDDVIQSQNALGKYNTSMALFESNSFEKTILESPYYVDLNQTLFVQVS
LHTSDPNLVVFLDTCRASPTSDFASPTYDLIKSGCSRDETCKVYPLFGHYGRFQFNAFKFL
RSMSSVYLQCKVLICDSSDHQSRCNQGCVSRSKRDISSYKWKTDSIIGPIRLKRDRSASGN
SGFQHETHAEETPNQPFNSVHLFSFMVLALNVVTVATITVRHFVNQRADYKYQKLQNY
```

Signal sequence:

amino acids 1-24

Transmembrane domain:

amino acids 571-586

N-glycosylation site.

amino acids 29-33, 57-61, 67-71, 148-152, 271-275, 370-374, 394-398, 419-423

Casein kinase II phosphorylation site.

amino acids 22-26, 108-112, 289-293, 348-352, 371-375, 379-383, 408-412, 463-467, 520-524, 556-560

Tyrosine kinase phosphorylation site.

amino acids 172-180, 407-415, 407-416, 519-528

N-myristoylation site.

amino acids 28-34, 38-44, 83-89, 95-101, 104-110, 226-232

Prokaryotic membrane lipoprotein lipid attachment site.

amino acids 7-18

FIGURE 5

GCAAGCGGCGAAATGGCGCCCTCCGGGAGTCTTGCAGTTCCCCTGGCAGTCCTGGTGCTGT
TGCTTTGGGGTGCTCCCTGGACGCACGGGCGGCGGAGCAACGTTCGCGTCATCACGGACGA
GAACTGGAGAGAACTGCTGGAAGGAGACTGGATGATAGAATTTTATGCCCCGTGGTGCCCT
GCTTGTCAAAATCTTCAACCGGAATGGGAAAGTTTTGCTGAATGGGGAGAAGATCTTGAGG
TTAATATTGCGAAAGTAGATGTCACAGAGCAGCCAGGACTGAGTGGACGGTTTATCATAAC
TGCTCTTCCTACTATTTATCATTGTAAAGATGGTGAATTTAGGCGCTATCAGGGTCCAAGG
ACTAAGAAGGACTTCATAAACTTTATAAGTGATAAAGAGTGGAAGAGTATTGAGCCCGTTT
CATCATGGTTTGGTCCAGGTTCTGTTCTGATGAGTAGTATGTCAGCACTCTTTCAGCTATC
TATGTGGATCAGGACGTGCCATAACTACTTTATTGAAGACCTTGGATTGCCAGTGTGGGA
TCATATACTGTTTTTGCTTTAGCAACTCTGTTTTCCGGACTGTTATTAGGACTCTGTATGA
TATTTGTGGCAGATTGCCTTTGTCCTTCAAAAAGGCGCAGACCACAGCCATACCCATACCC
TTCAAAAAAATTATTATCAGAATCTGCACAACCTTTGAAAAAAGTGGAGGAGGAACAAGAG
GCGGATGAAGAAGATGTTTCAGAAGAAGAAGCTGAAAGTAAAGAAGGAACAAACAAAGACT
TTCCACAGAATGCCATAAGACAACGCTCTCTGGGTCCATCATTGGCCACAGATAAATCCTA
GTTAAATTTTATAGTTATCTTAATATTATCATTTTGATAAAAACAGAAGATTCATCATTTT
GTTTGGTTTGAAGTGAACTGTGACTTTTTTGAATATTGCAGGGTTCAGTCTAGATTGTCAT
TAAATTGAAGAGTCTACATTCAGAACATAAAAGCACTAGGTATACAAGTTTGAAATATGAT
TTAAGCACAGTATGATGGTTTAAATAGTTCTCTAATTTTTGAAAAATCGTGCCAAGCAATA
AGATTTATGTATATTTGTTTAATAATAACCTATTTCAAGTCTGAGTTTTGAAAATTTACAT
TTCCCAAGTATTGCATTATTGAGGTATTTAACAAGATTATTTTAGACAAAAATATTTCTCA
TTTGATATAATTTTTCTCTGTTTCACTGTGTGAAAAAAAGAAGATATTTCCCATAAATGGG
AAGTTTGCCCATTGTCTCAAGAAATGTGTATTTCAGTGACAATTTCGTGGTCTTTTTAGAG
GTATATTCCAAAATTTCCTTGTATTTTTAGGTTATGCAACTAATAAAAACTACCTTACATT
AATTAATTACAGTTTTCTACACATGGTAATACAGGATATGCTACTGATTTAGGAAGTTTTT
AAGTTCATGGTATTCTCTTGATTCCAACAAAGTTTGATTTTCTCTTGTATTTTTCTTACTT
ACTATGGGTTACATTTTTTATTTTTCAAATTGGATGATAATTTCTTGGAAACATTTTTTAT
GTTTTAGTAAACAGTATTTTTTGTTGTTTCAAACTGAAGTTTACTGAGAGATCCATCAAA
TTGAACAATCTGTTGTAATTTAAAATTTTGGCCACTTTTTTCAGATTTTACATCATTCTTG
CTGAACTTCAACTTGAAATTGTTTTTTTTTCTTTTGGATGTGAAGGTGAACATTCCTGA
TTTTTGTCTGATGTGAAAAAGCCTTGGTATTTTACATTTTGAAAATTCAAAGAAGCTTAAT
ATAAAAGTTTGCATTCTACTCAGGAAAAGCATCTTCTTGTATATGTCTTAAATGTATTTT
TGTCCTCATATACAGAAAGTTCTTAATTGATTTACAGTCTGTAATGCTTGATGTTTTAAA
ATAATAACATTTTTATATTTTTAAAAGACAAACTTCATATTATCCTGTGTTCTTTCCTGA
CTGGTAATATTGTGTGGGATTTCACAGGTAAAGTCAGTAGGATGGAACATTTTAGTGTAT
TTTTACTCCTTAAAGAGCTAGAATACATAGTTTTCACCTTAAAAGAAGGGGGAAAATCATA
AATACAATGAATCAACTGACCATTACGTAGTAGACAATTTCTGTAATGTCCCCTTCTTTCT
AGGCTCTGTTGCTGTGTGAATCCATTAGATTTACAGTATCGTAATATACAAGTTTTCTTTA
AAGCCCTCTCCTTTAGAATTTAAAATATTGTACCATTAAAGAGTTTGGATGTGTAACTTGT
GATGCCTTAGAAAAATATCCTAAGCACAAAATAAACCTTTCTAACCACTTCATTAAAGCTG
AAAAAAAAAAAAAAAAAA

FIGURE 6

MAPSGSLAVPLAVLVLLLWGAPWTHGRRSNVRVITDENWRELLEGDWMIEFYAPWCPACQN
LQPEWESFAEWGEDLEVNIAKVDVTEQPGLSGRFIITALPTIYHCKDGEFRRYQGPRTKKD
FINFISDKEWKSIEPVSSWFGPGSVLMSSMSALFQLSMWIRTCHNYFIEDLGLPVWGSYTV
FALATLFSGLLLGLCMIFVADCLCPSKRRRPQPYPYPSKKLLSESAQPLKKVEEEQEADEE
DVSEEEAESKEGTNKDFPQNAIRQRSLGPSLATDKS

Signal sequence:

amino acids 1-26

Transmembrane domain:

amino acids 182-201

Casein kinase II phosphorylation site.

amino acids 68-72, 119-123, 128-132, 247-251, 257-261

Tyrosine kinase phosphorylation site.

amino acids 107-115

N-myristoylation site.

amino acids 20-26, 192-198

Amidation site.

amino acids 25-29

FIGURE 7

```
CCCACGCGTCCGCCCACGCGTCCGGCTGAACACCTCTTCTTTGGAGTCAGCCACTGATGAG
GCAGGGTCCCCACTTGCAGCTGCAGCAGCTGCAGCAGCTGCAGAGCGCTGCTCCTGGCTGG
TGCCACTGGTGCGCACGCTGCTAGACCGTGCCTATGAGCCGCTGGGGCTGCAGTGGGGACT
GCCCTCCCTGCCACCCACCAATGGCAGCCCCACCTTCTTTGAAGACTTCCAGGCTTTTTGT
GCCACACCCGAATGGCGCCACTTCATCGACAAACAGGTACAGCCAACCATGTCCCAGTTCG
AAATGGACACGTATGCTAAGAGCCACGACCTTATGTCAGGTTTCTGGAATGCCTGCTATGA
CATGCTTATGAGCAGTGGGCAGCGGCGCCAGTGGGAGCGCGCCCAGAGTCGTCGGGCCTTC
CAGGAGCTGGTGCTGGAACCTGCGCAGAGGCGGGCGCGCCTGGAGGGGCTACGCTACACGG
CAGTGCTGAAGCAGCAGGCAACGCAGCACTCCATGGCCCTGCTGCACTGGGGGGCGCTGTG
GCGCCAGCTCGCCAGCCCATGTGGGGCCTGGGCGCTGAGGGACACTCCCATCCCCGCTGG
AAACTGTCCAGCGCCGAGACATATTCACGCATGCGTCTGAAGCTGGTGCCCAACCATCACT
TCGACCCTCACCTGGAAGCCAGCGCTCTCCGAGACAATCTGGGTGAGGTTCCCCTGACACC
CACCGAGGAGGCCTCACTGCCTCTGGCAGTGACCAAAGAGGCCAAAGTGAGCACCCCACCC
GAGTTGCTGCAGGAGGACCAGCTCGGCGAGGACGAGCTGGCTGAGCTGGAGACCCCGATGG
AGGCAGCAGAACTGGATGAGCAGCGTGAGAAGCTGGTGCTGTCGGCCGAGTGCCAGCTGGT
GACGGTAGTGGCCGTGGTCCCAGGGCTGCTGGAGGTCACCACACAGAATGTATACTTCTAC
GATGGCAGCACTGAGCGCGTGGAAACCGAGGAGGGCATCGGCTATGATTTCCGGCGCCCAC
TGGCCCAGCTGCGTGAGGTCCACCTGCGGCGTTTCAACCTGCGCCGTTCAGCACTTGAGCT
CTTCTTTATCGATCAGGCCAACTACTTCCTCAACTTCCCATGCAAGGTGGGCACGACCCCA
GTCTCATCTCCTAGCCAGACTCCGAGACCCCAGCCTGGCCCCATCCCACCCCATACCCAGG
TACGGAACCAGGTGTACTCGTGGCTCCTGCGCCTACGGCCCCCCTCTCAAGGCTACCTAAG
CAGCCGCTCCCCCCAGGAGATGCTGCGTGCCTCAGGCCTTACCCAGAAATGGGTACAGCGT
GAGATATCCAACTTCGAGTACTTGATGCAACTCAACACCATTGCGGGGCGGACCTACAATG
ACCTGTCTCAGTACCCTGTGTTCCCCTGGGTCCTGCAGGACTACGTGTCCCCAACCCTGGA
CCTCAGCAACCCAGCCGTCTTCCGGGACCTGTCTAAGCCCATCGGTGTGGTGAACCCCAAG
CATGCCCAGCTCGTGAGGGAGAAGTATGAAAGCTTTGAGGACCCAGCAGGGACCATTGACA
AGTTCCACTATGGCACCCACTACTCCAATGCAGCAGGCGTGATGCACTACCTCATCCGCGT
GGAGCCCTTCACCTCCCTGCACGTCCAGCTGCAAAGTGGCCGCTTTGACTGCTCCGACCGG
CAGTTCCACTCGGTGGCGGCAGCCTGGCAGGCACGCCTGGAGAGCCCTGCCGATGTGAAGG
AGCTCATCCCGGAATTCTTCTACTTTCCTGACTTCCTGGAGAACCAGAACGGTTTTGACCT
GGGCTGTCTCCAGCTGACCAACGAGAAGGTAGGCGATGTGGTGCTACCCCCGTGGGCCAGC
TCTCCTGAGGACTTCATCCAGCAGCACCGCCAGGCTCTGGAGTCGGAGTATGTGTCTGCAC
ACCTACACGAGTGGATCGACCTCATCTTTGGCTACAAGCAGCGGGGCCAGCCGCCGAGGA
GGCCCTCAATGTCTTCTATTACTGCACCTATGAGGGGCTGTAGACCTGGACCATGTGACA
GATGAGCGGGAACGGAAGGCTCTGGAGGGCATTATCAGCAACTTTGGGCAGACTCCCTGTC
AGCTGCTGAAGGAGCCACATCCAACTCGGCTCTCAGCTGAGGAAGCAGCCCATCGCCTTGC
ACGCCTGGACACTAACTCACCTAGCATCTTCCAGCACCTGGACGAACTCAAGGCATTCTTC
GCAGAGGTGACTGTGAGTGCCAGTGGGCTGCTGGGCACCCACAGCTGGTTGCCCTATGACC
GCAACATAAGCAACTACTTCAGCTTCAGCAAAGACCCCACCATGGGCAGCCACAAGACGCA
GCGACTGCTGAGTGGCCCGTGGGTGCCAGGCAGTGGTGTGAGTGGACAAGCACTGGCAGTG
GCCCCGGATGGAAAGCTGCTATTCAGCGGTGGCCACTGGGATGGCAGCCTGCGGGTGACTG
CACTACCCCGTGGCAAGCTGTTGAGCCAGCTCAGCTGCCACCTTGATGTAGTAACCTGCCT
TGCACTGGACACCTGTGGCATCTACCTCATCTCAGGCTCCCGGGACACCACGTGCATGGTG
TGGCGGCTCCTGCATCAGGGTGGTCTGTCAGTAGGCCTGGCACCAAAGCCTGTGCAGGTCC
TGTATGGGCATGGGGCTGCAGTGAGCTGTGTGGCCATCAGCACTGAACTTGACATGGCTGT
GTCTGGATCTGAGGATGGAACTGTGATCATACACACTGTACGCCGCGGACAGTTTGTAGCG
GCACTACGGCCTCTGGGTGCCACATTCCCTGGACCTATTTTCCACCTGGCATTGGGGTCCG
AAGGCCAGATTGTGGTACAGAGCTCAGCGTGGGAACGTCCTGGGGCCCAGGTCACCTACTC
CTTGCACCTGTATTCAGTCAATGGGAAGTTGCGGGCTTCACTGCCCCTGGCAGAGCAGCCT
ACAGCCCTGACGGTGACAGAGGACTTTGTGTTGCTGGGCACCGCCCAGTGCGCCCTGCACA
TCCTCCAACTAAACACACTGCTCCCGGCCGCGCCTCCCTTGCCCATGAAGGTGGCCATCCG
CAGCGTGGCCGTGACCAAGGAGCCGACCACGTGCTGGTGGGCCTGGAGGATGGCAAGCTC
ATCGTGGTGGTCGCGGGCAGCCCTCTGAGGTGCGCAGCAGCCAGTTCGCGCGGAAGCTGT
GGCGGTCCTCGCGGCGCATCTCCCAGGTGTCCTCGGGAGAGACGGAATACAACCCTACTGA
GGCGCGCTGAACCTGGCCAGTCCGGCTGCTCGGGCCCGCCCCGGCAGGCCTGGCCCGGG
AGGCCCCGCCCAGAAGTCGGCGGGAACACCCCGGGGTGGGCAGCCCAGGGGGTGAGCGGGG
CCCACCCTGCCCAGCTCAGGGATTGGCGGGCGATGTTACCCCCTCAGGGATTGGCGGGCGG
AAGTCCCGCCCCTCGCCGGCTGAGGGGCCGCCCTGAGGGCCAGCACTGGCGTCT
```

FIGURE 8

MSQFEMDTYAKSHDLMSGFWNACYDMLMSSGQRRQWERAQSRRAFQELVLEPAQRRARLEG
LRYTAVLKQQATQHSMALLHWGALWRQLASPCGAWALRDTPTPRWKLSSAETYSRMRLKLV
PNHHFDPHLEASALRDNLGEVPLTPTEEASLPLAVTKEAKVSTPPELLQEDQLGEDELAEL
ETPMEAAELDEQREKLVLSAECQLVTVVAVVPGLLEVTTQNVYFYDGSTERVETEEGIGYD
FRRPLAQLREVHLRRFNLRRSALELFFIDQANYFLNFPCKVGTTPVSSPSQTPRPQPGPIP
PHTQVRNQVYSWLLRLRPPSQGYLSSRSPQEMLRASGLTQKWVQREISNFEYLMQLNTIAG
RTYNDLSQYPVFPWVLQDYVSPTLDLSNPAVFRDLSKPIGVVNPKHAQLVREKYESFEDPA
GTIDKFHYGTHYSNAAGVMHYLIRVEPFTSLHVQLQSGRFDCSDRQFHSVAAAWQARLESP
ADVKELIPEFFYFPDFLENQNGFDLGCLQLTNEKVGDVVLPPWASSPEDFIQQHRQALESE
YVSAHLHEWIDLIFGYKQRGPAAEEALNVFYYCTYEGAVDLDHVTDERERKALEGIISNFG
QTPCQLLKEPHPTRLSAEEAAHRLARLDTNSPSIFQHLDELKAFFAEVTVSASGLLGTHSW
LPYDRNISNYFSFSKDPTMGSHKTQRLLSGPWVPGSGVSGQALAVAPDGKLLFSGGHWDGS
LRVTALPRGKLLSQLSCHLDVVTCLALDTCGIYLISGSRDTTCMVWRLLHQGGLSVGLAPK
PVQVLYGHGAAVSCVAISTELDMAVSGSEDGTVIIHTVRRGQFVAALRPLGATFPGPIFHL
ALGSEGQIVVQSSAWERPGAQVTYSLHLYSVNGKLRASLPLAEQPTALTVTEDFVLLGTAQ
CALHILQLNTLLPAAPPLPMKVAIRSVAVTKERSHVLVGLEDGKLIVVVAGQPSEVRSSQF
ARKLWRSSRRISQVSSGETEYNPTEAR

N-glycosylation site.

amino acids 677-681 cAMP- and cGMP-dependent protein kinase phosphorylation site.

amino acids 985-989

Tyrosine kinase phosphorylation site.

amino acids 56-65, 367-376, 543-551

N-myristoylation site.

amino acids 61-67, 436-442, 604-610, 610-616, 664-670, 691-697,
706-712, 711-717, 769-775, 785-791, 802-808, 820-826, 834-840,
873-879, 912-918, 954-960

FIGURE 9

```
CATTGTGTTGGGCACAGCTCTCACTCACCCTCCGGCTTCCTGTCGGGGCTTTCTCAGCCC
CACCCCACGTTTGGACATTTGGAGCATTTCCTTCCCTGACAGCCGGACCTGGGACTGGGC
TGGGGCCCTGGCGGATGGAGACATGCTGCCCCTGCTGCTGCTGCCCCTGCTGTGGGGGGG
GTCCCTGCAGGAGAAGCCAGTGTACGAGCTGCAAGTGCAGAAGTCGGTGACGGTGCAGGA
GGGCCTGTGCGTCCTTGTGCCCTGCTCCTTCTCTTACCCCTGGAGATCCTGGTATTCCTC
TCCCCCACTCTACGTCTACTGGTTCCGGGACGGGGAGATCCCATACTACGCTGAGGTTGT
GGCCACAAACAACCCAGACAGAAGAGTGAAGCCAGAGACCCAGGGCCGATTCCGCCTCCT
TGGGGATGTCCAGAAGAAGAACTGCTCCCTGAGCATCGGAGATGCCAGAATGGAGGACAC
GGGAAGCTATTTCTTCCGCGTGGAGAGAGGAAGGGATGTAAAATATAGCTACCAACAGAA
TAAGCTGAACTTGGAGGTGACAGCCCTGATAGAGAAACCCGACATCCACTTTCTGGAGCC
TCTGGAGTCCGGCCGCCCCACAAGGCTGAGCTGCAGCCTTCCAGGATCCTGTGAAGCGGG
ACCACCTCTCACATTCTCCTGGACGGGGAATGCCCTCAGCCCCCTGGACCCCGAGACCAC
CCGCTCCTCGGAGCTCACCCTCACCCCCAGGCCCGAGGACCATGGCACCAACCTCACCTG
TCAGATGAAACGCCAAGGAGCTCAGGTGACCACGGAGAGAACTGTCCAGCTCAATGTCTC
CTATGCTCCACAGACCATCACCATCTTCAGGAACGGCATAGCCCTAGAGATCCTGCAAAA
CACCTCATACCTTCCGGTCCTGGAGGGCCAGGCTCTGCGGCTGCTCTGTGATGCTCCCAG
CAACCCCCCTGCACACCTGAGCTGGTTCCAGGGCTCCCCTGCCCTGAACGCCACCCCCAT
CTCCAATACCGGGATCTTGGAGCTTCGTCGAGTAAGGTCTGCAGAAGAAGGAGGCTTCAC
CTGCCGCGCTCAGCACCCGCTGGGCTTCCTGCAAATTTTTCTGAATCTCTCAGTTTACTC
CCTCCCACAGTTGCTGGGCCCCTCCTGCTCCTGGGAGGCTGAGGGTCTGCACTGCAGATG
CTCCTTTCGAGCCCGGCCGGCCCCCTCCCTGTGCTGGCGGCTTGAGGAGAAGCCGCTGGA
GGGGAACAGCAGCCAGGGCTCATTCAAGGTCAACTCCAGCTCAGCTGGGCCCTGGGCCAA
CAGCTCCCTGATCCTCCACGGGGGCTCAGCTCCGACCTCAAAGTCAGCTGCAAGGCCTG
GAACATCTATGGGTCCCAGAGCGGCTCTGTCCTGCTGCTGCAAGGGAGATCGAACCTCGG
GACAGGAGTGGTTCCTGCAGCCCTTGGTGGTGCTGGTGTCATGGCCCTGCTCTGTATCTG
TCTGTGCCTCATCTTCTTTTTAATAGTGAAAGCCCGCAGGAAGCAAGCAGCTGGGAGACC
AGAGAAAATGGATGATGAAGACCCCATTATGGGTACCATCACCTCGGGTTCCAGGAAGAA
GCCCTGGCCAGACAGCCCCGGAGATCAAGCATCTCCTCCTGGGGATGCCCCTCCCTTGGA
AGAACAAAAGGAGCTCCATTATGCCTCCCTTAGTTTTTCTGAGATGAAGTCGAGGGAGCC
TAAGGACCAGGAGGCCCCAAGCACCACGGAGTACTCGGAGATCAAGACAAGCAAGTGAGG
ATTTGCCCAGAGTTCAGTCCTGGCTGGAGGAGCCACAGCCTGTCTGGGGGAAAGGACAAG
TCAGGGACCACTTGCTGAAGCACGAAGAGCCCTTGTGGCAATGTTAACATTAACTGATGT
TTAAGTGCTCCAAGCAGAGCAGAAAGAAAACAGATGATGGAATTAGAGAGGTGGGCTCAA
ATCTAGGCCCTGGCACTGTCATCAAGCAATTCACTGCATCCCTCTGTGCCTCAGTTTCCC
ATTCTGTAAATCAGAGATCATGCATGCTACCTCAAAGGTTGTTGTGAACATTAAAGAAAT
CAACACATGGAAATCAAAAAAAAAAAAAAAA
```

FIGURE 10

```
leu> getseq ssp.DNA225543
><DNA225543 [min]
></usr/seqdb2/sst/DNA/Dnaseqs.min/ss.DNA225543
><subunit 1 of 1, 551 aa, 1 stop
><MW: 60715, pI: 7.44, NX(S/T): 9
MLPLLLLPLLWGGSLQEKPVYELQVQKSVTVQEGLCVLVPCSFSYPWRSWYSSPPLYVYW
FRDGEIPYYAEVVATNNPDRRVKPETQGRFRLLGDVQKKNCSLSIGDARMEDTGSYFFRV
ERGRDVKYSYQQNKLNLEVTALIEKPDIHFLEPLESGRPTRLSCSLPGSCEAGPPLTFSW
TGNALSPLDPETTRSSELTLTPRPEDHGTNLTCQMKRQGAQVTTERTVQLNVSYAPQTIT
IFRNGIALEILQNTSYLPVLEGQALRLLCDAPSNPPAHLSWFQGSPALNATPISNTGILE
LRRVRSAEEGGFTCRAQHPLGFLQIFLNLSVYSLPQLLGPSCSWEAEGLHCRCSFRARPA
PSLCWRLEEKPLEGNSSQGSFKVNSSSAGPWANSSLILHGGLSSDLKVSCKAWNIYGSQS
GSVLLLQGRSNLGTGVVPAALGGAGVMALLCICLCLIFFLIVKARRKQAAGRPEKMDDED
PIMGTITSGSRKKPWPDSPGDQASPPGDAPPLEEQKELHYASLSFSEMKSREPKDQEAPS
TTEYSEIKTSK
```

FIGURE 11

```
GCGCCGGGAGCCCATCTGCCCCCAGGGGCACGGGGCGCGGGGCCGGCTCCCGCCCGGCACA
TGGCTCCAGCCACCTCGCGCGCACCCCGAGGCGCCGCGCCCAGCTCGCCCGAGGTCCGTCG
GAGGCGCCCGGCCGCCCCGGAGCCAAGCAGCAACTGAGCGGGGAAGCGCCCGCGTCCGGGG
ATCGGGATGTCCCTCCTCCTTCTCCTCTTGCTAGTTTCCTACTATGTTGGAACCTTGGGGA
CTCACACTGAGATCAAGAGAGTGGCAGAGGAAAAGGTCACTTTGCCCTGCCACCATCAACT
GGGGCTTCCAGAAAAAGACACTCTGGATATTGAATGGCTGCTCACCGATAATGAAGGGAAC
CAAAAAGTGGTGATCACTTACTCCAGTCGTCATGTCTACAATAACTTGACTGAGGAACAGA
AGGGCCGAGTGGCCTTTGCTTCCAATTTCCTGGCAGGAGATGCCTCCTTGCAGATTGAACC
TCTGAAGCCCAGTGATGAGGGCCGGTACACCTGTAAGGTTAAGAATTCAGGGCGCTACGTG
TGGAGCCATGTCATCTTAAAAGTCTTAGTGAGACCATCCAAGCCCAAGTGTGAGTTGGAAG
GAGAGCTGACAGAAGGAAGTGACCTGACTTTGCAGTGTGAGTCATCCTCTGGCACAGAGCC
CATTGTGTATTACTGGCAGCGAATCCGAGAGAAAGAGGGAGAGGATGAACGTCTGCCTCCC
AAATCTAGGATTGACTACAACCACCCTGGACGAGTTCTGCTGCAGAATCTTACCATGTCCT
ACTCTGGACTGTACCAGTGCACAGCAGGCAACGAAGCTGGGAAGGAAAGCTGTGTGGTGCG
AGTAACTGTACAGTATGTACAAAGCATCGGCATGGTTGCAGGAGCAGTGACAGGCATAGTG
GCTGGAGCCCTGCTGATTTTCCTCTTGGTGTGGCTGCTAATCCGAAGGAAAGACAAAGAAA
GATATGAGGAAGAAGAGAGACCTAATGAAATTCGAGAAGATGCTGAAGCTCCAAAAGCCCG
TCTTGTGAAACCCAGCTCCTCTTCCTCAGGCTCTCGGAGCTCACGCTCTGGTTCTTCCTCC
ACTCGCTCCACAGCAAATAGTGCCTCACGCAGCCAGCGGACACTGTCAACTGACGCAGCAC
CCCAGCCAGGGCTGGCCACCCAGGCATACAGCCTAGTGGGGCCAGAGGTGAGAGGTTCTGA
ACCAAAGAAAGTCCACCATGCTAATCTGACCAAAGCAGAAACCACACCCAGCATGATCCCC
AGCCAGAGCAGAGCCTTCCAAACGGTCTGAATTACAATGGACTTGACTCCCACGCTTTCCT
AGGAGTCAGGCTCTTTGGACTCTTCTCGTCATTGGACCTCAAGTCACCACCCACACAACCA
GATGAGAGGTCATCTAAGTAGCAGTGAGCATTGCACGGAACAGATTCAGATGAGCATTTTC
CTTATACAATACCAAACAAGCAAAAGGATGTAAGCTGATTCATCTGTAAAAGGCATCTTA
TTGTGCCTTTAGACCAGAGTAAGGGAAAGCAGGAGTCCAAATCTATTTGTTGACCAGGACC
TGTGGTGAGAAGGTTGGGGAAAGGTGAGGTGAATATACCTAAAACTTTTAATGTGGGATAT
TTTGTATCAGTGCTTTGATTCACAATTTTCAAGAGGAAATGGGATGCTGTTTGTAAATTTT
CTATGCATTTCTGCAAACTTATTGGATTATTAGTTATTCAGACAGTCAAGCAGAACCCACA
GCCTTATTACACCTGTCTACACCATGTACTGAGCTAACCACTTCTAAGAAACTCCAAAAAA
GGAAACATGTGTCTTCTATTCTGACTTAACTTCATTTGTCATAAGGTTTGGATATTAATTT
CAAGGGGAGTTGAAATAGTGGGAGATGGAGAAGAGTGAATGAGTTTCTCCCACTCTATACT
AATCTCACTATTTGTATTGAGCCCAAAATAACTATGAAAGGAGACAAAAATTTGTGACAAA
GGATTGTGAAGAGCTTTCCATCTTCATGATGTTATGAGGATTGTTGACAAACATTAGAAAT
ATATAATGGAGCAATTGTGGATTTCCCCTCAAATCAGATGCCTCTAAGGACTTTCCTGCTA
GATATTTCTGGAAGGAGAAAATACAACATGTCATTTATCAACGTCCTTAGAAAGAATTCTT
CTAGAGAAAAAGGGATCTAGGAATGCTGAAAGATTACCCAACATACCATTATAGTCTCTTC
TTTCTGAGAAAATGTGAAACCAGAATTGCAAGACTGGGTGGACTAGAAAGGGAGATTAGAT
CAGTTTTCTCTTAATATGTCAAGGAAGGTAGCCGGGCATGGTGCCAGGCACCTGTAGGAAA
ATCCAGCAGGTGGAGGTTGCAGTGAGCCGAGATTATGCCATTGCACTCCAGCCTGGGTGAC
AGAGCGGGACTCCGTCTC
```

FIGURE 12

\></usr/seqdb2/sst/DNA/Dnaseqs.min/ss.DNA45419
\><subunit 1 of 1, 373 aa, 1 stop
\><MW: 41281, pI: 8.33, NX(S/T): 3
MSLLLLLLLVSYYVGTLGTHTETKRVAEEKVTLPCHHQLGLPEKDTLDIEWLLTDNEGNQK
VVITYSSRHVYNNLTEEQKGRVAFASNFLAGDASLQIEPLKPSDEGRYTCKVKNSGRYVWS
HVILKVLVRPSKPKCELEGELTEGSDLTLQCESSSGTEPIVYYWQRIREKEGEDERLPPKS
RIDYNHPGRVLLQNLTMSYSGLYQCTAGNEAGKESCVVRVTVQYVQSIGMVAGAVTGIVAG
ALLIFLLVWLLIRRKDKERYEEEERPNEIREDAEAPKARLVKPSSSSSGSRSSRSGSSSTR
STANSASRSQRTLSTDAAPQPGLATQAYSLVGPEVRGSEPKKVIIIANLTKAETTPSMIPSQ
SRAFQTV

Signal sequence:
amino acids 1-16

Transmembrane domain:
amino acids 232-251

FIGURE 13

```
GCGGCACCTGGAAGATGCGCCCATTGGCTGGTGGCCTGCTCAAGGTGGTGTTCGTGGTCTT
CGCCTCCTTGTGTGCCTGGTATTCGGGGTACCTGCTCGCAGAGCTCATTCCAGATGCACCC
CTGTCCAGTGCTGCCTATAGCATCCGCAGCATCGGGGAGAGGCCTGTCCTCAAAGCTCCAG
TCCCCAAAAGGCAAAAATGTGACCACTGGACTCCCTGCCCATCTGACACCTATGCCTACAG
GTTACTCAGCGGAGGTGGCAGAAGCAAGTACGCCAAAATCTGCTTTGAGGATAACCTACTT
ATGGGAGAACAGCTGGGAAATGTTGCCAGAGGAATAAACATTGCCATTGTCAACTATGTAA
CTGGGAATGTGACAGCAACACGATGTTTTGATATGTATGAAGGCGATAACTCTGGACCGAT
GACAAAGTTTATTCAGAGTGCTGCTCCAAAATCCCTGCTCTTCATGGTGACCTATGACGAC
GGAAGCACAAGACTGAATAACGATGCCAAGAATGCCATAGAAGCACTTGGAAGTAAAGAAA
TCAGGAACATGAAATTCAGGTCTAGCTGGGTATTTATTGCAGCAAAAGGCTTGGAACTCCC
TTCCGAAATTCAGAGAGAAAAGATCAACCACTCTGATGCTAAGAACAACAGATATTCTGGC
TGGCCTGCAGAGATCCAGATAGAAGGCTGCATACCCAAAGAACGAAGCTGACACTGCAGGG
TCCTGAGTAAATGTGTTCTGTATAAACAAATGCAGCTGGAATCGCTCAAGAATCTTATTTT
TCTAAATCCAACAGCCCATATTTGATGAGTATTTTGGGTTTGTTGTAAACCAATGAACATT
TGCTAGTTGTATCAAATCTTGGTACGCAGTATTTTTATACCAGTATTTTATGTAGTGAAGA
TGTCAATTAGCAGGAAACTAAAATGAATGGAAATTCTTAAAAAAAAAA
```

FIGURE 14

```
></usr/seqdb2/sst/DNA/Dnaseqs.min/ss.DNA46777
><subunit 1 of 1, 235 aa, 1 stop
><MW: 25982, pI: 9.09, NX(S/T): 2
MRPLAGGLLKVVFVVFASLCAWYSGYLLAELIPDAPLSSAAYSIRSIGERPVLKAPVPKRQ
KCDHWTPCPSDTYAYRLLSGGGRSKYAKICFEDNLLMGEQLGNVARGINIAIVNYVTGNVT
ATRCFDMYEGDNSGPMTKFIQSAAPKSLLFMVTYDDGSTRLNNDAKNAIEALGSKEIRNMK
FRSSWVFIAAKGLELPSEIQREKINHSDAKNNRYSGWPAEIQIEGCIPKERS
```

Signal sequence.
amino acids 1-20

N-glycosylation sites.
amino acids 120-124, 208-212

Glycosaminoglycan attachment site.
amino acids 80-84

N-myristoylation sites.
amino acids 81-87, 108-114, 119-125

FIGURE 15

```
ATGGGAAGCCAGTAACACTGTGGCCTACTATCTCTTCCGTGGTGCCATCTACATTTTTGGG
ACTCGGGAATTATGAGGTAGAGGTGGAGGCGGAGCCGGATGTCAGAGGTCCTGAAATAGTC
ACCATGGGGGAAAATGATCCGCCTGCTGTTGAAGCCCCCTTCTCATTCCGATCGCTTTTTG
GCCTTGATGATTTGAAAATAAGTCCTGTTGCACCAGATGCAGATGCTGTTGCTGCACAGAT
CCTGTCACTGCTGCCATTGAAGTTTTTTCCAATCATCGTCATTGGGATCATTGCATTGATA
TTAGCACTGGCCATTGGTCTGGGCATCCACTTCGACTGCTCAGGGAAGTACAGATGTCGCT
CATCCTTTAAGTGTATCGAGCTGATAGCTCGATGTGACGGAGTCTCGGATTGCAAAGACGG
GGAGGACGAGTACCGCTGTGTCCGGGTGGGTGGTCAGAATGCCGTGCTCCAGGTGTTCACA
GCTGCTTCGTGGAAGACCATGTGCTCCGATGACTGGAAGGGTCACTACGCAAATGTTGCCT
GTGCCCAACTGGGTTTCCCAAGCTATGTGAGTTCAGATAACCTCAGAGTGAGCTCGCTGGA
GGGGCAGTTCCGGGAGGAGTTTGTGTCCATCGATCACCTCTTGCCAGATGACAAGGTGACT
GCATTACACCACTCAGTATATGTGAGGGAGGGATGTGCCTCTGGCCACGTGGTTACCTTGC
AGTGCACAGCCTGTGGTCATAGAAGGGGCTACAGCTCACGCATCGTGGGTGGAAACATGTC
CTTGCTCTCGCAGTGGCCCTGGCAGGCCAGCCTTCAGTTCCAGGGCTACCACCTGTGCGGG
GGCTCTGTCATCACGCCCTGTGGATCATCACTGCTGCACACTGTGTTTATGACTTGTACC
TCCCCAAGTCATGGACCATCCAGGTGGGTCTAGTTTCCTGTTGGACAATCCAGCCCCATC
CCACTTGGTGGAGAAGATTGTCTACCACAGCAAGTACAAGCCAAAGAGGCTGGGCAATGAC
ATCGCCCTTATGAAGCTGGCCGGGCCACTCACGTTCAATGAAATGATCCAGCCTGTGTGCC
TGCCCAACTCTGAAGAGAACTTCCCCGATGGAAAGTGTGCTGGACGTCAGGATGGGGGGC
CACAGAGGATGGAGGTGACGCCTCCCCTGTCCTGAACCACGCGGCCGTCCCTTTGATTTCC
AACAAGATCTGCAACCACAGGGACGTGTACGGTGGCATCATCTCCCCCTCCATGCTCTGCG
CGGGCTACCTGACGGGTGGCGTGGACAGCTGCCAGGGGGACAGCGGGGGGCCCCTGGTGTG
TCAAGAGAGGAGGCTGTGGAAGTTAGTGGGAGCGACCAGCTTTGGCATCGGCTGCGCAGAG
GTGAACAAGCCTGGGGTGTACACCCGTGTCACCTCCTTCCTGGACTGGATCCACGAGCAGA
TGGAGAGAGACCTAAAAACCTGAAGAGGAAGGGGACAAGTAGCCACCTGAGTTCCTGAGGT
GATGAAGACAGCCCCGATCCTCCCCTGGACTCCCGTGTAGGAACCTGCACACGAGCAGACAC
CCTTGGAGCTCTGAGTTCCGGCACCAGTAGCAGGCCCGAAAGAGGCACCCTTCCATCTGAT
TCCAGCACAACCTTCAAGCTGCTTTTTGTTTTTTGTTTTTTTGAGGTGGAGTCTCGCTCTG
TTGCCCAGGCTGGAGTGCAGTGGCGAAATCCCTGCTCACTGCAGCCTCCGCTTCCCTGGTT
CAAGCGATTCTCTTGCCTCAGCTTCCCCAGTAGCTGGGACCACAGGTGCCCGCCACCACAC
CCAACTAATTTTTGTATTTTTAGTAGAGACAGGGTTTCACCATGTTGGCCAGGCTGCTCTC
AAACCCCTGACCTCAAATGATGTGCCTGCTTCAGCCTCCCACAGTGCTGGGATTACAGGCA
TGGGCCACCACGCCTAGCCTCACGCTCCTTTCTGATCTTCACTAAGAACAAAAGAAGCAGC
AACTTGCAAGGCGGCCTTTCCCACTGGTCCATCTGGTTTTCTCTCCAGGGTCTTGCAAAA
TTCCTGACGAGATAAGCAGTTATGTGACCTCACGTGCAAAGCCACCAACAGCCACTCAGAA
AAGACGCACCAGCCCAGAAGTGCAGAACTGCAGTCACTGCACGTTTTCATCTCTAGGGACC
AGAACCAAACCCACCCTTTCTACTTCCAAGACTTATTTTCACATGTGGGGAGGTTAATCTA
GGAATGACTCGTTTAAGGCCTATTTTCATGATTTCTTTGTAGCATTTGGTGCTTGACGTAT
TATTGTCCTTTGATTCCAAATAATATGTTTCCTTCCCTCATTGTCTGGCGTGTCTGCGTGG
ACTGGTGACGTGAATCAAAATCATCCACTGAAA
```

FIGURE 16

><\/usr\/seqdb2\/sst\/DNA\/Dnaseqs.min\/ss.DNA45234
><subunit 1 of 1, 453 aa, 1 stop
><MW: 49334, pI: 6.32, NX(S/T): 1
MGENDPPAVEAPFSFRSLFGLDDLKISPVAPDADAVAAQILSLLPLKFFPIIVIGIIALILALAIGLGIHFDCS
GKYRCRSSFKCIELIARCDGVSDCKDGEDEYRCVRVGGQNAVLQVFTAASWKTMCSDDWKGHYANVACAQLGFP
SYVSSDNLRVSSLEGQFREEFVSIDHLLPDDKVTALHHSVYVREGCASGHVVTLQCTACGHRRGYSSRIVGGNM
SLLSQWPWQASLQFQGYHLCGGSVITPLWIITAAHCVYDLYLPKSWTIQVGLVSLLDNPAPSHLVEKIVYHSKY
KPKRLGNDIALMKLAGPLTFNEMIQPVCLPNSEENFPDGKVCWTSGWGATEDGGDASPVLNHAAVPLISNKICN
HRDVYGGIISPSMLCAGYLTGGVDSCQGDSGGPLVCQERRLWKLVGATSFGIGCAEVNKPGVYTRVTSFLDWIH
EQMERDLKT

Signal Peptide:
amino acids 1-20

Transmembrane domain:
amino acids 240-284

FIGURE 17

```
CCCACGCGTCCGGCGCCGTGGCCTCGCGTCCATCTTTGCCGTTCTCTCGGACCTGTCACAA
AGGAGTCGCGCCGCCGCCGCCGCCCCCTCCCTCCGGTGGGCCCGGGAGGTAGAGAAAGTCA
GTGCCACAGCCCGACCGCGCTGCTCTGAGCCCTGGGCACGCGGAACGGGAGGGAGTCTGAG
GGTTGGGGACGTCTGTGAGGGAGGGGAACAGCCGCTCGAGCCTGGGGCGGGCGGACCGGAC
TGGGGCCGGGGTAGGCTCTGGAAAGGGCCCGGGAGAGAGGTGGCGTTGGTCAGAACCTGAG
AAACAGCCGAGAGGTTTTCCACCGAGGCCCGCGCTTGAGGGATCTGAAGAGGTTCCTAGAA
GAGGGTGTTCCCTCTTTCGGGGGTCCTCACCAGAAGAGGTTCTTGGGGGTCGCCCTTCTGA
GGAGCCTGCCGGCTAACACGGCCCAGAACTGCCATTGGATCTCCAGAATCCCCTGTAGTTGA
TAATGTTGGGAATAAGCTCTGCAACTTTCTTTGGCATTCAGTTGTTAAAAACAAATAGGAT
GCAAATTCCTCAACTCCAGGTTATGAAAACAGTACTTGGAAAACTGAAAACTACCTAAATG
ATCGTCTTTGGTTGGGCCGTGTTCTTAGCGAGCAGAAGCCTTGGCCAGGGTCTGTTGTTGA
CTCTCGAAGAGCACATAGCCCACTTCCTAGGGACTGGAGGTGCCGCTACTACCATGGGTAA
TTCCTGTATCTGCCGAGATGACAGTGGAACAGATGACAGTGTTGACACCCAACAGCAACAG
GCCGAGAACAGTGCAGTACCCACTGCTGACACAAGGAGCCAACCACGGGACCCTGTTCGGC
CACCAAGGAGGGGCCGAGGACCTCATGAGCCAAGGAGAAAGAAACAAAATGTGGATGGGCT
AGTGTTGGACACACTGGCAGTAATACGGACTCTTGTAGATAAGTAAGTATCTGACTCACGG
TCACCTCCAGTGGAATGAAAAGTGTTCTGCCCGGAACCATGACTTTAGGACTCCTTCAGTT
CCTTTAGGACATACTCGCCAAGCCTTGTGCTCACAGGGCAAAGGAGAATATTTTAATGCTC
CGCTGATGGCAGAGTAAATGATAAGATTTGATGTTTTTGCTTGCTGTCATCTACTTTGTCT
GGAAATGTCTAAATGTTTCTGTAGCAGAAAACACGATAAAGCTATGATCTTTATTAGAG
```

FIGURE 18

```
</usr/seqdb2/sst/DNA/Dnaseqs.min/ss.DNA26846
<subunit 1 of 1, 117 aa, 1 stop
<MW: 12692, pI: 7.50, NX(S/T): 0
MIVFGWAVFLASRSLGQGLLLTLEEHIAHFLGTGGAATTMGNSCICRDDSGTDDSVDTQQQ
Q
AENSAVPTADTRSQPRDPVRPPRRGRGPHEPRRKKQNVDGLVLDTLAVIRTLVDK
```

Important features:
Signal peptide:
amino acids 1-16

N-myristoylation sites.
amino acids 18-24, 32-38, 34-40, 35-41, 51-57

FIGURE 19

CCTGTGTTAAGCTGAGGTTTCCCCTAGATCTCGTATATCCCCAACACATACCTCCACGCAC
ACACATCCCCAAGAACCTCGAGCTCACACCAACAGACACACGCGCGCATACACACTCGCTC
TCGCTTGTCCATCTCCCTCCCGGGGGAGCCGGCGCGCGCTCCCACCTTTGCCGCACACTCC
GGCGAGCCGAGCCCGCAGCGCTCCAGGATTCTGCGGCTCGGAACTCGGATTGCAGCTCTGA
ACCCCCATGGTGGTTTTTTAAACACTTCTTTTCCTTCTCTTCCTCGTTTTGATTGCACCGT
TTCCATCTGGGGGCTAGAGGAGCAAGGCAGCAGCCTTCCCAGCCAGCCCTTGTTGGCTTGC
CATCGTCCATCTGGCTTATAAAAGTTTGCTGAGCGCAGTCCAGAGGGCTGCGCTGCTCGTC
CCCTCGGCTGGCAGAAGGGGGTGACGCTGGGCAGCGGCGAGGAGCGCGCCGCTGCCTCTGG
CGGGCTTTCGGCTTGAGGGGCAAGGTGAAGAGCGCACCGGCCGTGGGGTTTACCGAGCTGG
ATTTGTATGTTGCACCATGCCTTCTTGGATCGGGGCTGTGATTCTTCCCTCTTGGGGCTG
CTGCTCTCCCTCCCCGCCGGGGCGGATGTGAAGGCTCGGAGCTGCGGAGAGGTCCGCCAGG
CGTACGGTGCCAAGGGATTCAGCCTGGCGGACATCCCCTACCAGGAGATCGCAGGGGAACA
CTTAAGAATCTGTCCTCAGGAATATACATGCTGCACCACAGAAATGGAAGACAAGTTAAGC
CAACAAAGCAAACTCGAATTTGAAAACCTTGTGGAAGAGACAAGCCATTTTGTGCGCACCA
CTTTTGTGTCCAGGCATAAGAAATTTGACGAATTTTTCCGAGAGCTCCTGGAGAATGCAGA
AAAGTCACTAAATGATATGTTTGTACGGACCTATGGCATGCTGTACATGCAGAATTCAGAA
GTCTTCCAGGACCTCTTCACAGAGCTGAAAAGGTACTACACTGGGGGTAATGTGAATCTGG
AGGAAATGCTCAATGACTTTTGGGCTCGGCTCCTGGAACGGATGTTTCAGCTGATAAACCC
TCAGTATCACTTCAGTGAAGACTACCTGGAATGTGTGAGCAAATACACTGACCAGCTCAAG
CCATTTGGAGACGTGCCCCGGAAACTGAAGATTCAGGTTACCCGCGCCTTCATTGCTGCCA
GGACCTTTGTCCAGGGGCTGACTGTGGGCAGAGAAGTTGCAAACCGAGTTTCCAAGGTCAG
CCCAACCCCAGGGTGTATCCGTGCCCTCATGAAGATGCTGTACTGCCCATACTGTCGGGGG
CTTCCCACTGTGAGGCCCTGCAACAACTACTGTCTCAACGTCATGAAGGGCTGCTTGGCAA
ATCAGGCTGACCTCGACACAGAGTGGAATCTGTTTATAGATGCAATGCTCTTGGTGGCAGA
GCGACTGGAGGGGCCATTCAACATTGAGTCGGTCATGGACCCGATAGATGTCAAGATTTCT
GAAGCCATTATGAACATGCAAGAAAACAGCATGCAGGTGTCTGCAAAGGTCTTTCAGGGAT
GTGGTCAGCCCAAACCTGCTCCAGCCCTCAGATCTGCCCGCTCAGCTCCTGAAAATTTTAA
TACACGTTTCAGGCCCTACAATCCTGAGGAAAGACCAACAACTGCTGCAGGCACAAGCTTG
GACCGGCTGGTCACAGACATAAAAGAGAAATTGAAGCTCTCTAAAAAGGTCTGGTCAGCAT
TACCCTACACTATCTGCAAGGACGAGAGCGTGACAGCGGGCACGTCCAACGAGGAGGAATG
CTGGAACGGGCACAGCAAAGCCAGATACTTGCCTGAGATCATGAATGATGGGCTCACCAAC
CAGATCAACAATCCCGAGGTGGATGTGGACATCACTCGGCCTGACACTTTCATCAGACAGC
AGATTATGCTCTCCGTGTGATGACCAACAAACTAAAAAACGCCTACAATGGCAATGATGT
CAATTTCCAGGACACAAGTGATGAATCCAGTGGCTCAGGGAGTGGCAGTGGGTGCATGGAT
GACGTGTGTCCCACGGAGTTTGAGTTTGTCACCACAGAGGCCCCCGCAGTGGATCCCGACC
GGAGAGAGGTGGACTCTTCTGCAGCCCAGCGTGGCCACTCCCTGCTCTCCTGGTCTCTCAC
CTGCATTGTCCTGGCACTGCAGAGACTGTGCAGATAACTTGGGTTTTTGGTCAGATGAAA
CTGCATTTTAGCTATCTGAATGGCCAACTCACTTCTTTTCTTACACTCTTGGACAATGGAC
CATGCCACAAAAACTTACCGTTTTCTATGAGAAGAGAGCAGTAATGCAATCTGCCTCCCTT
TTTGTTTTCCCAAAGAGTACCGGGTGCCAGACTGAACTGCTTCCTCTTTCCTTCAGCTATC
TGTGGGACCTTGTTTATTCTAGAGAATTCTTACTCAAATTTTTCGTACCAGGAGATTT
TCTTACCTTCATTTGCTTTTATGCTGCAGAAGTAAAGGAATCTCACGTTGTGAGGGTTTTT
TTTTTCTCATTTAAAAT

FIGURE 20

><\/usr/seqdb2/sst/DNA/Dnaseqs.min/ss.DNA50914
><subunit 1 of 1, 555 aa, 1 stop
><MW: 62736, pI: 5.36, NX(S/T): 0
MPSWIGAVILPLLGLLLSLPAGADVKARSCGEVRQAYGAKGFSLADIPYQEIAGEHLRICPQEYTCCTTEMEDK
LSQQSKLEFENLVEETSHFVRTTFVSRHKKFDEFFRELLENAEKSLNDMFVRTYGMLYMQNSEVFQDLFTELKR
YYTGGNVNLEEMLNDFWARLLERMFQLINPQYHFSEDYLECVSKYTDQLKPFGDVPRKLKIQVTRAFIAARTFV
QGLTVGREVANRVSKVSPTPGCIRALMKMLYCPYCRGLPTVRPCNNYCLNVMKGCLANQADLDTEWNLFIDAML
LVAERLEGPFNIESVMDPIDVKISEAIMNMQENSMQVSAKVFQGCGQPKPAPALRSARSAPENFNTRFRPYNPE
ERPTTAAGTSLDRLVTDIKEKLKLSKKVWSALPYTICKDESVTAGTSNEEECWNGHSKARYLPEIMNDGLTNQI
NNPEVDVDITRPDTFIRQQIMALRVMTNKLKNAYNCNDVNFQDTSDESSGSCSGSCCMDDVCPTEFEFVTTEAP
AVDPDRREVDSSAAQRGHSLLSWSLTCIVLALQRLCR

Signal peptide:
amino acids 1-23

FIGURE 21

AATGTGAGAGGGGCTGATGGAAGCTGATAGGCAGGACTGGAGTGTTAGCACCAGTACTGGA
TGTGACAGCAGGCAGAGGAGCACTTAGCAGCTTATTCAGTGTCCGATTCTGATTCCGGCAA
GGATCCAAGCATGGAATGCTGCCGTCGGGCAACTCCTGGCACACTGCTCCTCTTTCTGGCT
TTCCTGCTCCTGAGTTCCAGGACCGCACGCTCCGAGGAGGACCGGGACGGCCTATGGGATG
CCTGGGGCCCATGGAGTGAATGCTCACGCACCTGCGGGGGAGGGCCTCCTACTCTCTGAG
GCGCTGCCTGAGCAGCAAGAGCTGTGAAGGAAGAAATATCCGATACAGAACATGCAGTAAT
GTGGACTGCCCACCAGAAGCAGGTGATTTCCGAGCTCAGCAATGCTCAGCTCATAATGATG
TCAAGCACCATGGCCAGTTTTATGAATGGCTTCCTGTGTCTAATGACCCTGACAACCCATG
TTCACTCAAGTGCCAAGCCAAAGGAACAACCCTGGTTGTTGAACTAGCACCTAAGGTCTTA
GATGGTACGCGTTGCTATACAGAATCTTTGGATATGTGCATCAGTGGTTTATGCCAAATTG
TTGGCTGCGATCACCAGCTGGGAAGCACCGTCAAGGAAGATAACTGTGGGGTCTGCAACGG
AGATGGGTCCACCTGCCGGCTGGTCCGAGGGCAGTATAAATCCCAGCTCTCCGCAACCAAA
TCGGATGATACTGTGGTTGCACTTCCCTATGGAAGTAGACATATTCGCCTTGTCTTAAAAG
GTCCTGATCACTTATATCTGGAAACCAAAACCCTCCAGGGGACTAAAGGTGAAAACAGTCT
CAGCTCCACAGGAACTTTCCTTGTGGACAATTCTAGTGTGGACTTCCAGAAATTTCCAGAC
AAAGAGATACTGAGAATGGCTGGACCACTCACAGCAGATTTCATTGTCAAGATTCGTAACT
CGGGCTCCGCTGACAGTACAGTCCAGTTCATCTTCTATCAACCCATCATCCACCGATGGAG
GGAGACGGATTTCTTTCCTTGCTCAGCAACCTGTGGAGGAGGTTATCAGCTGACATCGGCT
GAGTGCTACGATCTGAGGAGCAACCGTGTGGTTGCTGACCAATACTGTCACTATTACCCAG
AGAACATCAAACCCAAACCCAAGCTTCAGGAGTGCAACTTGGATCCTTGTCCAGCCAGTGA
CGGATACAAGCAGATCATGCCTTATGACCTCTACCATCCCCTTCCTCGGTGGGAGGCCACC
CCATGGACCGCGTGCTCCTCCTCGTGTGGGGGGGCATCCAGAGCCGGGCAGTTTCCTGTG
TGGAGGAGGACATCCAGGGGCATGTCACTTCAGTGGAAGAGTGGAAATGCATGTACACCCC
TAAGATGCCCATCGCGCAGCCCTGCAACATTTTTGACTGCCCTAAATGGCTGGCACAGGAG
TGGTCTCCGTGCACAGTGACATGTGGCCAGGGCCTCAGATACCGTGTGGTCCTCTGCATCG
ACCATCGAGGAATGCACACAGGAGGCTGTAGCCCAAAAACAAAGCCCCACATAAAAGAGGA
ATGCATCGTACCCACTCCCTGCTATAAACCCAAAGAGAAACTTCCAGTCGAGGCCAAGTTG
CCATGGTTCAAACAAGCTCAAGAGCTAGAAGAAGGAGCTGCTGTGTCAGAGGAGCCCTCGT
AAGTTGTAAAAGCACAGACTGTTCTATATTTGAAACTGTTTTGTTTAAAGAAAGCAGTGTC
TCACTGGTTGTAGCTTTCATGGGTTCTGAACTAAGTGTAATCATCTCACCAAAGCTTTTTG
GCTCTCAAATTAAAGATTGATTAGTTTCAAAAAAAAAAA

FIGURE 22

```
</usr/seqdb2/sst/DNA/Dnaseqs.min/ss.DNA58847
<subunit 1 of 1, 525 aa, 1 stop
<MW: 58416, pI: 6.62, NX(S/T): 1
MECCRRATPGTLLLFLAFLLLSSRTARSEEDRDGLWDAWGPWSECSRTCGGGASYSLRRCLSSKSCEGRNIRYR
TCSNVDCPPEAGDFRAQQCSAHNDVKHHGQFYEWLPVSNDPDNPCSLKCQAKGTTLVVELAPKVLDGTRCYTES
LDMCISGLCQIVGCDHQLGSTVKEDNCGVCNGDGSTCRLVRGQYKSQLSATKSDDTVVALPYGSRHIRLVLKGP
DHLYLETKTLQGTKGENSLSSTGTFLVDNSSVDFQKFPDKEILRMAGPLTADFIVKIRNSGSADSTVQFIFYQP
IIHRWRETDFFPCSATCGGGYQLTSAECYDLRSNRVVADQYCHYYPENIKPKPKLQECNLDPCPASDGYKQIMP
YDLYHPLPRWEATPWTACSSSCGGGIQSRAVSCVEEDIQGHVTSVEEWKCMYTPKMPIAQPCNIFDCPKWLAQE
WSPCTVTCGQGLRYRVVLCIDHRGMHTGGCSPKTKPHIKEECIVPTPCYKPKEKLPVEAKLPWFKQAQELEEGA
AVSEEPS
```

Important features:
Signal peptide:
amino acids 1-25

N-glycosylation site.
amino acids 251-254

Thrombospondin 1
amino acids 385-399 von Willebrand factor type C domain proteins
amino acids 385-399, 445-459 and 42-56

FIGURE 23

```
GGGCGCCCGCGTACTCACTAGCTGAGGTGGCAGTGGTTCCACCAACATGGAGCTCTCGCAG
ATGTCGGAGCTCATGGGGCTGTCGGTGTTGCTTGGGCTGCTGGCCCTGATGGCGACGGCGG
CGGTAGCGCGGGGGTGGCTGCGCGCGGGGGAGGAGAGGAGCGGCCGGCCCGCCTGCCAAAA
AGCAAATGGATTTCCACCTGACAAATCTTCGGGATCCAAGAAGCAGAAACAATATCAGCGG
ATTCGGAAGGAGAAGCCTCAACAACACAACTTCACCCACCGCCTCCTGGCTGCAGCTCTGA
AGAGCCACAGCGGGAACATATCTTGCATGGACTTTAGCAGCAATGGCAAATACCTGGCTAC
CTGTGCAGATGATCGCACCATCCGCATCTGGAGCACCAAGGACTTCCTGCAGCGAGAGCAC
CGCAGCATGAGAGCCAACGTGGAGCTGGACCACGCCACCCTGGTGCGCTTCAGCCCTGACT
GCAGAGCCTTCATCGTCTGGCTGGCCAACGGGGACACCCTCCGTGTCTTCAAGATGACCAA
GCGGGAGGATGGGGGCTACACCTTCACAGCCACCCCAGAGGACTTCCCTAAAAAGCACAAG
GCGCCTGTCATCGACATTGGCATTGCTAACACAGGGAAGTTTATCATGACTGCCTCCAGTG
ACACCACTGTCCTCATCTGGAGCCTGAAGGGTCAAGTGCTGTCTACCATCAACACCAACCA
GATGAACAACACACACGCTGCTGTATCTCCCTGTGGCAGATTTGTAGCCTCGTGTGGCTTC
ACCCCAGATGTGAAGGTTTGGAAGTCTGCTTTGGAAAGAAGGGGGAGTTCCAGGAGGTGG
TGCGAGCCTTCGAACTAAAGGGCCACTCCGCGGCTGTGCACTCGTTTGCTTTCTCCAACGA
CTCACGGAGGATGCTTCTGTCTCCAAGGATGGTACATGGAAACTGTGGGACACAGATGTG
GAATACAAGAAGAAGCAGGACCCCTACTTGCTGAAGACAGGCCGCTTTGAAGAGGCGGCGG
GTGCCGCGCCGTGCCGCCTGGCCCTCTCCCCAACGCCCAGGTCTTGGCCTTGGCCAGTGG
CAGTAGTATTCATCTCTACAATACCCGGCGGGCGAGAAGGAGGAGTGCTTTGAGCGGGTC
CATGGCGAGTGTATCGCCAACTTGTCCTTTGACATCACTGGCCGCTTTCTGGCCTCCTGTG
GGGACCGGGCGGTGCGGCTGTTTCACAACACTCCTGGCCACCGAGCCATGGTGGAGGAGAT
GCAGGGCCACCTGAAGCGGGCCTCCAACGAGAGCACCCGCCAGAGGCTGCAGCAGCAGCTG
ACCCAGGCCCAAGAGACCCTGAAGAGCCTGGGTGCCCTGAAGAAGTGACTCTGGGAGGGCC
CGGCGCAGAGGATTGAGGAGGAGGGATCTGGCCTCCTCATGGCACTGCTGCCATCTTTCCT
CCCAGGTGGAAGCCTTTCAGAAGGAGTCTCCTGGTTTTCTTACTGGTGGCCCTGCTTCTTC
CCATTGAAACTACTCTTGTCTACTTAGGTCTCTCTCTTCTTGCTGGCTGTGACTCCTCCCT
GACTAGTGGCCAAGGTGCTTTTCTTCCTCCCAGGCCCAGTGGGTGGAATCTGTCCCCACCT
GGCACTGAGGAGAATGGTAGAGAGGAGAGGAGAGAGAGAGAATGTGATTTTTGGCCTTG
TGGCAGCACATCCTCACACCCAAAGAAGTTTGTAAATGTTCCAGAACAACCTAGAGAACAC
CTGAGTACTAAGCAGCAGTTTTGCAAGGATGGGAGACTGGGATAGCTTCCCATCACAGAAC
TGTGTTCCATCAAAAGACACTAAGGGATTTCCTTCTGGGCCTCAGTTCTATTTGTAAGAT
GGAGAATAATCCTCTCTGTGAACTCCTTGCAAAGATGATATGAGGCTAAGAGAATATCAAG
TCCCCAGGTCTGGAAGAAAAGTAGAAAAGAGTAGTACTATTGTCCAATGTCATGAAAGTGG
TAAAAGTGGGAACCAGTGTGCTTTGAAACCAAATTAGAAACACATTCCTTGGGAAGGCAAA
GTTTTCTGGGACTTGATCATACATTTTATATGGTTGGGACTTCTCTCTTCGGGAGATGATA
TCTTGTTTAAGGAGACCTCTTTTCAGTTCATCAAGTTCATCAGATATTTGAGTGCCCACTC
TGTGCCCAAATAAATATGAGCTGGGGATTAAAAAAAAAAAAAAAAAAAAAAAAAAAAAA
AAAAAAAAAAAAAAAAAAAAAAA
```

FIGURE 24

MELSQMSELMGLSVLLGLLALMATAAVARGWLRAGEERSGRPACQKANGFPPDKSSGSKKQ
KQYQRIRKEKPQQHNFTHRLLAAALKSHSGNISCMDFSSNGKYLATCADDRTIRIWSTKDF
LQREHRSMRANVELDHATLVRFSPDCRAFIVWLANGDTLRVFKMTKREDGGYTFTATPEDF
PKKHKAPVIDIGIANTGKFIMTASSDTTVLIWSLKGQVLSTINTNQMNNTHAAVSPCGRFV
ASCGFTPDVKVWEVCFGKKGEFQEVVRAFELKGHSAAVHSFAFSNDSRRMASVSKDGTWKL
WDTDVEYKKKQDPYLLKTGRFEEAAGAAPCRLALSPNAQVLALASGSSIHLYNTRRGEKEE
CFERVHGECIANLSFDITGRFLASCGDRAVRLFHNTPGHRAMVEEMQGHLKRASNESTRQR
LQQQLTQAQETLKSLGALKK

Important features:
Signal peptide:
amino acids 1-25

N-glycosylation site.
amino acids 76-80, 92-96, 231-235, 289-293, 378-382, 421-425

Beta-transducin family Trp-Asp repeat protein.
amino acids 30-47, 105-118, 107-119, 203-216, 205-217,
296-308

FIGURE 25

GTGGGATTTATTTGAGTGCAAGATCGTTTTCTCAGTGGTGGTGGAAGTTGCCTCATCGCAG
GCAGATGTTGGGGCTTTGTCCGAACAGCTCCCCTCTGCCAGCTTCTGTAGATAAGGGTTAA
AAACTAATATTTATATGACAGAAGAAAAAGATGTCATTCCGTAAAGTAAACATCATCATCT
TGGTCCTGGCTGTTGCTCTCTTCTTACTGGTTTTGCACCATAACTTCCTCAGCTTGAGCAG
TTTGTTAAGGAATGAGGTTACAGATTCAGGAATTGTAGGGCCTCAACCTATAGACTTTGTC
CCAAATGCTCTCCGACATGCAGTAGATGGGAGACAAGAGGAGATTCCTGTGGTCATCGCTG
CATCTGAAGACAGGCTTGGGGGGGCCATTGCAGCTATAAACAGCATTCAGCACAACACTCG
CTCCAATGTGATTTTCTACATTGTTACTCTCAACAATACAGCAGACCATCTCCGGTCCTGG
CTCAACAGTGATTCCCTGAAAAGCATCAGATACAAAATTGTCAATTTTGACCCTAAACTTT
TGGAAGGAAAAGTAAAGGAGGATCCTGACCAGGGGGAATCCATGAAACCTTTAACCTTTGC
AAGGTTCTACTTGCCAATTCTGGTTCCCAGCGCAAAGAAGGCCATATACATGGATGATGAT
GTAATTGTGCAAGGTGATATTCTTGCCCTTTACAATACAGCACTGAAGCCAGGACATGCAG
CTGCATTTTCAGAAGATTGTGATTCAGCCTCTACTAAAGTTGTCATCCGTGGAGCAGGAAA
CCAGTACAATTACATTGGCTATCTTGACTATAAAAGGAAAGAATTCGTAAGCTTTCCATG
AAAGCCAGCACTTGCTCATTTAATCCTGGAGTTTTTGTTGCAAACCTGACGGAATGGAAAC
GACAGAATATAACTAACCAACTGGAAAAATGGATGAAACTCAATGTAGAAGAGGGACTGTA
TAGCAGAACCCTGGCTGGTAGCATCACAACACCTCCTCTGCTTATCGTATTTTATCAACAG
CACTCTACCATCGATCCTATGTGGAATGTCCGCCACCTTGGTTCCAGTGCTGGAAAACGAT
ATTCACCTCAGTTTGTAAAGGCTGCCAAGTTACTCCATTGGAATGGACATTTGAAGCCATG
GGGAAGGACTGCTTCATATACTGATGTTTGGGAAAAATGGTATATTCCAGACCCAACAGGC
AAATTCAACCTAATCCGAAGATATACCGAGATCTCAAACATAAAGTGAAACAGAATTTGAA
CTGTAAGCAAGCATTTCTCAGGAAGTCCTGGAAGATAGCATGCATGGGAAGTAACAGTTGC
TAGGCTTCAATGCCTATCGGTAGCAAGCCATGGAAAAAGATGTGTCAGCTAGGTAAAGATG
ACAAACTGCCCTGTCTGGCAGTCAGCTTCCAGACAGACTATAGACTATAAATATGTCTCC
ATCTGCCTTACCAAGTGTTTTCTTACTACAATGCTGAATGACTGGAAAGAAGAACTGATAT
GGCTAGTTCAGCTAGCTGGTACAGATAATTCAAAACTGCTGTTGGTTTTAATTTTGTAACC
TGTGGCCTGATCTGTAAATAAAACTTACATTTTTC

FIGURE 26

MSFRKVNIIILVLAVALFLLVLHHNFLSLSSLLRNEVTDSGIVGPQPIDFVPNALRHAVDG
RQEEIPVVIAASEDRLGGAIAAINSIQHNTRSNVIFYIVTLNNTADHLRSWLNSDSLKSIR
YKIVNFDPKLLEGKVKEDPDQGESMKPLTFARFYLPILVPSAKKAIYMDDDVIVQGDILAL
YNTALKPGHAAAFSEDCDSASTKVVIRGAGNQYNYIGYLDYKKERIRKLSMKASTCSFNPG
VFVANLTEWKRQNITNQLEKWMKLNVEEGLYSRTLAGSITTPPLLIVFYQQHSTIDPMWNV
RHLGSSAGKRYSPQFVKAAKLLHWNGHLKPWGRTASYTDVWEKWYIPDPTGKFNLIRRYTE
ISNIK

FIGURE 27

AGTGACTGCAGCCTTCCTAGATCCCCTCCACTCGGTTTCTCTCTTTGCAGGAGCACCGGCA
GCACCAGTGTGTGAGGGGAGCAGGCAGCGGTCCTAGCCAGTTCCTTGATCCTGCCAGACCA
CCCAGCCCCCGGCACAGAGCTGCTCCACAGGCACCATGAGGATCATGCTGCTATTCACAGC
CATCCTGGCCTTCAGCCTAGCTCAGAGCTTTGGGGCTGTCTGTAAGGAGCCACAGGAGGAG
GTGGTTCCTGGCGGGGCCGCAGCAAGAGGGATCCAGATCTCTACCAGCTGCTCCAGAGAC
TCTTCAAAAGCCACTCATCTCTGGAGGGATTGCTCAAAGCCCTGAGCCAGGCTAGCACAGA
TCCTAAGGAATCAACATCTCCCGAGAAACGTGACATGCATGACTTCTTTGTGGGACTTATG
GGCAAGAGGAGCGTCCAGCCAGAGGGAAAGACAGGACCTTTCTTACCTTCAGTGAGGGTTC
CTCGGCCCCTTCATCCCAATCAGCTTGGATCCACAGGAAAGTCTTCCCTGGGAACAGAGGA
GCAGAGACCTTTATAAGACTCTCCTACGGATGTGAATCAAGAGAACGTCCCCAGCTTTGGC
ATCCTCAAGTATCCCCCGAGAGCAGAATAGGTACTCCACTTCCGGACTCCTGGACTGCATT
AGGAAGACCTCTTTCCCTGTCCCAATCCCCAGGTGCGCACGCTCCTGTTACCCTTTCTCTT
CCCTGTTCTTGTAACATTCTTGTGCTTTGACTCCTTCTCCATCTTTTCTACCTGACCCTGG
TGTGGAAACTGCATAGTGAATATCCCCAACCCCAATGGGCATTGACTGTAGAATACCCTAG
AGTTCCTGTAGTGTCCTACATTAAAAATATAATGTCTCTCTCTATTCCTCAACAATAAAGG
ATTTTTGCATATGAAAAAAAAAAAAAAAAAAAAAAAAAAAAAAAAAAAAAAAAAAA

FIGURE 28

MRIMLLFTAILAFSLAQSFGAVCKEPQEEVVPGGGRSKRDPDLYQLLQRLFKSHSSLEGLL
KALSQASTDPKESTSPEKRDMHDFFVGLMGKRSVQPEGKTGPFLPSVRVPRPLHPNQLGST
GKSSLGTEEQRPL

Important features:
Signal peptide:
amino acids 1-18

Tyrosine kinase phosphorylation site.
amino acids 36-45

N-myristoylation site.
amino acids 33-39, 59-65

Amidation site.
amino acids 90-94

Leucine zipper pattern.
amino acids 43-65

Tachykinin family signature.
amino acids 86-92

FIGURE 29

```
GCCGAGCGCAAGAACCCTGCGCAGCCCAGAGCAGCTGCTGGAGGGGAATCGAGGCGCGGCT
CCGGGGATTCGGCTCGGGCCGCTGGCTCTGCTCTGCGGGGAGGGAGCGGGCCCGCCCGCGG
GGCCCGAGCCCTCCGGATCCGCCCCCTCCCCGGTCCCGCCCCCTCGGAGACTCCTCTGGCT
GCTCTGGGGGTTCGCCGGGGCCGGGGACCCGCGGTCCGGGCGCCATGCGGGCATCGCTGCT
GCTGTCGGTGCTGCGGCCCGCAGGGCCCGTGGCCGTGGGCATCTCCCTGGGCTTCACCCTG
AGCCTGCTCAGCGTCACCTGGGTGGAGGAGCCGTGCGGCCCAGGCCCGCCCCAACCTGGAG
ACTCTGAGCTGCCGCCGCGCGGCAACACCAACGCGGCGCGCCGGCCCAACTCGGTGCAGCC
CGGAGCGGAGCGCGAGAAGCCCGGGGCCGGCGAAGGCGCCGGGGAGAATTGGGAGCCGCGC
GTCTTGCCCTACCACCCTGCACAGCCCGGCCAGGCCGCCAAAAAGGCCGTCAGGACCCGCT
ACATCAGCACGGAGCTGGGCATCAGGCAGAGGCTGCTGGTGGCGGTGCTGACCTCTCAGAC
CACGCTGCCCACGCTGGGCGTGGCCGTGAACCGCACGCTGGGGCACCGGCTGGAGCGTGTG
GTGTTCCTGACGGGCGCACGGGGCCGCCGGGCCCCACCTGGCATGGCAGTGGTGACGCTGG
GCGAGGAGCGACCCATTGGACACCTGCACCTGGCGCTGCGCCACCTGCTGGAGCAGCACGG
CGACGACTTTGACTGGTTCTTCCTGGTGCCTGACACCACCTACACCGAGGCGCACGGCCTG
GCACGCCTAACTGGCCACCTCAGCCTGGCCTTCCGCCGCCCACCTGTACCTGGCCGGCCCC
AGGACTTCATCGGCGGAGAGCCCACCCCCGGCCGCTACTGCCACGGAGGCTTTGGGGTGCT
GCTGTCGCGCATGCTGCTGCAACAACTGCGCCCCCACCTGGAAGGCTGCCGCAACGACATC
GTCAGTGCGCGCCCTGACGAGTGGCTGGGTCGCTGCATTCTCGATGCCACCGGGGTGGGCT
GCACTGGTGACCACGAGGGGGTGCACTATAGCCATCTGGAGCTGAGCCCTGGGGAGCCAGT
GCAGGAGGGCCACCCTCATTTCCGAAGTGCCCTGACAGCCCACCCTGTGCGTGACCCTGTG
CACATGTACCAGCTGCACAAAGCTTTCGCCCGAGCTGAACTGGAACGCACGTACCAGGAGA
TCCAGGAGTTACAGTGGGAGATCCAGAATACCAGCCATCTGGCCGTTGATGGGGACCGGGC
AGCTGCTTGGCCCGTGGGTATTCCAGCACCATCCGCCCGGCCTCCCGCTTTGAGGTGCTG
CGCTGGGACTACTTCACGGAGCAGCACGCTTTCTCCTGCGCCGATGGCTCACCCCGCTGCC
CACTGCGTGGGGCTGACCGGGCTGATGTGGCCGATGTTCTGGGGACAGCTCTAGAGGAGCT
GAACCGCCGCTACCACCCGGCCTTGCGGCTCCAGAAGCAGCAGCTGGTGAATGGCTACCGA
CGCTTTGATCCGGCCCGGGGTATGGAATACACGCTGGACTTGCAGCTGGAGGCACTGACCC
CCCAGGGAGGCCGCCGGCCCCTCACTCGCCGAGTGCAGCTGCTCCGGCCGCTGAGCCGCGT
GGAGATCTTGCCTGTGCCCTATGTCACTGAGGCCTACGTCTCACTGTGCTGCTGCCTCTA
GCTGCGGCTGAGCGTGACCTGGCCCCTGGCTTCTTGGAGGCCTTTGCCACTGCAGCACTGG
AGCCTGGTGATGCTGCGGCACCCTGACCCTGCTGCTACTGTATGAGCCGCGCCAGGCCCA
GCGCGTGGCCCATGCAGATGTCTTCGCACCTGTCAAGGCCCACGTGGCAGAGCTGGAGCGG
CGTTTCCCCGGTGCCCGGGTGCCATGGCTCAGTGTGCAGACAGCCGCACCCTCACCACTGC
GCCTCATGGATCTACTCTCCAAGAAGCACCCGCTGGACACACTGTTCCTGCTGGCCGGGCC
AGACACGGTGCTCACGCCTGACTTCCTGAACCGCTGCCGCATGCATGCCATCTCCGGCTGG
CAGGCCTTCTTTCCCATGCATTTCCAAGCCTTCCACCCAGGTGTGGCCCCACCACAAGGGC
CTGGGCCCCAGAGCTGGGCCGTGACACTGGCCGCTTTGATCGCCAGGCAGCCAGCGAGGC
CTGCTTCTACAACTCCGACTACGTGGCAGCCCGTGGGCGCCTGGCGGCAGCCTCAGAACAA
GAAGAGGAGCTGCTGGAGAGCCTGGATGTGTACGAGCTGTTCCTCCACTTCTCCAGTCTGC
ATGTGCTGCGGGCGGTGGAGCCGGCGCTGCTGCAGCGCTACCGGGCCCAGACGTGCAGCGC
GAGGCTCAGTGAGGACCTGTACCACCGCTGCCTCCAGAGCGTGCTTGAGGGCCTCGGCTCC
CGAACCCAGCTGGCCATGCTACTCTTTGAACAGGAGCAGGGCAACAGCACCTGACCCCACC
CTGTCCCGTGGGCCGTGGCATGGCCACACCCCACCCCACTTCTCCCCAAAACCAGAGCC
ACCTGCCAGCCTCGCTGGGCAGGGCTGGCCGTAGCCAGACCCCAAGCTGGCCCACTGGTCC
CCTCTCTGGCTCTGTGGGTCCCTGGGCTCTGGACAAGCACTGGGGACGTGCCCCAGAGC
CACCCACTTCTCATCCCAAACCCAGTTTCCCTGCCCCTGACGCTGCTGATTCGGGCTGTG
GCCTCCACGTATTTATGCAGTACAGTCTGCCTGACGCCAGCCCTGCCTCTGGGCCCTGGGG
GCTGGGCTGTAGAAGAGTTGTTGGGGAAGGAGGGAGCTGAGGAGGGGGCATCTCCCAACTT
CTCCCTTTTGGACCCTGCCGAAGCTCCCTGCCTTTAATAAACTGGCAAGTGTGGAAAAA
```

FIGURE 30

MRASLLLSVLRPAGPVAVGISLGFTLSLLSVTWVEEPCGPGPPQPGDSELPPRGNTNAARR
PNSVQPGAEREKPGAGEGAGENWEPRVLPYHPAQPGQAAKKAVRTRYISTELGIRQRLLVA
VLTSQTTLPTLGVAVNRTLGHRLERVVFLTGARGRRAPPGMAVVTLGEERPIGHLHLALRH
LLEQHGDDFDWFFLVPDTTYTEAHGLARLTGHLSLASAAHLYLGRPQDFTGGEPTPGRYCH
GGFGVLLSRMLLQQLRPHLEGCRNDIVSARPDEWLGRCILDATGVGCTGDHEGVHYSHLEL
SPGEPVQEGDPHFRSALTAHPVRDPVHMYQLHKAFARAELERTYQEIQELQWEIQNTSHLA
VDGDRAAAWPVGIPAPSRPASRFEVLRWDYFTEQHAFSCADGSPRCPLRGADRADVADVLG
TALEELNRRYHPALRLQKQQLVNGYRRFDPARGMEYTLDLQLEALTPQGGRRPLTRRVQLL
RPLSRVEILPVPYVTEASRLTVLLPLAAAERDLAPGFLEAFATAALEPGDAAAALTLLLY
EPRQAQRVAHADVFAPVKAHVAELERRFPGARVPWLSVQTAAPSPLRLMDLLSKKHPLDTL
FLLAGPDTVLTPDFLNRCRMHAISGWQAFFPMHFQAFHPGVAPPQGPGPPELGRDTGRFDR
QAASEACFYNSDYVAARGRLAAASEQEEELLESLDVYELFLHFSSLHVLRAVEPALLQRYR
AQTCSARLSEDLYHRCLQSVLEGLGSRTQLAMLLFEQEQGNST

FIGURE 31

```
GGGAGAGAGGATAAATAGCAGCGTGGCTTCCCTGGCTCCTCTCTGCATCCTTCCCGACCTT
CCCAGCAATATGCATCTTGCACGTCTGGTCGGCTCCTGCTCCCTCCTTCTGCTACTGGGGG
CCCTGTCTGGATGGGCGGCCAGCGATGACCCCATTGAGAAGGTCATTGAAGGGATCAACCG
AGGGCTGAGCAATGCAGAGAGAGAGGTGGGCAAGGCCCTGGATGGCATCAACAGTGGAATC
ACGCATGCCGGAAGGGAAGTGGAGAAGGTTTTCAACGGACTTAGCAACATGGGGAGCCACA
CCGGCAAGGAGTTGGACAAAGGCGTCCAGGGGCTCAACCACGGCATGGACAAGGTTGCCCA
TGAGATCAACCATGGTATTGGACAAGCAGGAAAGGAAGCAGAGAAGCTTGGCCATGGGGTC
AACAACGCTGCTGGACAGGCCGGGAAGGAAGCAGACAAAGCGGTCCAAGGGTTCCACACTG
GGGTCCACCAGGCTGGGAAGGAAGCAGAGAAACTTGGCCAAGGGGTCAACCATGCTGCTGA
CCAGGCTGGAAAGGAAGTGGAGAAGCTTGGCCAAGGTGCCCACCATGCTGCTGGCCAGGCC
GGGAAGGAGCTGCAGAATGCTCATAATGGGGTCAACCAAGCCAGCAAGGAGGCCAACCAGC
TGCTGAATGGCAACCATCAAAGCGGATCTTCCAGCCATCAAGGAGGGCCACAACCACGCC
GTTAGCCTCTGGGGCCTCAGTCAACACGCCTTTCATCAACCTTCCCGCCCTGTGGAGGAGC
GTCGCCAACATCATGCCCTAAACTGGCATCCGGCCTTGCTGGGAGAATAATGTCGCCGTTG
TCACATCAGCTGACATGACCTGGAGGGGTTGGGGGTGGGGACAGGTTTCTGAAATCCCTG
AAGGGGGTTGTACTGGGATTTGTGAATAAACTTGATACACCA
```

FIGURE 32

```
></usr/seqdb2/sst/DNA/Dnaseqs.min/ss.DNA66675
><subunit 1 of 1, 247 aa, 1 stop
><MW: 25335, pI: 7.00, NX(S/T): 0
MHLARLVGSCSLLLLLGALSGWAASDDPIEKVIEGINRGLSNAEREVGKALDGINSGITHAGREVEKVFNGLSN
MGSHTGKELDKGVQGLNHGMDKVAHEINHGIGQAGKEAEKLGHGVNNAAGQAGKEADKAVQGFHTGVHQAGKEA
EKLGQGVNHAADQAGKEVEKLGQGAHHAAGQAGKELQNAHNGVNQASKEANQLLNGNHQSGSSSHQGGATTTPL
ASGASVNTPFINLPALWRSVANIMP Important features of the protein:
Signal peptide:
amino acids 1-25

Homologous region to circumsporozoite (CS) repeats:
amino acids 35-225
```

FIGURE 33

```
GCGGCGGCTATGCCGCTTGCTCTGCTCGTCCTGTTGCTCCTGGGGCCCGGCGGCTGGTGCC
TTGCAGAACCCCCACGCGACAGCCTGCGGGAGGAACTTGTCATCACCCCGCTGCCTTCCGG
GGACGTAGCCGCCACATTCCAGTTCCGCACGCGCTGGGATTCGGAGCTTCAGCGGGAAGGA
GTGTCCCATTACAGGCTCTTTCCCAAAGCCCTGGGGCAGCTGATCTCCAAGTATTCTCTAC
GGGAGCTGCACCTGTCATTCACACAAGGCTTTTGGAGGACCCGATACTGGGGCCACCCTT
CCTGCAGGCCCCATCAGGTGCAGAGCTGTGGGTCTGGTTCCAAGACACTGTCACTGATGTG
GATAAATCTTGGAAGGAGCTCAGTAATGTCCTCTCAGGGATCTTCTGCCTCTCTCAACT
TCATCGACTCCACCAACACAGTCACTCCCACTGCCTCCTTCAAACCCCTGGGTCTGGCCAA
TGACACTGACCACTACTTTCTGCGCTATGCTGTGCTGCCGCGGGAGGTGGTCTGCACCGAA
AACCTCACCCCCTGGAAGAAGCTCTTGCCCTGTAGTTCCAAGGCAGGCCTCTCTGTGCTGC
TGAAGGCAGATCGCTTGTTCCACACCAGCTACCACTCCCAGGCAGTGCATATCCGCCCTGT
TTGCAGAAATGCACGCTGTACTAGCATCTCCTGGGAGCTGAGGCAGACCCTGTCAGTTGTA
TTTGATGCCTTCATCACGGGGCAGGGAAAGAAAGACTGGTCCCTCTTCCGGATGTTCTCCC
GAACCCTCACGGAGCCCTGCCCCTGGCTTCAGAGAGCCGAGTCTATGTGGACATCACCAC
CTACAACCAGGACAACGAGACATTAGAGGTGCACCCACCCCCGACCACTACATATCAGGAC
GTCATCCTAGGCACTCGGAAGACCTATGCCATCTATGACTTGCTTGACACCGCCATGATCA
ACAACTCTCGAAACCTCAACATCCAGCTCAAGTGGAAGAGACCCCCAGAGAATGAGGCCCC
CCCAGTGCCCTTCCTGCATGCCCAGCGGTACGTGAGTGGCTATGGGCTGCAGAAGGGGGAG
CTGAGCACACTGCTGTACAACACCCACCCATACCGGGCCTTCCCGGTGCTGCTGCTGGACA
CCGTACCCTGGTATCTGCGGCTGTATGTGCACACCCTCACCATCACCTCCAAGGGCAAGGA
GAACAAACCAAGTTACATCCACTACCAGCCTGCCCAGGACCGGCTGCAACCCCACCTCCTG
GAGATGCTGATTCAGCTGCCGGCCAACTCAGTCACCAAGGTTTCCATCCAGTTTGAGCGGG
CGCTGCTGAAGTGGACCGAGTACACGCCAGATCCTAACCATGGCTTCTATGTCAGCCCATC
TGTCCTCAGCGCCCTTGTGCCCAGCATGGTAGCAGCCAAGCCAGTGGACTGGGAAGAGAGT
CCCCTCTTCAACAGCCTGTTCCCAGTCTCTGATGGCTCTAACTACTTTGTGCGGCTCTACA
CGGAGCCGCTGCTGGTGAACCTGCCGACACCGGACTTCAGCATGCCCTACAACGTGATCTG
CCTCACGTGCACTGTGGTGGCCGTGTGCTACGGCTCCTTCTACAATCTCCTCACCCGAACC
TTCCACATCCAGGAGCCCCGCACACGTGGCCTGCCCAAGCCGCTGGCCAACCTTATCCCGC
GCGCCCGAGGTGTCCCCCCACTCTGATTCTTGCCCTTTCCAGCAGCTGCAGCTGCCGTTTC
TCTCTGGGGAGGGGAGCCCAAGGGCTGTTTCTGCCACTTGCTCTCCTCAGAGTTGGCTTTT
GAACCAAAGTGCCCTGGACCAGGTCAGGGCCTACAGCTGTGTTGTCCAGTACAGGAGCCAC
GAGCCAAATGTGGCATTTGAATTTGAATTAACTTAGAAATTCATTTCCTCACCTGTAGTGG
CCACCTCTATATTGAGGTGCTCAATAAGCAAAAGTGGTCGGTGGCTGCTGTATTGGACAGC
ACAGAAAAAGATTTCCATCACCACAGAAAGGTCGGCTGGCAGCACTGGCCAAGGTGATGGG
GTGTGCTACACAGTGTATGTCACTGTGTAGTGGATGGAGTTTACTGTTTGTGGAATAAAAA
CGGCTGTTTCCGTGGAAAAAAAAAAAA
```

FIGURE 34

MPLALLVLLLLGPGGWCLAEPPRDSLREELVITPLPSGDVAATFQFRTRWDSELQREGVSH
YRLFPKALGQLISKYSLRELHLSFTQGFWRTRYWGPPFLQAPSGAELWVWFQDTVTDVDKS
WKELSNVLSGIFCASLNFIDSTNTVTPTASFKPLGLANDTDHYFLRYAVLPREVVCTENLT
PWKKLLPCSSKAGLSVLLKADRLFHTSYHSQAVHIRPVCRNARCTSISWELRQTLSVVFDA
FITGQGKKDWSLFRMFSRTLTEPCPLASESRVYVDITTYNQDNETLEVHPPPTTTYQDVIL
GTRKTYAIYDLLDTAMINNSRNLNIQLKWKRPPENEAPPVPFLHAQRYVSGYGLQKGELST
LLYNTHPYRAFPVLLLDTVPWYLRLYVHTLTITSKGKENKPSYIHYQPAQDRLQPHLLEML
IQLPANSVTKVSIQFERALLKWTEYTPDPNHGFYVSPSVLSALVPSMVAAKPVDWEESPLF
NSLFPVSDGSNYFVRLYTEPLLVNLPTPDFSMPYNVICLTCTVVAVCYGSFYNLLTRTFHI
EEPRTGGLAKRLANLTRRARGVPPL

FIGURE 35

CGCCGGAGGCAGCGGCGGCGTGGCGCAGCGGCGACATGGCCGTTGTCTCAGAGGACGACTT
TCAGCACAGTTCAAACTCCACCTACGGAACCACAAGCAGCAGTCTCCGAGCTGACCAGGAG
GCACTGCTTGAGAAGCTGCTGGACCGCCCGCCCCTGGCCTGCAGAGGCCCGAGGACCGCT
TCTGTGGCACATACATCATCTTCTTCAGCCTGGGCATTGGCAGTCTACTGCCATGGAACTT
CTTTATCACTGCCAAGGAGTACTGGATGTTCAAACTCCGCAACTCCTCCAGCCCAGCCACC
GGGGAGGACCCTGAGGGCTCAGACATCCTGAACTACTTTGAGAGCTACCTTGCCGTTGCCT
CCACCGTGCCCTCCATGCTGTGCCTGGTGGCCAACTTCCTGCTTGTCAACAGGGTTGCAGT
CCACATCCGTGTCCTGGCCTCACTGACGGTCATCCTGGCCATCTTCATGGTGATAACTGCA
CTGGTGAAGGTGGACACTTCCTCCTGGACCCGTGGTTTTTTGCGGTCACCATTGTCTGCA
TGGTGATCCTCAGCGGTGCCTCCACTGTCTTCAGCAGCAGCATCTACGGCATGACCGGCTC
CTTTCCTATGAGGAACTCCCAAGCACTGATATCAGGAGGAGCCATGGGCGGGACGGTCAGC
GCCGTGGCCTCATTGGTGGACTTGGCTGCATCCAGTGATGTGAGGAACAGCGCCCTGGCCT
TCTTCCTGACGGCCACCATCTTCCTCGTGCTCTGCATGGGACTCTACCTGCTGCTGTCCAG
GCTGGAGTATGCCAGGTACTACATGAGGCCTGTTCTTGCGGCCCATGTGTTTTCTGGTGAA
GAGGAGCTTCCCCAGGACTCCCTCAGTGCCCCTTCGGTGGCCTCCAGATTCATTGATTCCC
ACACACCCCCTCTCCGCCCCATCCTGAAGAAGACGGCCAGCCTGGGCTTCTGTGTCACCTA
CGTCTTCTTCATCACCAGCCTCATCTACCCCGCCGTCTGCACCAACATCGAGTCCCTCAAC
AAGGGCTCGGGCTCACTGTGGACCACCAAGTTTTTCATCCCCCTCACTACCTTCCTCCTGT
ACAACTTTGCTGACCTATGTGGCCGGCAGCTCACCGCCTGGATCCAGGTGCCAGGGCCCAA
CAGCAAGGCGCTCCCAGGGTTCGTGCTCCTCCGGACCTGCCTCATCCCCCTCTTCGTGCTC
TGTAACTACCAGCCCCGCGTCCACCTGAAGACTGTGGTCTTCCAGTCCGATGTGTACCCCG
CACTCCTCAGCTCCCTGCTGGGGCTCAGCAACGGCTACCTCAGCACCCTGGCCCTCCTCTA
CGGGCCTAAGATTGTGCCCAGGGAGCTGGCTGAGGCCACGGGAGTGGTGATGTCCTTTTAT
GTGTGCTTGGGCTTAACACTGGGCTCAGCCTGCTCTACCCTCCTGGTGCACCTCATCTAGA
AGGGAGGACACAAGGACATTGGTGCTTCAGAGCCTTTGAAGATGAGAAGAGAGTGCAGGAG
GGCTGGGGGCCATGGAGGAAAGGCCTAAAGTTTCACTTGGGGACAGAGAGCAGAGCACACT
CGGGCCTCATCCCTCCCAAGATGCCAGTGAGCCACGTCCATGCCCATTCCGTGCAAGGCAG
ATATTCCAGTCATATTAACAGAACACTCCTGAGACAGTTGAAGAAGAAATAGCACAAATCA
GGGGTACTCCCTTCACAGCTGATGGTTAACATTCCACCTTCTTTCTAGCCCTTCAAAGATG
CTGCCAGTGTTCGCCCTAGAGTTATTACAAAGCCAGTGCCAAAACCCAGCCATGGGCTCTT
TGCAACCTCCCAGCTGCGCTCATTCCAGCTGACAGCGAGATGCAAGCAAATGCTCAGCTCT
CCTTACCCTGAAGGGGTCTCCCTGGAATGGAAGTCCCCTGGCATGGTCAGTCCTCAGGCCC
AAGACTCAAGTGTGCACAGACCCCTGTGTTCTGCGGGTGAACAACTGCCCACTAACCAGAC
TGGAAAACCCAGAAAGATGGGCCTTCCATGAATGCTTCATTCCAGAGGGACCAGAGGGCCT
CCCTGTGCAAGGGATCAAGCATGTCTGGCCTGGGTTTTCAAAAAAGAGGGATCCTCATGA
CCTGGTGGTCTATGGCCTGGGTCAAGATGAGGGTCTTTCAGTGTTCCTGTTTACAACATGT
CAAAGCCATTGGTTCAAGGGCGTAATAAATACTTGCGTATTCAAAAA

FIGURE 36

MAVVSEDDFQHSSNSTYGTTSSSLRADQEALLEKLLDRPPPGLQRPEDRFCGTYIIFFSLGIGSLLPWNFFITA
KEYWMFKLRNSSSPATGEDPEGSDILNYFESYLAVASTVPSMLCLVANFLLVNRVAVHIRVLASLTVILAIFMV
ITALVKVDTSSWTRGFFAVTIVCMVILSGASTVFSSSIYGMTGSFPMRNSQALISGGAMGGTVSAVASLVDLAA
SSDVRNSALAFFLTATIFLVLCMGLYLLLSRLEYARYYMRPVLAAHVFSGEEELPQDSLSAPSVASRFIDSHTP
PLRPILKKTASLGFCVTYVFFITSLIYPAVCTNIESLNKGSGSLWTTKFFIPLTTFLLYNFADLCGRQLTAWIQ
VPGPNSKALPGFVLLRTCLIPLFVLCNYQPRVHLKTVVFQSDVYPALLSSLLGLSNGYLSTLALLYGPKIVPRE
LAEATGVVMSFYVCLGLTLGSACSTLLVHLI

Transmembrane domain:
amino acids 50-74 (type II), 105-127, 135-153, 163-183, 228-252, 305-330, 448-472

FIGURE 37

CGGCTCGAGTGCAGCTGTGGGGAGATTTCAGTGCATTGCCTCCCCTGGGTGCTCTTCATCT
TGGATTTGAAAGTTGAGAGCAGCATGTTTTGCCCACTGAAACTCATCCTGCTGCCAGTGTT
ACTGGATTATTCCTTGGGCCTGAATGACTTGAATGTTTCCCCGCCTGAGCTAACAGTCCAT
GTGGGTGATTCAGCTCTGATGGGATGTGTTTTCCAGAGCACAGAAGACAAATGTATATTCA
AGATAGACTGGACTCTGTCACCAGGAGAGCACGCCAAGGACGAATATGTGCTATACTATTA
CTCCAATCTCAGTGTGCCTATTGGGCGCTTCCAGAACCGCGTACACTTGATGGGGACATC
TTATGCAATGATGGCTCTCTCCTGCTCCAAGATGTGCAAGAGGCTGACCAGGGAACCTATA
TCTGTGAAATCCGCCTCAAAGGGGAGAGCCAGGTGTTCAAGAAGGCGGTGGTACTGCATGT
GCTTCCAGAGGAGCCCAAAGAGCTCATGGTCCATGTGGGTGGATTGATTCAGATGGGATGT
GTTTTCCAGAGCACAGAAGTGAAACACGTGACCAAGGTAGAATGGATATTTTCAGGACGGC
GCGCAAAGGAGGAGATTGTATTTCGTTACTACCACAAACTCAGGATGTCTGTGGAGTACTC
CCAGAGCTGGGGCCACTTCCAGAATCGTGTGAACCTGGTGGGGGACATTTTCCGCAATGAC
GGTTCCATCATGCTTCAAGGAGTGAGGGAGTCAGATGGAGGAAACTACACCTGCAGTATCC
ACCTAGGGAACCTGGTGTTCAAGAAAACCATTGTGCTGCATGTCAGCCCGGAAGAGCCTCG
AACACTGGTGACCCCGGCAGCCCTGAGGCCTCTGGTCTTGGGTGGTAATCAGTTGGTGATC
ATTGTGGGAATTGTCTGTGCCACAATCCTGCTGCTCCCTGTTCTGATATTGATCGTGAAGA
AGACCTGTGGAAATAAGAGTTCAGTGAATTCTACAGTCTTGGTGAAGAACACGAAGAAGAC
TAATCCAGAGATAAAAGAAAAACCCTGCCATTTTGAAAGATGTGAAGGGGAGAAACACATT
TACTCCCCAATAATTGTACGGGAGGTGATCGAGGAAGAAGAACCAAGTGAAAAATCAGAGG
CCACCTACATGACCATGCACCCAGTTTGGCCTTCTCTGAGGTCAGATCGGAACAACTCACT
TGAAAAAAGTCAGGTGGGGAATGCCAAAAACACAGCAAGCCTTTTTGAGAAGAATGGAGA
GTCCCTTCATCTCAGCAGCGGTGGAGACTCTCTCCTGTGTGTGTCCTGGGCCACTCTACCA
GTGATTTCAGACTCCCGCTCTCCCAGCTGTCCTCCTGTCTCATTGTTTGGTCAATACACTG
AAGATGGAGAATTTGGAGCCTGGCAGAGAGACTGGACAGCTCTGGAGGAACAGGCCTGCTG
AGGGGAGGGGAGCATGGACTTGGCCTCTGGAGTGGGACACTGGCCCTGGGAACCAGGCTGA
GCTGAGTGGCCTCAAACCCCCGTTGGATCAGACCCTCCTGTGGGCAGGGTTCTTAGTGGA
TGAGTTACTGGGAAGAATCAGAGATAAAAACCAACCCAAATCAA

FIGURE 38

MFCPLKLILLPVLLDYSLGLNDLNVSPPELTVHVGDSALMGCVFQSTEDKCIFKIDWTLSP
GEHAKDEYVLYYYSNLSVPIGRFQNRVHLMGDILCNDGSLLLQDVQEADQGTYICEIRLKG
ESQVFKKAVVLHVLPEEPKELMVHVGGLIQMGCVFQSTEVKHVTKVEWIFSGRRAKEEIVF
RYYHKLRMSVEYSQSWGHFQNRVNLVGDIFRNDGSTMLQGVRESDGGNYTCSTHLGNLVFK
KTIVLHVSPEEPRTLVTPAALRPLVLGGNQLVIIVGIVCATILLLPVLILIVKKTCGNKSS
VNSTVLVKNTKKTNPEIKEKPCHFERCEGEKHIYSPIIVREVIEEEEPSEKSEATYMTMHP
VWPSLRSDRNNSLEKKSGGGMPKTQQAF

FIGURE 39

```
TAAAACAGCTACAATATTCCAGGGCCAGTCACTTGCCATTTCTCATAACAGCGTCAGAGAG
AAAGAACTGACTGAAACGTTTGAGATGAAGAAAGTTCTCCTCCTGATCACAGCCATCTTGG
CAGTGGCTGTTGGTTTCCCAGTCTCTCAAGACCAGGAACGAGAAAAAAGAAGTATCAGTGA
CAGCGATGAATTAGCTTCAGGGTTTTTTGTGTTCCCTTACCCATATCCATTTCGCCCACTT
CCACCAATTCCATTTCCAAGATTTCCATGGTTTAGACGTAATTTTCCTATTCCAATACCTG
AATCTGCCCCTACAACTCCCCTTCCTAGCGAAAAGTAACAAGAAGGATAAGTCACGATAA
ACCTGGTCACCTGAAATTGAAATTGAGCCACTTCCTTGAAGAATCAAAATTCCTGTTAATA
AAAGAAAAACAAATGTAATTGAAATAGCACACAGCATTCTCTAGTCAATATCTTTAGTGAT
CTTCTTTAATAAACATGAAAGCAAAGATTTTGGTTTCTTAATTTCCACA
```

FIGURE 40

></usr/seqdb2/sst/DNA/Dnaseqs.min/ss.DNA71290
><subunit 1 of 1, 85 aa, 1 stop
><MW: 9700, pI: 9.55, NX(S/T): 0
MKKVLLLITAILAVAVGFPVSQDQEREKRSISDSDELASGFFVFPYPYPFRPLPPIPFPRF
PWFRRNFPIPIPESAPTTPLPSEK

Important features of the protein:
Signal peptide:
amino acids 1-17

Homologous region to B3-hordein:
amino acids 47-85

FIGURE 41

```
GCTGTTTCTCTCGCGCCACCACTGGCCGCCGGCCGCAGCTCCAGGTGTCCTAGCCGCCCAG
CCTCGACGCCGTCCCGGGACCCCTGTGCTCTGCGCGAAGCCCTGGCCCCGGGGCCGGGGC
ATGGGCCAGGGGCGCGGGGTGAAGCGGCTTCCCGCGGGGCCGTGACTGGGCGGGCTTCAGC
CATGAAGACCCTCATAGCCGCCTACTCCGGGGTCCTGCGCGGCGAGCGTCAGGCCGAGGCT
GACCGGAGCCAGCGCTCTCACGGAGGACCTGCGCTGTCGCGCGAGGGGTCTGGGAGATGGG
GCACTGGATCCAGCATCCTCTCCGCCCTCCAGGACCTCTTCTCTGTCACCTGGCTCAATAG
GTCCAAGGTGGAAAAGCAGCTACAGGTCATCTCAGTGCTCCAGTGGGTCCTGTCCTTCCTT
GTACTGGGAGTGGCCTGCAGTGCCATCCTCATGTACATATTCTGCACTGATTGCTGGCTCA
TCGCTGTGCTCTACTTCACTTGGCTGGTGTTTGACTGGAACACACCCAAGAAAGGTGGCAG
GAGGTCACAGTGGGTCCGAAACTGGGCTGTGTGGCGCTACTTTCGAGACTACTTTCCCATC
CAGCTGGTGAAGACACACAACCTGCTGACCACCAGGAACTATATCTTTGGATACCACCCCC
ATGGTATCATGGGCCTGGGTGCCTTCTGCAACTTCAGCACAGAGGCCACAGAAGTGAGCAA
GAAGTTCCCAGGCATACGGCCTTACCTGGCTACACTGGCAGGCAACTTCCGAATGCCTGTG
TTGAGGGAGTACCTGATGTCTGGAGGTATCTGCCCTGTCAGCCGGGACACCATAGACTATT
TGCTTTCAAAGAATGGGAGTGGCAATGCTATCATCATCGTGGTCGGGGGTGCGGCTGAGTC
TCTGAGCTCCATGCCTGGCAAGAATGCAGTCACCCTGCGGAACCGCAAGGGCTTTGTGAAA
CTGGCCCTGCGTCATGGAGCTGACCTGGTTCCCATCTACTCCTTGGAGAGAATGAAGTGT
ACAAGCAGGTGATCTTCGAGGAGGGCTCCTGGGGCCGATGGGTCCAGAAGAAGTTCCAGAA
ATACATTGGTTTCGCCCCATGCATCTTCCATGGTCGAGGCCTCTTCTCCTCCGACACCTGG
GGGCTGGTGCCCTACTCCAAGCCCATCACCACTGTTGTGGGAGAGCCCATCACCATCCCCA
AGCTGGAGCACCCAACCCAGCAAGACATCGACCTGTACCACACCATGTACATGGAGGCCCT
GGTGAAGCTCTTCGACAAGCACAAGACCAAGTTCGGCCTCCCGGAGACTGAGGTCCTGGAG
GTGAACTGAGCCAGCCTTCGGGGCCAATTCCCTGGAGGAACCAGCTGCAAATCACTTTTTT
GCTCTGTAAATTTGGAAGTGTCATGGGTGTCTGTGGGTTATTTAAAAGAAATTATAACAAT
TTTGCTAAACCAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAA
```

FIGURE 42

```
></usr/seqdb2/sst/DNA/Dnaseqs.min/ss.DNA71184
><subunit 1 of 1, 388 aa, 1 stop
><MW: 43831, pI: 9.64, NX(S/T): 3
MKTLIAAYSGVLRGERQAEADRSQRSHGGPALSREGSGRWGTGSSILSALQDLFSVTWLNRSKVEKQLQVISVL
QWVLSFLVLGVACSAILMYIFCTDCWLIAVLYFTWLVFDWNTPKKGGRRSQWVRNWAVWRYFRDYFPIQLVKTH
NLLTTRNYIFGYHPHGIMGLGAFCNFSTEATEVSKKFPGIRPYLATLAGNFRMPVLREYLMSGGICPVSRDTID
YLLSKNGSGNAIIIVVGGAAESLSSMPGKNAVTLRNRKGFVKLALRHGADLVPIYSFGENEVYKQVIFEEGSWG
RWVQKKFQKYIGFAPCIFHGRGLFSSDTWGLVPYSKPITTVVGEPITIPKLEHPTQQDIDLYHTMYMEALVKLF
DKHKTKFGLPETEVLEVN
```

Important features of the protein:
Transmembrane domain:
amino acids 76-97

N-glycosylation sites.
amino acids 60-63, 173-176, 228-231

N-myristoylation sites.
amino acids 10-15, 41-46, 84-89, 120-125, 169-174, 229-234, 240-245, 318-323, 378-383

FIGURE 43

AGTGACAATCTCAGAGCAGCTTCTACACCACAGCCATTTCCAGCATGAAGATCACTGGGGG
TCTCCTTCTGCTCTGTACAGTGGTCTATTTCTGTAGCAGCTCAGAAGCTGCTAGTCTGTCT
CCAAAAAAAGTGGACTGCAGCATTTACAAGAAGTATCCAGTGGTGGCCATCCCCTGCCCCA
TCACATACCTACCAGTTTGTGGTTCTGACTACATCACCTATGGGAATGAATGTCACTTGTG
TACCGAGAGCTTGAAAAGTAATGGAAGAGTTCAGTTTCTTCACGATGGAAGTTGCTAAATT
CTCCATGGACATAGAGAGAAAGGAATGATATTCTCATCATCATCTTCATCATCCCAGGCTC
TGACTGAGTTTCTTTCAGTTTTACTGATGTTCTGGGTGGGGGACAGAGCCAGATTCAGAGT
AATCTTGACTGAATGGAGAAAGTTTCTGTGCTACCCCTACAAACCCATGCCTCACTGACAG
ACCAGCATTTTTTTTTTTAACACGTCAATAAAAAAATAATCTCCCAGA

FIGURE 44

```
></usr/seqdb2/sst/DNA/Dnaseqs.min/ss.DNA/3739
><subunit 1 of 1, 85 aa, 1 stop
><MW: 9232, pI: 7.94, NX(S/T): 0
MKITGGLLLLCTVVYFCSSSEAASLSPKKVDCSIYKKYPVVAIPCPITYLPVCGSDYITYGNECHLCTESLKSN
GRVQFLHDGSC
```

Signal peptide:
amino acids 1-19

FIGURE 45

```
GGAGAGAGGCGCGCGGGTGAAAGGCGCATTGATGCAGCCTGCGGCGGCCTCGGAGCGCGGC
GGAGCCAGACGCTGACCACGTTCCTCTCCTCGGTCTCCTCCGCCTCCAGCTCCGCGCTGCC
CGGCAGCCGGGAGCCATGCGACCCCAGGGCCCCGCCGCCTCCCCGCAGCGGCTCCGCGGCC
TCCTGCTGCTCCTGCTGCTGCAGCTGCCCGCGCCGTCGAGCGCCTCTGAGATCCCCAAGGG
GAAGCAAAAGGCGCAGCTCCGGCAGAGGGAGGTGGTGGACCTGTATAATGGAATGTGCTTA
CAAGGGCCAGCAGGAGTGCCTGGTCGAGACGGGAGCCCTGGGGCCAATGTTATTCCGGGTA
CACCTGGGATCCCAGGTCGGGATGGATTCAAAGGAGAAAAGGGGGAATGTCTGAGGGAAAG
CTTTGAGGAGTCCTGGACACCCAACTACAAGCAGTGTTCATGGAGTTCATTGAATTATGGC
ATAGATCTTGGGAAAATTGCGGAGTGTACATTTACAAAGATGCGTTCAAATAGTGCTCTAA
GAGTTTTGTTCAGTGGCTCACTTCGGCTAAAATGCAGAAATGCATGCTGTCAGCGTTGGTA
TTTCACATTCAATGGAGCTGAATGTTCAGGACCTCTTCCCATTGAAGCTATAATTTATTTG
GACCAAGGAAGCCCTGAAATGAATTCAACAATTAATATTCATCGCACTTCTTCTGTGGAAG
GACTTTGTGAAGGAATTGGTGCTGGATTAGTGGATGTTGCTATCTGGGTTGGCACTTGTTC
AGATTACCCAAAAGGAGATGCTTCTACTGGATGGAATTCAGTTTCTCGCATCATTATTGAA
GAACTACCAAAATAAATGCTTTAATTTTCATTTGCTACCTCTTTTTTATTATGCCTTGGA
ATGGTTCACTTAAATGACATTTTAAATAAGTTTATGTATACATCTGAATGAAAGCAAAGC
TAAATATGTTTACAGACCAAAGTGTGATTTCACACTGTTTTAAATCTAGCATTATTCATT
TTGCTTCAATCAAAAGTGGTTTCAATATTTTTTTAGTTGGTTAGAATACTTTCTTCATAG
TCACATTCTCTCAACCTATAATTTGGAATATTGTTGTGGTCTTTTGTTTTTTCTCTTAGTA
TAGCATTTTAAAAAAATATAAAAGCTACCAATCTTTGTACAATTTGTAAATGTTAAGAAT
TTTTTTTATATCTGTTAAATAAAAATTATTTCCAACA
```

FIGURE 46

```
></usr/seqdb2/sst/DNA/Dnaseqs.min/ss.DNA76393
><subunit 1 of 1, 243 aa, 1 stop
><MW: 26266, pI: 8.43, NX(S/T): 1
MRPQGPAASPQRLRGLLLLLLLQLPAPSSASEIPKGKQKAQLRQREVVDLYNGMCLQGPAGVPGRDGSPGANVI
PGTPGIPGRDGFKGEKGECLRESFEESWTPNYKQCSWSSLNYGIDLGKIAECTFTKMRSNSALRVLFSGSLRLK
CRNACCQRWYFTFNGAECSGPLPIEAIIYLDQGSPEMNSTINIHRTSSVEGLCEGIGAGLVDVAIWVGTCSDYP
KGDASTGWNSVSRIIIEELPK
```

Signal peptide:
amino acids 1-30

Transmembrane domain:
amino acids 195-217

FIGURE 47

GCGGAACTGGCTCCGGCTGGCACCTGAGGAGCGGCGTGACCCCGAGGGCCCAGGGAGCTGC
CCGGCTGGCCTAGGCAGGCAGCCGCACCATGGCCAGCACGGCCGTGCAGCTTCTGGGCTTC
CTGCTCAGCTTCCTGGGCATGGTGGGCACGTTGATCACCACCATCCTGCCGCACTGGCGGA
GGACAGCGCACGTGGGCACCAACATCCTCACGGCCGTGTCCTACCTGAAAGGGCTCTGGAT
GGAGTGTGTGTGGCACAGCACAGGCATCTACCAGTGCCAGATCTACCGATCCCTGCTGGCG
CTGCCCCAAGACCTCCAGGCTGCCCGCGCCCTCATGGTCATCTCCTGCCTGCTCTCGGGCA
TAGCCTGCGCCTGCGCCGTCATCGGGATGAAGTGCACGCGCTGCGCCAAGGGCACACCCGC
CAAGACCACCTTTGCCATCCTCGGCGGCACCCTCTTCATCCTGGCCGGCCTCCTGTGCATG
GTGGCCGTCTCCTGGACCACCAACGACGTGGTGCAGAACTTCTACAACCCGCTGCTGCCCA
GCGGCATGAAGTTTGAGATTGGCCAGGCCCTGTACCTGGGCTTCATCTCCTCGTCCCTCTC
GCTCATTGGTGGCACCCTGCTTTGCCTGTCCTGCCAGGACGAGGCACCCTACAGGCCCTAC
CAGGCCCCGCCCAGGGCCACCACGACCACTGCAAACACCGCACCTGCCTACCAGCCACCAG
CTGCCTACAAAGACAATCGGGCCCCCTCAGTGACCTCGGCCACGCACAGCGGGTACAGGCT
GAACGACTACGTGTGAGTCCCCACAGCCTGCTTCTCCCCTGGGCTGCTGTGGGCTGGGTCC
CCGGCGGGACTGTCAATGGAGGCAGGGGTTCCAGCACAAAGTTTACTTCTGGGCAATTTTT
GTATCCAAGGAAATAATGTGAATGCGAGGAAATGTCTTTAGAGCACAGGGACAGAGGGGGA
AATAAGAGGAGGAGAAAGCTCTCTATACCAAAGACTGAAAAAAAAAATCCTGTCTGTTTTT
GTATTTATTATATATATTTATGTGGGTGATTTGATAACAAGTTTAATATAAAGTGACTTGG
GAGTTTGGTCAGTGGGGTTGGTTTGTGATCCAGGAATAAACCTTGCGGATGTGGCTGTTTA
TGAAAAAAAAAAAAAA

FIGURE 48

MASTAVQLLGFLLSFLGMVGTLITTILPHWRRTAHVGTNILTAVSYLKGLWMECVWHSTGIYQCQIYRSLLALP
QDLQAARALMVISCLLSGIACACAVIGMKCTRCAKGTPAKTTFAILGGTLFILAGLLCMVAVSWTTNDVVQNFY
NPLLPSGMKFEIGQALYLGFISSSLSLIGGTLLCLSCQDEAPYRPYQAPPRATTTTANTAPAYQPPAAYKDNRA
PSVTSATHSGYRLNDYV

Important features of the protein:
Signal peptide:
amino acids 1-21

Transmembrane domains:
amino acids 82-103, 115-141, 160-182

FIGURE 49

```
GAGCTCCCCTCAGGAGCGCGTTAGCTTCACACCTTCGGCAGCAGGAGGGCGGCAGCTTCTC
GCAGGCGGCAGGGCGGGCGGCCAGGATCATGTCCACCACCACATGCCAAGTGGTGGCGTTC
CTCCTGTCCATCCTGGGGCTGGCCGGCTGCATCGCGGCCACCGGGATGGACATGTGGAGCA
CCCAGGACCTGTACGACAACCCCGTCACCTCCGTGTTCCAGTACGAAGGGCTCTGGAGGAG
CTGCGTGAGGCAGAGTTCAGGCTTCACCGAATGCAGGCCCTATTTCACCATCCTGGGACTT
CCAGCCATGCTGCAGGCAGTGCGAGCCCTGATGATCGTAGGCATCGTCCTGGGTGCCATTG
GCCTCCTGGTATCCATCTTTGCCCTGAAATGCATCCGCATTGGCAGCATGGAGGACTCTGC
CAAAGCCAACATGACACTGACCTCCGGGATCATGTTCATTGTCTCAGGTCTTTGTGCAATT
GCTGGAGTGTCTGTGTTTGCCAACATGCTGGTGACTAACTTCTGGATGTCCACAGCTAACA
TGTACACCGGCATGGGTGGGATGGTGCAGACTGTTCAGACCAGGTACACATTTGGTGCGGC
TCTGTTCGTGGGCTGGGTCGCTGGAGGCCTCACACTAATTGGGGGTGTGATGATGTGCATC
GCCTGCCGGGGCCTGGCACCAGAAGAAACCAACTACAAAGCCGTTTCTTATCATGCCTCAG
GCCACAGTGTTGCCTACAAGCCTGGAGGCTTCAAGGCCAGCACTGGCTTTGGGTCCAACAC
CAAAAACAAGAAGATATACGATGGAGGTGCCCGCACAGAGGACGAGGTACAATCTTATCCT
TCCAAGCACGACTATGTGTAATGCTCTAAGACCTCTCAGCACGGGCGGAAGAAACTCCCGG
AGAGCTCACCCAAAAAACAAGGAGATCCCATCTAGATTTCTTCTTGCTTTTGACTCACAGC
TGGAAGTTAGAAAAGCCTCGATTTCATCTTTGGAGAGGCCAAATGGTCTTAGCCTCAGTCT
CTGTCTCTAAATATTCCACCATAAAACAGCTGAGTTATTTATGAATTAGAGGCTATAGCTC
ACATTTTCAATCCTCTATTTCTTTTTTAAATATAACTTTCTACTCTGATGAGAGAATGTG
GTTTTAATCTCTCTCTCACATTTTGATGATTTAGACAGACTCCCCCTCTTCCTCCTAGTCA
ATAAACCCATTGATGATCTATTTCCCAGCTTATCCCCAAGAAAACTTTTGAAAGGAAAGAG
TAGACCCAAAGATGTTATTTTCTGCTGTTTGAATTTTGTCTCCCCACCCCCAACTTGGCTA
GTAATAAACACTTACTGAAGAAGAAGCAATAAGAGAAAGATATTTGTAATCTCTCCAGCCC
ATGATCTCGGTTTTCTTACACTGTGATCTTAAAAGTTACCAAACCAAAGTCATTTTCAGTT
TGAGGCAACCAAACCTTTCTACTGCTGTTGACATCTTCTTATTACAGCAACACCATTCTAG
GAGTTTCCTGAGCTCTCCACTGGAGTCCTCTTTCTGTCGCGGGTCAGAAATTGTCCCTAGA
TGAATGAGAAAATTATTTTTTTAATTTAAGTCCTAAATATAGTTAAAATAAATAATGTTT
TAGTAAAATGATACACTATCTCTGTGAAATAGCCTCACCCCTACATGTGGATAGAAGGAAA
TGAAAAAATAATTGCTTTGACATTGTCTATATGGTACTTTGTAAAGTCATGCTTAAGTACA
AATTCCATGAAAAGCTCACACCTGTAATCCTAGCACTTTGGGAGGCTGAGGAGGAAGGATC
ACTTGAGCCCAGAAGTTCGAGACTAGCCTGGGCAACATGGAGAAGCCCTGTCTCTACAAAA
TACAGAGAGAAAAAATCAGCCAGTCATGGTGGCATACACCTGTAGTCCCAGCATTCCGGGA
GGCTGAGGTGGGAGGATCACTTGAGCCCAGGGAGGTTGGGCTGCAGTGAGCCATGATCAC
ACCACTGCACTCCAGCCAGGTGACATAGCGAGATCCTGTCTAAAAAAATAAAAAATAAATA
ATGGAACACAGCAAGTCCTAGGAAGTAGGTTAAAACTAATTCTTTAA
```

FIGURE 50

```
></usr/seqdb2/sst/DNA/Dnaseqs.min/ss.DNA73734
><subunit 1 of 1, 261 aa, 1 stop
><MW: 27856, pI: 8.50, NX(S/T): 1
MSTTTCQVVAFLLSILGLAGCIAATGMDMWSTQDLYDNPVTSVFQYEGLWRSCVRQSSGFTECRPYFTILGLPA
MLQAVRALMIVGIVLGAIGLLVSIFALKCIRIGSMEDSAKANMTLTSGIMFIVSGLCAIAGVSVFANMLVTNFW
MSTANMYTGMGGMVQTVQTRYTFGAALFVGWVAGGLTLIGGVMMCIACRGLAPEETNYKAVSYHASGHSVAYKP
GGFKASTGFGSNTKNKKIYDGGARTEDEVQSYPSKHDYV
```

Signal peptide:
amino acids 1-23

Transmembrane domains:
amino acids 81-100, 121-141, 173-194

FIGURE 51

```
GGAGCGCTGCTGGAACCCGAGCCGGAGCCGGAGCCACAGCGGGGAGGGTGGCCTGGCGGCC
TGGAGCCGGACGTGTCCGGGGCGTCCCCGCAGACCGGGGCAGCAGGTCGTCCGGGGGCCCA
CCATGCTGGTGACTGCCTACCTTGCTTTTGTAGGCCTCCTGGCCTCCTGCCTGGGGCTGGA
ACTGTCAAGATGCCGGGCTAAACCCCCTGGAAGGGCCTGCAGCAATCCCTCCTTCCTTCGG
TTTCAACTGGACTTCTATCAGGTCTACTTCCTGGCCCTGGCAGCTGATTGGCTTCAGGCCC
CCTACCTCTATAAACTCTACCAGCATTACTACTTCCTGGAAGGTCAAATTGCCATCCTCTA
TGTCTGTGGCCTTGCCTCTACAGTCCTCTTTGGCCTAGTGGCCTCCTCCCTTGTGGATTGG
CTGGGTCGCAAGAATTCTTGTGTCCTCTTCTCCCTGACTTACTCACTATGCTGCTTAACCA
AACTCTCTCAAGACTACTTTGTGCTGCTAGTGGGGCGAGCACTTGGTGGGCTGTCCACAGC
CCTGCTCTTCTCAGCCTTCGAGGCCTGGTATATCCATGAGCACGTGGAACGGCATGACTTC
CCTGCTGAGTGGATCCCAGCTACCTTTGCTCGAGCTGCCTTCTGGAACCATGTGCTGGCTG
TAGTGGCAGGTGTGGCAGCTGAGGCTGTAGCCAGCTGGATAGGGCTGGGGCCTGTAGCGCC
CTTTGTGGCTGCCATCCCTCTCCTGGCTCTGGCAGGGCCTTGGCCCTTCGAAACTGGGGG
GAGAACTATGACCGGCAGCGTGCCTTCTCAAGGACCTGTGCTGGAGGCCTGCGCTGCCTCC
TGTCGGACCGCCGCGTGCTGCTGCTGGGCACCATACAAGCTCTATTTGAGAGTGTCATCTT
CATCTTTGTCTTCCTCTGGACACCTGTGCTGGACCCACACGGGGCCCCTCTGGGCATTATC
TTCTCCAGCTTCATGGCAGCCAGCCTGCTTGGCTCTTCCCTGTACCGTATCGCCACCTCCA
AGAGGTACCACCTTCAGCCCATGCACCTGCTGTCCCTTGCTGTGCTCATCGTCGTCTTCTC
TCTCTTCATGTTGACTTTCTCTACCAGCCCAGGCCAGGAGAGTCCGGTGGAGTCCTTCATA
GCCTTTCTACTTATTGAGTTGGCTTGTGGATTATACTTTCCCAGCATGAGCTTCCTACGGA
GAAAGGTGATCCCTGAGACAGAGCAGGCTGGTGTACTCAACTGGTTCCGGGTACCTCTGCA
CTCACTGGCTTGCCTAGGGCTCCTTGTCCTCCATGACAGTGATCGAAAACAGGCACTCGG
AATATGTTCAGCATTTGCTCTGCTGTCATGGTGATGGCTCTGCTGGCAGTGGTGGGACTCT
TCACCGTGGTAAGGCATGATGCTGAGCTGCGGGTACCTTCACCTACTGAGGAGCCCTATGC
CCCTGAGCTGTAACCCCACTCCAGGACAAGATAGCTGGGACAGACTCTTGAATTCCAGCTA
TCCGGGATTGTACAGATCTCTCTGTGACTGACTTTGTGACTGTCCTGTGGTTTCTCCTGCC
ATTGCTTTGTCTTTGCCAGGACATGATGGGCCTGATCGACTGCAAACAAGGTCCCAAAGT
TCCCTCTGTGTTACTCCCATTTAGAAAATAAACACTTTTAAATGATCAAAAAAAAAAA
```

FIGURE 52

MLVTAYLAFVGLLASCLGLELSRCRAKPPGRACSNPSFLRFQLDFYQVYFLALAADWLQAPYLYKLYQHYYFLE
GQIAILYVCGLASTVLFGLVASSLVDWLGRKNSCVLFSLTYSLCCLTKLSQDYFVLLVGRALGGLSTALLFSAF
EAWYIHEHVERHDFPAEWIPATFARAAFWNHVLAVVAGVAAEAVASWIGLGPVAPFVAAIPLLALAGALALRNW
GENYDRQRAFSRTCAGGLRCLLSDRRVLLLGTIQALFESVIFIFVFLWTPVLDPHGAPLGIIFSSFMAASLLGS
SLYRIATSKRYHLQPMHLLSLAVLIVVFSLFMLTFSTSPGQESPVESFIAFLLIELACGLYFPSMSFLRRKVIP
ETEQAGVLNWFRVPLHSLACLGLLVLHDSDRKTGTRNMFSICSAVMVMALLAVVGLFTVVRHDAELRVPSPTEE
PYAPEL

Signal peptide:
amino acids 1-18

Transmembrane domain:
amino acids 41-55, 75-94, 127-143, 191-213, 249-270, 278-299, 314-330,
343-359, 379-394, 410-430

FIGURE 53

```
CGGACCACCAGCAACAGACAACATCTTCATTCGGCTCTCCTGAAGCTGTACTGCCTCGC
TGAGAGGATGAAGGTCTCCGAGGCTGCCCTGTCTCTCCTTGTCCTCATCCTTATCATTAC
TTCGGCTTCTCGCAGCCAGCCAAAAGTTCCTGAGTGGGTGAACACCCCATCCACCTGCTG
CCTGAAGTATTATGAGAAAGTGTTGCCAAGGAGACTAGTGGTGGGATACAGAAAGGCCCT
CAACTGTCACCTGCCAGCAATCATCTTCGTCACCAAGAGGAACCGAGAAGTCTGCACCAA
CCCCAATGACGACTGGGTCCAAGAGTACATCAAGGATCCCAACCTACCTTTGCTGCCTAC
CAGGAACTTGTCCACGGTTAAAATTATTACAGCAAAGAATGGTCAACCCCAGCTCCTCAA
CTCCCAGTGATGACCAGGCTTTAGTGGAAGCCCTTGTTTACAGAAGAGAGGGGTAAACCT
ATGAAAACAGGGGAAGCCTTATTAGGCTGAAACTAGCCAGTCACATTGAGAGAAGCAGAA
CAATGATCAAAATAAAGGAGAAGTATTTCGGAAAAAAAAAAAA
```

FIGURE 54

```
><Wed Dec  2 16:57:00 1998 DNA82372 [min]
></usr/seqdb2/sst/DNA/Dnaseqs.min/ss.DNA82372
><subunit 1 of 1, 120 aa, 1 stop
><MW: 13600, pI: 9.83, NX(S/T): 1
MKVSEAALSLLVLILIITSASRSQPKVPEWVNTPSTCCLKYYEKVLPRRLVVGYRKALNC
HLPAIIFVTKRNREVCTNPNDDWVQEYIKDPNLPLLPTRNLSTVKIITAKNGQPQLLNSQ
```

FIGURE 55

```
GCCATGGGGCGCTGGGCCTGGGTCCCCAGCCCCTGGCCCCCACCGGGGCTGGGCCCCTTC
CTCCTCCTCCTCCTGCTGCTGCTGCTGCTGCCACGGGGGTTCCAGCCCCAGCCTGGCGGG
AACCGTACGGAGTCCCCAGAACCTAATGCCACAGCGACCCCTGCGATCCCCACTATCCTG
GTGACCTCTGTGACCTCTGAGACCCCAGCAACAAGTGCTCCAGAGGCAGAGGGACCCCAA
AGTGGGGGGCTCCCGCCCCCGCCCAGGGCAGTTCCCTCGAGCAGTAGCCCCCAGGCCCAA
GCACTCACCGAGGACGGGAGGCCCTGCAGGTTCCCCTTCCGCTACGGGGCCGCATGCTG
CATGCCTGCACTTCGGAGGGCAGTGCACACAGGAAGTGGTGTGCCACAACTCACAACTAC
GACCGGGACAGGGCCTGGGGCTACTGTGTGGAGGCCACCCCGCCTCCAGGGGCCCAGCT
GCCCTGGATCCCTGTGCCTCCGGCCCCTGCCTCAATGGAGGCTCCTGCTCCAATACCCAG
GACCCCCAGTCCTATCACTGCAGCTGCCCCCGGGCCTTCACCGGCAAGGACTGCGGCACA
GAGAAATGCTTTGATGAGACCCGCTACGAGTACCTGGAGGGGGGCGACCGCTGGGCCCGC
GTGCGCCAGGGCCACGTGGAACAGTGCGAGTGCTTCGGGGGCCGGACCTGGTGCGAAGGC
ACCCGACATACAGCTTGTCTGAGCAGCCCTTGCCTGAACGGGGGCACCTGCCACCTGATC
GTGGCCACCGGGACCACCGTGTGTGCCTGCCCACCAGGCTTCGCTGGACGGCTCTGCAAC
ATCGAGCCTGATGAGCGCTGCTTCTTGGGGAACGGCACTGGGTACCGTGGCGTGGCCAGC
ACCTCAGCCTCGGGCCTCAGCTGCCTGGCCTGGAACTCCGATCTGCTCTACCAGGAGCTG
CACGTGGACTCCGTGGGCGCCGCGGCCCTGCTGGGCCTGGGCCCCATGCCTACTGCCGG
AATCCGGACAATGACGAGAGGCCCTGGTGCTACGTGGTGAAGGACAGCGCGCTCTCCTGG
GAGTACTGCCGCCTGGAGGCCTGCGAATCCCTCACCAGAGTCCAACTGTCACCGGATCTC
CTGGCGACCCTGCCTGAGCCAGCCTCCCCGGGGCGCCAGGCCTGCGGCAGGAGGCACAAG
AAGAGGACGTTCCTGCGGCCACGTATCATCGGCGGCTCCTCCTCGCTGCCCGGCTCGCAC
CCCTGGCTGGCCGCCATCTACATCGGGGACAGCTTCTGCGCCGGGAGCCTGGTCCACACC
TGCTGGGTGGTGTCGGCCGCCCACTGCTTCTCCCACAGCCCCCCAGGGACAGCGTCTCC
GTGGTGCTGGGCCAGCACTTCTTCAACCGCACGACGGACGTGACGCAGACCTTCGGCATC
GAGAAGTACATCCCGTACACCCTGTACTCGGTGTTCAACCCCAGCGACCACGACCTCGTC
CTGATCCGGCTGAAGAAGAAAGGGGACCGCTGTGCCACACGCTCGCAGTTCGTGCAGCCC
ATCTGCCTGCCCGAGCCCGGCAGCACCTTCCCCGCAGGACACAAGTGCCAGATTGCGGGC
TGGGGCCACTTGGATGAGAACGTGAGCGGCTACTCCAGCTCCCTGCGGGAGGCCCTGGTC
CCCCTGGTCGCCGACCACAAGTGCAGCAGCCCTGAGGTCTACGGCGCCGACATCAGCCCC
AACATGCTCTGTGCCGGCTACTTCGACTGCAAGTCCGACGCCTGCCAGGGGGACTCAGGG
GGGCCCCTGGCCTGCGAGAAGAACGGCGTGGCTTACCTCTACGGCATCATCAGCTGGGGT
GACGGCTGCGGGCGGCTCCACAAGCCGGGGGTCTACACCCGCGTGGCCAACTATGTGGAC
TGGATCAACGACCGGATACGGCCTCCCAGGCGGCTTGTGGCTCCCTCCTGACCCTCCAGC
GGGACACCCTGGTTCCCACCATTCCCTGCCTTGCTGACAATAAAGATATTTCCAAG
```

FIGURE 56

```
><DNA225681 [min]
></usr/seqdb2/sst/DNA/Dnaseqs.min/ss.DNA225681
><subunit 1 of 1, 655 aa, 1 stop
><MW: 70682, pI: 7.35, NX(S/T): 6
MGRWAWVPSPWPPPGLGPFLLLLLLLLLLPRGFQPQPGGNRTESPEPNATATPAIPTILV
TSVTSETPATSAPEAEGPQSGGLPPPPRAVPSSSSPQAQALTEDGRPCRFPFRYGGRMLH
ACTSEGSAHRKWCATTHNYDRDRAWGYCVEATPPPGGPAALDPCASGPCLNGGSCSNTQD
PQSYHCSCPRAFTGKDCGTEKCFDETRYEYLEGGDRWARVRQGHVEQCECFGGRTWCEGT
RHTACLSSPCLNGGTCHLIVATGTTVCACPPGFAGRLCNIEPDERCFLGNTGYRGVAST
SASGLSCLAWNSDLLYQELHVDSVGAAALLGLGPHAYCRNPDNDERPWCYVVKDSALSWE
YCRLEACESLTRVQLSPDLLATLPEPASPGRQACGRRHKKRTFLRPRIIGGSSSLPGSHP
WLAAIYIGDSFCAGSLVHTCWVVSAAHCFSHSPPRDSVSVVLGQHFFNRTTDVTQTFGIE
KYIPYTLYSVFNPSDHDLVLIRLKKKGDRCATRSQFVQPICLPEPGSTFPAGHKCQIAGW
GHLDENVSGYSSSLREALVPLVADHKCSSPEVYGADISPNMLCAGYFDCKSDACQGDSGG
PLACEKNGVAYLYGIISWGDGCGRLHKPGVYTRVANYVDWINDRIRPPRRLVAPS
```

FIGURE 57

AGGGCCCGCGGGTGGAGAGAGCGACGCCCGAGGGGATGGCGGCAGCGTCCCGGAGCGCCTC
TGGCTGGGCGCTACTGCTGCTGGTGGCACTTTGGCAGCAGCGCGCGGCCGGCTCCGGCGTC
TTCCAGCTGCAGCTGCAGGAGTTCATCAACGAGCGCGGCGTACTGGCCAGTGGGCGGCCTT
GCGAGCCCGGCTGCCGGACTTTCTTCCGCGTCTGCCTTAAGCACTTCCAGGCGGTCGTCTC
GCCCGGACCCTGCACCTTCGGGACCGTCTCCACGCCGGTATTGGGCACCAACTCCTTCGCT
GTCCGGGACGACAGTAGCGGCGGGGGGCGCAACCCTCTCCAACTGCCCTTCAATTTCACCT
GGCCGGGTACCTTCTCGCTCATCATCGAAGCTTGGCACGCGCCAGGAGACGACCTGCGGCC
AGAGGCCTTGCCACCAGATGCACTCATCAGCAAGATCGCCATCCAGGGCTCCCTAGCTGTG
GGTCAGAACTGGTTATTGGATGAGCAAACCAGCACCCTCACAAGGCTGCGCTACTCTTACC
GGGTCATCTGCAGTGACAACTACTATGGAGACAACTGCTCCCGCCTGTGCAAGAAGCGCAA
TGACCACTTCGGCCACTATGTGTGCCAGCCAGATGGCAACTTGTCCTGCCTGCCCGGTTGG
ACTGGGGAATATTGCCAACAGCCTATCTGTCTTTCGGGCTGTCATGAACAGAATGGCTACT
GCAGCAAGCCAGCAGAGTGCCTCTGCCGCCCAGGCTGGCAGGGCCGGCTGTGTAACGAATG
CATCCCCCACAATGGCTGTCGCCACGGCACCTGCAGCACTCCCTGGCAATGTACTTGTGAT
GAGGGCTGGGGAGGCCTGTTTTGTGACCAAGATCTCAACTACTGCACCCACCACTCCCCAT
GCAAGAATGGGGCAACGTGCTCCAACAGTGGGCAGCGAAGCTACACCTGCACCTGTCGCCC
AGGCTACACTGGTGTGGACTGTGAGCTGGAGCTCAGCGAGTGTGACAGCAACCCCTGTCGC
AATGGAGGCAGCTGTAAGGACCAGGAGGATGGCTACCACTGCCTGTGTCCTCCGGGCTACT
ATGGCCTGCACTGTGAACACAGCACCTTGAGCTGCGCCGACTCCCCCTGCTTCAATGGGGG
CTCCTGCCGGGAGCGCAACCAGGGGCCAACTATGCTTGTGAATGTCCCCCCAACTTCACC
GGCTCCAACTGCGAGAAGAAAGTGGACAGGTGCACCAGCAACCCCTGTGCCAACGGGGGAC
AGTGCCTGAACCGAGGTCCAAGCCGCATGTGCCGCTGCCGTCCTGGATTCACGGGCACCTA
CTGTGAACTCCACGTCAGCGACTGTGCCCGTAACCCTTGCGCCCACGGTGGCACTTGCCAT
GACCTGGAGAATGGGCTCATGTGCACCTGCCCTGCCGGCTTCTCTGGCCGACGCTGTGAGG
TGCGGACATCCATCGATGCCTGTGCCTCGAGTCCCTGCTTCAACAGGGCCACCTGCTACAC
CGACCTCTCCACAGACACCTTTGTGTGCAACTGCCCTTATGGCTTTGTGGGCAGCCGCTGC
GAGTTCCCCGTGGGCTTGCCGCCCAGCTTCCCCTGGGTGGCCGTCTCGCTGGGTGTGGGGC
TGGCAGTGCTGCTGGTACTGCTGGGCATGGTGGCAGTGGCTGTGCGGCAGCTGCGGCTTCG
ACGGCCGGACGACGGCAGCAGGGAAGCCATGAACAACTTGTCGGACTTCCAGAAGGACAAC
CTGATTCCTGCCGCCCAGCTTAAAAACACAAACCAGAAGAAGGAGCTGGAAGTGGACTGTG
GCCTGGACAAGTCCAACTGTGGCAAACAGCAAAACCACACATTGGACTATAATCTGGCCCC
AGGGCCCCTGGGGCGGGGGACCATGCCAGGAAAGTTTCCCCACAGTGACAAGAGCTTAGGA
GAGAAGGCGCCACTGCGGTTACACAGTGAAAAGCCAGAGTGTCGGATATCAGCGATATGCT
CCCCCAGGGACTCCATGTACCAGTCTGTGTGTTTGATATCAGAGGAGAGGAATGAATGTGT
CATTGCCACGGAGGTATAAGGCAGGAGCCTACCTGGACATCCCTGCTCAGCCCCGCGGCTG
GACCTTCCTTCTGCATTGTTTACA

FIGURE 58

MAAASRSASGWALLLLVALWQQRAAGSGVFQLQLQEFINERGVLASGRPCEPGCRTFFRVCLKHFQAVVSPGPC
TFGTVSTPVLGTNSFAVRDDSSGGGRNPLQLPFNFTWPGTFSLIIEAWHAPGDDLRPEALPPDALISKIAIQGS
LAVGQNWLLDEQTSTLTRLRYSYRVICSDNYYGDNCSRLCKKRNDHFGHYVCQPDGNLSCLPGWTGEYCQQPIC
LSGCHEQNGYCSKPAECLCRPGWQGRLCNECIPHNGCRHGTCSTPWQCTCDEGWGGLFCDQDLNYCTHHSPCKN
GATCSNSGQRSYTCTCRPCYTGVDCELELSECDSNPCRNGGSCKDQEDCYHCLCPPGYYGLHCEHSTLSCADSP
CFNGGSCRERNQGANYACECPPNFTGSNCEKKVDRCTSNPCANGGQCLNRGPSRMCRCRPGFTGTYCELHVSDC
ARNPCAHGGTCHDLENGLMCTCPAGFSGRRCEVRTSIDACASSPCFNRATCYTDLSTDTFVCNCPYGFVGSRCE
FPVGLPPSFPWVAVSLGVGLAVLLVLLGMVAVAVRQLRLRRPDDGSREAMNNLSDFQKDNLIPAAQLKNTNQKK
ELEVDCGLDKSNCGKQQNHTLDYNLAPGPLGRGTMPGKFPHSDKSLGEKAPLRLHSEKPECRISAICSPRDSMY
QSVCLISEERNECVIATEV

Important features of the protein:
Signal peptide:
amino acids 1-26
Transmembrane domain:
amino acids 530-552
N-glycosylation sites.
amino acids 108-112, 183-187, 205-209, 393-397, 570-574, 610-614
Glycosaminoglycan attachment site.
amino acids 96-100
Tyrosine kinase phosphorylation site.
amino acids 340-347
N-myristoylation sites.
amino acids 42-48, 204-210, 258-264, 277-283, 297-303, 383-389, 415-421, 461-467, 522-528, 535-541, 563-569, 599-605, 625-631
Amidation site.
amino acids 471-475
Aspartic acid and asparagine hydroxylation site.
amino acids 339-351
EGF-like domain cysteine pattern signature.
amino acids 173-185, 206-218, 239-251, 270-282, 310-322, 348-360, 388-400, 426-438, 464-476, 506-518
Calcium-binding EGF-like:
amino acids 224-245, 255-276, 295-316, 333-354, 373-394, 411-432, 449-470

FIGURE 59

```
TGCAATTAAAGGAGTCGGGTCTCTAACTGTTGATCTGTTTTTTTCCCTTCTGAGCAATGGA
GCTTACCATCTTTATCCTGAGACTGGCCATTTACATCCTGACATTTCCCTTGTACCTGCTG
AACTTTCTGGGCTTGTGGAGCTGGATATGCAAAAAATGGTTCCCCTACTTCTTGGTGAGGT
TCACTGTGATATACAACGAACAGATGGCAAGCAAGAAGCGGGAGCTCTTCAGTAACCTGCA
GGAGTTTGCGGGCCCCTCCGGGAAACTCTCCCTGCTGGAAGTGGGCTGTGGCACGGGGCC
AACTTCAAGTTCTACCCACCTGGGTGCAGGGTGACCTGTATTGACCCCAACCCCAACTTTG
AGAAGTTTTTGATCAAGAGCATTGCAGAGAACCGACACCTGCAGTTTGAGCGCTTTGTGGT
AGCTGCCGGGGAGAACATGCACCAGGTGGCTGATGGCTCTGTGGATGTGGTGGTCTGCACC
CTGGTGCTGTGCTCTGTGAAGAACCAGGAGCGGATTCTCCGCGAGGTGTGCAGAGTGCTGA
GACCGGGAGGGGCTTTCTATTTCATGGAGCATGTGGCAGCTGAGTGTTCGACTTGGAATTA
CTTCTGGCAACAAGTCCTGGATCCTGCCTGGCACCTTCTGTTTGATGGGTGCAACCTGACC
AGAGAGAGCTGGAAGGCCCTGGAGCGGGCCAGCTTCTCTAAGCTGAAGCTGCAGCACATCC
AGGCCCCACTGTCCTGGGAGTTGGTGCGCCCTCATATCTATGGATATGCTGTGAAATAGTG
TGAGCTGGCAGTTAAGAGCTGAATGGCTCAAAGAATTTAAAGCTTCAGTTTTACATTTAAA
ATGCTAAGTGGGAGAAGAGAAACCTTTTTTTGGGGGGCGGTTTTTTTGGTTTGTTGTTGG
TTTTTTTTTTTTTTGGCAGGAGAATCTCTTGAACCCAGAAGGCGAAGGTTGCAGTGAAC
CGAGATCATGCCATTGTACTCTAGCCTGGGTGACAAGAGCAAGACTCCGTCTCAAAAAAAA
AAAAAAAAAAAAAAGAAGTAGAGACAGGGAGACGGGGTCTCACTGTGTTGCCTAGGCCGG
TCTTGAACTCCTGGGCTCAAGTGATTCTCCCACCTTGACCTCCTAAATTGTTGGGATTACA
GGTGTGAGACAGTGCACCTGGCCGAAATAGCTCAAGTTTCTGAAAAACAAATCTGAATCTA
TTTGTTATTCTTAGCGTCACTGGTCTGGCTTTCAGAATTAACATACAAGGTTGCCACACCT
AGTTCTGCCCAGCTTTATGTCTTTTATTCCAGTATTCCACCAAAGTTTGTTTTCCTGCATT
CCAGTTCTCAAGTCTTAAGATAAAGATTGTACTTGACAGTTTAGTATATCCATAAAACTAT
TTGAGGTGGTTAAGGTTCTTGGGTTCATTTTCCTTAATACTTTGCTGAATATTGTAGATTG
TAGGCAATGAAAAAGTCTACTAAATTAGGAAAACCTTGAATAATTAGGTATCCTAGGTAAG
AGCCCCTAAACATCAAGCAATCTGTGAGTCTGTAAAGAAATAAATATTTTTGGATTATTC
TTATCTAATTCCACCCCTGTTGGAAGATGATTTCTTTGTTCTTTGCAACTATGGAAGCTGT
GAAAATCATCACAAGTGCCTCTGAAAGCGAGTGTTAGGTTGGTTAGAGGGTTTAATATTTT
CTGCAATGCTTTGTACGAATTTTAATAAATGTACTATATTTTCTCAGATCATTTTGTAAAA
GTACTATTTTAAATATCAAATCAACCAATAAATTCACATTTGTGTTAGGAACAAAA
```

FIGURE 60

MELTIFILRLAIYILTFPLYLLNFLGLWSWICKKWFPYFLVRFTVIYNEQMASKKRELFSNLQEFAGPSGKLSL
LEVGCGTGANFKFYPPGCRVTCIDPNPNFEKFLIKSIAENRHLQFERFVVAAGENMHQVADGSVDVVVCTLVLC
SVKNQERILREVCRVLRPGGAFYFMEHVAAECSTWNYFWQQVLDPAWHLLFDGCNLTRESWKALERASFSKLKL
QHIQAPLSWELVRPHIYGYAVK

Signal peptide:
amino acids 1-29

N-glycosylation site.
amino acids 203-207

N-myristoylation sites.
amino acids 78-84, 80-86, 91-97, 201-207

FIGURE 61

```
GGCGTGTGCAAGGCGGGGTCCGGCCCGCGCAGGTCGGGTAAGCGCGTCTAGGGCGCTGCGC
GGCGCAGCGAAAATGGCGGCTTCCAGGTGGGCGCGCAAGGCCGTGGTCCTGCTTTGTGCCT
CTGACCTGCTGCTGCTGCTGCTACTGCTACCACCGCCTGGGTCCTGCGCGGCCGAAGGCTC
GCCCGGGACGCCCGACGAGTCTACCCCACCTCCCCGGAAGAAGAAGAAGGATATTCGCGAT
TACAATGATGCAGACATGGCGCGTCTTCTGGAGCAATGGGAGAAAGATGATGACATTGAAG
AAGGAGATCTTCCAGAGCACAAGAGACCTTCAGCACCTGTCGACTTCTCAAAGATAGACCC
AAGCAAGCCTGAAAGCATATTGAAAATGACGAAAAAGGGAAGACTCTCATGATGTTTGTC
ACTGTATCAGGAAGCCCTACTGAGAAGGAGACAGAGGAAATTACGAGCCTCTGGCAGGGCA
GCCTTTTCAATGCCAACTATGACGTCCAGAGGTTCATTGTGGGATCAGACCGTGCTATCTT
CATGCTTCGCGATGGGAGCTACGCCTGGGAGATCAAGGACTTTTTGGTCGGTCAAGACAGG
TGTGCTGATGTAACTCTGGAGGGCCAGGTGTACCCCGGCAAAGGAGGAGGAAGCAAAGACA
AAAATAAAACAAAGCAAGACAAGGGCAAAAAAAGAAGGAAGGAGATCTGAAATCTCGGTC
TTCCAAGGAAGAAAATCGAGCTGGGAATAAAAGAGAAGACCTGTGATGGGGCAGCAGTGAC
GCGCTGTGGGGGACAGGTGGACGTGGAGAGCTCTTTGCCCAGCTCCTGGGGTGGGAGTGG
TCTCAGGCAACTGCACACCGGATGACATTCTAGTGTCTTCTAGAAAGGGTCTGCCACATGA
CCAGTTTGTGGTCAAAGAATTACTGCTTAATAGGCTTCAAGTAAGAAGACAGATGTTTTCT
AATTAATACTGGACACTGACAAATTCATGTTTACTATAAAATCTCCTTACATGGAAATGTG
ACTGTGTTGCTTTTTCCCATTTACACTTGGTGAGTCATCAACTCTACTGAGATTCCACTCC
CCTCCAAGCACCTGCTGTGATTGGGTGGCCTGCTCTGATCAGATAGCAAATTCTGATCAGA
GAAGACTTTAAAACTCTTGACTTAATTGAGTAAACTCTTCATGCCATATACATCATTTTCA
TTATGTTAAAGGTAAAATATGCTTTGTGAACTCAGATGTCTGTAGCCAGGAAGCCAGGGTG
TGTAAATCCAAAATCTATGCAGGAAATGCGGAGAATAGAAAATATGTCACTTGAAATCCTA
AGTAGTTTTGAATTTCTTTGACTTGAATCTTACTCATCAGTAAGAGAACTCTTGGTGTCTG
TCAGGTTTTATGTGGTCTGTAAAGTTAGGGGTTCTGTTTTGTTTCCTTATTTAGGAAAGAG
TACTGCTGGTGTCGAGGGGTTATATGTTCCATTTAATGTGACAGTTTTAAAGGATTTAAGT
AGGGAATCAGAGTCCTTTGCAGAGTGTGACAGACGACTCAATAACCTCATTTGTTTCTAAA
CATTTTCTTTGATAAAGTGCCTAAATCTGTGCTTTCGTATAGAGTAACATGATGTGCTAC
TGTTGATGTCTGATTTTGCCGTTCATGTTAGAGCCTACTGTGAATAAGAGTTAGAACATTT
ATATACAGATGTCATTTCTAAGAACTAAAATTCTTTGGGAAAAACCCTCAAAAAAAAAAA
AAAAAAAAAAAAAAAAA
```

FIGURE 62

```
></usr/seqdb2/sst/DNA/Dnaseqs.min/ss.DNA92289
><subunit 1 of 1, 234 aa, 1 stop
><MW: 26077, pI: 8.13, NX(S/T): 1
MAASRWARKAVVLLCASDLLLLLLLLPPPGSCAAEGSPGTPDESTPPPRKKKKDIRDYND
ADMARLLEQWEKDDDIEEGDLPEHKRPSAPVDFSKIDPSKPESILKMTKKGKTLMMFVTV
SGSPTEKETEEITSLWQGSLFNANYDVQRFIVGSDRAIFMLRDGSYAWEIKDFLVGQDRC
ADVTLEGQVYPGKGGGSKEKNKTKQDKGKKKKEGDLKSRSSKEENRAGNKREDL Important features of the protein:
Signal peptide:
Amino acids 1-32

N-glycosylation site:
Amino acids 201-205 cAMP- and cGMP-dependent protein kinase phosphorylation site:
Amino acids 85-89

Tyrosine kinase phosphorylation site:
Amino acids 50-59

N-myristoylation sites:
Amino acids 30-36;138-144;153-159;176-182

Amidation site:
Amino acids 207-211
```

FIGURE 63

ACGTCACTGTCTTGAAGCAGCAGTAGCCTGGGAAGTGAGGCAGGAGGAATTGAGAGGCAGG
AAGGGNGCTGGAGACACAGCTGAGCCTGGAAATGAGAGTGGGCATCGCCGTGGTCATCATG
ACTCCTCTGCGGCGTGGTCACCATGTTGGTTCACTGTGTTGGGCTCTTATTGACGGGTCTC
CTGCTAGGCCTGACCTTGGGTGCCGGAGCCCTGCTGGCTTCTGAGCCTATCTACCAACCAC
CTTCAGCCTGGGTGCCAGCTGGGGGGCTGGTGGGCTGGCGCTGCTGGGAGCCCTGCTCAC
ACTTCGGTGGCCACGTCCATTCACAGTTCTGGGCACAACCCTGCTGGGTTCTGCAGTGCTT
GTGGCCTGTGTTGACTACTTCCTGGAGGGGCTGGCACTGGGGAGTTGGCTGGGCCAACGCC
TGCAGACACTTCCAGCCTTGCCTTCTCTCTGCTGATATAGCTGGGTCTTACTGGGGATCTG
GCCAGCCTTGGGGGCCCTTGGAGCCCTGGCCCAGTGGAAGCTCGTGCCTGAGGAACATGGA
GGCCACGCTAATGGGTCTGTTCCTGGTTTCCCAGATGCATAAAGGAAGACATATCCCTCCC
CTGGGCAGCAAGGCTACAATGGGAGGGAGGGAGAACATGGGAGCATGTGAATAAAATGGCA
TTAAATACTGAAAAAAAAAAAAAAAAAAAAAAAAAAAAAAAAAAAAAAAAAAAAAAAAAAA
AAAAAAAAAAAAAAAAAAAAAAAA

FIGURE 64

MLVHCVGLLLTGLLLGLTLGAGALLASEPTYQPPSAWVPAGGLVGLALLGALLTLRWPRPFTVLGTTLLGSAVL
VACVDYFLEGLALGSWLGQRLQTLPALPSLC

Signal peptide:
amino acids 1-20

Transmembrane domain:
amino acids 38-55, 60-78

N-myristoylation sites.
amino acids 7-13, 12-18, 16-22, 22-28, 41-47, 50-56, 84-90, 88-94

Prokaryotic membrane lipoprotein lipid attachment site.
amino acids 67-78

FIGURE 65

ATGAAAGTGATAATCAGGCAGCCCAAATGATTGTTAATAAGGATCAAATGAGATCGTGTAT
GTGGGTCCAATCAATTGATTCTACACAAAGGAGCCTGGGGAGGGGCCATGGTGCCAATGCA
CTTACTGGGGAGACTGGAGAAGCCGCTTCTCCTCCTGTGCTGCGCCTCCTTCCTACTGGGG
CTGGCTTTGCTGGGCATAAAGACGGACATCACCCCCGTTGCTTATTTCTTTCTCACATTGG
GTGGCTTCTTCTTGTTTGCCTATCTCCTGGTCCGGTTTCTGGAATGGGGGCTTCGGTCCCA
GCTCCAATCAATGCAGACTGAGAGCCCAGGGCCCTCAGGCAATGCACGGGACAATGAAGCC
TTTGAAGTGCCAGTCTATGAAGAGGCCGTGGTGGGACTAGAATCCCAGTGCCGCCCCCAAG
AGTTGGACCAACCACCCCCTACAGCACTGTTGTGATACCCCCAGCACCTGAGGAGGAACA
ACCTAGCCATCCAGAGGGGTCCAGGAGAGCCAAACTGGAACAGAGGCGAATGGCCTCAGAG
GGGTCCATGGCCCAGGAAGGAAGCCCTGGAAGAGCTCCAATCAACCTTCGGCTTCGGGGAC
CACGGGCTGTGTCCACTGCTCCTGATCTGCAGAGCTTGGCGGCAGTCCCCACATTAGAGCC
TCTGACTCCACCCCCTGCCTATGATGTCTGCTTTGGTCACCCTGATGATGATAGTGTTTTT
TATGAGGACAACTGGGCACCCCCTTAAATGACTCTCCCAAGATTTCTCTTCTCCACACC
AGACCTCGTTCATTTGACTAACATTTTCCAGCGCCTACTATGTGTCAGAAACAAGTGTTTC
TGCCTGGACATCATAAATGGGGACTTGGACCCTGAGGAGAGTCAGGCCACGGTAAGCCCTT
CCCAGCTGAGATATGGGTGGCATAATTTGAGTCTTCTGGCAACATTTGGTGACCTACCCCA
TATCCAATATTTCCAGCGTTAGATTGAGGATGAGGTAGGGAGGTGATCCAGAGAAGGCGGA
GAAGGAAGAAGTAACCTCTGAGTGGCGGCTATTGCTTCTGTTCCAGGTGCTGTTCGAGCTG
TTAGAACCCTTAGGCTTGACAGCTTTGTGAGTTATTATTGAAAAATGAGGATTCCAAGAGT
CAGAGGAGTTTGATAATGTGCACGAGGGCACACTGCTAGTAAATAACATTAAAATAACTGG
AATGAA

FIGURE 66

> </usr/seqdb2/sst/DNA/Dnaseqs.min/ss.DNA92264
> <subunit 1 of 1, 216 aa, 1 stop
> <MW: 23729, pI: 4.73, NX(S/T): 0

MVPMHLLGRLEKPLLLLCCASFLLGLALLGIKT
DITPVAYFFLTLGGFFLFAYLLVRFLEWGLRSQL
QSMQTESPGPSGNARDNEAFEVPVYEEAVVGLE
SQCRPQELDQPPPYSTVVIPPAPEEEQPSHPEGSR
RAKLEQRRMASEGSMAQEGSPGRAPINLRLRGP
RAVSTAPDLQSLAAVPTLEPLTPPPAYDVCFGHP
DDDSVFYEDNWAPP

Important features of the protein:
Signal peptide:
Amino acids          1-25

Transmembrane domain:
Amino acids          41-59

N-myristoylation site:
Amino acids          133-139

FIGURE 67

GCGAGGCTGCACCAGCGCCTGGCACCATGAGGACGCCTGGGCCTCTGCCCGTGCTGCTGCT
GCTCCTGGCGGGAGCCCCCGCCGCGCGGCCCACTCCCCCGACCTGCTACTCCCGCATGCGG
GCCCTGAGCCAGGAGATCACCCGCGACTTCAACCTCCTGCAGGTCTCGGAGCCCTCGGAGC
CATGTGTGAGATACCTGCCCAGGCTGTACCTGGACATACACAATTACTGTGTGCTGGACAA
GCTGCGGGACTTTGTGGCCTCGCCCCGTGTTGGAAAGTGGCCCAGGTAGATTCCTTGAAG
GACAAAGCACGGAAGCTGTACACCATCATGAACTCGTTCTGCAGGAGAGATTTGGTATTCC
TGTTGGATGACTGCAATGCCTTGGAATACCCAATCCCAGTGACTACGGTCCTGCCAGATCG
TCAGCGCTAAGGGAACTGAGACCAGAGAAAGAACCCAAGAGAACTAAAGTTATGTCAGCTA
CCCAGACTTAATGGGCCAGAGCCATGACCCTCACAGGTCTTGTGTTAGTTGTATCTGAAAC
TGTTATGTATCTCTCTACCTTCTGGAAAACAGGGCTGGTATTCCTACCCAGGAACCTCCTT
TGAGCATAGAGTTAGCAACCATGCTTCTCATTCCCTTGACTCATGTCTTGCCAGGATGGTT
AGATACACAGCATGTTGATTTGGTCACTAAAAAGAAGAAAAGGACTAACAAGCTTCACTTT
TATGAACAACTATTTTGAGAACATGCACAATAGTATGTTTTTATTACTGGTTTAATGGAGT
AATGGTACTTTTATTCTTTCTTGATAGAAACCTGCTTACATTTAACCAAGCTTCTATTATG
CCTTTTTCTAACACAGACTTTCTTCACTGTCTTTCATTTAAAAGAAATTAATGCTCTTAA
GATATATATTTTACGTAGTGCTGACAGGACCCACTCTTTCATTGAAAGGTGATGAAAATCA
AATAAAGAATCTCTTCACATGGA

FIGURE 68

```
></usr/seqdb2/sst/DNA/Dnaseqs.min/ss.DNA93011
><subunit 1 of 1, 136 aa, 1 stop
><MW: 15577, pI: 8.88, NX(S/T): 0
MRTPGPLPVLLLLLAGAPAARPTPPTCYSRMRALSQEITRDFNLLQVSEPSEPCVRYLPRL
YLDIHNYCVLDKLRDFVASPPCWKVAQVDSLKDKARKLYTIMNSFCRRDLVFLLDDCNALE
YPIPVTTVLPDRQR
```

Important features of the protein:
Signal peptide:
amino acids 1-19

Tyrosine kinase phosphorylation site.
amino acids 60-69

N-myristoylation site.
amino acids 16-22

FIGURE 69

```
GGTGACTGAAGCGAGCCTGGCCTCTTGCATCCTCCGCCTGTGTACCTCCCTCCCCTTTTTTTCCGCC
TTCTGCCAGCAGAAGCAGCAGCCGCAGCACCTGAGCCGCTACTGCCGCTCACTCAGGACAACGCT**AT
G**CTGAGCCTGGGCACAGCCACCATCTCTCCGCCAGAGTCAGGAGAAGAACTGAGAGGCGCATACCC
CGGCTGTGGCGGCTGCTGCTCTGGGCTGGGACCGCCTTCCAGGTGACCCAGGGAACGGGACCGGAGC
TTCATGCCTGCAAAGAGTCTGAGTACCACTATGAGTACACGGCGTGTGACAGCACGGGTTCCAGGTG
GAGGGTCGCCGTGCCGCATACCCCGGGCCTGTGCACCAGCCTGTCTGACCCCGTCAAGGGCACCGAG
TGCTCCTTCTCCTGCAACGCCGGGGAGTTTCTGGATATGAAGGACCAGTCATGTAAGCCATGCGCTG
AGGGCCGCTACTCCCTCGGCACAGGCATTCGGTTTGATGAGTGGGATGAGCTGCCCCATGGCTTTGC
CAGCCTCTCAGCCAACATGGAGCTGGATGACAGTGCTGCTGAGTCCACCGGGAACTGTACTTCGTCC
AAGTGGGTTCCCCGGGCGACTACATCGCCTCCAACACGGACGAATGCACAGCCACACTGATGTACG
CCGTCAACCTGAAGCAATCTGGCACCGTTAACTTCGAATACTACTATCCAGACTCCAGCATCATCTT
TGAGTTTTTCGTTCAGAATGACCAGTGCCAGCCCAATGCAGATGACTCCAGGTGGATGAAGACCACA
GAGAAAGGATGGGAATTCCACAGTGTGGAGCTAAATCGAGGCAATAATGTCCTCTATTGGAGAACCA
CAGCCTTCTCAGTATGGACCAAAGTACCCAAGCCTGTGCTGGTGAGAAACATTGCCATAACAGGGGT
GGCCTACACTTCAGAATGCTTCCCCTGCAAACCTGGCACGTATGCAGACAAGCAGGGCTCCTCTTTC
TGCAAACTTTGCCCAGCCAACTCTTATTCAAATAAAGGAGAAACTTCTTGCCACCAGTGTGACCCTG
ACAAATACTCAGAGAAAGGATCTTCTTCCTGTAACGTGCGCCCAGCTTGCACAGACAAAGATTATTT
CTACACACACACGGCCTGCGATGCCAACGGAGAGACACAACTCATGTACAAATGGGCCAAGCCGAAA
ATCTGTAGCGAGGACCTTGAGGGGGCAGTGAAGCTGCCTGCCTCTGGTGTGAAGACCCACTGCCCAC
CCTGCAACCCAGGCTTCTTCAAAACCAACAACAGCACCTGCCAGCCCTGCCCATATGGTTCCTACTC
CAATGGCTCAGACTGTACCCGCTGCCCTGCAGGGACTGAACCTGCTGTGGGATTTGAATACAAATGG
TCCAACACCCTGCCCACAAACATGGAAACGACCGTTCTCAGTGGGATCAACTTCGAGTACAACCGCA
TGACAGGCTGGGAGGTGGCTGGTGATCACATTTACACAGCTGCTGGAGCCTCAGACAATGACTTCAT
GATTCTCACTCTGGTTGTGCCAGGATTTAGACCTCCGCAGTCGGTGATGGCAGACACAGAGAATAAA
GAGGTGGCCAGAATCACATTTGTCTTTGAGACCCTCTGTTCTGTGAACTGTGAGCTCTACTTCATGG
TGGGTGTGAATTCTAGGACCAACACTCCTGTGGAGACGTGGAAAGGTTCCAAAGGCAAACAGTCCTA
TACCTACATCATTGAGGAGAACACTACCACGAGCTTCACCTGGGCCTTCCAGAGGACCACTTTTCAT
GAGGCAAGCAGGAAGTACACCAATGACGTTGCCAAGATCTACTCCATCAATGTCACCAATGTTATGA
ATGGCGTGGCCTCCTACTGCCGTCCCTGTGCCCTAGAAGCCTCTGATGTGGGCTCCTCCTGCACCTC
TTGTCCTGCTGGTTACTATATTGACCGAGATTCAGGAACCTGCCACTCCTGCCCCCCTAACACAATT
CTGAAAGCCCACCAGCCTTATGGTGTCCAGGCCTGTGTGCCCTGTGGTCCAGGGACCAAGAACAACA
AGATCCACTCTCTGTGCTACAATGATTGCACCTTCTCACGCAACACTCCAACCAGGACTTTCAACTA
CAACTTCTCCGCTTTGGCAAACACCGTCACTCTTGCTGGAGGGCCAAGCTTCACTTCCAAAGGGTTG
AAATACTTCCATCACTTTACCCTCAGTCTCTGTGGAAACCAGGGTAGGAAAATGTCTGTGTGCACCG
ACAATGTCACTGACCTCCGGATTCCTGAGGGTGAGTCAGGGTTCTCCAAATCTATCACAGCCTACGT
CTGCCAGGCAGTCATCATCCCCCAGAGGTGACAGGCTACAAGGCCGGGGTTTCCTCACAGCCTGTC
AGCCTTGCTGATCGACTTATTGGGGTGACAACAGATATGACTCTGGATGGAATCACCTCCCCAGCTG
AACTTTTCCACCTGGAGTCCTTGGGAATACCGGACGTGATCTTCTTTTATAGGTCCAATGATGTGAC
CCAGTCCTGCAGTTCTGGGAGATCAACCACCATCCGCGTCAGGTGCAGTCCACAGAAAACTGTCCCT
GGAAGTTTGCTGCTGCCAGGAACGTGCTCAGATGGGACCTGTGATGGCTGCAACTTCCACTTCCTGT
GGGAGAGCGCGGCTGCTTGCCCGCTCTGCTCAGTGGCTGACTACCATGCTATCGTCAGCAGCTGTGT
GGCTGGGATCCAGANGACTACTTACGTGTGNCGAGAACCCAAGCTATGCTCTGGTGGCATTTCTCTG
CCTGAGCAGAGAGTCACCATCTGCAAACCATAGATTTCTGGCTGAAAGTGGGCATCTCTGCAGGCA
CCTGTACTGCCATCCTGCTCACCGTCTTGACCTGCTACTTTTGGAAAAAGAATCAAAAACTAGAGTA
CAAGTACTCCAAGCTGGTGATGAATGCTACTCTCAAGGACTGTGACCTGCCAGCAGCTGACAGCTGC
GCCATCATGGAAGGCGAGGATGTAGAGGACGACCTCATCTTTACCAGCAAGAAGTCACTTTTTGGGA
AGATCAAATCATTTACCTCCAAGAGGACTCCTGATGGATTTGACTCAGTGCCGCTGAAGACATCCTC
AGGAGGCCCAGACATGGACCTGTGAGAGGCACTGCCTGCCTCACCTGCCTCCTCACCTTGCATAGCA
CCTTTGCAAGCCTGCGGCGATTTGGGTGCCAGCATCCTGCAACACCCACTGCTGGAAATCTCTTCAT
TGTGGCCTTATCAGATGTTTGAATTTCAGATCTTTTTTTATAGAGTACCCAAACCCTCCTTTCTGCT
TGCCTCAAACCTGCCAAATATACCCACATTTTTTTTAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAA
AAAAAAAAAAAAAAAA
```

FIGURE 70

```
MAEPGHSHHLSARVRRRTERRIPRLWRLLLWAGTAFQVTQGTGPELHACKESEYHYEYTACDSTGSRWRVAVPH
TPGLCTSLSDPVKGTECSFSCNAGEFLDMKDQSCKPCAEGRYSLGTGIRFDEWDELPHGFASLSANMELDDSAA
ESTGNCTSSKWVPRGDYIASNTDECTATLMYAVNLKQSGTVNFEYYYPDSSIIFEFFVQNDQCQPNADDSRWMK
TTEKGWEFHSVELNRGNNVLYWRTTAFSVWTKVPKPVLVRNIAITGVAYTSECFPCKPGTYADKQGSSFCKLCP
ANSYSNKGETSCHQCDPDKYSEKGSSSCNVRPACTDKDYFYTHTACDANGETQLMYKWAKPKICSEDLEGAVKL
PASGVKTHCPPCNPGFFKTNNSTCQPCPYGSYSNGSDCTRCPAGTEPAVGFEYKWWNTLPTNMETTVLSGINFE
YKGMTGWEVAGDIIIYTAAGASDNDFMILTLVVPGFRPPQSVMADTENKEVARITFVFETLCSVNCELYFMVGVN
SRTNTPVETWKGSKGKQSYTYIIEENTTTSFTWAFQRTTFHEASRKYTNDVAKIYSINVTNVMNGVASYCRPCA
LEASDVGSSCTSCPAGYYIDRDSGTCHSCPPNTILKAHQPYGVQACVPCGPGTKNNKIHSLCYNDCTFSRNTPT
RTFNYNFSALANTVTLAGGPSFTSKGLKYFHHFTLSLCGNQGRKMSVCTDNVTDLRIPEGESGFSKSITAYVCQ
AVIIPPEVTGYKAGVSSQPVSLADRLIGVTTDMTLDGITSPAELFHLESLGIPDVIFFYRSNDVTQSCSSGRST
TIRVRCSPQKTVPGSLLLPGTCSDGTCDGCNFHFLWESAAACPLCSVADYHAIVSSCVAGIQXTTYVXREPKLC
SGGISLPEQRVTICKTIDFWLKVGISAGTCTAILLTVLTCYFWKKNQKLEYKYSKLVMNATLKDCDLPAADSCA
TMEGEDVEDDLIFTSKKSLFGKTKSFTSKRTPDGFDSVPLKTSSGGPDMDL
```

Important features of the protein:
N-glycosylation sites:
amino acids 153-156, 390-393, 391-394, 404-407, 544-547, 576-579, 672-675, 717-720, 947-950
cAMP- and cGMP-dependent protein kinase phosphorylation sites:
amino acids 15-18, 563-566, 709-712
Casein kinase II phosphorylation sites:
amino acids 42-45, 59-62, 81-84, 146-149, 168-171, 282-285, 331-334, 340-343, 431-434, 449-452, 465-468, 523-526, 557-560, 761-764, 780-783, 835-838, 860-863, 893-896, 949-952
Tyrosine kinase phosphorylation sites:
amino acids 50-56, 109-116
N-myristoylation sites:
amino acids 77-82, 88-93, 152-157, 268-273, 288-293, 320-325, 400-405, 405-410, 414-419, 463-468, 599-604, 616-621, 634-639, 644-649, 839-844, 874-879, 912-917, 916-921
Amidation site:
amino acids 707-710
Cell attachment sequence:
amino acids 162-164

FIGURE 71

```
GCTTGCACACATGGCTCCGGAGGCTCCGGTTGCCCATCCGAGCCCCTGCCAGGCTCTAACGTTCCCAACTGACA
ACACCAGTAACTAAATATAGGAGCAGATGGTGGGGACGGGCTGTCGCAGCGGCTCCTTTGCAGAGGTCTCCGGA
CTGCAGATAAGGCTCAGGCCCTTTTGTGAGAAGCAGACCAGCCTGGGGGCTGGCGGCAGGACACCTGTGTCTGC
ATGCTGAAGAAGATGGGTGAGGCCCGTGGCCAGAGTAGCAAGGAAGGTCAACGAGACGGTGGAGAGCGGCTCTGA
CACTCTGGACCTGGCCGAGTGCAAGCTGGTCTCCTTTCCCATTGGCATCTACAAGGTCCTGCGGAATGTCTCTG
GCCAGATCCACCTCATCACCCTGGCTAACAACGAGCTTAAGTCCCTCACCAGCAAGTTCATGACCACATTCAGT
CAGCTCCGAGAGCTCCACCTGGAGGGGAACTTCCTACACCGCCTCCCCAGCGAGGTCAGTGCCCTGCAGCACCT
CAAGGCCATTGACCTGTCCCGGAACCAGTTCCAGGACTTCCCTGAGCAGCTTACCGCCCTGCCGGCGCTGGAGA
CCATCAACCTGGAGGAGAACGAGATCGTAGATGTGCCCGTGGAGAAGCTGGCCGCCATGCCAGCCTTGCGCAGC
ATCAACCTCCGCTTCAACCCACTCAACGCCGAGGTGCGCGTGATCGCCCCGCCGCTCATCAAGTTTGACATGCT
CATGTCTCCGGAAGGCGCAAGAGCCCCCCTACCTTAGGCCACCCTCCTCATGCCCACCCAGCAAGGGACAGAGG
CCACAGGCCTGGAACCCTGGAAGGGAGGGAGGCCCATGGGAGGCCAAGCCTGGGGGCTGGGGGCGGGTGGGCCG
AGCAGCACGTGGTGGGTGGGGTGCAGCTGGTCTGGATAGATAGCTTACAGCAGTAGTGGGCTCTGGAATGCCCA
AGGGAAGAGGCAAGGTGGGGCCTGCAGCCTGGACTCGGCACTCACAGCTGCTGTGCAAACTCAGGCAGATCTCC
TGCCCTCTCTGAGCCTTGTCACTTGAAAAAAACAGGACCCTTTCCCTCCTTTGGGCTCCCTGGAGGTTTTAAG
CAGTACGTGCCTCCAAGTTACCTCCAGATCAGCAGGCACAGGTGGGCATTGCCAGGTATTTTCTGAGCCCCTGC
GGGTTTGAGGCCTTGTTTTTAGTGCTGAGAGCCAGTTGCTGCCCTGAGAAGAGAAGACAACCTCCATCTATTTA
TTGCTTCCTGAGAACTGACCTGGATGCGGCCCTCTGCAGGGCCCAGTCTTCAGTCCTGTGGTCCCTGGACTGGT
GGGAACCTGAACTAGGAGTCCTGGGAGAGCTGTGGTGGGAATATGGGCTGGCACTGCTGCAGGGCAAGAACATT
CATGTAGGAGCCCGAGGACCANCANGCTGGGAATGGGGAGCAAGTCACGTCAGCTCTGTCATTCCCCACAGTTA
ACAAATTGGCGGGGTGGGAAGTCCTGAGTGCTCCGTCCCTCTAGCATCACTCCTGAGCTGCGGGAGAGGTGGCC
CAGAGAACAGCAGAGTCAGTTACACCTGCAGCTCTTGTCTAAAGTGATTAGATGGCCACCCTCACCACTGTCCA
GTCCAGCAGCAGCCTGGCTGCCTTGTCATGGCCTCCTGGGGGCAGAAGGCGATGTGGACCACGGGATTTGTAGC
CAGCCAGCTCCCAGGCCAACGCCCAAAGCCCTGATGACCTGGTTCTTCTGAGGCCCTCAACCTGGCATCTTAGG
GTATGGTCAGGCAACAGGGTGACCAGCTGTCCTGGTTTCCCAGGACATGGAACTTTCAATGCTAAAACTGGGAC
ATTACCCAGCAAGTGGGGATGGTTGGTCCCCTACCAGGAGAGGGCCTGGGGCTCTTGCTTCCCGAGAACGCCTG
TGGCTTGAAGAACCTTGACTGCTTGGTCCTCAGGTATCTACCTCCCACCTTCTCCTCATCTGTGGAGCAAGCCA
ACTCAGTGCCCCAGACCCCACCTGATCTGCATCTTTGTTTGCTCCAGAGACACCTGAGGCCCCAGAGCTTGAGG
CAAAGCCAGGCCGTCCAAATCCTGTGTGCCGTGGACGAGTGGCCACTTTACTACTCCTAAGGCTAAGATGTTGA
GAGCTCAGACCACTGCTCAGAGCAGTAATCCCTGCTCAGAATGCTCCCAGTTCCCTCGTCCCTGCCCAGGTCTC
TTGTCTCTTCGGAAGGAACTCATACGTCCGGCCATTCTTGCGCCATCACTGACCGCTCACTATCTCAACAGACT
CTGTTCATTCTGCTCGTATCCCAAGGCCTGGTTGGTCAAACTCTGGGCAAAGGGTTTTCAGGATGAGGAGGTCA
AGACAGGATGTCCAGAGCTACCGAGTTCATCTGTGGGTGTTGGGGGCAAGTGGGGGCTGAAGTCCTGTGCAGGC
TGCGCTGGCCCCACCTGCCTTGTCCCTGGAGTGGGGTTTCTCCTTGTTGAAGAAGAGGCATCCTTCTCTGATG
TGCACAAACACAATGTATGACCAGAGCCTTGCAACTCAAAGTGTGGTCTGTGGACCAGCAGCGGCAGTGACACC
TGGGAGCTTGTTAGGAATGCAGAGTCTAGGCCTCACCCTATACCTCCCGACTCAGACCCTGCATTTTAGCAAGA
CCCCCAGCTGATTCCTATAAGCACTTTAGAGTTTGAGAAGCAAGGACCTAGGCTGGGGATGTCCTCCGAGCAGA
GGGTGAAGTTTCTCTCAGTTCTCTCCCTGCCACTTCCAGGGATCTGAGCCTGTGTTCAGCCTCCTCCCTAACCC
ACCCTGGGAGACACTTGGCCTGTTAGATTGTTCCAGAGTCTGCATGGCACTCCTGAAGAAGGGAGTGTGACCTG
CAGTCACCAGGAGATGAGGGTTAGGTGTGCCCAGCCCTCCAGACCCGGCCTTTCTGGTTAACCCCTGCATGCCA
AGCTGCCTGCTGCCCCAGGTCCTCACCTCAGGCCTTTGAAGGGGCAGCTTCTGGAAGTTGTTTTCTCCTCTGCT
TGGAGAGTTTGCCCTTGTCTGTCTTGGAAAGTGTGGGCAGCCACAGATGCCCCAAATCAGAGCTCACAGTGAG
TGAGCCCCTAAGCTTCAGTCTGCAATAAAGAATGCATTGGTTTCAAAAAAAAAAAAAAAAAAAAAAAAAAAAAA
AAAAAAAAA
```

FIGURE 72

MLKKMGEAVARVARKVNETVESGSDTLDLAECKLVSFPIGIYKVLRNVSGQIHLITLANNELKSLTSKFMTTFS
QLRELHLEGNFLHRLPSEVSALQHLKAIDLSRNQFQDFPEQLTALPALETINLEENEIVDVPVEKLAAMPALRS
INLRFNPLNAEVRVIAPPLIKFDMLMSPEGARAPLP

Important features of the protein:
N-glycosylation sites.
amino acids 17-21, 47-51

FIGURE 73

GTCGACCCACGCGTCCGAAGCTGCTGGAGCCACGATTCAGTCCCCTGGACTGTAGATAAAG
ACCCTTTCTTGCCAGGTGCTGAGACAACCACACTATGAGAGGCACTCCAGGAGACGCTGAT
GGTGGAGGAAGGGCCGTCTATCAATCAATCACTGTTGCTGTTATCACATGCAAGTATCCAG
AGGCTCTTGAGCAAGGCAGAGGGGATCCCATTTATTTGGGAATCCAGAATCCAGAAATGTG
TTTGTATTGTGAGAAGGTTGGAGAACAGCCCACATTGCAGCTAAAAGAGCAGAAGATCATG
GATCTGTATGGCCAACCCGAGCCCGTGAAACCCTTCCTTTTCTACCGTGCCAAGACTGGTA
GGACCTCCACCCTTGAGTCTGTGGCCTTCCCGGACTGGTTCATTGCCTCCTCCAAGAGAGA
CCAGCCCATCATTCTGACTTCAGAACTTGGGAAGTCATACAACACTGCCTTTGAATTAAAT
ATAAATGACTGAACTCAGCCTAGAGGTGGCAGCTTGGTCTTTGTCTTAAAGTTTCTGGTTC
CCAATGTGTTTTCGTCTACATTTTCTTAGTGTCATTTTCACGCTGGTGCTGAGACAGGAGC
AAGGCTGCTGTTATCATCTCATTTTATAATGAAGAAGAAGCAATTACTTCATAGCAACTGA
AGAACAGGATGTGGCCTCAGAAGCAGGAGAGCTGGGTGGTATAAGGCTGTCCTCTCAAGCT
GGTGCTGTGTAGGCCACAAGGCATCTGCATGAGTGACTTTAAGACTCAAAGACCAAACACT
GAGCTTTCTTCTAGGGGTGGGTATGAAGATGCTTCAGAGCTCATGCGCGTTACCCACGATG
GCATGACTAGCACAGAGCTGATCTCTGTTTCTGTTTTGCTTTATTCCCTCTTGGGATGATA
TCATCCAGTCTTTATATGTTGCCAATATACCTCATTGTGTGTAATAGAACCTTCTTAGCAT
TAAGACCTTGTAAACAAAAATAATTCTTGGGGTGGGTATGAAGATGCTTCAGAGCTCATGC
GCGTTACCCACGATGGCATGACTAGCACAGAGCTGATCTCTGTTTCTGTTTTGCTTTATTC
CCTCTTGGGATGATATCATCCAGTCTTTATATGTTGCCAATATACCTCATTGTGTGTAATA
GAACCTTCTTAGCATTAAGACCTTGTAAACAAAAATAATTCTTGTGTTAAGTTAAATCATT
TTTGTCCTAATTGTAATGTGTAATCTTAAAGTTAAATAAACTTTGTGTATTTATATAATAA
TAAAGCTAAAACTGATATAAAATAAAGAAAGAGTAAACTG

FIGURE 74

MRGTPGDADGGGRAVYQSITVAVITCKYPEALEQGRGDPIYLGIQNPEMCLYCEKVGEQPT
LQLKEQKIMDLYGQPEPVKPFLFYRAKTGRTSTLESVAFPDWFIASSKRDQPIILTSELGK
SYNTAFELNIND

Signal sequence:
amino acids 1-17

N-myristoylation site.
amino acids 10-16

Cell attachment sequence.
amino acids 36-39

FIGURE 75

```
CGGGTCATGCGCCGCCGCCTGTGGCTGGGCCTGGCCTGGCTGCTGCTGGCGCGGGCGCCGG
ACGCCGCGGGAACCCCGAGCGCGTCGCGGGGACCGCGCAGCTACCCGCACCTGGAGGGCGA
CGTGCGCTGGCGGCGCCTCTTCTCCTCCACTCACTTCTTCCTGCGCGTGGATCCCGGCGGC
CGCGTGCAGGGCACCCGCTGGCGCCACGGCCAGGACAGCATCCTGGAGATCCGCTCTGTAC
ACGTGGGCGTCGTGGTCATCAAAGCAGTGTCCTCAGGCTTCTACGTGGCCATGAACCGCCG
GGGCCGCCTCTACGGGTCGCGACTCTACACCGTGGACTGCAGGTTCCGGGAGCGCATCGAA
GAGAACGGCCACAACACCTACGCCTCACAGCGCTGGCGCCGCCGCGGCCAGCCCATGTTCC
TGGCGCTGGACAGGAGGGGGGGCCCCGGCCAGGCGGCCGGACGCGGCGGTACCACCTGTC
CGCCCACTTCCTGCCCGTCCTGGTCTCCTGAG
```

FIGURE 76

> </usr/seqdb2/sst/DNA/Dnaseqs.min/ss.DNA108912
> <subunit 1 of 1, 170 aa, 1 stop
> <MW: 19663, pI: 11.81, NX(S/T): 0

MRRRLWLGLAWLLLARAPDAAGTPSASRGPRS
YPHLEGDVRWRRLFSSTHFFLRVDPGGRVQGTR
WRHGQDSILEIRSVHVGVVVIKAVSSGFYVAMN
RRGRLYGSRLYTVDCRFRERIEENGHNTYASQR
WRRRGQPMFLALDRRGGPRPGGRTRRYHLSAH
FLPVLVS

Important features of the protein:
Signal peptide:
Amino acids          1-17

N-myristoylation site:
Amino acids          22-28

HBGF/FGF family proteins:
Amino acids          74-125;139-166

FIGURE 77

```
GGAAGGCGCTCAAGGTGCGCGGCCCGGGGCGCGCTACTGGGGGCGCCCTCCGCGGTGGGCA
GCGCGCCAGGGATCGGCCTGGGCAGCCGCGGGGCGCGCGAAGGCTGCGCTTTCCCTACGGC
CCCCCTCGCTTCCTCCGGCACGGCGGCAACGGAGATTTCCTCTCGGGGAAACTACGCGGAT
CCTTTTCGGGGATCCTCGCCCCGCCCCAGTTCTCCGCCCCCTCCCCTTTGCTGGGGCGCCT
GGGCTGGCCCGCGCAGGGGAGGAGGCTCTGGCAGCCTGGGCAGGGAGGCGGCGGGGGGCCG
CGGAGCCGCTGGCCATCGATTCTCCCCGCCATGTGACGCCGTCCTTAGCCCTGCGACCCCC
AGCGCGTCCCGGGCCTGCGCCTCCGCCCCGCCGCGCAGCGCACGATGCTTCTGCCGGGACG
CGCACGCCAACCGCCGACGCCCCAGCCCGTGCAGCATCCCGGCCTCCGCCGGCAGGTAGAG
CCGCCGGGGCAGCTCCTGCGCCTCTTCTACTGCACTGTCCTGGTCTGCTCCAAAGAGATCT
CAGCGCTCACCGACTTCTCTGGTTACCTAACCAAACTCCTGCAAAACCACACCACCTATGC
CTGTGATGGGGACTATTTGAATCTACAGTGCCCTCGGCATTCTACGATAAGTGTCCAATCG
GCATTTTATGGGCAAGATTACCAAATGTGTAGTTCCCAGAAGCCTGCCTCCCAGAGGGAAG
ACAGCTTAACCTGTGTGGCAGCCACCACCTTCCAGAAGGTGCTGGACGAATGCCAGAACCA
GCGGGCCTGCCACCTCCTGGTCAATAGCCGTGTTTTTGGACCTGACCTTTGTCCAGGAAGC
AGTAAATACCTCCTGGTCTCCTTTAAATGCCAACCTAATGAATTAAAAAACAAAACCGTGT
GTGAAGACCAGGAGCTGAAACTGCACTGCCATGAATCCAAGTTCCTCAACATCTACTCTGC
GACCTACGGCAGGAGGACCCAGGAAAGGGACATCTGCTCCTCCAAGGCAGAGCGGCTCCCC
CCTTTCGATTGCTTGTCTTACTCAGCTTTGCAAGTCCTATCCCGAAGGTGCTATGGGAAGC
AGAGATGCAAAATCATCGTCAACAATCACCATTTTGGAAGCCCCTGTTTGCCAGGCGTGAA
AAAATACCTCACTGTGACCTACGCATGTGTTCCCAAGAACATACTCACAGCGATTGATCCA
GCCATTGCTAATCTAAAACCTTCTTTGAAGCAGAAAGATGGTGAATATGGTATAAACTTCG
ACCCAAGCGGATCGAAGGTTCTGAGGAAAGATGGAATTCTTGTTAGCAACTCTCTGGCAGC
CTTTGCTTACATTAGAGCCCACCCAGAGAGAGCTGCCCTGCTGTTCGTGTCCAGTGTCTGC
ATCGGCCTGGCCCTCACACTGTGCGCCCTGGTCATCAGAGAGTCCTGTGCCAAGGACTTCC
GCGACTTGCAGCTGGGGAGGGAGCAGCTGGTGCCAGGAAGTGACAAGGTCGAGGAGGACAG
CGAGGATGAAGAAGAGGAGGAGGACCCCTCTGAGTCTGATTTCCCAGGGGAACTGTCGGGG
TTCTGTAGGACTTCATATCCTATATACAGTTCCATAGAAGCTGCAGAGCTCGCAGAAAGGA
TTGAGCGCAGGGAGCAAATCATTCAGGAAATATGGATGAACAGTGGTTTGGACACCTCGCT
CCCAAGAAACATGGGCCAGTTCTACTGAAAACCACATGCATCTTGATGCGATCGCACTTTC
TGAAGAAGGAAGGATCCCAAATGCCCCTCCAGTTCTGGTTCACCTGTACCTTCTATGAAGG
AGAATTCGTCATGTCATTCAACACTCGTGAGGCCAGGAAGCTATTAAAGGGATGTTTCAAG
CTGTTTCTAGCACATTCCAAAATAAATGAGGAGGGAGGAAAAAAAAAAAAAAAAAAAAAAA
AAAAAAAAAAAAAAAAAA
```

FIGURE 78

MLLPGRARQPPTPQPVQHPGLRRQVEPPGQLLRLFYCTVLVCSKEISALTDFSGYLTKLLQNHTTYACDGDYLN
LQCPRHSTISVQSAFYGQDYQMCSSQKPASQREDSLTCVAATTFQKVLDECQNQRACHLLVNSRVFGPDLCPGS
SKYLLVSFKCQPNELKNKTVCEDQELKLHCHESKFLNIYSATYGRRTQERDICSSKAERLPPFDCLSYSALQVL
SRRCYGKQRCKIIVNNHHFGSPCLPGVKKYLTVTYACVPKNILTAIDPAIANLKPSLKQKDGEYGINFDPSGSK
VLRKDGILVSNSLAAFAYIRAHPERAALLFVSSVCIGLALTLCALVIRESCAKDFRDLQLGREQLVPGSDKVEE
DSEDEEEEDPSESDFPGELSGFCRTSYPIYSSIEAAELAERIERREQIIQEIWMNSGLDTSLPRNMGQFY

Transmembrane domains:
amino acids 32-49, 322-343

N-glycosylation sites.
amino acids 62-66, 165-169

Tyrosine kinase phosphorylation site.
amino acids 280-287

N-myristoylation site.
amino acids 302-308, 333-339, 428-434

Amidation site.
amino acids 191-195

FIGURE 79

CAGCAGCCGAGACAGCAGCTGAGACGGCAGCGGCAGCTTCTCAGGGCCGGAGCCAGTTCTTGGAGGAGACTCTG
CACAGGGCATGGATCACTGTGGTGCCCTTTTCCTGTGCCTGTGCCTTCTGACTTTGCAGAATGCAACAACAGAG
ACATGGGAAGAACTCCTGAGCTACATGGAGAATATGCAGGTGTCCAGGGGCCGGAGCTCAGTTTTTTCCTCTCG
TCAACTCCACCAGCTGGAGCAGATGCTACTGAACACCAGCTTCCCAGGCTACAACCTGACCTTGCAGACACCCA
CCATCCAGTCTCTGGCCTTCAAGCTGAGCTGTGACTTCTCTGGCCTCTCGCTGACCAGTGCCACTCTGAAGCGG
GTGCCCCAGGCAGGAGGTCAGCATGCCCGGGGTCAGCACGCCATGCAGTTCCCCGCCGAGCTGACCCGGGACGC
CTGCAAGACCCGCCCCAGGGAGCTGCGGCTCATCTGTATCTACTTCTCCAACACCCACTTTTTCAAGGATGAAA
ACAACTCATCTCTGCTGAATAACTACGTCCTGGGGGCCCAGCTGAGTCATGGGCACGTGAACAACCTCAGGGAT
CCTGTGAACATCAGCTTCTGGCACAACCAAAGCCTGGAAGGCTACACCCTGACCTGTGTCTTCTGGAAGGAGGG
AGCCAGGAAACAGCCCTGGGGGGCTGGAGCCCTGAGGGCTGTCGTACAGAGCAGCCCTCCCACTCTCAGGTGC
TCTGCCGCTGCAACCACCTCACCTACTTTGCTGTTCTCATGCAACTCTCCCCAGCCCTGGTCCCTGCAGAGTTG
CTGGCACCTCTTACGTACATCTCCCTCGTGGGCTGCAGCATCTCCATCGTGGCCTCGCTGATCACAGTCCTGCT
GCACTTCCATTTCAGGAAGCAGAGTGACTCCTTAACACGTATCCACATGAACCTGCATGCCTCCGTGCTGCTCC
TGAACATCGCCTTCCTGCTGAGCCCCGCATTCGCAATGTCTCCTGTGCCCGGGTCAGCATGCACGGCTCTGGCC
GCTGCCCTGCACTACGCGCTGCTCAGCTGCCTCACCTGGATGGCCATCGAGGGCTTCAACCTCTACCTCCTCCT
CGGGCGTGTCTACAACATCTACATCCGCAGATATGTGTTCAAGCTTGGTGTGCTAGGCTGGGGGGCCCCAGCCC
TCCTGGTGCTGCTTTCCCTCTCTGTCAAGAGCTCGGTATACGGACCCTGCACAATCCCCGTCTTCGACAGCTGG
GAGAATGGCACAGGCTTCCAGAACATGTCCATATGCTGGGTGCGGAGCCCCGTGGTGCACAGTGTCCTGGTCAT
GGGCTACGGCGGCCTCACGTCCCTCTTCAACCTGGTGGTGCTGGCCTGGGCGCTGTGGACCCTGCGCAGGCTGC
GGGAGCGGGCGGATGCACCAAGTGTCAGGGCCTGCCATGACACTGTCACTGTGCTGGGCCTCACCGTGCTGCTG
GGAACCACCTGGGCCTTGGCCTTCTTTTCTTTTGGCGTCTTCCTGCTGCCCCAGCTGTTCCTCTTCACCATCTT
AAACTCGCTGTACGGTTTCTTCCTTTTCCTGTGGTTCTGCTCCCAGCGGTGCCGCTCAGAAGCAGAGGCCAAGG
CACAGATAGAGGCCTTCAGCTCCTCCCAAACAACACAGTAGTCCGGGCCTCCTGGCCTGGAATCCTCAGCCTCT
CTGGCCGCCAGTAGCCTGAGGCTACGGCTCCTGCTAGAGAGGGTGGCAGGCCTGCTGCTGGACCCCAGAGGCCA
CTGTGACCGCCAAGGGGCCTTTTCCACTTCCACGGCCTCTCCAGGCACTGAGGGGAAGGCATTGCTCTACCTCT
CCCTGACATTTTGCTCCGGGCAGATCCAACCTTACCTGGGGCAGCAAACTTTGTCCTGGTACCTGGGCCCAGC
TCGCCAGGGATGTGGGCAGAGCACCAGCCTGGGCATCAGGAAGCCAAGTTTCAAGGACTGTCTTTGAGTCTGTC
TGTATGACCTTGGGCCTGCCACTTCTCACAGACCCTAGGTATCCACAGCTGTGACATGGGGCAAGCAGCTTTG
TTTCAGCCTAACCCAGGAGCTTAGTAAAAATTGCATAAGACCAGGGGGAAGAGTGTCAGCGTGGGGTGGGAATT
CCCGCGGCCTCCACCTGCTTGCTAGGGGCAGGATCTCATTCAGGCTGCCCTGGAAGCACCTGCTTGGCCCTGCC
ACCTTCCTCCAGGCCAGGGCCACATGGCATCCTGGCTTCGGGCGCCTCGGACCTACCCAGGCTCTGAGACTTTA
CTGGCCTATGCCTGAGGCCTCTTTTCCTTTAACTCCCTAAATTATGATGACTCCAAGTCCAAGCCCACCCTTCC
CAAAGATTGGGAGGTTCCGCCGTTCCCAGAGGCCTCCTCCTGCGGTGCTCCCAAGACTTCCATAGACCATCTGGA
CCAGTAGCCCATCCCGCAGTTTTCTTGGGGGCAGAGGAAAAACGCTTCTTTCTCCTCCAGCTGAATCAGCTGGAT
CCCAGTGTCCTGGCTGTTTGGTGATTGGGCAAGATTGAATTTGCCCAGGTAGGCGTGAGAGTGTGGGTTTTAAA
TTCGAAGCTCAGGCCATAGTTTCAGAGAATCACCCTTACCCCAGACCTTCATGAGACAGTGCTCATGAAGCCAG
TGCGTTTCCCAGAACGAACACTAGGCGGCACCGTTGGTCCACACTCAGAGGCCCTTGGCGCCAAGACTGCATCT
AGAATCGCTCAAACACCTGTTTGCAGACCCCATGCACCGACGTGGAGGGGCCGTAACTGCAGGACTGCGCCTACT
GAGTGACCCATTTCCTCCAGGAGGAAAGGCAAGACACGCTTACACGGCCATTTGTCTCTTTTCCCAATGCGGCG
GTGCACTTTCGCTCTTGGGGGCTGCACCCCAGACATAGCTGGCACCAGAGCAGGGTGCTCAGGTGGTGGGTGCT
CAGG

FIGURE 79 CONTINUED

```
GCCCTGCCCCAGGCCACTGGGCCGTTTTGATGACCTCAAAGGTCACAGGCAGAAAATAGGAGCAGGATTTCCCC
TGGGGAAAAGTTATCCTGGGACATCTTCTGCTCTTCTGTACATTTCTAGATGCAAATAACTCCTTCACCAGGCA
GTGAGTGGCGTAGGCTCTGGAGCCAGGCTGCCTGGGCTCCAATGCCAGCTCTGCCACTTGCTAGCTGTGAGACT
GTGGACAAACCACTCAGCCTCTGTGTGCCTCAGTTTTCCTATTTGTAAAATAGAGACCATAGTGGTACCTATTT
TGAAGACTAAGTAAAAGAATTCAAATAAAGAGACTTGGCACAGAGTAAGTGCTCAGTAAAAA
```

FIGURE 80

```
></usr/seqdb2/sst/DNA/Dnaseqs.min/ss.DNA96860
><subunit 1 of 1, 528 aa, 1 stop
><MW: 59000, pI: 8.73, NX(S/T): 9
MDHCGALFLCLCLLTLQNATTETWEELLSYMENMQVSRGRSSVFSSRQLHQLEQMLLNTS
FPGYNLTLQTPTIQSLAFKLSCDFSGLSLTSATLKRVPQAGGQHARGQHAMQFPAELTRD
ACKTRPRELRLICIYFSNTHFFKDENNSSLLNNYVLGAQLSHGHVNNLRDPVNISFWHNQ
SLEGYTLTCVFWKEGARKQPWGGWSPEGCRTEQPSHSQVLCRCNHLTYFAVLMQLSPALV
PAELLAPLTYISLVGCSISIVASLITVLLHFHFRKQSDSLTRIHMNLHASVLLLNIAFLL
SPAFAMSPVPGSACTALAAALHYALLSCLTWMAIEGFNLYLLLGRVYNIYIRRYVFKLGV
LGWGAPALLVLLSLSVKSSVYGPCTIPVFDSWENGTGFQNMSICWVRSPVVHSVLVMGYG
GLTSLFNLVVLAWALWTLRRLRERADAPSVRACHDTVTVLGLTVLLGTTWALAFFSFGVF
LLPQLFLFTILNSLYGFFLFLWFCSQRCRSEAEAKAQIEAFSSSQTTQ Important features of the protein:
Signal peptide:
Amino acids 1-21
Transmembrane domains:
Amino acids 244-264;290-309;316-344;358-376;411-431;468-491
N-glycosylation sites:
Amino acids 18-22;58-62;65-69;146-150;147-151;173-177;
            179-183;394-398;400-404
cAMP- and cGMP-dependent protein kinase phosphorylation site:
Amino acids 274-278
N-myristoylation sites:
86   GLSLTS
101  GGQHAR
157  GAQLSH
255  GCSISI
311  GSACTA
420  GGLTSL
467  GTTWAL
Prokaryotic membrane lipoprotein lipid attachment sites:
Amino acids 246-257;318-329
Eukaryotic thiol (cysteine) proteases histidine active site:
Amino acids 410-421
G-protein coupled receptors family 2 proteins:
Amino acids 273-302;314-343
```

FIGURE 81

```
CGATGCCGGCGGTCAGTGGTCCAGGTCCCTTATTCTGCCTTCTCCTCCTGCTCCTGGACCC
CCACAGCCCTGAGACGGGGTGTCCTCCTCTACGCAGGTTTGAGTACAAGCTCAGCTTCAAA
GGCCCAAGGCTGGCATTGCCTGGGGCTGGAATACCCTTCTGGAGCCATCATGGAGACGCCA
TCCTGGGCCTGGAGGAAGTGCGGCTGACGCCATCCATGAGGAACCGGAGTGGCGCCGTGTG
GAGCAGGGCCTCTGTCCCCTTCTCTGCCTGGGAAGTAGAGGTGCAGATGAGGGTGACGGGA
CTGGGGCGCCGGGGAGCCCAGGGCATGGCCGTGTGGTACACCCGGGGCAGGGGCCATGTAG
GCTCTGTCCTTGGGGGCTGGCTTCGTGGGACGGCATCGGGATCTTCTTTGACTCTCCGGC
AGAGGATACTCAGGACAGTCCTGCCATCCGTGTGCTGGCCAGCGACGGGCACATCCCCTCT
GAGCAGCCTGGGGATGGAGCTAGCCAAGGGCTGGGCTCCTGTCATTGGGACTTCCGGAACC
GGCCACACTCCTTCAGAGCACGGATCACCTACTGGGGGCAGAGGCTGCGCATGTCCTTGAA
CAGTGGCCTCACTCCCAGTGATCCAGGTGAGTTCTGTGTGGATGTGGGGCCCCTGCTTTTG
GTCCCTGGAGGTTTCTTTGGGGTCTCAGCAGCCACCGGCACCCTGGCAGGTGAGGATCCCA
CTGGACAGGTTCCCCCTCAGCCCTTCCTGGAGATGCAGCAGCTCCGCCTGGCGAGGCAGCT
GGAAGGGCTGTGGGCAAGGCTGGGCTTGGGCACCAGGGAGGATGTAACTCCAAAATCAGAC
TCTGAAGCTCAAGGAGAAGGGGAAAGGCTCTTTGACCTGGAGGAGACGCTGGGCAGACACC
GCCGGATCCTGCAGGCTCTGCGGGTCTCTCCAAGCAGCTGGCCCAGGCTGAGAGACAATG
GAAGAAGCAGCTGGGGCCCCAGGCCAAGCCAGGCCTGACGGAGGCTGGGCCCTGGATGCT
TCCTGCCAGATTCCATCCACCCCAGGGAGGGGTGGCCACCTCTCCATGTCACTCAATAAGG
ACTCTGCCAAGGTCGGTGCCCTGCTCCATGGACAGTGGACTCTGCTCCAGGCCCTGCAAGA
GATGAGGGATGCAGCTGTCCGCATGGCTGCAGAAGCCCAGGTCTCCTACCTGCCTGTGGGC
ATTGAGCATCATTTCTTAGAGCTGGACCACATCCTGGGCCTCCTGCAGGAGGAGCTTCGGG
GCCCGGCGAAGGCAGCAGCCAAGGCCCCCGCCCACCTGGCCAGCCCCAAGGGCCTCCTC
GTGCCTGCAGCCTGGCATCTTCCTGTTCTACCTCCTCATTCAGACTGTAGGCTTCTTCGGC
TACGTGCACTTCAGGCAGGAGCTGAACAAGAGCCTTCAGGAGTGTCTGTCCACAGGCAGCC
TTCCTCTGGGTCCTGCACCACACACCCCAGGGCCCTGGGGATTCTGAGGAGGCAGCCTCT
CCCTGCCAGCATGCCTGCCTGACCCACCTCAGAGCCTGCTTTGCATCACTGGGAAGCAGGC
AGTGTCTTGGGTGGGGCTTGGTCAGTATCCTCTCCGTCTGGGTGCCCAGCTCCCACGCAC
ACCTGAGCTTTCGGCATGCTCCCACCTCGTTAAAGGTGATTTCCCTCTCCCCAAAAAAAAA
AAAAAAAAAAAAAAAAAAAAAAAAAAAAAAAAAAAAAAAAAAAAAAAAAAAA
```

FIGURE 82

```
></usr/seqdb2/sst/DNA/Dnaseqs.min/ss.DNA96883
><subunit 1 of 1, 514 aa, 1 stop
><MW: 55687, pI: 8.78, NX(S/T): 2
MPAVSGPGPLFCLLLLLLDPHSPETGCPPLRRFEYKLSFKGPRLALPGAGIPFWSHHGDAILGLEEVRLTPSMR
NRSGAVWSRASVPFSAWEVEVQMRVTGLGRRGAQGMAVWYTRGRGHVGSVLGGLASWDGIGIFFDSPAEDTQDS
PAIRVLASDGHIPSEQPGDGASQGLGSCHWDFRNRPHSFRARITYWGQRLRMSLNSGLTPSDPGEFCVDVGPLL
LVPGGFFGVSAATGTLAGEDPTGQVPPQPFLEMQQLRLARQLEGLWARLGLGTREDVTPKSDSEAQGEGERLFD
LEETLGRHRRILQALRGLSKQLAQAERQWKKQLGPPGQARPDGGWALDASCQIPSTPGRGGHLSMSLNKDSAKV
GALLHGQWTLLQALQEMRDAAVRMAAEAQVSYLPVGIEHHFLELDHILGLLQEELRGPAKAAAKAPRPPGQPPR
ASSCLQPGIFLFYLLIQTVGFFGYVHFRQELNKSLQECLSTGSLPLGPAPHTPRALGILRRQPLPASMPA Important features of the protein:
Signal peptide:
Amino acids    1-23

Transmembrane domain:
Amino acids    215-232;450-465

N-glycosylation sites:
Amino acids    75-79;476-480

Glycosaminoglycan attachment site:
Amino acids    5-9

N-myristoylation sites:
Amino acids    78-84;122-128;126-132;168-174;172-178;
               205-211;226-232;230-236;236-242;356-362

Amidation site:
Amino acids    102-106
```

FIGURE 83

```
GTAGAGAGTGAAGCAGCAAGACTGCAGAGCCTCATCAAGAAGTGTGGAGTGAAGGGAAGGCTTCAGATGGACAA
TTTGTGTGCTGGGGAAAAAATGGAATGTGCTGCAAATTCCCCTGTGGATAAGGGTGGACGGCTGCTCTGTCAAC
TTTGACCATTTTCAGATTCTGCGGGCCATTGGTAAAGGGAGTTTTGGAAAGGTATGCATCGTGCAGAAGCGAGA
CACTAAGAAAATGTATGCAATGAAGTACATGAACAAGCAGAAGTGCATCGAGAGGGATGAGGTTCGGAATGTTT
TCCGGGAGCTGCAGATCATGCAAGGGCTGGAGCACCCCTTCCTGGTCAATCTGTGGTACTCCTTCCAGGATGAG
GAGGACATGTTCATGGTGGTGGACCTGCTCCTGGGAGGCGACCTGCGCTACCATCTGCAGCAGAATGTGCATTT
CACAGAGGGGACTGTGAAACTCTACATCTGTGAGCTGGCACTGGCCCTGGAGTATCTTCAGAGGTACCACATCA
TCCACAGAGACATCAAGCCAGACAATATCCTGCTGGATGAACACGGACATGTTCACATTACAGACTTCAACATA
GCGACGGTAGTGAAAGGAGCAGAAAGGGCTTCCTCCATGGCTGGCACCAAGCCCTACATGGCTCCAGAAGTATT
CCAGGTGTACATGGACAGAGGCCCCGGATACTCGTACCCTGTCGACTGGTGGTCCCTGGGCATCACAGCCTATG
AGCTGCTGCGGGCTGGAGGCCGTACGAAATCCACTCGGTCACGCCCATCGATGAAATCCTTAACATGTTCAAG
GTGGAGCGTGTCCACTACTCCTCCACGTGGTGCAAGGGGATGGTGGCCCTGCTGAGGAAGCTCCTGACCAAGGA
TCCTGAGAGCCGCGTGTCCAGCCTTCATGACATACAGAGCGTGCCCTACTTGGCCGACATGAACTGGGACGCGG
TGTTCAAGAAGGCACTGATGCCCGGCTTTGTGCCCAATAAAGGGAGGTTGAACTGCGATCCCACATTTGAGCTT
GAAGAGATGATTCTAGAATCCAAGCCACTTCACAAAAGAAGAAGCGATTGGCAAGAACAGATCCAGGGATGG
CACAAAGGACAGCTGCCCGCTGAATGGACACCTGCAGCACTGTTTGGAGACTGTCCGGGAGGAATTCATCATAT
TCAACAGAGAGAAGCTCAGGAGGCAGCAGGGCAGGCAGCCAGCTCTTGGACACCGACAGCCGAGGGGGAGGC
CAGGCCCAAAGCAAGCTCCAGGACGGGTGCAACAACAACCTCCTCACCCACACCTGCACCCGTGGCTGCAGCAG
CTGAGCCCACACTTGTTGCTGCTCAACAGGACTGCACTCGTCTCTGCCCTGCCCACCCAGAGCCCCTCTTTGTG
CCCTGATGGTCCCTGTCTCACCCCTGAAAACATCAGATGCAGAAAAAGCCCTGGACTTGGAGCTGGGAAGCCTG
GGTTCTGGTCCCATCTCCATGACTGATTCACGTGTGACCTCAGACAAGTCACGCCCTCTCTGTGCCTCCGTTTT
CTGCATCTGCCAAAGGGGTTAAACACTTCTGCCCCACTTCAAATTACAAGATTATGGGGAGAACCCAATTAGGT
AGGAAACATGAAAAACCTTTGATATTTATAAAATCATTTTTACGTGCAAAATATAACCTTAATATTTGAAGTGA
CCCCCATTCCCCAAAGCAATCAAACCGTCATGACTTTGCAATTTCGCACATCCTAGCTTGTTAGAGGGCACTTC
CGAAAAACACAGCCCTGACAGCAAAATAAAGGTCTGATATGTTGGCCCCTTCTATGGAAACAACGCTGCCAAAT
CCTGGAGCAAAACCTGAAGTGTCTTCATGTGCATTCTCTGGCAGGCCACAGTCCTTCTGAGCTTGTAAGATGGT
GCAGCATGCAGACCAGACTTGTCCCCAAGGTCTCAGCGCTGCGGTCTCACTCCTCCCCTCATTTAAGAAGACTA
TCCTTACCTTTTAGTTTCAGCAGTCCTCACCACCACCATATCCCCAGTGCTGGGATGGCACACAGGTGTCCATT
CAGATGAGAGTTGGGTCGCTGAGCATTGGTTACTCCTGCAGAGTGTAATCAGCACCCCATCCAACTGGCCCGAA
AGCCCAGACCTGCAGCAGAACTCTCCAACTCTCTATCAGCTTTCAGGGTTTTCTCTCCTGGGAAGGGTGTAAAA
TCAGCTTGTCAGATTCTTCTTACAGAGAGTATCCAATCGGTATTGGTGGAGCGGCTCCCTATTTATACAATAGG
AAGCATGGGTGCTTAGAAAGTTTATTTCAGGAGGAAATGGGTTCACACAAAAGCAAACTACATTCTGATCTG
CTCAGGGAGAAGCTTGCCTTTGAACTGGAAGATGTTGGGATGAGCAGGGAAAGCTTAGACTTTGGAGTCAGGTT
TGTGTTCAGAATCCAGCCCTGCTGGCTACTAACTAACTGGGAGACCTTAGGCAAAGCATGCAATCGCTCTGAAT
GGCAGTTTCCTCATTTTTAAACAGGGATAATAAAACTAATATTGCAGGGGAGTTACAGGGTTAAATAAGATCCT
GTGTGTAACCCAAGCATTGGATGACTCATAGAATGGCCTTTTTGTCAGCATAATCGTCATCATTATTTAGAT
ACTTTCTTCCTTCACTCACCCAGCAGGTCAGTTTTCTGTGCAAACAAACCTGTTTAGGATTCTTCCAAATGTTC
TTCCTGGGGTCTTTGATATTTGTTTGTTACATCCTGCTGAAGTTCGACTGTGTTTTATTTTTTCATCCAACTT
CCATTTTTCACTTTTTACATGATTACTCAATCCTTGGGGCTGTCCATGTCATCTCTTAGATTTCTTAAAAGACA
TTTTAATGTATGGTTAGGTTTTATATTTTTATTTTTTAAAAAAGAAATAGTCAGTGTTTTCCTCCTTTCAACCG
AGAC
```

FIGURE 83 CONTINUED

```
TATTTCTGGATTGTGTGCTCCTCGTCAGTTGACTTGTTTTGCACACTTTTCTTTACTTCATGTCCCCATCAACA
ACCGTCCTGCTCCCCACCTCCCCCAGGAAATAAGGGGCCTGCTCCTCTCCCTACTGTGACCCTGGAGGCTCTTA
AGATGATGATGGTTTTTTTTATTGGGCTGAGTTCACGAATTAGGGGCAGGAGCTGGAAGTCGCCCTAGGAACAC
CAGATTTCCTGGTTCTGTTCAAGTTGGCATTTCTTGTTTGGAATAAACTATTTCTTGG
```

FIGURE 84

```
</usr/seqdb2/sst/DNA/Dnaseqs.min/ss.DNA136110
<subunit 1 of 1, 364 aa, 1 stop
<MW: 42195, pI: 7.40, NX(S/T): 1
MKYMNKQKCIERDEVRNVFRELQIMQGLEHPFLVNLWYSFQDEEDMFMVVDLLLGGDLRY
HLQQNVHFTEGTVKLYICELALALEYLQRYHIIHRDIKPDNILLDEHGHVHITDFNIATV
VKGAERASSMAGTKPYMAPEVFQVYMDRGPGYSYPVDWWSLGITAYELLRGWRPYEIHSV
TPIDEILNMFKVERVHYSSTWCKGMVALLRKLLTKDPESRVSSLHDIQSVPYLADMNWDA
VFKKALMPGFVPNKGRLNCDPTFELEEMILESKPLHKKKKRLAKNRSRDGTKDSCPLNGH
LQHCLETVREEFIIFNREKLRRQQGQGSQLLDTDSRGGGQAQSKLQDGCNNNLLTHTCTR
GCSS
```

Important features of the protein:

N-glycosylation site:
Amino acids    285-289

N-myristoylation sites:
Amino acids    123-129; 290-296; 337-343; 339-345; 348-354

Serine/Threonine protein kinases active-site signature:
Amino acids    92-105

FIGURE 85

CTGAGCTCCCGGGCTCCGGCAGCGCGCTGGCGGGGCGCCGCATTGCACACTCTGGGGGCG
CCGCAGTGTTCGTGGGATGGGGCAGCGGGCTGCAGCTGGCGGCCGGAATCCGCGCGCAGC
CCGGGTGCAAGTTCTCTCCTGTTGCCCTGAGTGCCCACTCCCAGGCCCTCTGTATGAGTG
ACACTTCAGTCTGCC
ATGGAACCTGGCCCTGCTCTGGCCTGGCTCCTGCTCCTGAGCCTGCTGGCGGATTGTCTG
AAAGCTGCTCAGTCCCGAGACTTCACAGTGAAAGACATTATCTACCTCCATCCTTCAACC
ACACCATATCCTGGTGGATTTAAATGTTTCACCTGTGAAAAGGCAGCAGACAATTATGAG
TGCAACCGATGGGCTCCAGACATCTACTGCCCTCGAGAGACCAGATACTGCTACACTCAG
CACACAATGGAAGTCACAGGAAACAGTATCTCAGTCACCAAACGCTGTGTCCCACTGGAA
GAGTGCTTATCCACTGGCTGCAGAGACTCCGAGCATGAAGGCCACAAGGTCTGCACTTCT
TGTTGTGAAGGAAATATCTGTAACTTGCCACTGCCCCGAAATGAAACTGATGCCACATTT
GCCACGACGTCACCTATAAATCAGACAAATGGGCACCCACGCTGTATGTCAGTGATAGTG
TCCTGCTTGTGGTTGTGGTTAGGGCTCATGTTATAGTGGCTCAGTGGCTCCATGTGTTAA
TAGCGATCCATGGGGATCTCGATGGTCCACAGACCTGCATGAGTCATTGGCCTGACAGTA
ATTACACATGTGAGACACAACACTCTTGGAGGTCATCACAGCCAAGCATTGCCACTTACC
ATGAGGAATAAATGTTGCTTCATTGTAGCCATTTTGAGTCTAACCGAGACTCATCAAAGC
CTTCTGTCAGTACAGCCCAAGTTCCATACCATAAACGTTTGTTTTCATTCCAAGAAGTAG
TTCTGCATTTATCGAGATCTGGGGTTCTTAATTTGGAAGAATACATGCATGAGATGCAGT
AGGTCCTGAGACTGTAAGATATTAGGAGTATGTTATAGGGCATGTATAGATGTGGGCTTT
TTCAGGAGAAAAGTAACCATTGGTTTAAATATAATCATGAGTTCATTTGTAGCTTTAGAA
TTTTAAAACATTGACTCCAAACTGAATGGACTATTTCCTTGGAAATTCTGACTGAGTCCC
TGGAAGAGTAGTAATTCCAACAATTCCAGCCATTTGTTCAATTAATTTTCCCAACATTCT
TCTCCCAGTGCTGGGAATCACATTTCCTCTGTTCTGTGCAGAAGACAAAAAGGCAATCAT
AAAAGTTTGTTATATTTGTGGGGGTGCCTGGAGGAGGATTTTCCTCAACTTAATGGAGCC
ACTGTCCATAAAGTGGCTGTTATCCCTTCATATAATTGGTGAGATCAGCCTTCTCCTTGA
CTTGGCACCTAATTATGCTTCATGAGATCCTAGATTCCACCTGAGTCAATTGTGTCCAGA
GCCCCAAACCAGGATGGAGTTGTTTTCCCCAGATATGGGGTTCTATTCAGCCATAGATAA
TCTAGACAGAGGATTTCAGAATGAAAGGAAAAATGTGTGGAGATTAGTCCTAGTTCATTC
TGAGGGCCGACTAAGTGGCTCAGCCAGCTTCTTACTCCATCTGCAGTTCATACTGCCAAA
GAGCTCCCACTTCCAAATCCCCAGTGACTTTATGGAGAAGATTCTGCATTAAATTGTCTT
TCGAATGATGGGGAAGCAAGGCATAATATGCGATGATGAGGAGAAAGTAGACCAGTGAGG
TGATTGCAAGACTAACAAGGAGACTCAATGGGAAGTTTTTCTTTCTTTTAGATATTGCTT
TTGAAGTAGATGGTAAAATTTTTGTCATCCTTCTTGTATTTTTTGTACCCCAAGTTACAA
TTTTTCTTCTTCCTTGTAAATAATTTAAACAGTATTTATTTTTGTAAGGCATAACTAGAA
ACTAAAATATATTCTAAAAAATTCATTATTCTGAACAAAGTGATCAAATTAGAATACATA
TTTTTCAACAGTGGTAGAGCTTTTAATATATGTTTATTGAAAGTTATCTATAATACTTGC
ACCAGTGTTGAAAAAGTTAACATGTAGGCAAGAGCAATATGTTTGTCTCAAGGATTTTT
CCATGGTTTCCTCAGTGATGGTGTCCTGGAATTATTCAGGTGGTGACCATCACTGGTCTA
AGTTTGTGTGCAGGGTTTTCAGACGTGTTTTTGTGAAACTTGGTAGAACCATGGCTAATA
AAGAGGACAGTGTTGTCAGGGTCCATCTGCCCTCCATAGAAAATGTCTCTGGCTCATAA
AATGAGACTCCCTCAGGGACTAAATATGAACTGACAGCAGTAACTCTGATACAGAATAAT
CTAAATTGCATCAAATGGCCTTAATTCAGAGTTTGTTAGGCTTATCAGTATGTTGCTTTT
AATTGGGGTGGGAAAGTAGAGGGAGAGAAAGCAAGACATTTATTAAGCACCTCGTATGTG
CCAGGCACTATGCTAAGCACTTTACATAAGTTAGGATTAATCCCTGCAAGAATCCTATAA

FIGURE 85 CONTINUED

```
AGAATGTTACTAGCATTTACACTTCCCAAATGAAGGTACCAAAGCTCAAACGCAATGTTG
TGAAGCTGTTTCCTTCAGATTTAGGTTATGTGGGATGATGTGGGATTGAAGAGGAAAGAA
AGGTGGGATTATCCCCCTAGGAAGACTTTCAGGCCTGACTTCATAGGAATTCATCCATCT
TATCATGTGGAGTTTATCTCACCCTGCTGTTGCAGGATGCTATTTGCATGTGTCCCCAGG
TGATGTTTTTCTTTGGGGAGTAGGGGTTTGGCTTCCTCATTCATCCCTCTTGCTAAAAG
AGGAGATAGTTGATGTTGCATCTAAAGATGCTATAAGACAATGAAAGTTTGATGTTGTAC
ATACCTACAAGTACCATTTTTGTGCATGATTACACTCCACTGACATCTTCCAAGTACTAC
ATGTGATTGAATAAGAAACAAGAAAGTGACCACACCAAAGCCTCCCTGGCTGGTGTACAG
GGATCAGGTCCACAGTGGTGCAGATTCAACCACCACCCAGGGAGTGCTTGCAGACTCTGC
ATAGATGTTGCTGCATGCGTCCCATGTGCCTGTCAGAATGGCAGTGTTTAATTCTCTTGA
AAGAAAGTTATTTGCTCACTATCCCCAGCCTCAAGGAGCCAAGGAAGAGTCATTCACATG
GAAGGTCCGGGACTGGTCAGCCACTCTGACTTTTCTACCACATTAAATTCTCCATTACAT
CTCACTATTGGTAATGGCTTAAGTGTAAAGAGCCATGATGTGTATATTAAGCTATGTGCC
ACATATTTATTTTTAGACTCTCCACAGCATTCATGTCAATATGGGATTAATGCCTAAACT
TTGTAAATATTGTACAGTTTGTAAATCAATGAATAAAGGTTTTGAGTGTAAAAAAAAAAA
AAAAAA
```

FIGURE 86

```
></usr/seqdb2/sst/DNA/Dnaseqs.min/ss.DNA108725
><subunit 1 of 1, 171 aa, 1 stop
><MW: 19118, pI: 5.99, NX(S/T): 2
MEPGPALAWLLLLSLLADCLKAAQSRDFTVKDIIYLHPSTTPYPGGFKCFTCEKAADNYE
CNRWAPDIYCPRETRYCYTQHTMEVTGNSISVTKRCVPLEECLSTGCRDSEHEGHKVCTS
CCEGNICNLPLPRNETDATFATTSPINQTNGHPRCMSVIVSCLWLWLGLML
```

Important features of the protein:
Signal peptide:
1-22

Transmembrane domain:

None

N-glycosylation site.

134-138
     147-151

N-myristoylation site.

45-51
      87-93
     106-112
     124-130

Ly-6 / u-PAR domain protein 115-128

FIGURE 87

ATGGCCCGCGGGACAACATGGCTGCGCCCGCACTAGGGCTGGTGTGTGGACGTTGCCCTG
AGCTGGGTCTCGTCCTCTTGCTGCTGCTGCTCTCGCTGCTGTGTGGAGCGGCAGGGAGCC
AGGAGGCCGGGACCGGTGCGGGCGCGGGGTCCCTTGCGGGTTCTTGCGGCTGCGGCACGC
CCCAGCGGCCTGGCGCCCATGGCAATTCGGCAGCCGCTCACCGATACTCGCGGGAGGCTA
ACGCTCCGGCCCCGTACCCGGAGAGCGGCAACTCGCGCACTCAAAGATGGTCCCCATCC
CTGCTGGAGTATTTACAATGGGCACAGATGATCCTCAGATAAAGCAGGATGGGGAAGCAC
CTGCGAGGAGAGTTACTATTGATGCCTTTTACATGGATGCCTATGAAGTCAGTAATACTG
AATTTGAGAAGTTTGTGAACTCAACTGGCTATTTGACAGAGGCTGAGAAGTTTGGCGACT
CCTTTGTCTTTGAAGGCATGTTGAGTGAGCAAGTGAAGACCAATATTCAACAGGCAGTTG
CAGCTGCTCCCTGGTGGTTACCTGTGAAAGGCGCTAACTGGAGACACCCAGAAGGGCCTG
ACTCTACTATTCTGCACAGGCCGGATCATCCAGTTCTCCATGTGTCCTGGAATGATGCGG
TTGCCTACTGCACTTGGGCAGGGAAGCGGCTGCCCACGGAAGCTGAGTGGGAATACAGCT
GTCGAGGAGGCCTGCATAATAGACTTTTCCCCTGGGGCAACAAACTGCAGCCCAAAGGCC
AGCATTATGCCAACATTTGGCAGGGCGAGTTTCCGGTGACCAACACTGGTGAGGATGGCT
TCCAAGGAACTGCGCCTGTTGATGCCTTCCCTCCCAATGGTTATGGCTTATACAACATAG
TGGGGAACGCATGGGAATGGACTTCAGACTGGTGGACTGTTCATCATTCTGTTGAAGAAA
CGCTTAACCCAAAAGGTCCCCCTTCTGGGAAAGACCGAGTGAAGAAAGGTGGATCCTACA
TGTGCCATAGGTCCCAAGAGTACTATGATCCCTATTTTCAAGATGTGGCATCTGAGATGT
TGAGAAGACACACAGCCAGCAGGTGGAAGGCCTTCTCATCTCTAGAACCATGCTGCTCAA
TACGTAGGCATCAGCAATATGCAGCTATTGAACGTTTGACATGTGGCAAGTTTGAATTGA
GATGTGCTAGTTTAAGAAAAATAGATTGCCTCAACACCAACATTGCCTGTAGCTACTCCA
TGAGGCAACATGGACCCAGACTCCACTGTGTGGACTGACCTCCCAGAAGGATCCTCCTGT
CCCTGAAGGCCACTCTGCCTTCAGCTACAGGCCCCAGTGCTGATTGTGATACTTAACAAG
GGCTTTCAGATGTCTGAAACAAGAGTATAGCATAAAGTTAAGAATGCGGCTTCTGGAGAG
ACAGACTTGGTTTCAAATTCAGCTCTGTGACCTTGGGTGCACAGCAAAGTCTTCTTCTCC
CCCCGATGAAAGAATGGGAAGGACTCAGGAAGGCTCAACTTGCAAACTCCCAGTATCAA
GTGGCTGCCTTCAAAATCCAACCCTTCTCTTCCAGCTCATTTCCAGTATGTATTTTCAA
AGGCCATGTCATTTTTGAAGTGCCTGAGAAGAAAACAGAACTGCCAGCAGACTATGGGAC
AAACGACTAAATGCCCTCCAGACGTTCCAGAGTCCTCTGCCTCTCAGGCTTCAGTTCTTC
CTGAAGGAATCTGGAGCTGGAAAGCAGGAAGCAATTTGCTGTGGAATTTTTTCCATCACA
GACTCCAAGTTCCTCAGCCTTTGGACTCTTGAACTTACACCAGTGTTTTGGCAGGAGCGC
TCGGGCCTTTGGCCACAGACTGAAGGCTGCATTGTCAGCTTTCCTACTTTTGAGGTTTTG
GGACTCAGACTGATCCACCACTGGCTTCCTTGCTCTTCAACTTGAAGACGGCCTATCGTG
AGACTTTACCTCGTGATTATGTGAGTCAATTCTCCTAATAAACTCCCCTTCGTATGTACA
TATACCCTATTACTTCTGTCCCTTTAGAGAACCCTGACTAATACAGTAGAGATTGCCTGG
ACTTATTAATAATAATGACTCTGTTTAGTTAATGTAACAGACAGATAAAGACAAATGAGT
GACACCCATGCAATTAATATAATTTTGGTGGGGAGTGAGAGGAGTTGGTTCTCCACTCAC

FIGURE 87 CONTINUED

AGTGGAAAGTTTTAGCGTATACTGCTGCACATGACATGGGAGTATTTTGCACTTCCACTG
GAAAAAAGTAAGGGGAATAAAAACCCCTGGATTCTACTTGCTGACTTGAGAGTGACTAAA
GCGATTTATCTGAAGGTTCCCCAGGGTGGATTCATAGTGGACTCAGGCCAGATTCTCTGC
TGATGCTTTGAACTTATGTCCAGAGCATCATCTCCACCACAAAAGAGCTTGCCTGCTCTG
TGTCCTGGCCAAAGAGATGCACGTGCTCTATCACTGGGTTGTGGCTCTTGAGTAACTCCT
GGAATTACCCAGCTGGAATTTCTATTCCTTTGGACCACAAATTTCATATCTTCACCTGCT
GCCTATATCATGCTAAAAGATGGAAATGTCTCAACTAAACCATGTAGGTGGACTAGCCTC
ATTAACAAGATAAGCAATGGGCCATTTTCTCACTGGTTATTAACTATGTACATTATCTAT
GAAATAACATATCTGGTCATGGTTACTACTCTATTCTGTAGGGTGGAATAGAAAAAGGTA
GAGGATATATATTTCAGTTGCATTTTTAAAATTGTTTATTTTGTTTTTTAATTGACAAAT
AATATTAGGTTGGTGCAAAAGTAATTGCAGTTTTTGCCATTAAAGGTAGACAAGGCTGGG
CACGGTGGCTCAGCACGCTTGTAATCCCAGCACTTTGGGAGGCAGAGGCGGGCAGATCAC
AAGGTCAGGAGACCGAGACCATCCTGGCTAACACGGTGAAACCCCATCTCTACTAAAAAT
ACAAAAAATTAGCCGGGTGTGGTGGTGGGCACCTGTAGTCCCAGCTACTCGGGAGGCTGA
GGCAGGAGAATGGCGTGAACCTGGGAGGTGGAGCTTGTAGTGAGCTGCACCACTGCACTC
CAGCCTGGGCAACAGAGCAAGACCCCATATC

FIGURE 88

```
MAAPALGLVCGRCPELGLVLLLLLLSLLCGAAGSQEAGTGAGAGSLAGSCGCGTPQRPGA
HGNSAAAHRYSREANAPGPVPGERQLAHSKMVPIPAGVFTMGTDDPQIKQDGEAPARRVT
IDAFYMDAYEVSNTEFEKFVNSTGYLTEAEKFGDSFVFEGMLSEQVKTNIQQAVAAAPWW
LPVKGANWRHPEGPDSTILHRPDHPVLHVSWNDAVAYCTWAGKRLPTEAEWEYSCRGGLH
NRLFPWGNKLQPKGQHYANIWQGEFPVTNTGEDGFQGTAPVDAFPPNGYGLYNIVGNAWE
WTSDWWTVHHSVEETLNPKGPPSGKDRVKKGGSYMCHRSQEYYDPYFQDVASEMLRRHTA
SRWKAFSSLEPCCSIRRHQQYAAIERLTCGKFELRCASLRKIDCLNTNIACSYSMRQHGP
RLHCVD
```

| | |
|---|---|
| 141-145 | N-glycosylation site |
| 117-123 | cAMP- and cGMP-dependent protein kinase phosphorylation site |
| 356-360 | cAMP- and cGMP-dependent protein kinase phosphorylation site |
| 118-126 | Tyrosine kinase phosphorylation site |
| 7-13 | N-myristoylation site |
| 30-36 | N-myristoylation site |
| 33-39 | N-myristoylation site |
| 38-44 | N-myristoylation site |
| 40-46 | N-myristoylation site |
| 44-50 | N-myristoylation site |
| 48-54 | N-myristoylation site |
| 59-65 | N-myristoylation site |
| 62-68 | N-myristoylation site |
| 237-243 | N-myristoylation site |
| 254-260 | N-myristoylation site |
| 332-338 | N-myristoylation site |
| 221-225 | Amidation site |
| 40-51 | Prokaryotic membrane lipoprotein lipid attachment site |
| 42-53 | Prokaryotic membrane lipoprotein lipid attachment site |

FIGURE 89

TTCCAGTCAGAGTTAAGTTAAAACAGAAAAAAGGAAGATGGCAAGAATATTGTTACTTTTC
CTCCCGGGTCTTGTGGCTGTATGTGCTGTGCATGGAATATTTATGGACCGTCTAGCTTCCA
AGAAGCTCTGTGCAGATGATGAGTGTGTCTATACTATTTCTCTGGCTAGTGCTCAAGAAGA
TTATAATGCCCCGGACTGTAGATTCATTAACGTTAAAAAAGGGCAGCAGATCTATGTGTAC
TCAAAGCTGGTAAAAGAAAATGGAGCTGGAGAATTTTGGGCTGGCAGTGTTTATGGTGATG
GCCAGGACGAGATGGGAGTCGTGGGTTATTTCCCCAGGAACTTGGTCAAGGAACAGCGTGT
GTACCAGGAAGCTACCAAGGAAGTTCCCACCACGGATATTGACTTCTTCTGCGAGTAATAA
ATTAGTTAAAACTGCAAATAGAAAGAAAACACCAAAAATAAAGAAAAGAGCAAAAGTGGCC
AAAAAATGCATGTCTGTAATTTTGGACTGACGT

FIGURE 90

\> </usr/seqdb2/sst/DNA/Dnaseqs.min/ss.DNA143076
\> <subunit 1 of 1, 128 aa, 1 stop
\> <MW: 14332, pI: 4.83, NX(S/T): 0
MARILLLFLPGLVAVCAVHGIFMDRLASKKLCADDECVYTISLASAQEDYNAPDC
RFINVKKGQQIYVYSKLVKENGAGEFWAGSVYGDGQDEMGVVGYFPRNLVKEQR
VYQEATKEVPTTDIDFFCE

Important features of the protein:
Signal peptide:
Amino acids   1-14

N-myristoylation site:
Amino acids   84-90

FIGURE 91

CTGTCAGCTGAGGATCCAGCCGAAAGAGGAGCCAGGCACTCAGGCCACCTGAGTCTACTCA
CCTGGACAACTGGAATCTGGCACCAATTCTAAACCACTCAGCTTCTCCGAGCTCACACCCC
GGAGATCACCTGAGGACCCGAGCCATTGATGGACTCGGACGAGACCGGGTTCGAGCACTCA
GGACTGTGGGTTTCTGTGCTGGCTGGTCTGCTGGGAGCCTGCCAGGCACACCCCATCCCTG
ACTCCAGTCCTCTCCTGCAATTCGGGGGCCAAGTCCGGCAGCGGTACCTCTACACAGATGA
TGCCCAGCAGACAGAAGCCCACCTGGAGATCAGGGAGGATGGGACGGTGGGGGGCGCTGCT
GACCAGAGCCCCGAAAGTCTCCTGCAGCTGAAAGCCTTGAAGCCGGGAGTTATTCAAATCT
TGGGAGTCAAGACATCCAGGTTCCTGTGCCAGCGGCCAGATGGGGCCCTGTATGGATCGCT
CCACTTTGACCCTGAGGCCTGCAGCTTCCGGGAGCTGCTTCTTGAGGACGGATACAATGTT
TACCAGTCCGAAGCCCACGGCCTCCCGCTGCACCTGCCAGGGAACAAGTCCCCACACCGGG
ACCCTGCACCCCGAGGACCAGCTCGCTTCCTGCCACTACCAGGCCTGCCCCCGCACTCCC
GGAGCCACCCGGAATCCTGGCCCCCAGCCCCCGATGTGGGCTCCTCGGACCCTCTGAGC
ATGGTGGGACCTTCCCAGGGCCGAAGCCCCAGCTACGCTTCCTGAAGCCAGAGGCTGTTTA
CTATGACATCTCCTCTTTATTTATTAGGTTATTTATCTTATTTATTTTTTATTTTTCTTA
CTTGAGATAATAAAGAGTTCCAGAGGAGAAAAAAAAAAAAAAAAAAAAAAAAAAAAAAAA
AAAAAAAAAAAAAAAAAAAAAG

FIGURE 92

\> </usr/seqdb2/sst/DNA/Dnaseqs.min/ss.DNA144841
\> <subunit 1 of 1, 208 aa, 1 stop
\> <MW: 22187, pI: 5.08, NX(S/T): 1
MDSDETGFEHSGLWVSVLAGLLGACQAHPIPDS
SPLLQFGGQVRQRYLYTDDAQQTEAHLEIREDG
TVGGAADQSPESLLQLKALKPGVIQILGVKTSRF
LCQRPDGALYGSLHFDPEACSFRELLLEDGYNV
YQSEAHGLPLHLPGNKSPHRDPAPRGPARFLPLP
GLPPALPEPPGILAPQPPDVGSSDPLSMVGPSQG
RSPSYAS

Important features of the protein:
Signal peptide:
Amino acids   1-27

N-myristoylation sites:
Amino acids 12-18;20-26;23-29;66-72;94-100;107-113;168-174

Prokaryotic membrane lipoprotein lipid attachment site:
Amino acids   15-26

HBGF/FGF family proteins:
Amino acids   57-73;80-131

FIGURE 93

```
CATCTAAAGCCTCCTCAGCCTTCTGAGTCAGCCTGAAAGGAACAGGCCGAACTGCTGTAT
GGGCTCTACTGCCAGTGTGACCTCACCCTCTCCAGTCACCCCTCCTCAGTTCCAGCTATG
AGTTCCTGCAACTTCACACATGCCACCTTTGTGCTTATTGGTATCCCAGGATTAGAGAAA
GCCCATTTCTGGGTTGGCTTCCCCCTCCTTTCCATGTATGTAGTGGCAATGTTTGGAAAC
TGCATCGTGGTCTTCATCGTAAGGACGGAACGCAGCCTGCACGCTCCGATGTACCTCTTT
CTCTGCATGCTTGCAGCCATTGACCTGGCCTTATCCACATCCACCATGCCTAAGATCCTT
GCCCTTTTCTGGTTTGATTCCCGAGAGATTAGCTTTGAGGCCTGTCTTACCCAGATGTTC
TTTATTCATGCCCTCTCAGCCATTGAATCCACCATCCTGCTGGCCATGGCCTTTGACCGT
TATGTGGCCATCTGCCACCCACTGCGCCATGCTGCAGTGCTCAACAATACAGTAACAGCC
CAGATTGGCATCGTGGCTGTGGTCCGCGGATCCCTCTTTTTTTCCCACTGCCTCTGCTG
ATCAAGCGGCTGGCCTTCTGCCACTCCAATGTCCTCTCGCACTCCTATTGTGTCCACCAG
GATGTAATGAAGTTGGCCTATGCAGACACTTTGCCCAATGTGGTATATGGTCTTACTGCC
ATTCTGCTGGTCATGGGCGTGGACGTAATGTTCATCTCCTTGTCCTATTTCTGATAATA
CGAACGGTTCTGCAACTGCCTTCCAAGTCGAGCGGGCCAAGGCCTTTGGAACCTGTGTG
TCACACATTGGTGTGGTACTCGCCTTCTATGTGCCACTTATTGGCCTCTCAGTTGTACAC
CGCTTTGGAAACAGCCTTCATCCCATTGTGCGTGTTGTCATGGGTGACATCTACCTGCTG
CTGCCTCCTGTCATCAATCCCATCATCTATGGTGCCAAAACCAAACAGATCAGAACACGG
GTGCTGGCTATGTTCAAGATCAGCTGTGACAAGGACTTGCAGGCTGTGGGAGGCAAGTGA
CCCTTAACACTACACTTCTCCTTATCTTTATTGGCTTGATAAACATAATTATTTCTAACA
CTAGCTTATTTCCAGTTGCCCATAAGCACATCAGTACTTTTCTCTGGCTGGAATAGTAAA
CTAAAGTATGGTACATCTACCTAAAGGACTATTATGTGGAATAATACATACTAATGAAGT
ATTACATGATTTAAAGACTACAATAAAACCAAACATGCTTATAACATTAAGAAAAACAAT
AAAGATACATGATTGAAACCAAGTTGAAAAATAGCATATGCCTTGGAGGAAATGTGCTCA
AATTACTAATGATTTAGTGTTGTCCCTACTTTCTCTCTCTTTTTTCTTTCTTTTTTTTTT
ATTATGGTTAGCTGTCACATACAACTTTTTTTTTTTTTGAGATGGGGTCTCCAGCCTGGG
CAACAGAGCAAGACCCTGTCTCAAAGCATAAAATGGAATAACATATCAAATGAAACAGGG
AAAATGAAGCTGACAATTTATGGGAGCCA
```

FIGURE 94

```
><Mon Mar 19 16:52:31 PST 2001 DNA220432 [min]
></usr/seqdb2/sst/DNA/Dnaseqs.min/ss.DNA220432
><subunit 1 of 1, 320 aa, 1 stop
><MW: 35493, pI: 9.26, NX(S/T): 2
MSSCNFTHATFVLIGIPGLEKAHFWVGFPLLSMYVVAMFGNCIVVFIVRTERSLHAPMYL
FLCMLAAIDLALSTSTMPKILALFWFDSREISFEACLTQMFFIHALSAIESTILLAMAFD
RYVAICHPLRHAAVLNNTVTAQIGIVAVVRGSLFFFPLPLLIKRLAFCHSNVLSHSYCVH
QDVMKLAYADTLPNVVYGLTAILLVMGVDVMFISLSYFLIIRTVLQLPSKSERAKAFGTC
VSHIGVVLAFYVPLIGLSVVHRFGNSLHPIVRVVMGDIYLLLPPVINPIIYGAKTKQIRT
RVLAMFKISCDKDLQAVGGK
```

FIGURE 95

```
GGGAGGGCTCTGTGCCAGCCCCGATGAGGACGCTGCTGACCATCTTGACTGTGGGATCCC
TGGCTGCTCACGCCCTGAGGACCCCTCGGATCTGCTCCAGCACGTGAAATTCCAGTCCA
GCAACTTTGAAAACATCCTGACGTGGGACAGCGGGCCAGAGGGCACCCCAGACACGGTCT
ACAGCATCGAGTATAAGACGTACGGAGAGAGGGACTGGGTGGCAAAGAAGGGCTGTCAGC
GGATCACCCGGAAGTCCTGCAACCTGACGGTGGAGACGGGCAACCTCACGGAGCTCTACT
ATGCCAGGGTCACCGCTGTCAGTGCGGGAGGCCGGTCAGCCACCAAGATGACTGACAGGT
TCAGCTCTCTGCAGCACACTACCCTCAAGCCACCTGATGTGACCTGTATCTCCAAAGTGA
GATCGATTCAGATGATTGTTCATCCTACCCCACGCCAATCCGTGCAGGCGATGGCCACC
GGCTAACCCTGGAAGACATCTTCCATGACCTGTTCTACCACTTAGAGCTCCAGGTCAACC
GCACCTACCAAATGCACCTTGGAGGGAAGCAGAGAGAATATGAGTTCTTCGGCCTGACCC
CTGACACAGAGTTCCTTGGCACCATCATGATTTGCGTTCCCACCTGGGCCAAGGAGAGTG
CCCCCTACATGTGCCGAGTGAAGACACTGCCAGACCGGACATGGACCTACTCCTTCTCCG
GAGCCTTCCTGTTCTCCATGGGCTTCCTCGTCGCAGTACTCTGCTACCTGAGCTACAGAT
ATGTCACCAAGCCGCCTGCACCTCCCAACTCCCTGAACGTCCAGCGAGTCCTGACTTTCC
AGCCGCTGCGCTTCATCCAGGAGCACGTCCTGATCCCTGTCTTTGACCTCAGCGGCCCCA
GCAGTCTGGCCCAGCCTGTCCAGTACTCCCAGATCAGGGTGTCTGGACCCAGGGAGCCCG
CAGGAGCTCCACAGCGGCATAGCCTGTCCGAGATCACCTACTTAGGGCAGCCAGACATCT
CCATCCTCCAGCCCTCCAACGTGCCACCTCCCCAGATCCTCTCCCCACTGTCCTATGCCC
CAAACGCTGCCCCTGAGGTCGGGCCCCATCCTATGCACCTCAGGTGACCCCGAAGCTC
AATTCCCATTCTACGCCCCACAGGCCATCTCTAAGGTCCAGCCTTCCTCCTATGCCCCTC
AAGCCACTCCGGACAGCTGGCCTCCCTCCTATGGGGTATGCATGGAAGGTTCTGGCAAAG
ACTCCCCCACTGGGACACTTTCTAGTCCTAAACACCTTAGGCCTAAAGGTCAGCTTCAGA
AAGAGCCACCAGCTGGAAGCTGCATGTTAGGTGGCCTTTCTCTGCAGGAGGTGACCTCCT
TGGCTATGGAGGAATCCCAAGAAGCAAAATCATTGCACCAGCCCCTGGGGATTTGCACAG
ACAGAACATCTGACCCAAATGTGCTACACAGTGGGGAGGAAGGGACACCACAGTACCTAA
AGGGCCAGCTCCCCCTCCTCTCCTCAGTCCAGATCGAGGGCCACCCCATGTCCCTCCCTT
TGCAACCTCCTTCCGGTCCATGTTCCCCCTCGGACCAAGGTCCAAGTCCCTGGGGCCTGC
TGGAGTCCCTTGTGTGTCCCAAGGATGAAGCCAAGAGCCCAGCCCCTGAGACCTCAGACC
TGGAGCAGCCCACAGAACTGGATTCTCTTTTCAGAGGCCTGGCCCTGACTGTGCAGTGGG
AGTCCTGAGGGGAATGGGAAAGGCTTGGTGCTTCCTCCCTGTCCCTACCCAGTGTCACAT
CCTTGGCTGTCAATCCCATGCCTGCCCATGCCACACACTCTGCGATCTGGCCTCAGACGG
GTGCCCTTGAGAGAAGCAGAGGGAGTGGCATGCAGGGCCCCTGCCATGGGTGCGCTCCTC
ACCGGAACAAAGCAGCATGATAAGGACTGCAGCGGGGAGCTCTGGGGAGCAGCTTGTGT
AGACAAGCGCGTGCTCGCTGAGCCCTGCAAGGCAGAAATGACAGTGCAAGGAGGAAATGC
AGGGAAACTCCCGAGGTCCAGAGCCCCACCTCCTAACACCATGGATTCAAAGTGCTCAGG
GAATTTGCCTCTCCTTGCCCCATTCCTGGCCAGTTTCACAATCTAGCTCGACAGAGCATG
AGGCCCCTGCCTCTTCTGTCATTGTTCAAAGGTGGGAAGAGAGCCTGGAAAAGAACCAGG
CCTGGAAAAGAACCAGAAGGAGGCTGGGCAGAACCAGAACAACCTGCACTTCTGCCAAGG
CCAGGGCCAGCAGGACGGCAGGACTCTAGGGAGGGGTGTGGCCTGCAGCTCATTCCCAGC
CAGGGCAACTGCCTGACGTTGCACGATTTCAGCTTCATTCCTCTGATAGAACAAAGCGAA
ATGCAGGTCCACCAGGGAGGGAGACACACAAGCCTTTTCTGCAGGCAGGAGTTTCAGACC
CTATCCTGAGAATGGGGTTTGAAAGGAAGGTGAGGGCTGTGGCCCCTGGACGGGTACAAT
AACACACTGTACTGATGTCACAACTTTGCAAGCTCTGCCTTGGGTTCAGCCCATCTGGGC
TCAAATTCCAGCCTCACCACTCACAAGCTGTGTGACTTCAAACAAATGAAATCAGTGCCC
AGAACCTCGGTTTCCTCATCTGTAATGTGGGGATCATAACACCTACCTCATGGAGTTGTG
GTGAAGATGAAATGAAGTCATGTCTTTAAAGTGCTTAATAGTGCCTGGTACATGGGCAGT
GCCCAATAAACGGTAGCTATTTAAAAAAAAAAAAA
```

FIGURE 96

```
><Fri Jun  9 10:59:57 2000 DNA165608 [min]
></usr/seqdb2/sst/DNA/Dnaseqs.min/ss.DNA165608
><subunit 1 of 1, 574 aa, 1 stop
><MW: 62977, pI: 6.02, NX(S/T): 3
MRTLLTILTVGSLAAHAPEDPSDLLQHVKFQSSNFENILTWDSGPEGTPDTVYSIEYKTY
GERDWVAKKGCQRITRKSCNLTVETGNLTELYYARVTAVSAGGRSATKMTDRFSSLQHTT
LKPPDVTCISKVRSIQMIVHPTPTPIRAGDGHRLTLEDIFHDLFYHLELQVNRTYQMHLG
GKQREYEFFGLTPDTEFLGTIMICVPTWAKESAPYMCRVKTLPDRTWTYSFSGAFLFSMG
FLVAVLCYLSYRYVTKPPAPPNSLNVQRVLTFQPLRFIQEHVLIPVFDLSGPSSLAQPVQ
YSQIRVSGPREPAGAPQRHSLSEITYLGQPDISILQPSNVPPPQILSPLSYAPNAAPEVG
PPSYAPQVTPEAQFPFYAPQAISKVQPSSYAPQATPDSWPPSYGVCMEGSGKDSPTGTLS
SPKHLRPKGQLQKEPPAGSCMLGGLSLQEVTSLAMEESQEAKSLHQPLGICTDRTSDPNV
LHSGEEGTPQYLKGQLPLLSSVQIEGHPMSLPLQPPSGPCSPSDQGPSPWGLLESLVCPK
DEAKSPAPETSDLEQPTELDSLFRGLALTVQWES
```

FIGURE 97

GCCAACACTGGCCAAAGAGCTGCGAGCTTGAGCGGCGCGAGGAGATGCTAGAGGGCGCAG
CGCCGCCAGCACCATGCGCCCCCGCCCGCGCTGGCCCTGGCCGGGCTCTGCCTGCTGGC
GCTGCCCGCCGCCGCCGCCTCCTACTTCGGCCTGACCGGGCGGGAAGTCCTGACGCCCTT
CCCAGGATTGGGCACTGCGGCAGCCCCGGCACAGGGCGGGGCCCACCTGAAGCAGTGTGA
CCTGCTGAAGCTGTCCCGGCGGCAGAAGCAGCTCTGCCGGAGGGAGCCCGGCCTGGCTGA
GACCCTGAGGGATGCTGCGCACCTCGGCCTGCTTGAGTGCCAGTTTCAGTTCCGGCATGA
GCGCTGGAACTGTAGCCTGGAGGGCAGGATGGGCCTGCTCAAGAGAGGCTTCAAAGAGAC
AGCTTTCCTGTACGCGGTGTCCTCTGCCGCCCTCACCCACACCCTGGCCCGGGCCTGCAG
CGCTGGGCGCATGGAGCGCTGCACCTGTGATGACTCTCCGGGGCTGGAGAGCCGGCAGGC
CTGGCAGTGGGGCGTGTGCGGTGACAACCTCAAGTACAGCACCAAGTTTCTGAGCAACTT
CCTGGGGTCCAAGAGAGGAAACAAGGACCTGCGGGCACGGGCAGACGCCCACAATACCCA
CGTGGGCATCAAGGCTGTGAAGAGTGGCCTCAGGACCACGTGTAAGTGCCATGGCGTATC
AGGCTCCTGTGCCGTGCGCACCTGCTGGAAGCAGCTCTCCCCGTTCCGTGAGACGGGCCA
GGTGCTGAAACTGCGCTATGACTCGGCTGTCAAGGTGTCCAGTGCCACCAATGAGGCCTT
GGGCCGCCTAGAGCTGTGGGCCCCTGCCAGGCAGGGCAGCCTCACCAAAGGCCTGGCCCC
AAGGTCTGGGGACCTGGTGTACATGGAGGACTCACCCAGCTTCTGCCGGCCCAGCAAGTA
CTCACCTGGCACAGCAGGTAGGGTGTGCTCCCGGGAGGCCAGCTGCAGCAGCCTGTGCTG
CGGGCGGGGCTATGACACCCAGAGCCGCCTGGTGGCCTTCTCCTGCCACTGCCAGGTGCA
GTGGTGCTGCTACGTGGAGTGCCAGCAATGTGTGCAGGAGGAGCTTGTGTACACCTGCAA
GCACTAGGCCTACTGCCCAGCAAGCCAGTCTGGCACTGCCAGGACCTCCTGTGGCACCCT
TCAAGCTGCCCAGCCGGCCCTCTGGGCAGACTGTCATCACATGCATGCATAAACCGGCAT
GTGTGCCAATGCACACGAGTGTGCCACTCACCACCATTCCTTGGCCAGCCTTTTGCCTCC
CTCGATACTCAACAAAGAGAAGCAAAGCCTCCTCCCTTAACCCAAGCATCCCCAACCTTG
TTGAGGACTTGGAGAGAA

FIGURE 98

MRPPPALALAGLCLLALPAAAASYFGLTGREVLTPFPGLGTAAAPAQGGAHLKQCDLLKL
SRRQKQLCRREPGLAETLRDAAHLGLLECQFQFRHERWNCSLEGRMGLLKRGFKETAFLY
AVSSAALTHTLARACSAGRMERCTCDDSPGLESRQAWQWGVCGDNLKYSTKFLSNFLGSK
RGNKDLRARADAHNTHVGIKAVKSGLRTTCKCHGVSGSCAVRTCWKQLSPFRETGQVLKL
RYDSAVKVSSATNEALGRLELWAPARQGSLTKGLAPRSGDLVYMEDSPSFCRPSKYSPGT
AGRVCSREASCSSLCCGRGYDTQSRLVAFSCHCQVQWCCYVECQQCVQEELVYTCKH

Signal peptide:
1-22
Transmembrane domain:
None

N-glycosylation site.

99-103

Tyrosine kinase phosphorylation site.
    277-283

N-myristoylation site.
    38-43
    73-78
    85-90
    178-183
    205-210
    214-219

Wnt-1 family proteins.
    64-102
    104-146
    171-213
    157-181
    187-239
    310-355 wnt family of developmental signaling proteins
    54-356

FIGURE 99

TCGCCCTTCGAGCAAATGGGTCTGGCCATGGAGCACGGAGGGTCCTACGCTCGGGCGGGG
GGCAGCTCTCGGGGCTGCTGGTATTACCTGCGCTACTTCTTCCTCTTCGTCTCCCTCATC
CAATTCCTCATCATCCTGGGGCTCGTGCTCTTCATGGTCTATGGCAACGTGCACGTGAGC
ACAGAGTCCAACCTGCAGGCCACCGAGCGCCGAGCCGAGGGCCTATACAGTCAGCTCCTA
GGGCTCACGGCCTCCCAGTCCAACTTGACCAAGGAGCTCAACTTCACCACCCGCGCCAAG
GATGCCATCATGCAGATGTGGCTGAATGCTCGCCGCGACCTGGACCGCATCAATGCCAGC
TTCCGCCAGTGCCAGGGTGACCGGGTCATCTACACGAACAATCAGAGGTACATGGCTGCC
ATCATCTTGAGTGAGAAGCAATGCAGAGATCAATTCAAGGACATGAACAAGAGCTGCGAT
GCCTTGCTCTTCATGCTGAATCAGAAGGTGAAGACGCTGGAGGTGGAGATAGCCAAGGAG
AAGACCATTTGCACTAAGGATAAGGAAAGCGTGCTGCTGAACAAACGCGTGGCGGAGGAA
CAGCTGGTTGAATGCGTGAAAACCCGGGAGCTGCAGCACCAAGAGCGCCAGCTGGCCAAG
GAGCAACTGCAAAAGGTGCAAGCCCTCTGCCTGCCCCTGGACAAGGACAAGTTTGAGATG
GACCTTCGTAACCTGTGGAGGGACTCCATTATCCCACGCAGCCTGGACAACCTGGGTTAC
AACCTCTACCATCCCCTGGGCTCGGAATTGGCCTCCATCCGCAGAGCCTGCGACCACATG
CCCAGCCTCATGAGCTCCAAGGTGGAGGAGCTGGCCCGGAGCCTCCGGGCGGATATCGAA
CGCGTGGCCCGCGAGAACTCAGACCTCCAACGCCAGAAGCTGGAAGCCCAGCAGGGCCTG
CGGGCCAGTCAGGAGGCGAAACAGAAGGTGGAGAAGGAGGCTCAGGCCCGGGAGGCCAAG
CTCCAAGCTGAATGCTCCCGGCAGACCCAGCTAGCGCTGGAGGAGAAGGCGGTGCTGCGG
AAGGAACGAGACAACCTGGCCAAGGAGCTGGAAGAGAAGAAGAGGGAGGCGGAGCAGCTC
AGGATGGAGCTGGCCATCAGAAACTCAGCCCTGGACACCTGCATCAAGACCAAGTCGCAG
CCGATGATGCCAGTGTCAAGGCCCATGGGCCCTGTCCCCAACCCCCAGCCCATCGACCCA
GCTAGCCTGGAGGAGTTCAAGAGGAAGATCCTGGAGTCCCAGAGGCCCCTGCAGGCATC
CCTGTAGCCCCATCCAGTGGCTGAGAAGGGCG

FIGURE 100

```
><Mon Nov 12 14:54:32 PST 2001 DNA269238 [min]
></usr/seqdb2/sst/DNA/Dnaseqs.min/ss.DNA269238
><subunit 1 of 1, 442 aa, 1 stop
><MW: 50594, pI: 9.17, NX(S/T): 4
MGLAMEHGGSYARAGGSSRGCWYYLRYFFLFVSLIQFLIILGLVLFMVYGNVHVSTESNL
QATERRAEGLYSQLLGLTASQSNLTKELNFTTRAKDAIMQMWLNARRDLDRINASFRQCQ
GDRVIYTNNQRYMAAIILSEKQCRDQFKDMNKSCDALLFMLNQKVKTLEVEIAKEKTICT
KDKESVLLNKRVAEEQLVECVKTRELQHQERQLAKEQLQKVQALCLPLDKDKFEMDLRNL
WRDSIIPRSLDNLGYNLYHPLGSELASIRRACDHMPSLMSSKVEELARSLRADIERVARE
NSDLQRQKLEAQQGLRASQEAKQKVEKEAQAREAKLQAECSRQTQLALEEKAVLRKERDN
LAKELEEKKREAEQLRMELAIRNSALDTCIKTKSQPMMPVSRPMGPVPNPQPIDPASLEE
FKRKILESQRPPAGIPVAPSSG
```

FIGURE 101

AGAAACCGTTGATGGGACTGAGAAACCAGAGTTAAAACCTCTTTGGAGCTTCTGAGGACT
CAGCTGGAACCAACGGGCACAGTTGGCAACACCATCATGACATCACAACCTGTTCCCAAT
GAGACCATCATAGTGCTCCCATCAAATGTCATCAACTTCTCCCAAGCAGAGAAACCCGAA
CCCACCAACCAGGGGCAGGATAGCCTGAAGAAACATCTACACGCAGAAATCAAAGTTATT
GGGACTATCCAGATCTTGTGTGGCATGATGGTATTGAGCTTGGGGATCATTTTGGCATCT
GCTTCCTTCTCTCCAAATTTTACCCAAGTGACTTCTACACTGTTGAACTCTGCTTACCCA
TTCATAGGACCCTTTTTTTTTATCATCTCTGGCTCTCTATCAATCGCCACAGAGAAAAGG
TTGACCAAGCTTTTGGTGCATAGCAGCCTGGTTGGAAGCATTCTGAGTGCTCTGTCTGCC
CTGGTGGGTTTCATTATCCTGTCTGTCAAACAGGCCACCTTAAATCCTGCCTCACTGCAG
TGTGAGTTGGACAAAAATAATATACCAACAAGAAGTTATGTTTCTTACTTTTATCATGAT
TCACTTTATACCACGGACTGCTATACAGCCAAAGCCAGTCTGGCTGGATCTCTCTCTCTG
ATGCTGATTTGCACTCTGCTGGAATTCTGCCTAGCTGTGCTCACTGCTGTGCTGCGGTGG
AAACAGGCTTACTCTGACTTCCCTGGGGTGAGTGTGCTGGCCGGCTTCACTTAACCTTGC
CTAGTGTATCTTATCCCTGCACTGTGTTGAGTATGTCACCAAGAGTGGTAGAAGGAACAA
CCAGCCAATCACGAGATCACATGGGAGGGCATTTGCATTGTGATGGAAGACAGAGAAGAA
AAGCAGATGGCAATTGAGTAGCTGATAAGCTGAAAATTCACTGGATATGAAAATAGTTAA
TCATGAGAAATCAACTGATTCAATCTTCCTATTTTGTCAGCGAAGGGAATGAGACTCTGG
GAAGTTAAATGACTGGCCTGGCATTATGCTATGAGTTTGTGCCTTTGCTGAGGACACTAG
AACCTGGCTTGCCTCCCTTATAAGCAGAAACAATTTCTGCCACAACCACTAGTCTCTTTA
ATAGTATTGACTTGGTAAAGGGCATTTACACACGTAACTGGATCCAGTGAATGTCTTATG
CTCTGCATTTGCCCCTGGTGATCTTAAAATTCGTTTGCCTTTTTAAAGCTATATTAAAAA
TGTATTGTTGAATCAAAAAAAAAAAAAAA

FIGURE 102

```
leu> getseq ssp.DNA228002
><DNA228002 [min]
></usr/seqdb2/sst/DNA/Dnaseqs.min/ss.DNA228002
><subunit 1 of 1, 225 aa, 1 stop
><MW: 24317, pI: 8.07, NX(S/T): 3
MTSQPVPNETIIVLPSNVINFSQAEKPEPTNQGQDSLKKHLHAEIKVIGTIQILCGMMVL
SLGIILASASFSPNFTQVTSTLLNSAYPFIGPFFFIISGSLSIATEKRLTKLLVHSSLVG
SILSALSALVGFIILSVKQATLNPASLQCELDKNNIPTRSYVSYFYHDSLYTTDCYTAKA
SLAGSLSLMLICTLLEFCLAVLTAVLRWKQAYSDFPGVSVLAGFT
```

FIGURE 103

```
GAGAGGGTCCTTCAGGGTCTGCTTATGCCCTTGTTCAAGAACACCAGTGTCAGCTCTCTG
TACTCTGGTTGCAGACTGACCTTGCTCAGGCCTGAGAAGGATGGGGCAGCCACCAGAGTG
GATGCTGTCTGCACCCATCGTCCTGACCCCAAAAGCCCTGGACTGGACAGAGAGCGGCTG
TACTGGAAGCTGAGCCAGCTGACCCACGGCATCACTGAGCTGGGCCCCTACACCCTGGAC
AGGCACAGTCTCTATGTCAATGGTTTCACCCATCAGAGCTCTATGACGACCACCAGAACT
CCTGATACCTCCACAATGCACCTGGCAACCTCGAGAACTCCAGCCTCCCTGTCTGGACCT
ACGACCGCCAGCCCTCTCCTGGTGCTATTCACAATTAACTTCACCATCACTAACCTGCGG
TATGAGGAGAACATGCATCACCCTGGCTCTAGAAAGTTTAACACCACGGAGAGAGTCCTT
CAGGGTCTGCTCAGGCCTGTGTTCAAGAACACCAGTGTTGGCCCTCTGTACTCTGGCTGC
AGACTGACCTTGCTCAGGCCCAAGAAGGATGGGGCAGCCACCAAAGTGGATGCCATCTGC
ACCTACCGCCCTGATCCCAAAAGCCCTGGACTGGACAGAGAGCAGCTATACTGGGAGCTG
AGCCAGCTAACCCACAGCATCACTGAGCTGGGCCCCTACACCCTGGACAGGGACAGTCTC
TATGTCAATGGTTTCACACAGCGGAGCTCTGTGCCCACCACTAGCATTCCTGGGACCCCC
ACAGTGGACCTGGGAACATCTGGGACTCCAGTTTCTAAACCTGGTCCCTCGGCTGCCAGC
CCTCTCCTGGTGCTATTCACTCTCAACTTCACCATCACCAACCTGCGGTATGAGGAGAAC
ATGCAGCACCCTGGCTCCAGGAAGTTCAACACCACGGAGAGGGTCCTTCAGGGCCTGCTC
AGGTCCCTGTTCAAGAGCACCAGTGTTGGCCCTCTGTACTCTGGCTGCAGACTGACTTTG
CTCAGGCCTGAAAAGGATGGGACAGCCACTGGAGTGGATGCCATCTGCACCCACCACCCT
GACCCCAAAAGCCCTAGGCTGGACAGAGCAGCTGTATTGGGAGCTGAGCCAGCTGACC
CACAATATCACTGAGCTGGGCCACTATGCCCTGGACAACGACAGCCTCTTTGTCAATGGT
TTCACTCATCGGAGCTCTGTGTCCACCACCAGCACTCCTGGGACCCCCACAGTGTATCTG
GGAGCATCTAAGACTCCAGCCTCGATATTTGGCCCTTCAGCTGCCAGCCATCTCCTGATA
CTATTCACCCTCAACTTCACCATCACTAACCTGCGGTATGAGGAGAACATGTGGCCTGGC
TCCAGGAAGTTCAACACTACAGAGAGGGTCCTTCAGGGCCTGCTAAGGCCCTTGTTCAAG
AACACCAGTGTTGGCCCTCTGTACTCTGGCTCCAGGCTGACCTTGCTCAGGCCAGAGAAA
GATGGGGAAGCCACCGGAGTGGATGCCATCTGCACCCACCGCCCTGACCCCACAGGCCCT
GGGCTGGACAGAGAGCAGCTGTATTGGAGCTGAGCCAGCTGACCCACAGCATCACTGAG
CTGGGCCCCTACACACTGGACAGGGACAGTCTCTATGTCAATGGTTTCACCCATCGGAGC
TCTGTACCCACCACCAGCACCGGGGTGGTCAGCGAGGAGCCATTCACACTGAACTTCACC
ATCAACAACCTGCGCTACATGGCGGACATGGGCCAACCCGGCTCCCTCAAGTTCAACATC
ACAGACAACGTCATGAAGCACCTGCTCAGTCCTTTGTTCCAGAGGAGCAGCCTGGGTGCA
CGGTACACAGGCTGCAGGGTCATCGCACTAAGGTCTGTGAAGAACGGTGCTGAGACACGG
GTGGACCTCCTCTGCACCTACCTGCAGCCCCTCAGCGGCCCAGGTCTGCCTATCAAGCAG
GTGTTCCATGAGCTGAGCCAGCAGACCCATGGCATCACCCGGCTGGGCCCCTACTCTCTG
GACAAAGACAGCCTCTACCTTAACGGTTACAATGAACCTGGTCTAGATGAGCCTCCTACA
ACTCCCAAGCCAGCCACCACATTCCTGCCTCCTCTGTCAGAAGCCACAACAGCCATGGGG
TACCACCTGAAGACCCTCACACTCAACTTCACCATCTCCAATCTCCAGTATTCACCAGAT
ATGGGCAAGGGCTCAGCTACATTCAACTCCACCGAGGGGGTCCTTCAGCACCTGCTCAGA
CCCTTGTTCCAGAAGAGCAGCATGGGCCCCTTCTACTTGGGTTGCCAACTGATCTCCCTC
AGGCCTGAGAAGGATGGGGCAGCCACTGGTGTGGACACCACCTGCACCTACCACCCTGAC
CCTGTGGGCCCCGGGCTGGACATACAGCAGCTTTACTGGGAGCTGAGTCAGCTGACCCAT
GGTGTCACCCAACTGGGCTTCTATGTCCTGGACAGGGATAGCCTCTTCATCAATGGCTAT
GCACCCCAGAATTTATCAATCCGGGGCGAGTACCAGATAAATTTCCACATTGTCAACTGG
AACCTCAGTAATCCAGACCCCACATCCTCAGAGTACATCACCCTGCTGAGGGACATCCAG
GACAAGGTCACCACACTCTACAAAGGCAGTCAACTACATGACACATTCCGCTTCTGCCTG
GTCACCAACTTGACGATGGACTCCGTGTTGGTCACTGTCAAGGCATTGTTCTCCTCCAAT
TTGGACCCCAGCCTGGTGGAGCAAGTCTTTCTAGATAAGACCCTGAATGCCTCATTCCAT
TGGCTGGGCTCCACCTACCAGTTGGTGGACATCCATGTGACAGAAATGGAGTCATCAGTT
TATCAACCAACAAGCAGCTCCAGCACCCAGCACTTCTACCCGAATTTCACCATCACCAAC
CTACCATATTCCCAGGACAAAGCCCAGCCAGGCACCACCAATTACCAGAGGAACAAAAGG
AATATTGAGGATGCGCTCAACCAACTCTTCCGAAACAGCAGCATCAAGAGTTATTTTCT
GACTGTCAAGTTTCAACATTCAGGTCTGTCCCAACAGGCACCACACCGGGGTGGACTCC
CTGTGTAACTTCTCGCCACTGGCTCGGAGAGTAGACAGAGTTGCCATCTATGAGGAATTT
CTGCGGATGACCCGGAATGGTACCCAGCTGCAGAACTTCACCCTGGACAGGAGCAGTGTC
CTTGTGGATGGGTATTCTCCCAACAGAAATGAGCCCTTAACTGGGAATTCTGACCTTCCC
TTCTGGGCTGTCATCTTCATCGGCTTGGCAGGACTCCTGGGACTCATCACATGCCTGATC
TGCGGTGTCCTGGTGACCACCCGCCGGCGGAAGAAGGAAGGAGAATACAACGTCCAGCAA
CAGTGCCCAGGCTACTACCAGTCACACCTAGACCTGGAGGATCTGCAATGACTGGAACTT
GCCGGTGCCTGGGGTGCCTTTCCCCCAGCCAGGGTCCAAAGAAGCTTGGCTGGGGCAGAA
ATAAACCATATTGGTCG
```

FIGURE 104

```
><Fri Aug 17 16:59:52 PDT 2001 DNA228199 [min]
></usr/seqdb2/sst/DNA/Dnaseqs.min/ss.DNA228199
><subunit 1 of 1, 1148 aa, 1 stop
><MW: 127958, pI: 8.04, NX(S/T): 24
MPLFKNTSVSSLYSGCRLTLLRPEKDGAATRVDAVCTHRPDPKSPGLDRERLYWKLSQLT
HGITELGPYTLDRHSLYVNGFTHQSSMTTTRTPDTSTMHLATSRTPASLSGPTTASPLLV
LFTINFTITNLRYEENMHHPGSRKFNTTERVLQGLLRPVFKNTSVGPLYSGCRLTLLRPK
KDGAATKVDAICTYRPDPKSPGLDREQLYWELSQLTHSITELGPYTLDRDSLYVNGFTQR
SSVPTTSIPGTPTVDLGTSGTPVSKPGPSAASPLLVLFTLNFTITNLRYEENMQHPGSRK
FNTTERVLQGLLRSLFKSTSVGPLYSGCRLTLLRPEKDGTATGVDAICTHHPDPKSPRLD
REQLYWELSQLTHNITELGHYALDNDSLFVNGFTHRSSVSTTSTPGTPTVYLGASKTPAS
IFGPSAASHLLILFTLNFTITNLRYEENMWPGSRKFNTTERVLQGLLRPLFKNTSVGPLY
SGSRLTLLRPEKDGEATGVDAICTHRPDPTGPGLDREQLYLELSQLTHSITELGPYTLDR
DSLYVNGFTHRSSVPTTSTGVVSEEPFTLNFTINNLRYMADMGQPGSLKFNITDNVMKHL
LSPLFQRSSLGARYTGCRVIALRSVKNGAETRVDLLCTYLQPLSGPGLPIKQVFHELSQQ
THGITRLGPYSLDKDSLYLNGYNEPGLDEPPTTPKPATTFLPPLSEATTAMGYHLKTLTL
NFTISNLQYSPDMGKGSATFNSTEGVLQHLLRPLFQKSSMGPFYLGCQLISLRPEKDGAA
TGVDTTCTYHPDPVGPGLDIQQLYWELSQLTHGVTQLGFYVLDRDSLFINGYAPQNLSIR
GEYQINFHIVNWNLSNPDPTSSEYITLLRDIQDKVTTLYKGSQLHDTFRFCLVTNLTMDS
VLVTVKALFSSNLDPSLVEQVFLDKTLNASFHWLGSTYQLVDIHVTEMESSVYQPTSSSS
TQHFYPNFTITNLPYSQDKAQPGTTNYQRNKRNIEDALNQLFRNSSIKSYFSDCQVSTFR
SVPNRHHTGVDSLCNFSPLARRVDRVAIYEEFLRMTRNGTQLQNFTLDRSSVLVDGYSPN
RNEPLTGNSDLPFWAVIFIGLAGLLGLITCLICGVLVTTRRRKKEGEYNVQQQCPGYYQS
HLDLEDLQ
```

FIGURE 105

```
GTTGGCATTCGGTGGTCCTGGCAGTTAGCTGAGCACGCCCTCTGAGCCGCTCGGTGGACA
CCAGGCACTCTAGTAGGCCTGGCCTACCCAGAAACAGCAGGAGAGAGAAGAAACAGGCCA
GCTGTGAGAAGCCAAGGACACCGAGTCAGTCATGGCACCTAAGGCGGCAAAGGGGGCCAA
GCCAGAGCCAGCACCAGCTCCACCTCCACCCGGGGCCAAACCCGAGGAAGACAAGAAGGA
CGGTAAGGAGCCATCGGACAAACCTCAAAAGGCGGTGCAGGACCATAAGGAGCCATCGGA
CAAACCTCAAAAGGCGGTGCAGCCCAAGCACGAAGTGGGCACGAGGAGGGGTGTCGCCG
CTACCGGTGGGAATTAAAAGACAGCAATAAAGAGTTCTGGCTCTTGGGGCACGCTGAGAT
CAAGATTCGGAGTTTGGGCTGCCTAATAGCTGCAATGATACTGTTGTCCTCACTCACCGT
GCACCCCATCTTGAGGCTTATCATCACCATGGAGATATCCTTCTTCAGCTTCTTCATCTT
ACTGTACAGCTTTGCCATTCATAGATACATACCCTTCATCCTGTGGCCCATTTCTGACCT
CTTCAACGACCTGATTGCTTGTGCGTTCCTTGTGGGAGCCGTGGTCTTTGCTGTGAGAAG
TCGGCGATCCATGAATCTCCACTACTTACTTGCTGTGATCCTTATTGGTGCGGCTGGAGT
TTTTGCTTTTATCGATGTGTGTCTTCAAAGAAACCACTTCAGAGGCAAGAAGGCCAAAAA
GCATATGCTGGTTCCTCCTCCAGGAAAGGAAAAAGGACCCCAGCAGGGCAAGGGACCAGA
ACCCGCCAAGCCACCAGAACCTGGCAAGCCACCAGGGCAGCAAAGGGAAAGAAATGACT
TGGAGGAGGCTCCTGGTGTCTGAAACGGCAGTGTATTTTACAGCAATATGTTTCCACTCT
CTTCCTTGTCTTCTTTCTGGAATGGTTTTCTTTTCCATTTTCATTACCACCTTTGCTTGG
AAAAGAATGGATTAATGGATTCTAAAAGCCTAAAAAAAAAAAAAAAAAAAA
```

FIGURE 106

```
><Sequence Version 1, Thu Jul 10 07:39:37 2003 DNA329632 [min]
></usr/seqdb2/sst/DNA/Dnaseqs.min/ss.DNA329632
><subunit 1 of 1, 248 aa, 1 stop
><MW: 27496, pI: 10.24, NX(S/T): 0
MAPKAAKGAKPEPAPAPPPPGAKPEEDKKDGKEPSDKPQKAVQDHKEPSDKPQKAVQPKH
EVGTRRGCRRYRWELKDSNKEFWLLGHAEIKIRSLGCLIAAMILLSSLTVHPILRLIITM
EISFFSFFILLYSFAIHRYIPFILWPISDLFNDLIACAFLVGAVVFAVRSRRSMNLHYLL
AVILIGAAGVFAFIDVCLQRNHFRGKKAKKHMLVPPPGKEKGPQQGKGPEPAKPPEPGKP
PGPAKGKK
```

US 8,207,396 B2

GENE DISRUPTIONS, COMPOSITIONS AND METHODS RELATING THERETO

RELATED APPLICATIONS

This application is a continuation application of, and claims the benefit under 35 U.S.C. §120 of, parent application Ser. No. 11/814,549, filed Jul. 23, 2007 now U.S. Pat. No. 7,931,902, which application is a US national stage application claiming priority under 35 USC §371 of international application PCT/US2006/027777, filed Jul. 18, 2006, which claims priority under 35 USC §119 to U.S. Provisional Application 60/708,312 filed Aug. 15, 2005.

INCORPORATION-BY-REFERENCE

The contents of the text file named "Sequence Listing P5208R1", created Jul. 23, 2007 and being 47.9 MB in size, which was filed with the United States Patent and Trademark Office on Jul. 23, 2007 regarding U.S. application Ser. No. 11/814,549, are hereby incorporated by reference in their entirety.

FIELD OF THE INVENTION

The present invention relates to compositions, including transgenic and knockout animals and methods of using such compositions for the diagnosis and treatment of diseases or disorders.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108-7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesion molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immuno-adhesions, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

Given the importance of secreted and membrane-bound proteins in biological and disease processes, in vivo studies and characterizations may provide valuable identification and discovery of therapeutics and/or treatments useful in the prevention, amelioration or correction of diseases or dysfunctions. In this regard, genetically engineered mice have proven to be invaluable tools for the functional dissection of biological processes relevant to human disease, including immunology, cancer, neuro-biology, cardiovascular biology, obesity and many others. Gene knockouts can be viewed as modeling the biological mechanism of drug action by presaging the activity of highly specific antagonists in vivo. Knockout mice have been shown to model drug activity; phenotypes of mice deficient for specific pharmaceutical target proteins can resemble the human clinical phenotype caused by the corresponding antagonist drug. Gene knockouts enable the discovery of the mechanism of action of the target, the predominant physiological role of the target, and mechanism-based side-effects that might result from inhibition of the target in mammals. Examples of this type include mice deficient in the angiotensin converting enzyme (ACE) [Esther, C. R. et al., *Lab. Invest.,* 74:953-965 (1996)] and cyclooxygenase-1 (COX1) genes [Langenbach, R. et al., *Cell,* 83:483-492 (1995)]. Conversely, knocking the gene out in the mouse can have an opposite phenotypic effect to that observed in humans after administration of an agonist drug to the corresponding target. Examples include the erythropoietin knockout [Wu, C. S. et al., *Cell,* 83:59-67 (1996)], in which a consequence of the mutation is deficient red blood cell production, and the GABA(A)-R-β3 knockout [DeLorey, T. M., *J. Neurosci.,* 18:8505-8514 (1998)], in which the mutant mice show hyperactivity and hyper-responsiveness. Both these phenotypes are opposite to the effects of erythropoietin and benzodiazepine administration in humans. A striking example of a target validated using mouse genetics is the ACC2 gene. Although the human ACC2 gene had been identified several years ago, interest in ACC2 as a target for drug development was stimulated only recently after analysis of ACC2 function using a knockout mouse. ACC2 mutant mice eat more than their wild-type littermates, yet burn more fat and store less fat in their adipocytes, making this enzyme a probable target for chemical antagonism in the treatment of obesity [Abu-El-heiga, L. et al., *Science*, 291:2613-2616 (2001)].

In the instant application, mutated gene disruptions have resulted in phenotypic observations related to various disease conditions or dysfunctions including: CNS/neurological disturbances or disorders such as anxiety; eye abnormalities and associated diseases; cardiovascular, endothelial or angiogenic disorders including atherosclerosis; abnormal metabolic disorders including diabetes and dyslipidemias associated with elevated serum triglycerides and cholesterol levels; immunological and inflammatory disorders; oncological disorders; bone metabolic abnormalities or disorders such as arthritis, osteoporosis and osteopetrosis; or a developmental disease such as embryonic lethality.

SUMMARY OF THE INVENTION

A. Embodiments

The invention provides an isolated nucleic acid molecule comprising a nucleotide sequence that encodes a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as disclosed herein, the coding sequence of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide lacking the signal peptide as disclosed herein, the coding sequence of an extracellular domain of a transmembrane PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect of the invention provides an isolated nucleic acid molecule comprising a nucleotide sequence encoding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides are contemplated.

The invention also provides fragments of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide coding sequence, or the complement thereof, that may find use as, for example, hybridization probes, for encoding fragments of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide that may optionally encode a polypeptide comprising a binding site for an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody or as antisense oligonucleotide probes. Such nucleic acid fragments usually are or are at least about 10 nucleotides in length, alternatively are or are at least about 15 nucleotides in length, alternatively are or are at least about 20 nucleotides in length, alternatively are or are at least about 30 nucleotides in length, alternatively are or are at least about 40 nucleotides in length, alternatively are or are at least about 50 nucleotides in length, alternatively are or are at least about 60 nucleotides in length, alternatively are or are at least about 70 nucleotides in length, alternatively are or are at least about 80 nucleotides in length, alternatively are or are at least about 90 nucleotides in length, alternatively are or are at least about 100 nucleotides in length, alternatively are or are at least about 110 nucleotides in length, alternatively are or are at least about 120 nucleotides in length, alternatively are or are at least about 130 nucleotides in length, alternatively are or are at least about 140 nucleotides in length, alternatively are or are at least about 150 nucleotides in length, alternatively are or are at least about 160 nucleotides in length, alternatively are or are at least about 170 nucleotides in length, alternatively are or are at least about 180 nucleotides in length, alternatively are or are at least about 190 nucleotides in length, alternatively are or are at least about 200 nucleotides in length, alternatively are or are at least about 250 nucleotides in length, alternatively are or are at least about 300 nucleotides in length, alternatively are or are at least about 350 nucleotides in length, alternatively are or are at least about 400 nucleotides in length, alternatively are or are at least about 450 nucleotides in length, alternatively are or are at least about 500 nucleotides in length, alternatively are or are at least about 600 nucleotides in length, alternatively are or are at least about 700 nucleotides in length, alternatively are or are at least about 800 nucleotides in length, alternatively are or are at least about 900 nucleotides in length and alternatively are or are at least about 1000 nucleotides in length, wherein in this context the term "about" means the referenced nucleotide sequence length plus or minus 10% of that referenced length. It is noted that novel fragments of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide-encoding nucleotide sequence may be determined in a routine manner by aligning the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide-encoding nucleotide sequence with other known nucleotide sequences using any of a number of well known sequence alignment programs and determining which PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide-encoding nucleotide sequence fragment(s) are novel. All of such PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide-encoding nucleotide sequences are contemplated herein. Also contemplated are the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide fragments encoded by these nucleotide molecule fragments, preferably those PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide fragments that comprise a binding site for an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

The invention provides isolated PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides encoded by any of the isolated nucleic acid sequences hereinabove identified.

In a certain aspect, the invention concerns an isolated PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In one aspect, the invention concerns PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant polypeptides which are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant polypeptides will have or have no more than one conservative amino acid substitution as compared to the native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence, alternatively will have or will have no more than 2, 3, 4, 5, 6, 7, 8, 9, or 10 conservative amino acid substitution as compared to the native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence.

In a specific aspect, the invention provides an isolated PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide and recovering the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide from the cell culture.

Another aspect the invention provides an isolated PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide and recovering the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide from the cell culture.

The invention provides agonists and antagonists of a native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as defined herein. In particular, the agonist or antagonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody or a small molecule.

The invention provides a method of identifying agonists or antagonists to a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide which comprise contacting the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide with a candidate molecule and monitoring a biological activity mediated by said PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Preferably, the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide is a native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

The invention provides a composition of matter comprising a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, or an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as herein described, or an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody, in combination with a carrier. Optionally, the carrier is a pharmaceutically acceptable carrier.

The invention provides the use of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, or an agonist or antagonist thereof as hereinbefore described, or an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody, for the preparation of a medicament useful in the treatment of a condition which is responsive to the anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

The invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

The invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

The invention provides an antibody which binds, preferably specifically, to any of the above or below described polypeptides. Optionally, the antibody is a monoclonal antibody, humanized antibody, antibody fragment or single-chain antibody.

The invention provides oligonucleotide probes which may be useful for isolating genomic and cDNA nucleotide sequences, measuring or detecting expression of an associated gene or as antisense probes, wherein those probes may be derived from any of the above or below described nucleotide sequences. Preferred probe lengths are described above.

The invention also provides a method of identifying a phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal. In one aspect, the non-human transgenic animal is a mammal. In another aspect, the mammal is a rodent. In still another aspect, the mammal is a rat or a mouse. In one aspect, the non-human transgenic animal is heterozygous for the disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In another aspect, the phenotype exhibited by the non-human transgenic animal as compared with gender matched wild-type littermates is at least one of the following: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histrionic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathyroidism or Conradi syndrome.

In still another aspect, the developmental abnormality comprises embryonic lethality or reduced viability.

In still yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In still another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety during open field testing; decreased locomotor activity during open field testing; abnormal circadian rhythm during home-cage activity testing (low activity during the light phase); abnormal circadian rhythm during home-cage activity testing including decreased ambulatory counts; hypoactivity with no circadian rhythm; abnormal circadian rhythm during home-cage activity testing including increased ambulatory counts; increased stress induced hyperthermia; decreased stress induced hyperthermia; impaired motor coordination during inverted screen testing; increased immobility in tail suspension (increased depressive-like response); increased depressive-like response during tail suspension testing; increased immobility or decreased depressive-like response during tail suspension testing; decreased startle response during prepulse inhibition testing; no startle response indicating deafness; or impaired hearing; decreased prepulse inhibition with impaired sensorimotor gating/attention; decreased responsiveness in hot plate testing; decreased latency to respond in hot plate testing; opthalmological abnormalities; increased mean artery-to-vein ratio; resistance to pupil dilating drug cyclopentolate hydrochloride; squinty eyes; squint eyes with white spots; cataracts; retinal degeneration; impaired vision; decreased basal body temperature; decreased heart rate; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; decreased mean serum triglyceride levels; enhanced glucose tolerance; impaired glucose tolerance; decreased mean serum insulin levels; increased mean serum calcium; increased urobilinogen, notable lipemia; increased albumin, alanine amino transferase, phosphorus and potassium levels; increased mean serum alkaline phosphatase levels; increased blood urea nitrogen; increased percentage of granulocyte; increased total white blood cell (WBC) count; increased mean absolute neutrophil count; neutropenia; increased absolute lymphocyte count; increased absolute monocyte count; increased monocytes and DC in spleen (CD11b+, CD11b+ c+); increased mean platelet count; increased natural killer (NK) cells in lymph node; decreased neutrophil count; decreased natural killer (NK) cells; decreased mean red blood cell (RBC) count, hemoglobin concentration, and hematocrit; increased mean red cell distribution width; decreased mean corpuscular volume and mean corpuscular hemoglobin; decreased mean platelet count and increased platelet volume; increase B cell number in lymph node; increase in B cell subtypes in Peyer's patches; increased percentage of B cells in lymph node; increase CD25+ cells; increased thymic DN, decreased DP T cells; increased CD19+ cells in lymph node; increased CD117 in bone marrow cells; increased mean percentage of CD4 cells; increased CD8 cells and decrease in B cells; increased percentage CD11b+ cells in peritoneal lavage; increased percentage of B220+CD11b Low CD23− cells; increased percentages of B220− CD11 Low and CD11b− cells in peritoneal lavage; increased percentage of B220−CD11bHi cells in peritoneal lavage; decreased percentage of B220+ CD11b− CD23+ cells in peritoneal lavage; increased percentage of B220− CD43 Hi cells in bone marrow; increased CD11b+ CD11c− cells in spleen; increase in CD62hi, CD44int subsets of CD4 and CD8 cells; increase in peritoneal CD117 cells; increase TcRbeta/CD38 cells in Peyer's patches; increased percentage of TcRbeta+ cells in thymus; increased percentages of CD11b+ CD11c+ in lymph node; decreased percentage of B220+ Hi CD23+ cells in peritoneal lavage; decreased percentage of B220+ Med CD23− cells in peritoneal lavage; decreased percentages of CD62L Hi CD44 Dim CD4+ and CD8+ cells in spleen; decreased percentage of B220−CD11b Hi cells; decreased mean percentages of CD4 and CD8 cells in lymph node and spleen; increased memory T cells [increased CD62L lo CD44hi]; decreased T cell:B cell ratio; decreased naive T cells; decreased CD117 cells in peritoneal lavage; decreased mean percentage of CD8 cells, increased IgG1 response to ovalbumin challenge; increased IgG2a response to ovalbumin challenge; increased mean serum IL-6 response to LPS challenge; increased TNF alpha response to LPS challenge; increased serum MCP-1 response to LPS challenge; increased mean serum IgM level; increased serum IgA; increase mean serum IgG1; increased mean serum IgG3; decreased serum IgG1 response to ovalbumin challenge; decreased serum IgG2a response to ovalbumin challenge; decreased mean serum IgA level; decreased serum IgG2a level; decrease in serum IgG3 level; increased skin fibroblast proliferation rate; decreased skin fibroblast proliferation rate; increased mean percent of total body fat and total fat mass; increased mean body weight; increased mean body length; increased total tissue mass (TTM); increased mean femoral midshaft cortical thickness and cross-sectional area;

increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD) in total body, femur and vertebrae; decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; osteopetrosis; osteoporosis; chronic inflammation in various tissues; bilateral hydronephrosis (moderate to severe) and inflammation; "pear shaped abdomen"; bilaterally enlarged kidneys, suggesting polycystic kidney disease; degeneration of the Organ of Corti; hepatocellular dysfunction; biliary obstruction; hepatosplenomegaly characterized by histiocytic infiltrate; histiocytosis in the small intestine, lymph nodes and spleen; splenomegaly, lymphadenopathy and lymphadenopathy; hyperplasia of adenoid and tonsils; mild-moderate extra medullary hematopoiesis; homozygous mice were small, dehydrated and exhibited decreased subcutaneous fat depots; lipopenia; ulcerous colitis; diffuse marked degeneration of sensory cochlear hair cells in the inner ear, characterized by a complete loss of both inner and outer cochlear hair cells on the basilar membrane; gastric mucosal hyperplasia and chronic inflammation; in creased stomach weight; defective spermatogenesis in the testes; hypospermia and defective spermatozoa in the epididymus; male infertility; lysosomal storage disease; anemia; growth retardation; reduced viability; perinatal lethality with decreased lymphocytes and lipopenia; homozygous embryonic lethality; and heterozygous embryonic lethality.

The invention also provides an isolated cell derived from a non-human transgenic animal whose genome comprises a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In one aspect, the isolated cell is a murine cell. In yet another aspect, the murine cell is an embryonic stem cell. In still another aspect, the isolated cell is derived from a non-human transgenic animal which exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality. The invention also provides a method of identifying an agent that modulates a phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

In one aspect, the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histrionic, narcissistic, obsessive-compulsive, schizoid, and schizotypal.

In yet another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathyroidism, or Conradi syndrome.

In still another aspect, the developmental abnormality comprises embryonic lethality or reduced viability.

In still another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety during open field testing; decreased locomotor activity during open field testing; abnormal circadian rhythm during home-cage activity testing (low activity during the light phase); abnormal circadian rhythm during home-cage activity testing including decreased ambulatory counts; hypoactivity with no circadian rhythm; abnormal circadian rhythm during home-cage activity testing including increased ambulatory counts; increased stress induced hyperthermia; decreased stress induced hyperthermia; impaired motor coordination during inverted screen testing; increased immobility in tail suspension (increased depressive-like response); increased depressive-like response during tail suspension testing; increased immobility or decreased depressive-like response during tail suspension testing; decreased startle response during prepulse inhibition testing; no startle response indicating deafness; or impaired hearing; decreased prepulse inhibition with impaired sensorimotor gating/attention; decreased responsiveness in hot plate testing; decreased latency to respond in hot plate testing; opthalmological abnormalities; increased mean artery-to-vein ratio; resistance to pupil dilating drug cyclopentolate hydrochloride; squinty eyes; squint eyes with white spots; cataracts; retinal degeneration; impaired vision; decreased basal body temperature; decreased heart rate; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; decreased mean serum triglyceride levels; enhanced glucose tolerance; impaired glucose tolerance; decreased mean serum insulin levels; increased mean serum calcium; increased urobilinogen, notable lipemia; increased albumin, alanine amino transferase, phosphorus and potassium levels; increased mean serum alkaline phosphatase levels; increased blood urea nitrogen; increased percentage of granulocyte; increased total white blood cell (WBC) count; increased mean absolute neutrophil count; neutropenia; increased absolute lymphocyte count; increased absolute monocyte count; increased monocytes and DC in spleen (CD11b+, CD11b+ c+); increased mean platelet count; increased natural killer (NK) cells in lymph node; decreased neutrophil count; decreased natural killer (NK) cells; decreased mean red blood cell (RBC) count, hemoglobin concentration, and hematocrit; increased mean red cell distribution width; decreased mean corpuscular volume and mean corpuscular hemoglobin; decreased mean platelet count and increased platelet volume; increase B cell number in lymph node; increase in B cell subtypes in Peyer's patches; increased percentage of B cells in lymph node; increase CD25+ cells; increased thymic DN, decreased DP T cells; increased CD19+ cells in lymph node; increased CD117 in bone marrow cells; increased mean percentage of CD4 cells; increased CD8 cells and decrease in B cells; increased percentage CD11b+ cells in peritoneal lavage; increased percentage of B220+ CD11b Low CD23– cells; increased percentages of B220– CD11 Low and CD11b– cells in peritoneal lavage; increased percentage of B220–CD11bHi cells in peritoneal lavage; decreased percentage of B220+ CD11b– CD23+ cells in peritoneal lavage; increased percentage of B220– CD43 Hi cells in bone marrow; increased CD11b+ CD11c– cells in spleen; increase in CD62hi, CD44int subsets of CD4 and CD8 cells; increase in peritoneal CD117 cells; increase TcRbeta/CD38 cells in Peyer's patches; increased percentage of TcRbeta+ cells in thymus; increased percentages of CD11b+ CD11c+ in lymph node; decreased percentage of B220+ Hi CD23+ cells in peritoneal lavage; decreased percentage of B220+ Med CD23–cells in peritoneal lavage; decreased percentages of CD62L Hi CD44 Dim CD4+ and CD8+ cells in spleen; decreased percentage of B220–CD11b Hi cells; decreased mean percentages of CD4 and CD8 cells in lymph node and spleen; increased memory T cells [increased CD62L lo CD44hi]; decreased T cell:B cell ratio; decreased naive T cells; decreased CD117 cells in peritoneal lavage; decreased mean percentage of CD8 cells, increased IgG1 response to ovalbumin challenge; increased IgG2a response to ovalbumin challenge; increased mean serum IL-6 response to LPS challenge; increased TNF alpha response to LPS challenge; increased serum MCP-1 response to LPS challenge; increased mean serum IgM level; increased serum IgA; increase mean serum IgG1; increased mean serum IgG3; decreased serum IgG1 response to ovalbumin challenge; decreased serum IgG2a response to ovalbumin challenge; decreased mean serum IgA level; decreased serum IgG2a level; decrease in serum IgG3 level; increased skin fibroblast proliferation rate; decreased skin fibroblast proliferation rate; increased mean percent of total body fat and total fat mass; increased mean body weight; increased mean body length; increased total tissue mass (TTM); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD) in total body, femur and vertebrae; decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; osteopetrosis; osteoporosis; chronic inflammation in various tissues; bilateral hydronephrosis (moderate to severe) and inflammation; "pear shaped abdomen"; bilaterally enlarged kidneys, suggesting polycystic kidney disease; degeneration of the Organ of Corti; hepatocellular dysfunction; biliary obstruction; hepatosplenomegaly characterized by histiocytic infiltrate; histiocytosis in the small intestine, lymph nodes and spleen; splenomegaly, lymphadenopathy and lymphadenopathy; hyperplasia of adenoid and tonsils; mild-moderate extra medullary hematopoiesis; homozygous mice were small, dehydrated and exhibited decreased subcutaneous fat depots; lipopenia; ulcerous colitis; diffuse marked degeneration of sensory cochlear hair cells in the inner ear, characterized by a complete loss of both inner and outer cochlear hair cells on the basilar membrane; gastric mucosal hyperplasia and chronic inflammation; in creased stomach weight; defective spermatogenesis in the testes; hypospermia and defective spermatozoa in the epididymus; male infertility; lysosomal storage disease; anemia; growth retardation; reduced viability; perinatal lethality with decreased lymphocytes and lipopenia; homozygous embryonic lethality; and heterozygous embryonic lethality.

The invention also provides an agent which modulates the phenotype associated with gene disruption. In one aspect, the agent is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody. In still another aspect, the antagonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti- PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

The invention also provides a method of identifying an agent that modulates a physiological characteristic associated with a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

In one aspect, the non-human transgenic animal exhibits at least one of the following physiological characteristics compared with gender matched wild-type littermates:

In another aspect, the non-human transgenic animal exhibits at least one of the following physiological characteristics compared with gender matched wild-type littermates: increased anxiety-like response during open field testing; decreased anxiety during open field testing; decreased locomotor activity during open field testing; abnormal circadian rhythm during home-cage activity testing (low activity during the light phase); abnormal circadian rhythm during home-cage activity testing including decreased ambulatory counts; hypoactivity with no circadian rhythm; abnormal circadian rhythm during home-cage activity testing including increased ambulatory counts; increased stress induced hyperthermia; decreased stress induced hyperthermia; impaired motor coordination during inverted screen testing; increased immobility in tail suspension (increased depressive-like response); increased depressive-like response during tail suspension testing; increased immobility or decreased depressive-like response during tail suspension testing; decreased startle response during prepulse inhibition testing; no startle response indicating deafness; or impaired hearing; decreased prepulse inhibition with impaired sensorimotor gating/attention; decreased responsiveness in hot plate testing; decreased latency to respond in hot plate testing; opthalmological abnormalities; increased mean artery-to-vein ratio; resistance to pupil dilating drug cyclopentolate hydrochloride; squinty eyes; squint eyes with white spots; cataracts; retinal degeneration; impaired vision; decreased basal body temperature; decreased heart rate; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; decreased mean serum triglyceride levels; enhanced glucose tolerance; impaired glucose tolerance; decreased mean serum insulin levels; increased mean serum calcium; increased urobilinogen, notable lipemia; increased albumin, alanine amino transferase, phosphorus and potassium levels; increased mean serum alkaline phosphatase levels; increased blood urea nitrogen; increased percentage of granulocyte; increased total white blood cell (WBC) count; increased mean absolute neutrophil count; neutropenia; increased absolute lymphocyte count; increased absolute monocyte count; increased monocytes and DC in spleen (CD11b+, CD11b+ c+); increased mean platelet count; increased natural killer (NK) cells in lymph node; decreased neutrophil count; decreased natural killer (NK) cells; decreased mean red blood cell (RBC) count, hemoglobin concentration, and hematocrit; increased mean red cell distribution width; decreased mean corpuscular volume and mean corpuscular hemoglobin; decreased mean platelet count and increased platelet volume; increase B cell number in lymph node; increase in B cell subtypes in Peyer's patches; increased percentage of B cells in lymph node; increase CD25+ cells; increased thymic DN, decreased DP T cells; increased CD19+ cells in lymph node; increased CD117 in bone marrow cells; increased mean percentage of CD4 cells; increased CD8 cells and decrease in B cells; increased percentage CD11b+ cells in peritoneal lavage; increased percentage of B220+ CD11b Low CD23– cells; increased percentages of B220– CD11 Low and CD11b– cells in peritoneal lavage; increased percentage of B220–CD11bHi cells in peritoneal lavage; decreased percentage of B220+ CD11b– CD23+ cells in peritoneal lavage; increased percentage of B220– CD43 Hi cells in bone marrow; increased CD11b+ CD11c– cells in spleen; increase in CD62hi, CD44int subsets of CD4 and CD8 cells; increase in peritoneal CD117 cells; increase TcRbeta/CD38 cells in Peyer's patches; increased percentage of TcRbeta+ cells in thymus; increased percentages of CD11b+ CD11c+ in lymph node; decreased percentage of B220+ Hi CD23+ cells in peritoneal lavage; decreased percentage of B220+ Med CD23–cells in peritoneal lavage; decreased percentages of CD62L Hi CD44 Dim CD4+ and CD8+ cells in spleen; decreased percentage of B220–CD11b Hi cells; decreased mean percentages of CD4 and CD8 cells in lymph node and spleen; increased memory T cells [increased CD62L lo CD44hi]; decreased T cell:B cell ratio; decreased naive T cells; decreased CD117 cells in peritoneal lavage; decreased mean percentage of CD8 cells, increased IgG1 response to ovalbumin challenge; increased IgG2a response to ovalbumin challenge; increased mean serum IL-6 response to LPS challenge; increased TNF alpha response to LPS challenge; increased serum MCP-1 response to LPS challenge; increased mean serum IgM level; increased serum IgA;

increase mean serum IgG1; increased mean serum IgG3; decreased serum IgG1 response to ovalbumin challenge; decreased serum IgG2a response to ovalbumin challenge; decreased mean serum IgA level; decreased serum IgG2a level; decrease in serum IgG3 level; increased skin fibroblast proliferation rate; decreased skin fibroblast proliferation rate; increased mean percent of total body fat and total fat mass; increased mean body weight; increased mean body length; increased total tissue mass (TTM); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD) in total body, femur and vertebrae; decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; osteopetrosis; osteoporosis; chronic inflammation in various tissues; bilateral hydronephrosis (moderate to severe) and inflammation; "pear shaped abdomen"; bilaterally enlarged kidneys, suggesting polycystic kidney disease; degeneration of the Organ of Corti; hepatocellular dysfunction; biliary obstruction; hepatosplenomegaly characterized by histiocytic infiltrate; histiocytosis in the small intestine, lymph nodes and spleen; splenomegaly, lymphadenopathy and lymphadenopathy; hyperplasia of adenoid and tonsils; mild-moderate extra medullary hematopoiesis; homozygous mice were small, dehydrated and exhibited decreased subcutaneous fat depots; lipopenia; ulcerous colitis; diffuse marked degeneration of sensory cochlear hair cells in the inner ear, characterized by a complete loss of both inner and outer cochlear hair cells on the basilar membrane; gastric mucosal hyperplasia and chronic inflammation; in creased stomach weight; defective spermatogenesis in the testes; hypospermia and defective spermatozoa in the epididymus; male infertility; lysosomal storage disease; anemia; growth retardation; reduced viability; perinatal lethality with decreased lymphocytes and lipopenia; homozygous embryonic lethality; and heterozygous embryonic lethality.

The invention also provides an agent that modulates a physiological characteristic which is associated with gene disruption. In one aspect, the agent is an agonist or antagonist of the phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agent is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody. In still another aspect, the antagonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

The invention also provides a method of identifying an agent which modulates a behavior associated with a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

In one aspect, the observed behavior is an increased anxiety-like response during open field activity testing. In yet another aspect, the observed behavior is a decreased anxiety-like response during open field activity testing. In yet another aspect, the observed behavior is an abnormal circadian rhythm during home-cage activity testing. In yet another aspect, the observed behavior is an enhanced motor coordination during inverted screen testing. In yet another aspect, the observed behavior is impaired motor coordination during inverted screen testing. In yet another aspect, the observed behavior includes depression, generalized anxiety disorders, attention deficit disorder, sleep disorder, hyperactivity disorder, obsessive compulsive disorder, schizophrenia, cognitive disorders, hyperalgesia and sensory disorders. Such disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, border line personality disorders, dependent, histrionic, narcissistic, obsessive-compulsive, schizoid, and schizotypal.

The invention also provides an agent that modulates a behavior which is associated with gene disruption. In one aspect, the agent is an agonist or antagonist of the phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agent is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody. In still another aspect, the antagonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) administering a test agent to said non-human transgenic animal; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality associated with the gene disruption in the non-human transgenic animal.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histrionic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathyroidism, or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety during open field testing; decreased locomotor activity during open field testing; abnormal circadian rhythm during home-cage activity testing (low activity during the light phase); abnormal circadian rhythm during home-cage activity testing including decreased ambulatory counts; hypoactivity with no circadian rhythm; abnormal circadian rhythm during home-cage activity testing including increased ambulatory counts; increased stress induced hyperthermia; decreased stress induced hyperthermia; impaired motor coordination during inverted screen testing; increased immobility in tail suspension (increased depressive-like response); increased depressive-like response during tail suspension testing; increased immobility or decreased depressive-like response during tail suspension testing; decreased startle response during prepulse inhibition testing; no startle response indicating deafness; or impaired hearing; decreased prepulse inhibition with impaired sensorimotor gating/attention; decreased responsiveness in hot plate testing; decreased latency to respond in hot plate testing; opthalmological abnormalities; increased mean artery-to-vein ratio; resistance to pupil dilating drug cyclopentolate hydrochloride; squinty eyes; squint eyes with white spots; cataracts; retinal degeneration; impaired vision; decreased basal body temperature; decreased heart rate; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; decreased mean serum triglyceride levels; enhanced glucose tolerance; impaired glucose tolerance; decreased mean serum insulin levels; increased mean serum calcium; increased urobilinogen, notable lipemia; increased albumin, alanine amino transferase, phosphorus and potassium levels; increased mean serum alkaline phosphatase levels; increased blood urea nitrogen; increased percentage of granulocyte; increased total white blood cell (WBC) count; increased mean absolute neutrophil count; neutropenia; increased absolute lymphocyte count; increased absolute monocyte count; increased monocytes and DC in spleen (CD11b+, CD11b+c+); increased mean platelet count; increased natural killer (NK) cells in lymph node; decreased neutrophil count; decreased natural killer (NK) cells; decreased mean red blood cell (RBC) count, hemoglobin concentration, and hematocrit; increased mean red cell distribution width; decreased mean corpuscular volume and mean corpuscular hemoglobin; decreased mean platelet count and increased platelet volume; increase B cell number in lymph node; increase in B cell subtypes in Peyer's patches; increased percentage of B cells in lymph node; increase CD25+ cells; increased thymic DN, decreased DP T cells; increased CD19+ cells in lymph node; increased CD117 in bone marrow cells; increased mean percentage of CD4 cells; increased CD8 cells and decrease in B cells; increased percentage CD11b+ cells in peritoneal lavage; increased percentage of B220+CD11b Low CD23− cells; increased percentages of B220− CD11 Low and CD11b− cells in peritoneal lavage; increased percentage of B220−CD11bHi cells in peritoneal lavage; decreased percentage of B220+ CD11b− CD23+ cells in peritoneal lavage; increased percentage of B220− CD43 Hi cells in bone marrow; increased CD11b+ CD11c− cells in spleen; increase in CD62hi, CD44int subsets of CD4 and CD8 cells; increase in peritoneal CD117 cells; increase TcRbeta/CD38 cells in Peyer's patches; increased percentage of TcRbeta+ cells in thymus; increased percentages of CD11b+ CD11c+ in lymph node; decreased percentage of B220+ Hi CD23+ cells in peritoneal lavage; decreased percentage of B220+ Med CD23−cells in peritoneal lavage; decreased percentages of CD62L Hi CD44 Dim CD4+ and CD8+ cells in spleen; decreased percentage of B220−CD11b Hi cells; decreased mean percentages of CD4 and CD8 cells in lymph node and spleen; increased memory T cells [increased CD62L lo CD44hi]; decreased T cell:B cell ratio; decreased naive T cells; decreased CD117 cells in peritoneal lavage; decreased mean percentage of CD8 cells, increased IgG1 response to ovalbumin challenge; increased IgG2a response to ovalbumin challenge; increased mean serum IL-6 response to LPS challenge; increased TNF alpha response to LPS challenge; increased serum MCP-1 response to LPS challenge; increased mean serum IgM level; increased serum IgA; increase mean serum IgG1; increased mean serum IgG3; decreased serum IgG1 response to ovalbumin challenge; decreased serum IgG2a response to ovalbumin challenge; decreased mean serum IgA level; decreased serum IgG2a level; decrease in serum IgG3 level; increased skin fibroblast proliferation rate; decreased skin fibroblast proliferation rate; increased mean percent of total body fat and total fat mass; increased mean body weight; increased mean body length; increased total tissue mass (TTM); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD) in total body, femur and vertebrae; decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; osteopetrosis; osteoporosis; chronic inflammation in various tissues; bilateral hydronephrosis (moderate to severe) and inflammation; "pear shaped abdomen"; bilaterally enlarged kidneys, suggesting polycystic kidney disease; degeneration of the Organ of Corti; hepatocellular dysfunction; biliary obstruction; hepatosplenomegaly characterized by histiocytic infiltrate; histiocytosis in the small intestine, lymph nodes and spleen; splenomegaly, lymphadenopathy and lymphadenopathy; hyperplasia of adenoid and tonsils; mild-moderate extra medullary hematopoiesis; homozygous mice were small, dehydrated and exhibited decreased subcutaneous fat depots; lipopenia; ulcerous colitis; diffuse marked degeneration of sensory cochlear hair cells in the inner ear, characterized by a complete loss of both inner and outer cochlear hair cells on the basilar membrane; gastric mucosal hyperplasia and chronic inflammation; in creased stomach weight; defective spermatogenesis in the testes; hypospermia and defective spermatozoa in the epididymus; male infertility; lysosomal storage disease; anemia; growth retardation; reduced viability; perinatal lethality with decreased lymphocytes and lipopenia; homozygous embryonic lethality; and heterozygous embryonic lethality.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption. In one aspect, the agent is an agonist or antagonist of the phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agent is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody. In still another aspect, the antagonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

The invention also provides a therapeutic agent for the treatment of a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a method of identifying an agent that modulates the expression of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) contacting a test agent with a host cell expressing a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide; and (b) determining whether the test agent modulates the expression of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide by the host cell.

The invention also provides an agent that modulates the expression of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In one aspect, the agent is an agonist or antagonist of the phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agent is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody. In still another aspect, the antagonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

The invention also provides a method of evaluating a therapeutic agent capable of affecting a condition associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

In one aspect, the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a therapeutic agent which is capable of affecting a condition associated with gene disruption. In one aspect, the agent is an agonist or antagonist of the phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agent is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO8516 antibody. In still another aspect, the antagonist agent is an anti-PRO226, anti-PRO257, anti-PRO268, anti- PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO8516 antibody.

The invention also provides a pharmaceutical composition comprising a therapeutic agent capable of affecting the condition associated with gene disruption.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO226, PRO257, PRO268, PRO290, PRO36006, PRO363, PRO365, PRO382, PRO444, PRO705, PRO171, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a subject in need of such treatment whom may already have the disorder, or may be prone to have the disorder or may be in whom the disorder is to be prevented, a therapeutically effective amount of a therapeutic agent, or agonists or antagonists thereof, thereby effectively treating or preventing or ameliorating said disorder or disease.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histrionic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathyroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect the therapeutic agent is an agonist or antagonist of the phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agent is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody. In still an other aspect, the antagonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal cell culture, each cell of said culture comprising a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) administering a test agent to said cell culture; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said culture. In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing.

In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histrionic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathyroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption in said culture. In one aspect, the agent is an agonist or antagonist of the phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agent is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In yet another aspect, the agonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody. In still another aspect, the antagonist agent is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

The invention also provides a method of modulating a phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a subject whom may already have the phenotype, or may be prone to have the phenotype or may be in whom the phenotype is to be prevented, an effective amount of an agent identified as modulating said phenotype, or agonists or antagonists thereof, thereby effectively modulating the phenotype.

The invention also provides a method of modulating a physiological characteristic associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a subject whom may already exhibit the physiological characteristic, or may be prone to exhibit the physiological characteristic or may be in whom the physiological characteristic is to be prevented, an effective amount of an agent identified as modulating said physiological characteristic, or agonists or antagonists thereof, thereby effectively modulating the physiological characteristic.

The invention also provides a method of modulating a behavior associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a subject whom may already exhibit the behavior, or may be prone to exhibit the behavior or may be in whom the exhibited behavior is to be prevented, an effective amount of an agent identified as modulating said behavior, or agonists or antagonists thereof, thereby effectively modulating the behavior.

The invention also provides a method of modulating the expression of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a host cell expressing said PRO226, PRO257, PRO268, PRO290, PRO36006, PRO363, PRO365, PRO382, PRO444, PRO705, PRO1071, PRO1125, PRO134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, an effective amount of an agent identified as modulating said expression, or agonists or antagonists thereof, thereby effectively modulating the expression of said polypeptide.

The invention also provides a method of modulating a condition associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a subject whom may have the condition, or may be prone to have the condition or may be in whom the condition is to be prevented, a therapeutically effective amount of a therapeutic agent identified as modulating said condition, or agonists or antagonists thereof, thereby effectively modulating the condition.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO226, PRO257, PRO268, PRO290, PRO36006, PRO363, PRO365, PRO382, PRO444, PRO705, PRO171, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a non-human transgenic animal cell culture, each cell of said culture comprising a disruption of the gene which encodes for a PRO226, PRO257, PRO268, PRO290, PRO36006, PRO363, PRO365, PRO382, PRO444, PRO705, PRO171, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, an effective amount of an agent identified as treating or preventing or ameliorating said disorder, or agonists or antagonists thereof, thereby effectively treating or preventing or ameliorating said disorder.

B. Further Embodiments

In yet further embodiments, the invention is directed to the following set of potential claims for this application:

1. A method of identifying a phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal.

2. The method of Claim 1, wherein the non-human transgenic animal is heterozygous for the disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

3. The method of Claim 1, wherein the phenotype exhibited by the non-human transgenic animal as compared with gender matched wild-type littermates is at least one of the following: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

4. The method of Claim 3, wherein the neurological disorder is an increased anxiety-like response during open field activity testing.

5. The method of Claim 3, wherein the neurological disorder is a decreased anxiety-like response during open field activity testing.

6. The method of Claim 3, wherein the neurological disorder is an abnormal circadian rhythm during home-cage activity testing.

7. The method of Claim 3, wherein the neurological disorder is an enhanced motor coordination during inverted screen testing.

8. The method of Claim 3, wherein the neurological disorder is an impaired motor coordination during inverted screen testing.

9. The method of Claim 3, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

10. The method of Claim 3, wherein the eye abnormality is a retinal abnormality.

11. The method of Claim 3, wherein the eye abnormality is consistent with vision problems or blindness.

12. The method of Claim 10, wherein the retinal abnormality is consistent with retinitis pigmentosa.

13. The method of Claim 10, wherein the retinal abnormality is characterized by retinal degeneration or retinal dysplasia.

14. The method of Claim 10, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congenita, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

15. The method of Claim 3, wherein the eye abnormality is a cataract.

16. The method of Claim 15, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathyroidism or Conradi syndrome.

17. The method of Claim 3, wherein the developmental abnormality comprises embryonic lethality or reduced viability.

18. The method of Claim 3, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

19. The method of Claim 3, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

20. The method of Claim 3, wherein the bone metabolic abnormality or disorder is arthritis, osteoporosis or osteopetrosis.

21. The method of Claim 1, wherein the non-human transgenic animal exhibits at least one of the following physiological characteristics compared with gender matched wild-type littermates: increased anxiety-like response during open field testing; decreased anxiety during open field testing; decreased locomotor activity during open field testing; abnormal circadian rhythm during home-cage activity testing (low activity during the light phase); abnormal circadian rhythm during home-cage activity testing including decreased ambulatory counts; hypoactivity with no circadian rhythm; abnormal circadian rhythm during home-cage activity testing including increased ambulatory counts; increased stress induced hyperthermia; decreased stress induced hyperthermia; impaired motor coordination during inverted screen testing; increased immobility in tail suspension (increased depressive-like response); increased depressive-like response during tail suspension testing; increased immobility or decreased depressive-like response during tail suspension testing; decreased startle response during prepulse inhibition testing; no startle response indicating deafness; or impaired hearing; decreased prepulse inhibition with impaired sensorimotor gating/attention; decreased responsiveness in hot-plate testing; decreased latency to respond in hot plate testing; opthalmological abnormalities; increased mean artery-to-vein ratio; resistance to pupil dilating drug cyclopentolate hydrochloride; squinty eyes; squint eyes with white spots; cataracts; retinal degeneration; impaired vision; decreased basal body temperature; decreased heart rate; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; decreased mean serum triglyceride levels; enhanced glucose tolerance; impaired glucose tolerance; decreased mean serum insulin levels; increased mean serum calcium; increased urobilinogen, notable lipemia; increased albumin, alanine amino transferase, phosphorus and potassium levels; increased mean serum alkaline phosphatase levels; increased blood urea nitrogen; increased percentage of granulocyte; increased total white blood cell (WBC) count; increased mean absolute neutrophil count; neutropenia; increased absolute lymphocyte count; increased absolute monocyte count; increased monocytes and DC in spleen (CD11b+, CD11b+c+); increased mean platelet count; increased natural killer (NK) cells in lymph node; decreased neutrophil count; decreased natural killer (NK) cells; decreased mean red blood cell (RBC) count, hemoglobin concentration, and hematocrit; increased mean red cell distribution width; decreased mean corpuscular volume and mean corpuscular hemoglobin; decreased mean platelet count and increased platelet volume; increase B cell number in lymph node; increase in B cell subtypes in Peyer's patches; increased percentage of B cells in lymph node; increase CD25+ cells; increased thymic DN, decreased DP T cells; increased CD19+ cells in lymph node; increased CD117 in bone marrow cells; increased mean percentage of CD4 cells; increased CD8 cells and decrease in B cells; increased percentage CD11b+ cells in peritoneal lavage; increased percentage of B220+ CD11b Low CD23– cells; increased percentages of B220– CD11 Low and CD11b– cells in peritoneal lavage; increased percentage of B220–CD11bHi cells in peritoneal lavage; decreased percentage of B220+ CD11b– CD23+ cells in peritoneal lavage; increased percentage of B220– CD43 Hi cells in bone marrow; increased CD11b+CD11c– cells in spleen; increase in CD62hi, CD44int subsets of CD4 and CD8 cells; increase in peritoneal CD117 cells; increase TcRbeta/CD38 cells in Peyer's patches; increased percentage of TcRbeta+ cells in thymus; increased percentages of CD11b+CD11c+ in lymph node; decreased percentage of B220+ Hi CD23+ cells in peritoneal lavage; decreased percentage of B220+ Med CD23–cells in peritoneal lavage; decreased percentages of CD62L Hi CD44 Dim CD4+ and CD8+ cells in spleen; decreased percentage of B220–CD11b Hi cells; decreased mean percentages of CD4 and CD8 cells in lymph node and spleen; increased memory T cells [increased CD62L lo CD44hi]; decreased T cell:B cell ratio; decreased naive T cells; decreased CD117 cells in peritoneal lavage; decreased mean percentage of CD8 cells, increased IgG1 response to ovalbumin challenge; increased IgG2a response to ovalbumin challenge; increased mean serum IL-6 response to LPS challenge; increased TNF alpha response to LPS challenge; increased serum MCP-1 response to LPS challenge; increased mean serum IgM level; increased serum IgA; increase mean serum IgG1; increased mean serum IgG3; decreased serum IgG1 response to ovalbumin challenge; decreased serum IgG2a response to ovalbumin challenge; decreased mean serum IgA level; decreased serum IgG2a level; decrease in serum IgG3 level; increased skin fibroblast proliferation rate; decreased skin fibroblast proliferation rate; increased mean percent of total body fat and total fat mass; increased mean body weight; increased mean body length; increased total tissue mass (TTM); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD) in total body, femur and vertebrae; decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; osteopetrosis; osteoporosis; chronic inflammation in various tissues; bilateral hydronephrosis (moderate to severe) and inflammation; "pear shaped abdomen"; bilaterally enlarged kidneys, suggesting polycystic kidney disease; degeneration of the Organ of Corti; hepatocellular dysfunction; biliary obstruction; hepatosplenomegaly characterized by histiocytic infiltrate; histiocytosis in the small intestine, lymph nodes and spleen; splenomegaly, lymphadenopathy and lymphadenopathy; hyperplasia of adenoid and tonsils; mild-moderate extra medullary hematopoiesis; homozygous mice were small, dehydrated and exhibited decreased subcutaneous fat depots; lipopenia; ulcerous colitis; diffuse marked degeneration of sensory cochlear hair cells in the inner ear, characterized by a complete loss of both inner and outer cochlear hair cells on the basilar membrane; gastric mucosal hyperplasia and chronic inflammation; in creased stomach weight; defective spermatogenesis in the testes; hypospermia and defective spermatozoa in the epididymus; male infertility; lysosomal storage disease; anemia; growth retardation; reduced viability; perinatal lethality with decreased lymphocytes and lipopenia; homozygous embryonic lethality; and heterozygous embryonic lethality.

22. An isolated cell derived from a non-human transgenic animal whose genome comprises a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

23. The isolated cell of Claim 22 which is a murine cell.

24. The isolated cell of Claim 23, wherein the murine cell is an embryonic stem cell.

25. The isolated cell of Claim 22, wherein the non-human transgenic animal exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

26. A method of identifying an agent that modulates a phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

27. The method of Claim 26, wherein the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

28. The method of Claim 27, wherein the neurological disorder is an increased anxiety-like response during open field activity testing.

29. The method of Claim 27, wherein the neurological disorder is a decreased anxiety-like response during open field activity testing.

30. The method of Claim 27, wherein the neurological disorder is an abnormal circadian rhythm during home-cage activity testing.

31. The method of Claim 27, wherein the neurological disorder is an enhanced motor coordination during inverted screen testing.

32. The method of Claim 27, wherein the neurological disorder is an impaired motor coordination during inverted screen testing.

33. The method of Claim 27, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

34. The method of Claim 27, wherein the eye abnormality is a retinal abnormality.

35. The method of Claim 27, wherein the eye abnormality is consistent with vision problems or blindness.

36. The method of Claim 34, wherein the retinal abnormality is consistent with retinitis pigmentosa.

37. The method of Claim 34, wherein the retinal abnormality is characterized by retinal degeneration or retinal dysplasia.

38. The method of Claim 34, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

39. The method of Claim 27, wherein the eye abnormality is a cataract.

40. The method of Claim 39, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathyroidism or Conradi syndrome.

41. The method of Claim 27, wherein the developmental abnormality comprises embryonic lethality or reduced viability.

42. The method of Claim 27, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

43. The method of Claim 27, wherein the immunological disorders are systemic lupus erythematosis; rheumatoid arthritis; juvenile chronic arthritis; spondyloarthropathies;

systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation-associated diseases including graft rejection and graft-versus-host disease.

44. The method of Claim 27, wherein said bone metabolic abnormality or disorder is arthritis, osteoporosis or osteopetrosis.

45. The method of Claim 26, wherein the non-human transgenic animal exhibits at least one of the following physiological characteristics compared with gender matched wild-type littermates: increased anxiety-like response during open field testing; decreased anxiety during open field testing; decreased locomotor activity during open field testing; abnormal circadian rhythm during home-cage activity testing (low activity during the light phase); abnormal circadian rhythm during home-cage activity testing including decreased ambulatory counts; hypoactivity with no circadian rhythm; abnormal circadian rhythm during home-cage activity testing including increased ambulatory counts; increased stress induced hyperthermia; decreased stress induced hyperthermia; impaired motor coordination during inverted screen testing; increased immobility in tail suspension (increased depressive-like response); increased depressive-like response during tail suspension testing; increased immobility or decreased depressive-like response during tail suspension testing; decreased startle response during prepulse inhibition testing; no startle response indicating deafness; or impaired hearing; decreased prepulse inhibition with impaired sensorimotor gating/attention; decreased responsiveness in hot plate testing; decreased latency to respond in hot plate testing; opthalmological abnormalities; increased mean artery-to-vein ratio; resistance to pupil dilating drug cyclopentolate hydrochloride; squinty eyes; squint eyes with white spots; cataracts; retinal degeneration; impaired vision; decreased basal body temperature; decreased heart rate; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; decreased mean serum triglyceride levels; enhanced glucose tolerance; impaired glucose tolerance; decreased mean serum insulin levels; increased mean serum calcium; increased urobilinogen, notable lipemia; increased albumin, alanine amino transferase, phosphorus and potassium levels; increased mean serum alkaline phosphatase levels; increased blood urea nitrogen; increased percentage of granulocyte; increased total white blood cell (WBC) count; increased mean absolute neutrophil count; neutropenia; increased absolute lymphocyte count; increased absolute monocyte count; increased monocytes and DC in spleen (CD11b+, CD11b+c+); increased mean platelet count; increased natural killer (NK) cells in lymph node; decreased neutrophil count; decreased natural killer (NK) cells; decreased mean red blood cell (RBC) count, hemoglobin concentration, and hematocrit; increased mean red cell distribution width; decreased mean corpuscular volume and mean corpuscular hemoglobin; decreased mean platelet count and increased platelet volume; increase B cell number in lymph node; increase in B cell subtypes in Peyer's patches; increased percentage of B cells in lymph node; increase CD25+ cells; increased thymic DN, decreased DP T cells; increased CD19+ cells in lymph node; increased CD117 in bone marrow cells; increased mean percentage of CD4 cells; increased CD8 cells and decrease in B cells; increased percentage CD11b+ cells in peritoneal lavage; increased percentage of B220+ CD11b Low CD23− cells; increased percentages of B220− CD11 Low and CD11b− cells in peritoneal lavage; increased percentage of B220−CD11bHi cells in peritoneal lavage; decreased percentage of B220+ CD11b− CD23+ cells in peritoneal lavage; increased percentage of B220− CD43 Hi cells in bone marrow; increased CD11b+ CD11c− cells in spleen; increase in CD62hi, CD44int subsets of CD4 and CD8 cells; increase in peritoneal CD117 cells; increase TcRbeta/CD38 cells in Peyer's patches; increased percentage of TcRbeta+ cells in thymus; increased percentages of CD11b+CD11c+ in lymph node; decreased percentage of B220+ Hi CD23+cells in peritoneal lavage; decreased percentage of B220+ Med CD23−cells in peritoneal lavage; decreased percentages of CD62L Hi CD44 Dim CD4+ and CD8+ cells in spleen; decreased percentage of B220−CD11b Hi cells; decreased mean percentages of CD4 and CD8 cells in lymph node and spleen; increased memory T cells [increased CD62L lo CD44hi]; decreased T cell:B cell ratio; decreased naive T cells; decreased CD117 cells in peritoneal lavage; decreased mean percentage of CD8 cells, increased IgG1 response to ovalbumin challenge; increased IgG2a response to ovalbumin challenge; increased mean serum IL-6 response to LPS challenge; increased TNF alpha response to LPS challenge; increased serum MCP-1 response to LPS challenge; increased mean serum IgM level; increased serum IgA; increase mean serum IgG1; increased mean serum IgG3; decreased serum IgG1 response to ovalbumin challenge; decreased serum IgG2a response to ovalbumin challenge; decreased mean serum IgA level; decreased serum IgG2a level; decrease in serum IgG3 level; increased skin fibroblast proliferation rate; decreased skin fibroblast proliferation rate; increased mean percent of total body fat and total fat mass; increased mean body weight; increased mean body length; increased total tissue mass (TTM); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD) in total body, femur and vertebrae; decreased bone mineral content (BMC); decreased bone mineral density index; decreased volumetric bone mineral density (vBMD);

decreased mean femoral midshaft cortical thickness and cross-sectional area; decreased mean vertebral trabecular bone volume, number and connectivity density; osteopetrosis; osteoporosis; chronic inflammation in various tissues; bilateral hydronephrosis (moderate to severe) and inflammation; "pear shaped abdomen"; bilaterally enlarged kidneys, suggesting polycystic kidney disease; degeneration of the Organ of Corti; hepatocellular dysfunction; biliary obstruction; hepatosplenomegaly characterized by histiocytic infiltrate; histiocytosis in the small intestine, lymph nodes and spleen; splenomegaly, lymphadenopathy and lymphadenopathy; hyperplasia of adenoid and tonsils; mild-moderate extra medullary hematopoiesis; homozygous mice were small, dehydrated and exhibited decreased subcutaneous fat depots; lipopenia; ulcerous colitis; diffuse marked degeneration of sensory cochlear hair cells in the inner ear, characterized by a complete loss of both inner and outer cochlear hair cells on the basilar membrane; gastric mucosal hyperplasia and chronic inflammation; in creased stomach weight; defective spermatogenesis in the testes; hypospermia and defective spermatozoa in the epididymus; male infertility; lysosomal storage disease; anemia; growth retardation; reduced viability; perinatal lethality with decreased lymphocytes and lipopenia; homozygous embryonic lethality; and heterozygous embryonic lethality.

46. An agent identified by the method of Claim 26.

47. The agent of Claim 46 which is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

48. The agent of Claim 47, wherein the agonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

49. The agent of Claim 47, wherein the antagonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

50. A method of identifying an agent that modulates a physiological characteristic associated with a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

51. The method of Claim 50, wherein the non-human transgenic animal exhibits at least one of the following physiological characteristics compared with gender matched wild-type littermates: increased anxiety-like response during open field testing; decreased anxiety during open field testing; decreased locomotor activity during open field testing; abnormal circadian rhythm during home-cage activity testing (low activity during the light phase); abnormal circadian rhythm during home-cage activity testing including decreased ambulatory counts; hypoactivity with no circadian rhythm; abnormal circadian rhythm during home-cage activity testing including increased ambulatory counts; increased stress induced hyperthermia; decreased stress induced hyperthermia; impaired motor coordination during inverted screen testing; increased immobility in tail suspension (increased depressive-like response); increased depressive-like response during tail suspension testing; increased immobility or decreased depressive-like response during tail suspension testing; decreased startle response during prepulse inhibition testing; no startle response indicating deafness; or impaired hearing; decreased prepulse inhibition with impaired sensorimotor gating/attention; decreased responsiveness in hot plate testing; decreased latency to respond in hot plate testing; opthalmological abnormalities; increased mean artery-to-vein ratio; resistance to pupil dilating drug cyclopentolate hydrochloride; squinty eyes; squint eyes with white spots; cataracts; retinal degeneration; impaired vision; decreased basal body temperature; decreased heart rate; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; decreased mean serum triglyceride levels; enhanced glucose tolerance; impaired glucose tolerance; decreased mean serum insulin levels; increased mean serum calcium; increased urobilinogen, notable lipemia; increased albumin, alanine amino transferase, phosphorus and potassium levels; increased mean serum alkaline phosphatase levels; increased blood urea nitrogen; increased percentage of granulocyte; increased total white blood cell (WBC) count; increased mean absolute neutrophil count; neutropenia; increased absolute lymphocyte count; increased absolute monocyte count; increased monocytes and DC in spleen (CD11b+, CD11b+c+); increased mean platelet count; increased natural killer (NK) cells in lymph node; decreased neutrophil count; decreased natural killer (NK) cells; decreased mean red blood cell (RBC) count, hemoglobin concentration, and hematocrit; increased mean red cell distribution width; decreased mean corpuscular volume and mean corpuscular hemoglobin; decreased mean platelet count and increased platelet volume; increase B cell number in lymph node; increase in B cell subtypes in Peyer's patches; increased percentage of B cells in lymph node; increase CD25+ cells; increased thymic DN, decreased DP T cells; increased CD19+ cells in lymph node; increased CD117 in bone marrow cells; increased mean percentage of CD4 cells; increased CD8 cells and decrease in B cells; increased percentage CD11b+ cells in peritoneal lavage; increased percentage of B220+CD11b Low CD23– cells; increased percentages of B220– CD11 Low and CD11b– cells in peritoneal lavage; increased percentage of B220–CD11bHi cells in peritoneal lavage; decreased percentage of B220+ CD11b– CD23+ cells in peritoneal lavage; increased percentage of B220– CD43 Hi cells in bone marrow; increased CD11b+ CD11c– cells in spleen; increase in CD62hi, CD44int subsets of CD4 and CD8 cells; increase in peritoneal CD117 cells; increase TcRbeta/CD38 cells in Peyer's patches; increased percentage of TcRbeta+ cells in thymus; increased percentages of CD11b+CD11c+ in lymph node; decreased percentage of B220+ Hi CD23+ cells in peritoneal lavage; decreased percentage of B220+ Med CD23–cells in peritoneal lavage; decreased percentages of CD62L Hi CD44 Dim CD4+ and CD8+ cells in spleen; decreased percentage of B220–CD11b Hi cells; decreased mean percentages of CD4 and CD8 cells in lymph node and spleen; increased memory T cells [increased CD62L lo CD44hi]; decreased T cell:B cell ratio; decreased naive T cells; decreased CD117 cells in peritoneal lavage; decreased mean percentage of CD8 cells, increased IgG1 response to ovalbumin challenge; increased IgG2a response to ovalbumin challenge; increased mean serum IL-6 response to LPS challenge; increased TNF alpha response to LPS challenge; increased serum MCP-1 response to LPS challenge; increased mean serum IgM level; increased serum IgA; increase mean serum IgG1; increased mean serum IgG3; decreased serum IgG1 response to ovalbumin challenge; decreased serum IgG2a response to ovalbumin challenge; decreased mean serum IgA level; decreased serum IgG2a level; decrease in serum IgG3 level; increased skin fibroblast proliferation rate; decreased skin fibroblast proliferation rate; increased mean percent of total body fat and total fat mass; increased mean body weight; increased mean body length; increased total tissue mass (TTM); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD) in total body, femur and vertebrae; decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; osteopetrosis; osteoporosis; chronic inflammation in various tissues; bilateral hydronephrosis (moderate to severe) and inflammation; "pear shaped abdomen"; bilaterally enlarged kidneys, suggesting polycystic kidney disease; degeneration of the Organ of Corti; hepatocellular dysfunction; biliary obstruction; hepatosplenomegaly characterized by histiocytic infiltrate; histiocytosis in the small intestine, lymph nodes and spleen; splenomegaly, lymphadenopathy and lymphadenopathy; hyperplasia of adenoid and tonsils; mild-moderate extra medullary hematopoiesis; homozygous mice were small, dehydrated and exhibited decreased subcutaneous fat depots; lipopenia; ulcerous colitis; diffuse marked degeneration of sensory cochlear hair cells in the inner ear, characterized by a complete loss of both inner and outer cochlear hair cells on the basilar membrane; gastric mucosal hyperplasia and chronic inflammation; in creased stomach weight; defective spermatogenesis in the testes; hypospermia and defective spermatozoa in the epididymus; male infertility; lysosomal storage disease; anemia; growth retardation; reduced viability; perinatal lethality with decreased lymphocytes and lipopenia; homozygous embryonic lethality; and heterozygous embryonic lethality.

52. An agent identified by the method of Claim 50.

53. The agent of Claim 52 which is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

54. The agent of Claim 53, wherein the agonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

55. The agent of Claim 53, wherein the antagonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

56. A method of identifying an agent which modulates a behavior associated with a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

57. The method of Claim 56, wherein the behavior is an increased anxiety-like response during open field activity testing.

58. The method of Claim 56, wherein the behavior is a decreased anxiety-like response during open field activity testing.

59. The method of Claim 56, wherein the behavior is an abnormal circadian rhythm during home-cage activity testing.

60. The method of Claim 56, wherein the behavior is an enhanced motor coordination during inverted screen testing.

61. The method of Claim 56, wherein the behavior is an impaired motor coordination during inverted screen testing.

62. The method of Claim 56, wherein the behavior is depression, generalized anxiety disorders, attention deficit disorder, sleep disorder, hyperactivity disorder, obsessive compulsive disorder, schizophrenia, cognitive disorders, hyperalgesia or sensory disorders.

63. An agent identified by the method of Claim 56.

64. The agent of Claim 63 which is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

65. The agent of Claim 64, wherein the agonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

66. The agent of Claim 64, wherein the antagonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

67. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) administering a test agent to said non-human transgenic animal; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in the non-human transgenic animal.

68. The method of Claim 67, wherein the neurological disorder is an increased anxiety-like response during open field activity testing.

69. The method of Claim 67, wherein the neurological disorder is a decreased anxiety-like response during open field activity testing.

70. The method of Claim 67, wherein the neurological disorder is an abnormal circadian rhythm during home-cage activity testing.

71. The method of Claim 67, wherein the neurological disorder is an enhanced motor coordination during inverted screen testing.

72. The method of Claim 67, wherein the neurological disorder is an impaired motor coordination during inverted screen testing.

73. The method of Claim 73, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

74. The method of Claim 67, wherein the eye abnormality is a retinal abnormality.

75. The method of Claim 67, wherein the eye abnormality is consistent with vision problems or blindness.

76. The method of Claim 74, wherein the retinal abnormality is consistent with retinitis pigmentosa.

77. The method of Claim 74, wherein the retinal abnormality is characterized by retinal degeneration or retinal dysplasia.

78. The method of Claim 74, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

79. The method of Claim 67, wherein the eye abnormality is a cataract.

80. The method of Claim 79, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathyroidism or Conradi syndrome.

81. The method of Claim 67, wherein the developmental abnormality comprises embryonic lethality or reduced viability.

82. The method of Claim 67, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

83. The method of Claim 67, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

84. The method of Claim 67, wherein said bone metabolic abnormality or disorder is arthritis, osteoporosis or osteopetrosis.

85. The method of Claim 67, wherein the non-human transgenic animal exhibits at least one of the following physiological characteristics compared with gender matched wild-type littermates: increased anxiety-like response during open field testing; decreased anxiety during open field testing; decreased locomotor activity during open field testing; abnormal circadian rhythm during home-cage activity testing (low activity during the light phase); abnormal circadian rhythm during home-cage activity testing including decreased ambulatory counts; hypoactivity with no circadian rhythm; abnormal circadian rhythm during home-cage activity testing including increased ambulatory counts; increased stress induced hyperthermia; decreased stress induced hyperthermia; impaired motor coordination during inverted screen testing; increased immobility in tail suspension (increased depressive-like response); increased depressive-like response during tail suspension testing; increased immobility or decreased depressive-like response during tail suspension testing; decreased startle response during prepulse inhibition testing; no startle response indicating deafness; or impaired hearing; decreased prepulse inhibition with impaired sensorimotor gating/attention; decreased responsiveness in hotplate testing; decreased latency to respond in hot plate testing; opthalmological abnormalities; increased mean artery-to-vein ratio; resistance to pupil dilating drug cyclopentolate hydrochloride; squinty eyes; squint eyes with white spots; cataracts; retinal degeneration; impaired vision; decreased basal body temperature; decreased heart rate; increased mean systolic blood pressure; increased insulin sensitivity; increased mean fasting serum glucose levels; decreased mean serum glucose levels; increased mean serum cholesterol levels; decreased mean serum cholesterol levels; increased mean serum triglyceride levels; decreased mean serum triglyceride levels; enhanced glucose tolerance; impaired glucose tolerance; decreased mean serum insulin levels; increased mean serum calcium; increased urobilinogen, notable lipemia; increased albumin, alanine amino transferase, phosphorus and potassium levels; increased mean serum alkaline phosphatase levels; increased blood urea nitrogen; increased percentage of granulocyte; increased total white blood cell (WBC) count; increased mean absolute neutrophil count; neutropenia; increased absolute lymphocyte count; increased absolute monocyte count; increased monocytes and DC in spleen (CD11b+, CD11b+c+); increased mean platelet count; increased natural killer (NK) cells in lymph node; decreased neutrophil count; decreased natural killer (NK) cells; decreased mean red blood cell (RBC) count, hemoglobin concentration, and hematocrit; increased mean red cell distribution width; decreased mean corpuscular volume and mean corpuscular hemoglobin; decreased mean platelet count and increased platelet volume; increase B cell number in lymph node; increase in B cell subtypes in Peyer's patches; increased percentage of B cells in lymph node; increase CD25+ cells; increased thymic DN, decreased DP T cells; increased CD19+ cells in lymph node; increased CD117 in bone marrow cells; increased mean percentage of CD4 cells; increased CD8 cells and decrease in B cells; increased percentage CD11b+ cells in peritoneal lavage; increased percentage of B220+CD11b Low CD23− cells; increased percentages of B220− CD11 Low and CD11b− cells in peritoneal lavage; increased percentage of B220−CD11bHi cells in peritoneal lavage; decreased percentage of B220+ CD11b− CD23+ cells in peritoneal lavage; increased percentage of B220− CD43 Hi cells in bone marrow; increased CD11b+CD11c− cells in spleen; increase in CD62hi, CD44int subsets of CD4 and CD8 cells; increase in peritoneal CD117 cells; increase TcRbeta/CD38 cells in Peyer's patches; increased percentage of TcRbeta+ cells in thymus; increased percentages of CD11b+CD11c+ in lymph node; decreased percentage of B220+ Hi CD23+ cells in peritoneal lavage; decreased percentage of B220+ Med CD23−cells in peritoneal lavage; decreased percentages of CD62L Hi CD44 Dim CD4+ and CD8+ cells in spleen; decreased percentage of B220−CD11b Hi cells; decreased mean percentages of CD4 and CD8 cells in lymph node and spleen; increased memory T cells [increased CD62L lo CD44hi]; decreased T cell:B cell ratio; decreased naive T cells; decreased CD117 cells in peritoneal lavage; decreased mean percentage of CD8 cells, increased IgG1 response to ovalbumin challenge; increased IgG2a response to ovalbumin challenge; increased mean serum IL-6 response to LPS challenge; increased TNF alpha response to LPS challenge; increased serum MCP-1 response to LPS challenge; increased mean serum IgM level; increased serum IgA; increase mean serum IgG1; increased mean serum IgG3; decreased serum IgG1 response to ovalbumin challenge; decreased serum IgG2a response to ovalbumin challenge; decreased mean serum IgA level; decreased serum IgG2a level; decrease in serum IgG3 level; increased skin fibroblast proliferation rate; decreased skin fibroblast proliferation rate; increased mean percent of total body fat and total fat mass; increased mean body weight; increased mean body length; increased total tissue mass (TTM); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased bone mineral density (BMD) in total body, femur and vertebrae; decreased bone mineral content (BMC); decreased bone mineral density index; decreased volumetric bone mineral density (vBMD); decreased mean femoral midshaft cortical thickness and cross-sectional area; decreased mean vertebral trabecular bone volume, number and connectivity density; osteopetrosis; osteoporosis; chronic inflammation in various tissues; bilateral hydronephrosis (moderate to severe) and inflammation; "pear shaped abdomen"; bilaterally enlarged kidneys, suggesting polycystic kidney disease; degeneration of the Organ of Corti; hepatocellular dysfunction; biliary obstruction; hepatosplenomegaly characterized by histiocytic infiltrate; histiocytosis in the small intestine, lymph nodes and spleen; splenomegaly, lymphadenopathy and lymphadenopathy; hyperplasia of adenoid and tonsils; mild-moderate extra medullary hematopoiesis; homozygous mice were small, dehydrated and exhibited decreased subcutaneous fat depots; lipopenia; ulcerous colitis; diffuse marked degeneration of sensory cochlear hair cells in the inner ear, characterized by a complete loss of both inner and outer cochlear hair cells on the basilar membrane; gastric mucosal hyperplasia and chronic inflammation; in creased stomach weight; defective spermatogenesis in the testes; hypospermia and defective spermatozoa in the epididymus; male infertility; lysosomal storage disease; anemia; growth retardation; reduced viability; perinatal lethality with decreased lymphocytes and lipopenia; homozygous embryonic lethality; and heterozygous embryonic lethality.

86. An agent identified by the method of Claim 67.

87. The agent of Claim 86 which is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

88. The agent of Claim 87, wherein the agonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

89. The agent of Claim 87, wherein the antagonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

90. A therapeutic agent identified by the method of Claim 67.

91. A method of identifying an agent that modulates the expression of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) contacting a test agent with a host cell expressing a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide; and (b) determining whether the test agent modulates the expression of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide by the host cell.

92. An agent identified by the method of Claim 91.

93. The agent of Claim 92 which is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

94. The agent of Claim 93, wherein the agonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

95. The agent of Claim 93, wherein the antagonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

96. A method of evaluating a therapeutic agent capable of affecting a condition associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal whose genome comprises a disruption of the gene which encodes for the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

97. The method of Claim 96, wherein the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

98. A therapeutic agent identified by the method of Claim 96.

99. The therapeutic agent of Claim 98 which is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

100. The therapeutic agent of Claim 99, wherein the agonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

101. The therapeutic agent of Claim 99, wherein the antagonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

102. A pharmaceutical composition comprising the therapeutic agent of Claim 98.

103. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a subject in need of such treatment whom may already have the disorder, or may be prone to have the disorder or may be in whom the disorder is to be prevented, a therapeutically effective amount of the therapeutic agent of Claim 94, or agonists or antagonists thereof, thereby effectively treating or preventing or ameliorating said disorder.

104. The method of Claim 103, wherein the neurological disorder is an increased anxiety-like response during open field activity testing.

105. The method of Claim 103, wherein the neurological disorder is a decreased anxiety-like response during open field activity testing.

106. The method of Claim 103, wherein the neurological disorder is an abnormal circadian rhythm during home-cage activity testing.

107. The method of Claim 103, wherein the neurological disorder is an enhanced motor coordination during inverted screen testing.

108. The method of Claim 103, wherein the neurological disorder is an impaired motor coordination during inverted screen testing.

109. The method of Claim 103, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

110. The method of Claim 103, wherein the eye abnormality is a retinal abnormality.

111. The method of Claim 103, wherein the eye abnormality is consistent with vision problems or blindness.

112. The method of Claim 110, wherein the retinal abnormality is consistent with retinitis pigmentosa.

113. The method of Claim 110, wherein the retinal abnormality is characterized by retinal degeneration or retinal dysplasia.

114. The method of Claim 110, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

115. The method of Claim 103, wherein the eye abnormality is a cataract.

116. The method of Claim 115, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathyroidism or Conradi syndrome.

117. The method of Claim 103, wherein the developmental abnormality comprises embryonic lethality or reduced viability.

118. The method of Claim 103, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

119. The method of Claim 103, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

120. The method of Claim 103, wherein said bone metabolic abnormality or disorder is arthritis, osteoporosis or osteopetrosis.

121. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising:

(a) providing a non-human transgenic animal cell culture, each cell of said culture comprising a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide;

(b) administering a test agent to said cell culture; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said cell culture.

122. The method of Claim 121, wherein the neurological disorder is an increased anxiety-like response during open field activity testing.

123. The method of Claim 121, wherein the neurological disorder is a decreased anxiety-like response during open field activity testing.

124. The method of Claim 121, wherein the neurological disorder is an abnormal circadian rhythm during home-cage activity testing.

125. The method of Claim 121, wherein the neurological disorder is an enhanced motor coordination during inverted screen testing.

126. The method of Claim 121, wherein the neurological disorder is an impaired motor coordination during inverted screen testing.

127. The method of Claim 121, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

128. The method of Claim 121, wherein the eye abnormality is a retinal abnormality.

129. The method of Claim 121, wherein the eye abnormality is consistent with vision problems or blindness.

130. The method of Claim 128, wherein the retinal abnormality is consistent with retinitis pigmentosa.

131. The method of Claim 128, wherein the retinal abnormality is characterized by retinal degeneration or retinal dysplasia.

132. The method of Claim 128, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

133. The method of Claim 121, wherein the eye abnormality is a cataract.

134. The method of Claim 133, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathyroidism or Conradi syndrome.

135. The method of Claim 121, wherein the developmental abnormality comprises embryonic lethality or reduced viability.

136. The method of Claim 121, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

137. The method of Claim 121, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

138. The method of Claim 121, wherein said bone metabolic abnormality or disorder is arthritis, osteoporosis or osteopetrosis.

139. An agent identified by the method of Claim 121.

140. The agent of Claim 139 which is an agonist or antagonist of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

141. The agent of Claim 140, wherein the agonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

142. The agent of Claim 140, wherein the antagonist is an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody.

143. A therapeutic agent identified by the method of Claim 121.

144. A method of modulating a phenotype associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a subject whom may already have the phenotype, or may be prone to have the phenotype or may be in whom the phenotype is to be prevented, an effective amount of the agent of Claim 46, or agonists or antagonists thereof, thereby effectively modulating the phenotype.

145. A method of modulating a physiological characteristic associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a subject whom may already exhibit the physiological characteristic, or may be prone to exhibit the physiological characteristic or may be in whom the physiological characteristic is to be prevented, an effective amount of the agent of Claim 52, or agonists or antagonists thereof, thereby effectively modulating the physiological characteristic.

146. A method of modulating a behavior associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a subject whom may already exhibit the behavior, or may be prone to exhibit the behavior or may be in whom the exhibited behavior is to be prevented, an effective amount of the agent of Claim 63, or agonists or antagonists thereof, thereby effectively modulating the behavior.

147. A method of modulating the expression of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a host cell expressing said PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, an effective amount of the agent of Claim 92, or agonists or antagonists thereof, thereby effectively modulating the expression of said polypeptide.

148. A method of modulating a condition associated with a disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a subject whom may have the condition, or may be prone to have the condition or may be in whom the condition is to be prevented, a therapeutically effective amount of the therapeutic agent of Claim 98, or agonists or antagonists thereof, thereby effectively modulating the condition.

149. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the method comprising administering to a non-human transgenic animal cell culture, each cell of said culture comprising a disruption of the gene which encodes for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, a therapeutically effective amount of the agent of Claim 139, or agonists or antagonists thereof, thereby effectively treating or preventing or ameliorating said disorder.

BRIEF DESCRIPTION OF THE DRAWINGS

FIG. 1 shows a nucleotide sequence (SEQ ID NO:1) of a native sequence PRO226 cDNA, wherein SEQ ID NO:1 is a clone designated herein as "DNA33460-1166" (UNQ200).

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO257 cDNA, wherein SEQ ID NO:3 is a clone designated herein as "DNA35841-1173" (UNQ224).

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO268 cDNA, wherein SEQ ID NO:5 is a clone designated herein as "DNA39427-1179" (UNQ235).

FIG. 6 shows the amino acid sequence (SEQ ID NO:6) derived from the coding sequence of SEQ ID NO:5 shown in FIG. 5.

FIG. 7 shows a nucleotide sequence (SEQ ID NO: 7) of a native sequence PRO290 cDNA, wherein SEQ ID NO:7 is a clone designated herein as "DNA35680-1212" (UNQ253).

FIG. 8 shows the amino acid sequence (SEQ ID NO: 8) derived from the coding sequence of SEQ ID NO:7 shown in FIG. 7.

FIG. 9 shows a nucleotide sequence (SEQ ID NO:9) of a native sequence PRO36006 cDNA, wherein SEQ ID NO:9 is a clone designated herein as "DNA225543" (UNQ294).

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO363 cDNA, wherein SEQ ID NO:11 is a clone designated herein as "DNA45419-1252" (UNQ318).

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO365 cDNA, wherein SEQ ID NO:13 is a clone designated herein as "DNA46777-1253" (UNQ320).

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO382 cDNA, wherein SEQ ID NO:15 is a clone designated herein as "DNA45234-1277" (UNQ323).

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO444 cDNA, wherein SEQ ID NO:17 is a clone designated herein as "DNA26846-1397" (UNQ328).

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO705 cDNA, wherein SEQ ID NO:19 is a clone designated herein as "DNA50914-1289" (UNQ369).

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO1071 cDNA, wherein SEQ ID NO:21 is a clone designated herein as "DNA58847-1383" (UNQ528).

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO1125 cDNA, wherein SEQ ID NO:23 is a clone designated herein as "DNA60619-1482" (UNQ563).

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO1134 cDNA, wherein SEQ ID NO:25 is a clone designated herein as "DNA56865-1491" (UNQ572).

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO1155 cDNA, wherein SEQ ID NO:27 is a clone designated herein as "DNA59849-1504" (UNQ585).

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO1281 cDNA, wherein SEQ ID NO:29 is a clone designated herein as "DNA59820-1549" (UNQ651).

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO1343 cDNA, wherein SEQ ID NO:31 is a clone designated herein as "DNA66675-1587" (UNQ698).

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO1379 cDNA, wherein SEQ ID NO:33 is a clone designated herein as "DNA59828-1608" (UNQ716).

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO1380 cDNA, wherein SEQ ID NO:35 is a clone designated herein as "DNA60740-1615" (UNQ717).

FIG. 36 shows the amino acid sequence (SEQ ID NO: 36) derived from the coding sequence of SEQ ID NO:35 shown in FIG. 35.

FIG. 37 shows a nucleotide sequence (SEQ ID NO:37) of a native sequence PRO1387 cDNA, wherein SEQ ID NO:37 is a clone designated herein as "DNA68872-1620" (UNQ722).

FIG. 38 shows the amino acid sequence (SEQ ID NO: 38) derived from the coding sequence of SEQ ID NO:37 shown in FIG. 37.

FIG. 39 shows a nucleotide sequence (SEQ ID NO:39) of a native sequence PRO1419 cDNA, wherein SEQ ID NO:39 is a clone designated herein as "DNA71290-1630" (UNQ733).

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO1433 cDNA, wherein SEQ ID NO:41 is a clone designated herein as "DNA71184-1634" (UNQ738).

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO1474 cDNA, wherein SEQ ID NO:43 is a clone designated herein as "DNA73739-1645" (UNQ745).

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO1550 cDNA, wherein SEQ ID NO:45 is a clone designated herein as "DNA76393-1664" (UNQ762).

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO1571 cDNA, wherein SEQ ID NO:47 is a clone designated herein as "DNA73730-1679" (UNQ777).

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO1572 cDNA, wherein SEQ ID NO:49 is a clone designated herein as "DNA73734-1680" (UNQ778).

FIG. 50 shows the amino acid sequence (SEQ ID NO: 50) derived from the coding sequence of SEQ ID NO:49 shown in FIG. 49.

FIG. 51 shows a nucleotide sequence (SEQ ID NO:51) of a native sequence PRO1759 cDNA, wherein SEQ ID NO:51 is a clone designated herein as "DNA76531-1701" (UNQ832).

FIG. 52 shows the amino acid sequence (SEQ ID NO: 52) derived from the coding sequence of SEQ ID NO:51 shown in FIG. 51.

FIG. 53 shows a nucleotide sequence (SEQ ID NO:53) of a native sequence PRO1904 cDNA, wherein SEQ ID NO:53 is a clone designated herein as "DNA82372" (UNQ886).

FIG. 54 shows the amino acid sequence (SEQ ID NO: 54) derived from the coding sequence of SEQ ID NO:53 shown in FIG. 53.

FIG. 55 shows a nucleotide sequence (SEQ ID NO:55) of a native sequence PRO35193 cDNA, wherein SEQ ID NO:55 is a clone designated herein as "DNA225681" (UNQ983).

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO4341 cDNA, wherein SEQ ID NO:57 is a clone designated herein as "DNA81761-2583" (UNQ1895).

FIG. 58 shows the amino acid sequence (SEQ ID NO:58) derived from the coding sequence of SEQ ID NO:57 shown in FIG. 57.

FIG. 59 shows a nucleotide sequence (SEQ ID NO:59) of a native sequence PRO4348 cDNA, wherein SEQ ID NO:59 is a clone designated herein as "DNA92232-2589" (UNQ1902).

FIG. 60 shows the amino acid sequence (SEQ ID NO:60) derived from the coding sequence of SEQ ID NO:59 shown in FIG. 59.

FIG. 61 shows a nucleotide sequence (SEQ ID NO:61) of a native sequence PRO4369 cDNA, wherein SEQ ID NO:61 is a clone designated herein as "DNA92289-2598" (UNQ1911).

FIG. 62 shows the amino acid sequence (SEQ ID NO: 62) derived from the coding sequence of SEQ ID NO:61 shown in FIG. 61.

FIG. 63 shows a nucleotide sequence (SEQ ID NO:63) of a native sequence PRO4381 cDNA, wherein SEQ ID NO:63 is a clone designated herein as "DNA92225-2603" (UNQ1916).

FIG. 64 shows the amino acid sequence (SEQ ID NO: 64) derived from the coding sequence of SEQ ID NO:63 shown in FIG. 63.

FIG. 65 shows a nucleotide sequence (SEQ ID NO:65) of a native sequence PRO4407 cDNA, wherein SEQ ID NO:65 is a clone designated herein as "DNA92264-2616" (UNQ1932).

FIG. 66 shows the amino acid sequence (SEQ ID NO: 66) derived from the coding sequence of SEQ ID NO:65 shown in FIG. 65.

FIG. 67 shows a nucleotide sequence (SEQ ID NO:67) of a native sequence PRO4425 cDNA, wherein SEQ ID NO:67 is a clone designated herein as "DNA93011-2637" (UNQ1942).

FIG. 68 shows the amino acid sequence (SEQ ID NO:68) derived from the coding sequence of SEQ ID NO:67 shown in FIG. 67.

FIG. 69 shows a nucleotide sequence (SEQ ID NO:69) of a native sequence PRO4985 cDNA, wherein SEQ ID NO:69 is a clone designated herein as "DNA59770-2652" (UNQ2426).

FIG. 70 shows the amino acid sequence (SEQ ID NO: 70) derived from the coding sequence of SEQ ID NO:69 shown in FIG. 69.

FIG. 71 shows a nucleotide sequence (SEQ ID NO:71) of a native sequence PRO4989 cDNA, wherein SEQ ID NO:71 is a clone designated herein as "DNA80135-2655" (UNQ2429).

FIG. 72 shows the amino acid sequence (SEQ ID NO: 72) derived from the coding sequence of SEQ ID NO:71 shown in FIG. 71.

FIG. 73 shows a nucleotide sequence (SEQ ID NO:73) of a native sequence PRO5737 cDNA, wherein SEQ ID NO:73 is a clone designated herein as "DNA92929-2534-1" (UNQ2456).

FIG. 74 shows the amino acid sequence (SEQ ID NO:74) derived from the coding sequence of SEQ ID NO:73 shown in FIG. 73.

FIG. 75 shows a nucleotide sequence (SEQ ID NO:75) of a native sequence PRO5800 cDNA, wherein SEQ ID NO:75 is a clone designated herein as "DNA108912-2680" (UNQ2500).

FIG. 76 shows the amino acid sequence (SEQ ID NO: 76) derived from the coding sequence of SEQ ID NO:75 shown in FIG. 75.

FIG. 77 shows a nucleotide sequence (SEQ ID NO:77) of a native sequence PRO5993 cDNA, wherein SEQ ID NO:77 is a clone designated herein as "DNA100276-2684" (UNQ2504).

FIG. 78 shows the amino acid sequence (SEQ ID NO:78) derived from the coding sequence of SEQ ID NO:77 shown in FIG. 77.

FIG. 79 shows a nucleotide sequence (SEQ ID NO:79) of a native sequence PRO6017 cDNA, wherein SEQ ID NO:79 is a clone designated herein as "DNA96860-2700" (UNQ2524).

FIG. 80 shows the amino acid sequence (SEQ ID NO: 80) derived from the coding sequence of SEQ ID NO:79 shown in FIG. 79.

FIG. 81 shows a nucleotide sequence (SEQ ID NO: 81) of a native sequence PRO7174 cDNA, wherein SEQ ID NO:81 is a clone designated herein as "DNA96883-2745" (UNQ2784).

FIG. 82 shows the amino acid sequence (SEQ ID NO: 82) derived from the coding sequence of SEQ ID NO:81 shown in FIG. 81.

FIG. 83 shows a nucleotide sequence (SEQ ID NO:83) of a native sequence PRO9744 cDNA, wherein SEQ ID NO:83 is a clone designated herein as "DNA136110-2763" (UNQ3003).

FIG. 84 shows the amino acid sequence (SEQ ID NO: 84) derived from the coding sequence of SEQ ID NO:83 shown in FIG. 83.

FIG. 85 shows a nucleotide sequence (SEQ ID NO:85) of a native sequence PRO9821 cDNA, wherein SEQ ID NO:85 is a clone designated herein as "DNA108725-2766" (UNQ3023).

FIG. 86 shows the amino acid sequence (SEQ ID NO: 86) derived from the coding sequence of SEQ ID NO:85 shown in FIG. 85.

FIG. 87 shows a nucleotide sequence (SEQ ID NO:87) of a native sequence PRO9852 cDNA, wherein SEQ ID NO:87 is a clone designated herein as "DNA129332-2775" (UNQ3037).

FIG. 88 shows the amino acid sequence (SEQ ID NO:88) derived from the coding sequence of SEQ ID NO:87 shown in FIG. 87.

FIG. 89 shows a nucleotide sequence (SEQ ID NO: 89) of a native sequence PRO9873 cDNA, wherein SEQ ID NO: 89 is a clone designated herein as "DNA143076-2787" (UNQ3054).

FIG. 90 shows the amino acid sequence (SEQ ID NO:90) derived from the coding sequence of SEQ ID NO:89 shown in FIG. 89.

FIG. 91 shows a nucleotide sequence (SEQ ID NO:91) of a native sequence PRO10196 cDNA, wherein SEQ ID NO:91 is a clone designated herein as "DNA144841-2816" (UNQ3115).

FIG. 92 shows the amino acid sequence (SEQ ID NO:92) derived from the coding sequence of SEQ ID NO:91 shown in FIG. 91.

FIG. 93 shows a nucleotide sequence (SEQ ID NO:93) of a native sequence PRO34778 cDNA, wherein SEQ ID NO:93 is a clone designated herein as "DNA220432" (UNQ3966).

FIG. 94 shows the amino acid sequence (SEQ ID NO:94) derived from the coding sequence of SEQ ID NO:93 shown in FIG. 93.

FIG. 95 shows a nucleotide sequence (SEQ ID NO:95) of a native sequence PRO20233 cDNA, wherein SEQ ID NO:95 is a clone designated herein as "DNA165608" (UNQ6208).

FIG. 96 shows the amino acid sequence (SEQ ID NO:96) derived from the coding sequence of SEQ ID NO:95 shown in FIG. 95.

FIG. 97 shows a nucleotide sequence (SEQ ID NO:97) of a native sequence PRO21956 cDNA, wherein SEQ ID NO:97 is a clone designated herein as "DNA178511-2986" (UNQ6973).

FIG. 98 shows the amino acid sequence (SEQ ID NO:98) derived from the coding sequence of SEQ ID NO:97 shown in FIG. 97.

FIG. 99 shows a nucleotide sequence (SEQ ID NO:99) of a native sequence PRO57290 cDNA, wherein SEQ ID NO:99 is a clone designated herein as "DNA269238" (UNQ8782).

FIG. 100 shows the amino acid sequence (SEQ ID NO:100) derived from the coding sequence of SEQ ID NO:99 shown in FIG. 99.

FIG. 101 shows a nucleotide sequence (SEQ ID NO:101) of a native sequence PRO38465 cDNA, wherein SEQ ID NO:101 is a clone designated herein as "DNA228002" (UNQ9128).

FIG. 102 shows the amino acid sequence (SEQ ID NO:102) derived from the coding sequence of SEQ ID NO:101 shown in FIG. 101.

FIG. 103 shows a nucleotide sequence (SEQ ID NO:103) of a native sequence PRO38683 cDNA, wherein SEQ ID NO:103 is a clone designated herein as "DNA228199" (UNQ9638).

FIG. 104 shows the amino acid sequence (SEQ ID NO:104) derived from the coding sequence of SEQ ID NO:103 shown in FIG. 103.

FIG. 105 shows a nucleotide sequence (SEQ ID NO:105) of a native sequence PRO85161 cDNA, wherein SEQ ID NO:105 is a clone designated herein as "DNA329632" (UNQ16168).

FIG. 106 shows the amino acid sequence (SEQ ID NO:106) derived from the coding sequence of SEQ ID NO:105 shown in FIG. 105.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide" comprises a polypeptide having the same amino acid sequence as the corresponding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide derived from nature. Such native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides can be isolated from nature or can be produced by recombinant or synthetic means. The term "native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide" specifically encompasses naturally-occurring truncated or secreted forms of the specific PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide (e.g., an extracellular domain sequence), naturally-occurring variant forms (e.g., alternatively spliced forms) and naturally-occurring allelic variants of the polypeptide. The invention provides native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides disclosed herein which are mature or full-length native sequence polypeptides comprising the full-length amino acids sequences shown in the accompanying figures. Start and stop codons are shown in bold font and underlined in the figures. However, while the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides.

The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide "extracellular domain" or "ECD" refers to a form of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide which is essentially free of the transmembrane and cytoplasmic domains. Ordinarily, a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide ECD will have less than 1% of such transmembrane and/or cytoplasmic domains and preferably, will have less than 0.5% of such domains. It will be understood that any transmembrane domains identified for the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide variant" means a PRO226, PRO257, PRO268, PRO290, PRO36006, PRO363, PRO365, PRO382, PRO444, PRO705, PRO1071, PRO1125, PRO1134, PRO155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, preferably an active PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, as defined herein having at least about 80% amino acid sequence identity with a full-length native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence as disclosed herein, a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence lacking the signal peptide as disclosed herein, an extracellular domain of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, with or without the signal peptide, as disclosed herein or any other fragment of a full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence as disclosed herein (such as those encoded by a nucleic acid that represents only a portion of the complete coding sequence for a full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide). Such PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide variants include, for instance, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides wherein one or more amino acid residues are added, or deleted, at the N- or C-terminus of the full-length native amino acid sequence. Ordinarily, a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide variant will have or will have at least about 80% amino acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence as disclosed herein, a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence lacking the signal peptide as disclosed herein, an extracellular domain of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, with or without the signal peptide, as disclosed herein or any other specifically defined fragment of a full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence as disclosed herein. Ordinarily, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant polypeptides are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant polypeptides will have no more than one conservative amino acid substitution as compared to the native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence, alternatively will have or will have no more than 2, 3, 4, 5, 6, 7, 8, 9, or 10 conservative amino acid substitution as compared to the native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence.

"Percent (%) amino acid sequence identity" with respect to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequences identified herein is defined as the percentage of amino acid residues in a candidate sequence that are identical with the amino acid residues in the specific PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X," "Y" and "Z" each represent different hypothetical amino acid residues. Unless specifically stated otherwise, all % amino acid sequence identity values used herein are obtained as described in the immediately preceding paragraph using the ALIGN-2 computer program.

"PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO617, PRO7174, PRO9744, PRO9821, PRO9852, PRO9873, PRO10196, PRO34778, PRO20233, PRO21956, PRO57290, PRO38465, PRO38683 or PRO85161 variant polynucleotide" or "PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant nucleic acid sequence" means a nucleic acid molecule which encodes a PRO226, PRO257, PRO268, PRO290, PRO36006, PRO363, PRO365, PRO382, PRO444, PRO705, PRO1071, PRO125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, preferably an active PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO1196, PRO34778, PRO20233, PRO21956, PRO57290, PRO38465, PRO38683 or PRO85161 polypeptide, as defined herein and which has at least about 80% nucleic acid sequence identity with a nucleotide acid sequence encoding a full-length native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence as disclosed herein, a full-length native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence lacking the signal peptide as disclosed herein, an extracellular domain of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, with or without the signal peptide, as disclosed herein or any other fragment of a full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence as disclosed herein (such as those encoded by a nucleic acid that represents only a portion of the complete coding sequence for a full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide). Ordinarily, a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant polynucleotide will have or will have at least about 80% nucleic acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence as disclosed herein, a full-length native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence lacking the signal peptide as disclosed herein, an extracellular domain of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, with or without the signal sequence, as disclosed herein or any other fragment of a full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide sequence as disclosed herein. Variants do not encompass the native nucleotide sequence.

Ordinarily, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant polynucleotides are or are at least about 5 nucleotides in length, alternatively are or are at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-encoding nucleic acid sequences identified herein is defined as the percentage of nucleotides in a candidate sequence that are identical with the nucleotides in the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

The invention also provides PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant polynucleotides which are nucleic acid molecules that encode a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide and which are capable of hybridizing, preferably under stringent hybridization and wash conditions, to nucleotide sequences encoding a full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as disclosed herein. PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant polypeptides may be those that are encoded by a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant polynucleotide.

The term "full-length coding region" when used in reference to a nucleic acid encoding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide refers to the sequence of nucleotides which encode the full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide of the invention (which is often shown between start and stop codons, inclusive thereof, in the accompanying figures). The term "full-length coding region" when used in reference to an ATCC deposited nucleic acid refers to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide-encoding portion of the cDNA that is inserted into the vector deposited with the ATCC (which is often shown between start and stop codons, inclusive thereof, in the accompanying figures).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. The invention provides that the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide natural environment will not be present. Ordinarily, however, isolated polypeptide will be prepared by at least one purification step.

An "isolated" PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues preferably, between about 10 and 20 amino acid residues).

"Active" or "activity" for the purposes herein refers to form(s) of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide which retain a biological and/or an immunological activity of native or naturally-occurring PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, wherein "biological" activity refers to a biological function (either inhibitory or stimulatory) caused by a native or naturally-occurring PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide other than the ability to induce the production of an antibody against an antigenic epitope possessed by a native or naturally-occurring PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide and an "immunological" activity refers to the ability to induce the production of an antibody against an antigenic epitope possessed by a native or naturally-occurring PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

The term "antagonist" is used in the broadest sense [unless otherwise qualified], and includes any molecule that partially or fully blocks, inhibits, or neutralizes a biological activity of a native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide disclosed herein. In a similar manner, the term "agonist" is used in the broadest sense [unless otherwise qualified] and includes any molecule that mimics a biological activity of a native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide disclosed herein. Suitable agonist or antagonist molecules specifically include agonist or antagonist antibodies or antibody fragments, fragments or amino acid sequence variants of native PRO226, PRO257, PRO268, PRO290, PRO36006, PRO363, PRO365, PRO382, PRO444, PRO705, PRO171, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides, peptides, antisense oligonucleotides, small organic molecules, etc. Methods for identifying agonists or antagonists of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may comprise contacting a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide with a candidate agonist or antagonist molecule and measuring a detectable change in one or more biological activities normally associated with the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

"Treating" or "treatment" or "alleviation" refers to both therapeutic treatment and prophylactic or preventative measures, wherein the object is to prevent or slow down (lessen) the targeted pathologic condition or disorder. A subject in need of treatment may already have the disorder, or may be prone to have the disorder or may be in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, rodents such as rats or mice, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. Depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "effective amount" of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody, a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding oligopeptide, a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody, a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding oligopeptide, a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

The phrases "cardiovascular, endothelial and angiogenic disorder", "cardiovascular, endothelial and angiogenic dysfunction", "cardiovascular, endothelial or angiogenic disorder" and "cardiovascular, endothelial or angiogenic dysfunction" are used interchangeably and refer in part to systemic disorders that affect vessels, such as diabetes mellitus, as well as diseases of the vessels themselves, such as of the arteries, capillaries, veins, and/or lymphatics. This would include indications that stimulate angiogenesis and/or cardiovascularization, and those that inhibit angiogenesis and/or cardiovascularization. Such disorders include, for example, arterial disease, such as atherosclerosis, hypertension, inflammatory vasculitides, Reynaud's disease and Reynaud's phenomenon, aneurysms, and arterial restenosis; venous and lymphatic disorders such as thrombophlebitis, lymphangitis, and lymphedema; and other vascular disorders such as peripheral vascular disease, cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma, tumor angiogenesis, trauma such as wounds, burns, and other injured tissue, implant fixation, scarring, ischemia reperfusion injury, rheumatoid arthritis, cerebrovascular disease, renal diseases such as acute renal failure, or osteoporosis. This would also include angina, myocardial infarctions such as acute myocardial infarctions, cardiac hypertrophy, and heart failure such as CHF.

"Hypertrophy", as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. Certain organs, such as the heart, lose the ability to divide shortly after birth. Accordingly, "cardiac hypertrophy" is defined as an increase in mass of the heart, which, in adults, is characterized by an increase in myocyte cell size and contractile protein content without concomitant cell division. The character of the stress responsible for inciting the hypertrophy, (e.g., increased preload, increased afterload, loss of myocytes, as in myocardial infarction, or primary depression of contractility), appears to play a critical role in determining the nature of the response. The early stage of cardiac hypertrophy is usually characterized morphologically by increases in the size of myofibrils and mitochondria, as well as by enlargement of mitochondria and nuclei. At this stage, while muscle cells are larger than normal, cellular organization is largely preserved. At a more advanced stage of cardiac hypertrophy, there are preferential increases in the size or number of specific organelles, such as mitochondria, and new contractile elements are added in localized areas of the cells, in an irregular manner. Cells subjected to long-standing hypertrophy show more obvious disruptions in cellular organization, including markedly enlarged nuclei with highly lobulated membranes, which displace adjacent myofibrils and cause breakdown of normal Z-band registration. The phrase "cardiac hypertrophy" is used to include all stages of the progression of this condition, characterized by various degrees of structural damage of the heart muscle, regardless of the underlying cardiac disorder. Hence, the term also includes physiological conditions instrumental in the development of cardiac hypertrophy, such as elevated blood pressure, aortic stenosis, or myocardial infarction.

"Heart failure" refers to an abnormality of cardiac function where the heart does not pump blood at the rate needed for the requirements of metabolizing tissues. The heart failure can be caused by a number of factors, including ischemic, congenital, rheumatic, or idiopathic forms.

"Congestive heart failure" (CHF) is a progressive pathologic state where the heart is increasingly unable to supply adequate cardiac output (the volume of blood pumped by the heart over time) to deliver the oxygenated blood to peripheral tissues. As CHF progresses, structural and hemodynamic damages occur. While these damages have a variety of manifestations, one characteristic symptom is ventricular hypertrophy. CHF is a common end result of a number of various cardiac disorders.

"Myocardial infarction" generally results from atherosclerosis of the coronary arteries, often with superimposed coronary thrombosis. It may be divided into two major types: transmural infarcts, in which myocardial necrosis involves the full thickness of the ventricular wall, and subendocardial (nontransmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

As a result of the increased stress or strain placed on the heart in prolonged hypertension due, for example, to the increased total peripheral resistance, cardiac hypertrophy has long been associated with "hypertension". A characteristic of the ventricle that becomes hypertrophic as a result of chronic pressure overload is an impaired diastolic performance. Fouad et al., *J. Am. Coll. Cardiol.*, 4: 1500-1506 (1984); Smith et al., *J. Am. Coll. Cardiol.*, 5: 869-874 (1985). A prolonged left ventricular relaxation has been detected in early essential hypertension, in spite of normal or supranormal systolic function. Hartford et al., *Hypertension*, 6: 329-338 (1984). However, there is no close parallelism between blood pressure levels and cardiac hypertrophy. Although improvement in left ventricular function in response to antihypertensive therapy has been reported in humans, patients variously treated with a diuretic (hydrochlorothiazide), a β-blocker (propranolol), or a calcium channel blocker (diltiazem), have shown reversal of left ventricular hypertrophy, without improvement in diastolic function. Inouye et al., *Am. J. Cardiol.*, 53: 1583-7 (1984).

Another complex cardiac disease associated with cardiac hypertrophy is "hypertrophic cardiomyopathy". This condition is characterized by a great diversity of morphologic, functional, and clinical features (Maron et al., *N. Engl. J. Med.*, 316: 780-789 (1987); Spirito et al., *N. Engl. J. Med.*, 320: 749-755 (1989); Louie and Edwards, *Prog. Cardiovasc. Dis.*, 36: 275-308 (1994); Wigle et al., *Circulation*, 92: 1680-1692 (1995)), the heterogeneity of which is accentuated by the fact that it afflicts patients of all ages. Spirito et al., *N. Engl. J. Med.*, 336: 775-785 (1997). The causative factors of hypertrophic cardiomyopathy are also diverse and little understood. In general, mutations in genes encoding sarcomeric proteins are associated with hypertrophic cardiomyopathy. Recent data suggest that β-myosin heavy chain mutations may account for approximately 30 to 40 percent of cases of familial hypertrophic cardiomyopathy. Watkins et al., *N. Engl. J. Med.*, 326: 1108-1114 (1992); Schwartz et al., *Circulation*, 91: 532-540 (1995); Marian and Roberts, *Circulation*, 92: 1336-1347 (1995); Thierfelder et al., *Cell*, 77: 701-712 (1994); Watkins et al., *Nat. Gen.*, 11: 434-437 (1995). Besides β-myosin heavy chain, other locations of genetic mutations include cardiac troponin T, alpha tropomyosin, cardiac myosin binding protein C, essential myosin light chain, and regulatory myosin light chain. See, Malik and Watkins, *Curr. Opin. Cardiol.*, 12: 295-302 (1997).

Supravalvular "aortic stenosis" is an inherited vascular disorder characterized by narrowing of the ascending aorta, but other arteries, including the pulmonary arteries, may also be affected. Untreated aortic stenosis may lead to increased intracardiac pressure resulting in myocardial hypertrophy and eventually heart failure and death. The pathogenesis of this disorder is not fully understood, but hypertrophy and possibly hyperplasia of medial smooth muscle are prominent features of this disorder. It has been reported that molecular variants of the elastin gene are involved in the development and pathogenesis of aortic stenosis. U.S. Pat. No. 5,650,282 issued Jul. 22, 1997.

"Valvular regurgitation" occurs as a result of heart diseases resulting in disorders of the cardiac valves. Various diseases, like rheumatic fever, can cause the shrinking or pulling apart of the valve orifice, while other diseases may result in endocarditis, an inflammation of the endocardium or lining membrane of the atrioventricular orifices and operation of the heart. Defects such as the narrowing of the valve stenosis or the defective closing of the valve result in an accumulation of blood in the heart cavity or regurgitation of blood past the valve. If uncorrected, prolonged valvular stenosis or insufficiency may result in cardiac hypertrophy and associated damage to the heart muscle, which may eventually necessitate valve replacement.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, or transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis, juvenile rheumatoid arthritis, osteoarthritis, psoriatic arthritis, and ankylosing spondylitis), psoriasis, dermatitis including atopic dermatitis; chronic idiopathic urticaria, including chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), and IBD with co-segregate of pyoderma gangrenosum, erythema nodosum, primary sclerosing cholangitis, and/or episcleritis), respiratory distress syndrome, including adult respiratory distress syndrome (ARDS), meningitis, IgE-mediated diseases such as anaphylaxis and allergic rhinitis, encephalitis such as Rasmussen's encephalitis, uveitis, colitis such as microscopic colitis and collagenous colitis, glomerulonephritis (GN) such as membranous GN, idiopathic membranous GN, membranous proliferative GN (MPGN), including Type I and Type II, and rapidly progressive GN, allergic conditions, eczema, asthma, conditions involving infiltration of T cells and chronic inflammatory responses, atherosclerosis, autoimmune myocarditis, leukocyte adhesion deficiency, systemic lupus erythematosus (SLE) such as cutaneous SLE, lupus (including nephritis, cerebritis, pediatric, non-renal, discoid, alopecia), juvenile onset diabetes, multiple sclerosis (MS) such as spino-optical MS, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including Large Vessel vasculitis (including Polymyalgia Rheumatica and Giant Cell (Takayasu's) Arteritis), Medium Vessel vasculitis (including Kawasaki's Disease and Polyarteritis Nodosa), CNS vasculitis, and ANCA-associated vasculitis, such as Churg-Strauss vasculitis or syndrome (CSS)), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, and rejection arising from renal transplantation, liver transplantation, intestinal transplantation, cardiac transplantation, etc.), graft versus host disease (GVHD), pemphigoid bullous, pemphigus (including vulgaris, foliaceus, and pemphigus mucus-membrane pemphigoid), autoimmune polyendocrinopathies, Reiter's disease, stiff-man syndrome, immune complex nephritis, IgM polyneuropathies or IgM mediated neuropathy, idiopathic thrombocytopenic purpura (ITP), thrombotic thrombocytopenic purpura (TTP), thrombocytopenia (as developed by myocardial infarction patients, for example), including autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM), including pediatric IDDM, and Sheehan's syndrome; autoimmune hepatitis, Lymphoid interstitial pneumonitis (HIV), bronchiolitis obliterans (non-transplant) vs NSIP, Guillain-Barré Syndrome, Berger's Disease (IgA nephropathy), primary biliary cirrhosis, celiac sprue (gluten enteropathy), refractory sprue with co-segregate dermatitis herpetiformis, cryoglobulinemia, amylotrophic lateral sclerosis (ALS; Lou Gehrig's disease), coronary artery disease, autoimmune inner ear disease (AIED), autoimmune hearing loss, opsoclonus myoclonus syndrome (OMS), polychondritis such as refractory polychondritis, pulmonary alveolar proteinosis, amyloidosis, giant cell hepatitis, scleritis, monoclonal gammopathy of uncertain/unknown significance (MGUS), peripheral neuropathy, paraneoplastic syndrome, channelopathies such as epilepsy, migraine, arrhythmia, muscular disorders, deafness, blindness, periodic paralysis, and channelopathies of the CNS; autism, inflammatory myopathy, and focal segmental glomerulosclerosis (FSGS).

The phrase "anxiety related disorders" refers to disorders of anxiety, mood, and substance abuse, including but not limited to: depression, generalized anxiety disorders, attention deficit disorder, sleep disorder, hyperactivity disorder, obsessive compulsive disorder, schizophrenia, cognitive disorders, hyperalgesia and sensory disorders. Such disorders include the mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histrionic, narcissistic, obsessive-compulsive, schizoid, and schizotypal.

The term "lipid metabolic disorder" refers to abnormal clinical chemistry levels of cholesterol and triglycerides, wherein elevated levels of these lipids is an indication for atherosclerosis. Additionally, abnormal serum lipid levels may be an indication of various cardiovascular diseases including hypertension, stroke, coronary artery diseases, diabetes and/or obesity.

The phrase "eye abnormality" refers to such potential disorders of the eye as they may be related to atherosclerosis or various opthalmological abnormalities. Such disorders include but are not limited to the following: retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis. Cataracts are also considered an eye abnormality and are associated with such systemic diseases as: Human Down's syndrome, Hallerman-Streiff syndrome, Lowe syndrome, galactosemia, Marfan syndrome, Trismoy 13-15 condition, Alport syndrome, myotonic dystrophy, Fabry disease, hypothyroidisms, or Conradi syndrome. Other ocular developmental anomalies include: Aniridia, anterior segment and dysgenesis syndrome. Cataracts may also occur as a result of an intraocular infection or inflammation (uveitis).

A "growth inhibitory amount" of an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding oligopeptide or PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding organic molecule is an amount capable of inhibiting the growth of a cell, especially tumor, e.g., cancer cell, either in vitro or in vivo. A "growth inhibitory amount" of an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding oligopeptide or PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding organic molecule for purposes of inhibiting neoplastic cell growth may be determined empirically and in a routine manner.

A "cytotoxic amount" of an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding oligopeptide or PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding organic molecule is an amount capable of causing the destruction of a cell, especially tumor, e.g., cancer cell, either in vitro or in vivo. A "cytotoxic amount" of an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding oligopeptide or PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding organic molecule for purposes of inhibiting neoplastic cell growth may be determined empirically and in a routine manner.

The term "antibody" is used in the broadest sense and specifically covers, for example, single anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody monoclonal antibodies (including agonist, antagonist, and neutralizing antibodies), anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody compositions with polyepitopic specificity, polyclonal antibodies, single chain anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies, and fragments of anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The invention provides that the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H$ 1). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$;

Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding oligopeptide" is an oligopeptide that binds, preferably specifically, to a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as described herein. PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding oligopeptides may be chemically synthesized using known oligopeptide synthesis methodology or may be prepared and purified using recombinant technology. PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding oligopeptides usually are or are at least about 5 amino acids in length, alternatively are or are at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as described herein. PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.,* 81:3998-4002 (1984); Geysen et al., *Proc. Natl. Acad. Sci. U.S.A.,* 82:178-182 (1985); Geysen et al., in *Synthetic Peptides as Antigens,* 130-149 (1986); Geysen et al., *J. Immunol. Meth.,* 102:259-274 (1987); Schoofs et al., *J. Immunol.,* 140:611-616 (1988), Cwirla, S. E. et al. (1990) *Proc. Natl. Acad. Sci. USA,* 87:6378; Lowman, H. B. et al. (1991) *Biochemistry,* 30:10832; Clackson, T. et al. (1991) *Nature,* 352:624; Marks, J. D. et al. (1991), *J. Mol. Biol.,* 222:581; Kang, A. S. et al. (1991) *Proc. Natl. Acad. Sci. USA,* 88:8363, and Smith, G. P. (1991) *Current Opin. Biotechnol.,* 2:668).

A "PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196,

PRO34778, PRO20233, PRO21956, PRO57290, PRO38465, PRO38683 or PRO85161 binding organic molecule" is an organic molecule other than an oligopeptide or antibody as defined herein that binds, preferably specifically, to a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as described herein. PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding organic molecules may be identified and chemically synthesized using known methodology (see, e.g., PCT Publication Nos. WO00/00823 and WO00/39585). PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding organic molecules are usually less than about 2000 daltons in size, alternatively less than about 1500, 750, 500, 250 or 200 daltons in size, wherein such organic molecules that are capable of binding, preferably specifically, to a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is preferably useful as a diagnostic and/or therapeutic agent in targeting a cell or tissue expressing the antigen, and does not significantly cross-react with other proteins. The extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. The term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a "PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161" or a "growth inhibitory" antibody, oligopeptide or other organic molecule is one which results in measurable growth inhibition of cancer cells expressing or overexpressing the appropriate PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may be a transmembrane polypeptide expressed on the surface of a cancer cell or may be a polypeptide that is produced and secreted by a cancer cell. Preferred growth inhibitory anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies, oligopeptides or organic molecules inhibit growth of PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-expressing tumor cells by or by greater than 20%, preferably from about 20% to about 50%, and even more preferably, by or by greater than 50% (e.g., from about 50% to about 100%) as compared to the appropriate control, the control typically being tumor cells not treated with the antibody, oligopeptide or other organic molecule being tested. Growth inhibition can be measured at an antibody concentration of about 0.1 to 30 µg/ml or about 0.5 nM to 200 nM in cell culture, where the growth inhibition is determined 1-10 days after exposure of the tumor cells to the antibody. Growth inhibition of tumor cells in vivo can be determined in various ways. The antibody is growth inhibitory in vivo if administration of the anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody at about 1 µg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in or in about 2 to 50 fold, preferably in or in about 5 to 50 fold, and most preferably in or in about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. U.S.A.* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD). Preferably, the cancer comprises a tumor that expresses an IGF receptor, more preferably breast cancer, lung cancer, colorectal cancer, or prostate cancer, and most preferably breast or prostate cancer.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omega1I (see, e.g., Agnew, *Chem. Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON• toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

The terms "cell proliferative disorder" and "proliferative disorder" refer to disorders that are associated with some degree of abnormal cell proliferation. In one aspect of the invention, the cell proliferative disorder is cancer.

"Tumor", as used herein, refers to all neoplastic cell growth and proliferation, whether malignant or benign, and all precancerous and cancerous cells and tissues.

An antibody, oligopeptide or other organic molecule which "induces cell death" is one which causes a viable cell to become nonviable. The cell is one which expresses a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, preferably a cell that overexpresses a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as compared to a normal cell of the same tissue type. The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may be a transmembrane polypeptide expressed on the surface of a cancer cell or may be a polypeptide that is produced and secreted by a cancer cell. Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

As used herein, the term "immunoadhesion" designates antibody-like molecules which combine the binding specificity of a heterologous protein (an "adhesion") with the effector functions of immunoglobulin constant domains. Structurally, the immunoadhesions comprise a fusion of an amino acid sequence with the desired binding specificity which is other than the antigen recognition and binding site of an antibody (i.e., is "heterologous"), and an immunoglobulin constant domain sequence. The adhesion part of an immunoadhesion molecule typically is a contiguous amino acid sequence comprising at least the binding site of a receptor or a ligand. The immunoglobulin constant domain sequence in the immunoadhesion may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

"Replication-preventing agent" is an agent wherein replication, function, and/or growth of the cells is inhibited or prevented, or cells are destroyed, no matter what the mechanism, such as by apoptosis, angiostasis, cytosis, tumoricide, mytosis inhibition, blocking cell cycle progression, arresting cell growth, binding to tumors, acting as cellular mediators, etc. Such agents include a chemotherapeutic agent, cytotoxic agent, cytokine, growth-inhibitory agent, or anti-hormonal agent, e.g., an anti-estrogen compound such as tamoxifen, an anti-progesterone such as onapristone (see, EP 616 812); or an anti-androgen such as flutamide, as well as aromidase inhibitors, or a hormonal agent such as an androgen.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, Sm$^{153}$, Bi$^{212}$, P$^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

Preferred cytotoxic agents herein for the specific tumor types to use in combination with the antagonists herein are as follows:
1. Prostate cancer: androgens, docetaxel, paclitaxel, estramustine, doxorubicin, mitoxantrone, antibodies to ErbB2 domain(s) such as 2C4 (WO01/00245; hybridoma ATCC HB-12697), which binds to a region in the extracellular domain of ErbB2 (e.g., any one or more residues in the region from about residue 22 to about residue 584 of ErbB2, inclusive), AVASTIN™ anti-vascular endothelial growth factor (VEGF), TARCEVA™ OSI-774 (erlotinib) (Genenetech and OSI Pharmaceuticals), or other epidermal growth factor receptor tyrosine kinase inhibitors (EGFR TKI's).
2. Stomach cancer: 5-fluorouracil (5FU), XELODA™ capecitabine, methotrexate, etoposide, cisplatin/carboplatin, pacliitaxel, docetaxel, gemcitabine, doxorubicin, and CPT-11 (camptothcin-11; irinotecan, USA Brand Name: CAMPTOSAR®).
3. Pancreatic cancer: gemcitabine, 5FU, XELODA™ capecitabine, CPT-11, docetaxel, paclitaxel, cisplatin, carboplatin, TARCEVA™ erlotinib, and other EGFR TKI's.
4. Colorectal cancer: 5FU, XELODA™ capecitabine, CPT-11, oxaliplatin, AVASTIN™ anti-VEGF, TARCEVA™ erlotinib and other EGFR TKI's, and ERBITUX™ (formerly known as IMC-C225) human:murine-chimerized monoclonal antibody that binds to EGFR and blocks the ability of EGF to initiate receptor activation and signaling to the tumor.
5. Renal cancer: IL-2, interferon alpha, AVASTIN™ anti-VEGF, MEGACE™ (Megestrol acetate) progestin, vinblastine, TARCEVA™ erlotinib, and other EGFR TKI's.

A "growth inhibitory agent" when used herein refers to a compound or composition which inhibits growth of a cell, especially a PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-expressing cancer cell, either in vitro or in vivo. Thus, the growth inhibitory agent may be one which significantly reduces the percentage of PRO226-, PRO257-, PRO268-, PRO290-, PRO36006-, PRO363-, PRO365-, PRO382-, PRO444-, PRO705-, PRO1071-, PRO1125-, PRO1134-, PRO155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

The term "gene" refers to (a) a gene containing at least one of the DNA sequences disclosed herein; (b) any DNA sequence that encodes the amino acid sequence encoded by the DNA sequences disclosed herein and/or; (c) any DNA sequence that hybridizes to the complement of the coding sequences disclosed herein. Preferably, the term includes coding as well as noncoding regions, and preferably includes all sequences necessary for normal gene expression.

The term "gene targeting" refers to a type of homologous recombination that occurs when a fragment of genomic DNA is introduced into a mammalian cell and that fragment locates and recombines with endogenous homologous sequences. Gene targeting by homologous recombination employs recombinant DNA technologies to replace specific genomic sequences with exogenous DNA of particular design.

The term "homologous recombination" refers to the exchange of DNA fragments between two DNA molecules or chromatids at the site of homologous nucleotide sequences.

The term "target gene" (alternatively referred to as "target gene sequence" or "target DNA sequence") refers to any nucleic acid molecule, polynucleotide, or gene to be modified by homologous recombination. The target sequence includes an intact gene, an exon or intron, a regulatory sequence or any region between genes. The target gene my comprise a portion of a particular gene or genetic locus in the individual's genomic DNA.

"Disruption" of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene occurs when a fragment of genomic DNA locates and recombines with an endogenous homologous sequence wherein the disruption is a deletion of the native gene or a portion thereof, or a mutation in the native gene or wherein the disruption is the functional inactivation of the native gene. Alternatively, sequence disruptions may be generated by nonspecific insertional inactivation using a gene trap vector (i.e. non-human transgenic animals containing and expressing a randomly inserted transgene; see for example U.S. Pat. No. 6,436,707 issued Aug. 20, 2002). These sequence disruptions or modifications may include insertions, missense, frameshift, deletion, or substitutions, or replacements of DNA sequence, or any combination thereof. Insertions include the insertion of entire genes, which may be of animal, plant, fungal, insect, prokaryotic, or viral origin. Disruption, for example, can alter the normal gene product by inhibiting its production partially or completely or by enhancing the normal gene product's activity. Preferably, the disruption is a null disruption, wherein there is no significant expression of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene.

The term "native expression" refers to the expression of the full-length polypeptide encoded by the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene, at expression levels present in the wild-type mouse. Thus, a disruption in which there is "no native expression" of the endogenous PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene refers to a partial or complete reduction of the expression of at least a portion of a polypeptide encoded by an endogenous PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene of a single cell, selected cells, or all of the cells of a mammal.

The term "knockout" refers to the disruption of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene wherein the disruption results in: the functional inactivation of the native gene; the deletion of the native gene or a portion thereof; or a mutation in the native gene.

The term "knock-in" refers to the replacement of the mouse ortholog (or other mouse gene) with a human cDNA encoding any of the specific human PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-encoding genes or variants thereof (ie. the disruption results in are placement of a native mouse gene with a native human gene).

The term "construct" or "targeting construct" refers to an artificially assembled DNA segment to be transferred into a target tissue, cell line or animal. Typically, the targeting construct will include a gene or a nucleic acid sequence of particular interest, a marker gene and appropriate control sequences. As provided herein, the targeting construct comprises a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 targeting construct. A "PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 targeting construct" includes a DNA sequence homologous to at least one portion of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene and is capable of producing a disruption in a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene in a host cell.

The term "transgenic cell" refers to a cell containing within its genome a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene that has been disrupted, modified, altered, or replaced completely or partially by the method of gene targeting.

The term "transgenic animal" refers to an animal that contains within its genome a specific gene that has been disrupted or otherwise modified or mutated by the methods described herein or methods otherwise well known in the art. Preferably the non-human transgenic animal is a mammal. More preferably, the mammal is a rodent such as a rat or mouse. In addition, a "transgenic animal" may be a heterozygous animal (i.e., one defective allele and one wild-type allele) or a homozygous animal (i.e., two defective alleles). An embryo is considered to fall within the definition of an animal. The provision of an animal includes the provision of an embryo or foetus in utero, whether by mating or otherwise, and whether or not the embryo goes to term.

As used herein, the terms "selective marker" and position selection marker" refer to a gene encoding a product that enables only the cells that carry the gene to survive and/or grow under certain conditions. For example, plant and animal cells that express the introduced neomycin resistance ($Neo^r$) gene are resistant to the compound G418. Cells that do not carry the $Neo^r$ gene marker are killed by G418. Other positive selection markers are known to, or are within the purview of, those of ordinary skill in the art.

The term "modulates" or "modulation" as used herein refers to the decrease, inhibition, reduction, amelioration, increase or enhancement of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene function, expression, activity, or alternatively a phenotype associated with PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene.

The term "ameliorates" or "amelioration" as used herein refers to a decrease, reduction or elimination of a condition, disease, disorder, or phenotype, including an abnormality or symptom.

The term "abnormality" refers to any disease, disorder, condition, or phenotype in which PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 is implicated, including pathological conditions and behavioral observations.

Table 1

```
/*
 *
 * C-C increased from 12 to 15
 * Z is average of EQ
 * B is average of ND
 * match with stop is _M; stop-stop = 0; J (joker) match = 0
 */
define   _M      -8        /* value of a match with a stop */ int       _day[26][26] = {
/*      A  B  C  D  E  F  G  H  I  J  K  L  M  N  O  P  Q  R  S  T  U  V  W  X  Y  Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2, _M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M, 0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0, M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
 */
#include <stdio.h>
include <ctype.h> define   MAXJMP    16      /* max jumps in a diag */
define   MAXGAP    24      /* don't continue to penalize gaps larger than this */
#define   JMPS      1024    /* max jmps in an path */
define   MX        4       /* save if there's at least MX-1 bases since last jmp */ define   DMAT      3       /* value of matching bases */
define   DMIS      0       /* penalty for mismatched bases */
#define   DINS0     8       /* penalty for a gap */
#define   DINS1     1       /* penalty per base */
#define   PINS0     8       /* penalty for a gap */
define   PINS1     4       /* penalty per residue */ struct jmp {
         short           n[MAXJMP];      /* size of jmp (neg for dely) */
         unsigned short  x[MAXJMP];      /* base no. of jmp in seq x */
};                                       /* limits seq to 2^16 -1 */ struct diag {
         int             score;          /* score at last jmp */
         long            offset;         /* offset of prev block */
         short           ijmp;           /* current jmp index */
         struct jmp      jp;             /* list of jmps */
};

struct path {
         int             spc;            /* number of leading spaces */
         short           n[JMPS];/* size of jmp (gap) */
         int             x[JMPS];/* loc of jmp (last elem before gap) */
};

char            *ofile;                  /* output file name */
char            *namex[2];               /* seq names: getseqs() */
char            *prog;                   /* prog name for err msgs */
char            *seqx[2];                /* seqs: getseqs() */
int             dmax;                    /* best diag: nw() */
int             dmax0;                   /* final diag */
int             dna;                     /* set if dna: main() */
int             endgaps;                 /* set if penalizing end gaps */
int             gapx, gapy;              /* total gaps in seqs */
int             len0, len1;              /* seq lens */
int             ngapx, ngapy;            /* total size of gaps */
int             smax;                    /* max score: nw() */
int             *xbm;                    /* bitmap for matching */
long            offset;                  /* current offset in jmp file */
struct  diag    *dx;                     /* holds diagonals */
struct  path    pp[2];                   /* holds path for seqs */ char            *calloc(), *malloc(), *index(), *strcpy();
char            *getseq(), *g_calloc();
```

Table 1 (cont')

```
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
include "nw.h"
#include "day.h"

static    _dbval[26] = {
          1,14,2,13,0,0,4,11,0,0,12,0,3,15,0,0,0,5,6,8,8,7,9,0,10,0
};

static    _pbval[26] = {
          1, 2|(1<<('D'-'A'))|(1<<('N'-'A')), 4, 8, 16, 32, 64,
          128, 256, 0xFFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};

main(ac, av)                                                                                    main
          int       ac;
          char      *av[];
{
          prog = av[0];
          if (ac != 3) {
                    fprintf(stderr,"usage: %s file1 file2\n", prog);
                    fprintf(stderr,"where file1 and file2 are two dna or two protein sequences.\n");
                    fprintf(stderr,"The sequences can be in upper- or lower-case\n");
                    fprintf(stderr,"Any lines beginning with ';' or '<' are ignored\n");
                    fprintf(stderr,"Output is in the file \"align.out\"\n");
                    exit(1);
          }
          namex[0] = av[1];
          namex[1] = av[2];
          seqx[0] = getseq(namex[0], &len0);
          seqx[1] = getseq(namex[1], &len1);
          xbm = (dna)? _dbval : _pbval;

endgaps = 0;              /* 1 to penalize endgaps */
          ofile = "align.out";      /* output file */ nw();                     /* fill in the matrix, get the possible jmps */
          readjmps();               /* get the actual jmps */
          print();                  /* print stats, alignment */ cleanup(0);               /* unlink any tmp files */}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                                nw
{
        char        *px, *py;        /* seqs and ptrs */
        int         *ndely, *dely;   /* keep track of dely */
        int         ndelx, delx;     /* keep track of delx */
        int         *tmp;            /* for swapping row0, row1 */
        int         mis;             /* score for each type */
        int         ins0, ins1;      /* insertion penalties */
        register    id;              /* diagonal index */
        register    ij;              /* jmp index */
        register    *col0, *col1;    /* score for curr, last row */
        register    xx, yy;          /* index into seqs */ dx = (struct diag *)g_calloc("to get diags", len0+len1+1, sizeof(struct diag));
        ndely = (int *)g_calloc("to get ndely", len1+1, sizeof(int));
        dely = (int *)g_calloc("to get dely", len1+1, sizeof(int));
        col0 = (int *)g_calloc("to get col0", len1-1, sizeof(int));
        col1 = (int *)g_calloc("to get col1", len1-1, sizeof(int));
        ins0 = (dna)? DINS0 : PINS0;
        ins1 = (dna)? DINS1 : PINS1;
        smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;         /* Waterman Bull Math Biol 84 */
        }
        else
                for (yy = 1; yy <= len1; yy++)
                        dely[yy] = -ins0;
        /* fill in match matrix
        */
        for (px = seqx[0], xx = 1; xx <= len0; px++, xx++) {
                /* initialize first entry in col
                */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (py = seqx[1], yy = 1; yy <= len1; py++, yy+-) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]+-;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]+-;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

...nw

```
        id = xx - yy + len1 - 1;
        if (mis >= delx && mis >= dely[yy])
                col1[yy] = mis;
```

Table 1 (cont')

```
                else if (delx >= dely[yy]) {
                        col1[yy] = delx;
                        ij = dx[id].ijmp;
                        if (dx[id].jp.n[0] && (!dna || (ndelx >= MAXJMP
                                && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;
if (dx[id].jp.n[0] && (!dna || (ndely[yy] >= MAXJMP
                                && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = -ndely[yy];
                        dx[id].jp.x[ij] = xx;
                        dx[id].score = dely[yy];
                }
                if (xx == len0 && yy < len1) {
                        /* last col
                        */
                        if (endgaps)
                                col1[yy] -= ins0+ins1*(len1-yy);
                        if (col1[yy] > smax) {
                                smax = col1[yy];
                                dmax = id;
                        }
                }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;                }
(void) free((char *)ndely);
(void) free((char *)dely);
(void) free((char *)col0);
(void) free((char *)col1);                              }
```

Table 1 (cont')

```
/*
*
* print() -- only routine visible outside this module
*
* static:
* getmat() -- trace back best path, count matches: print()
* pr_align() -- print alignment of described in array p[ ]: print()
* dumpblock() -- dump a block of lines with numbers, stars: pr_align()
* nums() -- put out a number line: dumpblock()
* putline() -- put out a line (name, [num], seq, [num]): dumpblock()
* stars() - -put a line of stars: dumpblock()
* stripname() -- strip any path and prefix from a seqname
*/ include "nw.h"

define SPC        3
#define P_LINE     256     /* maximum output line */
define P_SPC      3       /* space between name or num and seq */ extern    _day[26][26];
int       olen;            /* set output line length */
FILE      *fx;             /* output file */ print()
{
          int      lx, ly, firstgap, lastgap;    /* overlap */ if ((fx = fopen(ofile, "w")) == 0) {
                    fprintf(stderr,"%s: can't write %s\n", prog, ofile);
                    cleanup(1);
          }
          fprintf(fx, "<first sequence: %s (length = %d)\n", namex[0], len0);
          fprintf(fx, "<second sequence: %s (length = %d)\n", namex[1], len1);
          olen = 60;
          lx = len0;
          ly = len1;
          firstgap = lastgap = 0;
          if (dmax < len1 - 1) {           /* leading gap in x */
                    pp[0].spc = firstgap = len1 - dmax - 1;
                    ly -= pp[0].spc;
          }
          else if (dmax > len1 - 1) {      /* leading gap in y */
                    pp[1].spc = firstgap = dmax - (len1 - 1);
                    lx -= pp[1].spc;
          }
          if (dmax0 < len0 - 1) {          /* trailing gap in x */
                    lastgap = len0 - dmax0 -1;
                    lx -= lastgap;
          }
          else if (dmax0 > len0 - 1) {     /* trailing gap in y */
                    lastgap = dmax0 - (len0 - 1);
                    ly -= lastgap;
          }
          getmat(lx, ly, firstgap, lastgap);
          pr_align();              }
``` print

Table 1 (cont')

```
/*
 * trace back the best path, count matches
 */
static
getmat(lx, ly, firstgap, lastgap)
        int        lx, ly;                    /* "core" (minus endgaps) */
        int        firstgap, lastgap;         /* leading trailing overlap */
{
        int             nm, i0, i1, siz0, siz1;
        char            outx[32];
        double          pct;
        register        n0, n1;
        register char   *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
``` getmat

Table 1 (cont')

```
            fprintf(fx, "<gaps in first sequence: %d", gapx);                                    ...getmat
            if (gapx) {
                    (void) sprintf(outx, " (%d %s%s)",
                            ngapx, (dna)? "base":"residue", (ngapx == 1)? "":"s");
                    fprintf(fx,"%s", outx);
            fprintf(fx, ", gaps in second sequence: %d", gapy);
            if (gapy) {
                    (void) sprintf(outx, " (%d %s%s)",
                            ngapy, (dna)? "base":"residue", (ngapy == 1)? "":"s");
                    fprintf(fx,"%s", outx);
            }
            if (dna)
                    fprintf(fx,
                    "\n<score: %d (match = %d, mismatch = %d, gap penalty = %d + %d per base)\n",
                    smax, DMAT, DMIS, DINS0, DINS1);
            else
                    fprintf(fx,
                    "\n<score: %d (Dayhoff PAM 250 matrix, gap penalty - %d - %d per residue)\n",
                    smax, PINS0, PINS1);
            if (endgaps)
                    fprintf(fx,
                    "<endgaps penalized. left endgap: %d %s%s, right endgap: %d %s%s\n",
                    firstgap, (dna)? "base" : "residue", (firstgap == 1)? "" : "s",
                    lastgap, (dna)? "base" : "residue", (lastgap == 1)? "" : "s");
            else
                    fprintf(fx, "<endgaps not penalized\n");
    }
    static          nm;             /* matches in core -- for checking */
    static          lmax;           /* lengths of stripped file names */
    static          ij[2];          /* jmp index for a path */
    static          nc[2];          /* number at start of current line */
    static          ni[2];          /* current elem number -- for gapping */
    static          siz[2];
    static char     *ps[2];         /* ptr to current element */
    static char     *po[2];         /* ptr to next output char slot */
    static char     out[2][P_LINE]; /* output line */
    static char     star[P_LINE];   /* set by stars() */
    /*
    * print alignment of described in struct path pp[]
    */
    static
    pr_align()                                                                                   pr_align
    {
            int     nn;     /* char count */
            int     more;
            register I;

for (I = 0, lmax = 0; I < 2; I++) {
                    nn = stripname(namex[i]);
                    if (nn > lmax)
                            lmax = nn;
                    nc[i] = 1;
                    ni[i] = 1;
                    siz[i] = ij[i] = 0;
                    ps[i] = seqx[i];
                    po[i] = out[i];                         }
```

Table 1 (cont')

```
        for (nn = nm = 0, more = 1; more; ) {                                  ...pr_align
                for (I = more = 0; I < 2; I++) {
                        /*
                         * do we have more of this sequence?
                         */
                        if (!*ps[i])
                                continue;
                        more++;
                        if (pp[i].spc) {        /* leading space */
                                *po[i]++ = ' ';
                                pp[i].spc--;
                        }
                        else if (siz[i]) {      /* in a gap */
                                *po[i]++ = '-';
                                siz[i]--;
                        }
                        else {                  /* we're putting a seq element
                                                 */
                                *po[i] = *ps[i];
                                if (islower(*ps[i]))
                                        *ps[i] = toupper(*ps[i]);
                                po[i]++;
                                ps[i]++;
                                /*
                                 * are we at next gap for this seq?
                                 */
                                if (ni[i] == pp[i].x[ij[i]]) {
                                        /*
                                         * we need to merge all gaps
                                         * at this location
                                         */
                                        siz[i] = pp[i].n[ij[i]++];
                                        while (ni[i] == pp[i].x[ij[i]])
                                                siz[i] += pp[i].n[ij[i]++];
                                }
                                ni[i]++;
                        }
                }
                if (++nn == olen || !more && nn) {
                        dumpblock();
                        for (I = 0; I < 2; I++)
                                po[i] = out[i];
                        nn = 0;
                }
        }
}
/*
 * dump a block of lines, including numbers, stars: pr_align()
 */
static
dumpblock()                                                                    dumpblock
{
        register I;
        for (I = 0; I < 2; I++)
                *po[i]-- = '\0';
```

Table 1 (cont')

...dumpblock

```
            (void) putc('\n', fx);
            for (I = 0; I < 2; I++) {
                    if (*out[i] && (*out[i] != ' ' || *(po[i]) != ' ')) {
                            if (I == 0)
                                    nums(I);
                            if (I == 0 && *out[1])
                                    stars();
                            putline(I);
                            if (I == 0 && *out[1])
                                    fprintf(fx, star);
                            if (I == 1)
                                    nums(I);
                    }
            }
}
/*
 * put out a number line: dumpblock()
 */
static
nums(ix)
``` nums

```
        int       ix;         /* index in out[] holding seq line */
{
        char            nline[P_LINE];
        register        I, j;
        register char   *pn, *px, *py;
        for (pn = nline, I = 0; I < lmax+P_SPC; I++, pn++)
                *pn = ' ';
        for (I = nc[ix], py = out[ix]; *py; py++, pn++) {
                if (*py == ' ' || *py == '-')
                        *pn = ' ';
                else {
                        if (I%10 == 0 || (I == 1 && nc[ix] != 1)) {
                                j = (I < 0)? -I : I;
                                for (px = pn; j; j /= 10, px--)
                                        *px = j%10 + '0';
                                if (I < 0)
                                        *px = '-';
                        }
                        else
                                *pn = ' ';
                        I++;
                }
        }
        *pn = '\0';
        nc[ix] = I;
        for (pn = nline; *pn; pn++)
                (void) putc(*pn, fx);
        (void) putc('\n', fx);
}
/*
 * put out a line (name, [num], seq, [num]): dumpblock()
 */
static
putline(ix)
``` putline

```
        int       ix;                              {
```

Table 1 (cont')

...putline

```
        int         I;
        register char   *px;

for (px = namex[ix], I = 0; *px && *px != ':'; px++, I++)
                (void) putc(*px, fx);
        for (; I < lmax-P_SPC; I++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()
{
        int         I;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (I = lmax+P_SPC; I; I--)
                *px++ = ' ';

for (p0 = out[0], p1 = out[1]; *p0 && *p1; p0--, p1++) {
                if (isalpha(*p0) && isalpha(*p1)) { if (xbm[*p0-'A']&xbm[*p1-'A']) {
                                cx = '*';
                                nm+-;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px+- = '\n';
        *px = '\0';
}
``` stars

Table 1 (cont')

```
/*
 * strip path or prefix from pn, return len: pr_align()
 */
static
stripname(pn)                                                                stripname
        char       *pn;     /* file name (may be path) */
{
        register char      *px, *py;

py = 0;
        for (px = pn; *px; px++)
                if (*px == '/')
                        py = px + 1;
        if (py)
                (void) strcpy(pn, py);
        return(strlen(pn));

}
```

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char        *jname = "/tmp/homgXXXXXX";     /* tmp file for jmps */
FILE        *fj;
int         cleanup();                       /* cleanup tmp file */
long        lseek();
/*
 * remove any tmp file if we blow
 */
cleanup(I)                                                                      cleanup
        int     I;
{
        if (fj)
                (void) unlink(jname);
        exit(I);
}
/*
 * read, return ptr to seq, set dna, len, maxlen
 * skip lines starting with ';', '<', or '>'
 * seq in upper or lower case
 */
char    *
getseq(file, len)                                                               getseq
        char        *file;    /* file name */
        int         *len;     /* seq len */
{
        char            line[1024], *pseq;
        register char   *px, *py;
        int             natgc, tlen;
        FILE            *fp;
        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Table 1 (cont')

...getseq

```
        py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq-4);
}
char    *
g_calloc(msg, nx, sz)
        char    *msg;           /* program, calling routine */
        int     nx, sz;         /* number and size of elements */
{
        char            *px, *calloc();
        if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}

/*
 * get final jmps from dx[] or tmp file, set pp[], reset dmax: main()
 */
readjmps()
{
        int             fd = -1;
        int             siz, i0, i1;
        register        I, j, xx;
        if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (I = i0 = i1 = 0, dmax0 = dmax, xx = len0; ; I+-) {
                while (1) {
                        for (j = dx[dmax].ijmp; j >= 0 && dx[dmax].jp.x[j] >= xx; j--)
                                ;
``` g_calloc readjmps

Table 1 (cont')

...readjmps

```
                    if (j < 0 && dx[dmax].offset && fj) {
                            (void) lseek(fd, dx[dmax].offset, 0);
                            (void) read(fd, (char *)&dx[dmax].jp, sizeof(struct jmp));
                            (void) read(fd, (char *)&dx[dmax].offset, sizeof(dx[dmax].offset));
                            dx[dmax].ijmp = MAXJMP-1;                                   }
                    else
                            break;          }
            if (l >= JMPS) {
                    fprintf(stderr, "%s: too many gaps in alignment\n", prog);
                    cleanup(1);
            }
            if (j >= 0) {
                    siz = dx[dmax].jp.n[j];
                    xx = dx[dmax].jp.x[j];
                    dmax -= siz;
                    if (siz < 0) {                          /* gap in second seq */
                            pp[1].n[i1] = -siz;
                            xx += siz;
                            /* id = xx - yy + len1 - 1                                  */
                            pp[1].x[i1] = xx - dmax + len1 - 1;
                            gapy++;
                            ngapy -= siz;
/* ignore MAXGAP when doing endgaps */
                            siz = (-siz < MAXGAP || endgaps)? -siz : MAXGAP;
                            i1++;
                    }
                    else if (siz > 0) {     /* gap in first seq */
                            pp[0].n[i0] = siz;
                            pp[0].x[i0] = xx;
                            gapx++;
                            ngapx += siz;
/* ignore MAXGAP when doing endgaps */
                            siz = (siz < MAXGAP || endgaps)? siz : MAXGAP;
                            i0++;
                    }
            }
            else
                    break;
    }
    /* reverse the order of jmps    */
    for (j = 0, i0--; j < i0; j++, i0--) {
            I = pp[0].n[j]; pp[0].n[j] = pp[0].n[i0]; pp[0].n[i0] = I;
            I = pp[0].x[j]; pp[0].x[j] = pp[0].x[i0]; pp[0].x[i0] = I;
    }
    for (j = 0, i1--; j < i1; j++, i1--) {
            I = pp[1].n[j]; pp[1].n[j] = pp[1].n[i1]; pp[1].n[i1] = I;
            I = pp[1].x[j]; pp[1].x[j] = pp[1].x[i1]; pp[1].x[i1] = I;
    }
    if (fd >= 0)
            (void) close(fd);
    if (fj) {
            (void) unlink(jname);
            fj = 0;
            offset = 0;
    }                                       }
```

Table 1 (cont')

```
/*
 * write a filled jmp struct offset of the prev one (if any): nw()
 */
writejmps(ix)                                                                       writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| PRO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| PRO | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| PRO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| PRO-DNA | NNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 Polypeptides The present invention provides newly identified and isolated nucleotide sequences encoding polypeptides referred to in the present application as PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides. In particular, cDNAs encoding various PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides and encoding nucleic acids described herein, Applicants have identified what is believed to be the reading frame best identifiable with the sequence information available at the time.

B. PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 Polypeptide Variants In addition to the full-length native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides described herein, it is contemplated that PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variants can be prepared. PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variants can be prepared by introducing appropriate nucleotide changes into the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 DNA, and/or by synthesis of the desired PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Those skilled in the art will appreciate that amino acid changes may alter post-translational processes of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, such as changing the number or position of glycosylation sites or altering the membrane anchoring characteristics.

Variations in the native full-length sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or in various domains of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide that results in a change in the amino acid sequence of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as compared with the native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Optionally the variation is by substitution of at least one amino acid with any other amino acid in one or more of the domains of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Guidance in determining which amino acid residue may be inserted, substituted or deleted without adversely affecting the desired activity may be found by comparing the sequence of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 fragments may be prepared by any of a number of conventional techniques. Desired peptide fragments may be chemically synthesized. An alternative approach involves generating PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide fragments share at least one biological and/or immunological activity with the native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide disclosed herein.

Conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are preferably introduced and the products screened.

TABLE 6

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (O)
(3) acidic: Asp (D), Glu (E)
(4) basic: Lys (K), Arg (R), H is (H)
Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 Polypeptides Covalent modifications of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides are included within the scope of this invention. One type of covalent modification includes reacting targeted amino acid residues of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide with an organic derivatizing agent that is capable of reacting with selected side chains or the N or C-terminal residues of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Derivatization with bifunctional agents is useful, for instance, for crosslinking PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides to a water-insoluble support matrix or surface for use in the method for purifying anti- PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide included within the scope of this invention comprises altering the native glycosylation pattern of the polypeptide. "Altering the native glycosylation pattern" is intended for purposes herein to mean deleting one or more carbohydrate moieties found in native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides (either by removing the underlying glycosylation site or by deleting the glycosylation by chemical and/or enzymatic means), and/or adding one or more glycosylation sites that are not present in the native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. In addition, the phrase includes qualitative changes in the glycosylation of the native proteins, involving a change in the nature and proportions of the various carbohydrate moieties present.

Addition of glycosylation sites to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may be accomplished by altering the amino acid sequence. The alteration may be made, for example, by the addition of, or substitution by, one or more serine or threonine residues to the native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 (for O-linked glycosylation sites). The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 amino acid sequence may optionally be altered through changes at the DNA level, particularly by mutating the DNA encoding the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide at preselected bases such that codons are generated that will translate into the desired amino acids.

Another means of increasing the number of carbohydrate moieties on the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides comprises linking the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides of the present invention may also be modified in a way to form a chimeric molecule comprising the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide fused to another, heterologous polypeptide or amino acid sequence.

Such a chimeric molecule comprises a fusion of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide with a tag polypeptide which provides an epitope to which an anti-tag antibody can selectively bind. The epitope tag is generally placed at the amino- or carboxyl-terminus of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. The presence of such epitope-tagged forms of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide can be detected using an antibody against the tag polypeptide. Also, provision of the epitope tag enables the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

The chimeric molecule may comprise a fusion of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide in place of at least one variable region within an Ig molecule. In a particularly preferred aspect of the invention, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 Polypeptides The description below relates primarily to production of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides by culturing cells transformed or transfected with a vector containing PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 nucleic acid. It is, of course, contemplated that alternative methods, which are well known in the art, may be employed to prepare PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides. For instance, the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may be chemically synthesized separately and combined using chemical or enzymatic methods to produce the full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

1. Isolation of DNA Encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 Polypeptides DNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides may be obtained from a cDNA library prepared from tissue believed to possess the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 mRNA and to express it at a detectable level. Accordingly, human PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-DNA can be conveniently obtained from a cDNA library prepared from human tissue, such as described in the Examples. The PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-encoding gene may also be obtained from a genomic library or by known synthetic procedures (e.g., automated nucleic acid synthesis).

Libraries can be screened with probes (such as antibodies to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype to tonA ptr3; *E. coli* W3110 strain 27C7 (ATCC 55,244), which has the complete genotype tonA ptr3phoA E15 (argF-lac)169 degP ompT kan$^r$; *E. coli* W3110 strain 37D6, which has the complete genotype tonA ptr3phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fingi or yeast are suitable cloning or expression hosts for PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112: 284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp 1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides.

Still other methods, vectors, and host cells suitable for adaptation to the synthesis of PRO226, PRO257, PRO268, PRO290, PRO36006, PRO363, PRO365, PRO382, PRO444, PRO705, PRO1071, PRO125, PRO134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or against a synthetic peptide based on the DNA sequences provided herein or against exogenous sequence fused to PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 DNA and encoding a specific antibody epitope.

5. Purification of Polypeptide

Forms of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides may be recovered from culture medium or from host cell lysates. If membrane-bound, it can be released from the membrane using a suitable detergent solution (e.g. Triton-X 100) or by enzymatic cleavage. Cells employed in expression of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides can be disrupted by various physical or chemical means, such as freeze-thaw cycling, sonication, mechanical disruption, or cell lysing agents.

It may be desired to purify PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide produced.

E. Uses for PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 Polypeptides Nucleotide sequences (or their complement) encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides have various applications in the art of molecular biology, including uses as hybridization probes, in chromosome and gene mapping and in the generation of anti-sense RNA and DNA. PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 nucleic acid will also be useful for the preparation of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides by the recombinant techniques described herein.

The full-length native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene, or portions thereof, may be used as hybridization probes for a cDNA library to isolate the full-length PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 cDNA or to isolate still other cDNAs (for instance, those encoding naturally-occurring variants of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides or PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides from other species) which have a desired sequence identity to the native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161. By way of example, a screening method will comprise isolating the coding region of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene using the known DNA sequence to synthesize a selected probe of about 40 bases. Hybridization probes may be labeled by a variety of labels, including radionucleotides such as $^{32}$P or $^{35}$S, or enzymatic labels such as alkaline phosphatase coupled to the probe via avidin/biotin coupling systems. Labeled probes having a sequence complementary to that of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 nucleic acids include antisense or sense oligonucleotides comprising a singe-stranded nucleic acid sequence (either RNA or DNA) capable of binding to target PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 mRNA (sense) or PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 DNA (antisense) sequences. Antisense or sense oligonucleotides, according to the present invention, comprise a fragment of the coding region of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 coding sequences.

Nucleotide sequences encoding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide can also be used to construct hybridization probes for mapping the gene which encodes that PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 encode a protein which binds to another protein (for example, where the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 is a receptor), the PRO226, PRO257, PRO268, PRO290, PRO36006, PRO363, PRO365, PRO382, PRO444, PRO705, PRO1071, PRO1125, PRO134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 can be used to isolate correlative ligand(s). Screening assays can be designed to find lead compounds that mimic the biological activity of a native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or a receptor for PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. The invention provides cDNA encoding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide which can be used to clone genomic DNA encoding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide in accordance with established techniques and the genomic sequences used to generate transgenic animals that contain cells which express DNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides. Any technique known in the art may be used to introduce a target gene transgene into animals to produce the founder lines of transgenic animals. Such techniques include, but are not limited to pronuclear microinjection (U.S. Pat. Nos. 4,873,191, 4,736,866 and 4,870,009); retrovirus mediated gene transfer into germ lines (Van der Putten, et al., *Proc. Natl. Acad. Sci. USA,* 82:6148-6152 (1985)); gene targeting in embryonic stem cells (Thompson, et al., *Cell,* 56:313-321 (1989)); nonspecific insertional inactivation using a gene trap vector (U.S. Pat. No. 6,436,707); electroporation of embryos (Lo, *Mol. Cell. Biol.,* 3:1803-1814 (1983)); and sperm-mediated gene transfer (Lavitrano, et al., *Cell,* 57:717-723 (1989)); etc. Typically, particular cells would be targeted for a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 transgene incorporation with tissue-specific enhancers. Transgenic animals that include a copy of a transgene encoding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide introduced into the germ line of the animal at an embryonic stage can be used to examine the effect of increased expression of DNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition. Alternatively, non-human homologues of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides can be used to construct a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 "knock out" animal which has a defective or altered gene encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 proteins as a result of homologous recombination between the endogenous gene encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides and altered genomic DNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides introduced into an embryonic stem cell of the animal. Preferably the knock out animal is a mammal. More preferably, the mammal is a rodent such as a rat or mouse. For example, cDNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides can be used to clone genomic DNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides in accordance with established techniques. A portion of the genomic DNA encoding the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the gene encoding the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

In addition, knockout mice can be highly informative in the discovery of gene function and pharmaceutical utility for a drug target, as well as in the determination of the potential on-target side effects associated with a given target. Gene function and physiology are so well conserved between mice and humans, since they are both mammals and contain similar numbers of genes, which are highly conserved between the species. It has recently been well documented, for example, that 98% of genes on mouse chromosome 16 have a human ortholog (Mural et al., *Science* 296:1661-71 (2002)).

Although gene targeting in embryonic stem (ES) cells has enabled the construction of mice with null mutations in many genes associated with human disease, not all genetic diseases are attributable to null mutations. One can design valuable mouse models of human diseases by establishing a method for gene replacement (knock-in) which will disrupt the mouse locus and introduce a human counterpart with mutation, Subsequently one can conduct in vivo drug studies targeting the human protein (Kitamoto et. Al., *Biochemical and Biophysical Res. Commun.*, 222:742-47 (1996)).

Nucleic acid encoding the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides described herein may also be employed as molecular weight markers for protein electrophoresis purposes and the isolated nucleic acid sequences may be used for recombinantly expressing those markers.

The nucleic acid molecules encoding the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides or fragments thereof described herein are useful for chromosome identification. In this regard, there exists an ongoing need to identify new chromosome markers, since relatively few chromosome marking reagents, based upon actual sequence data are presently available. Each PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 nucleic acid molecule of the present invention can be used as a chromosome marker.

The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides and nucleic acid molecules of the present invention may also be used diagnostically for tissue typing, wherein the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides of the present invention may be differentially expressed in one tissue as compared to another, preferably in a diseased tissue as compared to a normal tissue of the same tissue type. PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 nucleic acid molecules will find use for generating probes for PCR, Northern analysis, Southern analysis and Western analysis.

The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides described herein may also be employed as therapeutic agents. The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides of the present invention can be formulated according to known methods to prepare pharmaceutically useful compositions, whereby the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide is desired in a formulation with release characteristics suitable for the treatment of any disease or disorder requiring administration of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, microencapsulation of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide (agonists) or prevent the effect of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide (antagonists). Agonists that mimic a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide would be especially valuable therapeutically in those instances where a negative phenotype is observed based on findings with the non-human transgenic animal whose genome comprises a disruption of the gene which encodes for the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Antagonists that prevent the effects of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide would be especially valuable therapeutically in those instances where a positive phenotype is observed based upon observations with the non-human transgenic knockout animal. Screening assays for antagonist drug candidates are designed to identify compounds that bind or complex with the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide encoded by the genes identified herein, or otherwise interfere with the interaction of the encoded polypeptide with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide encoded by a nucleic acid identified herein under conditions and for a time sufficient to allow these two components to interact.

In binding assays, the interaction is binding and the complex formed can be isolated or detected in the reaction mixture. The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide and drying. Alternatively, an immobilized antibody, e.g., a monoclonal antibody, specific for the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may be added to a cell along with the compound to be screened for a particular activity and the ability of the compound to inhibit the activity of interest in the presence of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide indicates that the compound is an antagonist to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Alternatively, antagonists may be detected by combining the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide and a potential antagonist with membrane-bound PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide receptors or recombinant receptors under appropriate conditions for a competitive inhibition assay. The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide can be labeled, such as by radioactivity, such that the number of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide and a cDNA library created from this RNA is divided into pools and used to transfect COS cells or other cells that are not responsive to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Transfected cells that are grown on glass slides are exposed to labeled PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, the labeled PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

Another approach in assessing the effect of an antagonist to a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, would be administering a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 antagonist to a wild-type mouse in order to mimic a known knockout phenotype. Thus, one would initially knockout the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene of interest and observe the resultant phenotype as a consequence of knocking out or disrupting the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene. Subsequently, one could then assess the effectiveness of an antagonist to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide by administering an antagonist to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide to a wild-type mouse. An effective antagonist would be expected to mimic the phenotypic effect that was initially observed in the knockout animal.

Likewise, one could assess the effect of an agonist to a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, by administering a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 agonist to a non-human transgenic mouse in order to ameliorate a known negative knockout phenotype. Thus, one would initially knockout the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene of interest and observe the resultant phenotype as a consequence of knocking out or disrupting the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 gene. Subsequently, one could then assess the effectiveness of an agonist to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide by administering an agonist to the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide to a the non-human transgenic mouse. An effective agonist would be expected to ameliorate the negative phenotypic effect that was initially observed in the knockout animal.

In another assay for antagonists, mammalian cells or a membrane preparation expressing the receptor would be incubated with a labeled PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide in the presence of the candidate compound. The ability of the compound to enhance or block this interaction could then be measured.

More specific examples of potential antagonists include an oligonucleotide that binds to the fusions of immunoglobulin with the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide that recognizes the receptor but imparts no effect, thereby competitively inhibiting the action of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

Another potential PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science,* 241: 456 (1988); Dervan et al., *Science,* 251:1360 (1991)), thereby preventing transcription and the production of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. The antisense RNA oligonucleotide hybridizes to the mRNA in vivo and blocks translation of the mRNA molecule into the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, thereby blocking the normal biological activity of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by anyone or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO226, Anti-PRO257, Anti-PRO268, Anti-PRO290, Anti-PRO36006, Anti-PRO363, Anti-PRO365, Anti-PRO382, Anti-PRO444, Anti-PRO705, Anti-PRO1071, Anti-PRO1125, Anti-PRO1134, Anti-PRO1155, Anti-PRO1281, Anti-PRO1343, Anti-PRO1379, Anti-PRO1380, Anti-PRO1387, Anti-PRO1419, Anti-PRO1433, Anti-PRO1474, Anti-PRO1550, Anti-PRO1571, Anti-PRO1572, Anti-PRO1759, Anti-PRO1904, Anti-PRO35193, Anti-PRO4341, Anti-PRO4348, Anti-PRO4369, Anti-PRO4381, Anti-PRO4407, Anti-PRO4425, Anti-PRO4985, Anti-PRO4989, Anti-PRO5737, Anti-PRO5800, Anti-PRO5993, Anti-PRO6017, Anti-PRO7174, Anti-PRO9744, Anti-PRO9821, Anti-PRO9852, Anti-PRO9873, Anti-PRO10196, Anti-PRO34778, Anti-PRO20233, Anti-PRO21956, Anti-PRO57290, Anti-PRO38465, Anti-PRO38683 or Anti-PRO85161, Antibodies The present invention provides anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-5, PRO20233, anti-PRO21956, anti-PRO57290, anti-PRO38465, anti-PRO38683 or anti-PRO85161 antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N\!\!=\!\!C\!\!=\!\!NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with 1/5 to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130: 151-188 (1992).

Monoclonal antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.* 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli,* thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. The antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering,* ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 protein as described herein. Other such antibodies may combine a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 binding site with a binding site for another protein. Alternatively, an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-expressing cell. Bispecific antibodies may also be used to localize cytotoxic agents to cells which express a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide. These antibodies possess a PRO226-, PRO257-, PRO268-, PRO290-, PRO36006-, PRO363-, PRO365-, PRO382-PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificity (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

The invention provides bispecific antibodies which are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise alight chain variable domain and, optionally, further comprise a CL domain.

8. Effector Function Engineering

It may be desirable to modify the antibody of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al, *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

The invention provides an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody (full length or fragments) which is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-PRO226, Anti-PRO257, Anti-PRO268, Anti-PRO290, Anti-PRO36006, Anti-PRO363, Anti-PRO365, Anti-PRO382, Anti-PRO444, Anti-PRO705, Anti-PRO1071, Anti-PRO1125, Anti-PRO1134, Anti-PRO1155, Anti-PRO1281, Anti-PRO1343, Anti-PRO1379, Anti-PRO1380, Anti-PRO1387, Anti-PRO1419, Anti-PRO1433, Anti-PRO1474, Anti-PRO1550, Anti-PRO1571, Anti-PRO1572, Anti-PRO1759, Anti-PRO1904, Anti-PRO35193, Anti-PRO4341, Anti-PRO4348, Anti-PRO4369, Anti-PRO4381, Anti-PRO4407, Anti-PRO4425, Anti-PRO4985, Anti-PRO4989, Anti-PRO5737, Anti-PRO5800, Anti-PRO5993, Anti-PRO6017, Anti-PRO7174, Anti-PRO9744, Anti-PRO9821, Anti-PRO9852, Anti-PRO9873, Anti-PRO10196, Anti-PRO34778, Anti-PRO20233, Anti-PRO21956, Anti-PRO57290, Anti-PRO38465, Anti-PRO38683 or Anti-PRO85161 Antibody-Maytansinoid Conjugates (Immunoconjugates)

Anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody-maytansinoid conjugates are prepared by chemically linking an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. The linkage is formed at the C-3 position of maytansinol or a maytansinol analogue.

Calicheamicin

Another immunoconjugate of interest comprises an anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

Alternatively, a fusion protein comprising the anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The invention provides that the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl. Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide interchange reaction. A chemotherapeutic agent is optionally contained within the liposome. See Gabizon et al., J. National Cancer Inst. 81(19): 1484 (1989).

11. Pharmaceutical Compositions of Antibodies

Antibodies specifically binding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide identified herein, as well as other molecules identified by the screening assays disclosed hereinbefore, can be administered for the treatment of various disorders in the form of pharmaceutical compositions.

If the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO226, Anti-PRO257, Anti-PRO268, Anti-PRO290, Anti-PRO36006, Anti-PRO363, Anti-PRO365, Anti-PRO382, Anti-PRO444, Anti-PRO705, Anti-PRO1071, Anti-PRO1125, Anti-PRO1134, Anti-PRO1155, Anti-PRO1281, Anti-PRO1343, Anti-PRO1379, Anti-PRO1380, Anti-PRO1387, Anti-PRO1419, Anti-PRO1433, Anti-PRO1474, Anti-PRO1550, Anti-PRO1571, Anti-PRO1572, Anti-PRO1759, Anti-PRO1904, Anti-PRO35193, Anti-PRO4341, Anti-PRO4348, Anti-PRO4369, Anti-PRO4381, Anti-PRO4407, Anti-PRO4425, Anti-PRO4985, Anti-PRO4989, Anti-PRO5737, Anti-PRO5800, Anti-PRO5993, Anti-PRO6017, Anti-PRO7174, Anti-PRO9744, Anti-PRO9821, Anti-PRO9852, Anti-PRO9873, Anti-PRO10196, Anti-PRO34778, Anti-PRO20233, Anti-PRO21956, Anti-PRO57290, Anti-PRO38465, Anti-PRO38683 or Anti-PRO85161 Antibodies The anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies of the invention have various therapeutic and/or diagnostic utilities for a neurological disorder; a cardiovascular, endothelial or angiogenic disorder; an immunological disorder; an oncological disorder; an embryonic developmental disorder or lethality, or a metabolic abnormality. For example, anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies may be used in diagnostic assays for PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13: 1014 (1974); Pain et al., *J. Immunol. Meth.*, 40:219 (1981); and Nygren, *J. Histochem. and Cytochem.*, 30:407 (1982).

Anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 antibodies also are useful for the affinity purification of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides from recombinant cell culture or natural sources. In this process, the antibodies against PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides are immobilized on a suitable support, such a Sephadex resin or filter paper, using methods well known in the art. The immobilized antibody then is contacted with a sample containing the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide to be purified, and thereafter the support is washed with a suitable solvent that will remove substantially all the material in the sample except the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, which is bound to the immobilized antibody. Finally, the support is washed with another suitable solvent that will release the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology*, 266:460-480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253: 1278-1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL$^+$, SUC$^+$, GAL$^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4-p) or the complex formation of these proteins may also be preferably employed in combination with the amylase-expressing yeast.

Transformation was performed based on the protocol outlined by Gietz et al., *Nucl. Acid. Res.*, 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about $2\times10^6$ cells/ml (approx. $OD_{600}$=0.1) into fresh YEPD broth (500 ml) and regrown to $1\times10^7$ cells/ml (approx. $OD_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 μl) with freshly denatured single stranded salmon testes DNA (Lofstrand Labs, Gaithersburg, Md.) and transforming DNA (1 μg, vol.<10 μl) in microfuge tubes. The mixture was mixed briefly by vortexing, then 40% PEG/TE (600 μl, 40% polyethylene glycol-4000, 10 mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.*, 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 µl) in a 96 well plate. At this time, the positive colonies were either frozen and stored for subsequent analysis or immediately amplified. An aliquot of cells (5 µl) was used as a template for the PCR reaction in a 25 µl volume containing: 0.5 µl Klentaq (Clontech, Palo Alto, Calif.); 4.0 µl 10 mM dNTP's (Perkin Elmer-Cetus); 2.5 µl Kentaq buffer (Clontech); 0.25 µl forward oligo 1; 0.25 µl reverse oligo 2; 12.5 µl distilled water. The sequence of the forward oligonucleotide 1 was:

```
                                        (SEQ ID NO: 107)
5'-TGTAAAACGACGGCCAGTTAAATAGACCTGCAATTATTAATCT-3'
```

The sequence of reverse oligonucleotide 2 was:

```
                                        (SEQ ID NO: 108)
5'-CAGGAAACAGCTATGACCACCTGCACACCTGCAAATCCATT-3'
```

PCR was then performed as follows:

| a. |              | Denature | 92° C., | 5 minutes  |
|----|--------------|----------|---------|------------|
| b. | 3 cycles of: | Denature | 92° C., | 30 seconds |
|    |              | Anneal   | 59° C., | 30 seconds |
|    |              | Extend   | 72° C., | 60 seconds |
| c. | 3 cycles of: | Denature | 92° C., | 30 seconds |
|    |              | Anneal   | 57° C., | 30 seconds |
|    |              | Extend   | 72° C., | 60 seconds |
| d. | 25 cycles of:| Denature | 92° C., | 30 seconds |
|    |              | Anneal   | 55° C., | 30 seconds |
|    |              | Extend   | 72° C., | 60 seconds |
| e. |              | Hold     | 4° C.   |            |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 µl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Using the techniques described in Examples 1 to 3 above, numerous full-length cDNA clones were identified as encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides as disclosed herein. These cDNAs were then deposited under the terms of the Budapest Treaty with the American Type Culture Collection, 10801 University Blvd., Manassas, Va. 20110-2209, USA (ATCC) as shown in Table 7 below. In addition, the sequence of DNA225543 encoding PRO36006 polypeptides was identified from GenBank accession no.: AF170484; the sequence of DNA82372 encoding PRO1904 polypeptides was identified from GenBank accession no.: AB007454; the sequence of DNA225681 encoding PRO35193 polypeptides was identified from GenBank accession no.: D14012; the sequence of DNA220432 encoding PRO34778 polypeptides was identified from GenBank accession no.: AF369708; the sequence of DNA165608 encoding PRO20233 polypeptides was identified from GenBank accession no.: AF286095; the sequence of DNA269238 encoding PRO57290 polypeptides was identified from GenBank accession no.: AF326591; the sequence of DNA228002 encoding PRO38465 polypeptides was identified from GenBank accession no.: AF412-409; the sequence of DNA228199 encoding PRO38683 polypeptides was identified from GenBank accession no.: AK024365; and the sequence of DNA329632 encoding PRO85161 polypeptides was identified from GenBank accession no.: AF479260.

Table 7

TABLE 7

| Material | ATCC Dep. No. | Deposit Date |
|---|---|---|
| DNA33460-1166 | 209376 | Oct. 16, 1997 |
| DNA35841-1173 | 209403 | Oct. 17, 1997 |
| DNA39427-1179 | 209395 | Oct. 17, 1997 |
| DNA35680-1212 | 209790 | Apr. 21, 1998 |
| DNA45419-1252 | 209616 | Feb. 5, 1998 |
| DNA46777-1253 | 209619 | Feb. 5, 1998 |
| DNA45234-1277 | 209654 | Mar. 5, 1998 |
| DNA26846-1397 | 203406 | Oct. 27, 1998 |
| DNA50914-1289 | 209722 | Mar. 31, 1998 |
| DNA58847-1383 | 209879 | May 20, 1998 |
| DNA60619-1482 | 209993 | Jun. 16, 1998 |
| DNA56865-1491 | 203022 | Jun. 23, 1998 |
| DNA59849-1504 | 209986 | Jun. 16, 1998 |
| DNA59820-1549 | 203129 | Aug. 18, 1998 |
| DNA66675-1587 | 203282 | Sep. 22, 1998 |
| DNA59828-1608 | 203158 | Aug. 25, 1998 |
| DNA60740-1615 | 203456 | Nov. 3, 1998 |
| DNA68872-1620 | 203160 | Aug. 25, 1998 |
| DNA71290-1630 | 203275 | Sep. 22, 1998 |
| DNA71184-1634 | 203266 | Sep. 22, 1998 |
| DNA73739-1645 | 203270 | Sep. 22, 1998 |
| DNA76393-1664 | 203323 | Oct. 6, 1998 |
| DNA73730-1679 | 203320 | Oct. 6, 1998 |
| DNA73734-1680 | 203363 | Oct. 20, 1998 |
| DNA76531-1701 | 203465 | Nov. 17, 1998 |
| DNA81761-2583 | 203862 | Mar. 23, 1999 |
| DNA92232-2589 | 203895 | Mar. 30, 1999 |
| DNA92289-2598 | PTA-131 | May 25, 1999 |
| DNA92225-2603 | 203950 | Apr. 20, 1999 |
| DNA92264-2616 | 203969 | Apr. 27, 1999 |
| DNA93011-2637 | PTA-20 | May 4, 1999 |
| DNA59770-2652 | PTA-427 | Jul. 27, 1999 |
| DNA80135-2655 | PTA-234 | Jun. 15, 1999 |
| DNA92929-2534-1 | 203586 | Jan. 12, 1999 |
| DNA108912-2680 | PTA-124 | May 25, 1999 |
| DNA100276-2684 | PTA-380 | Jul. 20, 1999 |
| DNA96860-2700 | PTA-478 | Aug. 3, 1999 |
| DNA96883-2745 | PTA-544 | Aug. 17, 1999 |
| DNA136110-2763 | PTA-652 | Sep. 14, 1999 |
| DNA108725-2766 | PTA-863 | Oct. 19, 1999 |
| DNA129332-2775 | PTA-944 | Nov. 9, 1999 |
| DNA143076-2787 | PTA-1028 | Dec. 7, 1999 |
| DNA144841-2816 | PTA-1188 | Jan. 11, 2000 |
| DNA178511-2986 | PTA-2452 | Sep. 12, 2000 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 4

Isolation of cDNA Clones Encoding Human PRO226 Polypeptides [UNQ200]

A consensus DNA sequence was assembled relative to other EST sequences using phrap as described in Example 1 above. This assembled consensus sequence encoding an EGF-like homologue is herein identified as DNA28744. Based on the DNA28744 consensus sequence, oligonucleotides were synthesized: 1) to identify by PCR a cDNA library that contained the sequence of interest, and 2) for use as probes to isolate a clone of the full-length coding sequence for PRO226.

PCR primers (forward and reverse) were synthesized:

```
forward PCR primer (28744.f) (OLI556):
5'-ATTCTGCGTGAACACTGAGGGC-3'   (SEQ ID NO: 109)

reverse PCR primer (28744.r) (OLI557):
5'-ATCTGCTTGTAGCCCTCGGCAC-3'   (SEQ ID NO: 110)
```

Additionally, a synthetic oligonucleotide hybridization probe was constructed from the DNA28744 consensus sequence which had the following nucleotide sequence:

```
hybridization probe (28744.p) (OLI555):
                                  (SEQ ID NO: 111)
5'-CCTGGCTATCAGCAGGTGGGCTCCAAGTGTCTCGATGTGGATGAGTGT
GA-3'
```

In order to screen several libraries for a source of a full-length clone, DNA from the libraries was screened by PCR amplification with the PCR primer pairs identified above. A positive library was then used to isolate clones encoding the PRO226 gene using the probe oligonucleotide and one of the PCR primers. RNA for construction of the cDNA libraries was isolated from human fetal lung tissue.

DNA sequencing of the isolated clones isolated as described above gave the full-length DNA sequence for DNA33460-1166 [FIG. 1, SEQ ID NO:1]; and the derived protein sequence for PRO226.

The entire coding sequence of DNA33460-1166 is included in FIG. 1 (SEQ ID NO: 1). Clone DNA33460-1166 contains a single open reading frame with an apparent translational initiation site at nucleotide positions 62-64, and an apparent stop codon at nucleotide positions 1391-1393. The predicted polypeptide precursor is 443 amino acids long. Analysis of the full-length PRO226 sequence shown in FIG. 2 (SEQ ID NO:2) evidences the presence of a variety of important polypeptide domains, wherein the locations given for those important polypeptide domains are approximate as described above. Analysis of the full-length PRO226 polypeptide shown in FIG. 2 evidences the presence of the following: a signal peptide from about amino acid 1 to about amino acid 25; N-glycosylation sites from about amino acid 198 to about amino acid 202 and from about amino acid 394 to about amino acid 398; N-myristoylation sites from about amino acid 76 to about amino acid 82, from about amino acid 145 to about amino acid 151, from about amino acid 182 to about amino acid 188, from about amino acid 222 to about amino acid 228, from about amino acid 290 to about amino acid 296, from about amino acid 305 to about amino acid 311, from about amino acid 371 to about amino acid 377 and from about amino acid 381 to about amino acid 387; and aspartic acid and asparagine hydroxylation sites from about amino acid 140 to about amino acid 152, from about amino acid 177 to about amino acid 189, from about amino acid 217 to about amino acid 229, and from about amino acid 258 to about amino acid 270. Clone DNA33460-1166 has been deposited with the ATCC on Oct. 16, 1997 and is assigned ATCC deposit no. 209376.

Based on a BLAST and FastA sequence alignment analysis of the full-length PRO226 sequence shown in FIG. 2 (SEQ ID NO:2), EGF-like homolog DNA33460-1166 shows amino acid sequence identity to HT protein and/or Fibulin (49% and 38%, respectively).

Example 5

Isolation of cDNA Clones Encoding Human PRO257 Polypeptides [UNQ224]

A consensus DNA sequence was assembled relative to other EST sequences using phrap as described in Example 1 above. This consensus sequence is herein designated DNA28731. Based on the DNA28731 consensus sequence, oligonucleotides were synthesized: 1) to identify by PCR a cDNA library that contained the sequence of interest, and 2) for use as probes to isolate a clone of the full-length coding sequence for PRO257.

A pair of PCR primers (forward and reverse) were synthesized:

```
                                         (SEQ ID NO: 112)
forward PCR primer 5'-TCTCTATTCCAAACTGTGGCG-3'

(SEQ ID NO: 113)
reverse PCR primer 5'-TTTGATGACGATTCGAAGGTGG-3'
```

Additionally, a synthetic oligonucleotide hybridization probe was constructed from the consensus DNA28731 sequence which had the following nucleotide sequence

```
hybridization probe
                                         (SEQ ID NO: 114)
5'-GGAAGGATCCTTCACCAGCCCCAATTACCCAAAGCCGCATCCTGAG
C-3'
```

In order to screen several libraries for a source of a full-length clone, DNA from the libraries was screened by PCR amplification with the PCR primer pair identified above. A positive library was then used to isolate clones encoding the PRO257 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO257 [herein designated as DNA35841-1173 (FIG. 3; SEQ ID NO:3) and the derived protein sequence for PRO257.

The entire nucleotide sequence of DNA35841-1173 is shown in FIG. 3 (SEQ ID NO:3). Clone DNA35841-1173 contains a single open reading frame with an apparent translational initiation site at nucleotide positions 964-966 and ending at the stop codon at nucleotide positions 2785-2787 (FIG. 3). The predicted polypeptide precursor is 607 amino acids long (FIG. 4; SEQ ID NO:4). Clone DNA35841-1173 has been deposited with ATCC on Oct. 17, 1997 and is assigned ATCC deposit no. ATCC 209403.

Analysis of the amino acid sequence of the full-length PRO257 polypeptide suggests that portions of it possess significant homology to the ebnerin protein, thereby indicating that PRO257 may be a novel protein member related to the ebnerin protein.

Example 6

Isolation of cDNA Clones Encoding Human PRO268 Polypeptides [UNQ235]

A consensus DNA sequence was assembled relative to other EST sequences using phrap as described in Example 1 above. This consensus sequence is herein designated DNA35698. Based on the DNA35698 consensus sequence, oligonucleotides were synthesized: 1) to identify by PCR a cDNA library that contained the sequence of interest, and 2) for use as probes to isolate a clone of the full-length coding sequence for PRO268.

Forward and reverse PCR primers were synthesized:

```
forward PCR primer 1
5'-TGAGGTGGGCAAGCGGCGAAATG-3'       (SEQ ID NO: 115)

forward PCR primer 2
5'-TATGTGGATCAGGACGTGCC-3'          (SEQ ID NO: 116)

forward PCR primer 3
5'-TGCAGGGTTCAGTCTAGATTG-3'         (SEQ ID NO: 117)

reverse PCR primer
5'-TTGAAGGACAAAGGCAATCTGCCAC-3'     (SEQ ID NO: 118)
```

Additionally, a synthetic oligonucleotide hybridization probe was constructed from the consensus DNA35698 sequence which had the following nucleotide sequence

```
hybridization probe
                                         (SEQ ID NO: 119)
5'-GGAGTCTTGCAGTTCCCCTGGCAGTCCTGGTGCTGTTGCTTTGGG-3'
```

In order to screen several libraries for a source of a full-length clone, DNA from the libraries was screened by PCR amplification with the PCR primer pair identified above. A positive library was then used to isolate clones encoding the PRO268 gene using the probe oligonucleotide and one of the PCR primers.

RNA for construction of the cDNA libraries was isolated from human fetal lung tissue.

DNA sequencing of the clones isolated as described above gave the full-length DNA sequence for PRO268 [herein designated as DNA39427-1179] (SEQ ID NO:5) and the derived protein sequence for PRO268.

The entire nucleotide sequence of DNA39427-1179 is shown in FIG. 5 (SEQ ID NO:5). Clone DNA39427-1179 contains a single open reading frame with an apparent translational initiation site at nucleotide positions 13-15 and ending at the stop codon at nucleotide positions 853-855 (FIG. 5). The predicted polypeptide precursor is 280 amino acids long (FIG. 6; SEQ ID NO:6). Clone DNA39427-1179 has been deposited with ATCC on Oct. 17, 1997 and is assigned ATCC deposit no. ATCC 209395.

Analysis of the amino acid sequence of the full-length PRO268 polypeptide suggests that it possess significant homology to protein disulfide isomerase, thereby indicating that PRO268 may be a novel protein disulfide isomerase.

Example 7

Isolation of cDNA Clones Encoding Human PRO290 Polypeptides [UNQ253]

An expressed sequence tag (EST) DNA database (LIFESEQ®, Incyte Pharmaceuticals, Palo Alto, Calif.) was searched and an EST was identified that had homology to beige and FAN. An oligonucleotide probe based upon the identified EST sequence was then synthesized and used to screen human fetal kidney cDNA libraries in an attempt to identify a full-length cDNA clone. The oligonucleotide probe had the following sequence:

```
                                           (SEQ ID NO: 120)
5'TGACTGCACTACCCCGTGGCAAGCTGTTGAGCCAGCTCAGCTG 3'.
```

RNA for construction of cDNA libraries was isolated from human fetal kidney tissue. The cDNA libraries used to isolate the cDNA clones encoding human PRO290 were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science 253:1278-1280 (1991)) in the unique XhoI and NotI.

A cDNA clone was identified and sequenced in entirety. The entire nucleotide sequence of DNA35680-1212 is shown in FIG. 7 (SEQ ID NO:7). Clone DNA35680-1212 contains a single open reading frame with an apparent translational initiation site at nucleotide positions 293-295, and a stop codon at nucleotide positions 3302-3304 (FIG. 7; SEQ ID NO:7). The predicted polypeptide precursor is 1003 amino acids long (FIG. 8; SEQ ID NO:8).

It is currently believed that the PRO290 polypeptide is related to FAN and/or beige. Clone DNA35680-1212 has been deposited with ATCC on Apr. 21, 1998 and is assigned ATCC deposit no. 209790. It is understood that the deposited clone has the actual correct sequence rather than the representations provided herein. The full-length PRO290 protein shown in FIG. 8 has an estimated molecular weight of about 112,013 daltons and a pI of about 6.4.

Example 8

Isolation of cDNA Clones Encoding Human PRO363 Polypeptides [UNQ318]

A consensus sequence was obtained relative to a variety of EST sequences as described in Example 1 above, wherein the consensus sequence obtained is herein designated DNA42828. Based on the DNA42828 consensus sequence, oligonucleotides were synthesized: 1) to identify by PCR a cDNA library that contained the sequence of interest, and 2) for use as probes to isolate a clone of the full-length coding sequence for PRO363.

A pair of PCR primers (forward and reverse) were synthesized:

```
forward PCR primer (42828.f1)
5'-CCAGTGCACAGCAGGCAACGAAGC-3'     (SEQ ID NO: 121)

reverse PCR primer (42828.r1)
5'-ACTAGGCTGTATGCCTGGGTGGGC-3'     (SEQ ID NO: 122)
```

Additionally, a synthetic oligonucleotide hybridization probe was constructed from the consensus DNA42828 sequence which had the following nucleotide sequence

```
hybridization probe (42828.p1)
                                           (SEQ ID NO: 123)
5'-GTATGTACAAAGCATCGGCATGGTTGCAGGAGCAGTGACAGGC-3'
```

In order to screen several libraries for a source of a full-length clone, DNA from the libraries was screened by PCR amplification with the PCR primer pair identified above. A positive library was then used to isolate clones encoding the PRO363 gene using the probe oligonucleotide and one of the PCR primers. RNA for construction of the cDNA libraries was isolated from human fetal kidney tissue (LIB227).

DNA sequencing of the clones isolated as described above gave the full-length DNA sequence for PRO363 [herein designated as UNQ318 (DNA45419-1252)] (SEQ ID NO:11) and the derived protein sequence for PRO363.

The entire nucleotide sequence of UNQ318 (DNA45419-1252) is shown in FIG. 11 (SEQ ID NO:11). Clone UNQ318 (DNA45419-1252) contains a single open reading frame with an apparent translational initiation site at nucleotide positions 190-192 and ending at the stop codon at nucleotide positions 1309-1311 (FIG. 11). The predicted polypeptide precursor is 373 amino acids long (FIG. 12). The full-length PRO363 protein shown in FIG. 12 has an estimated molecular weight of about 41,281 daltons and a pI of about 8.33. A transmembrane domain exists at amino acids 221 to 254 of the amino acid sequence shown in FIG. 12 (SEQ ID NO:12). The PRO363 polypeptide also possesses at least two myelin P0 protein domains from about amino acids 15 to 56 and from about amino acids 87 to 116. Clone UNQ318 (DNA45419-1252) has been deposited with ATCC on Feb. 5, 1998 and is assigned ATCC deposit no. 209616.

Analysis of the amino acid sequence of the full-length PRO363 polypeptide suggests that it possesses significant sequence similarity to the cell surface protein HCAR, thereby indicating that PRO363 may be a novel HCAR homolog. More specifically, an analysis of the Dayhoff database (version 35.45 SwissProt 35) evidenced significant homology between the PRO363 amino acid sequence and the following Dayhoff sequences, HS46KDA_1, HSU90716_1, MMCARH_1, MMCARHOM_1, MMU90715_1, A33_HUMAN, P_W14146, P_W14158, A42632 and B42632.

Example 9

Isolation of cDNA Clones Encoding Human PRO365 Polypeptides [UNQ320]

A consensus DNA sequence was assembled relative to other EST sequences using phrap as described in Example 1 above. This consensus sequence is herein designated DNA35613. Based on the DNA35613 consensus sequence, oligonucleotides were synthesized: 1) to identify by PCR a cDNA library that contained the sequence of interest, and 2) for use as probes to isolate a clone of the full-length coding sequence for PRO365.

Forward and reverse PCR primers were synthesized as follows:

```
                                        (SEQ ID NO: 124)
forward PCR primer 5'-AATGTGACCACTGGACTCCC-3'

(SEQ ID NO: 125)
forward PCR primer 5'-AGGCTTGGAACTCCCTTC-3'

(SEQ ID NO: 126)
reverse PCR primer 5'-AAGATTCTTGAGCGATTCCAGCTG-3'
```

Additionally, a synthetic oligonucleotide hybridization probe was constructed from the consensus DNA35613 sequence which had the following nucleotide sequence

```
hybridization probe
                                        (SEQ ID NO: 127)
5'-AATCCCTGCTCTTCATGGTGACCTATGACGACGGAAGCACAAGACT
G-3'
```

In order to screen several libraries for a source of a full-length clone, DNA from the libraries was screened by PCR amplification with one of the PCR primer pairs identified above. A positive library was then used to isolate clones encoding the PRO365 gene using the probe oligonucleotide and one of the PCR primers. RNA for construction of the cDNA libraries was isolated from human fetal kidney tissue.

DNA sequencing of the clones isolated as described above gave the full-length DNA sequence for PRO365 [herein designated as DNA46777-1253] (SEQ ID NO:13) and the derived protein sequence for PRO365.

The entire nucleotide sequence of DNA46777-1253 is shown in FIG. 13 (SEQ ID NO:13). Clone DNA46777-1253 contains a single open reading frame with an apparent translational initiation site at nucleotide positions 15-17 and ending at the stop codon at nucleotide positions 720-722 (FIG. 13). The predicted polypeptide precursor is 235 amino acids long (FIG. 14; SEQ ID NO:14). Important regions of the polypeptide sequence encoded by clone DNA46777-1253 have been identified and include the following: a signal peptide corresponding to amino acids 1-20, the start of the mature protein corresponding to amino acid 21, and multiple potential N-glycosylation sites as shown in FIG. 14. Clone DNA46777-1253 has been deposited with ATCC on Feb. 5, 1998 and is assigned ATCC deposit no. ATCC 209619.

Analysis of the amino acid sequence of the full-length PRO365 polypeptide suggests that portions of it possess significant homology to the human 2-19 protein, thereby indicating that PRO365 may be a novel human 2-19 protein homolog.

Example 10

Isolation of cDNA Clones Encoding Human PRO382 Polypeptides [UNQ323]

A consensus sequence was obtained relative to a variety of EST sequences as described in Example 1 above, wherein the consensus sequence obtained is herein designated DNA30892. Based on the DNA30892 consensus sequence, oligonucleotides were synthesized: 1) to identify by PCR a cDNA library that contained the sequence of interest, and 2) for use as probes to isolate a clone of the full-length coding sequence for PRO382.

A pair of PCR primers (forward and reverse) were synthesized:

```
                                        (SEQ ID NO: 128)
forward PCR primer 5'-TGACATCGCCCTTATGAAGCTGGC-3'

(SEQ ID NO: 129)
reverse PCR primer 5'-TACACGTCCCTGTGGTTGCAGATC-3'
```

Additionally, a synthetic oligonucleotide hybridization probe was constructed from the consensus DNA30892 sequence which had the following nucleotide sequence

```
hybridization probe
                                        (SEQ ID NO: 130)
5'-CGTTCAATGCAGAAATGATCCAGCCTGTGTGCCTGCCCAACTCTGAAG
AG-3'
```

In order to screen several libraries for a source of a full-length clone, DNA from the libraries was screened by PCR amplification with the PCR primer pair identified above. A positive library was then used to isolate clones encoding the PRO382 gene using the probe oligonucleotide and one of the PCR primers. RNA for construction of the cDNA libraries was isolated from human fetal kidney tissue (LIB227).

DNA sequencing of the clones isolated as described above gave the full-length DNA sequence for PRO382 [herein designated as UNQ323 (DNA45234-1277)] (SEQ ID NO:15) and the derived protein sequence for PRO382.

The entire nucleotide sequence of UNQ323 (DNA45234-1277) is shown in FIG. 15 (SEQ ID NO:15). Clone UNQ323 (DNA45234-1277) contains a single open reading frame with an apparent translational initiation site at nucleotide positions 126-128 and ending at the stop codon at nucleotide positions 1485-1487 (FIG. 15). The predicted polypeptide precursor is 453 amino acids long (FIG. 16; SEQ ID NO:16). The full-length PRO382 protein shown in FIG. 16 has an estimated molecular weight of about 49,334 daltons and a pI of about 6.32. Analysis of the native PRO382 amino acid sequence shown in FIG. 16 (SEQ ID NO:16) indicates the presence of a putative transmembrane domain from about amino acid 240 to about amino acid 284, a putative signal peptide at about amino acid 1 to about amino acid 20, a putative apple domain at about amino acid 386 to about amino acid 419, a putative Kringle domain at about amino acid 394 to about amino acid 406 and a histidine-containing protease active site at about amino acid 253 to about amino acid 258. Clone UNQ323 (DNA45234-1277) has been deposited with ATCC on Mar. 5, 1998 and is assigned ATCC deposit no. 209654.

Analysis of the amino acid sequence of the full-length PRO382 polypeptide suggests that it possess significant homology to serine protease proteins, thereby indicating that PRO382 may be a novel serine protease. Specifically, an analysis of the Dayhoff database (version 35.45 SwissProt 35) evidenced significant homology between the PRO382 amino acid sequence and the following Dayhoff sequences, HSU75329_1, ENTK_MOUSE, HEPS_HUMAN, AF030065_1, HEPS_RAT, PLMN_PIG, P_R89430, P_R89435, PLMN_HORSE, PLMN_BOVIN and P_R83959.

Example 11

Isolation of cDNA Clones Encoding Human PRO444 Polypeptides [UNQ328]

A cDNA sequence isolated in the amylase screen described in Example 2 above was designated DNA13121. Oligonucleotide probes were generated to this sequence and used to screen a human fetal lung library (LIB25) prepared as described in paragraph 1 of Example 2 above. The cloning vector was pRK5B (pRK5B is a precursor of pRK5D that does not contain the SfiI site; see, Holmes et al., Science, 253:1278-1280 (1991)), and the cDNA size cut was less than 2800 bp.

A full length clone was identified that contained a single open reading frame with an apparent translational initiation site at nucleotide positions 608-610 and ending at the stop codon found at nucleotide positions 959-961 (FIG. 17, SEQ ID NO:17). The predicted polypeptide precursor is 117 amino acids long, has a calculated molecular weight of approximately 12,692 daltons and an estimated pI of approximately 7.50. Analysis of the full-length PRO444 sequence shown in FIG. 18 (SEQ ID NO:18) evidences the presence of a signal peptide at amino acid 1 to about amino acid 16. An analysis of the Dayhoff database (version 35.45 SwissProt 35) evidenced homology between the PRO444 amino acid sequence and the following Dayhoff sequences: CEF44D12_8, P_R88452, YNE1_CAEEL, A47312, AF009957_1, and A06133_1.

Clone DNA26846-1397 was deposited with the ATCC on Oct. 27, 1998 and is assigned ATCC deposit no. 203406.

Example 12

Isolation of cDNA Clones Encoding Human PRO705 Polypeptides [UNQ369]

A consensus sequence was obtained relative to a variety of EST sequences as described in Example 1 above, wherein the consensus sequence obtained is herein designated DNA43437. Based on the DNA43437 consensus sequence, oligonucleotides were synthesized: 1) to identify by PCR a cDNA library that contained the sequence of interest, and 2) for use as probes to isolate a clone of the full-length coding sequence for PRO705.

A pair of PCR primers (forward and reverse) were synthesized:

```
forward PCR primer
5'-AAGCGTGACAGCGGGCACGTC-3'        (SEQ ID NO: 131)

reverse PCR primer
5'-TGCACAGTCTCTGCAGTGCCCAGG-3'     (SEQ ID NO: 132)
```

Additionally, a synthetic oligonucleotide hybridization probe was constructed from the consensus DNA43437 sequence which had the following nucleotide sequence

```
    hybridization probe (43437.p1)
                                    (SEQ ID NO: 133)
    5'-GAATGCTGGAACCGCCACACCAAAGCCAGATACTTGCCTG-3'
```

In order to screen several libraries for a source of a full-length clone, DNA from the libraries was screened by PCR amplification with the PCR primer pair identified above. A positive library was then used to isolate clones encoding the PRO705 gene using the probe oligonucleotide and one of the PCR primers. RNA for construction of the cDNA libraries was isolated from human fetal kidney tissue (LIB227).

DNA sequencing of the clones isolated as described above gave the full-length DNA sequence for PRO705 [herein designated as UNQ369 (DNA50914-1289)] (SEQ ID NO:19) and the derived protein sequence for PRO705.

The entire nucleotide sequence of UNQ369 (DNA50914-1289) is shown in FIG. 19 (SEQ ID NO:19). Clone UNQ369 (DNA50914-1289) contains a single open reading frame with an apparent translational initiation site at nucleotide positions 566-568 and ending at the stop codon at nucleotide positions 2231-2233 (FIG. 19). The predicted polypeptide precursor is 555 amino acids long (FIG. 20; SEQ ID NO:20). The full-length PRO705 protein shown in FIG. 20 has an estimated molecular weight of about 62,736 daltons and a pI of about 5.36. Analysis of the full-length PRO705 sequence as shown in FIG. 20 evidences the presence of the following: a signal peptide from about amino acid 1 to about amino acid 23, a eukaryotic DNA topoisomerase I active site from about amino acid 418 to about amino acid 436, and various regions that show homology to various glypican proteins from about amino acid 237 to about amino acid 279, about amino acid 421 to about amino acid 458, about amino acid 53 to about amino acid 74, about amino acid 466 to about amino acid 504, about amino acid 308 to about amino acid 355, about amino acid 104 to about amino acid 156 and about amino acid 379 to about amino acid 410. Clone UNQ369 (DNA50914-1289) has been deposited with ATCC on Mar. 31, 1998 and is assigned ATCC deposit no. 209722.

Analysis of the amino acid sequence of the full-length PRO705 polypeptide suggests that it possesses significant sequence similarity to the K-glypican protein, thereby indicating that PRO705 may be a novel glypican protein family member. More specifically, an analysis of the Dayhoff database (version 35.45 SwissProt 35) evidenced significant homology between the PRO705 amino acid sequence and the following Dayhoff sequences, GPCK_MOUSE, GLYP_CHICK, GLYP_RAT, GLYP_HUMAN, GPC2_RAT, GPC5_HUMAN, GPC3_HUMAN, GPC3_RAT, P_R30168 and CEC03H12_2.

Example 13

Isolation of cDNA Clones Encoding Human PRO1071 Polypeptides [UNQ528]

A consensus sequence was obtained relative to a variety of EST sequences as described in Example 1 above, wherein the consensus sequence obtained is herein designated DNA53035. Based on the DNA53035 consensus sequence, it was determined that that consensus sequence shared significant sequence identity with Incyte EST clone no. 2872569, a clone that upon review appeared to encode a full length protein. As such, Incyte EST clone no. 2872569 was purchased and its insert was obtained and sequenced so as to confirm the proper sequence. This sequence is herein designated UNQ528 or DNA58847-1383.

DNA sequencing of the clone isolated as described above gave the full-length DNA sequence for PRO1071 [herein designated as UNQ528 (DNA58847-1383)] (SEQ ID NO:21) and the derived protein sequence for PRO1071.

The entire nucleotide sequence of UNQ528 (DNA58847-1383) is shown in FIG. 21 (SEQ ID NO:21). Clone UNQ528 (DNA58848-1383) contains a single open reading frame with an apparent translational initiation site at nucleotide positions 133-135 and ending at the stop codon at nucleotide positions 1708-1710 (FIG. 21). The predicted polypeptide precursor is 525 amino acids long (FIG. 22; SEQ ID NO:22). The full-length PRO1071 protein shown in FIG. 22 has an estimated molecular weight of about 58,416 daltons and a pI of about 6.62. Analysis of the full-length PRO1071 sequence shown in FIG. 22 (SEQ ID NO:22) evidences the presence of the following: a signal peptide from about amino acid 1 to about amino acid 25, a potential N-glycosylation site from about amino acid 251 to about amino acid 254, a thrombospondin-1 homology block from about amino acid 385 to about amino acid 399 and von Willibrands factor type C homology blocks from about amino acid 385 to about amino acid 399, from about amino acid 445 to about amino acid 459 and from about amino acid 42 to about amino acid 56. Clone UNQ528 (DNA58847-1383) has been deposited with ATCC on May 20, 1998 and is assigned ATCC deposit no. 209879.

Analysis of the amino acid sequence of the full-length PRO1071 polypeptide suggests that it possesses significant sequence similarity to the thrombospondin protein, thereby indicating that PRO1071 may be a novel thrombospondin homolog. More specifically, an analysis of the Dayhoff database (version 35.45 SwissProt 35) evidenced significant homology between the PRO1071 amino acid sequence and the following Dayhoff sequences, AB002364_1, D67076_1, BTPCINPGN_1, CET13H10_1, CEF25H8_5, CEF53B6_2, CEC26C6_6, HSSEMG_1, CET21B6_4 and BTY08561_1.

Example 14

Isolation of cDNA Clones Encoding Human PRO1125 Polypeptides [UNQ563]

Use of the signal sequence algorithm described in Example 3 above allowed identification of a single EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56540.

In light of an observed sequence homology between the DNA56540 consensus sequence and an EST sequence encompassed within the Incyte EST clone no. 1486114, the Incyte EST clone 1486114 was purchased and the cDNA insert was obtained and sequenced. It was found that this insert encoded a full-length protein. The sequence of this cDNA insert is shown in FIG. 23 and is herein designated as DNA60615-1482.

The full length clone shown in FIG. 23 contained a single open reading frame with an apparent translational initiation site at nucleotide positions 47-49 and ending at the stop codon found at nucleotide positions 1388-1390 (FIG. 23; SEQ ID NO:23). The predicted polypeptide precursor (FIG. 24, SEQ ID NO:24) is 447 amino acids long. PRO1125 has a calculated molecular weight of approximately 49,798 daltons and an estimated pI of approximately 9.78. Clone DNA60619-1482 has been deposited with ATCC on Jun. 16, 1998 and is assigned ATCC deposit no. 209993. It is understood that the clone has the actual sequence and that the sequences herein are representations based on current techniques which may be prone to minor errors.

Based on a WU-BLAST2 sequence alignment analysis (using the ALIGN computer program) of the full-length sequence, PRO1125 shows some sequence identity with the following Dayhoff designations: RCO1NEUCR; S58306; PKWA_THECU; S76086; P_R85881; HET1_PODAN; SPU92792_1; APAF_HUMAN; S76414 and S59317.

Example 15

Isolation of cDNA Clones Encoding Human PRO1134 Polypeptides [UNQ572]

Use of the signal sequence algorithm described in Example 3 above allowed identification of an EST cluster sequence from the Incyte database, designated 7511. This EST cluster sequence was then compared to a variety of expressed sequence tag (EST) databases which included public EST databases (e.g., GenBank) and a proprietary EST DNA database (Lifeseq®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA55725. Two proprietary Genentech EST sequences were employed in the assembly.

In light of an observed sequence homology between the DNA55725 consensus sequence and an EST sequence encompassed within the Merck EST clone no. H94897, the Merck EST clone H94897 was purchased and the cDNA insert was obtained and sequenced. It was found that this insert encoded a full-length protein. The sequence of this cDNA insert is shown in FIG. 25 and is herein designated as DNA56865-1491.

Clone DNA56865-1491 contains a single open reading frame with an apparent translational initiation site at nucleotide positions 153-155 and ending at the stop codon at nucleotide positions 1266-1268 (FIG. 25; SEQ ID NO:25). The predicted polypeptide precursor is 371 amino acids long (FIG. 26; SEQ ID NO:26). The full-length PRO1134 protein shown in FIG. 26 has an estimated molecular weight of about 41,935 daltons and a pI of about 9.58. Analysis of the full-length PRO1134 sequence shown in FIG. 26 (SEQ ID NO:26) evidences the presence of the following: a signal peptide from about amino acid 1 to about amino acid 23, potential N-glycosylation sites from about amino acid 103 to about amino acid 106, from about amino acid 249 to about amino acid 252 and from about amino acid 257 to about amino acid 260, and an amino acid block having homology to tyrosinase CuA-binding region proteins from about amino acid 280 to about amino acid 306. Clone DNA56865-1491 has been deposited with ATCC on Jun. 23, 1998 and is assigned ATCC deposit no. 203022.

An analysis of the Dayhoff database (version 35.45 SwissProt 35), using a WU-BLAST-2 sequence alignment analysis of the full-length sequence shown in FIG. 26 (SEQ ID NO:26), evidenced significant homology between the PRO1134 amino acid sequence and the following Dayhoff sequences: F20P5_18, AC002396_10, S47847, C64146, GSPA_BACSU, P_W10564, RFAI_ECOLI, Y258_HAEIN, RFAJ_SALTY and P_R32985.

Example 16

Isolation of cDNA Clones Encoding Human PRO1155 Polypeptides [UNQ585]

Use of the signal sequence algorithm described in Example 3 above allowed identification of a single EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56102.

In light of an observed sequence homology between the DNA56102 consensus sequence and an EST sequence encompassed within the Incyte EST clone no. 2858870, the Incyte EST clone 2858870 was purchased and the cDNA insert was obtained and sequenced. It was found that this insert encoded a full-length protein. The sequence of this cDNA insert is shown in FIG. 27 and is herein designated as DNA59849-1504.

The full length clone shown in FIG. 27 contained a single open reading frame with an apparent translational initiation site at nucleotide positions 158-160 and ending at the stop codon found at nucleotide positions 563-565 (FIG. 27; SEQ ID NO:27). The predicted polypeptide precursor (FIG. 28, SEQ ID NO:28) is 135 amino acids long. PRO1155 has a calculated molecular weight of approximately 14,833 daltons and an estimated pI of approximately 9.78. Clone DNA59849-1504 has been deposited with ATCC on Jun. 16, 1998 and is assigned ATCC deposit no. 209986. It is understood that the actual clone has the correct sequence whereas herein are only representations which are prone to minor sequencing errors.

Based on a WU-BLAST2 sequence alignment analysis (using the ALIGN computer program) of the full-length sequence, PRO1155 shows some amino acid sequence identity with the following Dayhoff designations: TKNK_BOVIN; PVB19X587__1; AF019049__1; P_WO0948; S72864; P_WO0949; I62742; AF038501__1; TKNG_HUMAN; and YAT1_RHOBL. Based on the information provided herein, PRO1155 may play a role in providing neuroprotection and cognitive enhancement.

Example 17

Isolation of cDNA Clones Encoding Human PRO1281 Polypeptides [UNQ651]

A consensus DNA sequence was assembled relative to other EST sequences using phrap as described in Example 1 above. This consensus sequence is designated herein as DNA35720. Based on the DNA35720 sequence, oligonucleotides were synthesized: 1) to identify by PCR a cDNA library that contained the sequence of interest, and 2) for use as probes to isolate a clone of the full-length coding sequence for PRO1281.

PCR primers (forward and reverse) were synthesized:

```
forward PCR primers:
5'-TGGAAGGCTGCCGCAACGACAATC-3';    (SEQ ID NO: 134)

5'-CTGATGTGGCCGATGTTCTG-3';        (SEQ ID NO: 135)
and
```

```
-continued
5'-ATGGCTCAGTGTGCAGACAG-3'.        (SEQ ID NO: 136)

reverse PCR primers:
5'-GCATGCTGCTCCGTGAAGTAGTCC-3';    (SEQ ID NO: 137)
and

5'-ATGCATGGGAAAGAAGGCCTGCCC-3'.    (SEQ ID NO: 138)
```

Additionally, a synthetic oligonucleotide hybridization probe was constructed from the DNA35720 sequence which had the following nucleotide sequence:

```
hybridization probe:
                                   (SEQ ID NO: 139)
5'-TGCACTGGTGACCACGAGGGGGTGCACTATAGCCATCTGGAGCTGA
G-3'.
```

In order to screen several libraries for a source of a full-length clone, DNA from the libraries was screened by PCR amplification with the PCR primer pairs identified above. A positive library was then used to isolate clones encoding the PRO1281 gene using the probe oligonucleotide and one of the PCR primers. RNA for construction of the cDNA libraries was isolated human fetal liver.

DNA sequencing of the clones isolated as described above gave the full-length DNA sequence for PRO1281 (designated herein as DNA59820-1549 [FIG. 29, SEQ ID NO:29]; and the derived protein sequence for PRO1281.

The entire coding sequence of PRO1281 is shown in FIG. 29 (SEQ ID NO:29). Clone DNA59820-1549 contains a single open reading frame with an apparent translational initiation site at nucleotide positions 228-230 and an apparent stop codon at nucleotide positions 2553-2555. The predicted polypeptide precursor is 775 amino acids long. The full-length PRO1281 protein shown in FIG. 30 has an estimated molecular weight of about 85,481 daltons and a pI of about 6.92. Additional features include a signal peptide at about amino acids 1-15; and potential N-glycosylation sites at about amino acids 138-141 and 361-364.

An analysis of the Dayhoff database (version 35.45 SwissProt 35), using a WU-BLAST2 sequence alignment analysis of the full-length sequence shown in FIG. 30 (SEQ ID NO:30), revealed some sequence identity between the PRO1281 amino acid sequence and the following Dayhoff sequences: S44860, CET24D1__1, CEC38H2__3, CAC2_HAECO, B3A2_HUMAN, S22373, CEF38A3__2, CEC34F6__2, CEC34F6__3, and CELT22B11__3.

Clone DNA59820-1549 has been deposited with ATCC on Aug. 18, 1998 and is assigned ATCC deposit no. 203129.

Example 18

Isolation of cDNA Clones Encoding Human PRO1343 Polypeptides [UNQ698]

A cDNA sequence isolated in the amylase screen described in Example 2 above was found, by the WU-BLAST2 sequence alignment computer program, to have no significant sequence identity to any known human encoding nucleic acid. This cDNA sequence is herein designated DNA48921. Probes were generated from the sequence of the DNA48921 molecule and used to screen a human smooth muscle cell tissue library prepared as described in paragraph 1 above. The cloning vector was pRK5B (pRK5B is a precursor of pRK5D that does not contain the SfiI site; see, Holmes et al., Science, 253:1278-1280 (1991)), and the cDNA size cut was less than 2800 bp.

The oligonucleotide probes employed were as follows:

```
forward PCR primer (48921.f1)
                                        (SEQ ID NO: 140)
5'-CAATATGCATCTTGCACGTCTGG-3' reverse PCR primer (48921.r1)
                                        (SEQ ID NO: 141)
5'-AAGCTTCTCTGCTTCCTTTCCTGC-3' hybridization probe (48921.p1)
                                        (SEQ ID NO: 142)
5'-TGACCCCATTGAGAAGGTCATTGAAGGGATCAACCGAGGGCTG-3'
```

A full length clone was identified that contained a single open reading frame with an apparent translational initiation site at nucleotide positions 71-73 and a stop signal at nucleotide positions 812-814 (FIG. 31, SEQ ID NO:31). The predicted polypeptide precursor is 247 amino acids long, has a calculated molecular weight of approximately 25,335 daltons and an estimated pI of approximately 7.0. Analysis of the full-length PRO1343 sequence shown in FIG. 32 (SEQ ID NO:32) evidences the presence of the following: a signal peptide from about amino acid 1 to about amino acid 25 and a homologous region to circumsporozoite repeats from about amino acid 35 to about amino acid 225. Clone DNA66675-1587 has been deposited with ATCC on Sep. 22, 1998 and is assigned ATCC deposit no. 203282.

An analysis of the Dayhoff database (version 35.45 SwissProt 35), using a WU-BLAST2 sequence alignment analysis of the full-length sequence shown in FIG. 32 (SEQ ID NO:32), evidenced significant homology between the PRO1343 amino acid sequence and the following Dayhoff sequences: CSP_PLACC, CEF25H8_2, U88974_40, BNAMRNAA_1, BOBOPC3_1, S58135, AF061832_1, BHU52040_1, HUMPROFILE_1 and MTV023_14.

Additionally, an Incyte EST clone (Incyte EST clone no. 4701148) having homology to the DNA48921 sequence was obtained and the insert sequenced, thereby giving rise to the DNA66675-1587 sequence shown in FIG. 31.

Example 19

Isolation of cDNA Clones Encoding Human PRO1379 Polypeptides [UNQ716]

A consensus DNA sequence was assembled relative to other EST sequences using phrap as described in Example 1 above. This consensus sequence is designated herein DNA45232. Based on the DNA45232 consensus sequence, oligonucleotides were synthesized: 1) to identify by PCR a cDNA library that contained the sequence of interest, and 2) for use as probes to isolate a clone of the full-length coding sequence for PRO1379.

PCR primers (forward and reverse) were synthesized:

```
forward PCR primer
5'-TGGACACCGTACCCTGGTATCTGC-3'    (SEQ ID NO: 143)

reverse PCR primer
5'-CCAACTCTGAGGAGAGCAAGTGGC-3'    (SEQ ID NO: 144)
```

Additionally, a synthetic oligonucleotide hybridization probe was constructed from the consensus DNA45232 sequence which had the following nucleotide sequence:

```
hybridization probe
                                        (SEQ ID NO: 145)
5'-TGTATGTGCACACCCTCACCATCACCTCCAAGGGCAAGGAGAAC-3'.
```

In order to screen several libraries for a source of a full-length clone, DNA from the libraries was screened by PCR amplification with the PCR primer pair identified above. A positive library was then used to isolate clones encoding the PRO1379 gene using the probe oligonucleotide and one of the PCR primers. RNA for construction of the cDNA libraries was isolated human fetal kidney tissue.

DNA sequencing of the clones isolated as described above gave the full-length DNA sequence for PRO1379 which is designated herein as DNA59828-1608 and shown in FIG. 33 (SEQ ID NO:33); and the derived protein sequence for PRO1379 (SEQ ID NO:34).

The entire coding sequence of PRO1379 is shown in FIG. 33 (SEQ ID NO:33). Clone DNA59828-1608 contains a single open reading frame with an apparent translational initiation site at nucleotide positions 10-12 and an apparent stop codon at nucleotide positions 1732-1734. The predicted polypeptide precursor is 574 amino acids long. The full-length PRO1379 protein shown in FIG. 34 has an estimated molecular weight of about 65,355 daltons and a pI of about 8.73. Additional features include a signal peptide at about amino acids 1-17 and potential N-glycosylation sites at about amino acids 160-163, 287-290, and 323-326.

An analysis of the Dayhoff database (version 35.45 SwissProt 35), using a WU-BLAST2 sequence alignment analysis of the full-length sequence shown in FIG. 34 (SEQ ID NO:34), revealed some homology between the PRO1379 amino acid sequence and the following Dayhoff sequences: YHY8_YEAST, AF040625_1, HP714394_1, and HIV18U45630_1.

Clone DNA59828-1608 has been deposited with ATCC on Aug. 25, 1998 and is assigned ATCC deposit no. 203158.

Example 20

Isolation of cDNA Clones Encoding Human PRO1380 Polypeptides [UNQ717]

A cDNA sequence isolated in the amylase screen described in Example 2 above is herein designated DNA45776. Based on the DNA45776 sequence, oligonucleotide probes were generated and used to screen a human retina library prepared as described in paragraph 1 of Example 2 above. The cloning vector was pRK5B (pRK5B is a precursor of pRK5D that does not contain the SfiI site; see, Holmes et al., Science, 253:1278-1280 (1991)), and the cDNA size cut was less than 2800 bp.

PCR primers (forward and reverse) were synthesized:

```
forward PCR primer (45776.f1)
5'-TTTTGCGGTCACCATTGTCTGC-3'     (SEQ ID NO: 146)
and reverse PCR primer (45776.r1)
5'-CGTAGGTGACACAGAAGCCCAGG-3'.   (SEQ ID NO: 147)
```

Additionally, a synthetic oligonucleotide hybridization probe was constructed from the DNA45776 sequence which had the following nucleotide sequence:

```
hybridization probe (45776.p1)
                                        (SEQ ID NO: 148)
5'-TACGGCATGACCGGCTCCTTTCCTATGAGGAACTCCCAGGCACTGATA
T-3'.
```

In order to screen several libraries for a source of a full-length clone, DNA from the libraries was screened by PCR amplification with the PCR primer pair identified above. A positive library was then used to isolate clones encoding the PRO1380 gene using the probe oligonucleotide and one of the PCR primers.

A full length clone was identified that contained a single open reading frame with an apparent translational initiation site at nucleotide positions 36-38, and a stop signal at nucleotide positions 1461-1463 (FIG. 35; SEQ ID NO:35). The predicted polypeptide precursor is 470 amino acids long has a calculated molecular weight of approximately 51,715 daltons and an estimated pI of approximately 7.86. Additional features include transmembrane domains at about amino acids 50-74, 105-127, 135-153, 163-183, 228-252, 305-330, and 448-472; potential N-glycosylation sites at about amino acids 14-17 and 84-87; and a dihydrofolate reductase signature at about amino acids 60-68.

An analysis of the Dayhoff database (version 35.45 SwissProt 35), using a WU-BLAST2 sequence alignment analysis of the full-length sequence shown in FIG. 36 (SEQ ID NO:36), evidenced homology between the PRO1380 amino acid sequence and the following Dayhoff sequences: HSU81375_1, CEZK809_6, CEK02E11_1, AF034102_1, JC4196, CEF36H2_2, P_R92315, YAC2_YEAST, F1707_13, and CEF44D12_3.

Clone DNA60740-1615 was deposited with the ATCC on Nov. 3, 1998, and is assigned ATCC deposit no. 203456.

Example 21

Isolation of cDNA Clones Encoding Human PRO1387 Polypeptides [UNQ722]

Use of the signal sequence algorithm described in Example 3 above allowed identification of a single EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56259.

In light of an observed sequence homology between the DNA56259 consensus sequence and an EST sequence encompassed within the Incyte EST clone no. 3507924, the Incyte EST clone 3507924 was purchased and the cDNA insert was obtained and sequenced. It was found that this insert encoded a full-length protein. The sequence of this cDNA insert is shown in FIG. 37 and is herein designated as DNA68872-1620.

Clone DNA68872-1620 contains a single open reading frame with an apparent translational initiation site at nucleotide positions 85-87 and ending at the stop codon at nucleotide positions 1267-1269 (FIG. 37; SEQ ID NO:37). The predicted polypeptide precursor is 394 amino acids long (FIG. 38). The full-length PRO1387 protein shown in FIG. 38 has an estimated molecular weight of about 44,339 daltons and a pI of about 7.10. Analysis of the full-length PRO1387 sequence shown in FIG. 38 (SEQ ID NO:38) evidences the presence of the following: a signal peptide from about amino acid 1 to about amino acid 19, a transmembrane domain from about amino acid 275 to about amino acid 296, potential N-glycosylation sites from about amino acid 76 to about amino acid 79, from about amino acid 231 to about amino acid 234, from about amino acid 302 to about amino acid 305, from about amino acid 307 to about amino acid 310 and from about amino acid 376 to about amino acid 379, and amino acid sequence blocks having homology to myelin p0 protein from about amino acid 210 to about amino acid 239 and from about amino acid 92 to about amino acid 121. Clone DNA68872-1620 has been deposited with ATCC on Aug. 25, 1998 and is assigned ATCC deposit no. 203160.

An analysis of the Dayhoff database (version 35.45 SwissProt 35), using a WU-BLAST2 sequence alignment analysis of the full-length sequence shown in FIG. 38 (SEQ ID NO:38), evidenced significant homology between the PRO1387 amino acid sequence and the following Dayhoff sequences: P_W36955, MYP0_HETFR, HS46_KDA_1, AF049498_1, MYO0_HUMAN, AF030454_1, A53268, SHPTCRA_1, P_W14146 and GEN12838.

Example 22

Isolation of cDNA Clones Encoding Human PRO1419 Polypeptides [UNQ733]

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. One or more of the ESTs was derived from a diseased tonsil tissue library. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA59761.

In light of an observed sequence homology between the DNA59761 sequence and an EST sequence contained within the Incyte EST 3815008, the clone including this EST was purchased and the cDNA insert was obtained and sequenced. The sequence of this cDNA insert is shown in FIG. 39 and is herein designated as DNA71290-1630.

The full length clone shown in FIG. 39 contained a single open reading frame with an apparent translational initiation site at nucleotide positions 86-88 and ending at the stop codon found at nucleotide positions 341-343 (FIG. 39; SEQ ID NO:39). The predicted polypeptide precursor (FIG. 40, SEQ ID NO:40) is 85 amino acids long with the signal peptide at about amino acids 1-17 of SEQ ID NO:40. PRO1419 has a calculated molecular weight of approximately 9,700 daltons and an estimated pI of approximately 9.55. Clone DNA71290-1630 was deposited with the ATCC on Sep. 22, 1998 and is assigned ATCC deposit no. 203275.

An analysis of the Dayhoff database (version 35.45 SwissProt 35), using a WU-BLAST2 sequence alignment analysis of the full-length sequence shown in FIG. 40 (SEQ ID NO:40), revealed sequence identity between the PRO1419 amino acid sequence and the following Dayhoff sequences (data incorporated herein): S07975 (B3-hordein), C48232, HOR7_HORVU, GEN11764, S14970, AF020312_1, STAJ3220_1, CER07E3_1, CEY37A1B_4, and ATAC00423810.

Example 23

Isolation of cDNA Clones Encoding Human PRO1433 Polypeptides [UNQ738]

A consensus DNA sequence was assembled relative to other EST sequences using phrap as described in Example 1 above. This consensus sequence is herein designated DNA45230. Based on the DNA45230 consensus sequence, oligonucleotides were synthesized: 1) to identify by PCR a cDNA library that contained the sequence of interest, and 2) for use as probes to isolate a clone of the full-length coding sequence for PRO1433.

PCR primers (forward and reverse) were synthesized:

```
forward PCR primer (45230.f1)
5'-GCTGACCTGGTTCCCATCTACTCC-3'    (SEQ ID NO: 149)

reverse PCR primer (45230.r1)
5'-CCCACAGACACCCATGACACTTCC-3'    (SEQ ID NO: 150)
```

Additionally, a synthetic oligonucleotide hybridization probe was constructed from the consensus DNA45230 sequence which had the following nucleotide sequence

```
hybridization probe (45230.p1)
                                   (SEQ ID NO: 151)
5'-AAGAATGAATTGTACAAAGCAGGTGATCTTCGAGGAGGGCTCCTGGGG
CC-3'
```

In order to screen several libraries for a source of a full-length clone, DNA from the libraries was screened by PCR amplification with the PCR primer pair identified above. A positive library was then used to isolate clones encoding the PRO1433 gene using the probe oligonucleotide and one of the PCR primers. RNA for construction of the cDNA libraries was isolated from human adrenal gland tissue.

DNA sequencing of the clones isolated as described above gave the full-length DNA sequence for PRO1433 (designated herein as DNA71184-1634 [FIG. 41, SEQ ID NO:41]; and the derived protein sequence for PRO1433.

The entire nucleotide sequence of DNA71184-1634 is shown in FIG. 41 (SEQ ID NO:41). Clone DNA71184-1634 contains a single open reading frame with an apparent translational initiation site at nucleotide positions 185-187 and ending at the stop codon at nucleotide positions 1349-1351 (FIG. 41). The predicted polypeptide precursor is 388 amino acids long (FIG. 42). The full-length PRO1433 protein shown in FIG. 42 has an estimated molecular weight of about 43,831 daltons and a pI of about 9.64. Analysis of the full-length PRO1433 sequence shown in FIG. 42 (SEQ ID NO:42) evidences the presence of the following: a transmembrane domain from about amino acid 76 to about amino acid 97, potential N-glycosylation sites from about amino acid 60 to about amino acid 63, from about amino acid 173 to about amino acid 176 and from about amino acid 228 to about amino acid 231 and potential N-myristolation sites from about amino acid 10 to about amino acid 15, from about amino acid 41 to about amino acid 46, from about amino acid 84 to about amino acid 89, from about amino acid 120 to about amino acid 125, from about amino acid 169 to about amino acid 174, from about amino acid 229 to about amino acid 234, from about amino acid 240 to about amino acid 245, from about amino acid 318 to about amino acid 323 and from about amino acid 378 to about amino acid 383. Clone DNA71184-1634 has been deposited with ATCC on Sep. 22, 1998 and is assigned ATCC deposit no. 203266.

An analysis of the Dayhoff database (version 35.45 SwissProt 35), using a WU-BLAST2 sequence alignment analysis of the full-length sequence shown in FIG. 42 (SEQ ID NO:42), evidenced significant homology between the PRO1433 amino acid sequence and the following Dayhoff sequences: CELW01A11_4, CEF59A1_4, S67138, MTV050_3, S75135 and S12411.

Example 24

Isolation of cDNA Clones Encoding Human PRO1474 Polypeptides [UNQ745]

An expressed sequence tag (EST) DNA database (LIFESEQ®, Incyte Pharmaceuticals, Palo Alto, Calif.) was searched and an EST was identified. This EST showed homology to pancreatic secretory trypsin inhibitor.

The clone which included this EST was purchased from Incyte (it came from a uterine cervical tissue library) and sequenced in full to reveal the nucleic acid of SEQ ID NO:43, which encodes PRO1474.

The entire nucleotide sequence of PRO1474 is shown in FIG. 43 (SEQ ID NO:43). Clone DNA73739-1645 contains a single open reading frame with an apparent translational initiation site at nucleotide positions 45-47 and a stop codon at nucleotide positions 300-302 (FIG. 43; SEQ ID NO:43). The predicted polypeptide precursor is 85 amino acids long. As indicated in FIG. 44, the Kazal serine protease inhibitor family signature begins at about amino acid 45 of SEQ ID NO:44. Also indicated in FIG. 44 is a region conserved in integrin alpha chains (beginning at about amino acid 32 of SEQ ID NO:44). Clone DNA73739-1645 has been deposited with the ATCC on Sep. 22, 1998 and is assigned ATCC deposit no. 203270. The full-length PRO1474 protein shown in FIG. 44 has an estimated molecular weight of about 9,232 daltons and a pI of about 7.94.

An analysis of the Dayhoff database (version 35.45 SwissProt 35), using a WU-BLAST2 sequence alignment analysis of the full-length sequence shown in FIG. 44 (SEQ ID NO:44), revealed sequence identity between the PRO1474 amino acid sequence and the following Dayhoff sequences (all ovomucoids, data incorporated herein by reference): IOVO_FRAER, IOVO_FRAAF, IOVO_FRACO, IOVO_CYRMO, IOVO_STRCA, H61492, C61589, IOVO_POLPL, D61589, and IOVO_TURME.

Example 25

Isolation of cDNA Clones Encoding Human PRO1550 Polypeptides [UNQ762]

Use of the signal sequence algorithm described in Example 3 above allowed identification of an EST sequence from the Merck database, designated CELT15B7_12, also referred herein as "DNA10022". This EST sequence was then compared to a variety of expressed sequence tag (EST) databases which included public and proprietary EST databases (e.g., GenBank and LIFESEQ®) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated "DNA55708".

In light of the sequence homology between the DNA55708 sequence and a sequence contained within Incyte EST no. 3411659, the EST clone 3411659 was purchased and the cDNA insert was obtained and sequenced in its entirety. The sequence of this cDNA insert is shown in FIG. 45 and is herein designated as "DNA76393-1664".

The full length clone shown in FIG. 45 contained a single open reading frame with an apparent translational initiation site at nucleotide positions 138 to 140 and ending at the stop codon found at nucleotide positions 867 to 869 (FIG. 45; SEQ ID NO:45). The predicted polypeptide precursor (FIG. 46, SEQ ID NO:46) is 243 amino acids long. Other features of the PRO1550 protein include: a signal sequence at about amino acids 1-30; a hydrophobic domain at about amino acids 195-217; and a potential N-glycosylation site at about amino acids 186-189. PRO1550 has a calculated molecular weight of approximately 26,266 daltons and an estimated pI of approximately 8.43. Clone DNA76393-1664 was deposited with the ATCC on Oct. 6, 1998, and is assigned ATCC deposit no. 203323.

An analysis of the Dayhoff database (version 35.45 SwissProt 35), using a WU-BLAST2 sequence alignment analysis of the full-length sequence shown in FIG. 46 (SEQ ID NO:46), revealed some homology between the PRO1550 amino acid sequence and the following Dayhoff sequences: CELF59E12_11; CA24_ASCSU; AF018082_1; CA13_BOVIN; CA54_HUMAN; CA34_HUMAN; HUMCOL7A1X_1; P_W09643; AF053538_1; and HSEMCXIV2_1.

Example 26

Isolation of cDNA Clones Encoding Human PRO1571 Polypeptides [UNQ777]

A consensus DNA sequence was assembled relative to other EST sequences using phrap as described in Example 1 above. This consensus sequence is herein designated DNA69559. Based on homology observed between the DNA69559 consensus sequence and an EST sequence contained within the Incyte EST clone no. 3140760, Incyte EST clone no. 3140760 was purchased and the cDNA insert was obtained and sequenced. The sequence of this cDNA insert is shown in FIG. 47 and is herein designated as DNA73730-1679.

Clone DNA73730-1679 contains a single open reading frame with an apparent translational initiation site at nucleotide positions 90-92 and ending at the stop codon at nucleotide positions 807-809 (FIG. 47; SEQ ID NO:47). The predicted polypeptide precursor is 239 amino acids long (FIG. 48). The full-length PRO1571 protein shown in FIG. 48 has an estimated molecular weight of about 25,699 daltons and a pI of about 8.99. Analysis of the full-length PRO1571 sequence shown in FIG. 48 (SEQ ID NO:48) evidences the presence of the following: a signal peptide from about amino acid 1 to about amino acid 21 and transmembrane domains from about amino acid 82 to about amino acid 103, from about amino acid 115 to about amino acid 141 and from about amino acid 160 to about amino acid 182. Clone DNA73730-1679 has been deposited with ATCC on Oct. 6, 1998 and is assigned ATCC deposit no. 203320.

An analysis of the Dayhoff database (version 35.45 SwissProt 35), using a WU-BLAST2 sequence alignment analysis of the full-length sequence shown in FIG. 48 (SEQ ID NO:48), evidenced significant homology between the PRO1571 amino acid sequence and the following Dayhoff sequences: AF072128_1, AB000712_1, AB000714_1, AF007189_1, AF000959_1, AF068863_1, P_W15288, PM22_HUMAN, P_R30056 and LSU46824_1.

Example 27

Isolation of cDNA Clones Encoding Human PRO1572 Polypeptides [UNQ778]

Using the method described in Example 1 above, a consensus sequence was obtained. The consensus sequence is designated herein "DNA69560". Based on the DNA69560 consensus sequence and other information provided herein, a clone including another EST (Incyte DNA3051424) from the assembly was purchased and sequenced.

The entire coding sequence of PRO1573 is included in FIG. 49 (SEQ ID NO:49). Clone DNA73734-1680 contains a single open reading frame with an apparent translational initiation site at nucleotide positions 90-92 and an apparent stop codon at nucleotide positions 873-875. The predicted polypeptide precursor is 261 amino acids long. The signal peptide is at about amino acids 1-23 and the transmembrane domains are at about amino acids 81-100, 121-141, and 173-194 of SEQ ID NO: 50. One or more of the transmembrane domains can be deleted or inactivated. The locations of a N-glycosylation site, N-myristoylation sites, a tyrosine kinase phosphorylation site and a prokaryotic membrane lipoprotein lipid attachment site are indicated in FIG. 50. Clone DNA73734-1680 has been deposited with the ATCC on Oct. 20, 1998 and is assigned ATCC deposit no. 203363. The full-length PRO1572 protein shown in FIG. 50 has an estimated molecular weight of about 27,856 daltons and a pI of about 8.5.

An analysis of the Dayhoff database (version 35.45 SwissProt 35), using a WU-BLAST2 sequence alignment analysis of the full-length sequence shown in FIG. 50 (SEQ ID NO:50), revealed sequence identity between the PRO1572 amino acid sequence and the following Dayhoff sequences (incorporated herein): AF072127_1, HSU89916_1, AB000713_1, AB000714_1, AB000712_1, AF000959_1, AF072128_1, AF068863_1, P_W29881, and P_W58869.

Example 28

Isolation of cDNA Clones Encoding Human PRO1759 Polypeptides [UNQ832]

Use of the signal sequence algorithm described in Example 3 above allowed identification of an EST cluster sequence from the Incyte database, designated DNA10571. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. One or more of the ESTs was derived from pooled eosinophils of allergic asthmatic patients. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA57313.

In light of the sequence homology between the DNA57313 sequence and the Incyte EST 2434255, the clone including this EST was purchased and the cDNA insert was obtained and sequenced. The sequence of this cDNA insert is shown in FIG. 51 and is herein designated as DNA76531-1701.

The full length clone shown in FIG. 51 contained a single open reading frame with an apparent translational initiation site at nucleotide positions 125-127 and ending at the stop codon found at nucleotide positions 1475-1477 (FIG. 51; SEQ ID NO:51). The approximate locations of the signal peptide and transmembrane domains are indicated in FIG. 52, whereas the approximate locations for N-myristoylation sites, a lipid attachment site, an amidation site and a kinase phosphorylation site are indicated in FIG. 52. The predicted polypeptide precursor (FIG. 52, SEQ ID NO: 52) is 450 amino acids long. PRO1759 has a calculated molecular weight of approximately 49,765 daltons and an estimated pI of approximately 8.14. Clone DNA76531-1701 was deposited with the ATCC on Nov. 17, 1998 and is assigned ATCC deposit no. 203465.

An analysis of the Dayhoff database (version 35.45 SwissProt 35), using a WU-BLAST2 sequence alignment analysis of the full-length sequence shown in FIG. 52 (SEQ ID NO:52), revealed sequence identity between the PRO1759 amino acid sequence and the following Dayhoff sequences: OPDE_PSEAE, TH11_TRYBB, S67684, RGT2_YEAST, S68362, ATSUGTRPR__1, P_W17836 (Patent application WO9715668-A2), F69587, A48076, and A45611.

Example 29

Isolation of cDNA Clones Encoding Human PRO4341 Polypeptides [UNQ1895]

The extracellular domain (ECD) sequences (including the secretion signal sequence, if any) from about 950 known secreted proteins from the Swiss-Prot public database were used to search EST databases. The EST databases included public EST databases (e.g., GenBank), and a proprietary EST database (LIFESEQ®, Incyte Pharmaceuticals, Palo Alto, Calif.). The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence encoding PRO4341 was assembled relative to other EST sequences using phrap. This consensus sequence is designated herein "DNA45433".

Based on the DNA45433 consensus sequence oligonucleotides were synthesized: 1) to identify by PCR a cDNA library that contained the sequence of interest, and 2) for use as probes to isolate a clone of the full-length coding sequence for PRO4341. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'TTCTCTGGCCGACGCTGTGAGG3';       (SEQ ID NO: 152)
and reverse PCR primer
5'GCCATAAGGGCATTGCACACAAAGG3'.    (SEQ ID NO: 153)
```

Additionally, a synthetic oligonucleotide hybridization probe was constructed from the consensus 45433 sequence which had the following nucleotide sequence:

```
hybridization probe
                                  (SEQ ID NO: 154)
5'AGTCCCTGCTTCAACAGGGCCACCTGCTACCCGACCTCTCCAC3'.
```

In order to screen several libraries for a source of a full-length clone, DNA from the libraries was screened by PCR amplification with the PCR primer pair identified above. A positive library was then used to isolate clones encoding the PRO4341 gene using the probe oligonucleotide and one of the PCR primers.

RNA for construction of the cDNA libraries was isolated from human fetal lung. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for PRO4341 (designated herein as DNA81761-2583 [FIG. 57, SEQ ID NO:57]; and the derived protein sequence for PRO4341.

The entire coding sequence of PRO4341 is shown in FIG. 57 (SEQ ID NO:57). Clone DNA81761-2583 contains a single open reading frame with an apparent translational initiation site at nucleotide positions 36-38, and an apparent stop codon at nucleotide positions 2091-2093. The predicted polypeptide precursor is 685 amino acids long. Clone DNA81761-2583 (UNQ1895), designated as DNA81761-2583 has been deposited with ATCC on Mar. 23, 1999 and is assigned ATCC deposit no. 203862. The full-length PRO4341 protein shown in FIG. 58 has an estimated molecular weight of about 74605 daltons and a pI of about 6.89.

An analysis of the Dayhoff database (version 35.45 SwissProt 35), using a WU-BLAST2 sequence alignment analysis of the full-length sequence shown in FIG. 58 (SEQ ID NO: 58), revealed homology between the PRO4341 amino acid sequence and the following Dayhoff sequences (sequences and related text incorporated herein): P_W11719, I50719, P_WO0876, DLL1_HUMAN, P_W18348, AF030031__1, AF020201__1, AF028593__1, P_WO5833 and CRB_DROME. Therefore, it is believed that PRO4341 is related to Delta and useful in the treatment of cancer, wound repair, differentiation disorders or in assays to development compounds which are useful in such treatments.

Example 30

Isolation of cDNA Clones Encoding Human PRO4348 Polypeptides [UNQ1902]

The extracellular domain (ECD) sequences (including the secretion signal sequence, if any) from about 950 known secreted proteins from the Swiss-Prot public database were used to search EST databases. The EST databases included public EST databases (e.g., GenBank), and a proprietary EST database (LIFESEQ®, Incyte Pharmaceuticals, Palo Alto, Calif.). The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence encoding PRO4348 was assembled relative to other EST sequences using phrap. This consensus sequence is designated herein "DNA77500".

Based on the DNA77500 consensus sequence, DNA92232-2589 was identified. DNA sequencing gave the full-length DNA sequence for PRO4348 (designated herein as DNA92232-2589 [FIG. 59, SEQ ID NO:59]; and the derived protein sequence for PRO4348.

The entire coding sequence of PRO4348 is shown in FIG. 59 (SEQ ID NO:59). Clone DNA92232-2589 contains a single open reading frame with an apparent translational initiation site at nucleotide positions 57-59, and an apparent stop codon at nucleotide positions 789-791 of SEQ ID NO:59. The predicted polypeptide precursor is 244 amino acids long. Clone DNA92232-2589 (UNQ1902), designated as DNA92232-2589 has been deposited with ATCC ON Mar. 30, 1999 and is assigned ATCC deposit no. 203895. The full-length PRO4348 protein shown in FIG. 60 has an estimated molecular weight of about 28319 daltons and a pI of about 8.78.

An analysis of the Dayhoff database (version 35.45 SwissProt 35), using a WU-BLAST2 sequence alignment analysis of the full-length sequence shown in FIG. 60 (SEQ ID NO:60), revealed homology between the PRO4348 amino acid sequence and the following Dayhoff sequences: D70554, D69267, YH09_YEAST, D71620, AB019196_1, F71102, COQ5_YEAST, BIOC_SERMA, S61202, and PMTA_RHOSH.

Example 31

Isolation of cDNA Clones Encoding Human PRO4369 Polypeptides [UNQ1911]

DNA92289-2598 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA75180. In light of DNA75180, DNA92289 was identified.

The full length clone shown in FIG. 61 contained a single open reading frame with an apparent translational initiation site at nucleotide positions 74-76 and ending at the stop codon found at nucleotide positions 776-778 (FIG. 61; SEQ ID NO:61). The predicted polypeptide precursor (FIG. 62, SEQ ID NO:62) is 234 amino acids long. PRO4369 has a calculated molecular weight of approximately 26077 daltons and an estimated pI of approximately 8.13.

An analysis of the Dayhoff database (version 35.45 SwissProt 35), using a WU-BLAST2 sequence alignment analysis of the full-length sequence shown in FIG. 62 (SEQ ID NO:62), revealed homology between the PRO4369 amino acid sequence and the following Dayhoff sequences (sequences and related text incorporated herein): Y081_HUMAN, NUCL_CHICK, S64439, YG3A_YEAST, CELF12F3_3, ATGELSOLI_1, S55395, NFM_RABIT, PFAHSP86B_1 and NPM_XENLA.

Clone DNA92289-2598 (UNQ1911), designated as DNA92289-2598 was deposited with the ATCC on May 25, 1999 and is assigned ATCC deposit no. PTA-131.

Example 32

Isolation of cDNA Clones Encoding Human PRO4381 Polypeptides [UNQ1916]

DNA92225-2603 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST sequence from the Incyte database. This EST sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). One or more of the ESTs used in the assembly was derived from a thymus tissue library. The consensus sequence obtained therefrom is herein designated DNA79136. In light of the DNA79136 sequence DNA92225-2603 was identified and sequenced.

The full length clone shown in FIG. 63 contained a single open reading frame with an apparent translational initiation site at nucleotide positions 145-147 and ending at the stop codon found at nucleotide positions 460-462 (FIG. 63; SEQ ID NO: 63). The predicted polypeptide precursor (FIG. 64, SEQ ID NO: 64) is 105 amino acids long. PRO4381 has a calculated molecular weight of approximately 10803 daltons and an estimated pI of approximately 7.2.

An analysis of the Dayhoff database (version 35.45 SwissProt 35), using a WU-BLAST2 sequence alignment analysis of the full-length sequence shown in FIG. 64 (SEQ ID NO: 64), revealed homology between the PRO4381 amino acid sequence and the following Dayhoff sequences (sequences and related text incorporated herein): A2AC_CAVPO, P102 KB_39, S7123, I54343, HSL25A3_1, C71466, P_R62382, S76774, HS0934, and A64763.

Clone DNA92225-2603 (UNQ1916), designated as DNA92225-2603 was deposited with the ATCC on Apr. 20, 1999 and is assigned ATCC deposit no. 203950.

Example 33

Isolation of cDNA Clones Encoding Human PRO4407 Polypeptides [UNQ1932]

DNA92264-2616 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). Based upon the cluster sequence and the sequence alignments, DNA92264-2616 was identified and sequenced.

The full length clone shown in FIG. 65 contained a single open reading frame with an apparent translational initiation site at nucleotide positions 109-111 and ending at the stop codon found at nucleotide positions 757-759 (FIG. 65; SEQ ID NO: 65). The predicted polypeptide precursor (FIG. 66, SEQ ID NO: 66) is 216 amino acids long. PRO4407 has a calculated molecular weight of approximately 23729 daltons and an estimated pI of approximately 4.73.

An analysis of the Dayhoff database (version 35.45 SwissProt 35), using a WU-BLAST2 sequence alignment analysis of the full-length sequence shown in FIG. 66 (SEQ ID NO: 66), revealed homology between the PRO4407 amino acid sequence and the following Dayhoff sequences: SC1E6_12, D80003_1, HMGA_SOYBN, DROTRO12_1, HSU91934_1, GEN14338, AF051945_1, A45644, P_W60213, and P_W33807.

Clone DNA92264-2616 (UNQ1932), designated as DNA92264-2616 was deposited with the ATCC on Apr. 27, 1999 and is assigned ATCC deposit no. 203969.

Example 34

Isolation of cDNA Clones Encoding Human PRO4425 Polypeptides [UNQ1942]

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA81099.

In light of an observed sequence homology between the DNA81099 sequence and an EST sequence contained within the EST clone no. AA448744, the EST clone AA448744 was purchased from Merck and the cDNA insert was obtained and sequenced. The sequence of this cDNA insert is herein designated as DNA93011-2637.

The full length clone shown in FIG. 67 contained a single open reading frame with an apparent translational initiation site at nucleotide positions 27-29 and ending at the stop codon found at nucleotide positions 435-437 (FIG. 67; SEQ ID NO:67). The predicted polypeptide precursor (FIG. 68, SEQ ID NO:68) is 136 amino acids long. PRO4425 has a calculated molecular weight of approximately 15,577 daltons and an estimated pI of approximately 8.88.

An analysis of the Dayhoff database (version 35.45 SwissProt 35), using a WU-BLAST2 sequence alignment analysis of the full-length sequence shown in FIG. 68 (SEQ ID NO:68), revealed homology between the PRO4425 amino acid sequence and the following Dayhoff sequences: HGS_RE295, S44655, YOJ8_CAEEL, VBR1_CLVK, P_R39520, P_R65332, P_R39388, TGL4_HUMAN, YKAB_CAEEL, and S71105.

Clone DNA93011-2637 was deposited with the ATCC on May 4, 1999 and is assigned ATCC deposit no. 20-PTA.

Example 35

Isolation of cDNA Clones Encoding Human PRO4985 Polypeptides [UNQ2426]

The extracellular domain (ECD) sequences (including the secretion signal sequence, if any) from about 950 known secreted proteins from the Swiss-Prot public database were used to search EST databases. The EST databases included a proprietary EST database (LIFESEQ®, Incyte Pharmaceuticals, Palo Alto, Calif.). The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA42819. In some cases, the DNA42819 consensus sequence derives from an intermediate consensus DNA sequence which was extended using repeated cycles of BLAST and phrap to extend that intermediate consensus sequence as far as possible using the sources of EST sequences discussed above.

Based on the DNA42819 consensus sequence oligonucleotides were synthesized: 1) to identify by PCR a cDNA library that contained the sequence of interest, and 2) for use as probes to isolate a clone of the full-length coding sequence for PRO4985. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'-TGTCCTCTATTGGAGAACCACAGCC-3'    (SEQ ID NO: 155)

reverse PCR primer
5'-TAAAAGTTGGCTGGGCAAAGTTTGC-3'    (SEQ ID NO: 156)
```

Additionally, a synthetic oligonucleotide hybridization probe was constructed from the consensus DNA42819 sequence which had the following nucleotide sequence

```
hybridization probe
                                    (SEQ ID NO: 157)
5'-CTCAGTATGGACCAAAGTACCCAAGCCTGTGCTGGTGAGAAACATTGG
CA-3'
```

RNA for construction of the cDNA libraries was isolated from human thyroid tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO4985 polypeptide (designated herein as DNA59770-2652 [FIG. 69, SEQ ID NO: 69]) and the derived protein sequence for that PRO4985 polypeptide.

The full length clone identified above contained a single open reading frame with an apparent translational initiation site at nucleotide positions 133-135 and a stop signal at nucleotide positions 3172-3174 (FIG. 69, SEQ ID NO:69). The predicted polypeptide precursor is 1013 amino acids long, has a calculated molecular weight of approximately 111,348.50 daltons and an estimated pI of approximately 6.34. Analysis of the full-length PRO4985 sequence shown in FIG. 70 (SEQ ID NO:70) evidences the presence of a variety of important polypeptide domains as shown in FIG. 70, wherein the locations given for those important polypeptide domains are approximate as described above. Clone DNA59770-2652 has been deposited with ATCC on Jul. 27, 1999 and is assigned ATCC Deposit No. PTA-427.

An analysis of the Dayhoff database (version 35.45 SwissProt 35), using the ALIGN-2 sequence alignment analysis of the full-length sequence shown in FIG. 70 (SEQ ID NO:70), evidenced sequence identity between the PRO4985 amino acid sequence and the following Dayhoff sequences: CEF58E6_3; XELERTK_1; CELW02C12_2; I49071; I48653; EPB3_MOUSE; EPB3_HUMAN; LMG1_DROME; CVU90226_1; P_W57046.

Example 36

Isolation of cDNA Clones Encoding Human PRO4989 Polypeptides [UNQ2429]

The extracellular domain (ECD) sequences (including the secretion signal sequence, if any) from about 950 known secreted proteins from the Swiss-Prot public database were used to search EST databases. The EST databases included (1) public EST databases (e.g., Merck/Washington University), (2) a proprietary EST database (LIFESEQ®, Incyte Pharmaceuticals, Palo Alto, Calif.), and (3) a proprietary EST database from Genentech. The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA54206. In some cases, the DNA54206 consensus sequence derives from an intermediate consensus DNA sequence which was extended using repeated cycles of BLAST and phrap to extend that intermediate consensus sequence as far as possible using the sources of EST sequences discussed above.

Based on the DNA54206 consensus sequence oligonucleotides were synthesized: 1) to identify by PCR a cDNA library that contained the sequence of interest, and 2) for use as probes to isolate a clone of the full-length coding sequence for PRO4989. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'-CAAGGTCCTGCGGAATGTCTCTGG-3'     (SEQ ID NO: 158)

reverse PCR primer
5'-GGGAAGTCCTGGAACTGGTTCCGG-3'     (SEQ ID NO: 159)
```

Additionally, a synthetic oligonucleotide hybridization probe was constructed from the consensus DNA54206 sequence which had the following nucleotide sequence

```
hybridization probe
                                   (SEQ ID NO: 160)
5'-CCTCATCACCCTGGCTAACAACGAGCTTAAGTCCCTCACCAGCAA
G-3'
```

RNA for construction of the cDNA libraries was isolated from human testis tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO4989 polypeptide (designated herein as DNA80135-2655 [FIG. 71, SEQ ID NO: 71]) and the derived protein sequence for that PRO4989 polypeptide.

The full length clone identified above contained a single open reading frame with an apparent translational initiation site at nucleotide positions 223-225 and a stop signal at nucleotide positions 775-777 (FIG. 71, SEQ ID NO:71). The predicted polypeptide precursor is 184 amino acids long, has a calculated molecular weight of approximately 20,509 daltons and an estimated pI of approximately 6.47. Analysis of the full-length PRO4989 sequence shown in FIG. 72 (SEQ ID NO:72) evidences the presence of a variety of important polypeptide domains as shown in FIG. 72, wherein the locations given for those important polypeptide domains are approximate as described above. Clone DNA80135 has been deposited with ATCC on Jun. 15, 1999 and is assigned ATCC deposit no. PTA-234.

An analysis of the Dayhoff database (version 35.45 SwissProt 35), using the ALIGN-2 sequence alignment analysis of the full-length sequence shown in FIG. 72 (SEQ ID NO:72), evidenced sequence identity between the PRO4989-amino acid sequence and the following Dayhoff sequences: DDU82512_1; AF061443_1; AF054827_1; AF068919_1; AB016816_1; ATY16046_1; AF068920_1; AF054828_1; CYAA_YEAST; and CYAA_SCHPO.

Example 37

Isolation of cDNA Clones Encoding Human PRO5737 Polypeptides [UNQ2456]

An expressed sequence tag (EST) DNA database (LIFESEQ®, Incyte Pharmaceuticals, Palo Alto, Calif.) was searched with a human interleukin-1 receptor antagonist (hIL-1Ra) sequence, and an EST sequence, designated herein as 1433156 was identified, which showed homology with the hIL-1Ra known protein. EST clone 1433156 was purchased from Incyte Pharmaceuticals (Palo Alto, Calif.) and the cDNA insert was obtained and sequenced in its entirety, giving the DNA92929-2534 sequence.

The entire nucleotide sequence of DNA92929-2534 is shown in FIG. 73 (SEQ ID NO:73). Clone DNA92929-2534 contains a single open reading frame with an apparent translational initiation site at nucleotide positions 96-98 and a stop codon at nucleotide positions 498-500 (FIG. 73; SEQ ID NO:73). The predicted polypeptide precursor (hIL-1Ra2) is 134 amino acids long. The putative signal sequence extends from amino acid positions 1-17. Clone DNA92929-2534 was deposited with ATCC on Jan. 12, 1999 and was assigned ATCC deposit no. 203586. The full-length hIL-Ira2 protein shown in FIG. 74 has an estimated molecular weight of about 14,927 daltons and a pI of about 4.8.

Based on a BLAST and FastA sequence alignment analysis (using the ALIGN-2 computer program) of the full-length sequence, hIL-1Ra2 (FIG. 74, SEQ ID NO:74) shows significant amino acid sequence identity to hIL-1R protein. hIL-1Ra2 is believed to be a splice variant of hIL-1R.

Example 38

Isolation of cDNA Clones Encoding Human PRO5800 Polypeptides [UNQ2500]

The extracellular domain (ECD) sequences (including the secretion signal sequence, if any) from about 950 known secreted proteins from the Swiss-Prot public database were used to search EST databases. The EST databases included public EST databases (e.g., GenBank). The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA102836. In some cases, the consensus sequence derives from an intermediate consensus DNA sequence which was extended using repeated cycles of BLAST and phrap to extend that intermediate consensus sequence as far as possible using the sources of EST sequences discussed above.

Based on the DNA102836 consensus sequence oligonucleotides were synthesized: 1) to identify by PCR a cDNA library that contained the sequence of interest, and 2) for use as probes to isolate a clone of the full-length coding sequence for PRO5800. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer 1
                                         (SEQ ID NO: 161)
5'-CAGCGAACCGGGTGCCGGGTC-3' forward PCR primer 2
                                         (SEQ ID NO: 162)
5'-GAGCGACGAGCGCGCAGCGAAC-3' forward PCR primer 3
                                         (SEQ ID NO: 163)
5'-ATACTGCGATCGCTAAACCACCATGCGCCGCCGCCTGTGGCTG-3' reverse PCR primer 1
                                         (SEQ ID NO: 164)
5'-GCCGGCCTCTCAGGGCCTCAG-3' reverse PCR primer 2
                                         (SEQ ID NO: 165)
5'-CCCACGTGTACAGAGCGGATCTC-3' reverse PCR primer 3
                                         (SEQ ID NO: 166)
5'-GAGACCAGGACGGGCAGGAAGTG-3' reverse PCR primer 4
                                         (SEQ ID NO: 167)
5'-CAGGCACCTTGGGGAGCCGCC-3' reverse PCR primer 5
                                         (SEQ ID NO: 168)
5'-CCCACGTGTACAGAGCGGATCTC-3' reverse PCR primer 6
                                         (SEQ ID NO: 169)
5'-GAGACCAGGACGGGCAGGAAGTG-3'
```

Additionally, a synthetic oligonucleotide hybridization probe was constructed from the consensus DNA102836 sequence which had the following nucleotide sequence

```
hybridization probe
                                         (SEQ ID NO: 170)
5'-CTCTACGGGTACTGCAGGTTCCGGGAGCGCATCGAAGAGAACGG-3'
```

RNA for construction of the cDNA libraries was isolated from human fetal liver tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO5800 polypeptide (designated herein as DNA108912-2680 [FIG. 75, SEQ ID NO: 75]) and the derived protein sequence for that PRO5800 polypeptide.

The full length clone identified above contained a single open reading frame with an apparent translational initiation site at nucleotide positions 7-9 and a stop signal at nucleotide positions 517-519 (FIG. 75, SEQ ID NO:75). The predicted polypeptide precursor is 170 amino acids long, has a calculated molecular weight of approximately 19,663 daltons and an estimated pI of approximately 11.81. Analysis of the full-length PRO5800 sequence shown in FIG. 76 (SEQ ID NO:76) evidences the presence of a variety of important polypeptide domains as shown in FIG. 76, wherein the locations given for those important polypeptide domains are approximate as described above. Clone DNA108912-2680 has been deposited with ATCC on May 25, 1999 and is assigned ATCC deposit no. PTA-124.

An analysis of the Dayhoff database (version 35.45 SwissProt 35), using the ALIGN-2 sequence alignment analysis of the full-length sequence shown in FIG. 76 (SEQ ID NO:76), evidenced sequence identity between the PRO5800 amino acid sequence and the following Dayhoff sequences: P_W52595, P_W57313, FGFA_HUMAN, P_W57264, FGFA_RAT, P_W52597, MMU94517__1, FGFA_MOUSE, P_W57306 and D86333__1.

Example 39

Isolation of cDNA Clones Encoding Human PRO5993 Polypeptides [UNQ2504]

The extracellular domain (ECD) sequences (including the secretion signal sequence, if any) from about 950 known secreted proteins from the Swiss-Prot public database were used to search EST databases. The EST databases included (1) public EST databases (e.g., Merck/Washington University), (2) a proprietary EST database (LIFESEQ®, Incyte Pharmaceuticals, Palo Alto, Calif.), (3) a proprietary EST database from Genentech. The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

This consensus sequence is herein designated DNA91365. In some cases, the DNA91365 consensus sequence derives from an intermediate consensus DNA sequence which was extended using repeated cycles of BLAST and phrap to extend that intermediate consensus sequence as far as possible using the sources of EST sequences discussed above.

Based on the DNA91365 sequence oligonucleotides were synthesized: 1) to identify by PCR a cDNA library that contained the sequence of interest, and 2) for use as probes to isolate a clone of the full-length coding sequence for PRO5993. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'CGACCCAAGCGGATCGAAGGTTC 3'    (SEQ ID NO: 171)

reverse PCR primer
5'GTCACTTCCTGGCACCAGCTGCTC 3'   (SEQ ID NO: 172)
```

Additionally, a synthetic oligonucleotide hybridization probe was constructed from the consensus DNA91365 sequence which had the following nucleotide sequence

```
hybridization probe
                                (SEQ ID NO: 173)
5'GTTAGCAACTCTCTGGCAGCCTTTGCTTACATTAGAGACCACCCG 3'
```

RNA for construction of the cDNA libraries was isolated from human aortic endothelial tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO5993 polypeptide (designated herein as DNA100276-2684 [FIG. 77, SEQ ID NO: 77]) and the derived protein sequence for that PRO5993 polypeptide.

The full length clone identified above contained a single open reading frame with an apparent translational initiation site at nucleotide positions 411-413 and a stop signal at nucleotide positions 1734-1736 (FIG. 77, SEQ ID NO: 77). The predicted polypeptide precursor is 441 amino acids long, has a calculated molecular weight of approximately 49483 daltons and an estimated pI of approximately 6.91. Analysis of the full-length PRO5993 sequence shown in FIG. 78 (SEQ ID NO: 78) evidences the presence of a variety of important polypeptide domains as shown in FIG. 78, wherein the locations given for those important polypeptide domains are approximate as described above. Clone DNA100276-2684 has been deposited with ATCC on Jul. 20, 1999 and is assigned ATCC Deposit No. PTA-380.

An analysis of the Dayhoff database (version 35.45 SwissProt 35), using the ALIGN-2 sequence alignment analysis of the full-length sequence shown in FIG. 78 (SEQ ID NO: 78), evidenced sequence identity between the PRO5993 amino acid sequence and the following Dayhoff sequences: CEF32A7_4; CEF32A7_3; LEG_ANTCR; AF081149_1; P_W74585; HASA131581_1; RNU72487_1; AF111098_1; P_W59050.

Example 40

Isolation of cDNA Clones Encoding Human PRO6017 Polypeptides [UNQ2524]

DNA96860-2700 was identified by applying a proprietary signal sequence finding algorithm developed by Genentech, Inc. (South San Francisco, Calif.) upon ESTs as well as clustered and assembled EST fragments from public (e.g., Genbank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the LIFESEQ® database, Incyte Pharmaceuticals, Palo Alto, Calif., designated herein as CLU98611. This EST cluster sequence was then compared to a variety of expressed sequence tag (EST) databases which included public EST databases (e.g., Genbank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA82392.

In light of an observed sequence homology between the DNA82392 sequence and an EST sequence encompassed within clone no. 653153 from the LIFESEQ® database, Incyte Pharmaceuticals, Palo Alto, Calif., clone no. 653153 was purchased and the cDNA insert was obtained and sequenced. It was found herein that that cDNA insert encoded a full-length protein. The sequence of this cDNA insert is shown in FIG. 79 and is herein designated as DNA96860-2700.

Clone DNA96860-2700 contains a single open reading frame with an apparent translational initiation site at nucleotide positions 83-85 and ending at the stop codon at nucleotide positions 1667-1669 (FIG. 79; SEQ ID NO:79). The predicted polypeptide precursor is 528 amino acids long (FIG. 80). The full-length PRO6017 protein shown in FIG. 80 has an estimated molecular weight of about 59,000 daltons and a pI of about 8.73. Analysis of the full-length PRO6017 sequence shown in FIG. 80 (SEQ ID NO: 80) evidences the presence of a variety of important polypeptide domains as shown in FIG. 80, wherein the locations given for those important polypeptide domains are approximate as described above. Clone DNA96860-2700 has been deposited with ATCC on Aug. 3, 1999 and is assigned ATCC Deposit No. PTA-478.

An analysis of the Dayhoff database (version 35.45 SwissProt 35), using the ALIGN-2 sequence alignment analysis of the full-length sequence shown in FIG. 80 (SEQ ID NO: 80), evidenced sequence identity between the PRO6017 amino acid sequence and the following Dayhoff sequences: HSA011001_1; P_W36903; HSHE6_1; AF111092_1; GEN14046; P_W48756; AC004262_1; AF031573_1; P_WO7600; P_W37412.

Example 41

Isolation of cDNA Clones Encoding Human PRO7174 Polypeptides [UNQ2784]

DNA96883-2745 was identified by applying a proprietary signal sequence finding algorithm developed by Genentech, Inc. (South San Francisco, Calif.) upon ESTs as well as clustered and assembled EST fragments from public (e.g., Genbank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the LIFESEQ® database, Incyte Pharmaceuticals, Palo Alto, Calif., designated herein as CLU92188. This EST cluster sequence was then compared to a variety of expressed sequence tag (EST) databases which included public EST databases (e.g., Genbank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA83604.

In light of an observed sequence homology between the DNA83604 sequence and an EST sequence encompassed within clone no. 3362284 from the LIFESEQ® database, Incyte Pharmaceuticals, Palo Alto, Calif., clone no. 3362284 was purchased and the cDNA insert was obtained and sequenced. It was found herein that cDNA insert encoded a full-length protein. The sequence of this cDNA insert is shown in FIG. 81 and is herein designated as DNA96883-2745.

Clone DNA96883-2745 contains a single open reading frame with an apparent translational initiation site at nucleotide positions 3-5 and ending at the stop codon at nucleotide positions 1,545-1,547 (FIG. 81; SEQ ID NO:81). The predicted polypeptide precursor is 514 amino acids long (FIG. 82). The full-length PRO7174 protein shown in FIG. 82 has an estimated molecular weight of about 55,687 daltons and a pI of about 8.78. Analysis of the full-length PRO7174 sequence shown in FIG. 82 (SEQ ID NO: 82) evidences the presence of a variety of important polypeptide domains as shown in FIG. 82, wherein the locations given for those important polypeptide domains are approximate as described above. Clone DNA96883-2745 has been deposited with ATCC on Aug. 17, 1999 and is assigned ATCC Deposit No. PTA-544.

An analysis of the Dayhoff database (version 35.45 SwissProt 35), using the ALIGN-2 sequence alignment analysis of the full-length sequence shown in FIG. 82 (SEQ ID NO: 82), evidenced sequence identity between the PRO7174 amino acid sequence and the following Dayhoff sequences: RNU44129_1; ER53_HUMAN; XLU44130_1; P_W88699; VP36_CANFA; G01447; P_W67846; P_W67963; HSERGICP02_1; and CCAD_CHICK.

Example 42

Isolation of cDNA Clones Encoding Human PRO9744 Polypeptides [UNQ3003]

A cDNA clone (DNA136110-2763) encoding a native human PRO9744 polypeptide was identified using a CARD domain containing molecule, SOCA-1. More particularly, a cDNA fragment encoding the N-terminal portion of SOCA-1 was used to screen a human fetal kidney library. Several positive colonies were picked up, DNA were prepared and sequenced. DNA sequencing revealed that one of the cDNA clones contains a full length open reading frame that encodes a protein, homologous to the human Rac protein, designated herein DNA136110-2763.

Clone DNA136110-2763 contains a single open reading frame with an apparent translational initiation site at nucleotide positions 242-244 and ending at the stop codon at nucleotide positions 1334-1336 (FIG. 83; SEQ ID NO:83). The predicted polypeptide precursor is 364 amino acids long (FIG. 84; SEQ ID NO:84). The full-length PRO9744 protein shown in FIG. 84 has an estimated molecular weight of about 42195 daltons and a pI of about 7.4. Analysis of the full-length PRO9744 sequence shown in FIG. 84 (SEQ ID NO:84) evidences the presence of a variety of important polypeptide domains as shown in FIG. 84, wherein the locations given for those important polypeptide domains are approximate as described above. Clone DNA136110-2763 has been deposited with ATCC on Sep. 14, 1999 and is assigned ATCC deposit no. PTA-652.

An analysis of the Dayhoff database (version 35.45 SwissProt 35), using the ALIGN-2 sequence alignment analysis of the full-length sequence shown in FIG. 84 (SEQ ID NO: 84), evidenced sequence identity between the PRO9744 amino acid sequence and the following Dayhoff sequences: KRAC_DICDI, KAPC_DICDI, PK2_DICDI, KAPC_DROME, GEN13181, GEN12288, P_R95911, TCU63742_1, SGK_HUMAN, and AF135794_1.

Example 43

Isolation of cDNA Clones Encoding Human PRO9821 Polypeptides [UNQ3023]

DNA108725-2766 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST sequence from the Incyte database, designated herein as DNA21277. This EST sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA91971.

In light of an observed sequence homology between the DNA91971 sequence and an EST sequence encompassed within clone no. 3232833H1 from the Incyte database, clone no. 3232833 was purchased and the cDNA insert was obtained and sequenced. It was found herein that that cDNA insert encoded a full-length protein. The sequence of this cDNA insert is shown in FIG. 85 and is herein designated as DNA108725-2766.

Clone DNA108725-2766 contains a single open reading frame with an apparent translational initiation site at nucleotide positions 196-198 and ending at the stop codon at nucleotide positions 709-711 (FIG. 85; SEQ ID NO: 85). The predicted polypeptide precursor is shown in FIG. 86. The full-length PRO9821 protein shown in FIG. 86 has an estimated molecular weight of about 19118 daltons and a pI of about 5.99. Analysis of the full-length PRO9821 sequence shown in FIG. 86 (SEQ ID NO:86) evidences the presence of a variety of important polypeptide domains as shown in FIG. 86, wherein the locations given for those important polypeptide domains are approximate as described above. Clone DNA108725-2766 has been deposited with ATCC on Oct. 19, 1999 and is assigned ATCC deposit no. PTA-863.

An analysis of the Dayhoff database (version 35.45 SwissProt 35), using the ALIGN-2 sequence alignment analysis of the full-length sequence shown in FIG. 86 (SEQ ID NO: 86), evidenced sequence identity between the PRO9821 amino acid sequence and the following Dayhoff sequences: P_Y27573; UPAR_MOUSE; UPAR_RAT; S42152; SP63_STRPU; AF007789_1; CELR11F4_1; LY6A_MOUSE; P_Y02738; and AF141377_1.

Example 44

Isolation of cDNA Clones Encoding Human PRO9852 Polypeptides [UNQ3037]

DNA129332-2775 was identified by applying a proprietary signal sequence finding algorithm developed by Genentech, Inc. (South San Francisco, Calif.) upon ESTs as well as clustered and assembled EST fragments from public (e.g., Genbank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of the DNA124065 consensus sequence and oligonucleotides were synthesized based on this sequence. These oligonucleotides were used 1) to identify by PCR a cDNA library that contained the sequence of interest, and 2) for use as probes to isolate a clone of the full-length coding sequence for PRO9852. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'-CGATACTCGCGGGAGGCTAAC-3'        (SEQ ID NO: 174)

reverse PCR primer
5'-CCTTCTGGGTGTCTCCAGTTAGCG-3'     (SEQ ID NO: 175)
```

Additionally, a synthetic oligonucleotide hybridization probe was constructed from the consensus DNA124065 sequence which had the following nucleotide sequence

```
hybridization probe
                                   (SEQ ID NO: 176)
5'-CAACTCGCGCACTCAAAGATGGTCCCCATCCCTGCTG-3'
```

RNA for construction of the cDNA libraries was isolated from human Fetal Kidney tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO9852 polypeptide (designated herein as DNA129332-2775 [FIG. 87, SEQ ID NO: 87]) and the derived protein sequence for that PRO9852 polypeptide.

Clone DNA129332-2775 contains a single open reading frame with an apparent translational initiation site at nucleotide positions 18-20 and ending at the stop codon at nucleotide positions 1296-1298 (FIG. 87). The predicted polypeptide precursor is 426 amino acids long (FIG. 88). The full-length PRO9852 protein shown in FIG. 88 has an estimated molecular weight of about 46,884 daltons and a pI of about 7.01. Analysis of the full-length PRO9852 sequence shown in FIG. 88 (SEQ ID NO:88) evidences the presence of a variety of important polypeptide domains as shown in FIG. 88, wherein the locations given for those important polypeptide domains are approximate as described above. Clone DNA129332-2775 has been deposited with ATCC on Nov. 9, 1999 and is assigned ATCC Deposit No. PTA-944.

An analysis of the Dayhoff database (version 35.45 SwissProt 35), using the ALIGN-2 sequence alignment analysis of the full-length sequence shown in FIG. 88 (SEQ ID NO: 88), evidenced sequence identity between the PRO9852 amino acid sequence and the following Dayhoff sequences: C70643; P_Y19557; A72114; B71551; S74705; H70793; F69812; T08715; P_Y34750; P_W14450.

Example 45

Isolation of cDNA Clones Encoding Human PRO9873 Polypeptides [UNQ3054]

The extracellular domain (ECD) sequences (including the secretion signal sequence, if any) from about 950 known secreted proteins from the Swiss-Prot public database were used to search EST databases. The EST databases included a (1) public EST databases (e.g., GenBank), (2) a proprietary EST database (LIFESEQ®, Incyte Pharmaceuticals, Palo Alto, Calif.), and (3) a proprietary EST database from Genentech. The search was performed using the computer program BLAST or BLAST2 [Altschul et al., Methods in enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA117942. In some cases, the consensus sequence derives from an intermediate consensus DNA sequence which was extended using repeated cycles of BLAST and phrap to extend that intermediate consensus sequence as far as possible using the sources of EST sequences discussed above.

Based on the DNA 117942 consensus sequence oligonucleotides were synthesized: 1) to identify by PCR a cDNA library that contained the sequence of interest, and 2) for use as probes to isolate a clone of the full-length coding sequence for PRO9873. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'-CAGAAAAAAGGAAGATGGCAAG-3';        (SEQ ID NO: 177)

forward PCR primer
5'-GGCAAGAATATTGTTACTTTTCCTCCCG-3';(SEQ ID NO: 178)

reverse PCR primer
5'-TTACCAGCTTTGAGTACACATAGA-3';      (SEQ ID NO: 179)
and reverse PCR primer
5'-AACGTTAATGAATCTACAGTCCGGGGC-3'.  (SEQ ID NO: 180)
```

Additionally, a synthetic oligonucleotide hybridization probes were constructed from the consensus DNA 117942 sequence which had the following nucleotide sequence

```
hybridization probe
                                    (SEQ ID NO: 181)
5'-GGTCCATAAATATTCCATGCACAGCACATACAGCCACAAGACCCGGGA
GG-3'; and hybridization probe
                                    (SEQ ID NO: 182)
5'-TGTGCATGGAATATTTATGGACCGTCTAGCTTCCAAGAAG-3';
```

RNA for construction of the cDNA libraries was isolated from human brain tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO9873 polypeptide (designated herein as DNA143076-2787 [FIG. 89, SEQ ID NO: 89]) and the derived protein sequence for that PRO9873 polypeptide.

The full length clone identified above contained a single open reading frame with an apparent translational initiation site at nucleotide positions 38-40 and a stop signal at nucleotide positions 422-444 (FIG. 89, SEQ ID NO:89). The predicted polypeptide precursor is 128 amino acids long, has a calculated molecular weight of approximately 14332 daltons and an estimated pI of approximately 4.83. Analysis of the full-length PRO9873 sequence shown in FIG. 90 (SEQ ID NO:90) evidences the presence of a variety of important polypeptide domains as shown in FIG. 90, wherein the locations given for those important polypeptide domains are approximate as described above. Clone DNA143076-2787 has been deposited with ATCC on Dec. 7, 1999 and is assigned ATCC deposit no. PTA-1028.

An analysis of the Dayhoff database (version 35.45 SwissProt 35), using the ALIGN-2 sequence alignment analysis of the full-length sequence shown in FIG. 90 (SEQ ID NO:90), evidenced sequence identity between the PRO9873 amino acid sequence and the following Dayhoff sequences: MIA_HUMAN, A42965_1, P_R69811, MIA_BOVIN, RNU67884_1, GEN14164, MIA_MOUSE, P_R69812, P_Y24788, and P_Y22236.

Example 46

Isolation of cDNA Clones Encoding Human PRO10196 Polypeptides [UNQ3115]

The extracellular domain (ECD) sequences (including the secretion signal sequence, if any) from about 950 known secreted proteins from the Swiss-Prot public database were used to search EST databases. The EST databases included (1) public EST databases (e.g., GenBank), and (2) a proprietary EST database (LIFESEQ®, Incyte Pharmaceuticals, Palo Alto, Calif.). The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA139146. In some cases, the consensus sequence derives from an intermediate consensus DNA sequence which was extended using repeated cycles of BLAST and phrap to extend that intermediate consensus sequence as far as possible using the sources of EST sequences discussed above.

EST clone no. 5398353 was then purchased from LIFESEQ®, Incyte Pharmaceuticals, Palo Alto, Calif., and the cDNA insert of that clone was obtained and sequenced in entirety.

DNA sequencing of the insert obtained from the above clone gave the full-length DNA sequence for a full-length PRO10196 polypeptide (designated herein as DNA144841-2816 [FIG. 91, SEQ ID NO: 91]) and the derived protein sequence for that PRO10196 polypeptide.

The full length clone identified above contained a single open reading frame with an apparent translational initiation site at nucleotide positions 151-153 and a stop signal at nucleotide positions 775-777 (FIG. 91, SEQ ID NO:91). The predicted polypeptide precursor is 208 amino acids long, has a calculated molecular weight of approximately 22187 daltons and an estimated pI of approximately 5.08. Analysis of the full-length PRO10196 sequence shown in FIG. 92 (SEQ ID NO:92) evidences the presence of a variety of important polypeptide domains as shown in FIG. 92, wherein the locations given for those important polypeptide domains are approximate as described above. Clone DNA144841-2816 has been deposited with ATCC on Jan. 11, 2000 and is assigned ATCC deposit no. PTA-1188.

An analysis of the Dayhoff database (version 35.45 SwissProt 35), using the ALIGN-2 sequence alignment analysis of the full-length sequence shown in FIG. 92 (SEQ ID NO:92), evidenced sequence identity between the PRO10196 amino acid sequence and the following Dayhoff sequences: P_Y08581, rFGF19_1, AB018122_1, AF110400_1, P_Y08582, FGFF_MOUSE, FGF6_MOUSE, P_R80781 and P_R70825.

Example 47

Isolation of cDNA Clones Encoding Human PRO21956 Polypeptides [UNQ6973]

The extracellular domain (ECD) sequences (including the secretion signal sequence, if any) from about 950 known secreted proteins from the Swiss-Prot public database were used to search sequence databases. The databases included public databases (e.g., GenBank) In this instance, genomic DNA sequence from GenBank was analyzed using the gene prediction program GENSCAN, licensed from Stanford University. GENSCAN analysis predicts gene coding regions, creating sequences which can be subjected to the ECD search. The search was performed using the computer program BLAST or BLAST2 [Altschul et al., Methods in enzymology, 266:460-480 (1996)] as a comparison of the ECD protein sequences to a 6 frame translation of the sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.) if necessary.

A consensus DNA sequence was assembled. This consensus sequence is herein designated DNA146822.

Based on the DNA146822 consensus sequence, oligonucleotides were synthesized: 1) to identify by PCR a cDNA library that contained the sequence of interest, and 2) for use as probes to isolate a clone of the full-length coding sequence for PRO21956. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'-ACAGCACCAAGTTTCTGAGCAACTTCCT-3'   (SEQ ID NO: 183)

reverse PCR primer
5'-ACTTGAGGTTGTCACCGCACACG-3'        (SEQ ID NO: 184)
```

Additionally, a synthetic oligonucleotide hybridization probe was constructed from the consensus DNA146822 sequence which had the following nucleotide sequence

```
hybridization probe
                                     (SEQ ID NO: 185)
5'-AGAGAGGAAACAAGGACCTGCGGGCACGGGCAGACG-3'
```

A pool of 50 different human cDNA libraries from various tissues was used in cloning. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO21956 polypeptide (designated herein as DNA 178511-2986 [FIG. 97, SEQ ID NO: 97) and the derived protein sequence for that PRO21956 polypeptide.

The full length clone identified above contained a single open reading frame with an apparent translational initiation site at nucleotide positions 74-76 and a stop signal at nucleotide positions 1145-1147 (FIG. 97, SEQ ID NO:97). The predicted polypeptide precursor is 357 amino acids long, has a calculated molecular weight of approximately 39001 daltons and an estimated pI of approximately 9.28. Analysis of the full-length PRO21956 sequence shown in FIG. 98 (SEQ ID NO:98) evidences the presence of a variety of important polypeptide domains as shown in FIG. 98, wherein the locations given for those important polypeptide domains are approximate as described above. Clone DNA178511-2986 has been deposited with ATCC on Sep. 12, 2000 and is assigned ATCC deposit no. PTA-2452.

An analysis of the protein database (version 35.45 SwissProt 35), using the ALIGN-2 sequence alignment analysis of the full-length sequence shown in FIG. 98 (SEQ ID NO:98), evidenced sequence identity between the PRO21956 amino acid sequence and the following protein sequences: WN14_CHICK.

Example 48

Generation and Analysis of Mice Comprising PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 Gene Disruptions To investigate the role of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides, disruptions in PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 genes were produced by homologous recombination or retroviral insertion techniques. Specifically, transgenic mice comprising disruptions in PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 genes (i.e., knockout mice) were created by either gene targeting or gene trapping. Mutations were confirmed by southern blot analysis to confirm correct targeting on both the 5' and 3' ends. Gene-specific genotyping was also performed by genomic PCR to confirm the loss of the endogenous native transcript as demonstrated by RT-PCR using primers that anneal to exons flanking the site of insertion. Targeting vectors were electroporated into 129 strain ES cells and targeted clones were identified. Targeted clones were microinjected into host blastocysts to produce chimeras. Chimeras were bred with C57 animals to produce F1 heterozygotes. Heterozygotes were intercrossed to produce F2 wild-type, heterozygote and homozygote cohorts which were used for phenotypic analysis. Rarely, if not enough F1 heterozygotes were produced, the F1 hets were bred to wild-type C57 mice to produce sufficient heterozygotes to breed for cohorts to be analyzed for a phenotype. All phenotypic analysis was performed from 12-16 weeks after birth.

Overall Summary of Phenotypic Results 48.1. Generation and Analysis of Mice Comprising DNA33460-1166 (UNQ200) Gene Disruptions In these knockout experiments, the gene encoding PRO226 polypeptides (designated as DNA33460-1166) (UNQ200) was disrupted. The gene specific information for these studies is as follows: the mutated mouse gene corresponds to nucleotide reference: NM_021474 *Mus musculus* epidermal growth factor-containing fibulin-like extracellular matrix protein 2 (Efemp2); protein reference: Q9JM06 Q9JM06 Q9JM06 EGF-CONTAINING FIBULIN-LIKE EXTRACELLULAR M; the human gene sequence reference: NM_016938 ACCESSION:NM_016938 NID:8393298 *Homo sapiens* EGF-containing fibulin-like extracellular matrix protein 2 (EFEMP2); the human protein sequence corresponds to reference: 095967 FBL4_HUMAN 095967 EGF-CONTAINING FIBULIN-LIKE EXTRACELLUL.

The mouse gene of interest is Efemp2 (epidermal growth factor-containing fibulin-like extracellular matrix protein 2), ortholog of human EFEMP2. Aliases include MBP1, UPH1, FBLN4, 0610011K11Rik, fibulin 4, and fibulin-4.

EFEMP2 is a secreted protein that likely functions as an extracellular matrix protein. The protein contains a signal peptide, six epidermal growth factor (EGF)-like domains, and a globular fibulin-type module. EFEMP2 is prominently expressed in the medial layers of large veins and arteries as well as in a wide variety of other tissues. EFEMP2 may play a role in processes such as blood coagulation, complement activation, and cell fate determination during development. EFEMP2 is a candidate gene for retinopathies that map to chromosome 11 (Katsanis et al, *Hum Genet* 106(1):66-72 (2000); Argraves et al, *EMBO Rep* 4(12): 1127-31 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 15 | 43 | 0 | 58 |
| Expected | 14.5 | 29 | 14.5 | 58 |

Chi-Sq.=20.29 Significance=3.9271934E-5 (hom/n)=0.09
Avg. Litter Size=8
Mutation Information
Mutation Type Homologous Recombination (standard)
Description: Coding exons 1 through 3 were targeted (NCBI accession NM_021474.1).
1. Wild-type Expression Panel: Expression of the target gene was detected in embryonic stem (ES) cells and in all 13 adult tissue samples tested by RT-PCR.
2. QC Expression: Disruption of the target gene was confirmed by Southern hybridization analysis.
48.1.1. Phenotypic Analysis (for Disrupted Gene: DNA33460-1166 (UNQ200)
(a) Overall Phenotypic Summary:
Mutation of the gene encoding the ortholog of human epidermal growth factor-containing fibulin-like extracellular matrix protein 2 (EFEMP2) resulted in late embryonic lethality of (−/−) mutants. Gene disruption was confirmed by Southern blot.
(b) Pathology
Microscopic: Embryonic lethal. At 12.5 days there were 49 embryos observed: 12 (−/−) embryos, 19 (+/−) embryos, 9 (+/+) embryos, 8 inconclusive and 1 inc-het-hom. No structural developmental abnormalities were detected in these 12.5 d embryos by gross or histological examination.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.
48.2. Generation and Analysis of Mice Comprising DNA35841-1173 (UNQ224) Gene Disruptions In these knockout experiments, the gene encoding PRO257 polypeptides (designated as DNA35841-1173) (UNQ224) was disrupted. The gene specific information for these studies is as follows: the mutated mouse gene corresponds to nucleotide reference: NM_008411 ACCESSION:NM_008411 NID:11993940 *Mus musculus Mus musculus* integral membrane-associated protein 1 (Itmap1); protein reference: P70412 ACCESSION:P70412 NID: *Mus musculus* (Mouse). INTEGRAL MEMBRANE-ASSOCIATED PROTEIN 1; the human gene sequence reference: NM_022034 *Homo sapiens* CUB and zona pellucida-like domains 1 (CUZD1); the human protein sequence corresponds to reference: Q86UP6 ACCESSION:Q86UP6 NID: *Homo sapiens* (Human). Transmembrane protein UO-44D.

The mouse gene of interest is Cuzd1 (CUB and zona pellucida-like domains 1), ortholog of human CUZD1. Aliases include USG, ERG-1, UO-44, UTCZP, Itmap1, integral membrane-associated protein 1, and estrogen regulated gene 1.

CUZD1 is an integral membrane protein, containing a signal peptide, two CUB (complement subcomponents C1r/C1s, sea urchin Uegf protein, bone morphogenetic protein-1) domains, a zona pellucida (ZP) domain, and a transmembrane segment near the C-terminus (Kasik et al, *Biochem J* 330Pt 2):947-50 (1998); Chen et al, *J Biol Chem* 275(7):5248 (1999)). CUB (Inter Pro accession IPR000859) and ZP (Pfam accession PF00100) domains are generally found in extracellular proteins involved in protein-protein interactions. The precise function of CUZD1 is not clear. CUZD1 is expressed in epithelia of normal ovarian tissue and ovarian tumors and in epithelia from endometrium of pregnant uterus and oviduct, where CUZD1 is upregulated by estrogen and downregulated by progesterone (Chen et al, *J Biol Chem* 275(7): 5248 (1999); Huynh et al, *Endocrinology* 142(7):2985-95 (2001)). In these epithelia, CUZD1 may be located on the plasma membrane (Huynh et al, *Endocrinology* 142(7):2985-95 (2001); Leong et al, *Oncogene* 23(33):5707-18 (2004) or in granular structures in the apical region of uterine epithelium (Imamura e al, *J Biol Chem* 277(52):50725-33 (2002)). CUZD1 is also expressed on the membrane of trypsinogen-containing zymogen granules of pancreatic acinar cells (Imamura et al, *J Biol Chem* 277(52):50725-33 (2002)). CUZD1 may play a role in the reproductive cycle and pregnancy (Kasik, *Biochem J* 330Pt 2):947-50 (1998); Chen et al, *J Biol Chem* 275(7):5248 (1999), in cell motility and cell-cell interactions (Leong et al, *Oncogene* 23(33):5707-18 (2004), in epithelial cell proliferation and differentiation (Huynh et al, *Endocrinology* 142(7):2985-95 (2001), and in digestion (Imamura e al, *J Biol Chem* 277(52):50725-33 (2002)).

Imamura and coworkers (*J Biol Chem* 277(52):50725-33 2002)) investigated the physiological role of CUZD1 using knockout mice. They showed that secretagogue- and diet-induced pancreatitis susceptibility was much higher in CUZD1 homozygous null mice than in wild-type mice. Reproduction did not seem to be affected. Imamura and coworkers proposed that CUZD1 plays a role in modulating trypsinogen activation within the zymogen granule and that altered trypsinogen activation is associated with severity of pancreatitis.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 26 | 38 | 17 | 81 |
| Expected | 20.25 | 40.5 | 20.25 | 81 |

Chi-Sq.=1.75 Significance=0.416862 (hom/n)=0.22 Avg. Litter Size=9

Mutation Information

Mutation Type: Homologous Recombination (standard)

Description: Coding exon 1 was targeted (NCBI accession NM_008411.2).

1. Wild-type Expression Panel: Expression of the target gene was detected in brain; eye; spleen; kidney; skeletal muscle; stomach, small intestine, and colon; heart; adipose; banded heart; skin fibroblast; prostate; and MG 12 DPC among 26 adult tissue samples tested by RT-PCR.

2. QC Expression: Disruption of the Target Gene was Confirmed by Southern Hybridization Analysis.

48.2.1. Phenotypic Analysis (for Disrupted Gene: DNA35841-1173 (UNQ224)

(a) Overall Phenotypic Summary:

Mutation of the gene encoding the ortholog of human CUB and zona pellucida-like domains 1 (CUZD1) resulted in increased serum IgG3 levels in (−/−) mice as well as increased percentages of subsets of B cells. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (−/−) mice exhibited an increased mean serum IgG3 level when compared with that of their (+/+) littermates, the median for the (+/+) mice, and the cumulative (+/+) historical median.

Mutant (−/−) mice exhibited increased IgG3 serum immunoglobulins compared to their gender-matched (+/+) littermates. IgG3 immunoglobulins have neutralization effects and to a lesser extent are important for activation of the complement system. The observed phenotype suggests that the PRO257 polypeptide is a negative regulator of inflammatory responses. These immunological abnormalities suggest that antagonists or inhibitors of PRO257 polypeptides would be important agents which would stimulate the immune system (such as T cell proliferation) and would find utility in the cases wherein this effect would be beneficial to the individual such as in the case of leukemia, and other types of cancer, and in immuno-compromised patients, such as AIDS sufferers. Accordingly, PRO257 polypeptides would be useful in inhibiting the immune response and would be useful candidates for suppressing harmful immune responses, e.g. in the case of graft rejection or graft-versus-host diseases.

Fluorescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton- Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:
Tissue Specific FACS-Project: The (−/−) mice exhibited an increased percentage of B220+ CD11b Low CD23−cells and decreased percentage of B220+ CD11b− CD23+ cells in peritoneal lavage when compared with those of their (+/+) littermates.

48.3. Generation and Analysis of Mice Comprising DNA39427-1179 (UNQ235) Gene Disruptions In these knockout experiments, the gene encoding PRO268 polypeptides (designated as DNA39427-1179) (UNQ235) was disrupted. The gene specific information for these studies is as follows: the mutated mouse gene corresponds to nucleotide reference: BC017603 ACCESSION:BC017603 NID: 17160856 *Mus musculus*, RIKEN cDNA 2810425A04 gene, clone MGC:27603 IMAGE:4503129; protein reference: Q8VBT0 ACCESSION:Q8VBT0 NID: *Mus musculus* (Mouse). RIKEN cDNA 2810425A04 GENE; the human gene sequence reference: NM_030755 ACCESSION:NM_030755 NID:13559515 *Homo sapiens* thioredoxin domain-containing (TXNDC); the human protein sequence corresponds to reference: Q9Y4T6 ACCESSION:Q9Y4T6 NID: *Homo sapiens* (Human). HYPOTHETICAL 32.5 KDA PROTEIN (FRAGMENT).

The mouse gene of interest is Txndc1 (thioredoxin domain containing 1), ortholog of human TXNDC (thioredoxin domain containing). Aliases include 2810425A04Rik, TMX, TXNDC1, DKFZP564E1962, thioredoxin domain-containing, and thioredoxin-related transmembrane protein.

TXNDC is an integral membrane protein located primarily in the endoplasmic reticulum that likely functions as a protein disulfide isomerase. The protein contains a signal peptide, a thioredoxin domain, and one or possibly two transmembrane segments. The thioredoxin domain contains a dithiol active center that is capable of participating reversibly in a variety of oxidation-reduction reactions. Moreover, the thioredoxin domain projects into the lumen of the endoplasmic reticulum, where it is likely to participate with other enzymes in protein folding as well as in regulating redox state. Expression of TXNDC is ubiquitous but is particularly high in lung, kidney, liver, and placenta (Matsuo et al, *Arch Biochem Biophys* 423 (1):81-7 (2004); Matsuo et al, *J Biol Chem* 276(13):10032-8 (2001)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 11 | 23 | 13 | 47 |
| Expected | 11.75 | 23.5 | 11.75 | 47 |

Chi-Sq.=7.33 Significance=0.025604172 (hom/n)=0.27 Avg. Litter Size=10

Mutation Information
Mutation Type: Homologous Recombination (standard)
Description: Coding exon 1 was targeted (NCBI accession NM_028339.1).
1. Wild-type Expression Panel: Expression of the target gene was detected in embryonic stem (ES) cells and in all 13 adult tissue samples tested by RT-PCR.
2. QC Expression: Disruption of the target gene was confirmed by Southern hybridization analysis.

48.3.1. Phenotypic Analysis (for Disrupted Gene: DNA39427-1179 (UNQ235)
(a) Overall Phenotypic Summary:
Mutation of the gene encoding the ortholog of human thioredoxin domain containing (TXNDC) resulted in decreased bone mineral density measurements in the mutant (−/−) mice. Gene disruption was confirmed by Southern blot.
(b) Bone Metabolism & Body Diagnostics: Radiology Phenotypic Analysis
In the area of bone metabolism, targets were identified herein for the treatment of arthritis, osteoporosis, osteopenia and osteopetrosis as well as identifying targets that promote bone healing. Tests included:
DEXA for measurement of bone mineral density on femur and vertebra
MicroCT for very high resolution and very high sensitivity measurements of bone mineral density for both trabecular and cortical bone.

Dexa Analysis—Test Description:
Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:
Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased mean volumetric bone mineral density and bone mineral density in total body, femur, and vertebrae when compared with the levels for their gender-matched (+/+) littermates and the historical means.

Micro CT: The male (−/−) mice showed decreased mean femoral mid-shaft cortical thickness when compared with that of their gender-matched (+/+) littermates and the historical mean.

The (−/−) mice analyzed by DEXA and bone micro CT analysis exhibited decreased bone measurements when compared with their (+/+) littermates, suggestive of abnormal bone disorders. The negative bone phenotype indicates that PRO268 polypeptides or agonists thereof would be useful for maintaining bone homeostasis. In addition, PRO268 polypeptides would be useful in bone healing or for the treatment of arthritis or osteoporosis, whereas antagonists (or inhibitors) of PRO268 polypeptides or its encoding gene would lead to abnormal or pathological bone disorders including inflammatory diseases associated with abnormal bone metabolism including arthritis, osteoporosis and osteopenia.

48.4. Generation and Analysis of Mice Comprising DNA35680-1212 (UNQ253) Gene Disruptions In these knockout experiments, the gene encoding PRO290 polypeptides (designated as DNA35680-1212) (UNQ253) was disrupted. The gene specific information for these studies is as follows: the mutated mouse gene corresponds to nucleotide reference: XM_150243 PREDICTED: *Mus musculus* cDNA sequence BC042396 (BC042396); protein reference: XP_150243 mKIAA0540 protein [*Mus musculus*]; the human gene sequence reference: XM_291064 PREDICTED: *Homo sapiens* KIAA0540 protein (KIAA0540); the human protein sequence corresponds to reference: XP_291064 PREDICTED: KIAA0540 protein [*Homo sapiens*].

The mouse gene of interest is cDNA sequence BC042396, ortholog of human KIAA0540 protein. Aliases include mKIAA0540 and 1110014F23Rik.

KIAA0540 protein contains a putative signal peptide or signal anchor, a BEACH domain (PFAM accession PF02138), and four tandem WD40 repeats (SMART accession SM00320). Bioinformatic analyses suggest that the protein may be extracellular (Clark et al, *Genome Res* 13(10): 2265-70 (2003)). The domain organization of KIAA0540 protein is similar to that of LYST (lysosomal trafficking regulator), which may be involved in protein sorting to and from lysosomes and endosomes (Barbosa et al, *Nature* 385(6611): 97 (1996)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 19 | 40 | 9 | 68 |
| Expected | 17.0 | 34.0 | 17.0 | 68 |

Chi-Sq.=6.07 Significance=0.04807466 (hom/n)=0.19 Avg. Litter Size=8

Mutation Information

Mutation Type: Homologous Recombination (standard)

Description: Coding exons 4 through 11 were targeted (NCBI accession XM_150243.4).

1. Wild-type Expression Panel: Expression of the target gene was detected in embryonic stem (ES) cells and in all 26 adult tissue samples tested by RT-PCR, except bone.

2. QC Expression: Disruption of the target gene was confirmed by Southern hybridization analysis.

48.4.1. Phenotypic Analysis (for Disrupted Gene: DNA35680-1212 (UNQ253)

(a) Overall Phenotypic Summary:

The homozygous mutant mice exhibited numerous immunological abnormalities, including an increased percentage of granulocytes, an increased serum IL-6 response to LPS challenge, a decreased serum IgG2a level, increase mean serum IgM levels; decreased mean percentages of CD4 and CD8 cells in peripheral blood; and decreased T cell to B cell ratio in the spleen. In addition, the mutants exhibited neutrophils lacking the granulation normally present in these cells. Decreased neutrophils were also observed resulting in neutropenia. The (−/−) mice exhibited decreased platelets and increased platelet volume. Blood chemistry analysis resulted in the observation of decreased mean serum glucose levels and decreased mean serum triglycerides. The homozygous mutant mice also exhibited decreased bone measurements when compared with those of their gender-matched wild-type littermates. Disruption of the target gene was confirmed by Southern hybridization analysis.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (−/−) mice exhibited a decreased neutrophil count when compared with that of their (+/+) littermates and the historical mean. However, the neutropenia observed in the (−/−) mice by automated analysis was not confirmed by manual differentials. The (−/−) mice have a normal distribution of white blood cells, but the neutrophils do not exhibit the granulation normally present within the cells. The (−/−) mice also exhibited a decreased mean platelet count and increased mean platelet volume.

These results indicate that the mutant (−/−) mice exhibited an abnormality related to neutropenia with abnormal granulation within the neutrophils observed. Neutrophils are the chief phagocytic leukocytes of the blood. Therefore, the (−/−) mice have a compromised ability to fight infections.

In addition, the mutant mice deficient in the DNA35680-1212 gene resulted in a phenotype related to coagulation disorders. In this regard, PRO290 polypeptides or agonists thereof would be useful in treating disorders related to abnormal blood coagulation such as hemophilia.

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 µL sterile saline using a 26 gauge needle. The doses were based on the average weight of the mice tested at 1 µg/g body weight 3 hours after injection; a 100 ul blood sample was then taken and analyzed for the presence of TNFa, MCP-1, and IL-6 on the FACS Calibur instrument.

Results:

Acute Phase Response: The (−/−) mice exhibited an increased mean serum IL-6 response to LPS challenge when compared with that of their (+/+) littermates and the historical mean.

In summary, the LPS endotoxin challenge demonstrated that knockout mice deficient in the gene encoding PRO290 polypeptides exhibit immunological abnormalities when compared with their wild-type littermates. In particular, the mutant mice exhibited an increased ability to elicit an immunological response (IL-6 production) when challenged with the LPS endotoxin indicating a proinflammatory response. IL-6 contributes to the later stages of B cell activation. In addition, IL-6 plays a critical role in inducing the acute phase response and systemic inflammation. This suggests that inhibitors or antagonists to PRO290 polypeptides would stimulate the immune system and would find utility in the cases wherein this effect would be beneficial to the individual such as in the case of leukemia, and other types of cancer, and in immuno-compromised patients, such as AIDS sufferers. Accordingly, PRO290 polypeptides or agonists thereof would be useful in inhibiting the immune response and would be useful candidates for suppressing harmful immune responses, e.g. in the case of graft rejection or graft-versus-host diseases.

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (−/−) mice exhibited an increased mean serum IgM level and a decreased mean serum IgG2a level when compared with those of their (+/+) littermates, the (+/+) mice within the project run, and the historical medians for each.

Mutant (−/−) mice exhibited elevation of IgM serum immunoglobulins compared to their gender-matched (+/+) littermates. IgM immunoglobulins are the first to be produced in a humoral immune response for neutralization of bacterial toxins and are particularly important in activating the complement system. The observed phenotype suggests that the PRO290 polypeptide is a negative regulator of inflammatory responses. These immunological abnormalities suggest that inhibitors (antagonists) of PRO290 polypeptides would be useful in stimulating the immune system (such as T cell proliferation) and would find utility in the cases wherein this effect would be beneficial to the individual such as in the case of leukemia, and other types of cancer, and in immuno-compromised patients, such as AIDS sufferers. Accordingly, PRO290 polypeptides or agonists thereof would be useful in inhibiting the immune response and would be useful candidates for suppressing harmful immune responses, e.g. in the case of graft rejection or graft-versus-host diseases.

The serum immunoglobulin isotyping assay also showed decreased or reduced levels of mean serum IgG2a in the homozygous (−/−) mice compared to their gender-matched littermate (+/+) controls.

The serum immunoglobulin isotyping assay revealed that homozygous adults exhibited decreased serum IgG2a levels. Thus, homozygotes showed an abnormally low serum immunoglobulins compared with the (+/+) littermates. Thus, the gene encoding PRO290 is essential for making immunoglobulins (or gamma globulins). Likewise, IgG2a immunoglobulins have neutralization effects and to a lesser extent are important for activation of the complement system.

Fluorescence-Activated Cell-Sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

FACS3: The (−/−) mice exhibited an altered distribution of leukocyte subsets in the peripheral blood, characterized by decreased mean percentages of CD4 and CD8 cells when compared with those of their (+/+) littermates and the historical means.

Tissue Specific FACS-Project: The (−/−) mice also exhibited an increased percentage of granulocytes by scatter but not an increased percentage of B220− CD43 Hi cells in bone marrow when compared with that of their (+/+) littermates. The SSC-hi population was replaced by a large SSC-int population in the (−/−) mice. The (−/−) mice also exhibited an increased percentage of B220 Hi CD23+ cells in peritoneal lavage.

Tissue Specific FACS-Mouse: The (−/−) mice exhibited a decreased T cell:B cell ratio and decreased percentages of CD62L Hi CD44 Dim CD4+ and CD8+ cells in spleen when compared with that of their (+/+) littermates.

Thus, PRO290 polypeptides or agonists thereof act as a negative regulator of B cell production.

(c) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The $\mu$CT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Both the male and female (−/−) mice exhibited decreased mean total tissue mass and bone mineral content and density measurements when compared with the historical means, the differences being more notable in the females. Female (−/−) mice showed decreased total body volumetric bone mineral density (vBMD), vertebrae bone mineral density (BMD), and total body bone mineral density (large difference >2SD). The (−/−) mice also showed decreased femur bone mineral density (BMD) and total body bone mineral content (BMC).

Micro CT: The male (−/−) mice exhibited decreased mean vertebral trabecular bone volume, number, thickness, and connectivity density and decreased mean femoral mid-shaft cortical thickness and cross-sectional area when compared with their gender-matched (+/+) littermates and the historical means.

The (−/−) mice analyzed by DEXA and bone micro CT analysis exhibited decreased bone measurements and decreased body mass measurements when compared with their (+/+) littermates, suggestive of abnormal bone disorders. The (−/−) mice exhibited a negative bone phenotype with abnormal decreased bone measurements reflective of bone metabolic disorders. In addition, the decreased mean total tissue mass is indicative of a metabolic disorder related to tissue wasting disorders. The negative bone phenotype indicates that PRO290 polypeptides or agonists thereof would be useful for maintaining bone homeostasis. In addition, PRO290 polypeptides would be useful in bone healing or for the treatment of arthritis or osteoporosis, whereas antagonists (or inhibitors) of PRO290 polypeptides or its encoding gene would lead to abnormal or pathological bone disorders including inflammatory diseases associated with abnormal bone metabolism including arthritis, osteoporosis and osteopenia.

(d) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:
The female (−/−) mice also exhibited a notably decreased mean serum glucose level.

In these studies the mutant (−/−) mice showed a notably decreased serum glucose levels which could be due to an increased insulin sensitivity. Thus, antagonists (inhibitors) to PRO290 polypeptides or its encoding gene would be useful in the treatment of impaired glucose homeostasis.

(e) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygous and 8 homozygous mice were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The male (−/−) mice exhibited a decreased mean serum triglyceride level when compared with that of their gender-matched (+/+) littermates and the historical mean.

In summary, these knockout mutant mice exhibited a positive phenotype with regards to lipid metabolism. Thus, mutant mice deficient in the PRO290 gene can serve as a model for treatment of cardiovascular disease associated with dyslipidemia, hypertension, atherosclerosis, heart failure, stroke, or various coronary artery diseases.

48.5. Generation and Analysis of Mice Comprising DNA225543 (UNQ294) Gene Disruptions In these knockout experiments, the gene encoding PRO36006 polypeptides (designated as DNA225543) (UNQ294) was disrupted. The gene specific information for these studies is as follows: the mutated mouse gene corresponds to nucleotide reference: M_145581 ACCESSION: NM_145581 NID:21704167 Mus musculus sialic acid-binding lectin Siglec-F (LOC233186); protein reference: Q920G3 ACCESSION:Q920G3 NID:*Mus musculus* (Mouse). SIALIC ACID-BINDING LECTIN SIGLEC-F; the human gene sequence reference: NM_003830 ACCESSION:NM_ 003830 NID:4502658 *Homo sapiens* sialic acid binding Ig-like lectin 5 (SIGLEC5); the human protein sequence corresponds to reference: 015389 ACCESSION:015389 NID: *Homo sapiens* (Human). OB BINDING PROTEIN-2 (SIGLEC5).

The mouse gene of interest is Siglec5 (sialic acid binding Ig-like lectin 5), ortholog of human SIGLEC5. Aliases include mSiglec-F, sialic acid-binding lectin Siglec-F, OBBP2, CD33L2, OB-BP2, SIGLEC-5, CD33 antigen-like 2, OB binding protein-2, and sialic acid-binding immunoglobulin-like lectin 5.

SIGLEC5 is a type I integral plasma membrane protein expressed primarily on immature cells of the myelomonocytic lineage, particularly on eosinophils in blood and eosinophil precursors in bone marrow. The protein contains a signal peptide, four extracellular immunoglobulin-like domains, a transmembrane segment, and one or two cytoplasmic immunoreceptor tyrosine-based inhibitory motifs (ITIMs). When tyrosine-phosphorylated, ITIMs can bind with SH2 domains of several phosphatases. The extracellular domain of SIGLEC5 binds with alpha-2,3-linked sialic acid on lipopolysaccharides and likely functions as a cell adhesion molecule or signal-transducing receptor (Cornish et al, *Blood* 92(6):2123-32 (1998); Patel et al, *J Biol Chem* 274(32):22729-38 (1999); Angata et al, *J Biol Chem* 276(48): 45128-36 (2001); Zhang et al, *Eur J Immunol* 34(4):1175-84 (2004)). SIGLEC5 is expressed on eosinophils, neutrophils, monocytes, lung, spleen, and placenta (Zhang et al, *Eur J Immunol* 34(4):1175-84 (2004); Patel et al, *J Biol Chem* 274 (32):22729-38 (1999); Erickson-Miller et al, *Exp Hematol* 31(5):382-8 (2003)). Neutrophil SIGLEC5 expression is upregulated in response to treatment with fMLP and tumor necrosis factor-alpha, and SIGLEC5 is involved in augmenting neutrophil oxidative bursting in response to fMLP. These activities suggest that SIGLEC5 plays a role in immune cell function by participating in cell-cell interactions or phagocytosis after exposure to microbes (Erickson-Miller et al, *Exp Hematol* 31(5):382-8 (2003); Jones et al, *Mol Microbiol* 49(5):1213-25 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 14 | 47 | 30 | 91 |
| Expected | 22.75 | 45.5 | 22.75 | 91 |

Chi-Sq.=1.61 Significance=0.4470879 (hom/n)=0.25 Avg. Litter Size=9
Mutation Information
Mutation Type Homologous Recombination (standard)
Description: Coding exons 1 through 4 and the preceding noncoding exon were targeted (NCBI accession NM_145581.1).

1. Wild-type Expression Panel: Expression of the target gene was detected in brain, spinal cord, eye, thymus, spleen, lung, and kidney among the 13 adult tissue samples tested by RT-PCR.

2. QC Expression: Disruption of the target gene was confirmed by Southern hybridization analysis.

48.5.1. Phenotypic Analysis (for Disrupted Gene: DNA225543 (UNQ294)

(a) Overall Phenotypic Summary:

Mutation of the gene encoding the ortholog of human sialic acid binding Ig-like lectin 5 (SIGLEC5) resulted in an increased skin fibroblast proliferation rate in female (−/−) mice. In addition, the mutant (−/−) mice exhibited an increased percentage of B cells and B cell precursors both in the lymph nodes and in the peritoneal lavage. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:
Fluorescence-Activated Cell-Sorting (FACS) Analysis
Procedure:
FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:
Tissue Specific FACS-Project: The (−/−) mice exhibited an increased percentage of B cells in lymph node when compared with that of their (+/+) littermates. The (−/−) mice also exhibited a decreased percentage of B220− CD11b Hi cells and increased percentages of B220− CD11 Low and CD11b− cells in peritoneal lavage. Thus, it appears that UNQ294 is a negative regulator of B cell production and differentiation.

(c) Phenotypic Analysis: Metabolism—Blood Chemistry
In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:
Blood Chemistry: The female (−/−) mice exhibited an increased mean serum glucose level when compared with that of their gender-matched (+/+) littermates and the historical mean. However, all male (−/−) mice had higher than historical mean serum glucose levels.

Thus, the mutant (−/−) mice exhibited hyperglycemia which could be associated with an altered glucose metabolism or diabetes.

(d) Adult Skin Cell Proliferation:
Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:
Skin Proliferation: The female (−/−) mice exhibited an increased mean skin fibroblast proliferation rate when compared with that of their gender-matched (+/+) littermates and the historical mean.

Thus, homozygous mutant mice demonstrated a hyper-proliferative phenotype. As suggested by these observations, PRO36006 polypeptides or agonists thereof could function as tumor suppressors and would be useful in decreasing abnormal cell proliferation.

48.6. Generation and Analysis of Mice Comprising DNA45419-1252 (UNQ318) Gene Disruptions In these knockout experiments, the gene encoding PRO363 polypeptides (designated as DNA45419-1252) (UNQ318) was disrupted. The gene specific information for these studies is as follows: the mutated mouse gene corresponds to nucleotide reference: NM_133733 ACCESSION:NM_133733 NID:gi 31542034 ref NM_133733.2 *Mus musculus* RIKEN cDNA 9030425E11 gene (9030425E11Rik); protein reference:Q8R373 ACCESSION:Q8R373NID: *Mus musculus* (Mouse). CAR-like membrane protein (Adipocyte adhesion molecule) (*Mus musculus* adult male cecum cDNA, RIKEN full-length enriched library, clone:9130232O17 product: ADIPOCYTE-SPECIFIC PROTEIN 5, full insert sequence); the human gene sequence reference: NM_024769 *Homo sapiens* adipocyte-specific adhesion molecule (ASAM); the human protein sequence corresponds to reference: Q9H6B4 ACCESSION:Q9H6B4 NID:*Homo sapiens* (Human). cDNA:FLJ22415 FIS, CLONE HRC08561 (HYPOTHETICAL 41.3 KDA PROTEIN).

The mouse gene of interest is RIKEN cDNA 9030425E11 gene, ortholog of human ASAM (adipocyte-specific adhesion molecule). Aliases include ASAM, CLMP, FLJ22415, asp5, IGSF11, CAR-like membrane protein, and adipocyte-specific protein 5.

ASAM is a type I plasma membrane protein that likely functions as a cell adhesion molecule and tight junction component. The protein belongs to the immunoglobulin superfamily, consisting of a signal peptide, an immunoglobulin-like domain, an immunoglobulin constant-2 type domain, a transmembrane segment, and a cytoplasmic tail. ASAM is expressed primarily in epithelial cells from a wide variety of tissues and is likely to play a role cell-cell communication and tight junction formation (Raschperger et al, *J Biol Chem* 279(1):796-804 (2004); Katoh and Katoh, *Int J Oncol* 23(2): 525-31 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 28 | 52 | 9 | 89 |
| Expected | 22.25 | 44.5 | 22.5 | 89 |

Chi-Sq.=7.06 Significance=0.029304916 (hom/n)=0.17 Avg. Litter Size=10
Mutation Information
Mutation Type Homologous Recombination (standard)
1. Wild-type Expression Panel:
2. QC Expression:
  48.6.1. Phenotypic Analysis (for Disrupted Gene: DNA45419-1252 (UNQ318)
  (a) Overall Phenotypic Summary:
  Mutation of the gene encoding the ortholog of human adipocyte-specific adhesion molecule (ASAM) resulted in reduced viability of (−/−) mutants. Both CAT-Scan analysis and necropsy revealed bilateral hydronephrosis and inflammation in the surviving homozygous mutant mice, consistent with the notably increased mean systolic blood pressure observed clinically as well as the increase in blood urea nitrogen. The mutant (−/−) mice showed "pear shaped abdomens", as well as bilaterally enlarged kidneys with chronic inflammation noted as polycystic kidney disease. In addition, the mutants were smaller than their wild-type littermates and exhibited numerous blood chemistry, immunological and neurological abnormalities. Further evidence of growth retardation is shown by mutant (−/−) mice also exhibiting decreased body fat, lean body mass and total tissue mass with decreased bone mineral density measurements. Disruption of the target gene was confirmed by Southern hybridization analysis.
  (b) Pathology
  Gross: Reduced viability of the (−/−) mice was observed.
  Microscopic: At 12.5 days, there were 48 embryos observed: 11 (−/−) embryos, 18 (+/−) embryos, 10 (+/+) embryos, 5 resorption moles, and 4 inconclusive.
  All 3 (−/−) mice exhibited bilateral hydronephrosis. Suppurative and pyogranulomatous inflammation was also noted in 2/3 (−/−) mice, suggesting an increased susceptibility to bacterial infection in these mutants (urine analysis showed a possible urinary tract infection).
  (c) Immunology Phenotypic Analysis
  Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:
Hematology Analysis:
Test Description: Blood tests are carried out by Abbott's Cell-Dyn 3500R, an automated hematology analyzer. Some of its features include a five-part WBC differential. 'Patient' reports can cover over 22 parameters in all.
Results:
Hematology: The (−/−) mice exhibited an increased mean absolute neutrophil count when compared with that of their (+/+) littermates and the historical mean.
 (d) Bone Metabolism & Body Diagnostics
 (1) Tissue Mass & Lean Body Mass Measurements—Dexa
Dexa Analysis—Test Description:
Procedure: A cohort of wild type, heterozygous and homozygous mice were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):
Body Measurements: A measurement of body length and weight was performed at approximately 16 weeks of age.
Results:
Weight: The (−/−) mice exhibited decreased mean body weight when compared with that of their gender-matched (+/+) littermates and the historical mean.
Length: The (−/−) mice exhibited decreased mean body length when compared with that of their gender-matched (+/+) littermates and the historical mean.
In addition, 6 out of 8 (−/−) mice showed a "pear shaped" abdomen.
Fertility: The male (−/−) mouse available for analysis produced no pups after 40 days of breeding.
Basal Body Temperature: The male (−/−) mice exhibited a decreased median basal body temperature when compared with that of their gender-matched (+/+) littermates and the historical mean.
 (2) Bone Metabolism: Radiology Phenotypic Analysis
In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra
MicroCT for very high resolution and very high sensitivity measurements of bone mineral density for both trabecular and cortical bone.
Dexa Analysis—Test Description:
Procedure: A cohort of wild type, heterozygous and homozygous were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:
Procedure: MicroCT was also used to get very sensitive measurements of BMD. One vertebra and 1 femur were taken from a cohort of wild type and homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

CAT Scan Analysis:
Test Description: Mouse was injected with a CT contrast agent, Omnipaque 300 (Nycomed Amershan, 300 mg of iodine per ml, 0.25 ml per animal, or 2.50-3.75 g iodine/kg of body weight) intraperitoneally. After resting in the cage for ~10 minutes, the mouse was then sedated by intraperitoneal injection of Avertin (1.25% 2,2,2,-tribromoethanol, 20 ml/kg body weight). A CAT-scan was performed using a MicroCAT scanner (ImTek, Inc.) with the anesthetized animal lying prone on the test bed. Three dimensional images were reconstructed by the Feldkamp algorithm in a cluster of workstations using an ImTek 3D RECON software.

Results:
DEXA: The male (−/−) mice exhibited notably decreased mean total tissue mass and lean body mass. Both the male and female (−/−) mice exhibited notably decreased mean percent body fat, total fat mass, and all bone mineral density-related measurements when compared with those of their gender-matched (+/+) littermates and the historical means.
Micro CT: No notable difference. However, no (−/−) mice were available for analysis.
CATScan: All 3 (−/−) mice analyzed (M-154, F-81, and F-147) exhibited bilaterally enlarged kidneys with marked inflammation, suggesting polycystic kidney disease or severe hydronephrosis. These results are consistent with the increased blood urea nitrogen levels and systemic hypertension reported below. One (+/−) mice (F-76) also exhibited moderate hydronephrosis on the left side.

Mutant (−/−) mice deficient in the gene encoding PRO363 polypeptides show a phenotype consistent with growth retardation, marked by decreased body weight and length and tissue wasting diseases (decreased total body fat (%) and fat mass (g)). Thus, antagonists or inhibitors of PRO363 polypeptides or its encoding gene would mimic these metabolic and growth related effects. On the other hand, PRO363 polypeptides or agonists thereof would be useful in the prevention and/or treatment of such metabolic disorders as diabetes or other tissue wasting diseases.

In addition, the (−/−) mice analyzed by DEXA exhibited decreased bone measurements and decreased body mass measurements when compared with their (+/+) littermates, suggestive of abnormal bone disorders. The (−/−) mice exhibited a negative bone phenotype with abnormal decreased bone measurements reflective of bone metabolic disorders. In addition, the decreased mean total tissue mass and lean body mass is indicative of a metabolic disorder related to growth retardation and tissue wasting disorders. The negative bone phenotype indicates that PRO363 polypeptides or agonists thereof would be useful for maintaining bone homeostasis in addition to normal growth development. In addition, PRO363 polypeptides would be useful in bone healing or for the treatment of arthritis or osteoporosis, whereas antagonists (or inhibitors) of PRO363 polypeptides or its encoding gene would lead to abnormal or pathological bone disorders including inflammatory diseases associated with abnormal bone metabolism including arthritis, osteoporosis and osteopenia.

(e) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of wild type, heterozygous and homozygous mutant mice. All behavioral tests were done between 12 and 16 weeks of age unless reduced viability necessitates earlier testing. These tests included open field to measure anxiety, activity levels and exploration.

Functional Observational Battery (FOB) Test—Tail Suspension Testing:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Tail Suspension Testing:

The tail suspension test is a procedure that has been developed as a model for depressive-like behavior in rodents. In this particular setup, a mouse is suspended by its tail for 6 minutes, and in response the mouse will struggle to escape from this position. After a certain period of time the struggling of the mouse decreases and this is interpreted as a type of learned helplessness paradigm. Animals with invalid data (i.e. climbed their tail during the testing period) are excluded from analysis.

Results:

Tail Suspension2: The (−/−) mice exhibited increased median immobility time when compared with that of their (+/+) littermates and the historical mean, suggesting an increased depressive-like response in the mutants.

Thus, knockout mice demonstrated a phenotype consistent with depression, generalized anxiety disorders, cognitive disorders, hyperalgesia and sensory disorders and/or bipolar disorders. Thus, PRO363 polypeptides and agonists thereof would be useful for the treatment or amelioration of the symptoms associated with depressive disorders.

(f) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Results:

Blood Chemistry: The male (−/−) mice exhibited an increased mean serum alkaline phosphatase level when compared with that of their gender-matched (+/+) littermates and the historical mean. These results are consistent with the noted pathological findings of polycystic kidney disease and increased blood urea nitrogen.

The (−/−) mice also exhibited a decreased mean serum glucose level when compared with that of their gender-matched (+/+) littermates and the historical mean. In addition, both the male and female (−/−) mice exhibited an increased mean serum blood urea nitrogen level. Decreased mean serum glucose levels is consistent with the observation of an enhanced glucose tolerance in these mutant (−/−) mice. Likewise increased blood urea nitrogen levels are consistent with kidney malfunction and/or tissue wasting diseases.

(g) Phenotypic Analysis: Metabolism—Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism.

Abnormal glucose tolerance test results may indicate but may not be limited to the following disorders or conditions: Diabetes Type 1 and Type 2, Syndrome X, various cardiovascular diseases and/or obesity.

Procedure: A cohort of wild type and homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:
Oral Glucose Tolerance: The male (−/−) mouse available for analysis exhibited enhanced glucose tolerance when compared with that of its gender-matched (+/+) littermates and the historical mean.

(h) Cardiology—Blood Pressure
Description:
Systolic blood pressure is measured via a noninvasive tail-cuff method for four days on the Visitech BP-2000 Blood Pressure Analysis System. The blood pressure is measured ten times each day for four days. The four days are then averaged to obtain a mouse's conscious systolic blood pressure.

Results:
Blood Pressure: Both the male and female (−/−) mice exhibited notably increased mean systolic blood pressure when compared with that of their gender-matched (+/+) littermates and the historical mean suggesting systemic hypertension in the mutant (−/−) mice (consistent with the noted kidney pathology).

48.7. Generation and Analysis of Mice Comprising DNA46777-1253 (UNQ320) Gene Disruptions In these knockout experiments, the gene encoding PRO365 polypeptides (designated as DNA46777-1253) (UNQ320) was disrupted. The gene specific information for these studies is as follows: the mutated mouse gene corresponds to nucleotide reference: NM_020622 ACCESSION:NM_020622 NID: gi 22296879 ref NM_020622.1 *Mus musculus* RIKEN cDNA 9030624C24 gene (9030624C24Rik); protein reference: Q9D309 ACCESSION:Q9D309 NID: *Mus musculus* (Mouse). Protein FAM3B precursor; the human gene sequence reference: NM_058186 *Homo sapiens* family with sequence similarity 3, member B (FAM3B), transcript variant 1; the human protein sequence corresponds to reference: P58499 ACCESSION:P58499 NID: *Homo sapiens* (Human). Protein FAM3B precursor (Protein PRED44).

The mouse gene of interest is ORF9 (open reading frame 9), ortholog of human FAM3B (family with sequence similarity 3, member B). Aliases include 2-21, D16Jhu19e, 9030624C24Rik, PRED44, C21orf11, C21orf76, D21M16SJHU19e, cytokine-like protein 2-21, chromosome 21 open reading frame 11.

FAM3B is a secreted cytokine that likely functions as a signal-transducing ligand. The protein is expressed at high levels in alpha- and beta-cells of pancreatic islets and at lower levels in small intestine, prostate, round spermatids within seminiferous tubules, nerve cell bodies of numerous brain stem nuclei, and Purkinje cells of the cerebellum. FAM3B is capable of increasing basal levels of insulin secretion from beta-cells and inducing apoptosis in islet cells by a caspase-3-mediated pathway (Zhu et al, *Genomics* 80(2): 144-50 (2002); Cao et al, *Diabetes* 52(9):2296-303 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|          | wt   | het | hom  | Total |
|----------|------|-----|------|-------|
| Observed | 20   | 37  | 21   | 78    |
| Expected | 19.5 | 39  | 19.5 | 78    |

Chi-Sq.=0.91 Significance=0.63444793 (hom/n)=0.25 Avg. Litter Size=8
Mutation Information
Mutation Type Homologous Recombination (standard)
Description: Coding exons 1 and 2 were targeted (NCBI accession NM_020622.1).
1. Wild-type Expression Panel: Expression of the target gene was detected in all 13 adult tissue samples tested by RT-PCR, except bone and adipose.
2. QC Expression: Disruption of the target gene was confirmed by Southern hybridization analysis.

48.7.1. Phenotypic Analysis (for Disrupted Gene: DNA46777-1253 (UNQ320)
(a) Overall Phenotypic Summary:
Mutation of the gene encoding the ortholog of human family with sequence similarity 3, member B (FAM3B) resulted in the (−/−) mice exhibiting an increase percentage of CDb+CD11c− cells in the spleen (which contain monocytes/macrophages and neutrophils). The mutant (−/−) mice also exhibited a decreased mean heart rate. Gene disruption was confirmed by Southern blot.

(b) Immunology Phenotypic Analysis
Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:
Fluorescence-Activated Cell-Sorting (FACS) Analysis
Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:
Tissue Specific FACS-Mouse: The (−/−) mice exhibited an increased percentage of CD11b+ CD11c− cells in spleen when compared with that of their (+/+) littermates. Thus, the mutant (−/−) mice exhibited elevated levels of monocytes/macrophages and neutrophils in the spleen.

(c) Cardiology—Heart Rate
Description:
Heart rate is measured via a noninvasive tail-cuff method for four days on the Visitech BP-2000 Blood Pressure Analysis System. Heart rate is measured ten times each day for four days. The four days are then averaged to obtain a mouse's conscious heart rate.

Heart Rate: The (−/−) mice exhibited a decreased mean heart rate (1-2 SD below) when compared with that of their gender-matched (+/+) littermates and the historical mean.

48.8 Generation and Analysis of Mice Comprising DNA45234-1277 (UNQ323) Gene Disruptions In these knockout experiments, the gene encoding PRO382 polypeptides (designated as DNA45234-1277) (UNQ323) was disrupted. The gene specific information for these studies is as follows: the mutated mouse gene corresponds to nucleotide reference: NM_080727 ACCESSION:NM_080727 NID:18141558 *Mus musculus Mus musculus* transmembrane protease, serine 3 (Tmprss3); protein reference: Q8VDE0 ACCESSION:Q8VDE0 NID: *Mus musculus* (Mouse). TMPRSS3 PROTEIN; the human gene sequence reference: NM_024022 ACCESSION:NM_024022 NID:13173470 *Homo sapiens* transmembrane protease, serine 3 (TMPRSS3); the human protein sequence corresponds to reference: P57727 ACCESSION:P57727 NID: *Homo sapiens* (Human). TRANSMEMBRANE PROTEASE, SERINE 3 (EC 3.4.21.-) (SERINE PROTEASE TADG-12) (TUMOR ASSOCIATED DIFFERENTIALLY-EXPRESSED GENE-12 PROTEIN).

The mouse gene of interest is Tmprss3 (transmembrane protease, serine 3), ortholog of human TMPRS S3. Aliases include DFNB8, DFNB10, ECHOS1, TADG12, and serine protease TADG12.

TMPRSS3 is a type II integral membrane protein located primarily on the endoplasmic reticulum that likely functions as a channel-activating serine protease. The protein contains a transmembrane segment, an LDL receptor A domain, a scavenger receptor domain, a proteolytic activation site, and a C-terminal serine protease domain (Wallrapp et al, *Cancer Res* 60(10):2602-6 (2000); Guipponi et al, *Hum Mol Genet* 11(23):2829-36 (2002)). Bioinformatic analyses (Clark et al, *Genome Res* 13(10):2265-70 (2003)) suggest that TMPRSS3 may be an extracellular protein. TMPRSS3 catalyzes the cleavage of epithelial amiloride-sensitive sodium channel ENaC in vitro, activating the channel. TMPRSS3 is expressed in several tissues that also express ENaC, such as the spiral ganglion, which are cells that support the organ of Corti and the stria vascularis in the cochlea. TMPRSS3 is also expressed in thymus, stomach, testis and E19 mouse embryos. TMPRSS3 likely plays a role in hearing by regulating ENaC activity, which maintains the low concentration of sodium in endolymph of the inner ear (Guipponi et al, *Hum Mol Genet* 11(23):2829-36 (2002)). TMPRSS3 is often overexpressed in certain types of cancer, where it may play a role in metastasis and tumor invasion (Wallrapp et al, *Cancer Res* 60(10):2602-6 (2000); Underwood et al, *Biochim Biophys Acta* 1502(3):337-50 (2000); Sawasaki et al, *Tumour Biol* 25(3):141-8 (2004)). Mutations in the TMPRSS3 gene can cause sensorineural deafness (Wattenhofer et al, *J Mol Med* 80(2): 124-31 (2002); Lee et al, *J Med Genet* 40(8):629-31 (2003); Ahmed et al, *BMC Med Genet* 5(1):24 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 16 | 48 | 18 | 82 |
| Expected | 20.5 | 41 | 20.5 | 82 |

Chi-Sq.=0.76 Significance=0.68386143 (hom/n)=0.24 Avg. Litter Size=9
Mutation Information
Mutation Type: Homologous Recombination (standard)
Description: Coding exon 1 was targeted (NCBI accession NM_080727.1).
1. Wild-type Expression Panel: Expression of the target gene was detected in brain, spinal cord, eye, thymus, spleen, and blood among the 26 adult tissue samples tested by RT-PCR.
2. QC Expression: Disruption of the target gene was confirmed by Southern hybridization analysis.
  48.8.1. Phenotypic Analysis (for Disrupted Gene: DNA45234-1277 (UNQ323)
  (a) Overall Phenotypic Summary:
  Mutation of the gene encoding the ortholog of human transmembrane protease, serine 3 (TMPRSS3) resulted in no startle response in the (−/−) mice suggesting impaired hearing. Microscopic analysis revealed degeneration of the Organ of Corti in the homozygous mutant mice, consistent with the hearing impairment noted during prepulse inhibition testing. Disruption of the target gene was confirmed by Southern hybridization analysis.
  (b) Pathology
Microscopic: Of the 4 (−/−) mice available for analysis, 3 exhibited degeneration of the Organ of Corti; the organ was not in the level of the histological section in the remaining mutant. This is consistent with the possible hearing impairment noted clinically.
  (c) Phenotypic Analysis: CNS/Neurology
  In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.
  Procedure:
  Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.
  Prepulse Inhibition of the Acoustic Startle Reflex
  Prepulse inhibition of the acoustic startle reflex occurs when aloud 120 decibel (dB) startle-inducing tone is preceded by a softer (prepulse) tone. The PPI paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudorandom order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.
  Results:
PPI: All 8 (−/−) mice failed to exhibit a startle response, suggesting impaired hearing in the mutants. Therefore, prepulse inhibition could not be assessed. Degeneration of the Organ of Corti is consistent with these observations.
  Circadian Test Description:
  Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.
  Results:
Circadian: The female (−/−) mice exhibited a spike in activity in one of the light periods, but disruption of cycle was not consistent throughout the test period.
  48.9. Generation and Analysis of Mice Comprising DNA26846-1397 (UNQ328) Gene Disruptions
  In these knockout experiments, the gene encoding PRO444 polypeptides (designated as DNA26846-1397) (UNQ328) was disrupted. The gene specific information for these studies is as follows: the mutated mouse gene corresponds to nucleotide reference: NM_026274 ACCESSION:NM_026274 NID: gi 31541972 ref NM_026274.2 Mus musculus RIKEN cDNA 4930470D19 gene (4930470D19Rik); protein reference: Q8BVR6 ACCESSION:Q8BVR6NID: Mus musculus (Mouse). Mus musculus adult male testis cDNA, RIKEN full-length enriched library, clone:4930470D19 product:hypothetical SPla and the RYanodine Receptor (SPRY)/SPRY domain/RING finger containing protein, full insert sequence (RIKEN cDNA4930470D19) (MKIAA1972 protein); the human gene sequence reference: NM_133368 ACCESSION:NM_133368 NID: gi 45387948 refNM_133368.1 Homo sapiens KIAA1972 protein (KIAA1972); the human protein sequence corresponds to reference: Q96DX4 ACCESSION:Q96DX4 NID: Homo sapiens (Human). Hypothetical protein KIAA1972.
  The mouse gene of interest is RIKEN cDNA 4930470D19 gene, ortholog of human KIAA1972 protein.
  KIAA1972 protein is a putative E3 ubiquitin ligase, containing a signal peptide, a SPRY (splA and ryanodine receptor) domain (SMART accession SM00449), and a RING (Ring finger) domain (SMART accession SM00184). RING domains often possess E3 ubiquitin ligase activity and can be found in many E3 ubiquitin ligases (SMART accession SM00184). SPRY domains are likely involved in protein-protein interactions (Wang et al, *J Biol Chem* 280(16): 16393-401 (2005)). Bioinformatic analyses suggest that KIAA1972 protein is extracellular (Clark et al, *Genome Res* 13(10):2265-70 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 13 | 30 | 16 | 59 |
| Expected | 14.75 | 29.5 | 14.75 | 59 |

Chi-Sq.=0.83 Significance=0.6603403 (hom/n)=0.22 Avg. Litter Size=8
Mutation Information
Mutation Type: Homologous Recombination (standard)
Description: Coding exon 1 was targeted (NCBI accession NM_026274.1).
1. Wild-type Expression Panel: Expression of the target gene was detected in embryonic stem (ES) cells and in spinal cord; thymus; spleen; lung; liver; skeletal muscle; bone; stomach, small intestine, and colon; heart; adipose; asthmatic lung; and blood among the 26 adult tissue samples tested by RT-PCR.
2. QC Expression: Disruption of the target gene was confirmed by Southern hybridization analysis.

48.9.1. Phenotypic Analysis (for Disrupted Gene: DNA26846-1397 (UNQ328)
(a) Overall Phenotypic Summary:
Mutation of the gene encoding the ortholog of a putative human E3 ubiquitin ligase (KIAA1972) resulted in small (−/−) mice that exhibited numerous immunological abnormalities. The homozygous mutant mice were smaller than their gender-matched wild-type littermates, exhibiting decreased mean body weight and length, total tissue mass, and lean body mass. Numerous immunological abnormalities were noted in the homozygous mutant mice, including a decreased percentage of natural killer cells in peripheral blood and an increased mean serum IL-6 and TNF alpha response to LPS challenge when compared with that of their wild-type littermates and the historical means. The immunological abnormalities observed in the (−/−) mice could be due to mechanism of action mediated through UNQ328's E3 ubiquitin ligase activity. In addition, the mutants exhibited hypoactivity in open field testing or a depressive-like phenotype. The (−/−) mice showed systemic hypertension with an increased diastolic blood pressure and decreased heart rate. Blood chemistry results showed increased alkaline phosphatase levels possibly related to hepatocellular dysfunction or biliary obstruction. The male (−/−) mice exhibited notably decreased micro CT vertebral bone density measurements. Disruption of the target gene was confirmed by Southern hybridization analysis.
(b) Immunology Phenotypic Analysis
Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:
Acute Phase Response:
Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACSCalibur instrument.

Results:

Acute Phase Response: The (−/−) mice exhibited an increased mean serum IL-6 and TNFalpha response to LPS challenge when compared with that of their (+/+) littermates and the historical mean.

In summary, the LPS endotoxin challenge demonstrated that knockout mice deficient in the gene encoding PRO444 polypeptides exhibit immunological abnormalities when compared with their wild-type littermates. In particular, the mutant mice exhibited an increased ability to elicit an immunological response (IL-6 and TNFalpha production) when challenged with the LPS endotoxin indicating a proinflammatory response. Il-6 and TNFalpha contribute to the later stages of B cell activation. In addition, IL-6 plays a critical role in inducing the acute phase response and systemic inflammation. This suggests that inhibitors or antagonists to PRO444 polypeptides would stimulate the immune system and would find utility in the cases wherein this effect would be beneficial to the individual such as in the case of leukemia, and other types of cancer, and in immuno-compromised patients, such as AIDS sufferers. Accordingly, PRO444 polypeptides or agonists thereof would be useful in inhibiting the immune response and would be useful candidates for suppressing harmful immune responses, e.g. in the case of graft rejection or graft-versus-host diseases.

Fluorescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

FACS3: The (−/−) mice exhibited an altered distribution of leukocyte subsets in the peripheral blood, characterized by a decreased mean percentage of natural killer cells when compared with that of their (+/+) littermates and the historical mean.

These FACS results indicate that the homozygous mutant mice have a decreased mean percentage of natural killer cells. Natural killer cells are the first line of defense to viral infection since these cells have been implicated in viral immunity and in defense against tumors. Natural killer cells or NK cells act as effectors in antibody-dependent cell-mediated cytotoxicity and have been identified by their ability to kill certain lymphoid tumor cell lines in vitro without the need for prior immunization or activation. Thus, PRO444 polypeptides or agonists thereof, would be useful in stimulating or regulating this leukocyte production.

(c) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Results:

Blood Chemistry: Both the male and female (−/−) mice exhibited increased mean serum alkaline phosphatase levels when compared with those of their gender-matched (+/+) littermates and the historical means. These results may be due to hepatocellular dysfunction or biliary obstruction.

(d) Bone Metabolism & Body Diagnostics (1) Tissue Mass & Lean Body Mass Measurements—Dexa Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Weight: The (−/−) mice exhibited decreased mean body weight when compared with that of their gender-matched (+/+) littermates and the historical means.

Length: The (−/−) mice exhibited decreased mean body length when compared with that of their gender-matched (+/+) littermates and the historical means.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Both the male and female (−/−) mice exhibited decreased mean total tissue mass, lean body mass, and bone mineral content and density measurements when compared with those of their gender-matched (+/+) littermates and the historical means.

Micro CT: The male (−/−) mice exhibited notably decreased mean vertebral trabecular bone volume, number, thickness, and connectivity density and decreased mean femoral midshaft cortical thickness and cross-sectional area when compared with that of their gender-matched (+/+) littermates and the historical means.

Mutant (−/−) mice deficient in the gene encoding PRO444 polypeptides show a phenotype consistent with growth retardation, marked by decreased body weight and length. Thus, antagonists or inhibitors of PRO444 polypeptides or its encoding gene would mimic these metabolic and growth related effects. On the other hand, PRO444 polypeptides or agonists thereof would be useful in the prevention and/or treatment of such metabolic disorders as diabetes or other tissue wasting diseases.

In addition, the (−/−) mice analyzed by DEXA and micro CT exhibited decreased bone measurements and decreased body mass measurements when compared with their (+/+) littermates, suggestive of abnormal bone disorders. The (−/−) mice exhibited a negative bone phenotype with abnormal decreased bone measurements reflective of bone metabolic disorders. In addition, the decreased mean total tissue mass and lean body mass is indicative of a metabolic disorder related to growth retardation and tissue wasting disorders. The negative bone phenotype indicates that PRO444 polypeptides or agonists thereof would be useful for maintaining bone homeostasis in addition to normal growth development. In addition, PRO444 polypeptides would be useful in bone healing or for the treatment of arthritis or osteoporosis, whereas antagonists (or inhibitors) of PRO444 polypeptides or its encoding gene would lead to abnormal or pathological bone disorders including inflammatory diseases associated with abnormal bone metabolism including arthritis, osteoporosis and osteopenia.

(e) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

The male (−/−) mice exhibited hypoactivity during open field testing when compared with their gender-matched (+/+) littermates and the historical mean, suggesting a decreased anxiety-like response in the mutants.

A notable difference was observed during open field activity testing. The (−/−) mice exhibited an increased median sum time in the center (with hypoactivity) when compared with their gender-matched (+/+) littermates, which is indicative of a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO444 polypeptides and agonists thereof would be useful for the treatment or amelioration of the symptoms associated with depressive disorders.

(f) Cardiology—Blood Pressure/Heart Rate

Description:

Systolic blood pressure is measured via a noninvasive tail-cuff method for four days on the Visitech BP-2000 Blood Pressure Analysis System. The blood pressure is measured ten times each day for four days. The four days are then averaged to obtain a mouse's conscious systolic blood pressure.

Results:

Blood Pressure: The female (−/−) mice exhibited increased mean systolic blood pressure when compared with that of their gender-matched (+/+) littermates but within the historical mean.

Description:

Heart rate is measured via a noninvasive tail-cuff method for four days on the Visitech BP-2000 Blood Pressure Analysis System. Heart rate is measured ten times each day for four days. The four days are then averaged to obtain a mouse's conscious heart rate.

Heart Rate: The female (−/−) mice exhibited a decreased mean heart rate when compared with that of their gender-matched (+/+) littermates and the historical mean.

48.10. Generation and Analysis of Mice Comprising DNA50914-1289 (UNQ369) Gene Disruptions In these knockout experiments, the gene encoding PRO705 polypeptides (designated as DNA50914-1289) (UNQ369) was disrupted. The gene specific information for these studies is as follows: the mutated mouse gene corresponds to nucleotide reference: NM_011821 ACCESSION:NM_011821 NID:7106324 *Mus musculus Mus musculus* glypican 6 (Gpc6); protein reference: Q9R087 ACCESSION: Q9R087NID: *Mus musculus* (Mouse). GLYPICAN-6 PRECURSOR; the human gene sequence reference: NM_005708 ACCESSION:NM_005708 NID:8051601 *Homo sapiens* glypican 6 (GPC6); the human protein sequence corresponds to reference: Q9Y625 ACCESSION: Q9Y625 NID: *Homo sapiens* (Human). GLYPICAN-6 PRECURSOR.

The mouse gene of interest is Gpc6 (glypican 6), ortholog of human GPC6. Aliases include MGC32221, 6720429C22Rik, bA62D23.1 (glypican 6), bA632L2.2 (glypican 6), and bA158B14.1 (glypican 6).

GPC6 is an extracellular glycosylphosphatidylinositol (GPI)-anchored heparan sulfate proteoglycan that may function as a coreceptor or regulator of growth factor signaling. The protein is expressed in most tissues, especially kidney and ovary. GPC6 likely plays a role in morphogenesis during development (Veugelers et al, *J Biol Chem* 274(38):26968-77 (1999); Paine-Saunders et al, *Genomics* 57(3):455-8 (1999); De Cat and David, *Semin Cell Dev Biol* 12(2):117-25 (2001); Filmus, *Glycobiology* 11(3):19R-23R (2001)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 18 | 36 | 0 | 54 |
| Expected | 13.5 | 27 | 13.5 | 54 |

Chi-Sq.=12.36  Significance=0.002070428  (hom/n)=0.11
Avg. Litter Size=8
Mutation Information
Mutation Type: Homologous Recombination (standard)
Description: Coding exon 1 was targeted (NCBI accession NM_011821.1).
1. Wild-type Expression Panel: Expression of the target gene was detected in embryonic stem (ES) cells and in all 13 adult tissue samples tested by RT-PCR.
2. QC Expression: Disruption of the target gene was confirmed by Southern hybridization analysis.

48.10.1. Phenotypic Analysis (for Disrupted Gene: DNA50914-1289 (UNQ369)

(a) Overall Phenotypic Summary:

Mutation of the gene encoding the ortholog of human glypican 6 (GPC6) resulted in lethality of (−/−) mutants. However, even though all (−/−) mice showed embryonic lethality, the lethality was variable: some lethal before 12.5 days, some normal at 12.5 days. This observed lethality in the homozygous mice could possibly be due to defective or lack of growth factor signaling. Heterozygous (+/−) mice exhibited increased mean serum glucose levels as well as an increased platelet count. Gene disruption was confirmed by Southern blot.

(b) Pathology

Microscopic: At 12.5 days, 40 embryos were observed: 6 (−/−) embryos, 18 (+/−) embryos, 11 (+/+) embryos, 4 resorption moles, and 1 inconclusive. However, no structural developmental abnormalities were detected in the (−/−) embryos. Gene Expression: LacZ activity was not detected in the panel of tissues by immunohistochemical analysis.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (+/−) mice exhibited an increased mean platelet count when compared with that of their (+/+) littermates and the historical mean.

Thus, heterozygous mice resulted in a phenotype related to coagulation disorders.

(d) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:

Blood Chemistry: The female (+/−) mice exhibited an increased mean serum glucose level when compared with that of their gender-matched (+/+) littermates and the historical mean. Thus, the heterozygous (+/−) mice showed a negative phenotype related to abnormal glucose metabolism.

48.11. Generation and Analysis of Mice Comprising DNA58847-1383 (UNQ528) Gene Disruptions In these knockout experiments, the gene encoding PRO1071 polypeptides (designated as DNA58847-1383) (UNQ528) was disrupted. The gene specific information for these studies is as follows: the mutated mouse gene corresponds to nucleotide reference: AK045085 *Mus musculus* 9.5 days embryo parthenogenote cDNA, RIKEN full-length enriched library, clone:B130031C01 product:ADAM-TS RELATED PROTEIN 1 homolog [*Homo sapiens*]; protein reference: Q8BLI0 ADAMTS-like protein 1 precursor (Punctin) gi|26337059|dbj|BAC32213.1| unnamed protein product [*Mus musculus*]; the human gene sequence reference: NM_139238 Homo sapiens ADAMTS-like 1 (ADAMTSL1), transcript variant 1; the human protein sequence corresponds to reference: NP_640329 ADAMTS-like 1 isoform 1 *[Homo sapiens]*.

The mouse gene of interest is Adamtsl1 (ADAMTS-like 1), ortholog of human ADAMTSL1. Aliases include punctin-1, 6720426B09Rik, ADAMTSR1, MGC40193, punctin, ADAMTSL-1, ADAMTS-like, thrombospondin, and ADAM-TS related protein 1.

ADAMTSL1 is a secreted protein expressed primarily in skeletal muscle that likely functions as an extracellular matrix protein. ADAMTSL1 is similar in structure to ADAMTS family of proteases. The protein contains a signal peptide, a thrombospondin type 1 repeat (PFAM accession PF00090), an ADAM-TS spacer 1 region (PFAM accession PF05986), and two to four more thrombospondin type I repeats but lacks metalloprotease and disintegrin-like domains (Hirohata et al., *J Biol Chem* 277(14):12182-9 (2002)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 23 | 35 | 17 | 75 |
| Expected | 18.75 | 37.5 | 18.75 | 75 |

Chi-Sq.=0.92 Significance=0.63128364 (hom/n)=0.24 Avg. Litter Size=9
Mutation Information
Mutation Type: Homologous Recombination (standard)
Description: Coding exon 1 was targeted (NCBI accession AK045085).
1. Wild-type Expression Panel: Expression of the target gene was detected in all 26 adult tissue samples tested by RT-PCR, except bone, adipose, and blood.
2. QC Expression: Disruption of the target gene was confirmed by Southern hybridization analysis.

48.11.1. Phenotypic Analysis (for Disrupted Gene: DNA58847-1383 (UNQ528)

(a) Overall Phenotypic Summary:

Mutation of the gene encoding the ortholog of human ADAMTS-like 1 (ADAMTSL1) resulted in (−/−) mice exhibiting a decreased mean skin fibroblast proliferation rate. In addition, the mutant (−/−) mice exhibited decreased total tissue mass, lean body mass and decreased bone mineral density measurements. The homozygous mice also showed elevated mean serum glucose levels. Disruption of the target gene was confirmed by Southern hybridization analysis.

(b) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The female (−/−) mice exhibited decreased mean total tissue mass, lean body mass, and bone mineral content and density measurements when compared with those of their gender-matched (+/+) littermates and the historical means. However, the mean bone mineral content index (BMC/LBM) for the mutants was within the historical range.

Mutant (−/−) mice deficient in the gene encoding PRO1071 polypeptides show a phenotype consistent with tissue wasting diseases (decreased total tissue mass and lean body mass). Thus, antagonists or inhibitors of PRO1071 polypeptides or its encoding gene would mimic these metabolic related effects. On the other hand, PRO1071 polypeptides or agonists thereof would be useful in the prevention and/or treatment of such metabolic disorders as cachexia or other tissue wasting diseases.

In addition, the (−/−) mice analyzed by DEXA exhibited decreased bone measurements and decreased body bone mineral content and density measurements when compared with their (+/+) littermates, suggestive of abnormal bone disorders. The (−/−) mice exhibited a negative bone phenotype with abnormal decreased bone measurements reflective of bone metabolic disorders. The negative bone phenotype indicates that PRO1071 polypeptides or agonists thereof would be useful for maintaining bone homeostasis in addition to normal growth development. In addition, PRO1071 polypeptides would be useful in bone healing or for the treatment of arthritis or osteoporosis, whereas antagonists (or inhibitors) of PRO1071 polypeptides or its encoding gene would lead to abnormal or pathological bone disorders including inflammatory diseases associated with abnormal bone metabolism including arthritis, osteoporosis and osteopenia.

(c) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:

Blood Chemistry: The female (−/−) mice exhibited an increased mean serum glucose level when compared with that of their gender-matched (+/+) littermates and the historical mean.

Thus, the mutant (−/−) mice exhibited hyperglycemia which could be associated with an altered glucose metabolism or diabetes. PRO1071 polypeptides or agonists thereof would be useful in maintaining normal glucose levels/metabolism and possibly useful in the treatment of diabetes.

(d) Adult Skin Cell Proliferation:

Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:

Skin Proliferation: The female (−/−) mice exhibited a decreased mean skin fibroblast proliferation rate when compared with that of their gender-matched (+/+) littermates and the historical mean.

Thus, homozygous mutant mice demonstrated a hypo-proliferative phenotype. As suggested by these observations, antagonists or inhibitors of PRO1071 polypeptides would mimic this hypo-proliferative phenotype and could function as tumor suppressors and would be useful in decreasing abnormal cell proliferation.

48.12. Generation and Analysis of Mice Comprising DNA60619-1482 (UNQ563) Gene Disruptions In these knockout experiments, the gene encoding PRO1125 polypeptides (designated as DNA60619-1482) (UNQ563) was disrupted. The gene specific information for these studies is as follows: the mutated mouse gene corresponds to nucleotide reference: NM_013763 ACCESSION: NM_013763 NID: gi 31543844 ref NM_013763.2 *Mus musculus* transducin (beta)-like 2 (Tbl2); protein reference: Q8CFY0 ACCESSION: Q8CFY0 NID: *Mus musculus* (Mouse). Similar to transducin (Beta)-like 2; the human gene sequence reference: NM_032988 ACCESSION:NM_032988 NID: gi 14670378 refNM_032988.1 *Homo sapiens* transducin (beta)-like 2 (TBL2), transcript variant 2; the human protein sequence corresponds to reference: Q8N2L6 ACCESSION:Q8N2L6 NID: *Homo sapiens* (Human). Hypothetical protein FLJ90138.

The mouse gene of interest is Tbl2 (transducin [beta]-like 2), ortholog of human TBL2. Aliases include WS-bTRP, WBSCR13, WS-betaTRP, DKFZP43N024, and Williams-Beuren syndrome chromosome region 13.

TBL2 is a putative secreted protein (Clark et al, *Genome Res* 13(10):2265-70 (2003)), containing a signal peptide and five WD40 repeats. Proteins with WD40 repeats generally function as scaffolds for multi-protein complex assembly. Examples of proteins with WD40 repeats include G proteins, transcription factors, and E3 ubiquitin ligases (SMART accession SM00320). TBL2 is expressed primarily in testis, skeletal muscle, heart, and various endocrine tissues. TBL2 may be involved in Williams-Beuren syndrome (Meng et al, *Hum Genet* 103(5):590-9 (1998); Perez-Jurado et al, *Cytogenet Cell Genet* 86(3-4):277-84 (1999)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 18 | 29 | 16 | 63 |
| Expected | 15.75 | 31.5 | 15.75 | 63 |

Chi-Sq.=3.19 Significance=0.20290852 (hom/n)=0.2 Avg. Litter Size=8

Mutation Information

Mutation Type: Homologous Recombination (standard)

Description: Coding exon 1 was targeted (NCBI accession NM_013763.2).

1. Wild-type Expression Panel: Expression of the target gene was detected in all 13 adult tissue samples tested by RT-PCR, except skeletal muscle; bone; stomach, small intestine, and colon; and adipose.

2. QC Expression: Disruption of the target gene was confirmed by Southern hybridization analysis.

48.12.1. Phenotypic Analysis (for Disrupted Gene: DNA60619-1482 (UNQ563)

(a) Overall Phenotypic Summary:

Mutation of the gene encoding the ortholog of human transducin (beta)-like 2 (TBL2) resulted in the mutant (−/−) mice exhibiting increased microCT trabecular bone number and increased femoral mid-shaft cross-sectional area. The (−/−) mice also exhibited increased body weight and length compared with the (+/+) littermate controls. Male (−/−) mice showed fertility problems. Gene disruption was confirmed by Southern blot.

(b) Bone Metabolism & Body Diagnostics (1) Tissue Mass & Lean Body Mass Measurements—Dexa Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Weight: The (−/−) mice exhibited increased mean body weight when compared with that of their gender-matched (+/+) littermates and the historical mean, the difference being more notable in the males.

Length: The male (−/−) mice exhibited increased mean body length when compared with that of their gender-matched (+/+) littermates and the historical mean.

Fertility:

Fertility: The male (−/−) mouse available for analysis produced no pups after 40 days of breeding with female (+/+) mice.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro CT: The male (−/−) mice exhibited increased mean vertebral trabecular bone number and increased mean femoral mid-shaft cross-sectional area when compared with that of their gender-matched (+/+) littermates and the historical means.

In summary, the (−/−) mice exhibited increased vertebral and femoral bone measurements when compared with their gender-matched (+/+) littermates. These results indicate that the knockout mutant phenotype may be associated with such bone abnormalities as osteopetrosis. Osteopetrosis is a condition characterized by abnormal thickening and hardening of bone and abnormal fragility of the bones. As such, PRO1125 polypeptides or agonists thereof would be beneficial for the treatment of osteopetrosis or other osteo-related diseases. On the other hand, inhibitors or antagonists of PRO1125 polypeptides would be useful in bone healing.

In addition, the mutant (−/−) mice exhibited increased mean total tissue mass and lean body mass as well as increased body weight and length. These studies suggest that mutant (−/−) non-human transgenic animals exhibit a negative phenotype that would be associated with obesity. Thus, PRO1125 polypeptides or agonists thereof are essential for normal growth and metabolic processes and especially would be important in the prevention and/or treatment of obesity.

48.13. Generation and Analysis of Mice Comprising DNA56865-1491 (UNQ572) Gene Disruptions In these knockout experiments, the gene encoding PRO1134 polypeptides (designated as DNA56865-1491) (UNQ572) was disrupted. The gene specific information for these studies is as follows: the mutated mouse gene corresponds to nucleotide reference: NM_029626 *Mus musculus* RIKEN cDNA 2410004H05 gene (2410004H05Rik); protein reference: Q9CWT8 Q9CWT8 Q9CWT8 2410004H05RIK PROTEIN; the human gene sequence reference: NM_001010983 *Homo sapiens* glycosyltransferase 8 domain containing 1 (GLT8D1), transcript variant 3; the human protein sequence corresponds to reference: Q9P0I5 Q9P0I5 Q9P0I5 AD-017 PROTEIN GLYCOSYLTRANSFERASE.

The mouse gene of interest is RIKEN cDNA 2410004H05 gene, ortholog of human GLT8D1 (glycosyltransferase 8 domain containing 1). Aliases include 5430414N14Rik, AD-017, MSTP139, FLJ14611, and glycosyltransferase AD-017.

GLT8D1 is a putative glycosyltransferase, consisting of a signal anchor or signal peptide and a glycosyltransferase family 8 domain. Enzymes containing this domain typically catalyze the formation of O-glycosidic bonds between an acceptor molecule and an activated donor molecule. An example of an enzyme containing this domain is glycogenin, a protein tightly associated with glycogen synthase that catalyzes its self-glucosylation using UDP-glucose as a cosubstrate (Pfam accession PF01501). The cell location of GLT8D1 is ambiguous. Bioinformatic analyses suggest that the protein may be extracellular or may be located on the Golgi apparatus (Coutinho et al., *J Mol Biol* 328(2):307-17 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
| --- | --- | --- | --- | --- |
| Observed | 23 | 41 | 19 | 83 |
| Expected | 20.75 | 41.5 | 20.75 | 83 |

Chi-Sq.=0.79 Significance=0.67368 (hom/n)=0.23 Avg. Litter Size=8

Mutation Information

Mutation Type Homologous Recombination (standard)

Description: Coding exons 1 through 6 were targeted (NCBI accession NM_029626.1).

1. Wild-type Expression Panel: Expression of the target gene was detected in embryonic stem (ES) cells and in all 26 adult tissue samples tested by RT-PCR.

2. QC Expression: Disruption of the target gene was confirmed by Southern hybridization analysis.

48.13.1. Phenotypic Analysis (for Disrupted Gene: DNA56865-1491 (UNQ572)

(a) Overall Phenotypic Summary:

Mutation of the gene encoding the ortholog of human glycosyltransferase 8 domain containing 1 (GLT8D1) resulted in impaired sensorimotor gating/attention in male (−/−) mice. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Prepulse Inhibition of the Acoustic Startle Reflex

Prepulse inhibition of the acoustic startle reflex occurs when a loud 120 decibel (dB) startle-inducing tone is preceded by a softer (prepulse) tone. The PPI paradigm consists of six different trial types (70 dB background noise, 120 dB alone, 74 dB+120 dB-pp4, 78 dB+120 dB-pp8, 82 dB+120 dB-pp12, and 90 dB+120 dB-pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

PPI: The male (−/−) mice exhibited decreased inhibition during pp8, pp12, and pp20 when compared with that of their gender-matched (+/+) littermates and the historical means, suggesting impaired sensorimotor gating/attention in the mutants.

48.14. Generation and Analysis of Mice Comprising DNA59849-1504 (UNQ585) Gene Disruptions In these knockout experiments, the gene encoding PRO1155 polypeptides (designated as DNA59849-1504) (UNQ585) was disrupted. The gene specific information for these studies is as follows: the mutated mouse gene corresponds to nucleotide reference: NM_009312 ACCESSION: NM_009312 NID:na Mus musculus tachykinin 2 (Tac2); protein reference: P55099 TKNK_MOUSE P55099 NEUROKININ B PRECURSOR NKB NEUROMEDI; the human gene sequence reference: NM_013251 Homo sapiens tachykinin 3 (neuromedin K, neurokinin beta) (TAC3); the human protein sequence corresponds to reference: Q9UHF0 TKNK_HUMAN Q9UHF0 NEUROKININ B PRECURSOR NKB NEUROMEDI.

The mouse gene of interest is Tac2 (tachykinin 2), ortholog of human TAC3 (tachykinin 3 [neuromedin K, neurokinin beta]). Aliases include substance K, neurokinin 2, neurokinin A, neuromedin L, neuropeptide K, neurokinin alpha, NKB, NKNB, PRO1155, ZNEUROK1, neuromedin K, neurokinin beta, gamma tachykinin 3, and neurokinin B-like protein.

TAC3 is a peptide neurotransmitter that functions as a ligand for receptors TACR1, TACR2, or TACR3. TAC3 is released from peripheral neurons, interacting with its cognate receptors on a variety of tissues. TAC3 likely functions as paracrine hormone for regulation of vascular tone and blood pressure in the fetus and placenta. TAC3 dilates fetal vasculature and decreases fetal arterial blood pressure. TAC3 dilates placental vasculature by interacting with TACR1. Activation of TACR1 and consequent decreases in blood pressure involve neither nitric oxide synthesis nor prostacyclin synthesis (Brownbill et al, *J Clin Endocrinol Metab* 88(5):2164-70 (2003); Pinto et al, *Eur J Pharmacol* 494(2-3):233-9 (2004)). TAC3 likely plays a role in maintenance of high placental blood flow in normal pregnancy (Laliberte et al, *Regul Pept* 117(2):123-6 (2004)), and TAC3 production may be involved in preeclampsia (Schlembach et al, *Am J Obstet Gynecol* 189(5):1418-22 (2003); Page et al, *Nature* 405(6788):797-800 (2000)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 18 | 39 | 15 | 72 |
| Expected | 18 | 36 | 18 | 72 |

Chi-Sq.=1.15 Significance=0.56270486 (hom/n)=0.22 Avg. Litter Size=9

Mutation Information

Mutation Type Homologous Recombination (standard)

Description: The two noncoding exons preceding coding exon 1 and coding exon 1 were targeted (NCBI accession NM_009312.1).

1. Wild-type Expression Panel: Expression of the target gene was detected in brain, spinal cord, and eye among the 13 adult tissue samples tested by RT-PCR.

2. QC Expression: Disruption of the target gene was confirmed by Southern hybridization analysis.

48.14.1. Phenotypic Analysis (for Disrupted Gene: DNA59849-1504 (UNQ585)

(a) Overall Phenotypic Summary:

Mutation of the gene encoding the ortholog of human tachykinin 3 (neuromedin K, neurokinin beta) (TAC3) resulted in the (−/−) mice exhibiting decreased total body femur bone mineral density and bone mineral content and decreased connectivity density. Gene disruption was confirmed by Southern blot.

(b) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Female (−/−) mice exhibited decreased total body and femur bone mineral density as well as bone mineral content.

Micro CT: The (−/−) mice showed decreased connectivity density.

The (−/−) mice analyzed by DEXA and bone micro CT analysis exhibited decreased bone measurements when compared with their (+/+) littermates, suggestive of abnormal bone disorders. The (−/−) mice exhibited a negative bone phenotype with abnormal and decreased bone measurements reflective of bone metabolic disorders. The negative bone phenotype indicates that PRO1155 polypeptides or agonists thereof would be useful for maintaining bone homeostasis. In addition, PRO1155 polypeptides would be useful in bone healing or for the treatment of arthritis or osteoporosis, whereas antagonists (or inhibitors) of PRO1155 polypeptides or its encoding gene would lead to abnormal or pathological bone disorders including inflammatory diseases associated with abnormal bone metabolism including arthritis, osteoporosis and osteopenia.

48.15. Generation and Analysis of Mice Comprising DNA59820-1549 (UNQ651) Gene Disruptions In these knockout experiments, the gene encoding PRO1281 polypeptides (designated as DNA59820-1549) (UNQ651) was disrupted. The gene specific information for these studies is as follows: the mutated mouse gene corresponds to nucleotide reference: NM_001001566 *Mus musculus* DNA segment, Chr 1, Brigham & Women's Genetics 1363 expressed (D1Bwg1363e); protein reference: Q6IQX7 ACCESSION:Q6IQX7 NID: *Mus musculus* (Mouse). Chondroitin polymerizing factor, isoform a; the human gene sequencer reference: NM_024536 *Homo sapiens* chondroitin polymerizing factor (CHPF); the human protein sequence corresponds to reference: Q8IZ52 ACCESSION: Q8IZ52 NID: *Homo sapiens* (Human). Chondroitin polymerizing factor (Chondroitin sulfate synthase).

The mouse gene of interest is D1Bwg1363e (DNA segment, Chr 1, Brigham & Women's Genetics 1363 expressed), ortholog of human CHPF (chondroitin polymerizing factor). Aliases include 1700028N03Rik, CSS2, FLJ22678, and chondroitin sulfate synthase 2.

CHPF is a putative type II membrane protein that functions as an enzyme or enzyme subunit involved in the biosynthesis of chondroitin sulfate, a proteoglycan found on cell surfaces and in extracellular matrix. The protein contains either a signal peptide or signal anchor and a chondroitin N-acetylgalactosaminyltransferase domain (Pfam accession PF05679). CHPF participates in catalyzing the polymerization of alternating N-acetyl-D-galactosamine (GalNAc) and D-glucuronic acid (GlcUA) residues on chondroitin; however, it is not clear whether CHPF is capable of catalyzing this reaction alone or as a heterodimer with carbohydrate (chondroitin) synthase 1. Like other chondroitin sulfate synthesizing enzymes, CHPF is most likely located in the lumen of the Golgi apparatus (Kitagawa et al, *J Biol Chem* 278(26):23666-71 (2003); Yada et al, *J Biol Chem* 278(32):30235-47 (2003)). Bioinformatic analyses, however, suggests that CHPF is an extracellular protein (Clark et al, *Genome Res* 13(10):2265-70 (2003)). CHPF plays a role in physiological processes such as neural network formation, cell migration, organogenesis, and cytokine signaling (Kitagawa et al, *J Biol Chem* 278(26):23666-71 (2003); Yada et al, *J Biol Chem* 278(32): 30235-47 (2003); Izumikawa et al, *J Biol Chem* 279(51): 53755-61 (2004)). Moreover, CHPF, like other chondroitin sulfate biosynthesizing enzymes, may be a target for treatment of spinal cord injury (Kitagawa et al, *J Biol Chem* 278(26):23666-71 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
| --- | --- | --- | --- | --- |
| Observed | 15 | 30 | 18 | 63 |
| Expected | 15.75 | 31.5 | 15.75 | 63 |

Chi-Sq.=0.67 Significance=0.71533805 (hom/n)=0.27 Avg. Litter Size=9
Mutation Information
Mutation Type: Homologous Recombination (standard)
Description: Coding exons 1 through 3 as well as two non-coding exons preceding coding exon 1 were targeted (NCBI accession NM_001001565.1).
1. Wild-type Expression Panel: Expression of the target gene was detected in embryonic stem (ES) cells and in all 26 adult tissue samples tested by RT-PCR, except skeletal muscle and adipose.
2. QC Expression: Disruption of the target gene was confirmed by Southern hybridization analysis.

48.15.1. Phenotypic Analysis (for Disrupted Gene: DNA59820-1549 (UNQ651)

(a) Overall Phenotypic Summary:

Mutation of the gene encoding the ortholog of human chondroitin polymerizing factor (CHPF) resulted in the (−/−) mice exhibiting increased mean serum cholesterol and mean serum glucose levels. It is interesting to note that UNQ651 is required for chondroitin synthetase (CHSY1)-mediated chondroitin polymerization and acts in chondroitin sulfate biosynthesis. CHSY1 appears to be develop spontaneous arthritis. Gene disruption was confirmed by Southern blot.

(b) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygous and 8 homozygous mice were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The male (−/−) mice exhibited an increased mean serum cholesterol level when compared with that of their gender-matched (+/+) littermates and the historical mean.

As summarized above, the (−/−) mice exhibited increased mean serum cholesterol levels when compared with their gender-matched (+/+) littermates and the historical means. Thus, mutant mice deficient in the PRO1281 gene may serve as a model for cardiovascular disease. PRO1281 polypeptides or its encoding gene would be useful in regulating blood lipids such as cholesterol. Thus, PRO1281 polypeptides or agonists thereof would be useful in the treatment of such cardiovascular diseases as hypertension, atherosclerosis, heart failure, stroke, various coronary diseases, hypercholesterolemia, diabetes and/or obesity.

(c) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:

Both female heterozygous (+/−) and homozygous (−/−) mice exhibited increased mean serum glucose levels when compared with that of their gender-matched (+/+) littermates and the historical mean.

Thus, the mutant (+/−) and (−/−) mice exhibited hyperglycemia which could be associated with an altered glucose metabolism or diabetes. PRO1281 polypeptides or agonists thereof would be useful in maintaining normal glucose levels/metabolism and possibly useful in the treatment of diabetes.

48.16. Generation and Analysis of Mice Comprising DNA66675-1587 (UNQ698) Gene Disruptions In these knockout experiments, the gene encoding PRO1343 polypeptides (designated as DNA66675-1587) (UNQ698) was disrupted. The gene specific information for these studies is as follows: the mutated mouse gene corresponds to nucleotide reference: NM_172205 ACCESSION: NM_172205 NID: gi 26251306 ref NM_172205.1 *Mus musculus* suprabasin (Sbsn-pending); protein reference: 8CIT9 ACCESSION:Q8CIT9 NID: *Mus musculus* (Mouse). Suprabasal-specific protein suprabasin; the human gene sequence reference: BC063640 *Homo sapiens* HLAR698, mRNA (cDNA clone MGC:75533 IMAGE:4750640); the human protein sequence corresponds to reference: Q6UWP8 ACCESSION:Q6UWP8 NID: *Homo sapiens* (Human). HLAR698 (Hypothetical protein).

The mouse gene of interest is Sbsn (suprabasin), ortholog of human UNQ698 (HLAR698). Aliases include 1110005D19Rik and suprabasal-specific protein.

Sbsn is a secreted protein expressed primarily in differentiating suprabasal keratinocytes that likely functions as a structural component of skin. Sbsn contains a signal peptide and multiple regions of low complexity, consisting of a large percentage of glycine, glutamine, histidine, and alanine residues. Sbsn is a substrate for tissue transglutaminase 2 and epidermal transglutaminase 3, suggesting that the protein can cross-link with extracellular and cellular components to become part of the epidermal cornified cell envelope. Sbsn is expressed not only in the suprabasal epithelium of epidermis but also in the suprabasal epithelia of tongue and stomach. Sbsn likely plays a role in differentiation of the epidermis and formation of the highly stratified, water impermeable barrier that is skin (Park et al, *J Biol Chem* 277(47):45195-202 (2002); Moffatt et al, *Gene* 334:123-31 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 17 | 42 | 11 | 70 |
| Expected | 17.5 | 35 | 17.5 | 70 |

Chi-Sq.=0.38 Significance=0.82695913 (hom/n)=0.25 Avg. Litter Size=8

Mutation Information

Mutation Type: Homologous Recombination (standard)

Description: Coding exons 1 and 2 were targeted (NCBI accession NM_172205.1).

1. Wild-type Expression Panel: Expression of the target gene was detected in embryonic stem (ES) cells and in all 13 adult tissue samples tested by RT-PCR, except liver, skeletal muscle, bone, and adipose.

2. QC Expression: Disruption of the target gene was confirmed by Southern hybridization analysis.

48.16.1. Phenotypic Analysis (for Disrupted Gene: DNA66675-1587 (UNQ698)

(a) Overall Phenotypic Summary:

Mutation of the gene encoding the ortholog of human UNQ698 (HLAR698) resulted in the (−/−) mice exhibiting decreased bone mineral density measurements as well as elevated levels of mean serum cholesterol. Gene disruption was confirmed by Southern blot.

(b) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The male (−/−) mice exhibited decreased total body bone mineral density and femur bone mineral density as well as total body volumetric bone mineral density measurements when compared with those of their gender-matched (+/+) littermates and the historical means.

The (−/−) mice analyzed by DEXA exhibited decreased bone density measurements when compared with their (+/+) littermates, suggestive of abnormal bone disorders. The (−/−) mice exhibited a negative bone phenotype with abnormal decreased bone measurements reflective of bone metabolic disorders. The negative bone phenotype indicates that PRO1343 polypeptides or agonists thereof would be useful for maintaining bone homeostasis in addition to normal growth development. In addition, PRO1343 polypeptides would be useful in bone healing or for the treatment of arthritis or osteoporosis, whereas antagonists (or inhibitors) of PRO1343 polypeptides or its encoding gene would lead to abnormal or pathological bone disorders including inflammatory diseases associated with abnormal bone metabolism including arthritis, osteoporosis and osteopenia.

(c) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygous and 8 homozygous mice were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The female (−/−) mice exhibited increased mean serum cholesterol when compared with those of their gender-matched (+/+) littermates and the historical means.

As summarized above, the (−/−) mice exhibited increased mean serum cholesterol levels when compared with their gender-matched (+/+) littermates and the historical means. Thus, mutant mice deficient in the PRO1343 gene may serve as a model for cardiovascular disease. PRO1343 polypeptides or its encoding gene would be useful in regulating blood lipids such as cholesterol. Thus, PRO1343 polypeptides or agonists thereof would be useful in the treatment of such cardiovascular diseases as hypertension, atherosclerosis, heart failure, stroke, various coronary diseases, hypercholesterolemia, diabetes and/or obesity.

48.17. Generation and Analysis of Mice Comprising DNA59828-1608 (UNQ716) Gene Disruptions In these knockout experiments, the gene encoding PRO1379 polypeptides (designated as DNA59828-1608) (UNQ716) was disrupted. The gene specific information for these studies is as follows: the mutated mouse gene corresponds to nucleotide reference: NM_133779 ACCESSION: NM_133779 NID: gi 19527005 ref NM_133779.1 *Mus musculus* RIKEN cDNA 4930534E15 gene (4930534E15Rik); protein reference: Q99JA3 ACCESSION: Q99JA3 NID: *Mus musculus* (Mouse). Neuronal development-associated protein (Neuronal development-associated protein 7) (RIKEN cDNA 4930534E15 gene); the human gene sequence reference: NM_015937 ACCESSION:NM_015937 NID: gi 23397652 refNM_015937.2 *Homo sapiens* phosphatidyl inositol glycan class T (PIGT); the human protein sequence corresponds to reference: Q969N2 ACCESSION:Q969N2 NID: *Homo sapiens* (Human). Phosphatidyl inositol glycan class T precursor (DJ453C12.7) (Hypothetical protein PLACE1010330).

The mouse gene of interest is Pigt (phosphatidylinositol glycan, class T), ortholog of human PIGT. Aliases include CGI-06, 4930534E15Rik, MGC8909, and GPI transamidase component PIG-T.

PIGT is a type I integral membrane protein located in the endoplasmic reticulum that likely functions as a noncatalytic subunit of glycosylphosphatidylinositol (GPI) transamidase. GPI transamidase consists of five subunits and catalyzes the transfer of GPI to proteins. PIGT stabilizes the GPI transamidase complex and regulates access of substrate proteins to the active sites (Ohishi et al, *EMBO J.* 20(15):4088-98 (2001); Vainauskas et al, *J Biol Chem* 277(34):30535-42 (2002); Ohishi et al, *J Biol Chem* 278(16):13959-67 (2003); Eisenhaber et al, *Bioessays* 25(4):367-85 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 15 | 30 | 0 | 45 |
| Expected | 11.25 | 22.5 | 11.25 | 45 |

Chi-Sq.=47.2 Significance=5.6318367E-11 (hom/n)=0.0
Avg. Litter Size=7
Mutation Type: Homologous Recombination (standard)
Description: Coding exons 1 through 3 were targeted (NCBI accession NM_133779.1).
1. Wild-type Expression Panel: Expression of the target gene was detected in embryonic stem (ES) cells and in all 26 adult tissue samples tested by RT-PCR.
2. QC Expression: QC Images: Disruption of the target gene was confirmed by Southern hybridization analysis.

48.17.1. Phenotypic Analysis (for Disrupted Gene: DNA59828-1608 (UNQ716)
(a) Overall Phenotypic Summary:
UNQ716, DNA59828 Mutation of the gene encoding the ortholog of human phosphatidylinositol glycan, class T (PIGT) resulted in lethality of (−/−) mice. Heterozygous (+/−) mice exhibited decreased bone mineral content and density measurements. Gene disruption was confirmed by Southern blot.

(b) Pathology
Microscopic: Due to embryonic lethality, microscopic analysis was not performed. At 12.5 days, there were 44 embryos observed: 27 (+/−) embryos, 5 (+/+) embryos, and 12 resorption moles.

Discussion Related to Embryonic Developmental Abnormality of Lethality:
Embryonic lethality in knockout mice usually results from various serious developmental problems including but not limited to neurodegenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(c) Bone Metabolism & Body Diagnostics: Radiology Phenotypic Analysis
In the area of bone metabolism, targets were identified herein for the treatment of arthritis, osteoporosis, osteopenia and osteopetrosis as well as identifying targets that promote bone healing. Tests included:
DEXA for measurement of bone mineral density on femur and vertebra
MicroCT for very high resolution and very high sensitivity measurements of bone mineral density for both trabecular and cortical bone.

Dexa Analysis—Test Description:
Procedure: A cohort of 4 wild type, and 4 heterozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.
The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:
Procedure: MicroCT was also used to get very sensitive measurements of BMD. One vertebra and 1 femur were taken from a cohort of 4 wild type and 8 heterozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:
DEXA: The male (+/−) mice exhibited decreased mean bone mineral content (BMC), BMC/LBM, and total body bone mineral density (BMD) when compared with those of their gender-matched (+/+) littermates and the historical means.
Micro CT: The male (+/−) mice exhibited decreased mean vertebral trabecular bone volume, number, thickness, and connectivity density when compared with those of their gender-matched (+/+) littermates and the historical means.

The (+/−) mice analyzed by DEXA and bone micro CT analysis exhibited decreased bone measurements when compared with their (+/+) littermates, suggestive of abnormal bone disorders. The (+/−) mice exhibited a negative bone phenotype with abnormal and decreased bone measurements reflective of bone metabolic disorders. The negative bone phenotype indicates that PRO1379 polypeptides or agonists thereof would be useful for maintaining bone homeostasis. In addition, PRO1379 polypeptides would be useful in bone healing or for the treatment of arthritis or osteoporosis, whereas antagonists (or inhibitors) of PRO1379 polypeptides or its encoding gene would lead to abnormal or pathological bone disorders including inflammatory diseases associated with abnormal bone metabolism including arthritis, osteoporosis and osteopenia.

48.18. Generation and Analysis of Mice Comprising DNA60740-1615 (UNQ717) Gene Disruptions
In these knockout experiments, the gene encoding PRO1380 polypeptides (designated as DNA60740-1615) (UNQ717) was disrupted. The gene specific information for these studies is as follows: the mutated mouse gene corresponds to nucleotide reference: NM_023596 *Mus musculus* solute carrier family 29 (nucleoside transporters), member 3 (Slc29a3); protein reference: Q99P65 ACCESSION:Q99P65 NID: *Mus musculus* (Mouse). EQUILIBRATIVE NUCLEOSIDE TRANSPORTER 3; the human gene sequence reference: NM_018344 *Homo sapiens* solute carrier family 29 (nucleoside transporters), member 3 (SLC29A3); the human protein sequence corresponds to reference: Q9BZD2 ACCESSION:Q9BZD2 NID: *Homo sapiens* (Human). EQUILIBRATIVE NUCLEOSIDE TRANSPORTER 3.
The mouse gene of interest is Slc29a3 (solute carrier family 29 [nucleoside transporters], member 3), ortholog of human SLC29A3. Aliases include Ent3, 4933435C21Rik, FLJ1160, and equilibrative nucleoside transporter 3.

SLC29A3 is a lysosomal integral membrane protein that functions as an equilibrative transporter, mediating the passive influx and efflux of nucleosides (Baldwin et al, *J Biol Chem* 280(16): 15880-7 (2005)). The protein is expressed primarily in kidney and in Sertoli cells of the testis (Lu et al, *Drug Metab Dispos* 32(12): 1455-61 (2004); Kato et al, *J Pharmacol Exp Ther* 312(2):601-8 (2005)). SLC29A3 may play a role in release of nucleosides produced by breakdown of nucleic acids in lysosomes. SLC29A3 may also play a role in the disposition of anticancer and antiviral nucleoside analogs (Lu et al, *Drug Metab Dispos* 32(12):1455-61 (2004)) and in spermatogenesis (Kato et al, *J Pharmacol Exp Ther* 312(2):601-8 (2005)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 16 | 49 | 21 | 86 |
| Expected | 21.5 | 43 | 21.5 | 86 |

Chi-Sq.=5.5 Significance=0.06392786 (hom/n)=0.2 Avg. Litter Size=10
Mutation Type Homologous Recombination (standard)
Description: Coding exons 1 and 2 were targeted (NCBI accession NM_023596.1).
1. Wild-type Expression Panel: Expression of the target gene was detected in embryonic stem (ES) cells and in all 13 adult tissue samples tested by RT-PCR.
2. QC Expression: QC Images: Disruption of the target gene was confirmed by Southern hybridization analysis.
48.18.1. Phenotypic Analysis (for Disrupted Gene: DNA60740-1615 (UNQ717)
(a) Overall Phenotypic Summary:
Mutation of the gene encoding the ortholog of human solute carrier family 29 (nucleoside transporters), member 3 (SLC29A3) resulted in histiocytosis, lymphadenopathy, and hepatosplenomegaly in (−/−) mice with chronic inflammation. Necropsy revealed histiocytosis in the small intestine, spleen, and lymph nodes of the homozygous mutant mice, along with lymphadenopathy and splenomegaly. UNQ717 gene is expressed on monocytes and dendritic cells and is of special interest in immunological disorders (with a possible role in autoimmunity). The homozygous mutant mice were also anemic and exhibited numerous other immunological and blood chemistry abnormalities when compared with the levels for their wild-type littermates and the historical means. The (−/−) mice also exhibited a decreased stress induced hyperthermia response compared with their littermate (+/+) controls. Disruption of the target gene was confirmed by Southern hybridization analysis.
(b) Pathology
Gross: The (−/−) mice exhibited splenomegaly and lymphadenopathy.
Microscopic: All 6 (−/−) mice analyzed exhibited varying degrees of histiocytosis in the small intestine, lymph nodes, and spleen. The (−/−) mice also exhibited lymphoid depletion (T cell) in the spleen, lymph nodes, and thymus. In the earliest stages of disease, there was vacuolization of antigen presenting cells in the thymic cortex, associated with apoptosis of cortical thymocytes, and a minimal histiocytic infiltrate in the jejunum. In more advanced cases, the spleen was mildly enlarged with multifocal replacement of T-cells (periarteriolar lymphoid sheaths) by histiocytic cells. The B cell areas (follicles) were relatively normal. There was increased erythropoiesis in the splenic red pulp in most mutants; however, scattered erythroid cells had dark shrunken nuclei surrounded by an expanded clear cytoplasm. Lymph nodes were enlarged and contained a diffuse histiocytic infiltrate in the medullary cords and paracortical areas with concomitant decreases in T cell lymphocytes. The submucosa and lamina propria of the shortened jejunal villi was expanded by a cell infiltrate consisting primarily of histiocytes. The duodenum and ileum had similar but milder infiltrates. The thymic cortex contained increased numbers of body macrophages with abundant highly vacuolated cytoplasm. In the 2 most severe cases, there was marked enlargement of the spleen and all lymph nodes due to a massive infiltrate of histiocytic cells. The liver sinusoids and small intestinal mucosa were also diffusely infiltrated by histiocytes, and there was marked blunting and fusion of small intestinal villi. Again, the most severe lesions were in the jejunum. Histiocyte infiltrates extended into the interstitium of the pancreas, resulting in atrophy and a loss of acinar glands. There was a marked generalized loss of T cells in all lymphoid tissues. The distribution of the histiocytic cells in tissues suggests that they may be of T cell lineage.
(c) Immunology Phenotypic Analysis
Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:
Hematology Analysis:
Test Description: Blood tests are carried out by Abbott's Cell-Dyn 3500R, an automated hematology analyzer. Some of its features include a five-part WBC differential. 'Patient' reports can cover over 22 parameters in all.

Results:
Hematology: The (−/−) mice exhibited increased total white blood cell and absolute monocyte counts when compared with those of their (+/+) littermates and the historical means. In addition, the (−/−) mice exhibited a decreased mean red blood cell count, hemoglobin concentration, and hematocrit and an increased mean red cell distribution width. The (−/−) mice also exhibited a decreased mean platelet count and an increased mean platelet volume.

The increased total white blood cell and absolute monocyte counts are consistent with the pathological findings discussed above.

The (−/−) mice exhibited a decreased mean total red blood cell count, hemoglobin level, and hematocrit when compared with their (+/+) littermates and the historical means.

These results are related to a phenotype associated with anemia. Thus, PRO1380 polypeptides, agonists thereof or the encoding gene for PRO1380 polypeptides must be essential for normal red blood cell production and as such would be useful in the treatment of blood disorders associated with anemia or a low hematocrit.

The (−/−) mice also exhibited a decreased mean platelet count when compared with their (+/+) littermates and the historical mean.

Thus, mutant mice deficient in the DNA60740-1615 gene resulted in a phenotype related to coagulation disorders. In this regard, PRO1380 polypeptides or agonists thereof would be useful in treating disorders related to abnormal blood coagulation such as hemophilia.

Acute Phase Response:
Test Description: Bacterial lipopolysaccharide (LPS) is an endotoxin, and as such is a potent inducer of an acute phase response and systemic inflammation. The Level I LPS mice were injected intraperitoneally (i.p.) with a sub lethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACS Calibur instrument.

Results:
Acute Phase Response: The (−/−) mice exhibited increased mean serum IL-6, TNFalpha and MCP-1 responses to LPS challenge when compared with those of their (+/+) littermates and the historical means.

Ovalbumin Challenge
Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Results of this Challenge:
Ovalbumin: The (−/−) mice exhibited decreased mean serum IgG1 response to ovalbumin challenge when compared with those of their gender-matched (+/+) littermates and the historical means.

In summary, the ovalbumin challenge studies indicate that knockout mice deficient in the gene encoding PRO1380 polypeptides exhibit immunological abnormalities when compared with their wild-type littermates. In particular, the mutant mice exhibited a decreased ability to elicit an immunological response when challenged with the T-cell dependent OVA antigen. Accordingly, inhibitors or antagonists of PRO1380 polypeptides would mimic these immunological findings. These results are consistent with the pathology report indicating lymphoid depletion (T cell) in the spleen, lymph nodes and thymus.

Serum Immunoglobulin Isotyping Assay:
The Serum Immunoglobulin Isotyping Assay was performed using a Cytometric Bead Array (CBA) kit. This assay was used to rapidly identify the heavy and light chain isotypes of a mouse monoclonal antibody in a single sample. The values expressed are "relative fluorescence units" and are based on the detection of kappa light chains. Any value <6 is not significant.

Results:
Serum Imm. 2: The (−/−) mice exhibited an increased mean serum IgA level and IgM when compared with that of their (+/+) littermates, the (+/+) median for the project, and the cumulative (+/+) historical medians.

Mutant (−/−) mice exhibited elevation of IgA serum immunoglobulins compared to their gender-matched (+/+) littermates. IgA mainly functions as an epithelial cell protector which can neutralize bacterial toxins and viruses. Although no obvious disease susceptibility is associated with selective IgA defects, they are commoner in people with chronic lung disease than in the general population. This suggests that lack of IgA may result in a predisposition to lung infections with various pathogens and is consistent with the role of IgA in defense at the body surfaces. In this case, the phenotype observed for knockout mice resulted in an increase in IgA serum levels suggesting that inhibitors (antagonists) of PRO1380 polypeptides would mimic these immunological effects.

Fluorescence-Activated Cell-Sorting (FACS) Analysis
Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:
Tissue Specific FACS Overall Observations: The (−/−) mice exhibited an altered distribution of leukocyte subsets in the peripheral blood, characterized by a decreased mean percentage of CD4 and CD8 cells in lymph nodes and spleen (approximately ⅓ of the wild-type); increased memory T cells (approximately 5-fold—increase in CD62LloCD44hi cells (% CD4 or CD8 total); decreased naive T cells (approximately 2-fold); increased CD25+ cells: increased thymic DN, decreased DP T cells; and an increased mean percentage of monocytes and DC in spleen (CD11b+, CD11b+c+ (approximately 5-fold) and peritoneal lavage (CD11b+); increased CD19+ cells in LN; increased CD117 in bone marrow cells when compared with those of their (+/+) littermates and the historical mean.

These results are consistent with the pathological observations wherein the mutant (−/−) mice exhibited lymphoid depletion (T cells). histiocytosis, lymphadenopathy and splenomegaly.

(d) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:
Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

CAT-Scan Protocol:
Mice were injected with a CT contrast agent, Omnipaque 300 (Nycomed Amershan, 300 mg of iodine per ml, 0.25 ml per animal, or 2.50-3.75 g iodine/kg of body weight) intraperitoneally. After resting in the cage for ~10 minutes, the mouse was then sedated by intraperitoneal injection of Avertin (1.25% 2,2,2,-tribromoethanol, 20 ml/kg body weight). A CAT-scan was performed using a MicroCAT scanner (ImTek, Inc.) with the anesthetized animal lying prone on the test bed. Three dimensional images were reconstructed by the Feldkamp algorithm in a cluster of workstations using an ImTek 3D RECON software.

Results:
DEXA: Female (−/−) mice exhibited decreased mean percent total body fat and fat mass (g) when compared with that of their gender-matched (+/+) littermates and the historical means.

Mutant (−/−) mice deficient in the gene encoding PRO1380 polypeptides show a phenotype consistent with tissue wasting diseases (decreased total body fat (% and g)). Thus, antagonists or inhibitors of PRO1380 polypeptides or its encoding gene would mimic these metabolic and growth related effects. On the other hand, PRO1380 polypeptides or agonists thereof would be useful in the prevention and/or treatment of metabolic disorders related to abnormal fat metabolism or other tissue wasting diseases.

CATScan: All 3 (−/−) mice (M-95, M-103, and F-129) exhibited moderate splenomegaly.

(e) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids
Procedure: A cohort of 4 wild type, 4 heterozygous and 8 homozygous mice were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche).

Results:
Blood Chemistry: Both the male and female (−/−) mice exhibited decreased mean serum cholesterol levels when compared with those of their gender-matched (+/+) littermates and the historical means.

In summary, these knockout mutant mice exhibited a positive phenotype with regards to lipid metabolism. Thus, mutant mice deficient in the PRO1380 gene can serve as a model for treatment of cardiovascular disease associated with dyslipidemia, hypertension, atherosclerosis, heart failure, stroke, or various coronary artery diseases.

(f) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:

Both the male and female (−/−) mice exhibited decreased mean serum glucose levels when compared with those of their gender-matched (+/+) littermates and the historical means. These results may indicate an increased insulin sensitivity in the mutant (−/−) mice.

(g) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Functional Observational Battery (FOB) Test—Stress-Induced Hyperthermia:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

Anxiety: The male (−/−) mice exhibited a decreased response to stress-induced hyperthermia when compared with their gender-matched (+/+) littermates and the historical mean, suggesting a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO1380 polypeptides and agonists thereof would be useful for the treatment or amelioration of the symptoms associated with depressive disorders.

48.19. Generation and Analysis of Mice Comprising DNA68872-1620 (UNQ722) Gene Disruptions In these knockout experiments, the gene encoding PRO1387 polypeptides (designated as DNA68872-1620) (UNQ722) was disrupted. The gene specific information for these studies is as follows: the mutated mouse gene corresponds to nucleotide reference: NM_001005421 *Mus musculus* gene model 638, (NCBI) (Gm638); protein reference: Q80UL9 ACCESSION:Q80UL9 NID: *Mus musculus* (Mouse). Adhesion molecule AMICA; the human gene sequence reference: NM_153206 ACCESSION:NM_153206NID: gi 23397450 refNM_153206.1 *Homo sapiens* adhesion molecule AMICA (AMICA); the human protein sequence corresponds to reference: Q8N917 ACCESSION: Q8N917 NID: *Homo sapiens* (Human). Hypothetical protein FLJ37080.

The mouse gene of interest is AMICA (adhesion molecule AMICA), ortholog of human AMICA1 (adhesion molecule, interacts with CXADR antigen 1). Aliases include GM638, gene model 638, MGC61025, JAML, FLJ37080, junctional adhesion molecule, and adhesion molecule that interacts with CXADR antigen 1.

AMICA1 is a type I integral plasma membrane protein that likely functions as a cell adhesion molecule. The protein contains a signal peptide, two extracellular immunoglobulin-like domains, a transmembrane segment, and a cytoplasmic tail. AMICA1 is expressed primarily in granulocytes and other hematopoietic cells and is likely to play a role in leukocyte transmigration (Moog-Lutz et al, *Blood* 102(9):3371-8 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 20 | 40 | 12 | 72 |
| Expected | 18 | 36 | 18 | 72 |

Chi-Sq.=0.09 Significance=0.95599747 (hom/n)=0.24 Avg. Litter Size=8

Mutation Information

Mutation Type Homologous Recombination (standard)

Description: Coding exons 1 through 3 were targeted (NCBI accession NM_001005421.2).

1. Wild-type Expression Panel: Expression of the target gene was detected in embryonic stem (ES) cells and in all 13 adult tissue samples tested by RT-PCR, except skin fibroblast.

2. QC Expression: QC Images: Disruption of the target gene was confirmed by Southern hybridization analysis.

48.19.1. Phenotypic Analysis (for Disrupted Gene: DNA68872-1620 (UNQ722)

(a) Overall Phenotypic Summary:

Mutation of the gene encoding the ortholog of human adhesion molecule, interacts with CXADR antigen 1 (AMICA1) resulted in a decreased mean serum IgG2a response to ovalbumin challenge in (−/−) mice. Homozygous (−/−) mice also exhibited a decreased latency to respond during hot plate testing. The mutant female (−/−) mice showed increased total body fat. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Ovalbumin Challenge

Procedure: This assay was carried out on 7 wild types and 8 homozygous mice. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Results of this Challenge:

The (−/−) mice exhibited decreased mean serum IgG2a response when compared with their (+/+) littermates and the historical mean.

In summary, the ovalbumin challenge studies indicate that knockout mice deficient in the gene encoding PRO1387 polypeptides exhibit immunological abnormalities when compared with their wild-type littermates. In particular, the mutant mice exhibited a decreased ability to elicit an immunological response when challenged with the T-cell dependent OVA antigen. Thus, PRO1387 polypeptides or agonists thereof, would be useful for stimulating the immune system (such as T cell proliferation) and would find utility in the cases wherein this effect would be beneficial to the individual such as in the case of leukemia, and other types of cancer, and in immuno-compromised patients, such as AIDS sufferers. Accordingly, inhibitors (antagonists) of PRO1387 polypeptides would be useful for inhibiting the immune response and thus would be useful candidates for suppressing harmful immune responses, e.g. in the case of graft rejection or graft-versus-host diseases.

(c) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

The female (−/−) mice exhibited increased total body fat (% and g) when compared to their gender matched wild-type (+/+) littermates and historical mean.

These studies suggest that mutant (−/−) non-human transgenic animals exhibit a negative phenotype that would be associated with obesity. Thus, PRO1387 polypeptides or agonists thereof are essential for normal growth and metabolic processes and especially would be important in the prevention and/or treatment of obesity.

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Functional Observational Battery (FOB) Test—Hot Plate Testing:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Hot Plate Testing

Test Description: The hot plate test for nociception is carried out by placing each mouse on a small enclosed 55° C. hot plate. Latency to a hind limb response (lick, shake, or jump) is recorded, with a maximum time on the hot plate of 30 sec. Each animal is tested once.

Results:

The (−/−) mice exhibited a decreased latency in hot plate testing which indicates an increased pain perception compared with their gender-matched wild-type littermates and the historical means.

48.20. Generation and Analysis of Mice Comprising DNA71290-1630 (UNQ733) Gene Disruptions In these knockout experiments, the gene encoding PRO1419 polypeptides (designated as DNA71290-1630) (UNQ733) was disrupted. The gene specific information for these studies is as follows: the mutated mouse gene corresponds to nucleotide reference: BC037156 *Mus musculus* cDNA sequence BC037156; the human gene sequence reference: NM_152997 *Homo sapiens* chromosome 4 open reading frame 7 (C4orf7); the human protein sequence corresponds to reference: Q8NFU4 ACCESSION:Q8NFU4 NID: *Homo sapiens* (Human). Follicular dendritic cell secreted peptide precursor (FDC-SP) (FDC secreted protein).

The mouse gene of interest is cDNA sequence BC037156, ortholog of human C4orf7 (chromosome 4 open reading frame 7). Aliases include MGC71894, FDC-SP, FDCSP, and follicular dendritic cell secreted peptide.

C4orf7 is an 84-amino acid secreted protein expressed primarily by follicular dendritic cells of tonsils that likely functions as a signal-transducing ligand. C4orf7 expression can be stimulated by tumor necrosis factor-alpha in follicular dendritic cells and by lipopolysaccharides in blood leukocytes. Moreover, C4orf7 is expressed at very high levels in inflamed tonsillar crypts. In addition to tonsils, C4orf7 is also expressed in a number of other tissues, including lymph node, trachea, prostate, thyroid, stomach, colon, spleen, peripheral blood leukocytes, and bone marrow. The protein is capable of binding to activated B-cells, suggesting that C4orf7 plays a role in immune function (Marshall et al, *J Immunol* 169(5): 2381-9 (2002)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 26 | 43 | 17 | 86 |
| Expected | 21.5 | 43 | 21.5 | 86 |

Chi-Sq.=0.81 Significance=0.6669768 (hom/n)=0.23 Avg. Litter Size=10
Mutation Information
Mutation Type Homologous Recombination (standard)
Description: Coding exons 1 and 2 were targeted (NCBI accession BC037156).
1. Wild-type Expression Panel: Expression of the target gene was detected only in eye and thymus among the 13 adult tissue samples tested by RT-PCR.

2. QC Expression: QC Images: Disruption of the target gene was confirmed by Southern hybridization analysis.

48.20.1. Phenotypic Analysis (for Disrupted Gene: DNA71290-1630 (UNQ733)
(a) Overall Phenotypic Summary:

Mutation of the gene encoding the ortholog of human chromosome 4 open reading frame 7 (C4orf7) resulted in the mutant (−/−) mice exhibiting an increase in IgG2a response to the ovalbumin challenge. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:
Ovalbumin Challenge

Procedure: This assay was carried out on 7 wild types and 8 homozygous mice. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immuno-dominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Results of this Challenge:

The (−/−) mice exhibited an increased mean serum IgG2a response when compared with their (+/+) littermates and the historical mean.

In summary, the ovalbumin challenge studies indicate that knockout mice deficient in the gene encoding PRO1419 polypeptides exhibit immunological abnormalities when compared with their wild-type littermates. UNQ733 may play a role in inflammatory disorders since UNQ733 is secreted by follicular dendritic cells and it specifically binds B cells (which can be induced by TNF alpha). Hyperplasia of adenoid and tonsils have also been observed. In particular, the mutant mice exhibited a decreased ability to elicit an immunological response when challenged with the T-cell dependent OVA antigen. Thus, inhibitors (antagonists) of PRO1419 polypeptides would be useful for stimulating the immune system (such as T cell proliferation) and would find utility in the cases wherein this effect would be beneficial to the individual such as in the case of leukemia, and other types of cancer, and in immuno-compromised patients, such as AIDS sufferers. Accordingly, PRO1419 polypeptides or agonists thereof would be useful for inhibiting the immune response and thus would be useful candidates for suppressing harmful immune responses, e.g. in the case of graft rejection or graft-versus-host diseases.

48.21. Generation and Analysis of Mice Comprising DNA71184-1634 (UNQ738) Gene Disruptions In these knockout experiments, the gene encoding PRO1433 polypeptides (designated as DNA71184-1634) (UNQ738) was disrupted. The gene specific information for these studies is as follows: the mutated mouse gene corresponds to nucleotide reference: NM_026384 *Mus musculus* diacylglycerol O-acyltransferase 2 (Dgat2); protein reference: Q9DCV3 ACCESSION:Q9DCV3 NID: *Mus musculus* (Mouse). 0610010B06Rik protein (Diacylglycerol acyltransferase 2); the human gene sequence reference: NM_032564 ACCESSION:NM_032564 NID: gi 26024196 ref NM_032564.2 *Homo sapiens* diacylglycerol O-acyltransferase homolog 2 (mouse) (DGAT2); the human protein sequence corresponds to reference: Q96PD7 ACCESSION: Q96PD7 NID: *Homo sapiens* (Human). Diacylglycerol acyltransferase 2 (Hypothetical protein) (GS1999full protein).

The mouse gene of interest is Dgat2 (diacylglycerol O-acyltransferase 2), ortholog of human DGAT2 (diacylglycerol O-acyltransferase homolog 2 [mouse]). Aliases include DGAT-2, 0610010B06Rik, diacylglycerol acyltransferase 2, HMFN1045, and GS1999full.

DGAT2 is an integral membrane protein located on the endoplasmic reticulum that functions as an enzyme, catalyzing the formation of triglycerides from long-chain acyl-CoAs and diacylglycerol. Expression of DGAT2 is ubiquitous but seems most abundant in liver, white fat, mammary gland, small intestine, and sebaceous glands of skin. DGAT2 plays a role in energy metabolism and skin barrier function (Cases et al, *J Biol Chem* 276(42):38870-6 (2001); Wakimoto et al, *Biochem Biophys Res Commun* 310(2):296-302 (2003); Stone et al, *Biol Chem* 279(12):11767-76 (2004)). Moreover, DGAT2 may be associated with diabetes and psoriasis (Watermann and Zammit, *Int J Obes Relat Metab Disord* 26(5): 742-3 (2002); Meegalla et al, *Biochem Biophys Res Commun* 298(3):317-23 (2002); Wakimoto et al, *Biochem Biophys Res Commun* 310(2):296-302 (2003)).

Scot Stone and colleagues (2004) investigated the physiological role of DGAT2 using knockout mice. They showed that DGAT2 (−/−) mice were lipopenic and died early after birth. Tissue triglyceride and energy substrate content was severely lower in DGAT2 (−/−) mice than in (+/+) mice. Moreover, skin abnormalities and barrier maintenance function were evident in DGAT2 (−/−) mice but not (+/+) mice, suggesting that energy homeostasis abnormalities and dehydration contributed to early postnatal lethality of the DGAT2 (−/−) mice. Scot and colleagues concluded that the majority of triglyceride biosynthesis in mice involves DGAT2 and that inhibition of DGAT2 for therapeutic purposes should be approached with caution because DGAT2 function appears to be crucial for survival.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 20 | 36 | 14 | 70 |
| Expected | 17.5 | 35 | 17.5 | 70 |

Chi-Sq.=2.62 Significance=0.26982006 (hom/n)=0.18 Avg. Litter Size=8
Mutation Information
Mutation Type Homologous Recombination (standard)
Description: Coding exon 1 was targeted (NCBI accession NM_026384.2).
1. Wild-type Expression Panel: Expression of the target gene was detected in all 13 adult tissue samples tested by RT-PCR, except adipose.

2. QC Expression: QC Images: Disruption of the target gene was confirmed by Southern hybridization analysis.

48.21.1. Phenotypic Analysis (for Disrupted Gene: DNA71184-1634 (UNQ738)

(a) Overall Phenotypic Summary:

Mutation of the UNQ738 gene encoding the ortholog of human diacylglycerol O-acyltransferase homolog 2 (mouse) (DGAT2) resulted in perinatal lethality of (−/−) mutants. Genetic data indicate that this mutation resulted in perinatal lethality of the homozygous mutants. The homozygous mutant mice were small and frail, dying within 5 days of birth. Necropsy revealed that the mutants were dehydrated with decreased subcutaneous fat depots (suggesting abnormal lipid metabolism) and decreased lymphocytes in the spleen and thymus. Disruption of the target gene was confirmed by Southern hybridization analysis.

(b) Pathology

Gross: The (−/−) mice were small, dehydrated, and exhibited decreased subcutaneous fat depots.

Microscopic: Perinatal mortality was noted in the (−/−) mice. The (−/−) mice exhibited decreased lymphocytes in the thymus and spleen. External knockout mice were reportedly lipopenic and died soon after birth, apparently from a profound reduction in substrates for energy metabolism and from impaired permeability barrier function in the skin.

Gene Expression: LacZ activity was detected in testis and epididymis among the panel of tissues analyzed by immunohistochemistry.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(c) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, and 4 heterozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan.

Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 4 heterozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro CT: Male heterozygous (+/−) mice exhibited increased trabecular number and connectivity density when compared with their gender-matched wild-type littermates and the historical mean.

In summary, the (+/−) mice exhibited increased trabecular number and connectivity density when compared with their gender-matched (+/+) littermates. These results indicate that the knockout mutant phenotype may be associated with such bone abnormalities as osteopetrosis. Osteopetrosis is a condition characterized by abnormal thickening and hardening of bone and abnormal fragility of the bones. As such, PRO1433 polypeptides or agonists thereof would be beneficial for the treatment of osteopetrosis or other osteo-related diseases.

48.22. Generation and Analysis of Mice Comprising DNA73739-1645 (UNQ745) Gene Disruptions In these knockout experiments, the gene encoding PRO1474 polypeptides (designated as DNA73739-1645) (UNQ745) was disrupted. The gene specific information for these studies is as follows: the mutated mouse gene corresponds to nucleotide reference: NM_001001803 *Mus musculus* esophagus cancer-related gene-2 (Ecg2); protein reference: Q61E32 ACCESSION:Q61E32 NID: *Mus musculus* (Mouse). Esophagus cancer-related gene-2 precursor; the human gene sequence reference: NM_032566 *Homo sapiens* esophagus cancer-related gene-2 (ECG2); the human protein sequence corresponds to reference: P58062 Esophagus cancer-related gene-2 protein precursor (ECRG-2) (UNQ745/PRO1474).

The mouse gene of interest is Ecg2 (esophagus cancer-related gene-2), ortholog of human ECG2. Aliases include ECRG2.

ECG2 is a putative secreted protein that likely functions as a protease inhibitor (Puente and Lopez-Otin, *Genome Res* 14(4):609-22 (2004)). The protein contains a signal peptide and a Kazal-type serine protease inhibitor domain (SMART accession SM00280). ECG2 is also a tumor suppressor candidate that can associate with metallothionein 2A. Ectopically expressed ECG2 in esophageal cancer cells colocalizes with metallothionein in the nucleus and cytoplasm, inhibits cell proliferation, and induces apoptosis. Mutations in the ECG2 gene have been implicated in esophageal squamous cell carcinoma (Yue et al, *Int J Cancer* 108(2):232-6 (2004); Cui et al, *Biochem Biophys Res Commun* 302(4):904-15 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 16 | 42 | 22 | 80 |
| Expected | 20 | 40 | 20 | 80 |

Chi-Sq.=1.38 Significance=0.50157607 (hom/n)=0.28 Avg. Litter Size=9

Mutation Information

Mutation Type: Homologous Recombination (standard)

Description: Coding exons 1 through 3 were targeted (NCBI accession NM_001001803.1).

1. Wild-type Expression Panel: Expression of the target gene was detected only in eye among the 13 adult tissue samples tested by RT-PCR.

2. QC Expression: QC Images: Disruption of the target gene was confirmed by Southern hybridization analysis.

48.22.1. Phenotypic Analysis (for Disrupted Gene: DNA73739-1645 (UNQ745)

(a) Overall Phenotypic Summary:

Mutation of the gene encoding the ortholog of human esophagus cancer-related gene-2 (ECG2) resulted in the homozygous (−/−) mice exhibiting decreased total tissue mass and decreased bone mineral density measurements. Some of the female (−/−) mice were fat showing increased total body fat and high triglyceride levels. Gene disruption was confirmed by Southern blot.

(b) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased mean total body and femur bone mineral density (BMD) as well as a decrease in total tissue mass when compared with the those of their gender-matched (+/+) littermates and the historical means. In addition, a few of the female (−/−) mice showed high total body fat [One or two female (−/−) mice were fat with increased total body fat and showed high mean serum triglyceride levels]. Overall population did not display characteristics of obesity/type 2 diabetes.

The (−/−) mice analyzed by DEXA analysis exhibited decreased bone measurements when compared with their (+/+) littermates, suggestive of abnormal bone disorders. The (−/−) mice exhibited a negative bone phenotype with abnormal and decreased bone measurements reflective of bone metabolic disorders. The negative bone phenotype indicates that PRO1474 polypeptides or agonists thereof would be useful for maintaining bone homeostasis. In addition, PRO1474 polypeptides would be useful in bone healing or for the treatment of arthritis or osteoporosis, whereas antagonists (or inhibitors) of PRO1474 polypeptides or its encoding gene would lead to abnormal or pathological bone disorders including inflammatory diseases associated with abnormal bone metabolism including arthritis, osteoporosis and osteopenia.

48.23. Generation and Analysis of Mice Comprising DNA76393-1664 (UNQ762) Gene Disruptions In these knockout experiments, the gene encoding PRO1550 polypeptides (designated as DNA76393-1664) (UNQ762) was disrupted. The gene specific information for these studies is as follows: the mutated mouse gene corresponds to nucleotide reference: AK003674 *Mus musculus* 18-day embryo whole body cDNA, RIKEN full-length enriched library, clone:1110014B07 product:hypothetical Collagen triple helix repeat containing protein, full insert sequence; protein reference: Q9D1D6 ACCESSION: Q9D1D6 NID: *Mus musculus* (Mouse). 1110014B07Rik protein; the human gene sequence reference: NM_138455 ACCESSION:NM_138455 NID: gi 34147546 refNM_138455.2 *Homo sapiens* collagen triple helix repeat containing 1 (CTHRC1); the human protein sequence corresponds to reference: Q96CG8 ACCESSION:Q96CG8 NID: *Homo sapiens* (Human). Similar to RIKEN cDNA 1110014B07 gene (Collagen triple helix repeat-containing protein 1).

The mouse gene of interest is Cthrc1 (collagen triple helix repeat containing 1), ortholog of human CTHRC1. Aliases include 1110014B07Rik.

CTHRC1 is a secreted protein, containing a signal peptide and a collagen triple-helix repeat. CTHRC1 is expressed in fibroblasts of remodeling adventitia and smooth muscle cells of neointima of balloon-injured vascular tissue and is also found in the matrix of calcifying human atherosclerotic plaques. CTHRC1 is not expressed in normal arteries. Expression of CTHRC1 is upregulated in response to transforming growth factor-beta and bone morphogenic protein-4. CTHRC1 inhibits expression and secretion of collagen type I and enhances cell migration. Thus, CTHRC1 appears to play a role in vascular remodeling by inhibiting deposition of collagen and promoting migration of vascular cells (Pyagay et al, *Circ Res* 96(2):261-8 (2005)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|          | wt   | het | hom  | Total |
|----------|------|-----|------|-------|
| Observed | 16   | 33  | 17   | 66    |
| Expected | 16.5 | 33  | 16.5 | 66    |

Chi-Sq.=3.43 Significance=0.17996371 (hom/n)=0.27 Avg. Litter Size=9

Mutation Information

Mutation Type: Homologous Recombination (standard)

Description: Coding exons 1 and 2 were targeted (NCBI accession AK076498).

1. Wild-type Expression Panel: Expression of the target gene was detected in all 13 adult tissue samples tested by RT-PCR, except liver and bone.

2. QC Expression: QC Images: Disruption of the target gene was confirmed by Southern hybridization analysis.

48.23.1. Phenotypic Analysis (for Disrupted Gene: DNA76393-1664 (UNQ762)

(a) Overall Phenotypic Summary:

Mutation of the gene encoding the ortholog of human collagen triple helix repeat containing 1 (CTHRC1) resulted in increased serum alkaline phosphatase levels in both (+/−) and (−/−) mice. Female (−/−) mice also exhibited a notably decreased skin proliferation rate. Gene disruption was confirmed by Southern blot.

(b) Expression Patterns:

GeneLogic analysis shows UNQ762 being specifically expressed in skin and breast tissue. [See EXAMPLES 54 and 55 for protocol]

(c) Adult Skin Cell Proliferation:

Procedure: Skin cells were isolated from 16 week old animals (2 wild type and 4 homozygous mice). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:

The female (−/−) mice exhibited a notably decreased mean skin fibroblast proliferation rate when compared with their gender-matched (+/+) littermates.

Thus, homozygous mutant mice demonstrated a hypo-proliferative phenotype. As suggested by these observations, antagonists or inhibitors of PRO1550 polypeptides would mimic this hypo-proliferative phenotype and could function as tumor suppressors and would be useful in decreasing abnormal cell proliferation. Thus, UNQ762 plays a role in fibroblast activation and migration.

(d) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Results:

Both the male and female (−/−) mice exhibited notably increased mean serum alkaline phosphatase levels when compared with their gender-matched (+/+) littermates and the historical means. There is also elevation of alkaline phosphatase in heterozygous (+/−) animals, particularly males.

48.24. Generation and Analysis of Mice Comprising DNA73730-1679 (UNQ777) Gene Disruptions In these knockout experiments, the gene encoding PRO1571 polypeptides (designated as DNA73730-1679) (UNQ777) was disrupted. The gene specific information for these studies is as follows: the mutated mouse gene corresponds to nucleotide reference: NM_019500 *Mus musculus* claudin 14 (Cldn14); protein reference: Q9ZOS3 ACCESSION:Q9ZOS3 NID: *Mus musculus* (Mouse). Claudin-14; the human gene sequence reference: NM_144492 ACCESSION:NM_144492 NID: gi 21536293 ref NM_144492.1 *Homo sapiens* claudin 14 (CLDN14), transcript variant 1; the human protein sequence corresponds to reference: O95500 ACCESSION:O95500 NID: *Homo sapiens* (Human). Claudin-14.

The mouse gene of interest is Cldn14 (claudin 14), ortholog of human CLDN14. Aliases include DFNB29.

CLDN14 is an integral plasma membrane protein that likely functions as an adhesion molecule and component of tight junctions, structures that form a physical barrier around epithelial or endothelial cells. CLDN14 interacts with complementary proteins on adjacent cells and with itself, forming a lateral copolymer. Tight junctions prevent the movement of water and solutes through paracellular spaces as well as the movement of plasma membrane proteins between the apical and basolateral or abluminal surfaces of epithelial or endothelial cells. Tight junctions also recruit cytoskeletal proteins and signaling molecules and likely participate in signal transduction processes (Gonzalez-Mariscal et al, *Prog Biophys Mol Biol* 81(1): 1-44 (2003); Tsukita et al, *Nat Rev Mol Cell Biol* 2(4):285-93 (2001); Heiskala et al, *Traffic* 2(2): 93-8 (2001)). As a component of tight junctions, CLDN14 likely plays a role in paracellular transport and cellular asymmetry. Expression of CLDN14 is evident in cochlear inner and outer hair cells and supporting cells, in the collecting ducts of the kidney, and around the lobules of the liver (Yosef et al, *Hum Mol Genet* 12(16):2049-61 (2003)). Mutations in CLDN14 cause deafness in humans (Wilcox et al, *Cell* 104 (1):165-72 (2001)).

Ben-Yosef and colleagues (2003) investigated the physiological role of CLDN14 using knockout mice. They showed that the CLDN14 (−/−) mice displayed rapid degeneration of cochlear outer hair cells, slow degeneration of inner hair cells, and decreased paracellular permeability for cations, resulting in deafness. They also showed that CLDN14 is expressed in tight junctions of hair cells and supporting cells. Ben-Yosef and colleagues concluded that CLDN14 is required for restricting paracellular transport of cations, which is important for maintaining the proper ionic composition of the fluid surrounding the basolateral surface of outer hair cells.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
| --- | --- | --- | --- | --- |
| Observed | 16 | 40 | 26 | 82 |
| Expected | 20.5 | 41 | 20.5 | 82 |

Chi-Sq.=0.67 Significance=0.71533805 (hom/n)=0.27 Avg. Litter Size=9

Mutation Information

Mutation Type: Homologous Recombination (standard)

Description: Coding exon 1 was targeted (NCBI accession NM_019500.3).

1. Wild-type Expression Panel: Expression of the target gene was detected in brain, spinal cord, and eye among the 13 adult tissue samples tested by RT-PCR.

2. QC Expression: QC Images: Disruption of the target gene was confirmed by Southern hybridization analysis.

48.24.1. Phenotypic Analysis (for Disrupted Gene: DNA73730-1679 (UNQ777)

(a) Overall Phenotypic Summary:

Mutation of the gene encoding the ortholog of human claudin 14 (CLDN14) resulted in hearing impaired (−/−) mice, exhibiting cochlear hair cell degeneration. Microscopic analysis revealed degeneration and loss of sensory cochlear hair cells in the inner ear of the homozygous mutant mice, confirming the hearing impairment noted during prepulse inhibition testing. In addition, the mutants exhibited an increased mean platelet count and an increased subsets of CD4 and CD8 cells when compared with that of their wild-type littermates and the historical mean. The mutant (−/−) mice also exhibited decreased bone related measurements with decreased vertebral bone volume, number and connectivity density. The mutant (−/−) mice exhibited increased mean serum cholesterol and triglyceride levels. Disruption of the target gene was confirmed by Southern hybridization analysis.

(b) Expression:

Claudin 14 is a tight junction protein implicated in hearing function for its expression in the cochlea. Claudin 14's increased expression is also associated with synovial macrophages in rheumatoid arthritis and therefore plays an important role in the immune system.

(c) Pathology

Microscopic: The (−/−) mice exhibited diffuse marked degeneration sensory cochlear hair cells in the inner ear, characterized by a complete loss of both inner and outer cochlear hair cells on the basilar membrane.

Gene Expression: LacZ activity was not detected in the panel of tissues by immunohistochemical analysis.

(d) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (+/−) mice exhibited an increased mean platelet count when compared with that of their (+/+) littermates and the historical mean.

Thus, mutant mice deficient in the DNA73730-1679 gene resulted in a phenotype related to coagulation disorders. In this regard, inhibitors or antagonists of PRO1571 polypeptides would be useful in treating disorders related to abnormal blood coagulation such as hemophilia.

Fluorescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

The (−/−) mice exhibited an altered distribution of leukocyte subsets in the peripheral blood, characterized by an increased mean percentages of CD62hi, CD44int (subsets of CD4 and CD8) cells in the cell population when compared with their (+/+) littermates and the historical means.

Thus, knocking out the gene which encodes PRO1571 polypeptides causes an increase in the T cell population. From these observations, PRO1571 polypeptides or the gene encoding PRO1571 appears to act as a negative regulator of T cell proliferation. Thus, antagonists or inhibitors of PRO1571 polypeptides would be beneficial in enhancing T cell proliferation.

(e) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro CT: The male (−/−) mice exhibited decreased mean vertebral trabecular bone volume, number, and connectivity density when compared with that of their gender-matched (+/+) littermates and the historical means.

The (−/−) mice analyzed by Micro CT analysis exhibited decreased bone measurements when compared with their (+/+) littermates, suggestive of abnormal bone disorders. The negative bone phenotype indicates that PRO1571 polypeptides or agonists thereof would be useful for maintaining bone homeostasis. In addition, PRO1571 polypeptides would be useful in bone healing or for the treatment of arthritis or osteoporosis, whereas antagonists (or inhibitors) of PRO1571 polypeptides or its encoding gene would lead to abnormal or pathological bone disorders including inflammatory diseases associated with abnormal bone metabolism including arthritis, osteoporosis and osteopenia.

(f) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Prepulse Inhibition of the Acoustic Startle Reflex

Prepulse inhibition of the acoustic startle reflex occurs when a loud 120 decibel (dB) startle-inducing tone is preceded by a softer (prepulse) tone. The PPI paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

PPI: All 8 (−/−) mice failed to exhibit a startle response, suggesting hearing impairment in the mutants. Therefore, prepulse inhibition could not be assessed. These results are consistent with observation that the (−/−) mice exhibited diffuse marked degeneration sensory cochlear hair cells in the inner ear, characterized by a complete loss of both inner and outer cochlear hair cells on the basilar membrane.

(g) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygous and 8 homozygous mice were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:
Blood Chemistry: The male (−/−) mice exhibited increased mean serum cholesterol and triglyceride levels when compared with that of their gender-matched (+/+) littermates and the historical mean.

As summarized above, the (−/−) mice exhibited increased mean serum cholesterol and triglyceride levels when compared with their gender-matched (+/+) littermates and the historical means. Thus, mutant mice deficient in the PRO1571 gene may serve as a model for cardiovascular disease. PRO1571 polypeptides or its encoding gene would be useful in regulating blood lipids such as cholesterol and triglycerides. Thus, PRO1571 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

48.25. Generation and Analysis of Mice Comprising DNA73734-1680 (UNQ778) Gene Disruptions In these knockout experiments, the gene encoding PRO1572 polypeptides (designated as DNA73734-1680) (UNQ778) was disrupted. The gene specific information for these studies is as follows: the mutated mouse gene corresponds to nucleotide reference: NM_019815 ACCESSION: NM_019815 NID: gi 9790074 ref NM_019815.1 *Mus musculus* claudin 18 (Cldn18); protein reference: P56857 ACCESSION:P56857 NID: *Mus musculus* (Mouse). Claudin-18; the human gene sequence reference: NM_016369 *Homo sapiens* claudin 18 (CLDN18), transcript variant 1; the human protein sequence corresponds to reference: P56856 ACCESSION:P56856 NID: *Homo sapiens* (Human). Claudin-18.

The mouse gene of interest is Cldn18 (claudin 18), ortholog of human CLDN18.

CLDN18 is an integral plasma membrane protein expressed primarily in lung and stomach epithelial cells that functions as a component of tight junctions. CLDN18 likely plays a role in paracellular transport and cell polarity (Niimi et al, *Mol Cell Biol* 21(21):7380-90 (2001); Heiskala et al, *Traffic* 2(2):93-8 (2001); Gonzalez-Mariscal et al, *Prog Biophys Mol Biol* 81(1):1-44 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 24 | 37 | 23 | 84 |
| Expected | 21 | 42 | 21 | 84 |

Chi-Sq.=0.33 Significance=0.8478937 (hom/n)=0.24 Avg. Litter Size=9
Mutation Information
Mutation Type: Homologous Recombination (standard)
Description: Coding exons 2 through 4 were targeted (NCBI accession NM_019815.1).

1. Wild-type Expression Panel: Expression of the target gene was detected in spinal cord; lung; kidney; stomach, small intestine, and colon; and asthmatic lung among 26 adult tissue samples tested by RT-PCR.
2. QC Expression: QC Images: Disruption of the target gene was confirmed by Southern hybridization analysis.

48.25.1. Phenotypic Analysis (for Disrupted Gene: DNA73734-1680 (UNQ778)

(a) Overall Phenotypic Summary:

Mutation of the gene encoding the ortholog of human claudin 18 (CLDN18) resulted in decreased bone mineral content and density measurements in (−/−) mice. Both the male and female homozygous mutant mice exhibited notably decreased bone mineral content and density measurements when compared with those of their gender-matched wild-type littermates and the historical means. In addition, the homozygous mutants exhibited numerous immunological abnormalities, including increased white blood cell counts and an increased IL-6 response to LPS challenge. Necropsy revealed thickened gastric mucosa with abnormal differentiation of the gastric gland epithelium and chronic inflammation in the homozygous mutant mice. Disruption of the target gene was confirmed by Southern hybridization analysis.

(b) Expression:

Claudin 18 has a unique expression pattern limited largely to the lung and stomach with relatively low expression in other tissues. Expression is associated with rheumatoid arthritis with increased expression in synovial fibroblasts, macrophages and T cells.

(c) Pathology

Gross: The (−/−) mice exhibited markedly thickened gastric mucosa.

Microscopic: The (−/−) mice exhibited changes in the gastric mucosa, characterized by a marked loss of normal differentiation of gastric gland epithelium with decreased numbers of gastric chief cells and parietal cells and increased numbers of mucoid cells. Abnormal glands with multiple branches were present, and moderate inflammatory infiltrates were also present in the mucosa and lamina propria and extended to the tops of the glandular mucosa. These observations are consistent with specific expression in the stomach. GeneLogic data shows decreased expression of UNQ778 in human gastric adenocarcinoma. In many areas, the gastric glands contained numerous mucoid cells that replaced the parietal and chief cells. There was also a marked reduction in eosinophilic cytoplasmic granules in the striated ducts of the mandibular salivary glands in 2/3 male (−/−) mice. The (−/−) mice also exhibited an increase in stomach weight compared to the (+/+) littermates.

Gene Expression: LacZ activity was not detected in the panel of tissues by immunohistochemical analysis.

(d) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (−/−) mice exhibited increased mean white blood cell, absolute neutrophil, absolute lymphocyte, and platelet counts when compared with those of their (+/+) littermates and the historical means.

These results indicate that mutant (−/−) mice have several immunological abnormalities compared with their wild-type littermates. In summary, the hematology results indicate that the homozygous mutant mice exhibited an increased white blood cell count, neutrophils and lymphocytes count compared to their littermate controls indicating elevated levels of precursors of macrophages with increased phagocytic activity or ability to engulf or kill extracellular pathogens. Thus, PRO1572 polypeptides must be essential for maintaining a normal immunological profile especially for adaptive immunity. In addition, the mutant (−/−) mice exhibited an increased platelet count. Thus, mutant mice deficient in the DNA73734-1680 gene resulted in a phenotype related to coagulation disorders. In this regard, inhibitors or antagonists of PRO1572 polypeptides would be useful in treating disorders related to abnormal blood coagulation such as hemophilia.

Fluorescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

A significant decrease in CD117 cells were observed in the peritoneal lavage in the mutant (−/−) mice compared to the wild-type (+/+) littermates. Thus, hematopoietic progenitors are decreased in these knockout mice. Thus, the gene encoding PRO1572 polypeptides must be essential for hematopoietic progenitor development and/or production.

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 µL sterile saline using a 26 gauge needle. The doses were based on the average weight of the mice tested at 1 µg/g body weight 3 hours after injection; a 100 ul blood sample was then taken and analyzed for the presence of TNFa, MCP-1, and IL-6 on the FACS Calibur instrument.

Results:

Acute Phase Response: The (−/−) mice exhibited an increased IL-6 response to LPS challenge when compared with that of their (+/+) littermates and the historical mean.

In summary, the LPS endotoxin challenge demonstrated that knockout mice deficient in the gene encoding PRO1572 polypeptides exhibit immunological abnormalities when compared with their wild-type littermates. In particular, the mutant mice exhibited an increased ability to elicit an immunological response (IL-6 production) when challenged with the LPS endotoxin indicating a proinflammatory response. IL-6 contributes to the later stages of B cell activation. In addition, IL-6 plays a critical role in inducing the acute phase response and systemic inflammation. This suggests that inhibitors or antagonists to PRO1572 polypeptides would stimulate the immune system and would find utility in the cases wherein this effect would be beneficial to the individual such as in the case of leukemia, and other types of cancer, and in immuno-compromised patients, such as AIDS sufferers. Accordingly, PRO1572 polypeptides or agonists thereof would be useful in inhibiting the immune response and would be useful candidates for suppressing harmful immune responses, e.g. in the case of graft rejection or graft-versus-host diseases.

(e) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited notably decreased mean bone mineral content and density measurements when compared with those of their gender-matched (+/+) littermates and the historical means.

Micro CT: The male (−/−) mice exhibited notably decreased mean femoral mid-shaft cortical thickness, trabecular bone volume and trabecular bone thickness when compared with that of their gender-matched (+/+) littermates and the historical mean.

The (−/−) mice analyzed by DEXA and bone micro CT analysis exhibited decreased bone measurements when compared with their (+/+) littermates, suggestive of abnormal bone disorders. The (−/−) mice exhibited a negative bone phenotype with abnormal and decreased bone measurements reflective of bone metabolic disorders. The negative bone phenotype indicates that PRO1572 polypeptides or agonists thereof would be useful for maintaining bone homeostasis. In addition, PRO1572 polypeptides would be useful in bone healing or for the treatment of arthritis or osteoporosis, whereas antagonists (or inhibitors) of PRO1572 polypeptides or its encoding gene would lead to abnormal or pathological bone disorders including inflammatory diseases associated with abnormal bone metabolism including arthritis, osteoporosis and osteopenia.

48.26. Generation and Analysis of Mice Comprising DNA76531-1701 (UNQ832) Gene Disruptions In these knockout experiments, the gene encoding PRO1759 polypeptides (designated as DNA76531-1701) (UNQ832) was disrupted. The gene specific information for these studies is as follows: the mutated mouse gene corresponds to nucleotide reference: NM_134100 *Mus musculus* DNA Segment, Chr 15, Mouse Genome Informatics 27 (D15Mgi27); protein reference: Q921Y4 ACCESSION: Q921Y4 NID: *Mus musculus* (Mouse). D15Mgi27 protein (*Mus musculus* NOD-derived CD11c ve dendritic cells cDNA, RIKEN full-length enriched library, clone: F630109H06 product:hypothetical General substrate transporters containing protein, full insert sequence); the human gene sequence reference: NM_032889 *Homo sapiens* hypothetical protein MGC11308 (MGC11308); the human protein sequence corresponds to reference: Q961A5 ACCESSION: Q961A5 NID: *Homo sapiens* (Human). UNKNOWN (PROTEIN FOR MGC:111308).

The mouse gene of interest is D15Mgi27 (DNA Segment, Chr 15, Mouse Genome Informatics 27), ortholog of human hypothetical protein MGC11308.

Hypothetical protein MGC11308 is a putative integral plasma membrane protein (Clark et al, *Genome Res* 13(10): 2265-70 (2003)) and "major facilitator superfamily" (MFS) member that likely functions as a transporter (Pao et al, *Microbiol Mol Biol Rev* 62(1):1-34 (1998)). The protein consists primarily of a signal peptide and 10 transmembrane segments within a DUF791 ("protein of unknown function") domain (Pfam accession PF05631).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 18 | 32 | 18 | 68 |
| Expected | 17 | 34 | 17 | 68 |

Chi-Sq.=1.14 Significance=0.5655255 (hom/n)=0.26 Avg. Litter Size=9

Mutation Information

Mutation Type Homologous Recombination (standard)

Description: Coding exon 1 was targeted (NCBI accession NM_134100.2).

1. Wild-type Expression Panel: Expression of the target gene was detected in embryonic stem (ES) cells and in all 26 adult tissue samples tested by RT-PCR, except bone.

2. QC Expression: QC Images: Disruption of the target gene was confirmed by Southern hybridization analysis.

48.26.1. Phenotypic Analysis (for Disrupted Gene: DNA76531-1701 (UNQ832))

(a) Overall Phenotypic Summary:

Mutation of the gene encoding the ortholog of human hypothetical protein MGC11308 resulted in a decreased depressive-like response in (−/−) mice. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Functional Observational Battery (FOB) Test—Tail Suspension Testing:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Tail Suspension Testing:

The tail suspension test is a procedure that has been developed as a model for depressive-like behavior in rodents. In this particular setup, a mouse is suspended by its tail for 6 minutes, and in response the mouse will struggle to escape from this position. After a certain period of time the struggling of the mouse decreases and this is interpreted as a type of learned helplessness paradigm. Animals with invalid data (i.e. climbed their tail during the testing period) are excluded from analysis.

Results:

Tail Suspension2: The (−/−) mice exhibited a decreased median immobility time when compared with that of their (+/+) littermates and the historical mean, suggesting a decreased depressive-like response in the mutants.

In summary, the tail suspension testing revealed a phenotype associated with increased anxiety which could be associated with mild to moderate anxiety, anxiety due to a general medical condition, and/or bipolar disorders; hyperactivity; sensory disorders; obsessive-compulsive disorders; schizophrenia or a paranoid personality. Thus, PRO1759 polypeptides or agonists thereof would be useful in the treatment of such neurological disorders.

48.27. Generation and Analysis of Mice Comprising DNA82372 (UNQ886) Gene Disruptions In these knockout experiments, the gene encoding PRO1904 polypeptides (designated as DNA82372) (UNQ886) was disrupted. The gene specific information for these studies is as follows: the mutated mouse gene corresponds to nucleotide reference: MIS_UNQ886 LGID:15208; protein reference: MIS_UNQ886 ORF (LGID:15208); the human gene sequence reference: NM_004590 *Homo sapiens* chemokine (C-C motif) ligand 16 (CCL16); the human protein sequence corresponds to reference: O15467 ACCESSION:O15467 NID: *Homo sapiens* (Human). Small inducible cytokine A16 precursor (CCL16) (IL-10-inducible chemokine) (Chemokine LEC) (Liver-expressed chemokine) (Monotactin-1) (MTN-1) (Chemokine CC-4) (HCC-4) (NCC-4) (Lymphocyte and monocyte chemoattractant) (LMC) (LCC-1).

The mouse gene of interest is represented by a predicted transcript (Lexicon accession: MIS_UNQ886), which is orthologous with human CCL16 (chemokine [C-C motif] ligand 16). Aliases include LEC, LMC, NCC4, CKb12, HCC-4, LCC-1, Mtn-1, NCC-4, SCYL4, ILINCK, SCYA16, monotactin-1, chemokine LEC, chemokine CC-4, new CC chemokine 4, IL-10-inducible chemokine, liver-expressed chemokine, liver CC chemokine-1 precursor, and lymphocyte and monocyte chemoattractant.

CCL16 is a secreted protein that functions as a low-affinity ligand for cytokine receptors CCR1, CCR2, CCR5, and CCR8 (Howard et al, *Blood* 96(3):840-5 (2000); Nomiyama et al, *Int Immunol* 13(8): 1021-9 (2001)) and as a high-affinity ligand for histamine receptor H4 expressed on eosinophils (Nakayama et al, *J Immunol* 173(3):2078-83 (2004)). CCL16 is expressed constitutively by hepatocytes (Nomiyama et al, *Int Immunol* 13(8):1021-9 (2001); Shoudai et al, *Biochim Biophys Acta* 1396(3):273-7 (1998)), and CCL16 expression is upregulated by interleukin-10 in activated monocytes (Hedrick et al, *Blood* 91(11):4242-7 (1998)). CCL16 is a regulator of immune cell function. CCL16 stimulates chemotaxis of eosinophils, monocytes, T-cells, and dendritic cells, enhances the function of macrophages, and augments the lytic activity of T-cells (Nakayama et al, *J Immunol* 173(3):2078-83 (2004); Guiducci et al, *J Immunol* 172(7):4026-36 (2004); Cappello et al, *J Leukoc Biol* 75(1): 135-42 (2004)). CCL16 may play a role in angiogenesis by triggering angiogenic activities in endothelial cells (Strasly et al, *Blood* 103(1):40-9 (2004)). CCL16 can delay tumor growth and inhibit metastasis, suggesting that the cytokine may be useful for treatment of certain types of cancer (Li et al, *Cancer Res* 63(23):8384-92 (2003); Guiducci et al, *J Immunol* 172(7):4026-36 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
| --- | --- | --- | --- | --- |
| Observed | 27 | 30 | 22 | 79 |
| Expected | 19.75 | 39.5 | 19.75 | 79 |

Chi-Sq.=0.5 Significance=0.7788008 (hom/n)=0.26 Avg. Litter Size=9
Mutation Information
Mutation Type Homologous Recombination (standard)
Description: Coding exons 1 through 3 were targeted.
1. Wild-type Expression Panel: Expression of the target gene was detected in embryonic stem (ES) cells and in brain, spinal cord, and eye among the 13 adult tissue samples tested by RT-PCR.
2. QC Expression: QC Images: Disruption of the target gene was confirmed by Southern hybridization analysis.

48.27.1. Phenotypic Analysis (for Disrupted Gene: DNA82372 (UNQ886)

(a) Overall Phenotypic Summary:

Mutation of the gene encoding the ortholog of human chemokine (C-C motif) ligand 16 (CCL16) resulted in increased mean total tissue mass and total body fat in female (−/−) mice. The mutant (−/−) mice also exhibited increased peritoneal CD117 cells and TCRb/CD38 cells in Peyer's patches. The mice showed an increased IL-6 response to the LPS challenge as well as a decrease in mean serum IgG3 levels. Gene disruption was confirmed by Southern blot.

(b) Expression

HCC-4, also known as CCL-16, is a chemokine produced mainly in the liver. It is known to be a chemokine for monocytes and lymphocytes, but also has a function in the angiogenic program in vascular endothelial cells. HCC-4 is upregulated in ulcerous colitis and is implicated in eosinophil trafficking via binding to the H4 histamine receptor.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:
Fluorescence-Activated Cell-Sorting (FACS) Analysis
Procedure:
FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:
Tissue Specific FACS-Project: The (−/−) mice exhibited a phenotype in peritoneal CD117 cells (increase) and TCRb/CD38 cells in Peyer's patches. Thus, PRO1904 polypeptides or the gene encoding PRO1904 proteins appears to act as a negative regulator of hemopoietic progenitor development and/or production.

Acute Phase Response:
Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACS Calibur instrument.

Results:

Acute Phase Response: The (−/−) mice exhibited an increased IL-6 response to LPS challenge when compared with that of their (+/+) littermates and the historical mean.

In summary, the LPS endotoxin challenge demonstrated that knockout mice deficient in the gene encoding PRO1904 polypeptides exhibit immunological abnormalities when compared with their wild-type littermates. In particular, the mutant mice exhibited an increased ability to elicit an immunological response (IL-6 production) when challenged with the LPS endotoxin indicating a proinflammatory response. IL-6 contributes to the later stages of B cell activation. In addition, IL-6 plays a critical role in inducing the acute phase response and systemic inflammation. This suggests that inhibitors or antagonists to PRO1904 polypeptides would stimulate the immune system and would find utility in the cases wherein this effect would be beneficial to the individual such as in the case of leukemia, and other types of cancer, and in immuno-compromised patients, such as AIDS sufferers. Accordingly, PRO1904 polypeptides or agonists thereof would be useful in inhibiting the immune response and would be useful candidates for suppressing harmful immune responses, e.g. in the case of graft rejection or graft-versus-host diseases.

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (−/−) mice exhibited a decreased mean serum IgG3 level when compared with those of their (+/+) littermates, the (+/+) mice within the project run, and the historical medians for each.

The serum immunoglobulin isotyping assay showed decreased or reduced levels of mean serum IgG3 in the homozygous (−/−) mice compared to their gender-matched littermate (+/+) controls.

The serum immunoglobulin isotyping assay revealed that homozygous adults exhibited decreased serum IgG3 levels. Thus, homozygotes showed an abnormally low serum immunoglobulins compared with the (+/+) littermates. Thus, the gene encoding PRO1904 is essential for making immunoglobulins (or gamma globulins). Likewise, Igg3 immunoglobulins have neutralization effects and to a lesser extent are important for activation of the complement system.

(d) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The female (−/−) mice exhibited notably increased mean total tissue mass, percent total body fat, and total fat mass when compared with that of their gender-matched (+/+) littermates and the historical means. The female (−/−) mice also exhibited decreased mean total body bone mineral content, bone mineral content index BMC/LBM, and vertebrae bone mineral density (BMD). Increase in total tissue mass and total body fat with decreased bone-related measurements is significant since fat and bone cells arise from a common progenitor.

These studies suggest that mutant (−/−) non-human transgenic animals exhibit a negative phenotype that would be associated with obesity. Thus, PRO1904 polypeptides or agonists thereof are essential for normal growth and metabolic processes and especially would be important in the prevention and/or treatment of obesity.

In addition, the decreased bone density and content measurements is suggestive of abnormal bone disorders. The (−/−) mice exhibited a negative bone phenotype with abnormal decreased bone measurements reflective of bone metabolic disorders. The negative bone phenotype indicates that PRO1904 polypeptides or agonists thereof would be useful for maintaining bone homeostasis. In addition, PRO1904 polypeptides would be useful in bone healing or for the treatment of arthritis or osteoporosis, whereas antagonists (or inhibitors) of PRO1904 polypeptides or its encoding gene would lead to abnormal or pathological bone disorders including inflammatory diseases associated with abnormal bone metabolism including arthritis, osteoporosis and osteopenia.

48.28. Generation and Analysis of Mice Comprising DNA225681 (UNQ983) Gene Disruptions In these knockout experiments, the gene encoding PRO35193 polypeptides (designated as DNA225681)

(UNQ983) was disrupted. The gene specific information for these studies is as follows: the mutated mouse gene corresponds to nucleotide reference: NM_019447 ACCESSION: NM_019447 NID:9506778 *Mus musculus* hepatocyte growth factor activator (Hgfac); protein reference: Q9R098ACCESSION:Q9R098NID: *Mus musculus* (Mouse). HEPATOCYTE GROWTH FACTOR ACTIVATOR PRECURSOR (EC 3.4.21.-) (HGF ACTIVATOR) (HGFA); the human gene sequence reference: NM_001528 *Homo sapiens* HGF activator (HGFAC); the human protein sequence corresponds to reference: Q04756 ACCESSION: Q04756 NID: *Homo sapiens* (Human). HEPATOCYTE GROWTH FACTOR ACTIVATOR PRECURSOR (EC 3.4.21.-) (HGF ACTIVATOR) (HGFA).

The mouse gene of interest is Hgfac (hepatocyte growth factor activator), ortholog of human HGFAC. Aliases include HGFA.

HGFAC is a secreted protein expressed primarily in liver that functions as a serine protease, cleaving and activating hepatocyte growth factor. The protein is expressed as an inactive zymogen that can be cleaved and activated by thrombin. HGFAC is expressed not only in liver but also in ureteric bud of the developing kidney and in multiple myeloma cells. HGFAC plays an important role in HGF signaling, which is involved in development of the liver, kidney, placenta, lung, and mammary gland, in repair of intestinal mucosa, and in growth and survival of multiple myeloma cells (Itoh et al, *Biochim Biophys Acta* 1491(1-3):295-302 (2000); Miyazawa et al, *J Biol Chem* 268(14): 10024-8 (1992); Shimomura et al, *J Biol Chem* 268(30):22927-32 (1993); van Adelsberg et al, *J Biol Chem* 276(18):15099-106 (2001); Itoh et al, *Gastroenterology* 127(5):1423-35 (2004); Tjin et al, *Blood* 104(7): 2172-5 (2004).

Itoh and colleagues (2004) investigated the physiological role of HGFAC in knockout mice. They showed that death resulting from gastrointestinal injury by oral administration of dextran sodium sulfate was higher in HGFAC homozygous null mice than in wild-type mice. Moreover, they showed that HGF activation and repair of injured mucosa by regenerating epithelium was impaired in homozygous null mice but not in wild-type mice. Itoh and colleagues concluded that HGFAC is required for repair of injured intestinal mucosa but is not essential for normal development.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 24 | 44 | 20 | 88 |
| Expected | 22 | 44 | 22 | 88 |

Chi-Sq.=0.03 Significance=0.98511195 (hom/n)=0.25 Avg. Litter Size=9

Mutation Information

Mutation Type: Homologous Recombination (standard)

Description: Coding exons 1 through 9 were targeted (NCBI accession NM_019447.1).

1. Wild-type Expression Panel: Expression of the target gene was detected in embryonic stem (ES) cells and in all 13 adult tissue samples tested by RT-PCR, except skeletal muscle and bone.

2. QC Expression: QC Images: Disruption of the target gene was confirmed by Southern hybridization analysis.

48.28.1. Phenotypic Analysis (for Disrupted Gene: DNA225681 (UNQ983)

(a) Overall Phenotypic Summary:

Mutation of the gene encoding the ortholog of human hepatocyte growth factor activator (HGFAC) resulted in the (−/−) mice exhibiting increased mean serum glucose levels. Gene disruption was confirmed by Southern blot.

(b) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:

The female (−/−) mice exhibited an increased mean serum glucose level which could be related to abnormal glucose metabolism and/or diabetes.

Thus, the mutant (−/−) mice exhibited hyperglycemia which could be associated with an altered glucose metabolism or diabetes. PRO35193 polypeptides or agonists thereof would be useful in maintaining normal glucose levels/metabolism and possibly useful in the treatment of diabetes.

48.29. Generation and Analysis of Mice Comprising DNA81761-2583 (UNQ1895) Gene Disruptions In these knockout experiments, the gene encoding PRO4341 polypeptides (designated as DNA81761-2583) (UNQ1895) was disrupted. The gene specific information for these studies is as follows: the mutated mouse gene corresponds to nucleotide reference: NM_019454 ACCESSION: NM_019454NID:9506546 *Mus musculus Mus musculus* delta-like 4 (Drosophila) (Dl14); protein reference: Q9DBU9 ACCESSION:Q9DBU9 NID: *Mus musculus* (Mouse). DELTA-LIKE 4 HOMOLOG (DROSOPHILA); the human gene sequence reference: NM_019074 *Homo sapiens* delta-like 4 (Drosophila) (DLL4); the human protein sequence corresponds to reference: Q9NR61 ACCESSION: Q9NR61 NID: *Homo sapiens* (Human). DELTA-LIKE PROTEIN 4 PRECURSOR (DROSOPHILA DELTA HOMOLOG 4).

The mouse gene of interest is Dll4 (delta-like 4 *[Drosophila]*), ortholog of human DLL4. Aliases include Delta4, delta-like 4 protein, delta 4 precursor, delta ligand 4 precursor, notch ligand DLL4 precursor, notch ligand delta-2 precursor, delta-like 4 homolog (Drosophila), and hdelta2.

DLL4 is a type I plasma membrane protein belonging to the Delta family of Notch ligands. DLL4 contains a signal peptide, a delta serrate ligand (DSL) domain, at least seven epidermal growth factor (EGF)-like repeats, a transmembrane segment, and a cytoplasmic C-terminus. DLL4 is capable of activating receptors NOTCH 1 and NOTCH4 (Shutter et al, *Genes Dev* 14(11):1313-8 (2000)), which play an important role in angiogenesis (Krebs et al, *Genes Dev* 14(11):1343-52 (2000)). DLL4 is expressed primarily in vascular endothelium of arteries in the developing mouse embryo, in adult mice, and in tumor models (Shutter et al, *Genes Dev* 14(11): 1313-8 (2000); Mailhos et al, *Differentiation* 69(2-3):135-44 (2001)). DLL4 plays a role in hematopoietic and vascular development (Dorsch et al, *Blood* 100(6):2046-55 (2002); Lauret et al, *Leukemia* 18(4):788-97 (2004)) and may have therapeutic potential for treatment of certain types of cancer (Tohda et al, *Int J Oncol* 22(5): 1073-9 (2003)).

Several investigators have studied the physiological role of DLL4 using knockout mice. Krebs and coworkers [*Genes Dev* 18(20):2469-73 (2004)] as well as Gale and colleagues [*Proc Natl Acad Sci USA* 101(45):15949-54 (2004)] showed that vascular remodeling was defective in DLL4 heterozygous embryos, resulting in haplo-insufficient lethality. They concluded that vascular remodeling is sensitive to DLL4 gene dosage. Duarte and colleagues [*Genes Dev* 18(20):2474-8 (2004)] successfully generated DLL4 heterozygous mice by crossing germ line transmitting chimeras with ICR female mice. DLL4 heterozygous mice were produced with 27% frequency in the ICR background, whereas no DLL4 heterozygous mice were produced in a 129/Sv-CP background. Defects in arterial vascular development were evident to varying degrees in all DLL4 heterozygous embryos. Surviving male and female DLL4 heterozygous mice were apparently normal and fertile. Embryonic lethality was observed at day 10.5 in DLL4 homozygous null mice, showing severe defects primarily in arterial vascular development. Duarte and colleagues concluded that embryonic vascular development is very sensitive to DLL4 levels as evidenced in part by strain-dependent haplo-insufficiency. They suggested that DLL4 may have therapeutic utility for intervention in adult neovascularization.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 0 | 0 | 0 | 0 |
| Expected | 0 | 0 | 0 | 0 |

Chi-Sq.=0.0 Significance=0.0 (hom/n)=0.0 Avg. Litter Size=0

Mutation Information

Mutation Type: Homologous Recombination (standard)

Description: Coding exons 1 through 8 were targeted (NCBI accession NM_019454.1).

1. Wild-type Expression Panel: Expression of the target gene was detected in all 26 adult tissue samples tested by RT-PCR, except skeletal muscle, asthmatic lung, LPS liver, blood, skin fibroblast, MG 12 DPC, and MG 3 day post-weaning (lactating).

2. QC Expression: QC Images: Disruption of the target gene was confirmed by Southern hybridization analysis.

48.29.1. Phenotypic Analysis (for Disrupted Gene: DNA81761-1583 (UNQ1895))

(a) Overall Phenotypic Summary:

Mutation of the gene encoding the ortholog of human delta-like 4 (Drosophila) (DLL4) resulted in lethality of (+/−) and (−/−) mutants. Genetic data indicate that this mutation resulted in lethality of both the heterozygous and homozygous mutants. There were no structural developmental abnormalities detected in the heterozygous embryos examined at 11.5 and 12.5 days. No homozygous mutant embryos were observed. Disruption of the target gene was confirmed by Southern hybridization analysis.

(b) Pathology

Microscopic: Embryonic lethal. No (−/−) embryos were observed. There were no structural developmental abnormalities detected in the 11.5 day or 12.5 day (+/−) embryos.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

48.30. Generation and Analysis of Mice Comprising DNA92232-2589 (UNQ1902) Gene Disruptions In these knockout experiments, the gene encoding PRO4348 polypeptides (designated as DNA92232-2589) (UNQ1902) was disrupted. The gene specific information for these studies is as follows: the mutated mouse gene corresponds to nucleotide reference: NM_027334 ACCESSION: NM_027334 NID: gi 33563289 ref NM_027334.2 *Mus musculus* RIKEN cDNA 3300001H21 gene (3300001H21Rik); protein reference: Q8C6B0 ACCESSION:Q8C6B0 NID: *Mus musculus* (Mouse). *Mus musculus* 17 days embryo head cDNA, RIKEN full-length enriched library, clone:3300001H21 product:hypothetical S-adenosyl-L-methionine-dependent methyltransferases structure containing protein, full insert sequence (DKFZP586A0522 protein); the human gene sequence reference: NM_014033 *Homo sapiens* DKFZP586A0522 protein (DKFZP586A0522); the human protein sequence corresponds to reference: Q9H8H3 ACCESSION:Q9H8H3NID: *Homo sapiens* (Human). cDNA FLJ13631 FIS, CLONE PLACE1011090, HIGHLY SIMILAR TO HOMO SAPIENS mRNA; cDNA DKFZP586A0522 (FROM CLONE DKFZP586A0522) (UNKNOWN) (PROTEIN FOR MGC: 11081) (DKFZP586A0522 PROTEIN).

The mouse gene of interest is RIKEN cDNA 3300001H21 gene, ortholog of human DKFZP586A0522 protein. Aliases include 2210414H16Rik, UbiE, Aam-B, and AAM-B protein.

DKFZP586A0522 protein is a putative type II integral membrane protein that may function as a methyltransferase enzyme. The protein contains a signal anchor and an S-adenosyl-L-methionine-dependent methyltransferases superfamily domain (SCOP accession d1fp2a2; InterPro accessions IPR000051 and IPR001601). Proteins with this domain catalyze the methylation of specific DNA, RNA, proteins, or small molecule substrates, using S-adenosyl-L-methionine as the methyl donor. DKFZP586A0522 protein may be an extracellular protein (Clark et al, *Genome Res* 13(10):2265-70 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 24 | 40 | 19 | 83 |
| Expected | 20.75 | 41.5 | 20.75 | 83 |

Chi-Sq.=2.3 Significance=0.31663677 (hom/n)=0.23 Avg. Litter Size=9
Mutation Information
Mutation Type Homologous Recombination (standard)
Description: Coding exon 1 was targeted (NCBI accession NM_027334).
1. Wild-type Expression Panel: Expression of the target gene was detected in embryonic stem (ES) cells and in all 26 adult tissue samples tested by RT-PCR.
2. QC Expression: QC Images: Disruption of the target gene was confirmed by Southern hybridization analysis.

48.30.1. Phenotypic Analysis (for Disrupted Gene: DNA92232-2589 (UNQ1902)
(a) Overall Phenotypic Summary:
Mutation of the gene encoding the ortholog of a putative human type II integral membrane protein (DKFZP586A0522) resulted in the mutant (−/−) mice exhibiting decreased bone mineral content and bone mineral density measurements. Gene disruption was confirmed by Southern blot.
(b) Bone Metabolism & Body Diagnostics: Radiology Phenotypic Analysis
In the area of bone metabolism, targets were identified herein for the treatment of arthritis, osteoporosis, osteopenia and osteopetrosis as well as identifying targets that promote bone healing. Tests included:
DEXA for measurement of bone mineral density on femur and vertebra
MicroCT for very high resolution and very high sensitivity measurements of bone mineral density for both trabecular and cortical bone.
Dexa Analysis—Test Description:
Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.
The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].
Bone MicroCT Analysis:
Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.
Results:
DEXA: The female (−/−) mice exhibited decreased mean bone mineral content, total body bone mineral density, and vertebrae bone mineral density measurements when compared with those of their gender-matched (+/+) littermates and the historical means.

The decreased bone density and content measurements is suggestive of abnormal bone disorders. The (−/−) mice exhibited a negative bone phenotype with abnormal decreased bone measurements reflective of bone metabolic disorders. The negative bone phenotype indicates that PRO4348 polypeptides or agonists thereof would be useful for maintaining bone homeostasis. In addition, PRO4348 polypeptides would be useful in bone healing or for the treatment of arthritis or osteoporosis, whereas antagonists (or inhibitors) of PRO4348 polypeptides or its encoding gene would lead to abnormal or pathological bone disorders including inflammatory diseases associated with abnormal bone metabolism including arthritis, osteoporosis and osteopenia.

48.31. Generation and Analysis of Mice Comprising DNA92289-2598 (UNQ1911) Gene Disruptions
In these knockout experiments, the gene encoding PRO4369 polypeptides (designated as DNA92289-2598) (UNQ1911) was disrupted. The gene specific information for these studies is as follows: the mutated mouse gene corresponds to nucleotide reference: NM_023403 ACCESSION: NM_023403 NID: gi 12963664 ref NM_023403.1 *Mus musculus* mesoderm development candidate 2 (Mesdc2); protein reference: Q9ERE7 ACCESSION:Q9ERE7 NID: *Mus musculus* (Mouse). Mesoderm development candidate 2; the human gene sequence reference: BC009210 ACCESSION:BC009210 NID:14327971 *Homo sapiens*, Similar to mesoderm development candidate 2, clone MGC:16185 IMAGE:3637449; the human protein sequence corresponds to reference: Q14696 ACCESSION:Q14696 NID: *Homo sapiens* (Human). Mesoderm development candidate 2.

The mouse gene of interest is Mesdc2 (mesoderm development candidate 2), ortholog of human MESDC2. Aliases include MGC25959, mKIAA0081, 2210015O1Rik, BOCA, MESD, and KIAA0081.

MESDC2 is a protein located on the endoplasmic reticulum that likely functions as a chaperone protein for Wnt signaling coreceptors LRP5 and LRP6 or for other low-density lipoprotein receptor family members. MESDC2 may play a role in processes involving cargo transport or Wnt signaling, such as embryonic polarity and mesoderm induction during development and bone formation (Wines et al, *Genomics* 72(1):88-98 (2001); Hsieh et al, *Cell* 112(3):355-67 (2003); Culi and Mann, *Cell* 112(3):343-54 (2003); Herz and Marschang, *Cell* 112(3):289-92 (2003); Zhang et al, *Mol Cell Biol* 24(11):4677-84 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 21 | 32 | 0 | 53 |
| Expected | 13.25 | 26.5 | 13.25 | 53 |

Chi-Sq.=42.69 Significance=5.370127E-10 (hom/n)=0.0
Avg. Lifter Size=8
Mutation Information
Mutation Type Homologous Recombination (standard)
Description: Coding exon 1 was targeted (NCBI accession NM_023403.2).
1. Wild-type Expression Panel: Expression of the target gene was detected in embryonic stem (ES) cells and in all 13 adult tissue samples tested by RT-PCR.
2. QC Expression: QC Images: Disruption of the target gene was confirmed by Southern hybridization analysis.

48.31.1. Phenotypic Analysis (for Disrupted Gene: DNA92289-2598 (UNQ1911)

(a) Overall Phenotypic Summary:

Mutation of the UNQ1911 gene encoding the ortholog of human mesoderm development candidate 2 (MESDC2) resulted in lethality of (−/−) mutants. Genetic data indicate that this mutation resulted in lethality of the homozygous mutants. The heterozygous mice exhibited increased mean serum IgG1 and IgG2a responses to ovalbumin challenge when compared with those of their wild-type littermates and the historical means. Increased mean serum IgM levels were also observed in the (+/−) mice. Disruption of the target gene was confirmed by Southern hybridization analysis.

(b) Pathology
Microscopic: Due to embryonic lethality, microscopic analysis was not performed. At 12.5 days, there were 47 embryos observed: 27 (+/−) embryos, 4 (+/+) embryos, 14 resorption moles, and 2 inconclusive. UNQ1911 is a protein of unknown function that lies within a chromosomal region critical for the differentiation of mesoderm. UNQ1911 is likely to play a key role in regulating mesoderm differentiation which could explain the resultant embryonic lethality in the homozygous mice. Gene Expression: LacZ activity was not detected in the panel of tissues by immuno-histochemical analysis.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Ovalbumin Challenge

Procedure: This assay was carried out on 7 wild types and 8 heterozygous mice. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immuno-dominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Results of this Challenge:

Ovalbumin: The (+/−) mice exhibited increased mean serum IgG1 and IgG2a responses to ovalbumin challenge when compared with those of their (+/+) littermates and the historical means.

In summary, the ovalbumin challenge studies indicate that knockout heterozygous mice deficient in the gene encoding PRO4348 polypeptides exhibit immunological abnormalities when compared with their wild-type littermates. In particular, the mutant (+/−) mice exhibited an increased ability to elicit an immunological response when challenged with the T-cell dependent OVA antigen. Thus, antagonists (inhibitors) of PRO4348 polypeptides would be useful for stimulating the immune system (such as T cell proliferation) and would find utility in the cases wherein this effect would be beneficial to the individual such as in the case of leukemia, and other types of cancer, and in immuno-compromised patients, such as AIDS sufferers. Accordingly, PRO4348 polypeptides or agonists thereof, would be useful for inhibiting the immune response and thus would be useful candidates for suppressing harmful immune responses, e.g. in the case of graft rejection or graft-versus-host diseases.

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (+/−) mice exhibited an increased mean serum IgM level when compared with that of their (+/+) littermates, the (+/+) mice within the project run, and the historical range.

Mutant (+/−) mice exhibited elevation of IgM serum immunoglobulins compared to their gender-matched (+/+) littermates. IgM immunoglobulins are the first to be produced in a humoral immune response for neutralization of bacterial toxins and are particularly important in activating the complement system. The observed phenotype suggests that the PRO4348 polypeptide is a negative regulator of inflammatory responses. These immunological abnormalities suggest that inhibitors (antagonists) of PRO4348 polypeptides would be useful in stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO4348 polypeptides or agonists thereof would be useful in inhibiting the immune response and would be useful candidates for suppressing harmful immune responses, e.g. in the case of graft rejection or graft-versus-host diseases.

48.32. Generation and Analysis of Mice Comprising DNA92225-2603 (UNQ1916) Gene Disruptions In these knockout experiments, the gene encoding PRO4381 polypeptides (designated as DNA92225-2603) (UNQ1916) was disrupted. The gene specific information for these studies is as follows: the mutated mouse gene corresponds to nucleotide reference: NM_178066 *Mus musculus* RIKEN cDNA 1110012D08 gene (1110012D08Rik); protein reference: Q8CFU0 ACCESSION:Q8CFU0 NID: *Mus musculus* (Mouse). RIKEN cDNA 1110012D08; the human gene sequence reference: AK057179 ACCESSION:AK057179 NID:16552774 *Homo sapiens* cDNA FLJ32617 fis, clone STOMA2000257.

The mouse gene of interest is RIKEN cDNA 1110012D08 gene, which is orthologous with a human gene represented by "*Homo sapiens* cDNA FLJ32617 fis, clone STOMA2000257."

The hypothetical protein is a likely integral membrane protein, consisting of seven transmembrane domains. Bioinformatic analysis suggests that the hypothetical protein is located on the plasma membrane.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
| --- | --- | --- | --- | --- |
| Observed | 20 | 41 | 20 | 81 |
| Expected | 20.25 | 40.5 | 20.25 | 81 |

Chi-Sq.=0.83 Significance=0.6603403 (hom/0=0.27 Avg. Litter Size=9

Mutation Information

Mutation Type: Homologous Recombination (standard)

Description: The noncoding exon preceding coding exon 1 and coding exons 1 and 2 were targeted (NCBI accession NM_178066.2).

1. Wild-type Expression Panel: Expression of the target gene was detected in embryonic stem (ES) cells and in all 13 adult tissue samples tested by RT-PCR, except bone.

2. QC Expression: QC Images: Disruption of the target gene was confirmed by Southern hybridization analysis.

48.32.1. Phenotypic Analysis (for Disrupted Gene: DNA92225-2603 (UNQ1916)

(a) Overall Phenotypic Summary:

Mutation of the gene encoding the ortholog of a human hypothetical membrane protein resulted in impaired sensorimotor gating/attention in (−/−) mice. The male (−/−) mice exhibited increased mean body weight when compared with that of their gender-matched (+/+) littermates and the historical mean. Immunological abnormalities were also observed in the (−/−) mice since the homozygous mice exhibited increased platelet counts and decreased mean percentage of CD8 cells compared to their (+/+) littermate controls. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:
Fluorescence-Activated Cell-Sorting (FACS) Analysis
Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

FACS3: The (−/−) mice exhibited an altered distribution of leukocyte subsets in the peripheral blood, characterized by a decreased mean percentage of CD8 cells when compared with that of their (+/+) littermates and the historical mean.

Thus, knocking out the gene which encodes PRO4381 polypeptides causes a decrease in the T cell population. From these observations, PRO4381 polypeptides or the gene encoding PRO4381 appears to act as a positive regulator of T cell proliferation. Thus, PRO4381 polypeptides would be beneficial in enhancing T cell proliferation.

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (−/−) mice exhibited an increased mean platelet count when compared with their (+/+) littermates and the historical mean.

Thus, mutant mice deficient in the DNA92225-2603 gene resulted in a phenotype related to coagulation disorders. In this regard, inhibitors or antagonists of PRO4381 polypeptides would be useful in treating disorders related to abnormal blood coagulation such as hemophilia.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Prepulse Inhibition of the Acoustic Startle Reflex

Prepulse inhibition of the acoustic startle reflex occurs when a loud 120 decibel (dB) startle-inducing tone is preceded by a softer (prepulse) tone. The PPI paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

PPI: The (−/−) mice exhibited decreased inhibition during pp8, pp12, and pp20 when compared with that of their (+/+) littermates and the historical means, suggesting impaired sensorimotor gating/attention in the mutants.

48.33. Generation and Analysis of Mice Comprising DNA92264-2616 (UNQ1932) Gene Disruptions In these knockout experiments, the gene encoding PRO4407 polypeptides (designated as DNA92264-2616) (UNQ1932) was disrupted. The gene specific information for these studies is as follows: the mutated mouse gene corresponds to nucleotide reference: NM_175408 ACCESSION: NM_175408 NID: gi 31341822 ref NM_175408.2 *Mus musculus* RIKEN cDNA A930027H06 gene (A930027H06Rik); protein reference: Q8C6T0 ACCESSION:Q8C6T0 NID: *Mus musculus* (Mouse). Hypothetical protein; the human gene sequence reference: NM_153345 ACCESSION:NM_153345 NID:gi 23503270 refNM_153345.1 *Homo sapiens* hypothetical protein FLJ90586 (FLJ90586); the human protein sequence corresponds to reference: Q8IV31 ACCESSION: Q8IV31 NID: *Homo sapiens* (Human). Hypothetical protein.

The mouse gene of interest is RIKEN cDNA A930027H06 gene, ortholog of human hypothetical protein FLJ90586.

Hypothetical protein FLJ90586 contains a weakly predicted signal peptide and an overlapping transmembrane segment. The hypothetical protein may be secreted or may be located on the plasma membrane (Clark et al, *Genome Res* 13(10):2265-70 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
| --- | --- | --- | --- | --- |
| Observed | 26 | 40 | 13 | 79 |
| Expected | 19.75 | 39.5 | 19.75 | 79 |

Chi-Sq.=4.21 Significance=0.12184567 (hom/n)=0.21 Avg. Litter Size=9

Mutation Information

Mutation Type: Homologous Recombination (standard)

Description: Coding exons 1 and 2 were targeted (NCBI accessions BY032793 and NM_175408.2).

1. Wild-type Expression Panel: Expression of the target gene was detected in all 13 adult tissue samples tested by RT-PCR, except spinal cord, skeletal muscle, and adipose.

2. QC Expression: QC Images: Disruption of the target gene was confirmed by Southern hybridization analysis.

48.33.1. Phenotypic Analysis (for Disrupted Gene: DNA92264-2616 (UNQ1932)

(a) Overall Phenotypic Summary:

Mutation of the gene encoding the ortholog of human hypothetical protein FLJ90586 resulted in both heterozygous (+/−) and homozygous (−/−) mice exhibiting increased mean serum glucose levels. Immunological abnormalities were also observed in the mutant mice with decreased percentages of a subset of B cells in the peritoneal lavage. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:
Fluorescence-Activated Cell-Sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:
Tissue Specific FACS-Project: The (−/−) mice exhibited a decreased percentage of B220 Med CD23− cells in peritoneal lavage when compared with that of their (+/+) littermates.

These results indicate that the knockout mice exhibited a decrease in a subset of B cells. Thus, the mutant homozygous mice exhibited immunological abnormalities associated with decreased levels of B cell progenitor cells.

These results show that knockout (−/−) mice exhibit immunological abnormalities compared to their wild-type (+/+) littermates. Antagonists (inhibitors) of PRO4407 polypeptides would be expected to mimic this phenotype. PRO4407 polypeptides or agonists thereof appear to act as a positive regulator of B cell development and would be useful in the development or maturation of B cells which could then participate in fast immune responses.

(c) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:

Blood Chemistry: The female heterozygous (+/−) and homozygous (−/−) mice exhibited an increased mean serum glucose level (~2 SD above littermate wild-type mice) when compared with that of their gender-matched (+/+) littermates and the historical mean. Thus, both the heterozygous and homozygous (−/−) mice showed a negative phenotype related to abnormal glucose metabolism. However, female serum insulin and urine glucose levels were normal.

48.34. Generation and Analysis of Mice Comprising DNA93011-2637 (UNQ1942) Gene Disruptions In these knockout experiments, the gene encoding PRO4425 polypeptides (designated as DNA93011-2637) (UNQ1942) was disrupted. The gene specific information for these studies is as follows: the mutated mouse gene corresponds to nucleotide reference: XM_132070 ACCESSION: XM_132070 NID: gi 51710957 ref XM_132070.3 PREDICTED: *Mus musculus* RIKEN cDNA 4930443F05 gene (4930443F05Rik); protein reference:XP_132070 similar to Cytokine-like protein C17 precursor (UNQ1942/PRO4425) [*Mus musculus*]; the human gene sequence reference: NM_018659 *Homo sapiens* cytokine-like protein C17 (C17); the human protein sequence corresponds to reference: Q9NRR1 ACCESSION:Q9NRR1 NID: *Homo sapiens* (Human). Cytokine-like protein C17 precursor (UNQ1942/PRO4425)

The mouse gene of interest is RIKEN cDNA 4930443F05 gene, ortholog of human C17 (cytokine-like protein C17). Aliases include Gm147.

C17 is a protein secreted by CD34 mononuclear stem cells that likely functions as a signal-transducing ligand. The protein contains a signal peptide and generally shares structural similarities with other cytokines. Expression of C17 is upregulated by cytokines that maintain stem cells and is downregulated by hematopoietic colony-stimulating factors that stimulate differentiation of stem cells (Liu et al, *Genomics* 65(3):283-92 (2000)). C17 may play a role in hematopoiesis or immunity.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|          | wt | het | hom | Total |
|----------|----|----|----|------|
| Observed | 19 | 47 | 22 | 88 |
| Expected | 22 | 44 | 22 | 88 |

Chi-Sq.=3.43 Significance=0.17996371 (hom/n)=0.23 Avg. Litter Size=9
Mutation Information
Mutation Type: Homologous Recombination (standard)
Description: Coding exons 2 through 4 were targeted (NCBI accession BC063103.1).
1. Wild-type Expression Panel: Expression of the target gene was detected in embryonic stem (ES) cells and in all 13 adult tissue samples tested by RT-PCR, except skeletal muscle.
2. QC Expression: QC Images: Disruption of the target gene was confirmed by Southern hybridization analysis.

48.34.1. Phenotypic Analysis (for Disrupted Gene: DNA93011-2637 (UNQ1942)

(a) Overall Phenotypic Summary:

Mutation of the gene encoding the ortholog of human cytokine-like protein C17 (C17) resulted in an increased percentage of CD4 cells in the peripheral blood, increased TCR-beta+ in the thymus, increased CD11b+CD11c+ and increased natural killer cells in the lymph nodes, and increased percentage of CD117+ cells in the peritoneal lavage in the (−/−) mice. Decreased IgG2a and increased IgA mean serum levels were also shown in the (−/−) mice. The (−/−) mice also exhibited an increased retinal artery-to-vein ratio. The mutant (−/−) mice also exhibited increased trabecular number and connectivity density. Gene disruption was confirmed by Southern blot.

(b) Expression

C17 is expressed in arterial endothelium as shown by ISH studies. The Chr4 neighborhood is rich in genes implicated in bone development. [See EXAMPLE 57 for protocol]

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:
Fluorescence-Activated Cell-Sorting (FACS) Analysis
Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:
FACS3: The (−/−) mice exhibited an altered distribution of leukocyte subsets in the peripheral blood, characterized by an increased mean percentage of CD4 cells when compared with that of their (+/+) littermates and the historical mean.
Tissue Specific FACS-Project: The (−/−) mice exhibited an increased percentage of TcRbeta+ cells in thymus, increased percentages of CD11b+CD11c+ and NK cells in lymph node, and an increased percentage of CD117+ cells in peritoneal lavage when compared with those of their (+/+) littermates.

Thus, knocking out the gene which encodes PRO4425 polypeptides causes an increase in the T cell population. From these observations, PRO4425 polypeptides or the gene encoding PRO4425 appears to act as a negative regulator of T cell proliferation. Thus, PRO4425 polypeptides or agonists thereof would be beneficial as a negative regulator of T cell proliferation in those instances wherein a pronounced T-cell proliferation is present such as occurs in autoimmune diseases (for example rheumatoid arthritis patients). In addition, PRO4425 polypeptides would be especially useful in preventing skin graft rejections.

In addition, the FACS results indicate that the homozygous mutant mice have a increased mean percentage of natural killer cells. Natural killer cells are the first line of defense to viral infection since these cells have been implicated in viral immunity and in defense against tumors. Natural killer cells or NK cells act as effectors in antibody-dependent cell-mediated cytotoxicity and have been identified by their ability to kill certain lymphoid tumor cell lines in vitro without the need for prior immunization or activation. Thus, PRO4425 polypeptides act as a negative regulator for NK production.

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value <6 is not significant.

Results:

Serum Imm. 2: The (−/−) mice exhibited a decreased mean serum IgG2a level and a slightly increased mean serum IgA level when compared with that of their (+/+) littermates, the (+/+) mice within the project run, and the historical medians.

The serum immunoglobulin isotyping assay revealed that homozygous adults exhibited decreased serum IgG2a levels. Thus, homozygotes showed an abnormally low serum immunoglobulins compared with the (+/+) littermates. Thus, the gene encoding PRO4425 is essential for making immunoglobulins (or gamma globulins). Likewise, IgG2a immunoglobulins have neutralization effects and to a lesser extent are important for activation of the complement system.

(d) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to opthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygous and 8 homozygous mice were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct opthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Opthalmology analysis was performed on generated F2 wild type, heterozygous, and homozygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wild-type (+/+) littermates would be indicative of such pathological conditions.

Results:

Fundus: The (−/−) mice exhibited an increased mean retinal artery-to-vein ratio when compared with that of their (+/+) littermates and the historical mean.

In this study, the (−/−) exhibited an increased mean artery-to-vein (A/V) ratio when compared with their (+/+) littermates indicating retinal degeneration. In summary, by knocking out the gene identified as DNA93011-2637 encoding PRO4425 polypeptides, homozygous mutant progeny exhibit phenotypes which are associated with retinal degeneration. Such detected retinal changes are most commonly associated with cardiovascular systemic diseases or disorders that may be related to the vascular disease of hypertension (and any disease that causes hypertension, e.g. atherosclerosis), diabetes or other ocular diseases corresponding to opthalmological disorders such as retinal degeneration. Thus, antagonists (inhibitors) of PRO4425 encoding genes would lead to similar pathological retinal changes, whereas agonists may be useful as therapeutic agents in the treatment of hypertension, atherosclerosis or other opthalmological disorders including retinal degeneration and diseases associated with this condition (as indicated above).

(e) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro CT: Male (−/−) mice exhibited increased trabecular number and connectivity density.

In summary, the (−/−) mice exhibited increased trabecular bone mineral density when compared with their gender-matched (+/+) littermates. These results indicate that the knockout mutant phenotype may be associated with such bone abnormalities as osteopetrosis. Osteopetrosis is a condition characterized by abnormal thickening and hardening of bone and abnormal fragility of the bones. As such, PRO4425 polypeptides or agonists thereof would be beneficial for the treatment of osteopetrosis or other osteo-related diseases. On the other hand, inhibitors or antagonists of PRO4425 polypeptides would be useful in bone healing.

48.35. Generation and Analysis of Mice Comprising DNA59770-2652 (UNQ2426) Gene Disruptions In these knockout experiments, the gene encoding PRO4985 polypeptides (designated as DNA59770-2652) (UNQ2426) was disrupted. The gene specific information for these studies is as follows: the mutated mouse gene corresponds to nucleotide reference: XM_203978 PREDICTED: *Mus musculus* RIKEN cDNA 5330417C22 gene (5330417C22Rik); protein reference: XP_203978 RIKEN cDNA 5330417C22 gene [*Mus musculus*]; the human gene sequence reference: NM_020775 *Homo sapiens* maba1 (KIAA1324); the human protein sequence corresponds to reference: NP_065826 maba1 [*Homo sapiens*].

The mouse gene of interest is RIKEN cDNA 5330417C22 gene, ortholog of human maba1. Aliases include KIAA1324 and RP11-352P4.1.

Maba1 is a putative integral plasma membrane protein, consisting of a signal peptide, a large extracellular region containing a keratin/high sulfur B2 protein (B2) domain, a transmembrane segment, and a short cytoplasmic C-terminus. Proteins with B2 domains include the keratin/high sulfur B2 family of proteins, which function as components of hair fibers synthesized by differentiating hair cells (Mitsui et al, *Gene* 208(2): 123-9 (1998); Rogers et al, *J Biol Chem* 276 (22):19440-51 (2001); Shibuya et al, *Genomics* 83(4):679-93 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 18 | 43 | 30 | 91 |
| Expected | 22.75 | 45.5 | 22.75 | 91 |

Chi-Sq.=0.52 Significance=0.7710516 (hom/n)=0.26 Avg. Litter Size=9

Mutation Information

Mutation Type: Homologous Recombination (standard)

Description: Coding exon 1 was targeted (NCBI accession XM_203978.4).

1. Wild-type Expression Panel: Expression of the target gene was detected in all 26 adult tissue samples tested by RT-PCR, except skeletal muscle, bone, heart, adipose, blood, banded heart, aortic tree, MG 5 week virgin, MG mature virgin, MG 3 day post-partum (lactating), MG 3 day post-weaning (early involution), and MG 7 day post-weaning (late involution).

2. QC Expression: QC Images: Disruption of the target gene was confirmed by Southern hybridization analysis.

48.35.1. Phenotypic Analysis (for Disrupted Gene: DNA59770-2652 (UNQ2426)

(a) Overall Phenotypic Summary:

Mutation of the gene encoding the ortholog of human maba1 resulted in defective spermatogenesis in male (−/−) mice. Microscopic analysis revealed defective spermatogenesis in the testis and hypospermia and defective spermatozoa in the epididymus of the homozygous mutant mice, consistent with the infertility noted in the male homozygous mutant clinically. The (−/−) mice also exhibited decreased body fat. Disruption of the target gene was confirmed by Southern hybridization analysis.

(b) Pathology

Microscopic: The male (−/−) mice exhibited moderate diffuse defective spermatogenesis in the testes and hypospermia and defective spermatozoa in the epididymus. The male (−/−) mice exhibited a late-stage defect in spermatogenesis resulting in failure to develop beyond the round spermatid stage. The spermatocytes exhibited large rounded heads and large cytoplasmic droplets.

Gene Expression: LacZ activity was not detected in the panel of tissues by immunohistochemical analysis.

(c) Body Diagnostics

Fertility: The male (−/−) mouse produced no pups after 60 days of breeding and 4 matings with female (+/+) mice. The mouse appeared healthy, and a penile erection could be induced by abdominal pressure.

Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The male (−/−) mice exhibited decreased mean percent total body fat and total fat mass when compared with the levels for their gender-matched (+/+) littermates and the historical mean.

Mutant (−/−) mice deficient in the gene encoding PRO4985 polypeptides show a phenotype consistent with tissue wasting diseases (decreased total body fat (%) and fat mass (g)) or abnormal lipid metabolism. Thus, antagonists or inhibitors of PRO4985 polypeptides or its encoding gene would mimic these metabolic and developmental related effects. On the other hand, PRO4985 polypeptides or agonists thereof would be useful in the prevention and/or treatment of such metabolic disorders and for normal male reproductive development.

48.36. Generation and Analysis of Mice Comprising DNA80135-2655 (UNQ2429) Gene Disruptions In these knockout experiments, the gene encoding PRO4989 polypeptides (designated as DNA80135-2655) (UNQ2429) was disrupted. The gene specific information for these studies is as follows: the mutated mouse gene corresponds to nucleotide reference: NM_153542 ACCESSION: NM_153542 NID: gi 23956307 ref NM_153542.1 *Mus musculus* hypothetical protein MGC25719 (MGC25719); protein reference: Q8CI70 ACCESSION:Q8CI70 NID: *Mus musculus* (Mouse). Leucine rich repeat containing 20; the human gene sequence reference: NM_018205 ACCESSION:NM_018205 NID: gi 8922643 ref NM_018205.1 *Homo sapiens* hypothetical protein FLJ10751 (FLJ10751); the human protein sequence corresponds to reference: Q8TCA0 ACCESSION:Q8TCA0 NID: *Homo sapiens* (Human). Hypothetical protein FLJ37415.

The mouse gene of interest is Lrrc20 (leucine rich repeat containing 20), ortholog of human LRRC20. Aliases include MGC25719, cDNA sequence BC036304, FLJ10751, and FLJ10844.

LRRC20 is a putative extracellular protein of 184 amino acids, containing leucine-rich repeats (Clark et al, *Genome Res* 13(10):2265-70 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 21 | 40 | 23 | 84 |
| Expected | 21 | 42 | 21 | 84 |

Chi-Sq.=1.86 Significance=0.39455372 (hom/n)=0.26 Avg. Litter Size=10

Mutation Information

Mutation Type Homologous Recombination (standard)

Description: Coding exon 1 was targeted (NCBI accession NM_153542.1).

1. Wild-type Expression Panel: Expression of the target gene was detected in all 13 adult tissue samples tested by RT-PCR, except bone and adipose.

2. QC Expression: QC Images: Disruption of the target gene was confirmed by Southern hybridization analysis.

48.36.1. Phenotypic Analysis (for Disrupted Gene: DNA80135-2655 (UNQ2429)

(a) Overall Phenotypic Summary:

Mutation of the gene encoding the ortholog of human leucine rich repeat containing 20 (LRRC20) resulted in the (−/−) mice exhibited decreased anxiety during open filed testing. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

The (−/−) mice exhibited an increased median sum time and distance in-center during open field testing when compared with their gender-matched (+/+) littermates and the historical mean, suggesting a decreased anxiety-like response in the mutants.

The (−/−) mice exhibited an increased median sum time in the center area when compared with their gender-matched (+/+) littermates, which is indicative of a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO4989 polypeptides and agonists thereof would be useful for the treatment or amelioration of the symptoms associated with depressive disorders.

48.37. Generation and Analysis of Mice Comprising DNA92929-2534-1 (UNQ2456) Gene Disruptions In these knockout experiments, the gene encoding PRO5737 polypeptides (designated as DNA92929-2534-1) (UNQ2456) was disrupted. The gene specific information for these studies is as follows: the mutated mouse gene corresponds to nucleotide reference: NM_153511 ACCESSION: NM_153511 NID: gi 23943829 ref NM_153511.1 *Mus musculus* interleukin 1 family, member 9 (Il1F9); protein reference: Q8R460 ACCESSION:Q8R460NID: *Mus musculus* (Mouse). Interleukin 1 family member 9 (IL-1F9); the human gene sequence reference: NM_019618 *Homo sapiens* interleukin 1 family, member 9 (IL1F9); the human protein sequence corresponds to reference: Q9NZH8 ACCESSION: Q9NZH8 NID: *Homo sapiens* (Human). Interleukin 1 family member 9 (IL-1F9) (Interleukin-1 homolog 1) (IL-1H1) (Interleukin-1 epsilon) (IL-1 epsilon) (IL-1 related protein 2) (IL-1RP2).

The mouse gene of interest is Il1f9 (interleukin 1 family, member 9), ortholog of human IL1F9. Aliases include IL-1F9, IL1E, IL1H1, IL-1H1, IL1RP2, IL-1RP2, IL-1-epsilon, IL-1 (EPSILON), interleukin-1 epsilon, IL-1 related protein 2, interleukin-1 homolog 1, and interleukin 1-related protein 2.

IL1F9 is a secreted protein that functions as a ligand for receptor IL1RL2, activating nuclear factor kappaB. IL1F9 is expressed in epithelia from a variety of tissues, such as skin, lung, stomach and esophagus, and is induced by tumor necrosis factor-alpha and by interferon-gamma in keratinocytes. IL1F9 likely plays a role in immune function and inflammation (Debets et al, *J Immunol* 167(3):1440-6 (2001); Kumar et al, *J Biol Chem* 275(14):10308-14 (2000); Towne et al, *J Biol Chem* 279(14):13677-88 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 17 | 39 | 21 | 77 |
| Expected | 19.25 | 38.5 | 19.25 | 77 |

Chi-Sq.=1.41 Significance=0.4941086 (hom/n)=0.28 Avg. Litter Size=9

Mutation Information

Mutation Type: Homologous Recombination (standard)

Description: Coding exons 1 through 3 were targeted (NCBI accession NM_153511.1).

1. Wild-type Expression Panel: Expression of the target gene was detected in all 13 adult tissue samples tested by RT-PCR, except skeletal muscle and adipose.

2. QC Expression: QC Images: Disruption of the target gene was confirmed by Southern hybridization analysis.

48.37.1. Phenotypic Analysis (for Disrupted Gene: DNA92929-2534-1 (UNQ2456)

(a) Overall Phenotypic Summary:

Mutation of the gene encoding the ortholog of human interleukin 1 family, member 9 (IL1F9) resulted in the mutant (−/−) mice exhibiting decreased lean body mass. Gene disruption was confirmed by Southern blot.

(b) Expression

UNQ2456 is upregulated in squamous cell carcinoma or dysplasia (in head and neck); squamous cell carcinoma (in lung); and hyperplasia of adenoid tonsils. UNQ2456 is also upregulated in psoriasis. [See EXAMPLES 54 and 55 for protocol]

(c) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased mean lean body mass when compared with that of their gender-matched (+/+) littermates and the historical mean.

Mutant (−/−) mice deficient in the gene encoding PRO5737 polypeptides show a phenotype consistent with tissue wasting diseases (decreased lean body mass). Thus, antagonists or inhibitors of PRO5737 polypeptides or its encoding gene would mimic these metabolic related effects. On the other hand, PRO5737 polypeptides or agonists thereof would be useful in the prevention and/or treatment of such metabolic disorders as cachexia or other tissue wasting diseases.

48.38. Generation and Analysis of Mice Comprising DNA108912-2680 (UNQ2500) Gene Disruptions In these knockout experiments, the gene encoding PRO5800 polypeptides (designated as DNA108912-2680) (UNQ2500) was disrupted. The gene specific information for these studies is as follows: the mutated mouse gene corresponds to nucleotide reference: NM_023304 ACCESSION: NM_023304 NID: gi 12963626 ref NM_023304.1 *Mus musculus* fibroblast growth factor 22 (Fgf22); protein reference: Q9ESS2 ACCESSION:Q9ESS2 NID: *Mus musculus* (Mouse). FIBROBLAST GROWTH FACTOR-22 PRECURSOR (FGF-22); the human gene sequence reference: NM_020637 ACCESSION:NM_020637 NID: gi 10190671 ref NM_020637.1 *Homo sapiens* fibroblast growth factor 22 (FGF22); the human protein sequence corresponds to reference: Q9HCT0 ACCESSION:Q9HCT0 NID: *Homo sapiens* (Human). FIBROBLAST GROWTH FACTOR-22 PRECURSOR (FGF-22).

The mouse gene of interest is Fgf22 (fibroblast growth factor 22), ortholog of human FGF22. Aliases include FGF-22 and 2210414E06Rik.

FGF22 is a secreted protein that functions as a signal-transducing ligand. The protein consists of a signal peptide and a fibroblast growth factor (FGF) domain and is capable of binding with FGF receptor 2 (Umemori et al, *Cell* 118(2): 257-70 (2004); Boilly et al., *Cytokine Growth Factor Rev* 11(4):295-302 (2000); Eriksson et al., *Proc Natl Acad Sci USA* 88(8):3441-5 (1991); Murzin et al., *J Mol Biol* 223(2): 531-43 (1992)). FGF22 is expressed in skin epithelium and the inner root sheath of the hair follicle, where it likely plays a role in hair development and cutaneous development and repair (Nakatake et al, *Biochim Biophys Acta* 1517(3):460-3 (2001); Beyer et al, *Exp Cell Res* 287(2):228-36 (2003)); Wilkie et al, *Curr Biol* 5(5):500-7 (1995)). FGF22 is also expressed in tongue and in brain, where it plays a role in presynaptic organization (Umemori et al, *Cell* 118(2):257-70 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 19 | 34 | 16 | 69 |
| Expected | 17.25 | 34.5 | 17.25 | 69 |

Chi-Sq.=2.31 Significance=0.31505755 (hom/n)=0.25 Avg. Litter Size=10

Mutation Information

Mutation Type Homologous Recombination (standard)

Description: Coding exons 1 through 3 were targeted (NCBI accession NM_023304.1).

1. Wild-type Expression Panel: Expression of the target gene was detected in brain, spinal cord, eye, and thymus among 13 adult tissue samples tested by RT-PCR.

2. QC Expression: QC Images: Disruption of the target gene was confirmed by Southern hybridization analysis.

48.38.1. Phenotypic Analysis (for Disrupted Gene: DNA108912-2680 (UNQ2500)

(a) Overall Phenotypic Summary:

Mutation of the gene encoding the ortholog of human fibroblast growth factor 22 (FGF22) resulted in a decreased percentage of natural killer (NK) cells in the peripheral blood of (−/−) mice. Disruption of the target gene was confirmed by Southern hybridization analysis.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Fluorescence-Activated Cell-Sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

FACS3: The (−/−) mice exhibited an altered distribution of leukocyte subsets in the peripheral blood, characterized by a decreased mean percentage of natural killer cells when compared with that of their (+/+) littermates and the historical mean.

In summary, the FACS results indicate that the homozygous mutant mice have an impaired immune system, especially in view of the decreased mean percentage of natural killer cells which is an indicator of a negative phenotype associated with knocking out the DNA108912-2680 gene which encodes PRO5800 polypeptides. Natural killer cells are the first line of defense to viral infection since these cells have been implicated in viral immunity and in defense against tumors. Natural killer cells or NK cells act as effectors in antibody-dependent cell-mediated cytotoxicity and have been identified by their ability to kill certain lymphoid tumor cell lines in vitro without the need for prior immunization or activation. However, their known function in host defense is in the early phases of infection with several intracellular pathogens, particularly herpes viruses. Thus, PRO5800 polypeptides and agonists thereof would be important for a healthy immune system and would be useful in stimulating the immune system particularly during viral infections.

48.39. Generation and Analysis of Mice Comprising DNA100276-2684 (UNQ2504) Gene Disruptions In these knockout experiments, the gene encoding PRO5993 polypeptides (designated as DNA100276-2684) (UNQ2504) was disrupted. The gene specific information for these studies is as follows: the mutated mouse gene corresponds to nucleotide reference:AF358257 ACCESSION: AF358257 NID:17529688 *Mus musculus* C21orf63 protein (C21orf63); protein reference: P58659 ACCESSION: P58659 NID: *Mus musculus* (Mouse). PROTEIN C21ORF63 HOMOLOG PRECURSOR; the human gene sequence reference: NM_058187 *Homo sapiens* chromosome 21 open reading frame 63 (C21orf63); the human protein sequence corresponds to reference: P58658 ACCESSION:P58658 NID: *Homo sapiens* (Human). PROTEIN C21ORF63 PRECURSOR (PROTEIN PRED34) (SUE21).

The mouse gene of interest is RIKEN cDNA 4931408A02 gene, ortholog of human C21orf63 (chromosome 21 open reading frame 63). Aliases include 1700092M14Rik, B18, SUE21, and PRED34.

C21orf63 is a putative plasma membrane protein (Clark et al, *Genome Res* 13(10):2265-70 (2003)) that may function as a cell adhesion molecule or signal-transducing receptor. The protein contains two extracellular galactose-binding lectin domains (PFAM accession PF02140), a transmembrane segment, and a 100-amino acid cytoplasmic segment.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 17 | 45 | 24 | 86 |
| Expected | 21.5 | 43 | 21.5 | 86 |

Chi-Sq.=1.16 Significance=0.5598984 (hom/n)=0.27 Avg. Litter Size=9
Mutation Information
Mutation Type Homologous Recombination (standard)
Description: Coding exon 1 was targeted (NCBI accession AF358257).
1. Wild-type Expression Panel: Expression of the target gene was detected in embryonic stem (ES) cells and in all 13 adult tissue samples tested by RT-PCR, except skeletal muscle and bone.
2. QC Expression: QC Images: Disruption of the target gene was confirmed by Southern hybridization analysis.

48.39.1. Phenotypic Analysis (for Disrupted Gene: DNA100276-2684 (UNQ2504)

(a) Overall Phenotypic Summary:

UNQ2504, DNA100276 Mutation of the gene encoding the ortholog of human chromosome 21 open reading frame 63 (C21orf63) resulted in resistance to the pupil dilating drug cyclopentolate hydrochloride in (−/−) mice. The homozygous mutant mice exhibited resistance to the dilating drug used during fundus examination when compared with that of their wild-type littermates and the historical mean. In addition, the mutant (−/−) mice showed decreased lean body mass and decreased latency to respond in hot plate testing. Disruption of the target gene was confirmed by Southern hybridization analysis.

(b) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The (−/−) mice exhibited decreased mean lean body mass when compared with those of their gender-matched (+/+) littermates and the historical means.

Mutant (−/−) mice deficient in the gene encoding PRO5993 polypeptides show a phenotype consistent with tissue wasting diseases (decreased lean body mass). Thus, antagonists or inhibitors of PRO5993 polypeptides or its encoding gene would mimic these metabolic related effects. On the other hand, PRO5993 polypeptides or agonists thereof would be useful in the prevention and/or treatment of such metabolic disorders as cachexia or other tissue wasting diseases.

(c) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to opthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygous and 8 homozygous were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct opthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Opthalmology analysis was performed on generated F2 wild type, heterozygous, and homozygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wild-type (+/+) littermates would be indicative of such pathological conditions.

Results:
Fundus: The (−/−) mice exhibited resistance to the pupil dilating drug cyclopentolate hydrochloride. Only 4 males were examined; of these, only two images are interpretable; the pupils did not dilate normally in these animals. Two images show only cloudiness. One of the animals had cloudiness on fundus exam and was also reported to have "white spots" on the eyes. Functional observation battery testing resulted in one wild-type (+/+) mouse and two homozygous (−/−) mice having noted eye changes including small squinty eyes; one (−/−) mouse showed white spots on squinty eyes. The (−/−) mice exhibited body tremors and reduced exploratory behavior. Thus, the mutant (−/−) mice examined showed some retinal abnormalities which could be related to corneal changes and/or cataract formation.

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:
Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Hot Plate Testing

Test Description: The hot plate test for nociception is carried out by placing each mouse on a small enclosed 55° C. hot plate. Latency to a hindlimb response (lick, shake, or jump) is recorded, with a maximum time on the hot plate of 30 sec. Each animal is tested once.

Results:
Hot Plate: The (−/−) mice exhibited a decreased latency to respond, suggesting an increased sensitivity to acute pain in the mutants.

48.40. Generation and Analysis of Mice Comprising DNA96860-2700 (UNQ2524) Gene Disruptions In these knockout experiments, the gene encoding PRO6017 polypeptides (designated as DNA96860-2700) (UNQ2524) was disrupted. The gene specific information for these studies is as follows: the mutated mouse gene corresponds to nucleotide reference: XM_356118 PREDICTED: *Mus musculus* gene model 1109, (NCBI) (Gm1109); protein reference: XP_356118 PREDICTED: similar to G-protein coupled receptor 114 *[Mus musculus]*; the human gene sequence reference: NM_153837 ACCESSION:NM_153837 NID: gi 24475870 ref NM_153837.1 *Homo sapiens* G protein-coupled receptor 114 (GPR114); the human protein sequence corresponds to reference: NP_722579 G-protein coupled receptor 114 *[Homo sapiens]* gi|22749621|gb|AAH32401.1| G-protein coupled receptor 114 *[Homo sapiens]*.

The mouse gene of interest is Gpr114 (G protein-coupled receptor 114), ortholog of human GPR114. Aliases include PGR27 and Gm1109.

GPR114 is a G protein-coupled receptor of the secretin family (Fredriksson et al, *FEBS Lett* 531(3):407-14 (2002); Bjarnadottir et al, *Genomics* 84(1):23-33 (2004)). Members of this family generally consist of a large N-terminal segment, a G protein-coupled receptor proteolytic site (GPS) domain (SMART accession SM00303), and a secretin family seven-transmembrane receptor domain (Pfam accession PF00002). Secretin family G protein-coupled receptors include secretin, calcitonin, and vasoactive intestinal peptide receptors, which activate adenyl cyclase or phospholipase C (Pfam accession PF00002).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
| --- | --- | --- | --- | --- |
| Observed | 19 | 38 | 17 | 74 |
| Expected | 18.5 | 37 | 18.5 | 74 |

Chi-Sq.=1.16 Significance=0.5598984 (hom/n)=0.24 Avg. Litter Size=10

Mutation Information

Mutation Type: Homologous Recombination (standard)
Description: Coding exons 4 through 7 were targeted (NCBI accession XM_356118.2).

1. Wild-type Expression Panel: Expression of the target gene was detected in all 13 adult tissue samples tested by RT-PCR, except brain; lung; liver; skeletal muscle; bone; stomach, small intestine, and colon; and adipose.

2. QC Expression: QC Images: Disruption of the target gene was confirmed by Southern hybridization analysis.

48.40.1. Phenotypic Analysis (for Disrupted Gene: DNA96860-2700 (UNQ2524)

(a) Overall Phenotypic Summary:

Mutation of the gene encoding the ortholog of human G protein-coupled receptor 114 (GPR114) resulted in the (−/−) mice exhibiting decreased lean body mass and decreased bone mineral density measurements. Gene disruption was confirmed by Southern blot.

(b) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased mean lean body mass when compared with that of their gender-matched (+/+) littermates and the historical mean. The male (−/−) mice also exhibited decreased mean bone mineral content and density-related measurements.

Micro CT: The male (−/−) mice exhibited decreased mean femoral mid-shaft cross-sectional area when compared with that of their gender-matched (+/+) littermates and the historical mean.

Mutant (−/−) mice deficient in the gene encoding PRO6017 polypeptides show a phenotype consistent with tissue wasting diseases (decreased lean body mass). Thus, antagonists or inhibitors of PRO6017 polypeptides or its encoding gene would mimic these metabolic related effects. On the other hand, PRO6017 polypeptides or agonists thereof would be useful in the prevention and/or treatment of such metabolic disorders as cachexia or other tissue wasting diseases.

In addition, the (−/−) mice analyzed by DEXA exhibited decreased bone measurements and decreased body mass measurements when compared with their (+/+) littermates, suggestive of abnormal bone disorders. In addition, the decreased lean body mass is indicative of a metabolic disorder related to growth retardation and tissue wasting disorders. The negative bone phenotype indicates that PRO6017 polypeptides or agonists thereof would be useful for maintaining bone homeostasis in addition to normal growth development. In addition, PRO6017 polypeptides would be useful in bone healing or for the treatment of arthritis or osteoporosis, whereas antagonists (or inhibitors) of PRO6017 polypeptides or its encoding gene would lead to abnormal or pathological bone disorders including inflammatory diseases associated with abnormal bone metabolism including arthritis, osteoporosis and osteopenia.

48.41. Generation and Analysis of Mice Comprising DNA96883-2745 (UNQ2784) Gene Disruptions In these knockout experiments, the gene encoding PRO7174 polypeptides (designated as DNA96883-2745) (UNQ2784) was disrupted. The gene specific information for these studies is as follows: the mutated mouse gene corresponds to nucleotide reference: NM_199222 *Mus musculus* cDNA sequence BC020188 (BC020188); protein reference: Q8VCD3 ACCESSION:Q8VCD3 NID: *Mus musculus* (Mouse). ERGIC-53-like protein precursor (Lectin, mannose-binding 1 like); the human gene sequence reference: NM_021819 ACCESSION:NM_021819 NID: gi 11141890 ref NM_021819.1 *Homo sapiens* lectin, mannose-binding, 1 like (LMAN1L); the human protein sequence corresponds to reference: Q9HAT1 ACCESSION:Q9HAT1 NID: *Homo sapiens* (Human). ERGIC-53-like protein precursor (Lectin, mannose-binding 1 like).

The mouse gene of interest is "cDNA sequence BC020188," ortholog of human LMAN1L (lectin, mannose-binding, 1 like). Aliases include ERGL, CPLX3, CPXIII, FLJ13993, ERGIC-53L, complexin III, and ERGIC-53-like protein.

LMAN1L is a putative type I membrane protein, containing a signal peptide, a leguminous lectin-like domain (Pfam accession PF03388), and a transmembrane segment. The protein likely functions as a cargo receptor or regulator of cargo receptor ERGIC-53 located in the endoplasmic reticulum (ER)-Golgi intermediate compartment. ERGIC-53 binds with mannose-containing glycoproteins and participates in the sorting and transfer of glycoproteins from the endoplasmic reticulum to the Golgi complex (Yerushalmi et al, *Gene* 265(1-2):55-60 (2001); Hauri et al, *Biochem Soc Symp* 69:73-82 (2002); Schrag et al, *Trends Biochem Sci* 28(1):49-57 (2003)). Like ERGIC-53, LMAN1L is likely located in the ER-Golgi intermediate compartment; however, bioinformatic analyses suggest that LMAN1L is an extracellular protein (Clark et al, *Genome Res* 13(10):2265-70 (2003)). LMAN1L is expressed in prostate, cardiac atrium, salivary gland, spleen, and central nervous system and is likely to play a role in glycoprotein folding and secretion (Yerushalmi et al, *Gene* 265(1-2):55-60 (2001); Hauri et al, *Biochem Soc Symp* 69:73-82 (2002); Schrag et al, *Trends Biochem Sci* 28(1):49-57 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 19 | 24 | 15 | 58 |
| Expected | 14.5 | 29 | 14.5 | 58 |

Chi-Sq.=1.76 Significance=0.4147829 (hom/n)=0.26 Avg. Litter Size=8
Mutation Information
Mutation Type: Homologous Recombination (standard)
Description: Coding exons 2 through 4 were targeted (NCBI accession NM_021819.1 [human]).
1. Wild-type Expression Panel: Expression of the target gene was detected only in eye and spleen among the 13 adult tissue samples tested by RT-PCR.
2. QC Expression: QC Images: Disruption of the target gene was confirmed by Southern hybridization analysis.

48.41.1. Phenotypic Analysis (for Disrupted Gene: DNA96883-2745 (UNQ2784)

(a) Overall Phenotypic Summary:

Mutation of the gene encoding the ortholog of human lectin, mannose-binding, 1 like (LMAN1L) resulted in increased serum glucose as well as increased mean serum cholesterol levels in both (+/−) and (−/−) mice. Urinalysis showed increased urobilinogen levels. The mutant (−/−) mice exhibited extramedullary hematopoiesis. The mutant (−/−) mice also exhibited numerous immunological abnormalities. Circadian testing showed decreased ambulation counts or hypoactivity in the (−/−) mice. The mutant (−/−) mice also showed decreased trabecular bone volume, number and connectivity density. Gene disruption was confirmed by Southern blot.

(b) Expression

GeneLogic expression patterns showed high tissue expression in lymph and prostate. A specific signal was observed in the spleen by ISH. Signal strength was as strong as that observed in prostate carcinoma and was selective of the broad marginal zones of B cell splenic follicles. UNQ2784 expression and knockout phenotype supports a role in B cell function. [See EXAMPLES 57 for protocol]

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:
Hematology Analysis:
Test Description: Blood tests are carried out by Abbott's Cell-Dyn 3500R, an automated hematology analyzer. Some of its features include a five-part WBC differential. 'Patient' reports can cover over 22 parameters in all.
Results:
Hematology: The (−/−) mice exhibited an increased mean platelet count when compared with that of their (+/+) littermates and the historical mean.

Thus, mutant mice deficient in the DNA96883-2745 gene resulted in a phenotype related to coagulation disorders. In this regard, inhibitors or antagonists of PRO7174 polypeptides would be useful in treating disorders related to abnormal blood coagulation such as hemophilia.

Fluorescence-Activated Cell-Sorting (FACS) Analysis
Procedure:
FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:
Tissue Specific FACS-Project: The (−/−) mice exhibited a decreased T cell:B cell ratio in lymph node when compared with that of their (+/+) littermates. The (−/−) mice also exhibited increased percentages of B220+ CD38 Low IgM− and TCRbeta+ CD38+ cells in Peyer's patches. In addition, mild-moderate extramedullary hematopoiesis was reported in four homozygous (−/−) mice.

These observations indicate that there is a change of B cell subtypes in Peyer's patches. Also, an increase in B cell number in lymph nodes was observed. Thus, it appears that PRO7174 polypeptides acts as a negative regulator for B cell production and a positive regulator for T cell production.

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygous and 8 homozygous mice were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:
Blood Chemistry: The male (+/−) and (−/−) mice exhibited increased mean serum cholesterol when compared with those of their gender-matched (+/+) littermates and the historical means.

As summarized above, the (+/−) and (−/−) mice exhibited increased mean serum cholesterol levels when compared with their gender-matched (+/+) littermates and the historical means. Thus, mutant mice deficient in the PRO7174 gene may serve as a model for cardiovascular disease. PRO7174 polypeptides or its encoding gene would be useful in regulating blood lipids such as cholesterol. Thus, PRO7174 polypeptides or agonists thereof would be useful in the treatment of such cardiovascular diseases as hypertension, atherosclerosis, heart failure, stroke, various coronary diseases, hypercholesterolemia, diabetes and/or obesity.

(e) Phenotypic Analysis: Metabolism—Blood Chemistry/Urinalysis

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Results:
Both the male and female (+/−) and (−/−) mice exhibited increased mean serum glucose levels (~2SD above the historic mean) compared to their wild-type (+/+) littermates and the historical mean.

Thus, the mutant (+/−) and (−/−) mice exhibited hyperglycemia which is associated with an altered glucose metabolism or diabetes. PRO7174 polypeptides or agonists thereof would be useful in maintaining normal glucose levels/metabolism and possibly useful in the treatment of diabetes.

In addition to the elevated mean serum glucose levels in the heterozygous and homozygous mice, the male and female mutant mice also showed grossly elevated levels of urinary urobilinogen (~20 fold increase in two out of four heterozygous (+/−) mice and 3 out of 4 homozygous (−/−) mice). Serum bilirubin was normal. These results could be a function of an abnormal urine possibly associated with kidney dysfunction.

(f) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:
Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

The (−/−) mice exhibited decreased ambulatory counts (hypoactivity) during the 1-hour habituation period and both light periods of home-cage activity testing when compared with their gender-matched (+/+) littermates and the historical mean. These results are consistent with lethargy or depressive disorders. Antagonists or inhibitors of PRO7174 polypeptides or the PRO7174 encoding gene would be expected to mimic this behavior. Likewise, PRO7174 polypeptides or agonists thereof, would be useful in the treatment of such neurological disorders including depressive disorders or other decreased anxiety-like symptoms such as lethargy, cognitive disorders, hyperalgesia and sensory disorders.

(g) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and mid-shaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro CT: The male (−/−) mice exhibited decreased mean vertebral trabecular bone volume, number, and connectivity density when compared with that of their gender-matched (+/+) littermates and the historical means.

The (−/−) mice analyzed by Micro CT analysis exhibited decreased bone measurements when compared with their (+/+) littermates, suggestive of abnormal bone disorders. The (−/−) mice exhibited a negative bone phenotype with abnormal and decreased bone measurements reflective of bone metabolic disorders. The negative bone phenotype indicates that PRO7174 polypeptides or agonists thereof would be useful for maintaining bone homeostasis. In addition, PRO7174 polypeptides would be useful in bone healing or for the treatment of arthritis or osteoporosis, whereas antagonists (or inhibitors) of PRO7174 polypeptides or its encoding gene would lead to abnormal or pathological bone disorders including inflammatory diseases associated with abnormal bone metabolism including arthritis, osteoporosis and osteopenia.

48.42. Generation and Analysis of Mice Comprising DNA136110-2763 (UNQ3003) Gene Disruptions In these knockout experiments, the gene encoding PRO9744 polypeptides (designated as DNA136110-2763) (UNQ3003) was disrupted. The gene specific information for these studies is as follows: the mutated mouse gene corresponds to nucleotide reference: NM_022416 Mus musculus serine/threonine kinase 32B (Stk32b); protein reference: Q9JJX8 Q9JJX8 Q9JJX8 SERINE/THREONINE PROTEIN KINASE; the human gene sequence reference: NM_018401 Homo sapiens serine/threonine kinase 32B (STK32B); the human protein sequence corresponds to reference: Q9NY57 Q9NY57 Q9NY57 SERINE/THREONINE PROTEIN KINASE.

The mouse gene of interest is Stk32b (serine/threonine kinase 32B), ortholog of human STK32B. Aliases include STKG6, Stk32, YANK2, 2510009F08Rik, HSA250839, and serine threonine kinase 32.

STK32B is a putative cytosolic serine/threonine protein kinase, containing a serine/threonine protein kinase catalytic domain (SMART accession SM00220). Bioinformatic analysis suggests that STK32B may be an extracellular protein (Clark et al, Genome Res 13(10):2265-70 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 15 | 38 | 19 | 72 |
| Expected | 18 | 36 | 18 | 72 |

Chi-Sq.=0.44 Significance=0.8025188 (hom/n)=0.25 Avg. Litter Size=8
Mutation Information
Mutation Type Homologous Recombination (standard)
Description: Coding exon 3 was targeted (NCBI accession NM_022416.1).
1. Wild-type Expression Panel: Expression of the target gene was detected in all 26 adult tissue samples tested by RT-PCR, except spleen, lung, liver, skeletal muscle, bone, adipose, asthmatic lung, LPS liver, blood, aortic tree and skin fibroblast.
2. QC Expression: QC Images: Disruption of the target gene was confirmed by Southern hybridization analysis.

48.42.1. Phenotypic Analysis (for Disrupted Gene: DNA136110-2763 (UNQ3003)
(a) Overall Phenotypic Summary:
Mutation of the gene encoding the ortholog of human serine/threonine kinase 32B (STK32B) resulted in the (−/−) mice exhibiting increased mean serum triglyceride levels. Gene disruption was confirmed by Southern blot.
(b) Phenotypic Analysis: Cardiology
In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.
Blood Lipids
Procedure: A cohort of 4 wild type, 4 heterozygous and 8 homozygous mice were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).
Results:
Blood Chemistry: Both the male and female (−/−) mice exhibited increased mean serum triglyceride levels when compared with those of their gender-matched (+/+) littermates and the historical means.
As summarized above, the (−/−) mice exhibited notably increased mean serum triglyceride levels when compared with their gender-matched (+/+) littermates and the historical means. Thus, mutant mice deficient in the PRO9744 gene may serve as a model for cardiovascular disease. PRO9744 polypeptides or its encoding gene would be useful in regulating blood lipids such as triglycerides. Thus, PRO9744 polypeptides or agonists thereof would be useful in the treatment of such cardiovascular diseases as hypertension, atherosclerosis, heart failure, stroke, various coronary diseases, hypertriglyceridemia, diabetes and/or obesity.

48.43. Generation and Analysis of Mice Comprising DNA108725-2766 (UNQ3023) Gene Disruptions
In these knockout experiments, the gene encoding PRO9821 polypeptides (designated as DNA108725-2766) (UNQ3023) was disrupted. The gene specific information for these studies is as follows: the mutated mouse gene corresponds to nucleotide reference: NM_177139 *Mus musculus* RIKEN cDNA E130115E03 gene (E130115E03Rik); protein reference:Q8BPP5 ACCESSION:Q8BPP5 NID: *Mus musculus* (Mouse). Protein UNQ3023/PRO9821 precursor; the human gene sequence reference: NM_194317 *Homo sapiens* hypothetical protein MGC52057 (MGC52057); the human protein sequence corresponds to reference: Q86Y78 ACCESSION:Q86Y78 NID: *Homo sapiens* (Human). Protein UNQ3023/PRO9821 precursor.

The mouse gene of interest is RIKEN cDNA E130115E03 gene, ortholog of human hypothetical protein MGC52057.

Hypothetical protein MGC52057 is a putative extracellular protein (Clark et al, *Genome Res* 13(10):2265-70 (2003)) consisting of a signal peptide and an Ly-6 antigen/uPA receptor-like (LU) domain (SMART accession SM00134). Proteins with similar domain organization include CD59 antigen, which protects cells from complement-mediated lysis, and LY6D, which is involved in cell-cell adhesion in keratinocytes (Brakenhoff et al, *J Cell Biol* 129(6):1677-89 (1995); Clayton et al, *Eur J Immunol* 33(2):522-31 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|          | wt | het | hom | Total |
|----------|----|----|-----|-------|
| Observed | 26 | 29 | 17  | 72    |
| Expected | 18 | 36 | 18  | 72    |

Chi-Sq.=4.35 Significance=0.11360816 (hom/n)=0.22 Avg. Litter Size=9
Mutation Information
Mutation Type Homologous Recombination (standard)
Description: Coding exon 1 was targeted (NCBI accession NM_177139.3).
1. Wild-type Expression Panel: Expression of the target gene was detected in embryonic stem (ES) cells and in all 26 adult tissue samples tested by RT-PCR, except skeletal muscle, adipose, and LPS liver.
2. QC Expression: QC Images: Disruption of the target gene was confirmed by Southern hybridization analysis.

48.43.1. Phenotypic Analysis (for Disrupted Gene: DNA108725-2766 (UNQ3023)
(a) Overall Phenotypic Summary:
Mutation of the gene encoding the ortholog of human hypothetical protein MGC52057 resulted in the (−/−) mice exhibiting decreased bone mineral content and bone mineral density measurements. UNQ3023 is an unknown protein and has no immunological phenotype in the (−/−) mice. However, UNQ3023 appears to have a UPAR_LY6 domain in the ECD similar to that in CD59 which is important in the complement pathway. Gene disruption was confirmed by Southern blot.
(b) Bone Metabolism & Body Diagnostics: Radiology Phenotypic Analysis
In the area of bone metabolism, targets were identified herein for the treatment of arthritis, osteoporosis, osteopenia and osteopetrosis as well as identifying targets that promote bone healing. Tests included:
DEXA for measurement of bone mineral density on femur and vertebra
MicroCT for very high resolution and very high sensitivity measurements of bone mineral density for both trabecular and cortical bone.

Dexa Analysis—Test Description:
Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:
DEXA: Both the male and female (−/−) mice exhibited decreased bone mineral content, BMC/LBM index and total body bone mineral density measurements when compared with that of their gender-matched (+/+) littermates and the historical means.

The (−/−) mice analyzed by DEXA analysis exhibited decreased bone measurements when compared with their (+/+) littermates, suggestive of abnormal bone disorders. The negative bone phenotype indicates that PRO9821 polypeptides or agonists thereof would be useful for maintaining bone homeostasis. In addition, PRO9821 polypeptides would be useful in bone healing or for the treatment of arthritis or osteoporosis, whereas antagonists (or inhibitors) of PRO9821 polypeptides or its encoding gene would lead to abnormal or pathological bone disorders including inflammatory diseases associated with abnormal bone metabolism including arthritis, osteoporosis and osteopenia.

48.44. Generation and Analysis of Mice Comprising DNA129332-2775 (UNQ3037) Gene Disruptions In these knockout experiments, the gene encoding PRO9852 polypeptides (designated as DNA129332-2775) (UNQ3037) was disrupted. The gene specific information for these studies is as follows: the mutated mouse gene corresponds to nucleotide reference:NM_145937 ACCESSION: NM_145937 NID: gi 22122360 ref NM_145937.1 Mus musculus EST AI463102 (AI463102); protein reference: Q8R0F3 ACCESSION:Q8ROF3 NID: Mus musculus (Mouse). Sulfatase modifying factor 1 precursor (C-alpha-formlyglycine-generating enzyme 1); the human gene sequence reference: NM_182760 Homo sapiens sulfatase modifying factor 1 (SUMF1); the human protein sequence corresponds to reference: Q8NBK3 ACCESSION:Q8NBK3 NID: Homo sapiens (Human). Sulfatase modifying factor 1 precursor (C-alpha-formyglycine-generating enzyme 1).

The mouse gene of interest is Sumf1 (sulfatase modifying factor 1), ortholog of human SUMF1. Aliases include FGE, MGC39076, EST AI463102, and C-alpha-formylglycine-generating enzyme.

SUMF1 is an enzyme in the lumen of the endoplasmic reticulum that catalyzes the conversion of cysteine to C-alpha-formylglycine in the catalytic site of various sulfatases, such as GALNS (galactosamine [N-acetyl]-6-sulfate sulfatase), ARSA (arylsulfatase A), STS (steroid sulfatase [microsomal], arylsulfatase C, isozyme S), and ARSE (arylsulfatase E [chondrodysplasia punctata 1]). This post-translational modification is required for enzymatic activity of these sulfatases. SUMF1 is expressed in a number of tissues, including heart, brain, placenta, lung, liver, skeletal muscle, kidney, and pancreas as well as in skin fibroblasts.

Mutations in SUMF1 can cause multiple sulfatase deficiency, a lysosomal storage disorder (OMIM 272200) (Cosma et al, Cell 113(4):421-2 (2003); Dierks et al, Cell 113(4):435-44 (2003); Cosma et al, Hum Mutat 23(6):576-81 (2004); Preusser-Kunze et al, J Biol Chem 280(15):14900-10 (2005)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 23 | 42 | 8 | 73 |
| Expected | 18.25 | 36.5 | 18.25 | 73 |

Chi-Sq.=13.92 Significance=9.490965E-4 (liom/n)=0.12
Avg. Litter Size=9
Mutation Information
Mutation Type: Homologous Recombination (standard)
Description: Coding exon 1 was targeted (NCBI accession NM_145937.1).
1. Wild-type Expression Panel: Expression of the target gene was detected in embryonic stem (ES) cells and in all 13 adult tissue samples tested by RT-PCR.
2. QC Expression: QC Images: Disruption of the target gene was confirmed by Southern hybridization analysis.

48.44.1. Phenotypic Analysis (for Disrupted Gene: DNA129332-2775 (UNQ3037)

(a) Overall Phenotypic Summary:
Mutation of the gene encoding the ortholog of human sulfatase modifying factor 1 (SUMF1) resulted in reduced viability and a lysosomal storage disease in (−/−) mice. Genetic data indicate that this mutation resulted in reduced viability of the homozygous mutant mice. No homozygous mutant mice underwent complete Level 1 testing. The female mutant mice available for partial analysis exhibited signs of growth retardation and blood chemistry, immunological, and neurological abnormalities. Microscopic analysis revealed a lysosomal storage disease in the mutants, characterized by macrophages distended by large intracytoplasmic vesicles in all tissues. Disruption of the target gene was confirmed by Southern hybridization analysis.

(b) Pathology
Gross: The (−/−) mice exhibited several skeletal abnormalities, including convex sternum, vertebral kyphosis, shortened limbs.
Microscopic: The (−/−) mice exhibited a lysosomal storage disease, characterized by macrophages that were distended by large intracytoplasmic vacuoles in all tissues. The affected macrophages were most numerous in the red pulp of the spleen and lymph node sinuses, but diffusely within the bones of the skull and the epiphyses of long bones. Kupffer cells in the liver and glial cells (primarily microglia) in the brain and spinal cord were also distended by large cytoplasmic vacuoles. The large distended Kupffer cells bulged into and expanded the hepatic sinusoids. Some Ito cells also appeared to be hypertrophic. In the central nervous system, the affected microglial cells were most numerous in white tracts in the brain and spinal cord. Arterial (aortic) smooth muscle cells were frequently distended by clear cytoplasmic vacuoles. In the more severely affected mutants, distended cells replaced the normal marrow in the bones of the skull and surrounded and compressed the vestibulocochlear nerves. The lesions in long bones were most severe at the metaphyses, where there was often complete absence of osteoblasts and trabecular bone, and increased numbers of osteoclasts. At the epiphyses, normal cellular elements were replaced by large distended macrophages, loose pale staining extracellular matrix, and scattered detached chondrocytes. The normal maturation sequence of epiphyseal cartilage was completely disrupted, characterized by an absence of the normal columnar arrays of proliferating and hypertrophic chondrocytes. There was also reduced ossification of the epiphyseal cartilage template of long bones and dysarthrosis. The grossly evident skeletal abnormalities reflect the defective bone development and maturation.

Gene Expression: LacZ activity was not detected in the panel of tissues by immunohistochemical analysis.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The female (−/−) mice exhibited decreased hemoglobin, hematocrit, mean corpuscular volume, mean corpuscular volume and mean corpuscular hemoglobin when compared with those of their (+/+) littermates and the historical means. The female (−/−) mice also exhibited an increased red cell distribution width.

The (−/−) mice exhibited a hemoglobin level, hematocrit and a decrease in corpuscular volume when compared with their (+/+) littermates and the historical means.

These results are related to a phenotype associated with anemia. Thus, PRO9852 polypeptides, agonists thereof or the encoding gene for PRO9852 polypeptides must be essential for normal red blood cell production and as such would be useful in the treatment of blood disorders associated with anemia or a low hematocrit.

Fluorescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on wild type and homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

FACS3: The (−/−) mice exhibited an altered distribution of leukocyte subsets in the peripheral blood, characterized by a decreased mean percentage of B cells and an increased mean percentage of CD8 cells when compared with those of their (+/+) littermates and the historical means.

These results show that knockout (−/−) mice exhibit immunological abnormalities compared to their wild-type (+/+) littermates. Antagonists (inhibitors) of PRO9852 polypeptides would be expected to mimic this phenotype. PRO9852 polypeptides or agonists thereof appear to act as a negative regulator of T cell production and a positive regulator of B cell development and would be useful in the development or maturation of B cells which could then participate in fast immune responses.

Ovalbumin Challenge

Procedure: This assay was carried out on wild type mice and homozygous mice. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Results of this Challenge:

The (−/−) mice exhibited decreased mean serum IgG1 and IgG2a responses when compared with their (+/+) littermates and the historical mean.

In summary, the ovalbumin challenge studies indicate that knockout mice deficient in the gene encoding PRO9852 polypeptides exhibit immunological abnormalities when compared with their wild-type littermates. In particular, the mutant mice exhibited a decreased ability to elicit an immunological response when challenged with the T-cell dependent OVA antigen. Thus, PRO9852 polypeptides or agonists thereof, would be useful for stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, inhibitors (antagonists) of PRO9852 polypeptides would be useful for inhibiting the immune response and thus would be useful candidates for suppressing harmful immune responses, e.g. in the case of graft rejection or graft-versus-host diseases.

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of wild type, heterozygous and homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

The (−/−) mice exhibited an increased median sum time and distance in-center during open field testing when compared with their gender-matched (+/+) littermates and the historical mean, suggesting a decreased anxiety-like response in the mutants.

A notable difference was observed during open field activity testing. The (−/−) mice exhibited an increased median sum time in the center area when compared with their gender-matched (+/+) littermates, which is indicative of a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO9852 polypeptides and agonists thereof would be useful for the treatment or amelioration of the symptoms associated with depressive disorders.

Functional Observational Battery (FOB) Test—Tail Suspension Testing:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Tail Suspension Testing:

The tail suspension test is a procedure that has been developed as a model for depressive-like behavior in rodents. In this particular setup, a mouse is suspended by its tail for 6 minutes, and in response the mouse will struggle to escape from this position. After a certain period of time the struggling of the mouse decreases and this is interpreted as a type of learned helplessness paradigm. Animals with invalid data (i.e. climbed their tail during the testing period) are excluded from analysis.

Results:
Tail Suspension2: The female (−/−) mice exhibited increased immobility time when compared with that of their gender-matched (+/+) littermates and the historical mean, suggesting an increased depressive-like response in the mutants.

Thus, knockout mice demonstrated a phenotype consistent with depression, generalized anxiety disorders, cognitive disorders, hyperalgesia and sensory disorders and/or bipolar disorders. Thus, PRO9852 polypeptides and agonists thereof would be useful for the treatment or amelioration of the symptoms associated with depressive disorders.

Prepulse Inhibition of the Acoustic Startle Reflex

Prepulse inhibition of the acoustic startle reflex occurs when a loud 120 decibel (dB) startle-inducing tone is preceded by a softer (prepulse) tone. The PPI paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:
PPI: The (−/−) mice failed to exhibit a startle response, suggesting hearing impairment in the mutants. Therefore, prepulse inhibition could not be assessed.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:
Circadian: The female (−/−) mice exhibited decreased ambulatory counts during the 1- and 12-hour habituation periods and all light/dark periods when compared with their gender-matched (+/+) littermates and the historical means.

These results are consistent with lethargy or depressive disorders. Antagonists or inhibitors of PRO9852 polypeptides or the PRO9852 encoding gene would be expected to mimic this behavior. Likewise, PRO9852 polypeptides or agonists thereof, would be useful in the treatment of such neurological disorders including depressive disorders or other decreased anxiety-like symptoms such as lethargy, cognitive disorders, hyperalgesia and sensory disorders.

Inverted Screen Testing:

Behavioral screens were performed on a cohort of wild type, heterozygous and homozygous mutant mice. All behavioral tests were done between 12 and 16 weeks of age unless reduced viability necessitates earlier testing. These tests included open field to measure anxiety, activity levels and exploration.

Inverted Screen Test Data:

The Inverted Screen is used to measure motor strength/coordination. Untrained mice were placed individually on top of a square (7.5 cm×7.5 cm) wire screen which was mounted horizontally on a metal rod. The rod was then rotated 180 degrees so that the mice were on the bottom of the screens. The following behavioral responses were recorded over a 1 min testing session: fell off, did not climb, and climbed up.

Results:

| Genotype | Ratio Fell Down | % | Ratio Climbed up | % |
| --- | --- | --- | --- | --- |
| +/+ (n = 8) | 1/8 | 13 | 7/8 | 87.5 |
| −/− (n = 8) | 5/8 | 63 | 0/8 | 0 |

WT Population Fell Down 3.62 Climbed Up 60.04
A motor strength deficit is apparent when there is a 50% point difference between (−/−) or (+/−) mice and (+/+) mice for the fell down response. 0/8 or 1/8 (−/−) or (+/−) mice not climbing indicates impaired motor coordination. 7/8 or 8/8(−/−) or (+/−) mice climbing up indicates enhanced motor coordination.

The Inverted Screen Test is designed to measure basic sensory & motor observations:

Among the 8 (−/−) mice analyzed, 5 fell off the inverted screen whereas only 1/8 (+/+) mice fell off. These results indicate an impaired motor strength in the mutants. These results are consistent with the observations in bone-related measurements as shown below.

(e) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed:

Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Results:

Blood Chemistry: The female (−/−) mice exhibited increased alkaline phosphatase, albumin, alanine amino transferase, phosphorus, and potassium levels when compared with those of their (+/+) littermates and the historical means. These blood chemistry abnormalities are consistent with the reduced viability consequences when the PRO9852 encoding gene is knocked out in mice.

(f) Bone Metabolism & Body Diagnostics (1) Tissue Mass & Lean Body Mass Measurements—Dexa Dexa Analysis—Test Description:

Procedure: A cohort of wild type, heterozygous and homozygous mice were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Weight: The (−/−) mice exhibited decreased mean body weight when compared with that of their gender-matched (+/+) littermates and the historical mean.

Length: The 2 female (−/−) mice analyzed exhibited decreased mean body length when compared with that of their gender-matched (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of wild type, heterozygous and homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The 2 female (−/−) mice available for analysis exhibited decreased total tissue mass, lean body mass, percent total body fat, total fat mass, and total body bone mineral content when compared with the historical means. However, the 2 female (+/+) mice also exhibited similarly decreased measurements.

Micro CT: No notable difference. However, no (−/−) mice were available for analysis.

Mutant (−/−) mice deficient in the gene encoding PRO9852 polypeptides show a phenotype consistent with growth retardation, marked by decreased body weight and length and tissue wasting diseases (decreased total body fat (%) and fat mass (g)). Thus, antagonists or inhibitors of PRO9852 polypeptides or its encoding gene would mimic these metabolic and growth related effects. On the other hand, PRO9852 polypeptides or agonists thereof would be useful in the prevention and/or treatment of such metabolic disorders as diabetes or other tissue wasting diseases.

In addition, the (−/−) mice analyzed by DEXA exhibited decreased bone measurements and decreased body mass measurements when compared with their (+/+) littermates, suggestive of abnormal bone disorders. In addition, the decreased mean total tissue mass and lean body mass is indicative of a metabolic disorder related to growth retardation and tissue wasting disorders. The negative bone phenotype indicates that PRO9852 polypeptides or agonists thereof would be useful for maintaining bone homeostasis in addition to normal growth development. In addition, PRO9852 polypeptides would be useful in bone healing or for the treatment of arthritis or osteoporosis, whereas antagonists (or inhibitors) of PRO9852 polypeptides or its encoding gene would lead to abnormal or pathological bone disorders including inflammatory diseases associated with abnormal bone metabolism including arthritis, osteoporosis and osteopenia.

These findings are consistent with the pathology report and the microscopic observations.

(g) Cardiology/Diagnostics—Blood Pressure

Description:

Systolic blood pressure is measured via a noninvasive tail-cuff method for four days on the Visitech BP-2000 Blood Pressure Analysis System. The blood pressure is measured ten times each day for four days. The four days are then averaged to obtain a mouse's conscious systolic blood pressure.

Results:

Blood Pressure: The 2 female (−/−) mice available for analysis exhibited increased mean systolic blood pressure when compared with that of their gender-matched (+/+) littermates and the historical mean which is indicative of hypertension.

48.45. Generation and Analysis of Mice Comprising DNA143076-2787 (UNQ3054) Gene Disruptions In these knockout experiments, the gene encoding PRO9873 polypeptides (designated as DNA143076-2787) (UNQ3054) was disrupted. The gene specific information for these studies is as follows: the mutated mouse gene corresponds to nucleotide reference: NM_020595 *Mus musculus* otoraplin (Otor); protein reference: Q9JIE3 ACCESSION: Q9JIE3 NID: *Mus musculus* (Mouse). Otoraplin precursor (Melanoma inhibitory activity-like protein); the human gene sequence reference:NM_020157 ACCESSION:NM_020157 NID: gi 21618345 ref NM_020157.2 *Homo sapiens* otoraplin (OTOR); the human protein sequence corresponds to reference: Q9NRC9 ACCESSION:Q9NRC9 NID: *Homo sapiens* (Human). Otoraplin precursor (Fibrocyte-derived protein) (Melanoma inhibitory activity like protein).

The mouse gene of interest is Otor (otoraplin), ortholog of human OTOR. Aliases include Fdp, MIA, MIAL, CDRAP, fibrocyte-derived protein, and melanoma inhibitory activity-like protein.

OTOR is a secreted protein expressed primarily by the mesenchymal cell layer beneath sensory epithelium of the cochlea and vestibule of the inner ear. The protein consists of a signal peptide and an SH3 domain and undergoes post-translational modification, resulting in sulfation and covalent homodimerization (Rendtorff et al, *Genomics* 71(1):40-52 (2001); Stoll et al, *Protein Sci* 12(3):510-9 (2003); Robertson et al, *Genomics* 66(3):242-8 (2000)). OTOR may function as a component of extracellular matrix or as a signal-transducing ligand (Bosserhoff and Buettner, *Histol Histonathol* 17(1):289-300 (2002)). OTOR likely plays a role in periotic mesenchyme chondrogenesis, participating in formation of the otic capsule during development (Cohen-Salmon et al, *J Biol Chem* 275(51):40036-41 (2000)). Mutations in OTOR may cause deafness (Cohen-Salmon et al, *J Biol Chem* 275(51):40036-41 (2000); Rendtorff et al, *Genomics* 71(1):40-52 (2001).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 20 | 30 | 29 | 79 |
| Expected | 19.75 | 39.5 | 19.75 | 79 |

Chi-Sq.=0.81 Significance=0.6669768 (hom/n)=0.27 Avg. Litter Size=9
Mutation Information
Mutation Type: Homologous Recombination (standard)
Description: Coding exons 1 through 3 were targeted (NCBI accession NM_020595.1).
1. Wild-type Expression Panel: Expression of the target gene was detected in brain, spinal cord, eye, and thymus among 13 adult tissue samples tested by RT-PCR.
2. QC Expression: QC Images: Disruption of the target gene was confirmed by Southern hybridization analysis.

48.45.1. Phenotypic Analysis (for Disrupted Gene: DNA143076-2787 (UNQ3054)

(a) Overall Phenotypic Summary:

Mutation of the gene encoding the ortholog of human otoraplin (OTOR) resulted in an increased anxiety-related response in male (−/−) mice. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

Anxiety: The male (−/−) mice exhibited decreased median sum time-in-center during open field testing when compared with their gender-matched (+/+) littermates and the historical mean, suggesting an increased anxiety-like response in the mutants.

The (−/−) mice demonstrated a decrease median sum time-in-center at intervals 2,3, and 5 when compared to the (+/+) mice, suggesting an increased anxiety-like response in the (−/−) mice. In summary, the open field testing revealed a phenotype associated with increased anxiety which could be associated with mild to moderate anxiety, anxiety due to a general medical condition, and/or bipolar disorders; hyperactivity; sensory disorders; obsessive-compulsive disorders, schizophrenia or a paranoid personality. Thus, PRO9873 polypeptides or agonists thereof would be useful in the treatment of such neurological disorders.

48.46. Generation and Analysis of Mice Comprising DNA144841-2816 (UNQ3115) Gene Disruptions In these knockout experiments, the gene encoding PRO10196 polypeptides (designated as DNA144841-2816) (UNQ3115) was disrupted. The gene specific information for these studies is as follows: the mutated mouse gene corresponds to nucleotide reference: NM_020013 *Mus musculus* fibroblast growth factor 21 (Fgf21); protein reference: Q9JJN1 ACCESSION:Q9JJN1 NID: *Mus musculus* (Mouse). Fibroblast growth factor-21 precursor (FGF-21); the human gene sequence reference: NM_019113 ACCESSION:NM_019113 NID:9506596 *Homo sapiens* fibroblast growth factor 21 (FGF21); the human protein sequence corresponds to reference: Q9NSA1 ACCESSION:Q9NSA1 NID: *Homo sapiens* (Human). FIBROBLAST GROWTH FACTOR-21 PRECURSOR (FGF-21).

The mouse gene of interest is Fgf21 (fibroblast growth factor 21), ortholog of human FGF21. Aliases include FGF-21 and UNQ3115.

FGF21 is a putative secreted protein expressed primarily in liver. The 209-amino acid protein contains a signal peptide and a fibroblast growth factor (FGF) domain (Pfam accession PF00167). FGF21 may function as a signal-transducing ligand (Nishimura et al, *Biochim Biophys Acta* 1492(1):203-6 (2000)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 17 | 49 | 21 | 87 |
| Expected | 21.75 | 43.5 | 21.75 | 87 |

Chi-Sq.=2.45 Significance=0.2937577 (hom/n)=0.25 Avg. Litter Size=9
Mutation Information
Mutation Type Homologous Recombination (standard)

Description: Coding exons 1 through 3 were targeted (NCBI accession NM_020013.2).

1. Wild-type Expression Panel: Expression of the target gene was detected only in brain among the 13 adult tissue samples tested by RT-PCR.
2. QC Expression: QC Images: Disruption of the target gene was confirmed by Southern hybridization analysis.

48.46.1. Phenotypic Analysis (for Disrupted Gene: DNA144841-2816 (UNQ3115)

(a) Overall Phenotypic Summary:

Mutation of the gene encoding the ortholog of human fibroblast growth factor 21 (FGF21) resulted in the (−/−) mice exhibiting increased mean serum cholesterol and glucose levels. The mutant (−/−) mice also showed increased total tissue mass and total body fat. Gene disruption was confirmed by Southern blot.

(b) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygous and 8 homozygous mice were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

Blood Chemistry: The (−/−) mice exhibited an increased mean serum cholesterol level when compared with that of their gender-matched (+/+) littermates and the historical mean.

As summarized above, the (−/−) mice exhibited increased mean serum cholesterol levels when compared with their gender-matched (+/+) littermates and the historical means. Thus, mutant mice deficient in the PRO10196 gene may serve as a model for cardiovascular disease. PRO10196 polypeptides or its encoding gene would be useful in regulating blood lipids such as cholesterol. Thus, PRO10196 polypeptides or agonists thereof would be useful in the treatment of such cardiovascular diseases as hypertension, atherosclerosis, heart failure, stroke, various coronary diseases, hypercholesterolemia, diabetes and/or obesity.

(c) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:

The homozygous (−/−) mice exhibited increased mean serum glucose levels when compared with that of their gender-matched (+/+) littermates and the historical mean.

Thus, the mutant (−/−) mice exhibited hyperglycemia which could be associated with an altered glucose metabolism or diabetes. PRO10196 polypeptides or agonists thereof would be useful in maintaining normal glucose levels/metabolism and possibly useful in the treatment of diabetes.

(d) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

The male (−/−) mice exhibited increased total tissue mass and total body fat (% and g) when compared to their gender matched wild-type (+/+) littermates and historical mean.

These studies suggest that mutant (−/−) non-human transgenic animals exhibit a negative phenotype that would be associated with obesity. Thus, PRO10196 polypeptides or agonists thereof are essential for normal growth and metabolic processes and especially would be important in the prevention and/or treatment of obesity.

48.47. Generation and Analysis of Mice Comprising DNA220432 (UNQ3966) Gene Disruptions In these knockout experiments, the gene encoding PRO34778 polypeptides (designated as DNA220432) (UNQ3966) was disrupted. The gene specific information for these studies is as follows: the mutated mouse gene corresponds to nucleotide reference:NM_130866 *Mus musculus* olfactory receptor 78 (Olfr78); protein reference: Q8VBV9 Q8VBV9 Q8VBV9 OLFACTORY RECEPTOR MOR18-2 PROSTATE-SPECIF; the human gene sequence reference: NM_030774 ACCESSION:NM_030774 NID:19923630 *Homo sapiens* olfactory receptor, family 51, subfamily E, member 2 (ORS1E2); the human protein sequence corresponds to reference: Q9H255 OXE2_HUMAN Q9H255 OLFACTORY RECEPTOR 51E2 PROSTATE SPECI.

The mouse gene of interest is Olfr78 (olfactory receptor 78), ortholog of human OR51E2 (olfactory receptor, family 51, subfamily E, member 2). Aliases include PSGR; RA1c; MOL2.3; MOR18-2; 4633402A21Rik; olfactory receptor MOR18-2; GA_x6K02T2PBJ9-5459657-5458695; OR52A2; OR51E3P; olfactory receptor OR11-16; prostate specific G-protein coupled receptor; olfactory receptor, family 52, subfamily A, member 2; olfactory receptor, family 51, subfamily E, member 3 pseudogene.

OR51E2 is an integral membrane protein expressed primarily in prostate gland that likely functions as a G protein-coupled receptor. The protein contains a seven-transmembrane receptor (rhodopsin family) domain (PFAM accession PF00001), displays marked similarity with olfactory receptor family members, and interacts with GNA12 (guanine nucleotide binding protein [G protein] alpha 12). OR51E2 is also expressed in olfactory tissue and the medulla oblongata of the brain in humans, in brain and colon in mice, and in brain and liver in rats (Xu et al, *Cancer Res* 60(23):6568-72 (2000); Yuan et al, *Gene* 278(1-2):41-51 (2001); Xia et al, *Oncogene* 20(41):5903-7 (2001)). Expression of OR51E2 is frequently upregulated in prostate cancer, suggesting that the protein may be useful for early detection and treatment of prostate cancer (Weng et al, *Int J Cancer* 113(5):811-8 (2005)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
| --- | --- | --- | --- | --- |
| Observed | 18 | 25 | 18 | 61 |
| Expected | 15.25 | 30.5 | 15.25 | 61 |

Chi-Sq.=0.32 Significance=0.85214376 (hom/n)=0.27 Avg. Litter Size=8
Mutation Information
Mutation Type: Homologous Recombination (standard)
Description: Coding exon 1 was targeted (NCBI accession NM_130866.2).
1. Wild-type Expression Panel: Expression of the target gene was detected in embryonic stem (ES) cells and in all 26 adult tissue samples tested by RT-PCR, except liver and adipose.
2. QC Expression: QC Images: Disruption of the target gene was confirmed by Southern hybridization analysis.

48.47.1. Phenotypic Analysis (for Disrupted Gene: DNA220432 (UNQ3966)

(a) Overall Phenotypic Summary:

Mutation of the gene encoding the ortholog of human olfactory receptor, family 51, subfamily E, member 2 (OR51E2) resulted in the (−/−) mice exhibiting increased total tissue mass and total body fat as well as increased cholesterol levels. An enhanced glucose tolerance was also observed in the mutant (−/−) mice. Neurological testing showed increased stress induced hyperthermia in the homozygous mice. Gene disruption was confirmed by Southern blot.

(b) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygous and 8 homozygous mice were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:
Blood Chemistry: The (−/−) mice exhibited an increased mean serum cholesterol level when compared with that of their gender-matched (+/+) littermates and the historical mean.

As summarized above, the (−/−) mice exhibited increased mean serum cholesterol levels when compared with their gender-matched (+/+) littermates and the historical means. Thus, mutant mice deficient in the PRO34778 gene may serve as a model for cardiovascular disease. PRO34778 polypeptides or its encoding gene would be useful in regulating blood lipids such as cholesterol. Thus, PRO34778 polypeptides or agonists thereof would be useful in the treatment of such cardiovascular diseases as hypertension, atherosclerosis, heart failure, stroke, various coronary diseases, hypercholesterolemia, diabetes and/or obesity.

(c) Phenotypic Analysis: Metabolism—Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:
Glucose Tolerance Test: The mutant (−/−) mice tested exhibited enhanced glucose tolerance when compared with their gender-matched (+/+) littermates.

In these studies the mutant (−/−) mice showed an increased or enhanced glucose tolerance in the presence of normal fasting glucose at all 3 intervals tested when compared with their gender-matched (+/+) littermates and the historical means. Thus, knockout mice exhibited an increased insulin sensitivity or the opposite phenotypic pattern of an impaired glucose homeostasis, and as such antagonists (inhibitors) to PRO34778 polypeptides or its encoding gene would be useful in the treatment of an impaired glucose homeostasis.

(d) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:
Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:
The male (−/−) mice exhibited increased total tissue mass and total body fat (% and g) when compared to their gender matched wild-type (+/+) littermates and historical mean.

These studies suggest that mutant (−/−) non-human transgenic animals exhibit a negative phenotype that would be associated with obesity. Thus, PRO34778 polypeptides or agonists thereof are essential for normal growth and metabolic processes and especially would be important in the prevention and/or treatment of obesity.

(e) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:
Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Functional Observational Battery (FOB) Test—Stress-Induced Hyperthermia:

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

Anxiety: The (−/−) mice exhibited increased sensitivity to stress-induced hyperthermia when compared with their gender-matched (+/+) littermates and the historical mean, suggesting an increased anxiety-like response in the mutants. In summary, the functional observation testing revealed a phenotype associated with increased anxiety which could be associated with mild to moderate anxiety, anxiety due to a general medical condition, and/or bipolar disorders; hyperactivity; sensory disorders; obsessive-compulsive disorders, schizophrenia or a paranoid personality. Thus, PRO34778 polypeptides or agonists thereof would be useful in the treatment of such neurological disorders.

48.48. Generation and Analysis of Mice Comprising DNA165608 (UNQ6208) Gene Disruptions In these knockout experiments, the gene encoding PRO20233 polypeptides (designated as DNA165608) (UNQ6208) was disrupted. The gene specific information for these studies is as follows: the mutated mouse gene corresponds to nucleotide reference: NM_178257 ACCESSION: NM_178257 NID: gi 30142708 ref NM_178257.1 *Mus musculus* interleukin 22 receptor, alpha 1 (Il22ra1); protein reference: Q80XZ4 ACCESSION:Q80XZ4 NID: *Mus musculus* (Mouse). Interleukin-22 receptor alpha chain; the human gene sequence reference: NM_021258 ACCESSION:NM_021258 NID: gi 31317238 refNM_021258.2 *Homo sapiens* interleukin 22 receptor, alpha 1 (IL22RA1); the human protein sequence corresponds to reference: Q9HB22 ACCESSION:Q9HB22 NID: *Homo sapiens* (Human). IL-22 receptor.

The mouse gene of interest is Il22ra1 (interleukin 22 receptor, alpha 1), ortholog of human IL22RA1. Aliases include Il22r, IL-22R, CRF2-9, and interleukin-22 receptor alpha chain.

IL22RA1 is a type I integral plasma membrane protein that functions as a subunit of IL22 receptor complex. IL22 receptor complex consists of both IL22RA1 and interleukin 10 receptor beta (IL10RB), which bind with interleukin 22 (IL22) released by T-cells (Xie et al, *J Biol Chem* 275(40): 31335-9 (2000); Kotenko et al, *J Biol Chem* 276(4):2725-32 (2001)). Activation of the IL22 receptor complex can stimulate gene transcription through the JAK/STAT pathways and can activate several MAP kinase pathways (Xie et al, *J Biol Chem* 275(40):31335-9 (2000); Aggarwal et al, *J Interferon Cytokine Res* 21(12): 1047-53 (2001); Lejeune et al, *J Biol Chem* 277(37): 33676-82 (2002)). IL22RA1 is expressed in liver, kidney, pancreas, small intestine, colon, vascular endothelium, and skin keratinocytes (Kotenko et al, *J Biol Chem* 276(4):2725-32 (2001); Aggarwal et al, *J Interferon Cytokine Res* 21(12):1047-53 (2001); Ramesh et al, *Cancer Res* 63(16):5105-13 (2003); Wolk et al, *Immunity* 21(2):241-54 (2004). Moreover, IL22RA1 expression is upregulated in liver in response to stimulation with lipopolysaccharides (Tachiiri et al, *Genes Immun* 4(2):153-9 (2003)) and in keratinocytes in response to interferon-gamma (Wolk et al, *Immunity* 21(2):241-54 (2004)). IL22RA1 may play a role in innate immunity (Wolk et al, *Immunity* 21(2):241-54 (2004)), prevention and repair of liver injury (Radaeva et al, *Hepatology* 39(5):1332-42 (2004)), angiogenesis (Ramesh et al, *Cancer Res* 63(6):5105-13 (2003)), and apoptosis of cancer cells (Sauane et al, *J Cell Physiol* 196(2):334-45 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 17 | 37 | 13 | 67 |
| Expected | 16.75 | 33.5 | 16.75 | 67 |

Chi-Sq.=0.46 Significance=0.7945336 (hom/n)=0.23 Avg. Litter Size=7

Mutation Information

Mutation Type: Homologous Recombination (standard)

Description: Coding exons 2 through 4 were targeted (NCBI accession NM_178257.1).

1. Wild-type Expression Panel: Expression of the target gene was detected in embryonic stem (ES) cells and in all 13 adult tissue samples tested by RT-PCR, except skeletal muscle and bone.

2. QC Expression: QC Images: Disruption of the target gene was confirmed by Southern hybridization analysis.

48.48.1. Phenotypic Analysis (for Disrupted Gene: DNA165608 (UNQ6208)

(a) Overall Phenotypic Summary:

Mutation of the gene encoding the ortholog of human interleukin 22 receptor, alpha 1 (IL22RA1) resulted in small female (−/−) mice. The female homozygous mutant mice were smaller than their gender-matched wild-type littermates, exhibiting decreased body weight and length, decreased total tissue mass, and decreased lean body mass as well as decreased bone mineral content and bone mineral density measurements. Disruption of the target gene was confirmed by Southern hybridization analysis.

(b) Expression

UNQ6208 is overexpressed in pancreatic tumors. [See EXAMPLES 54 and 55 for protocol]

(c) Bone Metabolism & Body Diagnostics (1) Tissue Mass & Lean Body Mass Measurements—Dexa Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Weight: The (−/−) mice exhibited decreased mean body weight when compared with that of their (+/+) littermates and the historical mean, the difference being more notable in the females.

Length: The female (−/−) mice exhibited decreased mean body length when compared with that of their (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The female (−/−) mice exhibited notably decreased mean total tissue mass, lean body mass, bone mineral content, and bone mineral density (total body BMD, femur BMD, and vertebrae BMD) when compared with that of their gender-matched (+/+) littermates and the historical means.

Mutant female (−/−) mice deficient in the gene encoding PRO20233 polypeptides show a phenotype consistent with growth retardation, marked by decreased body weight and length and total tissue mass and lean body mass. Thus, antagonists or inhibitors of PRO20233 polypeptides or its encoding gene would mimic these metabolic and growth related effects. On the other hand, PRO20233 polypeptides or agonists thereof would be useful in the prevention and/or treatment of such metabolic disorders as diabetes or other tissue wasting diseases.

In addition, the (−/−) mice analyzed by DEXA exhibited decreased bone measurements and decreased body mass measurements when compared with their (+/+) littermates, suggestive of abnormal bone disorders. The (−/−) mice exhibited a negative bone phenotype with abnormal decreased bone measurements reflective of bone metabolic disorders. In addition, the decreased mean total tissue mass and lean body mass is indicative of a metabolic disorder related to growth retardation and tissue wasting disorders. The negative bone phenotype indicates that PRO20233 polypeptides or agonists thereof would be useful for maintaining bone homeostasis in addition to normal growth development. In addition, PRO20233 polypeptides would be useful in bone healing or for the treatment of arthritis or osteoporosis, whereas antagonists (or inhibitors) of PRO20233 polypeptides or its encoding gene would lead to abnormal or pathological bone disorders including inflammatory diseases associated with abnormal bone metabolism including arthritis, osteoporosis and osteopenia.

48.49. Generation and Analysis of Mice Comprising DNA178511-2986 (UNQ6973) Gene Disruptions In these knockout experiments, the gene encoding PRO21956 polypeptides (designated as DNA178511-2986) (UNQ6973) was disrupted. The gene specific information for these studies is as follows: the mutated mouse gene corresponds to nucleotide reference: NM_011719 *Mus musculus* wingless-type MMTV integration site 9B (Wnt9b); protein reference:O35468 Wnt-9b protein precursor (Wnt-15) (Wnt-14b) gi|18181917|dbj|BAB83866.1| Wnt14b [*Mus musculus*]; the human gene sequence reference: NM_003396 ACCESSION:NM_003396 NID: gi 17017975 refNM_003396.1 *Homo sapiens* wingless-type MMTV integration site family, member 15 (WNT15); the human protein sequence corresponds to reference: O14905 ACCESSION: O14905 NID: *Homo sapiens* (Human). WNT-15 PROTEIN PRECURSOR (WNT-14B).

The mouse gene of interest is Wnt9b (wingless-type MMTV integration site 9B), ortholog of human WNT9B (wingless-type MMTV integration site family, member 9B). Aliases include Wnt14b, Wnt15, wingless-type MMTV integration site 15, and wingless-type MMTV integration site family member 15.

WNT9B is a secreted protein that likely functions as a ligand for members of the frizzled family of G protein-coupled receptors (Katoh, *Int J Mol Med* 9(6):579-84 (2002)). The protein is expressed in most tissues during development and in kidney and brain during adulthood (Qian et al, *Genomics* 81(1):34-46 (2003); Kirikoshi et al, *Int J Oncol* 19(5):947-52 (2001); Kirikoshi and Katoh, *Int J Mol Med* 9(2):135-9 (2002)). WNT9B may play a role in embryogenesis and neuronal differentiation (Kirikoshi et al, *Int J Oncol* 19(5):947-52 (2001); Kirikoshi and Katoh, *Int J Mol Med* 9(2):135-9 (2002)). Overexpression of WNT9B may play a role in certain types of mammary cancer (Qian et al, *Genomics* 81(1):34-46 (2003)), and disruption of the WNT9B gene may cause cleft lip and palate in mice (Juriloff et al, *Birth Defects Res A Clin Mol Teratol* 73(2):103-13 (2005)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 19 | 38 | 0 | 57 |
| Expected | 14.25 | 28.5 | 14.2 | 57 |

Chi-Sq.=15.61 Significance=4.076915E-4 (hom/n)=0.09
Avg. Litter Size=8
Mutation Information
Mutation Type: Homologous Recombination (standard)
Description: Coding exons 2 through 4 were targeted (NCBI accession NM_011719.2).
1. Wild-type Expression Panel: Expression of the target gene was detected in embryonic stem (ES) cells and in all 13 adult tissue samples tested by RT-PCR, except lung; skeletal muscle; bone; and stomach, small intestine, and colon.

2. QC Expression: QC Images: Disruption of the target gene was confirmed by Southern hybridization analysis.

48.49.1. Phenotypic Analysis (for Disrupted Gene: DNA178511-2986 (UNQ6973)

(a) Overall Phenotypic Summary:

Mutation of the gene encoding the ortholog of human wingless-type MMTV integration site family, member 9B (WNT9B) resulted in lethality of (−/−) mutants. Genetic data indicate that this mutation resulted in lethality of the homozygous mutants. No notable phenotype was observed for the heterozygous mice. Disruption of the target gene was confirmed by Southern hybridization analysis.

(b) Pathology

Microscopic: At 12.5 days, 41 embryos were observed: 10 (−/−) embryos, 18 (+/−) embryos, 7 (+/+) embryos, 5 resorption moles, and 1 inconclusive. However, no structural developmental abnormalities were detected in the (−/−) embryos. Gene Expression: LacZ activity was not detected in the panel of tissues by immunohistochemical analysis.

Discussion Related to Embryonic Developmental Abnormality of Lethality:

Embryonic lethality in knockout mice usually results from various serious developmental problems including but not limited to neurodegenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

48.50. Generation and Analysis of Mice Comprising DNA269238 (UNQ8782) Gene Disruptions In these knockout experiments, the gene encoding PRO57290 polypeptides (designated as DNA269238) (UNQ8782) was disrupted. The gene specific information for these studies is as follows: the mutated mouse gene corresponds to nucleotide reference: NM_032398 ACCESSION: NM_032398 NID: gi 14161697 ref NM_032398.1 *Mus musculus* plasmalemma vesicle associated protein (Plvap); protein reference: Q99JB1 ACCESSION:Q99JB1 NID: *Mus musculus* (Mouse). PV1 protein; the human gene sequence reference: NM_031310 ACCESSION:NM_031310 NID: gi13775237 refNM_031310.1 *Homo sapiens* plasmalemma vesicle associated protein (PLVAP); the human protein sequence corresponds to reference: Q9BX97 ACCESSION: Q9BX97 NID: *Homo sapiens* (Human). PV1 protein.

The mouse gene of interest is Plvap (plasmalemma vesicle associated protein), ortholog of human PLVAP. Aliases include PV-1, MECA32, PV1, FELS, gp68, and fenestrated-endothelial linked structure protein.

PLVAP is a type II integral plasma membrane protein that is associated with both the stomatal diaphragms of caveolae, transendothelial channels, and vesiculovacuolar organelles as well as the diaphragms of endothelial fenestrae. The protein likely plays a role in the formation and structure of these diaphragms, which function as a selective barrier for solutes. PLVAP may play a role in processes such as blood brain barrier development and microvascular permeability (Hallmann et al, *Dev Dyn* 202(4):325-32 (1995); Stan et al, *Genomics* 72(3):304-13 (2001); Stan, *Am J Physiol Heart Circ Physiol* 286(4):H1347-53 (2004)). PLVAP is also expressed in a variety of endocrine and non-endocrine cells, such as pancreatic islet delta cells, neural lobe pituicytes, corpus luteal cells, germ cells within the adult seminiferous tubule, interstitial cells of the neonatal testis, and the thecal cell layer of developing follicles (Hnasko et al, *J Endocrinol* 175(3):649-61 (2002)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|          | wt   | het | hom  | Total |
|----------|------|-----|------|-------|
| Observed | 22   | 42  | 18   | 82    |
| Expected | 20.5 | 41  | 20.5 | 82    |

Chi-Sq.=1.77 Significance=0.41271418 (hom/n)=0.22 Avg. Litter Size=8
Mutation Information
Mutation Type Homologous Recombination (standard)
Description: Coding exon 1 was targeted (NCBI accession NM_032398.1).

1. Wild-type Expression Panel: Expression of the target gene was detected in embryonic stem (ES) cells and in all 13 adult tissue samples tested by RT-PCR, except bone.

2. QC Expression: QC Images: Disruption of the target gene was confirmed by Southern hybridization analysis.

48.50.1. Phenotypic Analysis (for Disrupted Gene: DNA269238 (UNQ8782)

(a) Overall Phenotypic Summary:

Mutation of the gene encoding the ortholog of human plasmalemma vesicle associated protein (PLVAP) resulted in the mutant (−/−) mice exhibiting decreased anxiety in open field testing. The mutant (−/−) mice also showed decreased mean serum glucose levels. Gene disruption was confirmed by Southern blot.

(b) Expression

UNQ8782 is overexpressed in kidney clear cell carcinoma. [See EXAMPLES 54 and 55 for protocol]

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

The female (−/−) mice exhibited an increased median sum time-in-center during open field testing when compared with their gender-matched (+/+) littermates and the historical mean, suggesting a decreased anxiety-like response in the mutants.

A notable difference was observed during open field activity testing. The female (−/−) mice exhibited an increased median sum time in the center area when compared with their gender-matched (+/+) littermates, which is indicative of a decreased anxiety-like response in the mutants. Thus, knockout mice demonstrated a phenotype consistent with depression, generalized anxiety disorders, cognitive disorders, hyperalgesia and sensory disorders and/or bipolar disorders. Thus, PRO57290 polypeptides and agonists thereof would be useful for the treatment or amelioration of the symptoms associated with depressive disorders.

(d) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:

The male (−/−) mice also exhibited a decreased mean serum glucose level which could be related to abnormal glucose metabolism and/or diabetes.

In these studies the mutant (−/−) mice showed a decreased serum glucose levels which could be due to an increased insulin sensitivity. Thus, antagonists (inhibitors) to PRO57290 polypeptides or its encoding gene would be useful in the treatment of impaired glucose homeostasis.

48.51. Generation and Analysis of Mice Comprising DNA228002 (UNQ9128) Gene Disruptions In these knockout experiments, the gene encoding PRO38465 polypeptides (designated as DNA228002) (UNQ9128) was disrupted. The gene specific information for these studies is as follows: the mutated mouse gene corresponds to nucleotide reference:NM_027209 *Mus musculus* membrane-spanning 4-domains, subfamily A, member 6B (Ms4a6b); protein reference: Q99N09 Membrane-spanning 4-domains subfamily A member 6B gi|13649409|gb|AAK37418.1|MS4A6B protein [*Mus musculus*]; the human gene sequence reference: NM_152852 *Homo sapiens* membrane-spanning 4-domains, subfamily A, member 6A (MS4A6A), transcript variant 1; the human protein sequence corresponds to reference: Q9H2W1 ACCESSION:Q9H2W1 NID: *Homo sapiens* (Human). CDA01 (MS4A6A-POLYMORPH) (MS4A6A protein).

The mouse gene of interest is Ms4a6b (membrane-spanning 4-domains, subfamily A, member 6B), ortholog of human MS4A6A (membrane-spanning 4-domains, subfamily A, member 6A). Aliases include 1810027D10Rik, CDA01, MS4A6, 4SPAN3, CD20L3, MST090, MSTP090, 4SPAN3.2, MGC22650, HAIRB-iso, MS4A6A-polymorph, CD20-like precursor, four-span transmembrane protein 3.1, and four-span transmembrane protein 3.2.

MS4A6A is an integral plasma membrane protein that likely functions as a component of a signal-transducing receptor complex. The protein consists of four transmembrane segments within a CD20/IgE Fc receptor beta subunit family domain. Proteins with this domain include cell surface receptor subunits CD20, high-affinity IgE receptor beta chain, and HTm4, which are expressed on hematopoietic cells. Variable expression of MS4A6A was evident in some B-cell, myelomonocytic, and erythroleukemia cell lines (Liang and Tedder, *Genomics* 72(2):119-27 (2001); Ishibashi et al, *Gene* 264(1):87-93 (2001)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
| --- | --- | --- | --- | --- |
| Observed | 25 | 35 | 18 | 78 |
| Expected | 19.5 | 39 | 19.5 | 78 |

Chi-Sq.=0.21 Significance=0.9003245 (hom/n)=0.25 Avg. Litter Size=9
Mutation Information
Mutation Type: Homologous Recombination (standard)
Description: Coding exons 1 through 3 were targeted (NCBI accession NM_027209.2).
1. Wild-type Expression Panel: Expression of the target gene was detected in all 26 adult tissue samples tested by RT-PCR, except bone and asthmatic lung.
2. QC Expression: Disruption of the target gene was confirmed by Southern hybridization analysis.

48.51.1. Phenotypic Analysis (for Disrupted Gene: DNA228002 (UNQ9128)

(a) Overall Phenotypic Summary:
Mutation of the gene encoding the ortholog of human membrane-spanning 4-domains, subfamily A, member 6A (MS4A6A) resulted in the (−/−) mice exhibiting decreased insulin levels accompanied by increase mean serum glucose and an impaired glucose tolerance. The mutant (−/−) mice also showed decreased skin fibroblast proliferation. Gene disruption was confirmed by Southern blot.

(b) Expression
UNQ9128 is overexpressed in ovarian tumors (serous cystadenocarcinoma including papillary). [See EXAMPLES 54 and 55 for protocol]

(c) Blood Chemistry/Glucose Tolerance
In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:
Blood Glucose Levels/Glucose Tolerance Test:
The (−/−) mice exhibited impaired glucose tolerance when compared with their gender-matched (+/+) littermates and the historical means. The (−/−) mice also exhibited an increased mean fasting serum glucose level.

These studies indicated that (−/−) mice exhibit a decreased or impaired glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefor PRO38496 polypeptides (or agonists thereof) or its encoding gene would be useful in the treatment of conditions associated with an impaired glucose homeostasis and/or various cardiovascular diseases, including diabetes.

Insulin Data:
Test Description: Lexicon Genetics uses the Cobra II Series Auto-Gamma Counting System in its clinical settings for running quantitative Insulin assays on mice.
Results:
The (−/−) mice exhibited a decreased mean serum insulin level when compared with their gender-matched (+/+) littermates and the historical mean.
Serum Glucose Levels
Results:
The homozygous (−/−) mice exhibited increased mean serum glucose levels when compared with that of their gender-matched (+/+) littermates and the historical mean.

Thus, the mutant (−/−) mice exhibited hyperglycemia which is associated with an altered glucose metabolism or diabetes. PRO38465 polypeptides or agonists thereof would be useful in maintaining normal glucose levels/metabolism and possibly useful in the treatment of diabetes. These results are consistent with the observed decrease in insulin levels in the mutant (−/−) mice.

(d) Adult Skin Cell Proliferation:
Procedure: Skin cells were isolated from 16 week old animals (2 wild type and 4 homozygous mice). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:
The female (−/−) mice exhibited a decreased mean skin fibroblast proliferation rate when compared with their gender-matched (+/+) littermates.

Thus, homozygous mutant mice demonstrated a hypo-proliferative phenotype. As suggested by these observations, antagonists or inhibitors of PRO38465 polypeptides would mimic this hypo-proliferative phenotype and could function as tumor suppressors and would be useful in decreasing abnormal cell proliferation.

48.52. Generation and Analysis of Mice Comprising DNA228199 (UNQ9638) Gene Disruptions In these knockout experiments, the gene encoding PRO38683 polypeptides (designated as DNA228199) (UNQ9638) was disrupted. The gene specific information for these studies is as follows: the mutated mouse gene corresponds to nucleotide reference: XM_357986 PREDICTED: *Mus musculus* RIKEN cDNA 1110008I14 gene (1110008I14Rik); protein reference: XP_357986 MUC16 [*Mus musculus*]; the human gene sequence reference: AF414442 *Homo sapiens* ovarian cancer related tumor marker CA125 mRNA, complete cds; the human protein sequence corresponds to reference: Q8WX17 ACCESSION: Q8WX17 NID: *Homo sapiens* (Human). Ovarian cancer related tumor marker CA125.

The mouse gene of interest is RIKEN cDNA 1110008I14 gene, ortholog of human MUC16 (mucin 16). Aliases include CA125, FLJ14303, and CA125 ovarian cancer antigen.

MUC16 is a giant integral plasma membrane glycoprotein expressed in a variety of epithelia and over-expressed in epithelial ovarian cancer cells. The protein consists of a large N-terminal extracellular segment, a transmembrane segment, and a short C-terminal cytoplasmic domain. The extracellular N-terminal segment varies in length due to alternative splicing but can consist of as many as 20,000 amino acids. This segment is heavily O-glycosylated, containing many serine and threonine residues. The extracellular segment consists of an N-terminal domain and as many as 40-60 tandem repeats of SEA domains (domain found in sea urchin sperm protein, enterokinase, agrin) near the plasma membrane. SEA domains are generally found in heavily glycosylated proteins and are likely involved in binding with carbohydrate side chains on neighboring molecules (SMART accession SM00200). The extracellular segment of MUC16 can be released into the extracellular space by proteolytic cleavage (O'Brien et al, *Tumour Biol* 22(6):348-66 (2001); O'Brien et al, *Tumour Biol* 23(3):154-69 (2002)). MUC16 is likely involved in immune suppression and reproduction, protecting the embryo from the maternal immune response. Upregulation of MUC16 in epithelial ovarian tumor cells may enable escape from cytotoxic T-cells and natural killer cells (Kui Wong et al, *J Biol Chem* 278(31):28619-34 (2003)). Moreover, MUC16 may play a role in heterotypic cell adhesion and metastasis (Rump et al, *J Biol Chem* 279(10):9190-8 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 16 | 41 | 21 | 78 |
| Expected | 19.5 | 39 | 19.5 | 78 |

Chi-Sq.=1.26 Significance=0.5325918 (hom/n)=0.22 Avg. Litter Size=9

Mutation Information

Mutation Type Homologous Recombination (standard)

Description: Coding exons 60-63 were targeted (NCBI accession XM_357986.2).

1. Wild-type Expression Panel: Expression of the target gene was detected in embryonic stem (ES) cells and in all 13 adult tissue samples tested by RT-PCR, except brain, skeletal muscle, and bone. Further RT-PCR studies showed expression in normal RNA tissue derived from (+/+) mice as follows: male (+/+) mice in heart, lung, testis and vas deferens; female (+/+) mice heart, lung, ovary/oviduct (including fallopian tube), and uterus.

2. QC Expression: Disruption of the target gene was confirmed by Southern hybridization analysis.

48.52.1. Phenotypic Analysis (for Disrupted Gene: DNA228199 (UNQ9638))

(a) Overall Phenotypic Summary:

Mutation of the gene encoding the ortholog of human mucin 16 (MUC16) resulted in the (−/−) mice exhibiting a decreased skin fibroblast proliferation rate. Gene disruption was confirmed by Southern blot.

(b) Adult Skin Cell Proliferation:

Procedure: Skin cells were isolated from 16 week old animals (2 wild type and 4 homozygous mice). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results: The female (−/−) mice exhibited a decreased mean skin fibroblast proliferation rate when compared with their gender-matched (+/+) littermates.

Thus, homozygous mutant mice demonstrated a hypo-proliferative phenotype. As suggested by these observations, antagonists or inhibitors of PRO38683 polypeptides would mimic this hypo-proliferative phenotype and could function as tumor suppressors and would be useful in decreasing abnormal cell proliferation.

48.53. Generation and Analysis of Mice Comprising DNA329632 (UNQ16168) Gene Disruptions In these knockout experiments, the gene encoding PRO85161 polypeptides (designated as DNA329632) (UNQ16168) was disrupted. The gene specific information for these studies is as follows: the mutated mouse gene corresponds to nucleotide reference: NM_027022 *Mus musculus* chemokine-like factor super family 2A (Cklfsf2a); protein reference: Q9DAR1 ACCESSION:Q9DAR1 NID: *Mus musculus* (Mouse). 1700001K04Rik protein; the human gene sequence reference: NM_144673 *Homo sapiens* chemokine-like factor super family 2 (CKLFSF2); the human protein sequence corresponds to reference: Q8TAZ6 ACCESSION: Q8TAZ6 NID: *Homo sapiens* (Human). Similar to putative (Chemokine-like factor super family 2).

The mouse gene of interest is Cklfsf2a (chemokine-like factor super family 2A), ortholog of human CKLFSF2 (chemokine-like factor super family 2). Aliases include C32, Cklf, ARR19, CKLF3, CKLF4, CKLF5, Cklf1, UCK-1, Cklfsf2-1b, 1700001K04Rik, 1700041N15Rik, 1700063K20Rik, chemokine-like factor, chemokine-like factor superfamily 2-1b, FLJ25732, MGC39436, and CKLFSF2-v2.

CKLFSF2 is an integral membrane protein expressed primarily in testis and prostate. The protein contains four transmembrane segments within a MARVEL (membrane-associating) domain. Proteins with MARVEL domains may function in membrane apposition events, such as transport vesicle biogenesis (PFAM accession PF01284). CKLFSF2 is located in the cytoplasm but translocates to the nucleus after forming a complex with androgen-activated androgen receptors. CKLFSF2 is capable of repressing androgen receptor transactivation by recruiting histone deacetylase 4. Thus, CKLFSF2 appears to function as an androgen receptor corepressor. Bioinformatic analyses suggest that CKLFSF2 is located in the plasma membrane. CKLFSF2 may be involved in cell proliferation, cell differentiation, and male reproductive processes (Xia et al, *Biochim Biophys Acta* 1591 (1-3): 163-173 (2002); Rui et al, *Mol Biol Rep* 30(4):229-37 (2003); Han et al, *Genomics* 81(6):609-17 (2003); Jeong et al, *Mol Endocrinol* 18(1):13-25 (2004)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 12 | 27 | 13 | 52 |
| Expected | 13 | 26 | 13 | 52 |

Chi-Sq.=2.41 Significance=0.29969198 (hom/n)=0.25 Avg. Litter Size=8

Mutation Information

Mutation Type: Homologous Recombination (standard)

Description: Coding exons 1 and 2 were targeted (NCBI accession NM_027022.2).

1. Wild-type Expression Panel: Expression of the target gene was detected only in brain among the 13 adult tissue samples tested by RT-PCR.

2. QC Expression: QC Images: Disruption of the target gene was confirmed by Southern hybridization analysis.

48.53.1. Phenotypic Analysis (for Disrupted Gene: DNA329632 (UNQ16168)

(a) Overall Phenotypic Summary:

Mutation of the gene encoding the ortholog of human chemokine-like factor super family 2 (CKLFSF2) resulted in the (−/−) mice exhibiting increased alkaline phosphatase levels and increased body fat. Gene disruption was confirmed by Southern blot.

(b) Phenotypic Analysis: Metabolism—Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In addition to measuring blood glucose levels the following blood chemistry tests are also routinely performed: Alkaline Phosphatase; Alanine Amino-Transferase; Albumin; Bilirubin; Phosphorous; Creatinine; BUN=Blood Urea Nitrogen; Calcium; Uric Acid; Sodium; Potassium; and Chloride. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Results:

The male (−/−) mice exhibited increased mean serum alkaline phosphatase when compared with their gender-matched (+/+) littermates and the historical means.

(c) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygous and 8 homozygous mice were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The female (−/−) mice exhibited increased mean percent total body fat and total fat mass when compared with their gender-matched (+/+) littermates and the historical means.

These studies suggest that mutant (−/−) non-human transgenic animals exhibit a negative phenotype that would be associated with obesity. Thus, PRO85161 polypeptides or agonists thereof are essential for normal growth and metabolic processes and especially would be important in the prevention and/or treatment of obesity.

Example 49

Use of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 as a hybridization Probe The following method describes use of a nucleotide sequence encoding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide as a hybridization probe.

DNA comprising the coding sequence of full-length or mature PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides as disclosed herein is employed as a probe to screen for homologous DNAs (such as those encoding naturally-occurring variants of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides) in human tissue cDNA libraries or human tissue genomic libraries.

Hybridization and washing of filters containing either library DNAs is performed under the following high stringency conditions. Hybridization of radiolabeled PRO226-, PRO257-, PRO268-, PRO290-, PRO36006-, PRO363-, PRO365-, PRO382-, PRO444-, PRO705-, PRO1071-, PRO1125-, PRO1134-, PRO1155-, PRO1281-, PRO1343-, PRO1379-, PRO1380-, PRO1387-, PRO1419-, PRO1433-, PRO1474-, PRO1550-, PRO1571-, PRO1572-, PRO1759-, PRO1904-, PRO35193-, PRO4341-, PRO4348-, PRO4369-, PRO4381-, PRO4407-, PRO4425-, PRO4985-, PRO4989-, PRO5737-, PRO5800-, PRO5993-, PRO6017-, PRO7174-, PRO9744-, PRO9821-, PRO9852-, PRO9873-, PRO10196-, PRO34778-, PRO20233-, PRO21956-, PRO57290-, PRO38465-, PRO38683- or PRO85161-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides can then be identified using standard techniques known in the art.

Example 50

Expression of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 in *E. coli*

This example illustrates preparation of an unglycosylated form of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides by recombinant expression in *E. coli*.

The DNA sequence encoding a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 protein can then be purified using a metal chelating column under conditions that allow tight binding of the protein.

PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 may be expressed in *E. coli* in a poly-His tagged form, using the following procedure. The DNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA (tonA) lon galE rpoHts (htpRts) clpP (lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1 M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 51

Expression of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 in Mammalian Cells This example illustrates preparation of a potentially glycosylated form of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide by recombinant expression in mammalian cells.

The vector, pRK5 (see EP 307,247, published Mar. 15, 1989), is employed as the expression vector. Optionally, the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 DNA is ligated into pRK5 with selected restriction enzymes to allow insertion of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 DNA using ligation methods such as described in Sambrook et al., supra. The resulting vector is called pRK5-PRO226, pRK5-PRO257, pRK5-PRO268, pRK5-PRO290, pRK5-PRO36006, pRK5-PRO363, pRK5-PRO365, pRK5-PRO382, pRK5-PRO444, pRK5-PRO705, pRK5-PRO1071, pRK5-PRO1125, pRK5-PRO1134, pRK5-PRO1155, pRK5-PRO1281, pRK5-PRO1343, pRK5-PRO1379, pRK5-PRO1380, pRK5-PRO1387, pRK5-PRO1419, pRK5-PRO1433, pRK5-PRO1474, pRK5-PRO1550, pRK5-PRO1571, pRK5-PRO1572, pRK5-PRO1759, pRK5-PRO1904, pRK5-PRO35193, pRK5-PRO4341, pRK5-PRO4348, pRK5-PRO4369, pRK5-PRO4381, pRK5-PRO4407, pRK5-PRO4425, pRK5-PRO4985, pRK5-PRO4989, pRK5-PRO5737, pRK5-PRO5800, pRK5-PRO5993, pRK5-PRO6017, pRK5-PRO7174, pRK5-PRO9744, pRK5-PRO9821, pRK5-PRO9852, pRK5-PRO9873, pRK5-PRO10196, pRK5-PRO34778, pRK5-PRO20233, pRK5-PRO21956, pRK5-PRO57290, pRK5-PRO38465, pRK5-PRO38683 or pRK5-PRO85161.

The selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO226, pRK5-PRO257, pRK5-PRO268, pRK5-PRO290, pRK5-PRO36006, pRK5-PRO363, pRK5-PRO365, pRK5-PRO382, pRK5-PRO444, pRK5-PRO705, pRK5-PRO1071, pRK5-PRO1125, pRK5-PRO1134, pRK5-PRO1155, pRK5-PRO1281, pRK5-PRO1343, pRK5-PRO1379, pRK5-PRO1380, pRK5-PRO1387, pRK5-PRO1419, pRK5-PRO1433, pRK5-PRO1474, pRK5-PRO1550, pRK5-PRO1571, pRK5-PRO1572, pRK5-PRO1759, pRK5-PRO1904, pRK5-PRO35193, pRK5-PRO4341, pRK5-PRO4348, pRK5-PRO4369, pRK5-PRO4381, pRK5-PRO4407, pRK5-PRO4425, pRK5-PRO4985, pRK5-PRO4989, pRK5-PRO5737, pRK5-PRO5800, pRK5-PRO5993, pRK5-PRO6017, pRK5-PRO7174, pRK5-PRO9744, pRK5-PRO9821, pRK5-PRO9852, pRK5-PRO9873, pRK5-PRO10196, pRK5-PRO34778, pRK5-PRO20233, pRK5-PRO21956, pRK5-PRO57290, pRK5-PRO38465, pRK5-PRO38683 or pRK5-PRO85161 DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides. The cultures containing transfected cells may undergo further incubation (in serum free medium) and the medium is tested in selected bioassays.

In an alternative technique, PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-PRO226, pRK5-PRO257, pRK5-PRO268, pRK5-PRO290, pRK5-PRO36006, pRK5-PRO363, pRK5-PRO365, pRK5-PRO382, pRK5-PRO444, pRK5-PRO705, pRK5-PRO1071, pRK5-PRO1125, pRK5-PRO1134, pRK5-PRO1155, pRK5-PRO1281, pRK5-PRO1343, pRK5-PRO1379, pRK5-PRO1380, pRK5-PRO1387, pRK5-PRO1419, pRK5-PRO1433, pRK5-PRO1474, pRK5-PRO1550, pRK5-PRO1571, pRK5-PRO1572, pRK5-PRO1759, pRK5-PRO1904, pRK5-PRO35193, pRK5-PRO4341, pRK5-PRO4348, pRK5-PRO4369, pRK5-PRO4381, pRK5-PRO4407, pRK5-PRO4425, pRK5-PRO4985, pRK5-PRO4989, pRK5-PRO5737, pRK5-PRO5800, pRK5-PRO5993, pRK5-PRO6017, pRK5-PRO7174, pRK5-PRO9744, pRK5-PRO9821, pRK5-PRO9852, pRK5-PRO9873, pRK5-PRO10196, pRK5-PRO34778, pRK5-PRO20233, pRK5-PRO21956, pRK5-PRO57290, pRK5-PRO38465, pRK5-PRO38683 or pRK5-PRO85161 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 can then be concentrated and purified by any selected method, such as dialysis and/or column chromatography.

PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 can be expressed in CHO cells. The pRK5-PRO226, pRK5-PRO257, pRK5-PRO268, pRK5-PRO290, pRK5-PRO36006, pRK5-PRO363, pRK5-PRO365, pRK5-PRO382, pRK5-PRO444, pRK5-PRO705, pRK5-PRO1071, pRK5-PRO1125, pRK5-PRO1134, pRK5-PRO1155, pRK5-PRO1281, pRK5-PRO1343, pRK5-PRO1379, pRK5-PRO1380, pRK5-PRO1387, pRK5-PRO1419, pRK5-PRO1433, pRK5-PRO1474, pRK5-PRO1550, pRK5-PRO1571, pRK5-PRO1572, pRK5-PRO1759, pRK5-PRO1904, pRK5-PRO35193, pRK5-PRO4341, pRK5-PRO4348, pRK5-PRO4369, pRK5-PRO4381, pRK5-PRO4407, pRK5-PRO4425, pRK5-PRO4985, pRK5-PRO4989, pRK5-PRO5737, pRK5-PRO5800, pRK5-PRO5993, pRK5-PRO6017, pRK5-PRO7174, pRK5-PRO9744, pRK5-PRO9821, pRK5-PRO9852, pRK5-PRO9873, pRK5-PRO10196, pRK5-PRO34778, pRK5-PRO20233, pRK5-PRO21956, pRK5-PRO57290, pRK5-PRO38465, pRK5-PRO38683 or pRK5-PRO85161 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the culture medium may be replaced with serum free medium. Preferably, the cultures are incubated for about 6 days, and then the conditioned medium is harvested. The medium containing the expressed PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 can then be concentrated and purified by any selected method.

Epitope-tagged PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 may also be expressed in host CHO cells. The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 may be subcloned out of the pRK5 vector. The subclone insert can undergo PCR to fuse in frame with a selected epitope tag such as a poly-his tag into a Baculovirus expression vector. The poly-his tagged PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 can then be concentrated and purified by any selected method, such as by $Ni^{2+}$-chelate affinity chromatography.

PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3\times10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2\times10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 52

Expression of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 in Yeast

The following method describes recombinant expression of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 in yeast.

First, yeast expression vectors are constructed for intracellular production or secretion of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 from the ADH2/GAPDH promoter. DNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 and the promoter is inserted into suitable restriction enzyme sites in the selected plasmid to direct intracellular expression of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161. For secretion, DNA encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 can be cloned into the selected plasmid, together with DNA encoding the ADH2/GAPDH promoter, a native PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 signal peptide or other mammalian signal peptide, or, for example, a yeast alpha-factor or invertase secretory signal/leader sequence, and linker sequences (if needed) for expression of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 can subsequently be isolated and purified by removing the yeast cells from the fermentation medium by centrifugation and then concentrating the medium using selected cartridge filters. The concentrate containing PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290,

Example 53

Expression of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 in Baculovirus-Infected Insect Cells

The following method describes recombinant expression of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 in Baculovirus-infected insect cells.

The sequence coding for PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 or the desired portion of the coding sequence of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO38465, PRO38683 or PRO85161 may further be purified using selected column chromatography resins.

PRO57290, PRO38465, PRO38683 or PRO85161 are pooled and dialyzed against loading buffer.

Alternatively, purification of the IgG tagged (or Fc tagged) PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 can be performed using known chromatography techniques, including for instance, Protein A or protein G column chromatography.

Example 54

Tissue Expression Profiling Using GeneExpress®

A proprietary database containing gene expression information (GeneExpress®, Gene Logic Inc., Gaithersburg, Md.) was analyzed in an attempt to identify polypeptides (and their encoding nucleic acids) whose expression is significantly upregulated in a particular tumor tissue(s) of interest as compared to other tumor(s) and/or normal tissues. Specifically, analysis of the GeneExpress® database was conducted using either software available through Gene Logic Inc., Gaithersburg, Md., for use with the GeneExpress® database or with proprietary software written and developed at Genentech, Inc. for use with the GeneExpress® database. The rating of positive hits in the analysis is based upon several criteria including, for example, tissue specificity, tumor specificity and expression level in normal essential and/or normal proliferating tissues. The following is a list of molecules whose tissue expression profile as determined from an analysis of the GeneExpress® database evidences high tissue expression and significant upregulation of expression in a specific tumor or tumors as compared to other tumor(s) and/or normal tissues and optionally relatively low expression in normal essential and/or normal proliferating tissues. Tissue expression profiling was performed on several UNQ genes the results of which are disclosed in Example 48.

Example 55

Microarray Analysis to Detect Upregulation of UNQ Genes in Cancerous Tumors

Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In one example, the specific preparation of nucleic acids for hybridization and probes, slides, and hybridization conditions are all detailed in PCT Patent Application Serial No. PCT/US01/10482, filed on Mar. 30, 2001 and which is herein incorporated by reference.

In the present example, cancerous tumors derived from various human tissues were studied for upregulated gene expression relative to cancerous tumors from different tissue types and/or non-cancerous human tissues in an attempt to identify those polypeptides which are overexpressed in a particular cancerous tumor(s). In certain experiments, cancerous human tumor tissue and non-cancerous human tumor tissue of the same tissue type (often from the same patient) were obtained and analyzed for UNQ polypeptide expression. Additionally, cancerous human tumor tissue from any of a variety of different human tumors was obtained and compared to a "universal" epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described UNQ polypeptide-encoding nucleic acid sequences were used in the creation of the microarray and RNA from various tumor tissues were used for the hybridization thereto. Below is shown the results of these experiments, demonstrating that various UNQ polypeptides of the present invention are significantly overexpressed in various human tumor tissues as compared to their normal counterpart tissue(s). Moreover, all of the molecules shown below are significantly overexpressed in their specific tumor tissue(s) as compared to in the "universal" epithelial control. As described above, these data demonstrate that the UNQ polypeptides of the present invention are useful not only as diagnostic markers for the presence of one or more cancerous tumors, but also serve as therapeutic targets for the treatment of those tumors. Microarray analysis was performed on several UNQ genes the results of which are disclosed in Example 48.

Example 56

Quantitative Analysis of UNQ mRNA Expression

In this assay, a 5' nuclease assay (for example, TaqMan®) and real-time quantitative PCR (for example, ABI Prizm 7700 Sequence Detection System® (Perkin Elmer, Applied Biosystems Division, Foster City, Calif.)), were used to find genes that are significantly overexpressed in a cancerous tumor or tumors as compared to other cancerous tumors or normal non-cancerous tissue. The 5' nuclease assay reaction is a fluorescent PCR-based technique which makes use of the 5' exonuclease activity of Taq DNA polymerase enzyme to monitor gene expression in real time. Two oligonucleotide primers (whose sequences are based upon the gene or EST sequence of interest) are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the PCR amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 7700™ Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The starting material for the screen was mRNA isolated from a variety of different cancerous tissues. The mRNA is quantitated precisely, e.g., fluorometrically. As a negative control, RNA was isolated from various normal tissues of the same tissue type as the cancerous tissues being tested.

5' nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer mRNA results to normal human mRNA results. As one Ct unit corresponds to 1 PCR cycle or approximately a 2-fold relative increase relative to normal, two units corresponds to a 4-fold relative increase, 3 units corresponds to an 8-fold relative increase and so on, one can quantitatively measure the relative fold increase in mRNA expression between two or more different tissues. Using this technique, the molecules have been identified as being significantly overexpressed in a particular tumor(s) as compared to their normal non-cancerous counterpart tissue(s) (from both the same and different tissue donors) and thus, represent excellent polypeptide targets for the diagnosis and therapy of cancer in mammals. Specific results for a UNQ gene are disclosed in Example 48.

Example 57

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [3-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:

2.0 µl 5× transcription buffer
1.0 µl DTT (100 mM)
2.0 µl NTP mix (2.5 mM: 10µ; each of 10 mM GTP, CTP & ATP+10 µl H$_2$O)
1.0 µl UTP (50 µM)
1.0 µl Rnasin
1.0 µl DNA template (1 µg)
1.0 µl H$_2$O
1.0 µl RNA polymerase (for PCR products T3=AS, T7=S, usually)

The tubes were incubated at 37° C. for one hour. 1.0 µl RQ1 DNase were added, followed by incubation at 37° C. for 15 minutes. 90 µl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1-3 µl of the probe or 5 µl of RNA Mrk III were added to 3 µl of loading buffer. After heating on a 95° C. heat block for three minutes, the probe was immediately placed on ice. The wells of gel were flushed, the sample loaded, and run at 180-250 volts for 45 minutes. The gel was wrapped in saran wrap and exposed to XAR film with an intensifying screen in −70° C. freezer one hour to overnight.

$^{33}$P-Hybridization

A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+ 975 ml SQ H$_2$O). After deproteination in 0.5 µg/ml proteinase K for 10 minutes at 37° C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-Embedded Sections

The slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes)—human embryo, or 8× proteinase K (100 µl in 250 ml Rnase buffer, 37° C., 30 minutes)—formalin tissues. Subsequent rinsing in 0.5×SSC and dehydration were performed as described above.

C. Prehybridization

The slides were laid out in a plastic box lined with Box buffer (4×SSC, 50% formamide)—saturated filter paper.

D. Hybridization $1.0 \times 10^6$ cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

E. Washes

Washing was done 2×10 minutes with 2×SSC, EDTA at room temperature (400 ml 20×SSC+16 ml 0.25M EDTA, $V_f$=4 L), followed by RNaseA treatment at 37° C. for 30 minutes (500 µl of 10 mg/ml in 250 ml Rnase buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4 L).

F. Oligonucleotides

In situ analysis was performed on a variety of DNA sequences disclosed herein. The oligonucleotides employed for these analyses were obtained so as to be complementary to the nucleic acids (or the complements thereof) as shown in the accompanying figures.

G. Results

In situ analysis was performed on a variety of DNA sequences disclosed herein the results of which are disclosed in Example 48.

Example 58

Preparation of Antibodies that Bind PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161

This example illustrates preparation of monoclonal antibodies which can specifically bind PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161.

Techniques for producing the monoclonal antibodies are known in the art and are described, for instance, in Goding, supra. Immunogens that may be employed include purified PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides, fusion proteins containing PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides, and cells expressing recombinant PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides on the cell surface. Selection of the immunogen can be made by the skilled artisan without undue experimentation.

Mice, such as Balb/c, are immunized with the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti- PRO34778, anti-PRO20233, anti-PRO21956, anti-PRO57290, anti-PRO38465, anti-PRO38683 or anti-PRO85161 antibodies.

After a suitable antibody titer has been detected, the animals "positive" for antibodies can be injected with a final intravenous injection of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161. Determination of "positive" hybridoma cells secreting the desired monoclonal antibodies against PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 is within the skill in the art.

The positive hybridoma cells can be injected intraperitoneally into syngeneic Balb/c mice to produce ascites containing the anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 59

Purification of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 Polypeptides Using Specific Antibodies Native or recombinant PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides may be purified by a variety of standard techniques in the art of protein purification. For example, pro-PRO226, pro-PRO257, pro-PRO268, pro-PRO290, pro-PRO36006, pro-PRO363, pro-PRO365, pro-PRO382, pro-PRO444, pro-PRO705, pro-PRO1071, pro-PRO1125, pro-PRO1134, pro-PRO1155, pro-PRO1281, pro-PRO1343, pro-PRO1379, pro-PRO1380, pro-PRO1387, pro-PRO1419, pro-PRO1433, pro-PRO1474, pro-PRO1550, pro-PRO1571, pro-PRO1572, pro-PRO1759, pro-PRO1904, pro-PRO35193, pro-PRO4341, pro-PRO4348, pro-PRO4369, pro-PRO4381, pro-PRO4407, pro-PRO4425, pro-PRO4985, pro-PRO4989, pro-PRO5737, pro-PRO5800, pro-PRO5993, pro-PRO6017, pro-PRO7174, pro-PRO9744, pro-PRO9821, pro-PRO9852, pro-PRO9873, pro-PRO10196, pro-PRO34778, pro-PRO20233, pro-PRO21956, pro-PRO57290, pro-PRO38465, pro-PRO38683 or pro-PRO85161 polypeptide, mature PRO226, mature PRO257, mature PRO268, mature PRO290, mature PRO36006, mature PRO363, mature PRO365, mature PRO382, mature PRO444, mature PRO705, mature PRO1071, mature PRO1125, mature PRO1134, mature PRO1155, mature PRO1281, mature PRO1343, mature PRO1379, mature PRO1380, mature PRO1387, mature PRO1419, mature PRO1433, mature PRO1474, mature PRO1550, mature PRO1571, mature PRO1572, mature PRO1759, mature PRO1904, mature PRO35193, mature PRO4341, mature PRO4348, mature PRO4369, mature PRO4381, mature PRO4407, mature PRO4425, mature PRO4985, mature PRO4989, mature PRO5737, mature PRO5800, mature PRO5993, mature PRO6017, mature PRO7174, mature PRO9744, mature PRO9821, mature PRO9852, mature PRO9873, mature PRO10196, mature PRO34778, mature PRO20233, mature PRO21956, mature PRO57290, mature PRO38465, mature PRO38683 or mature PRO85161 polypeptide, or pre-PRO226, pre-PRO257, pre-PRO268, pre-PRO290, pre-PRO36006, pre-PRO363, pre-PRO365, pre-PRO382, pre-PRO444, pre-PRO705, pre-PRO1071, pre-PRO1125, pre-PRO1134, pre-PRO1155, pre-PRO1281, pre-PRO1343, pre-PRO1379, pre-PRO1380, pre-PRO1387, pre-PRO1419, pre-PRO1433, pre-PRO1474, pre-PRO1550, pre-PRO1571, pre-PRO1572, pre-PRO1759, pre-PRO1904, pre-PRO35193, pre-PRO4341, pre-PRO4348, pre-PRO4369, pre-PRO4381, pre-PRO4407, pre-PRO4425, pre-PRO4985, pre-PRO4989, pre-PRO5737, pre-PRO5800, pre-PRO5993, pre-PRO6017, pre-PRO7174, pre-PRO9744, pre-PRO9821, pre-PRO9852, pre-PRO9873, pre-PRO10196, pre-PRO34778, pre-PRO20233, pre-PRO21956, pre-PRO57290, pre-PRO38465, pre-PRO38683 or pre-PRO85161 polypeptide is purified by immunoaffinity chromatography using antibodies specific for the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide of interest. In general, an immunoaffinity column is constructed by covalently coupling the anti-PRO226, anti-PRO257, anti-PRO268, anti-PRO290, anti-PRO36006, anti-PRO363, anti-PRO365, anti-PRO382, anti-PRO444, anti-PRO705, anti-PRO1071, anti-PRO1125, anti-PRO1134, anti-PRO1155, anti-PRO1281, anti-PRO1343, anti-PRO1379, anti-PRO1380, anti-PRO1387, anti-PRO1419, anti-PRO1433, anti-PRO1474, anti-PRO1550, anti-PRO1571, anti-PRO1572, anti-PRO1759, anti-PRO1904, anti-PRO35193, anti-PRO4341, anti-PRO4348, anti-PRO4369, anti-PRO4381, anti-PRO4407, anti-PRO4425, anti-PRO4985, anti-PRO4989, anti-PRO5737, anti-PRO5800, anti-PRO5993, anti-PRO6017, anti-PRO7174, anti-PRO9744, anti-PRO9821, anti-PRO9852, anti-PRO9873, anti-PRO10196, anti-PRO34778, anti-PRO20233, anti-PRO21956, anti-PRO57290, anti-PRO38465, anti-PRO38683 or anti-PRO85161 polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide by preparing a fraction from cells containing PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide in a soluble form. This preparation is derived by solubilization of the whole cell or of a subcellular fraction obtained via differential centrifugation by the addition of detergent or by other methods well known in the art. Alternatively, soluble polypeptide containing a signal sequence may be secreted in useful quantity into the medium in which the cells are grown.

A soluble PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide-containing preparation is passed over the immunoaffinity column, and the column is washed under conditions that allow the preferential absorbance of PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide (e.g., high ionic strength buffers in the presence of detergent). Then, the column is eluted under conditions that disrupt antibody/PRO226, antibody/PRO257, antibody/PRO268, antibody/PRO290, antibody/PRO36006, antibody/PRO363, antibody/PRO365, antibody/PRO382, antibody/PRO444, antibody/PRO705, antibody/PRO1071, antibody/PRO1125, antibody/PRO1134, antibody/PRO1155, antibody/PRO1281, antibody/PRO1343, antibody/PRO1379, antibody/PRO1380, antibody/PRO1387, antibody/PRO1419, antibody/PRO1433, antibody/PRO1474, antibody/PRO1550, antibody/PRO1571, antibody/PRO1572, antibody/PRO1759, antibody/PRO1904, antibody/PRO35193, antibody/PRO4341, antibody/PRO4348, antibody/PRO4369, antibody/PRO4381, antibody/PRO4407, antibody/PRO4425, antibody/PRO4985, antibody/PRO4989, antibody/PRO5737, antibody/PRO5800, antibody/PRO5993, antibody/PRO6017, antibody/PRO7174, antibody/PRO9744, antibody/PRO9821, antibody/PRO9852, antibody/PRO9873, antibody/PRO10196, antibody/PRO34778, antibody/PRO20233, antibody/PRO21956, antibody/PRO57290, antibody/PRO38465, antibody/PRO38683 or antibody/PRO85161 polypeptide binding (e.g., a low pH buffer such as approximately pH 2-3, or a high concentration of a chaotrope such as urea or thiocyanate ion), and PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide is collected.

Example 60

Drug Screening

This invention is particularly useful for screening compounds by using PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptides or binding fragment thereof in any of a variety of drug screening techniques. The PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or fragment. Drugs are screened against such transformed cells in competitive binding assays. Such cells, either inviable or fixed form, can be used for standard binding assays. One may measure, for example, the formation of complexes between PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or a fragment and the agent being tested. Alternatively, one can examine the diminution in complex formation between the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide and its target cell or target receptors caused by the agent being tested.

Thus, the present invention provides methods of screening for drugs or any other agents which can affect a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide-associated disease or disorder. These methods comprise contacting such an agent with an PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or fragment thereof and assaying (I) for the presence of a complex between the agent and the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or fragment, or (ii) for the presence of a complex between the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or fragment and the cell, by methods well known in the art. In such competitive binding assays, the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or fragment is typically labeled. After suitable incubation, free PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or fragment is separated from that present in bound form, and the amount of free or uncomplexed label is a measure of the ability of the particular agent to bind to PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or to interfere with the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, the peptide test compounds are reacted with PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide and washed. Bound PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide is detected by methods well known in the art. Purified PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide specifically compete with a test compound for binding to PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or fragments thereof. In this manner, the antibodies can be used to detect the presence of any peptide which shares one or more antigenic determinants with PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide.

Example 61

Rational Drug Design

The goal of rational drug design is to produce structural analogs of biologically active polypeptide of interest (i.e., a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide) or of small molecules with which they interact, e.g., agonists, antagonists, or inhibitors. Any of these examples can be used to fashion drugs which are more active or stable forms of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide or which enhance or interfere with the function of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide in vivo (c.f, Hodgson, Bio/Technology, 9: 19-21 (1991)).

In one approach, the three-dimensional structure of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide, or of a PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide-inhibitor complex, is determined by x-ray crystallography, by computer modeling or, most typically, by a combination of the two approaches. Both the shape and charges of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide must be ascertained to elucidate the structure and to determine active site(s) of the molecule. Less often, useful information regarding the structure of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may be gained by modeling based on the structure of homologous proteins. In both cases, relevant structural information is used to design analogous PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide-like molecules or to identify efficient inhibitors. Useful examples of rational drug design may include molecules which have improved activity or stability as shown by Braxton and Wells, Biochemistry, 31:7796-7801 (1992) or which act as inhibitors, agonists, or antagonists of native peptides as shown by Athauda et al., J. Biochem., 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide may be made available to perform such analytical studies as X-ray crystallography. In addition, knowledge of the PRO226, PRO257, PRO268, PRO290, PRO36006, PRO363, PRO365, PRO382, PRO444, PRO705, PRO1071, PRO1125, PRO1134, PRO1155, PRO1281, PRO1343, PRO1379, PRO1380, PRO1387, PRO1419, PRO1433, PRO1474, PRO1550, PRO1571, PRO1572, PRO1759, PRO1904, PRO35193, PRO4341, PRO4348, PRO4369, PRO4381, PRO4407, PRO4425, PRO4985, PRO4989, PRO5737, PRO5800, PRO5993, PRO6017, PRO7174, PRO9744, PRO9821, PRO9852, PRO9873, PRO10196, PRO34778, PRO20233, PRO21956, PRO57290, PRO38465, PRO38683 or PRO85161 polypeptide amino acid sequence provided herein will provide guidance to those employing computer modeling techniques in place of or in addition to x-ray crystallography.

What is claimed is:

1. A method of identifying an agent that modulates a phenotype associated with a disruption of a gene which encodes for a PRO1071 polypeptide, the method comprising:

(a) providing a non-human transgenic animal whose genome comprises a disruption of a gene which is an ortholog of a human gene that encodes for the PRO1071 polypeptide (SEQ ID NO:22) and which, compared with gender matched wild-type littermates, exhibits a phenotype associated with said gene disruption, said phenotype comprising at least one of the following physiological characteristics: decreased mean skin fibroblast proliferation rate, decreased total tissue mass, lean body mass and bone mineral content and density measurements, and increased mean serum glucose levels;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

2. The method of claim 1, wherein the phenotype associated with the gene disruption comprises a bone metabolic abnormality or disorder; a metabolic or growth related disorder; or a glucose metabolism abnormality.

3. The method of claim 2, wherein said bone metabolic abnormality or disorder is arthritis, osteoporosis or osteopenia.

4. The method of claim 2, wherein said metabolic or growth related disorder is cachexia or other tissue wasting disease.

5. The method of claim 2, wherein said glucose metabolism abnormality is diabetes.

* * * * *

UNITED STATES PATENT AND TRADEMARK OFFICE
CERTIFICATE OF CORRECTION

PATENT NO. : 8,207,396 B2  Page 1 of 1
APPLICATION NO. : 13/031009
DATED : June 26, 2012
INVENTOR(S) : Payne et al.

It is certified that error appears in the above-identified patent and that said Letters Patent is hereby corrected as shown below:

On the Title page, in the "Related U.S. Application Data": (63) please correct the related application data as follows:

-- Continuation of application Serial No. 11/814,549, filed July 23, 2007, which is a US national stage application claiming priority of international application PCT/US2006/027777, filed July 18, 2006 --

Signed and Sealed this
Twenty-eighth Day of August, 2012

David J. Kappos
*Director of the United States Patent and Trademark Office*

SEQUENCE LISTING

<160> NUMBER OF SEQ ID NOS: 185

<210> SEQ ID NO 1
<211> LENGTH: 1875
<212> TYPE: DNA
<213> ORGANISM: Homo sapiens

<400> SEQUENCE: 1

```
cccaagccag ccgagccgcc agagccgcgg gccgcggggg tgtcgcgggc         50 ccaacccag gatgctcccc tgcgcctcct gcctaccgg gtctctactg          100 ctctgggcgc tgctactgtt gctcttggga tcagcttctc ctcaggattc        150
tgaagagccc gacagctaca cggaatgcac agatggctat gagtgggacc        200
cagacagcca gcactgccgg gatgtcaacg agtgtctgac catccctgag        250
gcctgcaagg gggaaatgaa gtgcatcaac cactacgggg gctacttgtg        300
cctgccccgc tccgctgccg tcatcaacga cctacatggc gagggacccc        350
cgccaccagt gcctcccgct caacacccca accctgccc accaggctat         400 gagcccgacg atcaggacag ctgtgtggat gtggacgagt gtgcccaggc        450
cctgcacgac tgtcgcccca gccaggactg ccataacttg cctggctcct        500
atcagtgcac ctgccctgat ggttaccgca agatcgggcc cgagtgtgtg        550
gacatagacg agtgccgcta ccgctactgc cagcaccgct gcgtgaacct        600
gcctggctcc ttccgctgcc agtgcgagcc gggcttccag ctggggccta        650
acaaccgctc ctgtgttgat gtgaacgagt gtgacatggg ggccccatgc        700
gagcagcgct gcttcaactc ctatgggacc ttcctgtgtc gctgccacca        750
gggctatgag ctgcatcggg atggcttctc ctgcagtgat attgatgagt        800
gtagctactc cagctacctc tgtcagtacc gctgcgtcaa cgagccaggc        850
cgtttctcct gccactgccc acaggttac cagctgctgg ccacacgcct         900
ctgccaagac attgatgagt gtgagtctgg tgcgcaccag tgctccgagg        950
cccaaacctg tgtcaacttc catgggggct accgctgcgt ggacaccaac        1000
cgctgcgtgg agccctacat ccaggtctct gagaaccgct gtctctgccc        1050
ggcctccaac cctctatgtc gagagcagcc ttcatccatt gtgcaccgct        1100
acatgaccat cacctcggag cggagcgtgc ccgctgacgt gttccagatc        1150
caggcgacct ccgtctaccc cggtgcctac aatgcctttc agatccgtgc        1200
tggaaactcg caggggact tttacattag gcaaatcaac aacgtcagcg         1250
ccatgctggt cctcgcccgg ccggtgacgg gccccgggga gtacgtgctg        1300
```

-continued

```
gacctggaga tggtcaccat gaattccctc atgagctacc gggccagctc          1350
tgtactgagg ctcaccgtct ttgtaggggc ctacaccttc tgaggagcag          1400
gagggagcca ccctccctgc agctacccta gctgaggagc ctgttgtgag          1450
gggcagaatg agaaaggcaa taaagggaga agaaagtcc tggtggctga           1500 ggtgggcggg tcacactgca ggaagcctca ggctggggca gggtggcact          1550
tgggggggca ggccaagttc acctaaatgg gggtctctat atgttcaggc          1600 ccagggccc ccattgacag gagctgggag ctctgcacca cgagcttcag           1650
tcaccccgag aggagaggag gtaacgagga gggcggactc caggccccgg          1700
cccagagatt tggacttggc tggcttgcag gggtcctaag aaactccact          1750
ctggacagcg ccaggaggcc ctgggttcca ttcctaactc tgcctcaaac          1800
tgtacatttg ataagccct agtagttccc tgggcctgtt tttctataaa           1850
acgaggcaac tggaaaaaaa  aaaaa                                    1875

<210> SEQ ID NO 2
<211> LENGTH: 443
<212> TYPE: PRT
<213> ORGANISM: Homo sapiens

<400> SEQUENCE: 2

Met Leu Pro Cys Ala Ser Cys Leu Pro Gly Ser Leu Leu Leu Trp
  1               5                  10                  15

Ala Leu Leu Leu Leu Leu Leu Gly Ser Ala Ser Pro Gln Asp Ser
                 20                  25                  30

Glu Glu Pro Asp Ser Tyr Thr Glu Cys Thr Asp Gly Tyr Glu Trp
                 35                  40                  45

Asp Pro Asp Ser Gln His Cys Arg Asp Val Asn Glu Cys Leu Thr
                 50                  55                  60

Ile Pro Glu Ala Cys Lys Gly Glu Met Lys Cys Ile Asn His Tyr
                 65                  70                  75

Gly Gly Tyr Leu Cys Leu Pro Arg Ser Ala Ala Val Ile Asn Asp
                 80                  85                  90

Leu His Gly Glu Gly Pro Pro Pro Val Pro Pro Ala Gln His
                 95                 100                 105

Pro Asn Pro Cys Pro Pro Gly Tyr Glu Pro Asp Gln Asp Ser
                110                 115                 120

Cys Val Asp Val Asp Glu Cys Ala Gln Ala Leu His Asp Cys Arg
                125                 130                 135

Pro Ser Gln Asp Cys His Asn Leu Pro Gly Ser Tyr Gln Cys Thr
                140                 145                 150

Cys Pro Asp Gly Tyr Arg Lys Ile Gly Pro Glu Cys Val Asp Ile
                155                 160                 165

Asp Glu Cys Arg Tyr Arg Tyr Cys Gln His Arg Cys Val Asn Leu
                170                 175                 180

Pro Gly Ser Phe Arg Cys Gln Cys Glu Pro Gly Phe Gln Leu Gly
                185                 190                 195

Pro Asn Asn Arg Ser Cys Val Asp Val Asn Glu Cys Asp Met Gly
                200                 205                 210

Ala Pro Cys Glu Gln Arg Cys Phe Asn Ser Tyr Gly Thr Phe Leu
                215                 220                 225

Cys Arg Cys His Gln Gly Tyr Glu Leu His Arg Asp Gly Phe Ser
                230                 235                 240
```

```
Cys Ser Asp Ile Asp Glu Cys Ser Tyr Ser Ser Tyr Leu Cys Gln
            245                 250                 255

Tyr Arg Cys Val Asn Glu Pro Gly Arg Phe Ser Cys His Cys Pro
        260                 265                 270

Gln Gly Tyr Gln Leu Leu Ala Thr Arg Leu Cys Gln Asp Ile Asp
        275                 280                 285

Glu Cys Glu Ser Gly Ala His Gln Cys Ser Glu Ala Gln Thr Cys
        290                 295                 300

Val Asn Phe His Gly Gly Tyr Arg Cys Val Asp Thr Asn Arg Cys
        305                 310                 315

Val Glu Pro Tyr Ile Gln Val Ser Glu Asn Arg Cys Leu Cys Pro
        320                 325                 330

Ala Ser Asn Pro Leu Cys Arg Glu Gln Pro Ser Ser Ile Val His
        335                 340                 345

Arg Tyr Met Thr Ile Thr Ser Glu Arg Ser Val Pro Ala Asp Val
        350                 355                 360

Phe Gln Ile Gln Ala Thr Ser Val Tyr Pro Gly Ala Tyr Asn Ala
        365                 370                 375

Phe Gln Ile Arg Ala Gly Asn Ser Gln Gly Asp Phe Tyr Ile Arg
        380                 385                 390

Gln Ile Asn Asn Val Ser Ala Met Leu Val Leu Ala Arg Pro Val
        395                 400                 405

Thr Gly Pro Arg Glu Tyr Val Leu Asp Leu Glu Met Val Thr Met
        410                 415                 420

Asn Ser Leu Met Ser Tyr Arg Ala Ser Ser Val Leu Arg Leu Thr
        425                 430                 435

Val Phe Val Gly Ala Tyr Thr Phe
        440

<210> SEQ ID NO 3
<211> LENGTH: 2917
<212> TYPE: DNA
<213> ORGANISM: Homo sapiens

<400> SEQUENCE: 3
cccacgcgtc cggccttctc tctggacttt gcatttccat tccttttcat          50
tgacaaactg actttttta tttctttttt tccatctctg ggccagcttg           100
ggatcctagg ccgccctggg aagacatttg tgttttacac acataaggat          150
ctgtgtttgg ggtttcttct tcctcccctg acattggcat tgcttagtgg          200
ttgtgtgggg agggagacca cgtgggctca gtgcttgctt gcacttatct          250
gcctaggtac atcgaagtct tttgacctcc atacagtgat tatgcctgtc          300
atcgctggtg gtatcctggc ggccttgctc ctgctgatag ttgtcgtgct          350
ctgtctttac ttcaaaatac acaacgcgct aaaagctgca aaggaacctg          400
aagctgtggc tgtaaaaaat cacaacccag acaaggtgtg gtgggccaag          450
aacagccagg ccaaaaccat tgccacggag tcttgtcctg ccctgcagtg          500
ctgtgaagga tatagaatgt gtgccagttt tgattccctg ccaccttgct          550
gttgcgacat aaatgagggc ctctgagtta ggaaaggctc ccttctcaaa          600
gcagagccct gaagacttca atgatgtcaa tgaggccacc tgtttgtgat          650
gtgcaggcac agaagaaagg cacagctccc catcagtttc atggaaaata          700
actcagtgcc tgctgggaac cagctgctgg agatccctac agagagcttc          750
```

```
cactgggggc aacccttcca ggaaggagtt ggggagagag aaccctcact        800
gtggggaatg ctgataaacc agtcacacag ctgctctatt ctcacacaaa        850
tctacccctt gcgtggctgg aactgacgtt tccctggagg tgtccagaaa        900
gctgatgtaa cacagagcct ataaaagctg tcggtcctta aggctgccca        950
gcgccttgcc aaaatggagc ttgtaagaag gctcatgcca ttgaccctct       1000
taattctctc ctgtttggcg gagctgacaa tggcggaggc tgaaggcaat       1050
gcaagctgca cagtcagtct aggggtgcc aatatggcag agacccacaa        1100
agccatgatc ctgcaactca atcccagtga aactgcacc tggacaatag        1150 aaagaccaga aaacaaaagc atcagaatta tcttttccta tgtccagctt       1200
gatccagatg aagctgtga aagtgaaaac attaaagtct ttgacggaac        1250
ctccagcaat gggcctctgc tagggcaagt ctgcagtaaa aacgactatg       1300
ttcctgtatt tgaatcatca tccagtacat tgacgtttca aatagttact       1350
gactcagcaa gaattcaaag aactgtcttt gtcttctact acttcttctc       1400
tcctaacatc tctattccaa actgtggcgg ttacctggat accttggaag       1450
gatccttcac cagccccaat tacccaaagc cgcatcctga gctggcttat       1500
tgtgtgtggc acataccagt ggagaaagat tacaagataa aactaaactt       1550
caaagagatt ttcctagaaa tagacaaaca gtgcaaattt gattttcttg       1600
ccatctatga tggccctcc accaactctg gcctgattgg acaagtctgt        1650
ggccgtgtga ctcccacctt cgaatcgtca tcaaactctc tgactgtcgt       1700
gttgtctaca gattatgcca attcttaccg gggattttct gcttcctaca       1750
cctcaattta tgcagaaaac atcaacacta catctttaac ttgctcttct       1800
gacaggatga gagttattat aagcaaatcc tacctagagg cttttaactc       1850
taatgggaat aacttgcaac taaaagaccc aacttgcaga ccaaaattat       1900
caaatgttgt ggaattttct gtccctctta atggatgtgg tacaatcaga       1950
aaggtagaag atcagtcaat tacttacacc aatataatca cctttttctgc      2000 atcctcaact tctgaagtga tcacccgtca gaaacaactc cagattattg       2050
tgaagtgtga aatgggacat aattctacag tggagataat atacataaca       2100
gaagatgatg taatacaaag tcaaaatgca ctgggcaaat ataacaccag       2150
catggctctt tttgaatcca attcatttga aaagactata cttgaatcac       2200
catattatgt ggatttgaac caaactcttt ttgttcaagt tagtctgcac       2250
acctcagatc caaatttggt ggtgtttctt gatacctgta gagcctctcc       2300
cacctctgac tttgcatctc caacctacga cctaatcaag agtggatgta       2350
gtcgagatga aacttgtaag gtgtatccct tatttggaca ctatgggaga       2400
ttccagttta atgcctttaa attcttgaga agtatgagct ctgtgtatct       2450
gcagtgtaaa gttttgatat gtgatagcag tgaccaccag tctcgctgca       2500
atcaaggttg tgtctccaga agcaaacgag acatttcttc atataaatgg       2550
aaaacagatt ccatcatagg acccattcgt ctgaaaaggg atcgaagtgc       2600
aagtggcaat tcaggatttc agcatgaaac acatgcggaa gaaactccaa       2650
accagccttt caacagtgtg catctgtttt ccttcatggt tctagctctg       2700
aatgtggtga ctgtagcgac aatcacagtg aggcattttg taaatcaacg       2750
```

```
ggcagactac aaataccaga agctgcagaa ctattaacta acaggtccaa              2800
ccctaagtga acatgtttc tccaggatgc caaggaaat gctacctcgt               2850 ggctacacat attatgaata aatgaggaag ggcctgaaag tgacacacag              2900
gcctgcatgt aaaaaaa                                                 2917

<210> SEQ ID NO 4
<211> LENGTH: 607
<212> TYPE: PRT
<213> ORGANISM: Homo sapiens

<400> SEQUENCE: 4

Met Glu Leu Val Arg Arg Leu Met Pro Leu Thr Leu Leu Ile Leu
 1               5                  10                  15

Ser Cys Leu Ala Glu Leu Thr Met Ala Glu Ala Glu Gly Asn Ala
                20                  25                  30

Ser Cys Thr Val Ser Leu Gly Gly Ala Asn Met Ala Glu Thr His
                35                  40                  45

Lys Ala Met Ile Leu Gln Leu Asn Pro Ser Glu Asn Cys Thr Trp
                50                  55                  60

Thr Ile Glu Arg Pro Glu Asn Lys Ser Arg Ile Ile Phe Ser
                65                  70                  75

Tyr Val Gln Leu Asp Pro Asp Gly Ser Cys Glu Ser Glu Asn Ile
                80                  85                  90

Lys Val Phe Asp Gly Thr Ser Ser Asn Gly Pro Leu Leu Gly Gln
                95                  100                 105

Val Cys Ser Lys Asn Asp Tyr Val Pro Val Phe Glu Ser Ser Ser
                110                 115                 120

Ser Thr Leu Thr Phe Gln Ile Val Thr Asp Ser Ala Arg Ile Gln
                125                 130                 135

Arg Thr Val Phe Val Phe Tyr Tyr Phe Ser Pro Asn Ile Ser
                140                 145                 150

Ile Pro Asn Cys Gly Gly Tyr Leu Asp Thr Leu Glu Gly Ser Phe
                155                 160                 165

Thr Ser Pro Asn Tyr Pro Lys Pro His Pro Glu Leu Ala Tyr Cys
                170                 175                 180

Val Trp His Ile Gln Val Glu Lys Asp Tyr Lys Ile Lys Leu Asn
                185                 190                 195

Phe Lys Glu Ile Phe Leu Glu Ile Asp Lys Gln Cys Lys Phe Asp
                200                 205                 210

Phe Leu Ala Ile Tyr Asp Gly Pro Ser Thr Asn Ser Gly Leu Ile
                215                 220                 225

Gly Gln Val Cys Gly Arg Val Thr Pro Thr Phe Glu Ser Ser Ser
                230                 235                 240

Asn Ser Leu Thr Val Val Leu Ser Thr Asp Tyr Ala Asn Ser Tyr
                245                 250                 255

Arg Gly Phe Ser Ala Ser Tyr Thr Ser Ile Tyr Ala Glu Asn Ile
                260                 265                 270

Asn Thr Thr Ser Leu Thr Cys Ser Ser Asp Arg Met Arg Val Ile
                275                 280                 285

Ile Ser Lys Ser Tyr Leu Glu Ala Phe Asn Ser Gly Asn Asn
                290                 295                 300

Leu Gln Leu Lys Asp Pro Thr Cys Arg Pro Lys Leu Ser Asn Val
                305                 310                 315

Val Glu Phe Ser Val Pro Leu Asn Gly Cys Gly Thr Ile Arg Lys
```

```
                    320                 325                 330
Val Glu Asp Gln Ser Ile Thr Tyr Thr Asn Ile Ile Thr Phe Ser
                335                 340                 345
Ala Ser Ser Thr Ser Glu Val Ile Thr Arg Gln Lys Gln Leu Gln
                350                 355                 360
Ile Ile Val Lys Cys Glu Met Gly His Asn Ser Thr Val Glu Ile
                365                 370                 375
Ile Tyr Ile Thr Glu Asp Asp Val Ile Gln Ser Gln Asn Ala Leu
                380                 385                 390
Gly Lys Tyr Asn Thr Ser Met Ala Leu Phe Glu Ser Asn Ser Phe
                395                 400                 405
Glu Lys Thr Ile Leu Glu Ser Pro Tyr Val Asp Leu Asn Gln
                410                 415                 420
Thr Leu Phe Val Gln Val Ser Leu His Thr Ser Asp Pro Asn Leu
                425                 430                 435
Val Val Phe Leu Asp Thr Cys Arg Ala Ser Pro Thr Ser Asp Phe
                440                 445                 450
Ala Ser Pro Thr Tyr Asp Leu Ile Lys Ser Gly Cys Ser Arg Asp
                455                 460                 465
Glu Thr Cys Lys Val Tyr Pro Leu Phe Gly His Tyr Gly Arg Phe
                470                 475                 480
Gln Phe Asn Ala Phe Lys Phe Leu Arg Ser Met Ser Ser Val Tyr
                485                 490                 495
Leu Gln Cys Lys Val Leu Ile Cys Asp Ser Ser Asp His Gln Ser
                500                 505                 510
Arg Cys Asn Gln Gly Cys Val Ser Arg Ser Lys Arg Asp Ile Ser
                515                 520                 525
Ser Tyr Lys Trp Lys Thr Asp Ser Ile Ile Gly Pro Ile Arg Leu
                530                 535                 540
Lys Arg Asp Arg Ser Ala Ser Gly Asn Ser Gly Phe Gln His Glu
                545                 550                 555
Thr His Ala Glu Glu Thr Pro Asn Gln Pro Phe Asn Ser Val His
                560                 565                 570
Leu Phe Ser Phe Met Val Leu Ala Leu Asn Val Val Thr Val Ala
                575                 580                 585
Thr Ile Thr Val Arg His Phe Val Asn Gln Arg Ala Asp Tyr Lys
                590                 595                 600
Tyr Gln Lys Leu Gln Asn Tyr
                605

<210> SEQ ID NO 5
<211> LENGTH: 2397
<212> TYPE: DNA
<213> ORGANISM: Homo sapiens

<400> SEQUENCE: 5
gcaagcggcg aaatggcgcc ctccgggagt cttgcagttc ccctggcagt          50
cctggtgctg ttgctttggg gtgctccctg acgcacggg cggcggagca           100 acgttcgcgt catcacggac gagaactgga gagaactgct ggaaggagac          150 tgatgatag aatttatgc cccgtggtgc cctgcttgtc aaaatcttca            200
accggaatgg gaaagttttg ctgaatgggg agaagatctt gaggttaata          250
ttgcgaaagt agatgtcaca gagcagccag gactgagtgg acggtttatc          300
ataactgctc ttcctactat ttatcattgt aaagatggtg aatttaggcg          350
```

```
ctatcagggt ccaaggacta agaaggactt cataaacttt ataagtgata      400
aagagtggaa gagtattgag cccgtttcat catggtttgg tccaggttct      450
gttctgatga gtagtatgtc agcactcttt cagctatcta tgtggatcag      500
gacgtgccat aactacttta ttgaagacct tggattgcca gtgtggggat      550
catatactgt ttttgcttta gcaactctgt tttccggact gttattagga      600
ctctgtatga tatttgtggc agattgcctt tgtccttcaa aaaggcgcag      650
accacagcca tacccatacc cttcaaaaaa attattatca gaatctgcac      700
aacctttgaa aaaagtggag gaggaacaag aggcggatga agaagatgtt      750
tcagaagaag aagctgaaag taaagaagga acaaacaaag actttccaca      800
gaatgccata agacaacgct ctctgggtcc atcattggcc acagataaat      850
cctagttaaa ttttatagtt atcttaatat tatgattttg ataaaaacag      900
aagattgatc attttgtttg gtttgaagtg aactgtgact tttttgaata      950
ttgcagggtt cagtctagat tgtcattaaa ttgaagagtc tacattcaga     1000
acataaaagc actaggtata caagtttgaa atatgattta agcacagtat     1050
gatggtttaa atagttctct aattttgaa aaatcgtgcc aagcaataag     1100
atttatgtat atttgtttaa taataaccta tttcaagtct gagttttgaa     1150
aatttacatt tcccaagtat tgcattattg aggtatttaa gaagattatt     1200
ttagagaaaa atatttctca tttgatataa ttttctctg tttcactgtg     1250
tgaaaaaaag aagatatttc ccataaatgg gaagtttgcc cattgtctca     1300
agaaatgtgt atttcagtga caatttcgtg gtcttttag aggtatattc     1350
caaaatttcc ttgtattttt aggttatgca actaataaaa actaccttac     1400
attaattaat tacagttttc tacacatggt aatacaggat atgctactga     1450
tttaggaagt ttttaagttc atggtattct cttgattcca acaaagtttg     1500
attttctctt gtatttttct tacttactat gggttacatt ttttattttt     1550
caaattggat gataatttct tggaaacatt ttttatgttt tagtaaacag     1600
tatttttttg ttgtttcaaa ctgaagttta ctgagagatc catcaaattg     1650
aacaatctgt tgtaatttaa aattttggcc acttttttca gattttacat     1700
cattcttgct gaacttcaac ttgaaattgt tttttttttc tttttggatg     1750
tgaaggtgaa cattcctgat ttttgtctga tgtgaaaaag ccttggtatt     1800
ttacattttg aaaattcaaa gaagcttaat ataaaagttt gcattctact     1850
caggaaaaag catcttcttg tatatgtctt aaatgtattt ttgtcctcat     1900
atacagaaag ttcttaattg attttacagt ctgtaatgct tgatgtttta     1950
aaataataac attttatat ttttaaaag acaaacttca tattatcctg     2000
tgttctttcc tgactggtaa tattgtgtgg gatttcacag gtaaaagtca     2050
gtaggatgga acatttagt gtattttac tccttaaaga gctagaatac     2100
atagttttca ccttaaaaga aggggaaaa tcataaatac aatgaatcaa     2150
ctgaccatta cgtagtagac aatttctgta atgtccccctt ctttctaggc     2200
tctgttgctg tgtgaatcca ttagatttac agtatcgtaa tatacaagtt     2250
ttctttaaag ccctctcctt tagaatttaa aatattgtac cattaaagag     2300
tttggatgtg taacttgtga tgccttagaa aaatatccta agcacaaaat     2350
```
aaacctttct aaccacttca ttaaagctga aaaaaaaaaa aaaaaaa            2397

<210> SEQ ID NO 6
<211> LENGTH: 280
<212> TYPE: PRT
<213> ORGANISM: Homo sapiens

<400> SEQUENCE: 6

Met Ala Pro Ser Gly Ser Leu Ala Val Pro Leu Ala Val Leu Val
1               5                   10                  15

Leu Leu Leu Trp Gly Ala Pro Trp Thr His Gly Arg Arg Ser Asn
                20                  25                  30

Val Arg Val Ile Thr Asp Glu Asn Trp Arg Glu Leu Leu Glu Gly
                35                  40                  45

Asp Trp Met Ile Glu Phe Tyr Ala Pro Trp Cys Pro Ala Cys Gln
                50                  55                  60

Asn Leu Gln Pro Glu Trp Glu Ser Phe Ala Glu Trp Gly Glu Asp
                65                  70                  75

Leu Glu Val Asn Ile Ala Lys Val Asp Val Thr Glu Gln Pro Gly
                80                  85                  90

Leu Ser Gly Arg Phe Ile Ile Thr Ala Leu Pro Thr Ile Tyr His
                95                  100                 105

Cys Lys Asp Gly Glu Phe Arg Arg Tyr Gln Gly Pro Arg Thr Lys
                110                 115                 120

Lys Asp Phe Ile Asn Phe Ile Ser Asp Lys Glu Trp Lys Ser Ile
                125                 130                 135

Glu Pro Val Ser Ser Trp Phe Gly Pro Gly Ser Val Leu Met Ser
                140                 145                 150

Ser Met Ser Ala Leu Phe Gln Leu Ser Met Trp Ile Arg Thr Cys
                155                 160                 165

His Asn Tyr Phe Ile Glu Asp Leu Gly Leu Pro Val Trp Gly Ser
                170                 175                 180

Tyr Thr Val Phe Ala Leu Ala Thr Leu Phe Ser Gly Leu Leu Leu
                185                 190                 195

Gly Leu Cys Met Ile Phe Val Ala Asp Cys Leu Cys Pro Ser Lys
                200                 205                 210

Arg Arg Arg Pro Gln Pro Tyr Pro Tyr Pro Ser Lys Lys Leu Leu
                215                 220                 225

Ser Glu Ser Ala Gln Pro Leu Lys Lys Val Glu Glu Gln Glu
                230                 235                 240

Ala Asp Glu Glu Asp Val Ser Glu Glu Glu Ala Glu Ser Lys Glu
                245                 250                 255

Gly Thr Asn Lys Asp Phe Pro Gln Asn Ala Ile Arg Gln Arg Ser
                260                 265                 270

Leu Gly Pro Ser Leu Ala Thr Asp Lys Ser
                275                 280

<210> SEQ ID NO 7
<211> LENGTH: 3531
<212> TYPE: DNA
<213> ORGANISM: Homo sapiens

<400> SEQUENCE: 7
cccacgcgtc cgcccacgcg tccggctgaa cacctcttct ttggagtcag           50
ccactgatga ggcagggtcc ccacttgcag ctgcagcagc tgcagcagct           100

-continued

| | |
|---|---|
| gcagagcgct gctcctggct ggtgccactg gtgcgcacgc tgctagaccg | 150 |
| tgcctatgag ccgctggggc tgcagtgggg actgccctcc ctgccaccca | 200 |
| ccaatggcag ccccaccttc tttgaagact tccaggcttt ttgtgccaca | 250 |
| cccgaatggc gccacttcat cgacaaacag gtacagccaa ccatgtccca | 300 |
| gttcgaaatg gacacgtatg ctaagagcca cgaccttatg tcaggtttct | 350 |
| ggaatgcctg ctatgacatg cttatgagca gtgggcagcg cgccagtggg | 400 |
| gagcgcgccc agagtcgtcg ggccttccag gagctggtgc tggaacctgc | 450 |
| gcagaggcgg gcgcgcctgg aggggctacg ctacacggca gtgctgaagc | 500 |
| agcaggcaac gcagcactcc atggccctgc tgcactgggg ggcgctgtgg | 550 |
| cgccagctcg ccagcccatg tggggcctgg gcgctgaggg acactcccat | 600 |
| cccccgctgg aaactgtcca gcgccgagac atattcacgc atgcgtctga | 650 |
| agctggtgcc caaccatcac ttcgaccctc acctggaagc cagcgctctc | 700 |
| cgagacaatc tgggtgaggt tcccctgaca cccaccgagg aggcctcact | 750 |
| gcctctggca gtgaccaaag aggccaaagt gagcacccca cccgagttgc | 800 |
| tgcaggagga ccagctcggc gaggacgagc tggctgagct ggagaccccg | 850 |
| atggaggcag cagaactgga tgagcagcgt gagaagctgg tgctgtcggc | 900 |
| cgagtgccag ctggtgacgg tagtggccgt ggtcccaggg ctgctggagg | 950 |
| tcaccacaca gaatgtatac ttctacgatg gcagcactga gcgcgtggaa | 1000 |
| accgaggagg gcatcggcta tgatttccgg cgcccactgg cccagctgcg | 1050 |
| tgaggtccac ctgcggcgtt tcaacctgcg ccgttcagca cttgagctct | 1100 |
| tctttatcga tcaggccaac tacttcctca acttcccatg caaggtgggc | 1150 |
| acgaccccag tctcatctcc tagccagact ccgagacccc agcctggccc | 1200 |
| catcccaccc catacccagg tacgaaacca ggtgtactcg tggctcctgc | 1250 |
| gcctacggcc cccctctcaa ggctacctaa gcagccgctc cccccaggag | 1300 |
| atgctgcgtg cctcaggcct tacccagaaa tgggtacagc gtgagatatc | 1350 |
| caacttcgag tacttgatgc aactcaacac cattgcgggg cggacctaca | 1400 |
| atgacctgtc tcagtaccct gtgttcccct gggtcctgca ggactacgtg | 1450 |
| tccccaaccc tggacctcag caacccagcc gtcttccggg acctgtctaa | 1500 |
| gcccatcggt gtggtgaacc ccaagcatgc ccagctcgtg agggagaagt | 1550 |
| atgaaagctt tgaggaccca gcagggacca ttgacaagtt ccactatggc | 1600 |
| acccactact ccaatgcagc aggcgtgatg cactacctca tccgcgtgga | 1650 |
| gcccttcacc tccctgcacg tccagctgca aagtggccgc tttgactgct | 1700 |
| ccgaccggca gttccactcg gtggcggcag cctggcaggc acgcctggag | 1750 |
| agccctgccg atgtgaagga gctcatcccg gaattcttct actttcctga | 1800 |
| cttcctggag aaccagaacg gttttgacct gggctgtctc cagctgacca | 1850 |
| acgagaaggt aggcgatgtg gtgctacccc cgtgggccag ctctcctgag | 1900 |
| gacttcatcc agcagcaccg ccaggctctg gagtcggagt atgtgtctgc | 1950 |
| acacctacac gagtggatcg acctcatctt tggctacaag cagcgggggc | 2000 |
| cagccgccga ggaggccctc aatgtcttct attactgcac ctatgagggg | 2050 |
| gctgtagacc tggaccatgt gacagatgag cgggaacgga aggctctgga | 2100 |

-continued

| | |
|---|---|
| gggcattatc agcaactttg ggcagactcc ctgtcagctg ctgaaggagc | 2150 |
| cacatccaac tcggctctca gctgaggaag cagcccatcg ccttgcacgc | 2200 |
| ctggacacta actcacctag catcttccag cacctggacg aactcaaggc | 2250 |
| attcttcgca gaggtgactg tgagtgccag tgggctgctg gcacccaca | 2300 |
| gctggttgcc ctatgaccgc aacataagca actacttcag cttcagcaaa | 2350 |
| gaccccacca tgggcagcca caagacgcag cgactgctga gtggcccgtg | 2400 |
| ggtgccaggc agtggtgtga gtggacaagc actggcagtg cccccggatg | 2450 |
| gaaagctgct attcagcggt ggccactggg atggcagcct gcgggtgact | 2500 |
| gcactacccc gtggcaagct gttgagccag ctcagctgcc accttgatgt | 2550 |
| agtaacctgc cttgcactgg acacctgtgg catctacctc atctcaggct | 2600 |
| cccgggacac cacgtgcatg gtgtggcggc tcctgcatca gggtggtctg | 2650 |
| tcagtaggcc tggcaccaaa gcctgtgcag gtcctgtatg ggcatggggc | 2700 |
| tgcagtgagc tgtgtggcca tcagcactga acttgacatg gctgtgtctg | 2750 |
| gatctgagga tggaactgtg atcatacaca ctgtacgccg cggacagttt | 2800 |
| gtagcggcac tacggcctct gggtgccaca ttccctggac ctattttcca | 2850 |
| cctggcattg gggtccgaag gccagattgt ggtacagagc tcagcgtggg | 2900 |
| aacgtcctgg ggcccaggtc acctactcct tgcacctgta ttcagtcaat | 2950 |
| gggaagttgc gggcttcact gccctggca gagcagccta cagccctgac | 3000 |
| ggtgacagag gactttgtgt tgctgggcac cgcccagtgc gccctgcaca | 3050 |
| tcctccaact aaacacactg ctcccggccg cgcctccctt gcccatgaag | 3100 |
| gtggccatcc gcagcgtggc cgtgaccaag gagcgcagcc acgtgctggt | 3150 |
| gggcctggag gatggcaagc tcatcgtggt ggtcgcgggg cagccctctg | 3200 |
| aggtgcgcag cagccagttc gcgcggaagc tgtggcggtc ctcgcggcgc | 3250 |
| atctcccagg tgtcctcggg agagacggaa tacaaccccta ctgaggcgcg | 3300 |
| ctgaacctgg ccagtccggc tgctcgggcc ccgcccccgg caggcctggc | 3350 |
| ccgggaggcc ccgcccagaa gtcggcggga acaccccggg gtgggcagcc | 3400 |
| caggggtga gcggggccca ccctgcccag ctcaggatt ggcgggcgat | 3450 |
| gttacccct cagggattgg cgggcggaag tcccgcccct cgccggctga | 3500 |
| ggggccgccc tgagggccag cactggcgtc t | 3531 |

<210> SEQ ID NO 8
<211> LENGTH: 1003
<212> TYPE: PRT
<213> ORGANISM: Homo sapiens

<400> SEQUENCE: 8

Met Ser Gln Phe Glu Met Asp Thr Tyr Ala Lys Ser His Asp Leu
1               5                   10                  15

Met Ser Gly Phe Trp Asn Ala Cys Tyr Asp Met Leu Met Ser Ser
                20                  25                  30

Gly Gln Arg Arg Gln Trp Glu Arg Ala Gln Ser Arg Arg Ala Phe
                35                  40                  45

Gln Glu Leu Val Leu Glu Pro Ala Gln Arg Arg Ala Arg Leu Glu
                50                  55                  60

Gly Leu Arg Tyr Thr Ala Val Leu Lys Gln Gln Ala Thr Gln His
                65                  70                  75

```
Ser Met Ala Leu Leu His Trp Gly Ala Leu Trp Arg Gln Leu Ala
                 80                  85                  90

Ser Pro Cys Gly Ala Trp Ala Leu Arg Asp Thr Pro Ile Pro Arg
                 95                 100                 105

Trp Lys Leu Ser Ser Ala Glu Thr Tyr Ser Arg Met Arg Leu Lys
                110                 115                 120

Leu Val Pro Asn His His Phe Asp Pro His Leu Glu Ala Ser Ala
                125                 130                 135

Leu Arg Asp Asn Leu Gly Glu Val Pro Leu Thr Pro Thr Glu Glu
                140                 145                 150

Ala Ser Leu Pro Leu Ala Val Thr Lys Glu Ala Lys Val Ser Thr
                155                 160                 165

Pro Pro Glu Leu Leu Gln Glu Asp Gln Leu Gly Glu Asp Glu Leu
                170                 175                 180

Ala Glu Leu Glu Thr Pro Met Glu Ala Glu Leu Asp Glu Gln
                185                 190                 195

Arg Glu Lys Leu Val Leu Ser Ala Glu Cys Gln Leu Val Thr Val
                200                 205                 210

Val Ala Val Val Pro Gly Leu Leu Glu Val Thr Thr Gln Asn Val
                215                 220                 225

Tyr Phe Tyr Asp Gly Ser Thr Glu Arg Val Glu Thr Glu Glu Gly
                230                 235                 240

Ile Gly Tyr Asp Phe Arg Arg Pro Leu Ala Gln Leu Arg Glu Val
                245                 250                 255

His Leu Arg Arg Phe Asn Leu Arg Arg Ser Ala Leu Glu Leu Phe
                260                 265                 270

Phe Ile Asp Gln Ala Asn Tyr Phe Leu Asn Phe Pro Cys Lys Val
                275                 280                 285

Gly Thr Thr Pro Val Ser Ser Pro Ser Gln Thr Pro Arg Pro Gln
                290                 295                 300

Pro Gly Pro Ile Pro Pro His Thr Gln Val Arg Asn Gln Val Tyr
                305                 310                 315

Ser Trp Leu Leu Arg Leu Arg Pro Pro Ser Gln Gly Tyr Leu Ser
                320                 325                 330

Ser Arg Ser Pro Gln Glu Met Leu Arg Ala Ser Gly Leu Thr Gln
                335                 340                 345

Lys Trp Val Gln Arg Glu Ile Ser Asn Phe Glu Tyr Leu Met Gln
                350                 355                 360

Leu Asn Thr Ile Ala Gly Arg Thr Tyr Asn Asp Leu Ser Gln Tyr
                365                 370                 375

Pro Val Phe Pro Trp Val Leu Gln Asp Tyr Val Ser Pro Thr Leu
                380                 385                 390

Asp Leu Ser Asn Pro Ala Val Phe Arg Asp Leu Ser Lys Pro Ile
                395                 400                 405

Gly Val Val Asn Pro Lys His Ala Gln Leu Val Arg Glu Lys Tyr
                410                 415                 420

Glu Ser Phe Glu Asp Pro Ala Gly Thr Ile Asp Lys Phe His Tyr
                425                 430                 435

Gly Thr His Tyr Ser Asn Ala Ala Gly Val Met His Tyr Leu Ile
                440                 445                 450

Arg Val Glu Pro Phe Thr Ser Leu His Val Gln Leu Gln Ser Gly
                455                 460                 465

Arg Phe Asp Cys Ser Asp Arg Gln Phe His Ser Val Ala Ala Ala
```

```
                    470             475             480
Trp Gln Ala Arg Leu Glu Ser Pro Ala Asp Val Lys Glu Leu Ile
                485             490             495
Pro Glu Phe Phe Tyr Phe Pro Asp Phe Leu Glu Asn Gln Asn Gly
                500             505             510
Phe Asp Leu Gly Cys Leu Gln Leu Thr Asn Glu Lys Val Gly Asp
                515             520             525
Val Val Leu Pro Pro Trp Ala Ser Ser Pro Glu Asp Phe Ile Gln
                530             535             540
Gln His Arg Gln Ala Leu Glu Ser Glu Tyr Val Ser Ala His Leu
                545             550             555
His Glu Trp Ile Asp Leu Ile Phe Gly Tyr Lys Gln Arg Gly Pro
                560             565             570
Ala Ala Glu Glu Ala Leu Asn Val Phe Tyr Tyr Cys Thr Tyr Glu
                575             580             585
Gly Ala Val Asp Leu Asp His Val Thr Asp Glu Arg Glu Arg Lys
                590             595             600
Ala Leu Glu Gly Ile Ile Ser Asn Phe Gly Gln Thr Pro Cys Gln
                605             610             615
Leu Leu Lys Glu Pro His Pro Thr Arg Leu Ser Ala Glu Glu Ala
                620             625             630
Ala His Arg Leu Ala Arg Leu Asp Thr Asn Ser Pro Ser Ile Phe
                635             640             645
Gln His Leu Asp Glu Leu Lys Ala Phe Phe Ala Glu Val Thr Val
                650             655             660
Ser Ala Ser Gly Leu Leu Gly Thr His Ser Trp Leu Pro Tyr Asp
                665             670             675
Arg Asn Ile Ser Asn Tyr Phe Ser Phe Ser Lys Asp Pro Thr Met
                680             685             690
Gly Ser His Lys Thr Gln Arg Leu Leu Ser Gly Pro Trp Val Pro
                695             700             705
Gly Ser Gly Val Ser Gly Gln Ala Leu Ala Val Ala Pro Asp Gly
                710             715             720
Lys Leu Leu Phe Ser Gly Gly His Trp Asp Gly Ser Leu Arg Val
                725             730             735
Thr Ala Leu Pro Arg Gly Lys Leu Leu Ser Gln Leu Ser Cys His
                740             745             750
Leu Asp Val Val Thr Cys Leu Ala Leu Asp Thr Cys Gly Ile Tyr
                755             760             765
Leu Ile Ser Gly Ser Arg Asp Thr Thr Cys Met Val Trp Arg Leu
                770             775             780
Leu His Gln Gly Gly Leu Ser Val Gly Leu Ala Pro Lys Pro Val
                785             790             795
Gln Val Leu Tyr Gly His Gly Ala Ala Val Ser Cys Val Ala Ile
                800             805             810
Ser Thr Glu Leu Asp Met Ala Val Ser Gly Ser Glu Asp Gly Thr
                815             820             825
Val Ile Ile His Thr Val Arg Arg Gly Gln Phe Val Ala Ala Leu
                830             835             840
Arg Pro Leu Gly Ala Thr Phe Pro Gly Pro Ile Phe His Leu Ala
                845             850             855
Leu Gly Ser Glu Gly Gln Ile Val Val Gln Ser Ser Ala Trp Glu
                860             865             870
```

```
Arg Pro Gly Ala Gln Val Thr Tyr Ser Leu His Leu Tyr Ser Val
                875                 880                 885

Asn Gly Lys Leu Arg Ala Ser Leu Pro Leu Ala Glu Gln Pro Thr
            890                 895                 900

Ala Leu Thr Val Thr Glu Asp Phe Val Leu Leu Gly Thr Ala Gln
        905                 910                 915

Cys Ala Leu His Ile Leu Gln Leu Asn Thr Leu Leu Pro Ala Ala
    920                 925                 930

Pro Pro Leu Pro Met Lys Val Ala Ile Arg Ser Val Ala Val Thr
935                 940                 945

Lys Glu Arg Ser His Val Leu Val Gly Leu Glu Asp Gly Lys Leu
                950                 955                 960

Ile Val Val Val Ala Gly Gln Pro Ser Glu Val Arg Ser Ser Gln
            965                 970                 975

Phe Ala Arg Lys Leu Trp Arg Ser Ser Arg Arg Ile Ser Gln Val
        980                 985                 990

Ser Ser Gly Glu Thr Glu Tyr Asn Pro Thr Glu Ala Arg
    995                 1000
```

```
<210> SEQ ID NO 9
<211> LENGTH: 2130
<212> TYPE: DNA
<213> ORGANISM: Homo sapiens

<400> SEQUENCE: 9
```

| | | | | |
|---|---|---|---|---|
| cattgtgttg | ggcacagctc | tcactcaccc | tccggcttcc | tgtcggggct | 50 |
| ttctcagccc | caccccacgt | ttggacattt | ggagcatttc | cttccctgac | 100 |
| agccggacct | gggactgggc | tggggccctg | gcggatggag | acatgctgcc | 150 |
| cctgctgctg | ctgccccctgc | tgtggggggg | gtccctgcag | agaagccag | 200 |
| tgtacgagct | gcaagtgcag | aagtcggtga | cggtgcagga | gggcctgtgc | 250 |
| gtccttgtgc | cctgctcctt | ctcttacccc | tggagatcct | ggtattcctc | 300 |
| tcccccactc | tacgtctact | ggttccggga | cggggagatc | ccatactacg | 350 |
| ctgaggttgt | ggccacaaac | aacccagaca | gaagagtgaa | gccagagacc | 400 |
| cagggccgat | tccgcctcct | tggggatgtc | cagaagaaga | actgctccct | 450 |
| gagcatcgga | gatgccagaa | tggaggacac | gggaagctat | ttcttccgcg | 500 |
| tggagagagg | aagggatgta | aaatatagct | accaacagaa | taagctgaac | 550 |
| ttggaggtga | cagccctgat | agagaaaccc | gacatccact | ttctggagcc | 600 |
| tctggagtcc | ggccgcccca | caaggctgag | ctgcagcctt | ccaggatcct | 650 |
| gtgaagcggg | accacctctc | acattctcct | ggacggggaa | tgccctcagc | 700 |
| cccctggacc | ccgagaccac | ccgctcctcg | gagctcaccc | tcacccccag | 750 |
| gcccgaggac | catggcacca | acctcacctg | tcagatgaaa | cgccaaggag | 800 |
| ctcaggtgac | cacggagaga | actgtccagc | tcaatgtctc | ctatgctcca | 850 |
| cagaccatca | ccatcttcag | gaacggcata | gccctagaga | tcctgcaaaa | 900 |
| cacctcatac | cttccggtcc | tggagggcca | ggctctgcgg | ctgctctgtg | 950 |
| atgctcccag | caacccccct | gcacacctga | gctggttcca | gggctccctt | 1000 |
| gccctgaacg | ccaccccat | ctccaatacc | gggatcttgg | agcttcgtcg | 1050 |
| agtaaggtct | gcagaagaag | gaggcttcac | ctgccgcgct | cagcacccgc | 1100 |
| tgggcttcct | gcaaattttt | ctgaatctct | cagtttactc | cctcccacag | 1150 |

-continued

```
ttgctgggcc cctcctgctc ctgggaggct gagggtctgc actgcagatg         1200
ctcctttcga gcccggccgg ccccctccct gtgctggcgg cttgaggaga         1250
agccgctgga ggggaacagc agccagggct cattcaaggt caactccagc         1300
tcagctgggc cctgggccaa cagctccctg atcctccacg gggggctcag         1350
ctccgacctc aaagtcagct gcaaggcctg gaacatctat gggtcccaga         1400
gcggctctgt cctgctgctg caagggagat cgaacctcgg gacaggagtg         1450
gttcctgcag cccttggtgg tgctggtgtc atggccctgc tctgtatctg         1500
tctgtgcctc atcttctttt taatagtgaa agcccgcagg aagcaagcag         1550
ctgggagacc agagaaaatg gatgatgaag accccattat gggtaccatc         1600
acctcgggtt ccaggaagaa gccctggcca gacagccccg gagatcaagc         1650
atctcctcct ggggatgccc ctcccttgga agaacaaaag gagctccatt         1700
atgcctccct tagttttttct gagatgaagt cgagggagcc taaggaccag         1750
gaggccccaa gcaccacgga gtactcggag atcaagacaa gcaagtgagg         1800 attgccag agttcagtcc tggctggagg agccacagcc tgtctggggg          1850
aaaggacaag tcagggacca cttgctgaag cacgaagagc ccttgtggca         1900
atgttaacat taactgatgt ttaagtgctc caagcagagc agaaagaaaa         1950
cagatgatgg aattagagag gtgggctcaa atctaggccc tggcactgtc         2000
atcaagcaat tcactgcatc cctctgtgcc tcagtttccc attctgtaaa         2050
tcagagatca tgcatgctac ctcaaaggtt gttgtgaaca ttaaagaaat         2100
caacacatgg aaatcaaaaa aaaaaaaaa                               2130
```

<210> SEQ ID NO 10
<211> LENGTH: 551
<212> TYPE: PRT
<213> ORGANISM: Homo sapiens

<400> SEQUENCE: 10

```
Met Leu Pro Leu Leu Leu Pro Leu Leu Trp Gly Gly Ser Leu
  1               5                   10                  15

Gln Glu Lys Pro Val Tyr Glu Leu Gln Val Gln Lys Ser Val Thr
                 20                  25                  30

Val Gln Glu Gly Leu Cys Val Leu Val Pro Cys Ser Phe Ser Tyr
                 35                  40                  45

Pro Trp Arg Ser Trp Tyr Ser Ser Pro Pro Leu Tyr Val Tyr Trp
                 50                  55                  60

Phe Arg Asp Gly Glu Ile Pro Tyr Tyr Ala Glu Val Val Ala Thr
                 65                  70                  75

Asn Asn Pro Asp Arg Arg Val Lys Pro Glu Thr Gln Gly Arg Phe
                 80                  85                  90

Arg Leu Leu Gly Asp Val Gln Lys Lys Asn Cys Ser Leu Ser Ile
                 95                  100                 105

Gly Asp Ala Arg Met Glu Asp Thr Gly Ser Tyr Phe Phe Arg Val
                 110                 115                 120

Glu Arg Gly Arg Asp Val Lys Tyr Ser Tyr Gln Gln Asn Lys Leu
                 125                 130                 135

Asn Leu Glu Val Thr Ala Leu Ile Glu Lys Pro Asp Ile His Phe
                 140                 145                 150

Leu Glu Pro Leu Glu Ser Gly Arg Pro Thr Arg Leu Ser Cys Ser
```

-continued

```
                    155                 160                 165
Leu Pro Gly Ser Cys Glu Ala Gly Pro Leu Thr Phe Ser Trp
                170                 175                 180
Thr Gly Asn Ala Leu Ser Pro Leu Asp Pro Glu Thr Thr Arg Ser
                185                 190                 195
Ser Glu Leu Thr Leu Thr Pro Arg Pro Glu Asp His Gly Thr Asn
                200                 205                 210
Leu Thr Cys Gln Met Lys Arg Gln Gly Ala Gln Val Thr Thr Glu
                215                 220                 225
Arg Thr Val Gln Leu Asn Val Ser Tyr Ala Pro Gln Thr Ile Thr
                230                 235                 240
Ile Phe Arg Asn Gly Ile Ala Leu Glu Ile Leu Gln Asn Thr Ser
                245                 250                 255
Tyr Leu Pro Val Leu Glu Gly Gln Ala Leu Arg Leu Leu Cys Asp
                260                 265                 270
Ala Pro Ser Asn Pro Ala His Leu Ser Trp Phe Gln Gly Ser
                275                 280                 285
Pro Ala Leu Asn Ala Thr Pro Ile Ser Asn Thr Gly Ile Leu Glu
                290                 295                 300
Leu Arg Arg Val Arg Ser Ala Glu Glu Gly Gly Phe Thr Cys Arg
                305                 310                 315
Ala Gln His Pro Leu Gly Phe Leu Gln Ile Phe Leu Asn Leu Ser
                320                 325                 330
Val Tyr Ser Leu Pro Gln Leu Leu Gly Pro Ser Cys Ser Trp Glu
                335                 340                 345
Ala Glu Gly Leu His Cys Arg Cys Ser Phe Arg Ala Arg Pro Ala
                350                 355                 360
Pro Ser Leu Cys Trp Arg Leu Glu Glu Lys Pro Leu Glu Gly Asn
                365                 370                 375
Ser Ser Gln Gly Ser Phe Lys Val Asn Ser Ser Ser Ala Gly Pro
                380                 385                 390
Trp Ala Asn Ser Ser Leu Ile Leu His Gly Gly Leu Ser Ser Asp
                395                 400                 405
Leu Lys Val Ser Cys Lys Ala Trp Asn Ile Tyr Gly Ser Gln Ser
                410                 415                 420
Gly Ser Val Leu Leu Leu Gln Gly Arg Ser Asn Leu Gly Thr Gly
                425                 430                 435
Val Val Pro Ala Ala Leu Gly Gly Ala Gly Val Met Ala Leu Leu
                440                 445                 450
Cys Ile Cys Leu Cys Leu Ile Phe Phe Leu Ile Val Lys Ala Arg
                455                 460                 465
Arg Lys Gln Ala Ala Gly Arg Pro Glu Lys Met Asp Asp Glu Asp
                470                 475                 480
Pro Ile Met Gly Thr Ile Thr Ser Gly Ser Arg Lys Lys Pro Trp
                485                 490                 495
Pro Asp Ser Pro Gly Asp Gln Ala Ser Pro Pro Gly Asp Ala Pro
                500                 505                 510
Pro Leu Glu Glu Gln Lys Glu Leu His Tyr Ala Ser Leu Ser Phe
                515                 520                 525
Ser Glu Met Lys Ser Arg Glu Pro Lys Asp Gln Glu Ala Pro Ser
                530                 535                 540
Thr Thr Glu Tyr Ser Glu Ile Lys Thr Ser Lys
                545                 550
```

<210> SEQ ID NO 11
<211> LENGTH: 2458
<212> TYPE: DNA
<213> ORGANISM: Homo sapiens

<400> SEQUENCE: 11

| | | | | |
|---|---|---|---|---|
| gcgccgggag | cccatctgcc | cccaggggca | cggggcgcgg | ggccggctcc | 50 |
| cgcccggcac | atggctgcag | ccacctcgcg | cgcaccccga | ggcgccgcgc | 100 |
| ccagctcgcc | cgaggtccgt | cggaggcgcc | cggccgcccc | ggagccaagc | 150 |
| agcaactgag | cggggaagcg | cccgcgtccg | gggatcggga | tgtccctcct | 200 |
| ccttctcctc | ttgctagttt | cctactatgt | tggaaccttg | gggactcaca | 250 |
| ctgagatcaa | gagagtggca | gaggaaaagg | tcactttgcc | ctgccaccat | 300 |
| caactggggc | ttccagaaaa | agacactctg | gatattgaat | ggctgctcac | 350 |
| cgataatgaa | gggaaccaaa | aagtggtgat | cacttactcc | agtcgtcatg | 400 |
| tctacaataa | cttgactgag | gaacagaagg | gccgagtggc | ctttgcttcc | 450 |
| aatttcctgg | caggagatgc | ctccttgcag | attgaacctc | tgaagcccag | 500 |
| tgatgagggc | cggtacacct | gtaaggttaa | gaattcaggg | cgctacgtgt | 550 |
| ggagccatgt | catcttaaaa | gtcttagtga | gaccatccaa | gcccaagtgt | 600 |
| gagttggaag | gagagctgac | agaaggaagt | gacctgactt | gcagtgtga | 650 |
| gtcatcctct | ggcacagagc | ccattgtgta | ttactggcag | cgaatccgag | 700 |
| agaaagaggg | agaggatgaa | cgtctgcctc | ccaaatctag | gattgactac | 750 |
| aaccaccctg | gacgagttct | gctgcagaat | cttaccatgt | cctactctgg | 800 |
| actgtaccag | tgcacagcag | gcaacgaagc | tgggaaggaa | agctgtgtgg | 850 |
| tgcgagtaac | tgtacagtat | gtacaaagca | tcggcatggt | tgcaggagca | 900 |
| gtgacaggca | tagtggctgg | agcccctgctg | atttttcctct | tggtgtggct | 950 |
| gctaatccga | aggaaagaca | agaaagata | tgaggaagaa | gagagaccta | 1000 |
| atgaaattcg | agaagatgct | gaagctccaa | aagcccgtct | tgtgaaaccc | 1050 |
| agctcctctt | cctcaggctc | tcggagctca | cgctctggtt | cttcctccac | 1100 |
| tcgctccaca | gcaaatagtg | cctcacgcag | ccagcggaca | ctgtcaactg | 1150 |
| acgcagcacc | ccagccaggg | ctggccaccc | aggcatacag | cctagtgggg | 1200 |
| ccagaggtga | gaggttctga | accaaagaaa | gtccaccatg | ctaatctgac | 1250 |
| caaagcagaa | accacaccca | gcatgatccc | cagccagagc | agagccttcc | 1300 |
| aaacggtctg | aattacaatg | gacttgactc | ccacgctttc | ctaggagtca | 1350 |
| gggtctttgg | actcttctcg | tcattggagc | tcaagtcacc | agccacacaa | 1400 |
| ccagatgaga | ggtcatctaa | gtagcagtga | gcattgcacg | gaacagattc | 1450 |
| agatgagcat | tttccttata | caataccaaa | caagcaaaag | gatgtaagct | 1500 |
| gattcatctg | taaaaaggca | tcttattgtg | cctttagacc | agagtaaggg | 1550 |
| aaagcaggag | tccaaatcta | tttgttgacc | aggacctgtg | gtgagaaggt | 1600 |
| tggggaaagg | tgaggtgaat | atacctaaaa | cttttaatgt | gggatatttt | 1650 |
| gtatcagtgc | tttgattcac | aattttcaag | aggaaatggg | atgctgtttg | 1700 |
| taaatttttct | atgcatttct | gcaaacttat | tggattatta | gttattcaga | 1750 |
| cagtcaagca | gaacccacag | ccttattaca | cctgtctaca | ccatgtactg | 1800 |

-continued

```
agctaaccac ttctaagaaa ctccaaaaaa ggaaacatgt gtcttctatt       1850
ctgacttaac ttcatttgtc ataaggtttg gatattaatt tcaaggggag       1900
ttgaaatagt gggagatgga gaagagtgaa tgagtttctc ccactctata       1950
ctaatctcac tatttgtatt gagcccaaaa taactatgaa aggagacaaa       2000
aatttgtgac aaaggattgt gaagagcttt ccatcttcat gatgttatga       2050
ggattgttga caaacattag aaatatataa tggagcaatt gtggatttcc       2100
cctcaaatca gatgcctcta aggactttcc tgctagatat ttctggaagg       2150
agaaaataca acatgtcatt tatcaacgtc cttagaaaga attcttctag       2200
agaaaaaggg atctaggaat gctgaaagat tacccaacat accattatag       2250
tctcttcttt ctgagaaaat gtgaaaccag aattgcaaga ctgggtggac       2300
tagaaaggga gattagatca gttttctctt aatatgtcaa ggaaggtagc       2350
cgggcatggt gccaggcacc tgtaggaaaa tccagcaggt ggaggttgca       2400
gtgagccgag attatgccat tgcactccag cctgggtgac agagcgggac       2450
tccgtctc                                                     2458
```

<210> SEQ ID NO 12
<211> LENGTH: 373
<212> TYPE: PRT
<213> ORGANISM: Homo sapiens

<400> SEQUENCE: 12

```
Met Ser Leu Leu Leu Leu Leu Leu Val Ser Tyr Tyr Val Gly
  1               5                  10                  15

Thr Leu Gly Thr His Thr Glu Ile Lys Arg Val Ala Glu Glu Lys
             20                  25                  30

Val Thr Leu Pro Cys His His Gln Leu Gly Leu Pro Glu Lys Asp
             35                  40                  45

Thr Leu Asp Ile Glu Trp Leu Leu Thr Asp Asn Glu Gly Asn Gln
             50                  55                  60

Lys Val Val Ile Thr Tyr Ser Ser Arg His Val Tyr Asn Asn Leu
             65                  70                  75

Thr Glu Glu Gln Lys Gly Arg Val Ala Phe Ala Ser Asn Phe Leu
             80                  85                  90

Ala Gly Asp Ala Ser Leu Gln Ile Glu Pro Leu Lys Pro Ser Asp
             95                 100                 105

Glu Gly Arg Tyr Thr Cys Lys Val Lys Asn Ser Gly Arg Tyr Val
            110                 115                 120

Trp Ser His Val Ile Leu Lys Val Leu Val Arg Pro Ser Lys Pro
            125                 130                 135

Lys Cys Glu Leu Glu Gly Glu Leu Thr Glu Gly Ser Asp Leu Thr
            140                 145                 150

Leu Gln Cys Glu Ser Ser Ser Gly Thr Glu Pro Ile Val Tyr Tyr
            155                 160                 165

Trp Gln Arg Ile Arg Glu Lys Glu Gly Glu Asp Glu Arg Leu Pro
            170                 175                 180

Pro Lys Ser Arg Ile Asp Tyr Asn His Pro Gly Arg Val Leu Leu
            185                 190                 195

Gln Asn Leu Thr Met Ser Tyr Ser Gly Leu Tyr Gln Cys Thr Ala
            200                 205                 210

Gly Asn Glu Ala Gly Lys Glu Ser Cys Val Val Arg Val Thr Val
            215                 220                 225
```

| | | | | | | | | | | |
|---|---|---|---|---|---|---|---|---|---|---|
| Gln | Tyr | Val | Gln | Ser | Ile | Gly | Met | Val | Ala | Gly | Ala | Val | Thr | Gly |
| | | | 230 | | | | 235 | | | | | | 240 | |
| Ile | Val | Ala | Gly | Ala | Leu | Leu | Ile | Phe | Leu | Leu | Val | Trp | Leu | Leu |
| | | | 245 | | | | 250 | | | | | | 255 | |
| Ile | Arg | Arg | Lys | Asp | Lys | Glu | Arg | Tyr | Glu | Glu | Glu | Glu | Arg | Pro |
| | | | 260 | | | | 265 | | | | | | 270 | |
| Asn | Glu | Ile | Arg | Glu | Asp | Ala | Glu | Ala | Pro | Lys | Ala | Arg | Leu | Val |
| | | | 275 | | | | 280 | | | | | | 285 | |
| Lys | Pro | Ser | Ser | Ser | Ser | Gly | Ser | Arg | Ser | Ser | Arg | Ser | Gly |
| | | | 290 | | | | 295 | | | | | | 300 | |
| Ser | Ser | Ser | Thr | Arg | Ser | Thr | Ala | Asn | Ser | Ala | Ser | Arg | Ser | Gln |
| | | | 305 | | | | 310 | | | | | | 315 | |
| Arg | Thr | Leu | Ser | Thr | Asp | Ala | Ala | Pro | Gln | Pro | Gly | Leu | Ala | Thr |
| | | | 320 | | | | 325 | | | | | | 330 | |
| Gln | Ala | Tyr | Ser | Leu | Val | Gly | Pro | Glu | Val | Arg | Gly | Ser | Glu | Pro |
| | | | 335 | | | | 340 | | | | | | 345 | |
| Lys | Lys | Val | His | His | Ala | Asn | Leu | Thr | Lys | Ala | Glu | Thr | Thr | Pro |
| | | | 350 | | | | 355 | | | | | | 360 | |
| Ser | Met | Ile | Pro | Ser | Gln | Ser | Arg | Ala | Phe | Gln | Thr | Val |
| | | | 365 | | | | 370 | | | | | | | |

<210> SEQ ID NO 13
<211> LENGTH: 963
<212> TYPE: DNA
<213> ORGANISM: Homo sapiens

<400> SEQUENCE: 13

```
gcggcacctg gaagatgcgc ccattggctg gtggcctgct caaggtggtg         50
ttcgtggtct tcgcctcctt gtgtgcctgg tattcggggt acctgctcgc         100
agagctcatt ccagatgcac ccctgtccag tgctgcctat agcatccgca         150
gcatcgggga gaggcctgtc ctcaaagctc cagtccccaa aaggcaaaaa         200
tgtgaccact ggactccctg cccatctgac acctatgcct acaggttact         250
cagcggaggt ggcagaagca agtacgccaa atctgctttt gaggataacc         300
tacttatggg agaacagctg ggaaatgttg ccagaggaat aaacattgcc         350
attgtcaact atgtaactgg gaatgtgaca gcaacacgat gttttgatat         400
gtatgaaggc gataactctg gaccgatgac aaagtttatt cagagtgctg         450
ctccaaaatc cctgctcttc atggtgacct atgacgacgg aagcacaaga         500
ctgaataacg atgccaagaa tgccatagaa gcacttggaa gtaaagaaat         550
caggaacatg aaaattcaggt ctagctgggt atttattgca gcaaaaggct         600
tggaactccc ttccgaaatt cagagagaaa agatcaacca ctctgatgct         650
aagaacaaca gatattctgg ctggcctgca gagatccaga tagaaggctg         700
catacccaaa gaacgaagct gacactgcag ggtcctgagt aaatgtgttc         750
tgtataaaca aatgcagctg gaatcgctca agaatcttat ttttctaaat         800
ccaacagccc atatttgatg agtatttttgg gtttgttgta aaccaatgaa         850
catttgctag ttgtatcaaa tcttggtacg cagtattttt ataccagtat         900
tttatgtagt gaagatgtca attagcagga aactaaaatg aatggaaatt         950
cttaaaaaaa aaa                                                963
```

-continued

<210> SEQ ID NO 14
<211> LENGTH: 235
<212> TYPE: PRT
<213> ORGANISM: Homo sapiens

<400> SEQUENCE: 14

```
Met Arg Pro Leu Ala Gly Gly Leu Leu Lys Val Val Phe Val Val
 1               5                  10                  15

Phe Ala Ser Leu Cys Ala Trp Tyr Ser Gly Tyr Leu Leu Ala Glu
                20                  25                  30

Leu Ile Pro Asp Ala Pro Leu Ser Ser Ala Ala Tyr Ser Ile Arg
                35                  40                  45

Ser Ile Gly Glu Arg Pro Val Leu Lys Ala Pro Val Pro Lys Arg
                50                  55                  60

Gln Lys Cys Asp His Trp Thr Pro Cys Pro Ser Asp Thr Tyr Ala
                65                  70                  75

Tyr Arg Leu Leu Ser Gly Gly Arg Ser Lys Tyr Ala Lys Ile
                80                  85                  90

Cys Phe Glu Asp Asn Leu Leu Met Gly Glu Gln Leu Gly Asn Val
                95                 100                 105

Ala Arg Gly Ile Asn Ile Ala Ile Val Asn Tyr Val Thr Gly Asn
               110                 115                 120

Val Thr Ala Thr Arg Cys Phe Asp Met Tyr Glu Gly Asp Asn Ser
               125                 130                 135

Gly Pro Met Thr Lys Phe Ile Gln Ser Ala Ala Pro Lys Ser Leu
               140                 145                 150

Leu Phe Met Val Thr Tyr Asp Asp Gly Ser Thr Arg Leu Asn Asn
               155                 160                 165

Asp Ala Lys Asn Ala Ile Glu Ala Leu Gly Ser Lys Glu Ile Arg
               170                 175                 180

Asn Met Lys Phe Arg Ser Ser Trp Val Phe Ile Ala Ala Lys Gly
               185                 190                 195

Leu Glu Leu Pro Ser Glu Ile Gln Arg Glu Lys Ile Asn His Ser
               200                 205                 210

Asp Ala Lys Asn Asn Arg Tyr Ser Gly Trp Pro Ala Glu Ile Gln
               215                 220                 225

Ile Glu Gly Cys Ile Pro Lys Glu Arg Ser
               230                 235
```

<210> SEQ ID NO 15
<211> LENGTH: 2412
<212> TYPE: DNA
<213> ORGANISM: Homo sapiens

<400> SEQUENCE: 15

| | | | | | |
|---|---|---|---|---|---|
| atgggaagcc | agtaacactg | tggcctacta | tctcttccgt | ggtgccatct | 50 |
| acattttttgg | gactcgggaa | ttatgaggta | gaggtggagg | cggagccgga | 100 |
| tgtcagaggt | cctgaaatag | tcaccatggg | ggaaaatgat | ccgcctgctg | 150 |
| ttgaagcccc | cttctcattc | cgatcgcttt | ttggccttga | tgatttgaaa | 200 |
| ataagtcctg | ttgcaccaga | tgcagatgct | gttgctgcac | agatcctgtc | 250 |
| actgctgcca | ttgaagtttt | ttccaatcat | cgtcattggg | atcattgcat | 300 |
| tgatattagc | actggccatt | ggtctgggca | tccacttcga | ctgctcaggg | 350 |
| aagtacagat | gtcgctcatc | ctttaagtgt | atcgagctga | tagctcgatg | 400 |
| tgacggagtc | tcggattgca | aagacgggga | ggacgagtac | cgctgtgtcc | 450 |

-continued

```
gggtgggtgg tcagaatgcc gtgctccagg tgttcacagc tgcttcgtgg       500
aagaccatgt gctccgatga ctggaagggt cactacgcaa atgttgcctg       550
tgcccaactg ggtttcccaa gctatgtgag ttcagataac ctcagagtga       600
gctcgctgga ggggcagttc cgggaggagt ttgtgtccat cgatcacctc       650
ttgccagatg acaaggtgac tgcattacac cactcagtat atgtgaggga       700
gggatgtgcc tctggccacg tggttacctt gcagtgcaca gcctgtggtc       750
atagaagggg ctacagctca cgcatcgtgg gtggaaacat gtccttgctc       800
tcgcagtggc cctggcaggc cagccttcag ttccagggct accacctgtg       850
cgggggctct gtcatcacgc ccctgtggat catcactgct gcacactgtg       900
tttatgactt gtacctcccc aagtcatgga ccatccaggt gggtctagtt       950
tccctgttgg acaatccagc cccatccac ttggtggaga agattgtcta       1000
ccacagcaag tacaagccaa agaggctggg caatgacatc gcccttatga       1050
agctggccgg gccactcacg ttcaatgaaa tgatccagcc tgtgtgcctg       1100
cccaactctg aagagaactt ccccgatgga aaagtgtgct ggacgtcagg       1150
atggggggcc acagaggatg gaggtgacgc ctcccctgtc ctgaaccacg       1200
cggccgtccc tttgatttcc aacaagatct gcaaccacag ggacgtgtac       1250
ggtggcatca tctccccctc catgctctgc gcgggctacc tgacgggtgg       1300
cgtggacagc tgccaggggg acagcggggg gcccctggtg tgtcaagaga       1350
ggaggctgtg gaagttagtg ggagcgacca gctttggcat cggctgcgca       1400
gaggtgaaca gcctggggt gtacacccgt gtcacctcct tcctggactg       1450
gatccacgag cagatggaga gagacctaaa aacctgaaga ggaaggggac       1500
aagtagccac ctgagttcct gaggtgatga agacagcccg atcctcccct       1550
ggactcccgt gtaggaacct gcacacgagc agacacccett ggagctctga       1600
gttccggcac cagtagcagg cccgaaagag gcacccttcc atctgattcc       1650
agcacaacct tcaagctgct ttttgttttt tgttttttg aggtggagtc       1700
tcgctctgtt gcccaggctg gagtgcagtg gcgaaatccc tgctcactgc       1750
agcctccgct tccctggttc aagcgattct cttgcctcag cttccccagt       1800
agctgggacc acaggtgccc gccaccacac ccaactaatt tttgtatttt       1850
tagtagagac agggtttcac catgttggcc aggctgctct caaacccctg       1900
acctcaaatg atgtgcctgc ttcagcctcc cacagtgctg ggattacagg       1950
catgggccac cacgcctagc ctcacgctcc tttctgatct tcactaagaa       2000
caaaagaagc agcaacttgc aagggcggcc tttcccactg gtccatctgg       2050
ttttctctcc agggtcttgc aaaattcctg acgagataag cagttatgtg       2100
acctcacgtg caaagccacc aacagccact cagaaaagac gcaccagccc       2150
agaagtgcag aactgcagtc actgcacgtt ttcatctcta gggaccagaa       2200
ccaaacccac cctttctact tccaagactt attttcacat gtggggaggt       2250
taatctagga atgactcgtt taaggcctat tttcatgatt tctttgtagc       2300
atttggtgct tgacgtatta ttgtcctttg attccaaata atatgtttcc       2350
ttccctcatt gtctggcgtg tctgcgtgga ctggtgacgt gaatcaaaat       2400
catccactga aa                                              2412
```

<210> SEQ ID NO 16
<211> LENGTH: 453
<212> TYPE: PRT
<213> ORGANISM: Homo sapiens

<400> SEQUENCE: 16

```
Met Gly Glu Asn Asp Pro Pro Ala Val Glu Ala Pro Phe Ser Phe
 1               5                  10                  15

Arg Ser Leu Phe Gly Leu Asp Asp Leu Lys Ile Ser Pro Val Ala
                20                  25                  30

Pro Asp Ala Asp Ala Val Ala Ala Gln Ile Leu Ser Leu Leu Pro
                35                  40                  45

Leu Lys Phe Phe Pro Ile Ile Val Ile Gly Ile Ala Leu Ile
                50                  55                  60

Leu Ala Leu Ala Ile Gly Leu Gly Ile His Phe Asp Cys Ser Gly
                65                  70                  75

Lys Tyr Arg Cys Arg Ser Ser Phe Lys Cys Ile Glu Leu Ile Ala
                80                  85                  90

Arg Cys Asp Gly Val Ser Asp Cys Lys Asp Gly Glu Asp Glu Tyr
                95                 100                 105

Arg Cys Val Arg Val Gly Gly Gln Asn Ala Val Leu Gln Val Phe
               110                 115                 120

Thr Ala Ala Ser Trp Lys Thr Met Cys Ser Asp Asp Trp Lys Gly
               125                 130                 135

His Tyr Ala Asn Val Ala Cys Ala Gln Leu Gly Phe Pro Ser Tyr
               140                 145                 150

Val Ser Ser Asp Asn Leu Arg Val Ser Ser Leu Glu Gly Gln Phe
               155                 160                 165

Arg Glu Glu Phe Val Ser Ile Asp His Leu Leu Pro Asp Asp Lys
               170                 175                 180

Val Thr Ala Leu His His Ser Val Tyr Val Arg Glu Gly Cys Ala
               185                 190                 195

Ser Gly His Val Val Thr Leu Gln Cys Thr Ala Cys Gly His Arg
               200                 205                 210

Arg Gly Tyr Ser Ser Arg Ile Val Gly Gly Asn Met Ser Leu Leu
               215                 220                 225

Ser Gln Trp Pro Trp Gln Ala Ser Leu Gln Phe Gln Gly Tyr His
               230                 235                 240

Leu Cys Gly Gly Ser Val Ile Thr Pro Leu Trp Ile Ile Thr Ala
               245                 250                 255

Ala His Cys Val Tyr Asp Leu Tyr Leu Pro Lys Ser Trp Thr Ile
               260                 265                 270

Gln Val Gly Leu Val Ser Leu Leu Asp Asn Pro Ala Pro Ser His
               275                 280                 285

Leu Val Glu Lys Ile Val Tyr His Ser Lys Tyr Lys Pro Lys Arg
               290                 295                 300

Leu Gly Asn Asp Ile Ala Leu Met Lys Leu Ala Gly Pro Leu Thr
               305                 310                 315

Phe Asn Glu Met Ile Gln Pro Val Cys Leu Pro Asn Ser Glu Glu
               320                 325                 330

Asn Phe Pro Asp Gly Lys Val Cys Trp Thr Ser Gly Trp Gly Ala
               335                 340                 345

Thr Glu Asp Gly Gly Asp Ala Ser Pro Val Leu Asn His Ala Ala
               350                 355                 360
```

```
Val Pro Leu Ile Ser Asn Lys Ile Cys Asn His Arg Asp Val Tyr
            365                 370                 375

Gly Gly Ile Ile Ser Pro Ser Met Leu Cys Ala Gly Tyr Leu Thr
            380                 385                 390

Gly Gly Val Asp Ser Cys Gln Gly Asp Ser Gly Gly Pro Leu Val
            395                 400                 405

Cys Gln Glu Arg Arg Leu Trp Lys Leu Val Gly Ala Thr Ser Phe
            410                 415                 420

Gly Ile Gly Cys Ala Glu Val Asn Lys Pro Gly Val Tyr Thr Arg
            425                 430                 435

Val Thr Ser Phe Leu Asp Trp Ile His Glu Gln Met Glu Arg Asp
            440                 445                 450

Leu Lys Thr

<210> SEQ ID NO 17
<211> LENGTH: 1218
<212> TYPE: DNA
<213> ORGANISM: Homo sapiens

<400> SEQUENCE: 17
cccacgcgtc cggcgccgtg gcctcgcgtc catctttgcc gttctctcgg          50
acctgtcaca aaggagtcgc gccgccgccg ccgcccctc cctccggtgg          100 gcccgggagg tagagaaagt cagtgccaca gcccgaccgc gctgctctga          150
gccctgggca cgcggaacgg gagggagtct gagggttggg gacgtctgtg          200
agggagggga acagccgctc gagcctgggg cgggcggacc ggactggggc          250
cggggtaggc tctggaaagg gcccgggaga gaggtggcgt tggtcagaac          300
ctgagaaaca gccgagaggt tttccaccga ggcccgcgct tgagggatct          350
gaagaggttc ctagaagagg gtgttccctc tttcggggt cctcaccaga          400 agaggttctt gggggtcgcc cttctgagga ggctgcggct aacagggccc          450
agaactgcca ttggatgtcc agaatcccct gtagttgata atgttgggaa          500
taagctctgc aactttcttt ggcattcagt tgttaaaaac aaataggatg          550
caaattcctc aactccaggt tatgaaaaca gtacttggaa aactgaaaac          600
tacctaaatg atcgtctttg gttgggccgt gttcttagcg agcagaagcc          650
ttggccaggg tctgttgttg actctcgaag agcacatagc ccacttccta          700
gggactggag gtgccgctac taccatgggt aattcctgta tctgccgaga          750
tgacagtgga acagatgaca gtgttgacac ccaacagcaa caggccgaga          800
acagtgcagt acccactgct gacacaagga gccaaccacg ggaccctgtt          850
cggccaccaa ggaggggccg aggacctcat gagccaagga gaaagaaaca          900
aaatgtggat gggctagtgt tggacacact ggcagtaata cggactcttg          950
tagataagta agtatctgac tcacggtcac ctccagtgga atgaaaagtg          1000
ttctgcccgg aaccatgact ttaggactcc ttcagttcct ttaggacata          1050
ctcgccaagc cttgtgctca cagggcaaag gagaatattt taatgctccg          1100
ctgatggcag agtaaatgat aagatttgat gtttttgctt gctgtcatct          1150
actttgtctg gaaatgtcta aatgtttctg tagcagaaaa cacgataaag          1200
ctatgatctt tattagag                                             1218
```

```
<210> SEQ ID NO 18
<211> LENGTH: 117
<212> TYPE: PRT
<213> ORGANISM: Homo sapiens

<400> SEQUENCE: 18

Met Ile Val Phe Gly Trp Ala Val Phe Leu Ala Ser Arg Ser Leu
 1               5                  10                  15

Gly Gln Gly Leu Leu Leu Thr Leu Glu Glu His Ile Ala His Phe
             20                  25                  30

Leu Gly Thr Gly Gly Ala Ala Thr Thr Met Gly Asn Ser Cys Ile
             35                  40                  45

Cys Arg Asp Asp Ser Gly Thr Asp Asp Ser Val Asp Thr Gln Gln
             50                  55                  60

Gln Gln Ala Glu Asn Ser Ala Val Pro Thr Ala Asp Thr Arg Ser
             65                  70                  75

Gln Pro Arg Asp Pro Val Arg Pro Pro Arg Gly Arg Gly Pro
             80                  85                  90

His Glu Pro Arg Arg Lys Lys Gln Asn Val Asp Gly Leu Val Leu
             95                 100                 105

Asp Thr Leu Ala Val Ile Arg Thr Leu Val Asp Lys
            110                 115

<210> SEQ ID NO 19
<211> LENGTH: 2579
<212> TYPE: DNA
<213> ORGANISM: Homo sapiens

<400> SEQUENCE: 19
cctgtgttaa gctgaggttt ccctagatc tcgtatatcc ccaacacata          50
cctccacgca cacacatccc caagaacctc gagctcacac caacagacac        100
acgcgcgcat acacactcgc tctcgcttgt ccatctccct cccggggag         150 ccggcgcgcg ctcccacctt tgccgcacac tccggcgagc cgagcccgca        200
gcgctccagg attctgcggc tcggaactcg gattgcagct ctgaaccccc        250
atggtggttt tttaaacact tcttttcctt ctcttcctcg ttttgattgc        300
accgtttcca tctgggggct agaggagcaa ggcagcagcc ttcccagcca        350
gcccttgttg gcttgccatc gtccatctgg cttataaaag tttgctgagc        400
gcagtccaga gggctgcgct gctcgtcccc tcggctggca aaggggggtg        450
acgctgggca gcggcgagga gcgcgccgct gcctctggcg ggctttcggc        500
ttgaggggca aggtgaagag cgcaccggcc gtggggttta ccgagctgga        550
tttgtatgtt gcaccatgcc ttcttggatc ggggctgtga ttcttcccct        600 cttgggctg ctgctctccc tccccgccgg ggcggatgtg aaggctcgga         650
gctgcggaga ggtccgccag gcgtacggtg ccaagggatt cagcctggcg        700
gacatcccct accaggagat cgcaggggaa cacttaagaa tctgtcctca        750
ggaatataca tgctgcacca cagaaatgga agacaagtta agccaacaaa        800
gcaaactcga atttgaaaac cttgtggaag agacaagcca ttttgtgcgc        850 accactttg tgtccaggca taagaaattt gacgaatttt ccgagagct         900 cctggagaat gcagaaaagt cactaaatga tatgtttgta cggacctatg        950
gcatgctgta catgcagaat tcagaagtct tccaggacct cttcacagag       1000
ctgaaaaggt actacactgg gggtaatgtg aatctggagg aaatgctcaa       1050
```

```
tgacttttgg gctcggctcc tggaacggat gtttcagctg ataaaccctc      1100
agtatcactt cagtgaagac tacctggaat gtgtgagcaa atacactgac      1150
cagctcaagc catttggaga cgtgccccgg aaactgaaga ttcaggttac      1200
ccgcgccttc attgctgcca ggacctttgt ccaggggctg actgtgggca      1250
gagaagttgc aaaccgagtt tccaaggtca gcccaacccc agggtgtatc      1300
cgtgccctca tgaagatgct gtactgccca tactgtcggg ggcttcccac      1350
tgtgaggccc tgcaacaact actgtctcaa cgtcatgaag ggctgcttgg      1400
caaatcaggc tgacctcgac acagagtgga atctgtttat agatgcaatg      1450
ctcttggtgg cagagcgact ggaggggcca ttcaacattg agtcggtcat      1500
ggacccgata gatgtcaaga tttctgaagc cattatgaac atgcaagaaa      1550
acagcatgca ggtgtctgca aaggtctttc agggatgtgg tcagcccaaa      1600
cctgctccag ccctcagatc tgcccgctca gctcctgaaa attttaatac      1650
acgtttcagg ccctacaatc ctgaggaaag accaacaact gctgcaggca      1700
caagcttgga ccggctggtc acagacataa agagaaatt gaagctctct       1750 aaaaaggtct ggtcagcatt accctacact atctgcaagg acgagagcgt      1800
gacagcgggc acgtccaacg aggaggaatg ctggaacggg cacagcaaag      1850
ccagatactt gcctgagatc atgaatgatg ggctcaccaa ccagatcaac      1900
aatcccgagt ggatgtggga catcactcgg cctgacactt tcatcagaca      1950
gcagattatg gctctccgtg tgatgaccaa caaactaaaa aacgcctaca      2000
atggcaatga tgtcaatttc caggacacaa gtgatgaatc cagtggctca      2050
gggagtggca gtgggtgcat ggatgacgtg tgtcccacgg agtttgagtt      2100
tgtcaccaca gaggccccg cagtggatcc cgaccggaga gaggtggact       2150
cttctgcagc ccagcgtggc cactccctgc tctcctggtc tctcacctgc      2200
attgtcctgg cactgcagag actgtgcaga taatcttggg ttttttggtca     2250 gatgaaactg cattttagct atctgaatgg ccaactcact tcttttctta      2300
cactcttgga caatggacca tgccacaaaa acttaccgtt ttctatgaga      2350
agagagcagt aatgcaatct gcctcccttt tgttttttccc aaagagtacc     2400 gggtgccaga ctgaactgct tcctctttcc ttcagctatc tgtggggacc      2450
ttgtttattc tagagagaat tcttactcaa attttttcgta ccaggagatt     2500 ttcttacctt catttgcttt tatgctgcag aagtaaagga atctcacgtt      2550
gtgagggttt tttttttctc atttaaaat                             2579
```

<210> SEQ ID NO 20
<211> LENGTH: 555
<212> TYPE: PRT
<213> ORGANISM: Homo sapiens

<400> SEQUENCE: 20

```
Met Pro Ser Trp Ile Gly Ala Val Ile Leu Pro Leu Leu Gly Leu
 1               5                  10                  15

Leu Leu Ser Leu Pro Ala Gly Ala Asp Val Lys Ala Arg Ser Cys
                20                  25                  30

Gly Glu Val Arg Gln Ala Tyr Gly Ala Lys Gly Phe Ser Leu Ala
                35                  40                  45
```

```
Asp Ile Pro Tyr Gln Glu Ile Ala Gly Glu His Leu Arg Ile Cys
                 50                  55                  60

Pro Gln Glu Tyr Thr Cys Cys Thr Thr Glu Met Glu Asp Lys Leu
                 65                  70                  75

Ser Gln Gln Ser Lys Leu Glu Phe Glu Asn Leu Val Glu Glu Thr
                 80                  85                  90

Ser His Phe Val Arg Thr Thr Phe Val Ser Arg His Lys Lys Phe
                 95                 100                 105

Asp Glu Phe Phe Arg Glu Leu Leu Glu Asn Ala Glu Lys Ser Leu
                110                 115                 120

Asn Asp Met Phe Val Arg Thr Tyr Gly Met Leu Tyr Met Gln Asn
                125                 130                 135

Ser Glu Val Phe Gln Asp Leu Phe Thr Glu Leu Lys Arg Tyr Tyr
                140                 145                 150

Thr Gly Gly Asn Val Asn Leu Glu Glu Met Leu Asn Asp Phe Trp
                155                 160                 165

Ala Arg Leu Leu Glu Arg Met Phe Gln Leu Ile Asn Pro Gln Tyr
                170                 175                 180

His Phe Ser Glu Asp Tyr Leu Glu Cys Val Ser Lys Tyr Thr Asp
                185                 190                 195

Gln Leu Lys Pro Phe Gly Asp Val Pro Arg Lys Leu Lys Ile Gln
                200                 205                 210

Val Thr Arg Ala Phe Ile Ala Ala Arg Thr Phe Val Gln Gly Leu
                215                 220                 225

Thr Val Gly Arg Glu Val Ala Asn Arg Val Ser Lys Val Ser Pro
                230                 235                 240

Thr Pro Gly Cys Ile Arg Ala Leu Met Lys Met Leu Tyr Cys Pro
                245                 250                 255

Tyr Cys Arg Gly Leu Pro Thr Val Arg Pro Cys Asn Asn Tyr Cys
                260                 265                 270

Leu Asn Val Met Lys Gly Cys Leu Ala Asn Gln Ala Asp Leu Asp
                275                 280                 285

Thr Glu Trp Asn Leu Phe Ile Asp Ala Met Leu Leu Val Ala Glu
                290                 295                 300

Arg Leu Glu Gly Pro Phe Asn Ile Glu Ser Val Met Asp Pro Ile
                305                 310                 315

Asp Val Lys Ile Ser Glu Ala Ile Met Asn Met Gln Glu Asn Ser
                320                 325                 330

Met Gln Val Ser Ala Lys Val Phe Gln Gly Cys Gly Gln Pro Lys
                335                 340                 345

Pro Ala Pro Ala Leu Arg Ser Ala Arg Ser Ala Pro Glu Asn Phe
                350                 355                 360

Asn Thr Arg Phe Arg Pro Tyr Asn Pro Glu Glu Arg Pro Thr Thr
                365                 370                 375

Ala Ala Gly Thr Ser Leu Asp Arg Leu Val Thr Asp Ile Lys Glu
                380                 385                 390

Lys Leu Lys Leu Ser Lys Lys Val Trp Ser Ala Leu Pro Tyr Thr
                395                 400                 405

Ile Cys Lys Asp Glu Ser Val Thr Ala Gly Thr Ser Asn Glu Glu
                410                 415                 420

Glu Cys Trp Asn Gly His Ser Lys Ala Arg Tyr Leu Pro Glu Ile
                425                 430                 435

Met Asn Asp Gly Leu Thr Asn Gln Ile Asn Asn Pro Glu Val Asp
                440                 445                 450
```

```
Val Asp Ile Thr Arg Pro Asp Thr Phe Ile Arg Gln Gln Ile Met
        455                 460                 465

Ala Leu Arg Val Met Thr Asn Lys Leu Lys Asn Ala Tyr Asn Gly
        470                 475                 480

Asn Asp Val Asn Phe Gln Asp Thr Ser Asp Glu Ser Ser Gly Ser
        485                 490                 495

Gly Ser Gly Ser Gly Cys Met Asp Asp Val Cys Pro Thr Glu Phe
        500                 505                 510

Glu Phe Val Thr Thr Glu Ala Pro Ala Val Asp Pro Asp Arg Arg
        515                 520                 525

Glu Val Asp Ser Ser Ala Ala Gln Arg Gly His Ser Leu Leu Ser
        530                 535                 540

Trp Ser Leu Thr Cys Ile Val Leu Ala Leu Gln Arg Leu Cys Arg
        545                 550                 555

<210> SEQ ID NO 21
<211> LENGTH: 1869
<212> TYPE: DNA
<213> ORGANISM: Homo sapiens

<400> SEQUENCE: 21
aatgtgagag gggctgatgg aagctgatag gcaggactgg agtgttagca            50
ccagtactgg atgtgacagc aggcagagga gcacttagca gcttattcag           100
tgtccgattc tgattccggc aaggatccaa gcatggaatg ctgccgtcgg           150
gcaactcctg gcacactgct cctctttctg gctttcctgc tcctgagttc           200
caggaccgca cgctccgagg aggaccggga cggcctatgg gatgcctggg           250
gcccatggag tgaatgctca cgcacctgcg ggggagggc ctcctactct            300 ctgaggcgct gcctgagcag caagagctgt gaaggaagaa atatccgata           350
cagaacatgc agtaatgtgg actgcccacc agaagcaggt gatttccgag           400
ctcagcaatg ctcagctcat aatgatgtca agcaccatgg ccagttttat           450
gaatggcttc ctgtgtctaa tgaccctgac aacccatgtt cactcaagtg           500
ccaagccaaa ggaacaaccc tggttgttga actagcacct aaggtcttag           550
atggtacgcg ttgctataca gaatctttgg atatgtgcat cagtggttta           600
tgccaaattg ttggctgcga tcaccagctg ggaagcaccg tcaaggaaga           650
taactgtggg gtctgcaacg agatgggtc cacctgccgg ctggtccgag            700
ggcagtataa atcccagctc tccgcaacca atcggatga tactgtggtt           750 gcacttccct atgaagtag acatattcgc cttgtcttaa aaggtcctga           800
tcacttatat ctggaaacca aaaccctcca ggggactaaa ggtgaaaaca           850
gtctcagctc cacaggaact ttccttgtgg acaattctag tgtggacttc           900
cagaaatttc cagacaaaga gatactgaga atggctggac cactcacagc           950
agatttcatt gtcaagattc gtaactcggg ctccgctgac agtacagtcc          1000
agttcatctt ctatcaaccc atcatccacc gatggaggga gacggatttc          1050
tttccttgct cagcaacctg tggaggaggt tatcagctga catcggctga          1100
gtgctacgat ctgaggagca accgtgtggt tgctgaccaa tactgtcact          1150
attacccaga gaacatcaaa cccaaaccca gcttcagga gtgcaacttg           1200 gatccttgtc cagccagtga cggatacaag cagatcatgc cttatgacct          1250
```

```
ctaccatccc cttcctcggt gggaggccac cccatggacc gcgtgctcct      1300
cctcgtgtgg gggggcatc cagagccggg cagtttcctg tgtggaggag       1350
gacatccagg ggcatgtcac ttcagtggaa gagtggaaat gcatgtacac      1400
ccctaagatg cccatcgcgc agccctgcaa cattttgac tgccctaaat       1450 ggctggcaca ggagtggtct ccgtgcacag tgacatgtgg ccagggcctc      1500
agataccgtg tggtcctctg catcgaccat cgaggaatgc acacaggagg      1550
ctgtagccca aaaacaaagc cccacataaa agaggaatgc atcgtaccca      1600
ctccctgcta taaacccaaa gagaaacttc cagtcgaggc caagttgcca      1650
tggttcaaac aagctcaaga gctagaagaa ggagctgctg tgtcagagga      1700
gccctcgtaa gttgtaaaag cacagactgt tctatatttg aaactgtttt      1750
gtttaaagaa agcagtgtct cactggttgt agctttcatg ggttctgaac      1800
taagtgtaat catctcacca aagcttttg gctctcaaat taaagattga       1850
ttagtttcaa aaaaaaaaa                                        1869
```

<210> SEQ ID NO 22
<211> LENGTH: 525
<212> TYPE: PRT
<213> ORGANISM: Homo sapiens

<400> SEQUENCE: 22

```
Met Glu Cys Cys Arg Arg Ala Thr Pro Gly Thr Leu Leu Phe
 1               5                  10                  15

Leu Ala Phe Leu Leu Leu Ser Ser Arg Thr Ala Arg Ser Glu Glu
                20                  25                  30

Asp Arg Asp Gly Leu Trp Asp Ala Trp Gly Pro Trp Ser Glu Cys
                35                  40                  45

Ser Arg Thr Cys Gly Gly Gly Ala Ser Tyr Ser Leu Arg Arg Cys
                50                  55                  60

Leu Ser Ser Lys Ser Cys Glu Gly Arg Asn Ile Arg Tyr Arg Thr
                65                  70                  75

Cys Ser Asn Val Asp Cys Pro Pro Glu Ala Gly Asp Phe Arg Ala
                80                  85                  90

Gln Gln Cys Ser Ala His Asn Asp Val Lys His His Gly Gln Phe
                95                 100                 105

Tyr Glu Trp Leu Pro Val Ser Asn Asp Pro Asp Asn Pro Cys Ser
               110                 115                 120

Leu Lys Cys Gln Ala Lys Gly Thr Thr Leu Val Val Glu Leu Ala
               125                 130                 135

Pro Lys Val Leu Asp Gly Thr Arg Cys Tyr Thr Glu Ser Leu Asp
               140                 145                 150

Met Cys Ile Ser Gly Leu Cys Gln Ile Val Gly Cys Asp His Gln
               155                 160                 165

Leu Gly Ser Thr Val Lys Glu Asp Asn Cys Gly Val Cys Asn Gly
               170                 175                 180

Asp Gly Ser Thr Cys Arg Leu Val Arg Gly Gln Tyr Lys Ser Gln
               185                 190                 195

Leu Ser Ala Thr Lys Ser Asp Asp Thr Val Val Ala Leu Pro Tyr
               200                 205                 210

Gly Ser Arg His Ile Arg Leu Val Leu Lys Gly Pro Asp His Leu
               215                 220                 225

Tyr Leu Glu Thr Lys Thr Leu Gln Gly Thr Lys Gly Glu Asn Ser
```

| | | | 230 | | | | 235 | | | | 240 |

Leu Ser Ser Thr Gly Thr Phe Leu Val Asp Asn Ser Ser Val Asp
                        245                 250                 255

Phe Gln Lys Phe Pro Asp Lys Glu Ile Leu Arg Met Ala Gly Pro
                        260                 265                 270

Leu Thr Ala Asp Phe Ile Val Lys Ile Arg Asn Ser Gly Ser Ala
                        275                 280                 285

Asp Ser Thr Val Gln Phe Ile Phe Tyr Gln Pro Ile Ile His Arg
                        290                 295                 300

Trp Arg Glu Thr Asp Phe Phe Pro Cys Ser Ala Thr Cys Gly Gly
                        305                 310                 315

Gly Tyr Gln Leu Thr Ser Ala Glu Cys Tyr Asp Leu Arg Ser Asn
                        320                 325                 330

Arg Val Val Ala Asp Gln Tyr Cys His Tyr Tyr Pro Glu Asn Ile
                        335                 340                 345

Lys Pro Lys Pro Lys Leu Gln Glu Cys Asn Leu Asp Pro Cys Pro
                        350                 355                 360

Ala Ser Asp Gly Tyr Lys Gln Ile Met Pro Tyr Asp Leu Tyr His
                        365                 370                 375

Pro Leu Pro Arg Trp Glu Ala Thr Pro Trp Thr Ala Cys Ser Ser
                        380                 385                 390

Ser Cys Gly Gly Gly Ile Gln Ser Arg Ala Val Ser Cys Val Glu
                        395                 400                 405

Glu Asp Ile Gln Gly His Val Thr Ser Val Glu Glu Trp Lys Cys
                        410                 415                 420

Met Tyr Thr Pro Lys Met Pro Ile Ala Gln Pro Cys Asn Ile Phe
                        425                 430                 435

Asp Cys Pro Lys Trp Leu Ala Gln Glu Trp Ser Pro Cys Thr Val
                        440                 445                 450

Thr Cys Gly Gln Gly Leu Arg Tyr Arg Val Val Leu Cys Ile Asp
                        455                 460                 465

His Arg Gly Met His Thr Gly Gly Cys Ser Pro Lys Thr Lys Pro
                        470                 475                 480

His Ile Lys Glu Glu Cys Ile Val Pro Thr Pro Cys Tyr Lys Pro
                        485                 490                 495

Lys Glu Lys Leu Pro Val Glu Ala Lys Leu Pro Trp Phe Lys Gln
                        500                 505                 510

Ala Gln Glu Leu Glu Glu Gly Ala Ala Val Ser Glu Glu Pro Ser
                        515                 520                 525

<210> SEQ ID NO 23
<211> LENGTH: 2281
<212> TYPE: DNA
<213> ORGANISM: Homo sapiens

<400> SEQUENCE: 23

| | | |
|---|---|---|
| gggcgcccgc gtactcacta gctgaggtgg cagtggttcc accaacatgg | | 50 |
| agctctcgca gatgtcggag ctcatggggc tgtcggtgtt gcttgggctg | | 100 |
| ctggccctga tggcgacggc ggcggtagcg cggggtggc tgcgcgcggg | | 150 |
| ggaggagagg agcggccggc ccgcctgcca aaaagcaaat ggatttccac | | 200 |
| ctgacaaatc ttcgggatcc aagaagcaga acaatatca gcggattcgg | | 250 |
| aaggagaagc tcaacaaca caacttcacc caccgcctcc tggctgcagc | | 300 |
| tctgaagagc cacagcggga acatatcttg catggacttt agcagcaatg | | 350 |

```
gcaaatacct ggctacctgt gcagatgatc gcaccatccg catctggagc       400
accaaggact tcctgcagcg agagcaccgc agcatgagag ccaacgtgga       450
gctggaccac gccaccctgg tgcgcttcag ccctgactgc agagccttca       500
tcgtctggct ggccaacggg gacaccctcc gtgtcttcaa gatgaccaag       550
cgggaggatg ggggctacac cttcacagcc accccagagg acttccctaa       600
aaagcacaag gcgcctgtca tcgacattgg cattgctaac acagggaagt       650
ttatcatgac tgcctccagt gacaccactg tcctcatctg gagcctgaag       700
ggtcaagtgc tgtctaccat caacaccaac cagatgaaca acacacacgc       750
tgctgtatct ccctgtggca gatttgtagc ctcgtgtggc ttcacccag        800 atgtgaaggt ttgggaagtc tgctttggaa agaagggggga gttccaggag      850 gtggtgcgag ccttcgaact aaagggccac tccgcggctg tgcactcgtt       900
tgctttctcc aacgactcac ggaggatggc ttctgtctcc aaggatggta       950
catggaaact gtgggacaca gatgtggaat acaagaagaa gcaggacccc      1000
tacttgctga agacaggccg ctttgaagag gcggcgggtg ccgcgccgtg      1050
ccgcctggcc ctctccccca acgcccaggt cttggccttg gccagtggca      1100
gtagtattca tctctacaat acccggcggg gcgagaagga ggagtgcttt      1150
gagcgggtcc atggcgagtg tatcgccaac ttgtcctttg acatcactgg      1200 ccgcttctg gcctcctgtg gggaccgggc ggtgcggctg tttcacaaca       1250
ctcctggcca ccgagccatg gtggaggaga tgcagggcca cctgaagcgg      1300
gcctccaacg agagcaccg ccagaggctg cagcagcagc tgacccaggc       1350
ccaagagacc ctgaagagcc tgggtgccct gaagaagtga ctctgggagg      1400
gcccggcgca gaggattgag gaggagggat ctggcctcct catggcactg      1450
ctgccatctt tcctcccagg tggaagcctt tcagaaggag tctcctggtt      1500
ttcttactgg tggccctgct tcttcccatt gaaactactc ttgtctactt      1550
aggtctctct cttcttgctg gctgtgactc ctccctgact agtggccaag      1600 gtgctttttct tcctcccagg cccagtgggt ggaatctgtc cccacctggc     1650
actgaggaga atggtagaga ggagaggaga gagagagaga atgtgatttt      1700
tggccttgtg gcagcacatc ctcacaccca aagaagtttg taaatgttcc      1750
agaacaacct agagaacacc tgagtactaa gcagcagttt tgcaaggatg      1800
ggagactggg atagcttccc atcacagaac tgtgttccat caaaaagaca      1850
ctaagggatt tccttctggg cctcagttct atttgtaaga tggagaataa      1900
tcctctctgt gaactccttg caaagatgat atgaggctaa gagaatatca      1950
agtccccagg tctggaagaa aagtagaaaa gagtagtact attgtccaat      2000
gtcatgaaag tggtaaaagt gggaaccagt gtgctttgaa accaaattag      2050
aaacacattc cttgggaagg caaagttttc tgggacttga tcatacattt      2100
tatatggttg ggacttctct cttcgggaga tgatatcttg tttaaggaga      2150
cctcttttca gttcatcaag ttcatcagat atttgagtgc ccactctgtg      2200
cccaaataaa tatgagctgg ggattaaaaa aaaaaaaaa aaaaaaaaa        2250 aaaaaaaaaa aaaaaaaaaa aaaaaaaaa  a                         2281
```

<210> SEQ ID NO 24
<211> LENGTH: 447
<212> TYPE: PRT
<213> ORGANISM: Homo sapiens

<400> SEQUENCE: 24

```
Met Glu Leu Ser Gln Met Ser Glu Leu Met Gly Leu Ser Val Leu
 1               5                  10                  15

Leu Gly Leu Leu Ala Leu Met Ala Thr Ala Ala Val Ala Arg Gly
                20                  25                  30

Trp Leu Arg Ala Gly Glu Arg Ser Gly Arg Pro Ala Cys Gln
                35                  40                  45

Lys Ala Asn Gly Phe Pro Pro Asp Lys Ser Gly Ser Lys Lys
                50                  55                  60

Gln Lys Gln Tyr Gln Arg Ile Arg Lys Glu Lys Pro Gln Gln His
                65                  70                  75

Asn Phe Thr His Arg Leu Leu Ala Ala Ala Leu Lys Ser His Ser
                80                  85                  90

Gly Asn Ile Ser Cys Met Asp Phe Ser Ser Asn Gly Lys Tyr Leu
                95                 100                 105

Ala Thr Cys Ala Asp Asp Arg Thr Ile Arg Ile Trp Ser Thr Lys
               110                 115                 120

Asp Phe Leu Gln Arg Glu His Arg Ser Met Arg Ala Asn Val Glu
               125                 130                 135

Leu Asp His Ala Thr Leu Val Arg Phe Ser Pro Asp Cys Arg Ala
               140                 145                 150

Phe Ile Val Trp Leu Ala Asn Gly Asp Thr Leu Arg Val Phe Lys
               155                 160                 165

Met Thr Lys Arg Glu Asp Gly Gly Tyr Thr Phe Thr Ala Thr Pro
               170                 175                 180

Glu Asp Phe Pro Lys Lys His Lys Ala Pro Val Ile Asp Ile Gly
               185                 190                 195

Ile Ala Asn Thr Gly Lys Phe Ile Met Thr Ala Ser Ser Asp Thr
               200                 205                 210

Thr Val Leu Ile Trp Ser Leu Lys Gly Gln Val Leu Ser Thr Ile
               215                 220                 225

Asn Thr Asn Gln Met Asn Asn Thr His Ala Ala Val Ser Pro Cys
               230                 235                 240

Gly Arg Phe Val Ala Ser Cys Gly Phe Thr Pro Asp Val Lys Val
               245                 250                 255

Trp Glu Val Cys Phe Gly Lys Lys Gly Glu Phe Gln Glu Val Val
               260                 265                 270

Arg Ala Phe Glu Leu Lys Gly His Ser Ala Ala Val His Ser Phe
               275                 280                 285

Ala Phe Ser Asn Asp Ser Arg Arg Met Ala Ser Val Ser Lys Asp
               290                 295                 300

Gly Thr Trp Lys Leu Trp Asp Thr Asp Val Glu Tyr Lys Lys Lys
               305                 310                 315

Gln Asp Pro Tyr Leu Leu Lys Thr Gly Arg Phe Glu Glu Ala Ala
               320                 325                 330

Gly Ala Ala Pro Cys Arg Leu Ala Leu Ser Pro Asn Ala Gln Val
               335                 340                 345

Leu Ala Leu Ala Ser Gly Ser Ser Ile His Leu Tyr Asn Thr Arg
               350                 355                 360

Arg Gly Glu Lys Glu Glu Cys Phe Glu Arg Val His Gly Glu Cys
```

```
                            365                 370                 375
Ile Ala Asn Leu Ser Phe Asp Ile Thr Gly Arg Phe Leu Ala Ser
                380                 385                 390

Cys Gly Asp Arg Ala Val Arg Leu Phe His Asn Thr Pro Gly His
                395                 400                 405

Arg Ala Met Val Glu Glu Met Gln Gly His Leu Lys Arg Ala Ser
                410                 415                 420

Asn Glu Ser Thr Arg Gln Arg Leu Gln Gln Leu Thr Gln Ala
                425                 430                 435

Gln Glu Thr Leu Lys Ser Leu Gly Ala Leu Lys Lys
                440                 445

<210> SEQ ID NO 25
<211> LENGTH: 1621
<212> TYPE: DNA
<213> ORGANISM: Homo sapiens

<400> SEQUENCE: 25
gtgggattta tttgagtgca agatcgtttt ctcagtggtg gtggaagttg          50
cctcatcgca ggcagatgtt ggggctttgt ccgaacagct cccctctgcc         100
agcttctgta gataagggtt aaaaactaat atttatatga cagaagaaaa         150
agatgtcatt ccgtaaagta aacatcatca tcttggtcct ggctgttgct         200
ctcttcttac tggttttgca ccataacttc ctcagcttga gcagtttgtt         250
aaggaatgag gttacagatt caggaattgt agggcctcaa cctatagact         300
ttgtcccaaa tgctctccga catgcagtag atgggagaca agaggagatt         350
cctgtggtca tcgctgcatc tgaagacagg cttgggggg ccattgcagc          400
tataaacagc attcagcaca acactcgctc caatgtgatt ttctacattg         450
ttactctcaa caatacagca gaccatctcc ggtcctggct caacagtgat         500
tccctgaaaa gcatcagata caaaattgtc aattttgacc ctaaactttt         550
ggaaggaaaa gtaaaggagg atcctgacca gggggaatcc atgaaaccctt        600
taacctttgc aaggttctac ttgccaattc tggttcccag cgcaaagaag         650
gccatataca tggatgatga tgtaattgtg caaggtgata ttcttgccct         700
ttacaataca gcactgaagc aggacatgc agctgcattt tcagaagatt          750
gtgattcagc ctctactaaa gttgtcatcc gtggagcagg aaaccagtac         800
aattacattg gctatcttga ctataaaaag gaaagaattc gtaagctttc         850
catgaaagcc agcacttgct catttaatcc tggagttttt gttgcaaacc         900
tgacggaatg gaaacgacag aatataacta accaactgga aaaatggatg         950
aaactcaatg tagaagaggg actgtatagc agaacccctgg ctggtagcat       1000
cacaacacct cctctgctta tcgtatttta tcaacagcac tctaccatcg        1050
atcctatgtg gaatgtccgc caccttggtt ccagtgctgg aaaacgatat        1100
tcacctcagt ttgtaaaggc tgccaagtta ctccattgga atggacattt        1150
gaagccatgg ggaaggactg cttcatatac tgatgtttgg gaaaaatggt       1200
atattccaga cccaacaggc aaattcaacc taatccgaag ataccgag          1250
atctcaaaca taaagtgaaa cagaatttga actgtaagca agcatttctc       1300
aggaagtcct ggaagatagc atgcatggga agtaacagtt gctaggcttc        1350
aatgcctatc ggtagcaagc catggaaaaa gatgtgtcag ctaggtaaag        1400
```

```
atgacaaact gccctgtctg gcagtcagct tcccagacag actatagact         1450
ataaatatgt ctccatctgc cttaccaagt gtttttcttac tacaatgctg        1500 aatgactgga agaagaact gatatggcta gttcagctag ctggtacaga          1550
taattcaaaa ctgctgttgg ttttaatttt gtaacctgtg gcctgatctg         1600
taaataaaac ttacattttt  c                                       1621

<210> SEQ ID NO 26
<211> LENGTH: 371
<212> TYPE: PRT
<213> ORGANISM: Homo sapiens

<400> SEQUENCE: 26
```

| Met | Ser | Phe | Arg | Lys | Val | Asn | Ile | Ile | Ile | Leu | Val | Leu | Ala | Val |
|---|---|---|---|---|---|---|---|---|---|---|---|---|---|---|
| 1 |  |  |  | 5 |  |  |  |  | 10 |  |  |  |  | 15 |

Ala Phe Leu Leu Val Leu His His Asn Phe Leu Ser Leu Ser
            20                  25                  30

Ser Leu Leu Arg Asn Glu Val Thr Asp Ser Gly Ile Val Gly Pro
        35                  40                  45

Gln Pro Ile Asp Phe Val Pro Asn Ala Leu Arg His Ala Val Asp
    50                  55                  60

Gly Arg Gln Glu Glu Ile Pro Val Val Ile Ala Ala Ser Glu Asp
65                  70                  75

Arg Leu Gly Gly Ala Ile Ala Ala Ile Asn Ser Ile Gln His Asn
            80                  85                  90

Thr Arg Ser Asn Val Ile Phe Tyr Ile Val Thr Leu Asn Asn Thr
        95                 100                 105

Ala Asp His Leu Arg Ser Trp Leu Asn Ser Asp Ser Leu Lys Ser
    110                 115                 120

Ile Arg Tyr Lys Ile Val Asn Phe Asp Pro Lys Leu Leu Glu Gly
125                 130                 135

Lys Val Lys Glu Asp Pro Asp Gln Gly Glu Ser Met Lys Pro Leu
            140                 145                 150

Thr Phe Ala Arg Phe Tyr Leu Pro Ile Leu Val Pro Ser Ala Lys
        155                 160                 165

Lys Ala Ile Tyr Met Asp Asp Asp Val Ile Val Gln Gly Asp Ile
    170                 175                 180

Leu Ala Leu Tyr Asn Thr Ala Leu Lys Pro Gly His Ala Ala Ala
185                 190                 195

Phe Ser Glu Asp Cys Asp Ser Ala Ser Thr Lys Val Val Ile Arg
            200                 205                 210

Gly Ala Gly Asn Gln Tyr Asn Tyr Ile Gly Tyr Leu Asp Tyr Lys
        215                 220                 225

Lys Glu Arg Ile Arg Lys Leu Ser Met Lys Ala Ser Thr Cys Ser
    230                 235                 240

Phe Asn Pro Gly Val Phe Val Ala Asn Leu Thr Glu Trp Lys Arg
245                 250                 255

Gln Asn Ile Thr Asn Gln Leu Glu Lys Trp Met Lys Leu Asn Val
            260                 265                 270

Glu Glu Gly Leu Tyr Ser Arg Thr Leu Ala Gly Ser Ile Thr Thr
        275                 280                 285

Pro Pro Leu Leu Ile Val Phe Tyr Gln Gln His Ser Thr Ile Asp
    290                 295                 300

Pro Met Trp Asn Val Arg His Leu Gly Ser Ser Ala Gly Lys Arg

```
                305                 310                 315
Tyr Ser Pro Gln Phe Val Lys Ala Ala Lys Leu Leu His Trp Asn
            320                 325                 330

Gly His Leu Lys Pro Trp Gly Arg Thr Ala Ser Tyr Thr Asp Val
            335                 340                 345

Trp Glu Lys Trp Tyr Ile Pro Asp Pro Thr Gly Lys Phe Asn Leu
            350                 355                 360

Ile Arg Arg Tyr Thr Glu Ile Ser Asn Ile Lys
            365                 370

<210> SEQ ID NO 27
<211> LENGTH: 972
<212> TYPE: DNA
<213> ORGANISM: Homo sapiens

<400> SEQUENCE: 27
agtgactgca gccttcctag atcccctcca ctcggtttct ctctttgcag            50
gagcaccggc agcaccagtg tgtgagggga gcaggcagcg gtcctagcca           100
gttccttgat cctgccagac acccagcccc cggcacagag ctgctccac            150 aggcaccatg aggatcatgc tgctattcac agccatcctg gccttcagcc           200
tagctcagag ctttggggct gtctgtaagg agccacagga ggaggtggtt           250
cctggcgggg gccgcagcaa gagggatcca gatctctacc agctgctcca           300
gagactcttc aaaagccact catctctgga gggattgctc aaagccctga           350
gccaggctag cacagatcct aaggaatcaa catctcccga gaaacgtgac           400
atgcatgact tctttgtggg acttatgggc aagaggagcg tccagccaga           450
gggaaagaca ggacctttct taccttcagt gagggttcct cggcccctt            500 atcccaatca gcttggatcc acaggaaagt cttccctggg aacagaggag           550
cagagaccct tataagactc tcctacggat gtgaatcaag agaacgtccc           600
cagctttggc atcctcaagt atcccccgag agcagaatag gtactccact           650
tccggactcc tggactgcat taggaagacc tctttccctg tcccaatccc           700
caggtgcgca cgctcctgtt acccttctc ttccctgttc ttgtaacatt            750
cttgtgcttt gactccttct ccatcttttc tacctgaccc tggtgtggaa           800
actgcatagt gaatatcccc aaccccaatg ggcattgact gtagaatacc           850
ctagagttcc tgtagtgtcc tacattaaaa atataatgtc tctctctatt           900
cctcaacaat aaaggatttt tgcatatgaa aaaaaaaaa aaaaaaaaa            950 aaaaaaaaaa aaaaaaaaaa aa                                         972

<210> SEQ ID NO 28
<211> LENGTH: 135
<212> TYPE: PRT
<213> ORGANISM: Homo sapiens

<400> SEQUENCE: 28

Met Arg Ile Met Leu Leu Phe Thr Ala Ile Leu Ala Phe Ser Leu
1               5                   10                  15

Ala Gln Ser Phe Gly Ala Val Cys Lys Glu Pro Gln Glu Glu Val
            20                  25                  30

Val Pro Gly Gly Gly Arg Ser Lys Arg Asp Pro Asp Leu Tyr Gln
            35                  40                  45

Leu Leu Gln Arg Leu Phe Lys Ser His Ser Ser Leu Glu Gly Leu
```

```
                     50                  55                  60
Leu Lys Ala Leu Ser Gln Ala Ser Thr Asp Pro Lys Glu Ser Thr
                 65                  70                  75

Ser Pro Glu Lys Arg Asp Met His Asp Phe Phe Val Gly Leu Met
                 80                  85                  90

Gly Lys Arg Ser Val Gln Pro Glu Gly Lys Thr Gly Pro Phe Leu
                 95                 100                 105

Pro Ser Val Arg Val Pro Arg Pro Leu His Pro Asn Gln Leu Gly
                110                 115                 120

Ser Thr Gly Lys Ser Ser Leu Gly Thr Glu Glu Gln Arg Pro Leu
                125                 130                 135

<210> SEQ ID NO 29
<211> LENGTH: 2988
<212> TYPE: DNA
<213> ORGANISM: Homo sapiens

<400> SEQUENCE: 29
gccgagcgca agaaccctgc gcagcccaga gcagctgctg gaggggaatc            50
gaggcgcggc tccggggatt cggctcgggc cgctggctct gctctgcggg           100
gagggagcgg gcccgcccgc ggggcccgag ccctccggat ccgccccctc           150
cccggtcccg cccccctcgga gactcctctg gctgctctgg gggttcgccg           200
gggccgggga cccgcggtcc gggcgccatg cgggcatcgc tgctgctgtc           250
ggtgctgcgg cccgcagggc ccgtggccgt gggcatctcc ctgggcttca           300
ccctgagcct gctcagcgtc acctgggtgg aggagccgtg cggcccaggc           350
ccgccccaac ctggagactc tgagctgccg ccgcgcggca acaccaacgc           400
ggcgcgccgg cccaactcgg tgcagcccgg agcggagcgc gagaagcccg           450 gggcggcga aggcgccggg gagaattggg agccgcgcgt cttgccctac            500
caccctgcac agcccggcca ggccgccaaa aaggccgtca ggacccgcta           550
catcagcacg gagctgggca tcaggcagag gctgctggtg gcggtgctga           600
cctctcagac cacgctgccc acgctgggcg tggccgtgaa ccgcacgctg           650
gggcaccggc tggagcgtgt ggtgttcctg acgggcgcac ggggccgccg           700
ggccccacct ggcatggcag tggtgacgct gggcgaggag cgacccattg           750
gacacctgca cctggcgctg cgccacctgc tggagcagca cggcgacgac           800
tttgactggt tcttcctggt gcctgacacc acctacaccg aggcgcacgg           850
cctggcacgc ctaactggcc acctcagcct ggcctccgcc gcccacctgt           900
acctgggccg gccccaggac ttcatcggcg agagcccac ccccggccgc            950 tactgccacg gaggctttgg ggtgctgctg tcgcgcatgc tgctgcaaca          1000
actgcgcccc cacctggaag gctgccgcaa cgacatcgtc agtgcgcgcc          1050
ctgacgagtg gctgggtcgc tgcattctcg atgccaccgg ggtgggctgc          1100
actggtgacc acgagggggt gcactatagc catctggagc tgagccctgg          1150
ggagccagtg caggaggggg accctcattt ccgaagtgcc ctgacagccc          1200
accctgtgcg tgaccctgtg cacatgtacc agctgcacaa gctttcgcc           1250 cgagctgaac tggaacgcac gtaccaggag atccaggagt tacagtggga          1300
gatccagaat accagccatc tggccgttga tgggaccgg gcagctgctt           1350 ggcccgtggg tattccagca ccatcccgcc cggcctcccg ctttgaggtg          1400
```

```
ctgcgctggg actacttcac ggagcagcac gctttctcct gcgccgatgg      1450
ctcaccccgc tgcccactgc gtggggctga ccgggctgat gtggccgatg      1500
ttctggggac agctctagag gagctgaacc gccgctacca cccggccttg      1550
cggctccaga agcagcagct ggtgaatggc taccgacgct ttgatccggc      1600
ccggggtatg gaatacacgc tggacttgca gctggaggca ctgaccccc      1650 agggaggccg ccggcccctc actcgccgag tgcagctgct ccggccgctg      1700
agccgcgtgg agatcttgcc tgtgcccat gtcactgagg cctcacgtct       1750
cactgtgctg ctgcctctag ctgcggctga gcgtgacctg gcccctggct      1800
tcttggaggc cttTgccact gcagcactgg agcctggtga tgctgcggca      1850
gccctgaccc tgctgctact gtatgagccg cgccaggccc agcgcgtggc      1900
ccatgcagat gtcttcgcac ctgtcaaggc ccacgtggca gagctggagc      1950
ggcgtttccc cggtgcccgg gtgccatggc tcagtgtgca gacagccgca      2000
ccctcaccac tgcgcctcat ggatctactc tccaagaagc acccgctgga      2050
cacactgttc ctgctggccg ggccagacac ggtgctcacg cctgacttcc      2100
tgaaccgctg ccgcatgcat gccatctccg gctggcaggc cttctttccc      2150
atgcatttcc aagccttcca cccaggtgtg gccccaccac aagggcctgg      2200 gccccagag ctgggccgtg acactggccg ctttgatcgc caggcagcca       2250
gcgaggcctg cttctacaac tccgactacg tggcagcccg tggcgcctg      2300 gcggcagcct cagaacaaga gaggagctg ctggagagcc tggatgtgta       2350
cgagctgttc ctccacttct ccagtctgca tgtgctgcgg gcggtggagc      2400
cggcgctgct gcagcgctac cgggcccaga cgtgcagcgc gaggctcagt      2450
gaggacctgt accaccgctg cctccagagc gtgcttgagg gcctcggctc      2500
ccgaacccag ctggccatgc tactctttga acaggagcag ggcaacagca      2550
cctgacccca ccctgtcccc gtgggccgtg gcatggccac accccacccc      2600
acttctcccc caaaaccaga gccacctgcc agcctcgctg ggcagggctg      2650
gccgtagcca gaccccaagc tggcccactg gtccctctc tggctctgtg       2700 ggtccctggg ctctggacaa gcactggggg acgtgccccc agagccaccc      2750
acttctcatc ccaaacccag tttccctgcc ccctgacgct gctgattcgg      2800
gctgtggcct ccacgtattt atgcagtaca gtctgcctga cgccagccct      2850
gcctctgggc cctgggggct gggctgtaga agagttgttg gggaaggagg      2900
gagctgagga gggggcatct cccaacttct ccctttgga ccctgccgaa       2950 gctccctgcc tttaataaac tggccaagtg tggaaaaa                   2988
```

<210> SEQ ID NO 30
<211> LENGTH: 775
<212> TYPE: PRT
<213> ORGANISM: Homo sapiens

<400> SEQUENCE: 30

Met Arg Ala Ser Leu Leu Leu Ser Val Leu Arg Pro Ala Gly Pro
1               5                   10                  15

Val Ala Val Gly Ile Ser Leu Gly Phe Thr Leu Ser Leu Leu Ser
                20                  25                  30

Val Thr Trp Val Glu Glu Pro Cys Gly Pro Gly Pro Pro Gln Pro

-continued

```
                35                  40                  45
Gly Asp Ser Glu Leu Pro Pro Arg Gly Asn Thr Asn Ala Ala Arg
            50                  55                  60
Arg Pro Asn Ser Val Gln Pro Gly Ala Glu Arg Glu Lys Pro Gly
            65                  70                  75
Ala Gly Glu Gly Ala Gly Glu Asn Trp Glu Pro Arg Val Leu Pro
            80                  85                  90
Tyr His Pro Ala Gln Pro Gly Gln Ala Ala Lys Lys Ala Val Arg
            95                 100                 105
Thr Arg Tyr Ile Ser Thr Glu Leu Gly Ile Arg Gln Arg Leu Leu
           110                 115                 120
Val Ala Val Leu Thr Ser Gln Thr Thr Leu Pro Thr Leu Gly Val
           125                 130                 135
Ala Val Asn Arg Thr Leu Gly His Arg Leu Glu Arg Val Val Phe
           140                 145                 150
Leu Thr Gly Ala Arg Gly Arg Arg Ala Pro Pro Gly Met Ala Val
           155                 160                 165
Val Thr Leu Gly Glu Glu Arg Pro Ile Gly His Leu His Leu Ala
           170                 175                 180
Leu Arg His Leu Leu Glu Gln His Gly Asp Asp Phe Asp Trp Phe
           185                 190                 195
Phe Leu Val Pro Asp Thr Thr Tyr Thr Glu Ala His Gly Leu Ala
           200                 205                 210
Arg Leu Thr Gly His Leu Ser Leu Ala Ser Ala Ala His Leu Tyr
           215                 220                 225
Leu Gly Arg Pro Gln Asp Phe Ile Gly Gly Glu Pro Thr Pro Gly
           230                 235                 240
Arg Tyr Cys His Gly Gly Phe Gly Val Leu Leu Ser Arg Met Leu
           245                 250                 255
Leu Gln Gln Leu Arg Pro His Leu Glu Gly Cys Arg Asn Asp Ile
           260                 265                 270
Val Ser Ala Arg Pro Asp Glu Trp Leu Gly Arg Cys Ile Leu Asp
           275                 280                 285
Ala Thr Gly Val Gly Cys Thr Gly Asp His Glu Gly Val His Tyr
           290                 295                 300
Ser His Leu Glu Leu Ser Pro Gly Glu Pro Val Gln Glu Gly Asp
           305                 310                 315
Pro His Phe Arg Ser Ala Leu Thr Ala His Pro Val Arg Asp Pro
           320                 325                 330
Val His Met Tyr Gln Leu His Lys Ala Phe Ala Arg Ala Glu Leu
           335                 340                 345
Glu Arg Thr Tyr Gln Glu Ile Gln Glu Leu Gln Trp Glu Ile Gln
           350                 355                 360
Asn Thr Ser His Leu Ala Val Asp Gly Asp Arg Ala Ala Ala Trp
           365                 370                 375
Pro Val Gly Ile Pro Ala Pro Ser Arg Pro Ala Ser Arg Phe Glu
           380                 385                 390
Val Leu Arg Trp Asp Tyr Phe Thr Glu Gln His Ala Phe Ser Cys
           395                 400                 405
Ala Asp Gly Ser Pro Arg Cys Pro Leu Arg Gly Ala Asp Arg Ala
           410                 415                 420
Asp Val Ala Asp Val Leu Gly Thr Ala Leu Glu Glu Leu Asn Arg
           425                 430                 435
```

```
Arg Tyr His Pro Ala Leu Arg Leu Gln Lys Gln Gln Leu Val Asn
            440                 445                 450

Gly Tyr Arg Arg Phe Asp Pro Ala Arg Gly Met Glu Tyr Thr Leu
        455                 460                 465

Asp Leu Gln Leu Glu Ala Leu Thr Pro Gln Gly Gly Arg Arg Pro
    470                 475                 480

Leu Thr Arg Arg Val Gln Leu Leu Arg Pro Leu Ser Arg Val Glu
485                 490                 495

Ile Leu Pro Val Pro Tyr Val Thr Glu Ala Ser Arg Leu Thr Val
            500                 505                 510

Leu Leu Pro Leu Ala Ala Ala Glu Arg Asp Leu Ala Pro Gly Phe
        515                 520                 525

Leu Glu Ala Phe Ala Thr Ala Ala Leu Glu Pro Gly Asp Ala Ala
    530                 535                 540

Ala Ala Leu Thr Leu Leu Leu Tyr Glu Pro Arg Gln Ala Gln
545                 550                 555

Arg Val Ala His Ala Asp Val Phe Ala Pro Val Lys Ala His Val
            560                 565                 570

Ala Glu Leu Glu Arg Arg Phe Pro Gly Ala Arg Val Pro Trp Leu
        575                 580                 585

Ser Val Gln Thr Ala Ala Pro Ser Pro Leu Arg Leu Met Asp Leu
    590                 595                 600

Leu Ser Lys Lys His Pro Leu Asp Thr Leu Phe Leu Leu Ala Gly
605                 610                 615

Pro Asp Thr Val Leu Thr Pro Asp Phe Leu Asn Arg Cys Arg Met
            620                 625                 630

His Ala Ile Ser Gly Trp Gln Ala Phe Phe Pro Met His Phe Gln
        635                 640                 645

Ala Phe His Pro Gly Val Ala Pro Pro Gln Gly Pro Gly Pro Pro
    650                 655                 660

Glu Leu Gly Arg Asp Thr Gly Arg Phe Asp Arg Gln Ala Ala Ser
665                 670                 675

Glu Ala Cys Phe Tyr Asn Ser Asp Tyr Val Ala Ala Arg Gly Arg
            680                 685                 690

Leu Ala Ala Ala Ser Glu Gln Glu Glu Leu Leu Glu Ser Leu
        695                 700                 705

Asp Val Tyr Glu Leu Phe Leu His Phe Ser Ser Leu His Val Leu
    710                 715                 720

Arg Ala Val Glu Pro Ala Leu Leu Gln Arg Tyr Arg Ala Gln Thr
725                 730                 735

Cys Ser Ala Arg Leu Ser Glu Asp Leu Tyr His Arg Cys Leu Gln
            740                 745                 750

Ser Val Leu Glu Gly Leu Gly Ser Arg Thr Gln Leu Ala Met Leu
        755                 760                 765

Leu Phe Glu Gln Glu Gln Gly Asn Ser Thr
    770                 775

<210> SEQ ID NO 31
<211> LENGTH: 957
<212> TYPE: DNA
<213> ORGANISM: Homo sapiens

<400> SEQUENCE: 31
gggagagagg ataaatagca gcgtggcttc cctggctcct ctctgcatcc          50
ttcccgacct tcccagcaat atgcatcttg cacgtctggt cggctcctgc         100
```

```
tccctccttc tgctactggg ggccctgtct ggatgggcgg ccagcgatga        150
ccccattgag aaggtcattg aagggatcaa ccgagggctg agcaatgcag        200
agagagaggt gggcaaggcc ctggatggca tcaacagtgg aatcacgcat        250
gccggaaggg aagtggagaa ggttttcaac ggacttagca acatggggag        300
ccacaccggc aaggagttgg acaaaggcgt ccagggctc aaccacggca         350 tggacaaggt tgcccatgag atcaaccatg gtattggaca gcaggaaag         400 gaagcagaga agcttggcca tggggtcaac aacgctgctg acaggccgg         450 gaaggaagca gacaaagcgg tccaagggtt ccacactggg gtccaccagg        500
ctgggaagga agcagagaaa cttggccaag gggtcaacca tgctgctgac        550
caggctggaa aggaagtgga gaagcttggc caaggtgccc accatgctgc        600
tggccaggcc gggaaggagc tgcagaatgc tcataatggg gtcaaccaag        650
ccagcaagga ggccaaccag ctgctgaatg caaccatca aagcggatct         700 tccagccatc aaggaggggc cacaaccacg ccgttagcct ctggggcctc        750
agtcaacacg cctttcatca accttcccgc cctgtggagg agcgtcgcca        800
acatcatgcc ctaaactggc atccggcctt gctgggagaa taatgtcgcc        850
gttgtcacat cagctgacat gacctggagg ggttgggggt gggggacagg        900
tttctgaaat ccctgaaggg ggttgtactg ggatttgtga ataaacttga        950
tacacca                                                      957
```

<210> SEQ ID NO 32
<211> LENGTH: 247
<212> TYPE: PRT
<213> ORGANISM: Homo sapiens

<400> SEQUENCE: 32

```
Met His Leu Ala Arg Leu Val Gly Ser Cys Ser Leu Leu Leu Leu
  1               5                  10                  15

Leu Gly Ala Leu Ser Gly Trp Ala Ala Ser Asp Asp Pro Ile Glu
             20                  25                  30

Lys Val Ile Glu Gly Ile Asn Arg Gly Leu Ser Asn Ala Glu Arg
         35                  40                  45

Glu Val Gly Lys Ala Leu Asp Gly Ile Asn Ser Gly Ile Thr His
     50                  55                  60

Ala Gly Arg Glu Val Glu Lys Val Phe Asn Gly Leu Ser Asn Met
 65                  70                  75

Gly Ser His Thr Gly Lys Glu Leu Asp Lys Gly Val Gln Gly Leu
             80                  85                  90

Asn His Gly Met Asp Lys Val Ala His Glu Ile Asn His Gly Ile
             95                 100                 105

Gly Gln Ala Gly Lys Glu Ala Glu Lys Leu Gly His Gly Val Asn
            110                 115                 120

Asn Ala Ala Gly Gln Ala Gly Lys Glu Ala Asp Lys Ala Val Gln
            125                 130                 135

Gly Phe His Thr Gly Val His Gln Ala Gly Lys Glu Ala Glu Lys
            140                 145                 150

Leu Gly Gln Gly Val Asn His Ala Ala Asp Gln Ala Gly Lys Glu
            155                 160                 165

Val Glu Lys Leu Gly Gln Gly Ala His His Ala Ala Gly Gln Ala
            170                 175                 180
```

```
Gly Lys Glu Leu Gln Asn Ala His Asn Gly Val Asn Gln Ala Ser
            185                 190                 195
Lys Glu Ala Asn Gln Leu Leu Asn Gly Asn His Gln Ser Gly Ser
            200                 205                 210
Ser Ser His Gln Gly Gly Ala Thr Thr Thr Pro Leu Ala Ser Gly
            215                 220                 225
Ala Ser Val Asn Thr Pro Phe Ile Asn Leu Pro Ala Leu Trp Arg
            230                 235                 240
Ser Val Ala Asn Ile Met Pro
            245

<210> SEQ ID NO 33
<211> LENGTH: 2162
<212> TYPE: DNA
<213> ORGANISM: Homo sapiens

<400> SEQUENCE: 33
gcggcggcta tgccgcttgc tctgctcgtc ctgttgctcc tggggcccgg          50
cggctggtgc cttgcagaac ccccacgcga cagcctgcgg gaggaacttg         100
tcatcacccc gctgccttcc ggggacgtag ccgccacatt ccagttccgc         150
acgcgctggg attcggagct tcagcgggaa ggagtgtccc attacaggct         200
ctttcccaaa gccctggggc agctgatctc caagtattct ctacgggagc         250
tgcacctgtc attcacacaa ggcttttgga ggacccgata ctgggggcca         300
cccttcctgc aggccccatc aggtgcagag ctgtgggtct ggttccaaga         350
cactgtcact gatgtggata aatcttggaa ggagctcagt aatgtcctct         400
cagggatctt ctgcgcctct ctcaacttca tcgactccac caacacagtc         450
actcccactg cctccttcaa accctgggt ctggccaatg acactgacca          500
ctactttctg cgctatgctg tgctgccgcg ggaggtggtc tgcaccgaaa         550
acctcacccc ctggaagaag ctcttgccct gtagttccaa ggcaggcctc         600
tctgtgctgc tgaaggcaga tcgcttgttc cacaccagct accactccca         650
ggcagtgcat atccgccctg tttgcagaaa tgcacgctgt actagcatct         700
cctgggagct gaggcagacc ctgtcagttg tatttgatgc cttcatcacg         750
gggcagggaa agaaagactg gtccctcttc cggatgttct cccgaaccct         800
cacggagccc tgccccctgg cttcagagag ccgagtctat gtggacatca         850
ccacctacaa ccaggacaac gagacattag aggtgcaccc acccccgacc         900
actacatatc aggacgtcat cctaggcact cggaagacct atgccatcta         950
tgacttgctt gacaccgcca tgatcaacaa ctctcgaaac ctcaacatcc        1000
agctcaagtg gaagagaccc ccagagaatg aggcccccc agtgcccttc         1050 ctgcatgccc agcggtacgt gagtggctat gggctgcaga aggggagct          1100 gagcacactg ctgtacaaca cccacccata ccgggccttc ccggtgctgc        1150
tgctggacac cgtaccctgg tatctgcggc tgtatgtgca ccctcacc           1200 atcacctcca agggcaagga gaacaaacca agttacatcc actaccagcc        1250
tgcccaggac cggctgcaac cccacctcct ggagatgctg attcagctgc        1300
cggccaactc agtcaccaag gtttccatcc agtttgagcg ggcgctgctg        1350
aagtggaccg agtacacgcc agatcctaac catggcttct atgtcagccc        1400
```

```
atctgtcctc agcgcccttg tgcccagcat ggtagcagcc aagccagtgg    1450
actgggaaga gagtcccctc ttcaacagcc tgttcccagt ctctgatggc    1500
tctaactact ttgtgcggct ctacacggag ccgctgctgg tgaacctgcc    1550
gacaccggac ttcagcatgc cctacaacgt gatctgcctc acgtgcactg    1600
tggtggccgt gtgctacggc tccttctaca atctcctcac ccgaaccttc    1650
cacatcgagg agccccgcac aggtggcctg gccaagcggc tggccaacct    1700
tatccggcgc gcccgaggtg tccccccact ctgattcttg ccctttccag    1750
cagctgcagc tgccgtttct ctctggggag gggagcccaa gggctgtttc    1800
tgccacttgc tctcctcaga gttggctttt gaaccaaagt gccctggacc    1850
aggtcagggc ctacagctgt gttgtccagt acaggagcca cgagccaaat    1900
gtggcatttg aatttgaatt aacttagaaa ttcatttcct cacctgtagt    1950
ggccacctct atattgaggt gctcaataag caaaagtggt cggtggctgc    2000
tgtattggac agcacagaaa aagatttcca tcaccacaga aaggtcggct    2050
ggcagcactg gccaaggtga tggggtgtgc tacacagtgt atgtcactgt    2100
gtagtggatg gagtttactg tttgtggaat aaaaacggct gtttccgtgg    2150
aaaaaaaaaa aa                                             2162
```

<210> SEQ ID NO 34
<211> LENGTH: 574
<212> TYPE: PRT
<213> ORGANISM: Homo sapiens

<400> SEQUENCE: 34

```
Met Pro Leu Ala Leu Leu Val Leu Leu Leu Gly Pro Gly Gly
  1               5                  10                  15

Trp Cys Leu Ala Glu Pro Pro Arg Asp Ser Leu Arg Glu Glu Leu
                 20                  25                  30

Val Ile Thr Pro Leu Pro Ser Gly Asp Val Ala Ala Thr Phe Gln
             35                  40                  45

Phe Arg Thr Arg Trp Asp Ser Glu Leu Gln Arg Glu Gly Val Ser
         50                  55                  60

His Tyr Arg Leu Phe Pro Lys Ala Leu Gly Gln Leu Ile Ser Lys
     65                  70                  75

Tyr Ser Leu Arg Glu Leu His Leu Ser Phe Thr Gln Gly Phe Trp
                 80                  85                  90

Arg Thr Arg Tyr Trp Gly Pro Pro Phe Leu Gln Ala Pro Ser Gly
                 95                 100                 105

Ala Glu Leu Trp Val Trp Phe Gln Asp Thr Val Thr Asp Val Asp
            110                 115                 120

Lys Ser Trp Lys Glu Leu Ser Asn Val Leu Ser Gly Ile Phe Cys
        125                 130                 135

Ala Ser Leu Asn Phe Ile Asp Ser Thr Asn Thr Val Thr Pro Thr
        140                 145                 150

Ala Ser Phe Lys Pro Leu Gly Leu Ala Asn Asp Thr Asp His Tyr
        155                 160                 165

Phe Leu Arg Tyr Ala Val Leu Pro Arg Glu Val Val Cys Thr Glu
        170                 175                 180

Asn Leu Thr Pro Trp Lys Lys Leu Leu Pro Cys Ser Ser Lys Ala
        185                 190                 195

Gly Leu Ser Val Leu Leu Lys Ala Asp Arg Leu Phe His Thr Ser
```

```
                    200                 205                 210
Tyr His Ser Gln Ala Val His Ile Arg Pro Val Cys Arg Asn Ala
            215                 220                 225
Arg Cys Thr Ser Ile Ser Trp Glu Leu Arg Gln Thr Leu Ser Val
            230                 235                 240
Val Phe Asp Ala Phe Ile Thr Gly Gln Gly Lys Lys Asp Trp Ser
            245                 250                 255
Leu Phe Arg Met Phe Ser Arg Thr Leu Thr Glu Pro Cys Pro Leu
            260                 265                 270
Ala Ser Glu Ser Arg Val Tyr Val Asp Ile Thr Thr Tyr Asn Gln
            275                 280                 285
Asp Asn Glu Thr Leu Glu Val His Pro Pro Thr Thr Thr Tyr
            290                 295                 300
Gln Asp Val Ile Leu Gly Thr Arg Lys Thr Tyr Ala Ile Tyr Asp
            305                 310                 315
Leu Leu Asp Thr Ala Met Ile Asn Asn Ser Arg Asn Leu Asn Ile
            320                 325                 330
Gln Leu Lys Trp Lys Arg Pro Pro Glu Asn Glu Ala Pro Val
            335                 340                 345
Pro Phe Leu His Ala Gln Arg Tyr Val Ser Gly Tyr Gly Leu Gln
            350                 355                 360
Lys Gly Glu Leu Ser Thr Leu Leu Tyr Asn Thr His Pro Tyr Arg
            365                 370                 375
Ala Phe Pro Val Leu Leu Leu Asp Thr Val Pro Trp Tyr Leu Arg
            380                 385                 390
Leu Tyr Val His Thr Leu Thr Ile Thr Ser Lys Gly Lys Glu Asn
            395                 400                 405
Lys Pro Ser Tyr Ile His Tyr Gln Pro Ala Gln Asp Arg Leu Gln
            410                 415                 420
Pro His Leu Leu Glu Met Leu Ile Gln Leu Pro Ala Asn Ser Val
            425                 430                 435
Thr Lys Val Ser Ile Gln Phe Glu Arg Ala Leu Leu Lys Trp Thr
            440                 445                 450
Glu Tyr Thr Pro Asp Pro Asn His Gly Phe Tyr Val Ser Pro Ser
            455                 460                 465
Val Leu Ser Ala Leu Val Pro Ser Met Val Ala Lys Pro Val
            470                 475                 480
Asp Trp Glu Glu Ser Pro Leu Phe Asn Ser Leu Phe Pro Val Ser
            485                 490                 495
Asp Gly Ser Asn Tyr Phe Val Arg Leu Tyr Thr Glu Pro Leu Leu
            500                 505                 510
Val Asn Leu Pro Thr Pro Asp Phe Ser Met Pro Tyr Asn Val Ile
            515                 520                 525
Cys Leu Thr Cys Thr Val Val Ala Val Cys Tyr Gly Ser Phe Tyr
            530                 535                 540
Asn Leu Leu Thr Arg Thr Phe His Ile Glu Glu Pro Arg Thr Gly
            545                 550                 555
Gly Leu Ala Lys Arg Leu Ala Asn Leu Ile Arg Arg Ala Arg Gly
            560                 565                 570
Val Pro Pro Leu

<210> SEQ ID NO 35
<211> LENGTH: 2243
<212> TYPE: DNA
```

-continued

<213> ORGANISM: Homo sapiens

<400> SEQUENCE: 35

| | |
|---|---|
| cgccggaggc agcggcggcg tggcgcagcg gcgacatggc cgttgtctca | 50 |
| gaggacgact ttcagcacag ttcaaactcc acctacggaa ccacaagcag | 100 |
| cagtctccga gctgaccagg aggcactgct tgagaagctg ctggaccgcc | 150 |
| cgcccctgg cctgcagagg cccgaggacc gcttctgtgg cacatacatc | 200 |
| atcttcttca gcctgggcat tggcagtcta ctgccatgga acttctttat | 250 |
| cactgccaag gagtactgga tgttcaaact ccgcaactcc tccagcccag | 300 |
| ccaccgggga ggaccctgag ggctcagaca tcctgaacta ctttgagagc | 350 |
| taccttgccg ttgcctccac cgtgccctcc atgctgtgcc tggtggccaa | 400 |
| cttcctgctt gtcaacaggg ttgcagtcca catccgtgtc ctggcctcac | 450 |
| tgacggtcat cctggccatc ttcatggtga taactgcact ggtgaaggtg | 500 |
| gacacttcct cctggacccg tggtttttt gcggtcacca ttgtctgcat | 550 |
| ggtgatcctc agcggtgcct ccactgtctt cagcagcagc atctacggca | 600 |
| tgaccggctc ctttcctatg aggaactccc aagcactgat atcaggagga | 650 |
| gccatgggcg ggacggtcag cgccgtggcc tcattggtgg acttggctgc | 700 |
| atccagtgat gtgaggaaca cgccctggc cttcttcctg acggccacca | 750 |
| tcttcctcgt gctctgcatg ggactctacc tgctgctgtc caggctggag | 800 |
| tatgccaggt actacatgag gcctgttctt gcggcccatg tgttttctgg | 850 |
| tgaagaggag cttccccagg actccctcag tgcccttcg gtggcctcca | 900 |
| gattcattga ttcccacaca cccctctcc gccccatcct gaagaagacg | 950 |
| gccagcctgg gcttctgtgt cacctacgtc ttcttcatca ccagcctcat | 1000 |
| ctaccccgcc gtctgcacca acatcgagtc cctcaacaag ggctcgggct | 1050 |
| cactgtggac caccaagttt ttcatccccc tcactacctt cctcctgtac | 1100 |
| aactttgctg acctatgtgg ccggcagctc accgcctgga tccaggtgcc | 1150 |
| agggcccaac agcaaggcgc tcccaggggtt cgtgctcctc cggacctgcc | 1200 |
| tcatccccct cttcgtgctc tgtaactacc agccccgcgt ccacctgaag | 1250 |
| actgtggtct ccagtccga tgtgtacccc gcactcctca gctccctgct | 1300 |
| ggggctcagc aacggctacc tcagcaccct ggccctcctc tacgggccta | 1350 |
| agattgtgcc cagggagctg gctgaggcca cgggagtggt gatgtcctt | 1400 |
| tatgtgtgct tgggcttaac actgggctca gcctgctcta ccctcctggt | 1450 |
| gcacctcatc tagaagggag gacacaagga cattggtgct tcagagcctt | 1500 |
| tgaagatgag aagagagtgc aggagggctg ggggccatgg aggaaaggcc | 1550 |
| taaagtttca cttggggaca gagagcagag cacactcggg cctcatccct | 1600 |
| cccaagatgc cagtgagcca cgtccatgcc cattccgtgc aaggcagata | 1650 |
| ttccagtcat attaacagaa cactcctgag acagttgaag aagaaatagc | 1700 |
| acaaatcagg ggtactccct tcacagctga tggttaacat tccaccttct | 1750 |
| ttctagccct tcaaagatgc tgccagtgtt cgccctagag ttattacaaa | 1800 |
| gccagtgcca aaaccagcc atgggctctt tgcaacctcc cagctgcgct | 1850 |
| cattccagct gacagcgaga tgcaagcaaa tgctcagctc tccttaccct | 1900 |

```
gaagggtct ccctggaatg gaagtcccct ggcatggtca gtcctcaggc         1950
ccaagactca agtgtgcaca gaccctgtg ttctgcgggt gaacaactgc          2000
ccactaacca gactggaaaa cccagaaaga tgggccttcc atgaatgctt         2050
cattccagag ggaccagagg gcctcccgt gcaagggatc aagcatgtct          2100
ggcctgggtt tcaaaaaaa gagggatcct catgacctgg tggtctatgg          2150
cctgggtcaa gatgagggtc tttcagtgtt cctgtttaca acatgtcaaa         2200
gccattggtt caagggcgta ataaatactt gcgtattcaa  aaa               2243
```

<210> SEQ ID NO 36
<211> LENGTH: 475
<212> TYPE: PRT
<213> ORGANISM: Homo sapiens

<400> SEQUENCE: 36

```
Met Ala Val Val Ser Glu Asp Asp Phe Gln His Ser Ser Asn Ser
  1               5                  10                  15

Thr Tyr Gly Thr Thr Ser Ser Ser Leu Arg Ala Asp Gln Glu Ala
                 20                  25                  30

Leu Leu Glu Lys Leu Leu Asp Arg Pro Pro Gly Leu Gln Arg
             35                  40                  45

Pro Glu Asp Arg Phe Cys Gly Thr Tyr Ile Ile Phe Phe Ser Leu
             50                  55                  60

Gly Ile Gly Ser Leu Leu Pro Trp Asn Phe Phe Ile Thr Ala Lys
             65                  70                  75

Glu Tyr Trp Met Phe Lys Leu Arg Asn Ser Ser Ser Pro Ala Thr
             80                  85                  90

Gly Glu Asp Pro Glu Gly Ser Asp Ile Leu Asn Tyr Phe Glu Ser
             95                 100                 105

Tyr Leu Ala Val Ala Ser Thr Val Pro Ser Met Leu Cys Leu Val
            110                 115                 120

Ala Asn Phe Leu Leu Val Asn Arg Val Ala Val His Ile Arg Val
            125                 130                 135

Leu Ala Ser Leu Thr Val Ile Leu Ala Ile Phe Met Val Ile Thr
            140                 145                 150

Ala Leu Val Lys Val Asp Thr Ser Ser Trp Thr Arg Gly Phe Phe
            155                 160                 165

Ala Val Thr Ile Val Cys Met Val Ile Leu Ser Gly Ala Ser Thr
            170                 175                 180

Val Phe Ser Ser Ser Ile Tyr Gly Met Thr Gly Ser Phe Pro Met
            185                 190                 195

Arg Asn Ser Gln Ala Leu Ile Ser Gly Gly Ala Met Gly Gly Thr
            200                 205                 210

Val Ser Ala Val Ala Ser Leu Val Asp Leu Ala Ala Ser Ser Asp
            215                 220                 225

Val Arg Asn Ser Ala Leu Ala Phe Phe Leu Thr Ala Thr Ile Phe
            230                 235                 240

Leu Val Leu Cys Met Gly Leu Tyr Leu Leu Leu Ser Arg Leu Glu
            245                 250                 255

Tyr Ala Arg Tyr Tyr Met Arg Pro Val Leu Ala Ala His Val Phe
            260                 265                 270

Ser Gly Glu Glu Glu Leu Pro Gln Asp Ser Leu Ser Ala Pro Ser
            275                 280                 285

Val Ala Ser Arg Phe Ile Asp Ser His Thr Pro Pro Leu Arg Pro
```

```
                    290                 295                 300
Ile Leu Lys Lys Thr Ala Ser Leu Gly Phe Cys Val Thr Tyr Val
                305                 310                 315
Phe Phe Ile Thr Ser Leu Ile Tyr Pro Ala Val Cys Thr Asn Ile
                320                 325                 330
Glu Ser Leu Asn Lys Gly Ser Gly Ser Leu Trp Thr Thr Lys Phe
                335                 340                 345
Phe Ile Pro Leu Thr Thr Phe Leu Leu Tyr Asn Phe Ala Asp Leu
                350                 355                 360
Cys Gly Arg Gln Leu Thr Ala Trp Ile Gln Val Pro Gly Pro Asn
                365                 370                 375
Ser Lys Ala Leu Pro Gly Phe Val Leu Leu Arg Thr Cys Leu Ile
                380                 385                 390
Pro Leu Phe Val Leu Cys Asn Tyr Gln Pro Arg Val His Leu Lys
                395                 400                 405
Thr Val Val Phe Gln Ser Asp Val Tyr Pro Ala Leu Leu Ser Ser
                410                 415                 420
Leu Leu Gly Leu Ser Asn Gly Tyr Leu Ser Thr Leu Ala Leu Leu
                425                 430                 435
Tyr Gly Pro Lys Ile Val Pro Arg Glu Leu Ala Glu Ala Thr Gly
                440                 445                 450
Val Val Met Ser Phe Tyr Val Cys Leu Gly Leu Thr Leu Gly Ser
                455                 460                 465
Ala Cys Ser Thr Leu Leu Val His Leu Ile
                470                 475

<210> SEQ ID NO 37
<211> LENGTH: 1630
<212> TYPE: DNA
<213> ORGANISM: Homo sapiens

<400> SEQUENCE: 37
cggctcgagt gcagctgtgg ggagatttca gtgcattgcc tcccctgggt            50
gctcttcatc ttggatttga agttgagag cagcatgttt tgcccactga            100
aactcatcct gctgccagtg ttactggatt attccttggg cctgaatgac            150
ttgaatgttt ccccgcctga gctaacagtc catgtgggtg attcagctct            200
gatgggatgt gttttccaga gcacagaaga caaatgtata ttcaagatag            250
actggactct gtcaccagga gagcacgcca aggacgaata tgtgctatac            300
tattactcca atctcagtgt gcctattggg cgcttccaga accgcgtaca            350
cttgatgggg gacatcttat gcaatgatgg ctctctcctg ctccaagatg            400
tgcaagaggc tgaccaggga acctatatct gtgaaatccg cctcaagggg            450
gagagccagt tgttcaagaa ggcggtggta ctgcatgtgc ttccagagga            500
gcccaaagag ctcatggtcc atgtgggtgg attgattcag atgggatgtg            550
ttttccagag cacagaagtg aaacacgtga ccaaggtaga atggatattt            600
tcaggacggc gcgcaaagga ggagattgta tttcgttact accacaaact            650
caggatgtct gtggagtact cccagagctg gggccacttc agaatcgtgt            700
tgaacctggt gggggacatt ttccgcaatg acggttccat catgcttcaa            750
ggagtgaggg agtcagatgg aggaaactac acctgcagta tccacctagg            800
gaacctggtg ttcaagaaaa ccattgtgct gcatgtcagc ccggaagagc            850
```

```
ctcgaacact ggtgacccng gcagccctga ggcctctggt cttgggtggt        900
aatcagttgg tgatcattgt gggaattgtc tgtgccacaa tcctgctgct        950
ccctgttctg atattgatcg tgaagaagac ctgtggaaat aagagttcag       1000
tgaattctac agtcttggtg aagaacacga agaagactaa tccagagata       1050
aaagaaaaac cctgccattt tgaaagatgt gaaggggaga aacacattta       1100
ctccccaata attgtacggg aggtgatcga ggaagaagaa ccaagtgaaa       1150
aatcagaggc cacctacatg accatgcacc cagtttggcc ttctctgagg       1200
tcagatcgga acaactcact tgaaaaaaag tcaggtgggg gaatgccaaa       1250
aacacagcaa gccttttgag aagaatggag agtcccttca tctcagcagc       1300
ggtggagact ctctcctgtg tgtgtcctgg gccactctac cagtgatttc       1350
agactcccgc tctcccagct gtcctcctgt ctcattgttt ggtcaataca       1400
ctgaagatgg agaatttgga gcctggcaga gagactggac agctctggag       1450
gaacaggcct gctgagggga ggggagcatg gacttggcct ctggagtggg       1500
acactggccc tgggaaccag gctgagctga gtggcctcaa accccccgtt       1550
ggatcagacc ctcctgtggg cagggttctt agtggatgag ttactgggaa       1600
gaatcagaga taaaaaccaa cccaaatcaa                             1630
```

<210> SEQ ID NO 38
<211> LENGTH: 394
<212> TYPE: PRT
<213> ORGANISM: Homo sapiens

<400> SEQUENCE: 38

```
Met Phe Cys Pro Leu Lys Leu Ile Leu Leu Pro Val Leu Leu Asp
  1               5                  10                  15

Tyr Ser Leu Gly Leu Asn Asp Leu Asn Val Ser Pro Pro Glu Leu
             20                  25                  30

Thr Val His Val Gly Asp Ser Ala Leu Met Gly Cys Val Phe Gln
         35                  40                  45

Ser Thr Glu Asp Lys Cys Ile Phe Lys Ile Asp Trp Thr Leu Ser
     50                  55                  60

Pro Gly Glu His Ala Lys Asp Glu Tyr Val Leu Tyr Tyr Tyr Ser
 65                  70                  75

Asn Leu Ser Val Pro Ile Gly Arg Phe Gln Asn Arg Val His Leu
             80                  85                  90

Met Gly Asp Ile Leu Cys Asn Asp Gly Ser Leu Leu Leu Gln Asp
         95                 100                 105

Val Gln Glu Ala Asp Gln Gly Thr Tyr Ile Cys Glu Ile Arg Leu
        110                 115                 120

Lys Gly Glu Ser Gln Val Phe Lys Lys Ala Val Val Leu His Val
        125                 130                 135

Leu Pro Glu Glu Pro Lys Glu Leu Met Val His Val Gly Gly Leu
        140                 145                 150

Ile Gln Met Gly Cys Val Phe Gln Ser Thr Glu Val Lys His Val
        155                 160                 165

Thr Lys Val Glu Trp Ile Phe Ser Gly Arg Arg Ala Lys Glu Glu
        170                 175                 180

Ile Val Phe Arg Tyr Tyr His Lys Leu Arg Met Ser Val Glu Tyr
        185                 190                 195

Ser Gln Ser Trp Gly His Phe Gln Asn Arg Val Asn Leu Val Gly
```

```
                    200                 205                 210
Asp Ile Phe Arg Asn Asp Gly Ser Ile Met Leu Gln Gly Val Arg
                215                 220                 225
Glu Ser Asp Gly Gly Asn Tyr Thr Cys Ser Ile His Leu Gly Asn
                230                 235                 240
Leu Val Phe Lys Lys Thr Ile Val Leu His Val Ser Pro Glu Glu
                245                 250                 255
Pro Arg Thr Leu Val Thr Pro Ala Ala Leu Arg Pro Leu Val Leu
                260                 265                 270
Gly Gly Asn Gln Leu Val Ile Ile Val Gly Ile Val Cys Ala Thr
                275                 280                 285
Ile Leu Leu Leu Pro Val Leu Ile Leu Ile Val Lys Lys Thr Cys
                290                 295                 300
Gly Asn Lys Ser Ser Val Asn Ser Thr Val Leu Val Lys Asn Thr
                305                 310                 315
Lys Lys Thr Asn Pro Glu Ile Lys Glu Lys Pro Cys His Phe Glu
                320                 325                 330
Arg Cys Glu Gly Glu Lys His Ile Tyr Ser Pro Ile Ile Val Arg
                335                 340                 345
Glu Val Ile Glu Glu Glu Pro Ser Glu Lys Ser Glu Ala Thr
                350                 355                 360
Tyr Met Thr Met His Pro Val Trp Pro Ser Leu Arg Ser Asp Arg
                365                 370                 375
Asn Asn Ser Leu Glu Lys Lys Ser Gly Gly Met Pro Lys Thr
                380                 385                 390
Gln Gln Ala Phe

<210> SEQ ID NO 39
<211> LENGTH: 537
<212> TYPE: DNA
<213> ORGANISM: Homo sapiens

<400> SEQUENCE: 39
taaaacagct acaatattcc agggccagtc acttgccatt tctcataaca        50
gcgtcagaga gaaagaactg actgaaacgt ttgagatgaa gaaagttctc       100
ctcctgatca cagccatctt ggcagtggct gttggtttcc cagtctctca       150
agaccaggaa cgagaaaaaa gaagtatcag tgacagcgat gaattagctt       200
cagggttttt tgtgttccct tacccatatc catttcgccc acttccacca       250
attccatttc caagatttcc atggtttaga cgtaattttc ctattccaat       300
acctgaatct gccctacaa ctccccttcc tagcgaaaag taaacaagaa        350
ggataagtca cgataaacct ggtcacctga aattgaaatt gagccacttc       400
cttgaagaat caaaattcct gttaataaaa gaaaaacaaa tgtaattgaa       450
atagcacaca gcattctcta gtcaatatct ttagtgatct tctttaataa       500
acatgaaagc aaagattttg gtttcttaat ttccaca                     537

<210> SEQ ID NO 40
<211> LENGTH: 85
<212> TYPE: PRT
<213> ORGANISM: Homo sapiens

<400> SEQUENCE: 40

Met Lys Lys Val Leu Leu Leu Ile Thr Ala Ile Leu Ala Val Ala
  1               5                  10                  15
```

```
Val Gly Phe Pro Val Ser Gln Asp Gln Glu Arg Glu Lys Arg Ser
             20                  25                  30

Ile Ser Asp Ser Asp Glu Leu Ala Ser Gly Phe Val Phe Pro
         35                  40                  45

Tyr Pro Tyr Pro Phe Arg Pro Leu Pro Pro Ile Pro Phe Pro Arg
             50                  55                  60

Phe Pro Trp Phe Arg Arg Asn Phe Pro Ile Pro Ile Pro Glu Ser
             65                  70                  75

Ala Pro Thr Thr Pro Leu Pro Ser Glu Lys
             80                  85

<210> SEQ ID NO 41
<211> LENGTH: 1570
<212> TYPE: DNA
<213> ORGANISM: Homo sapiens

<400> SEQUENCE: 41
```

| | | | | | |
|---|---|---|---|---|---|
| gctgtttctc | tcgcgccacc | actggccgcc | ggccgcagct | ccaggtgtcc | 50 |
| tagccgccca | gcctcgacgc | cgtcccggga | cccctgtgct | ctgcgcgaag | 100 |
| ccctggcccc | gggggccggg | gcatgggcca | ggggcgcggg | gtgaagcggc | 150 |
| ttcccgcggg | gccgtgactg | ggcgggcttc | agccatgaag | accctcatag | 200 |
| ccgcctactc | cggggtcctg | cgcggcgagc | gtcaggccga | ggctgaccgg | 250 |
| agccagcgct | ctcacggagg | acctgcgctg | tcgcgcgagg | ggtctgggag | 300 |
| atggggcact | ggatccagca | tcctctccgc | cctccaggac | ctcttctctg | 350 |
| tcacctggct | caataggtcc | aaggtggaaa | agcagctaca | ggtcatctca | 400 |
| gtgctccagt | gggtcctgtc | cttccttgta | ctgggagtgg | cctgcagtgc | 450 |
| catcctcatg | tacatattct | gcactgattg | ctggctcatc | gctgtgctct | 500 |
| acttcacttg | gctggtgttt | gactggaaca | cacccaagaa | aggtggcagg | 550 |
| aggtcacagt | gggtccgaaa | ctgggctgtg | tggcgctact | ttcgagacta | 600 |
| ctttcccatc | cagctggtga | agacacacaa | cctgctgacc | accaggaact | 650 |
| atatctttgg | ataccacccc | catggtatca | tgggcctggg | tgccttctgc | 700 |
| aacttcagca | cagaggccac | agaagtgagc | aagaagttcc | aggcatacg | 750 |
| gccttacctg | gctacactgg | caggcaactt | ccgaatgcct | gtgttgaggg | 800 |
| agtacctgat | gtctggaggt | atctgccctg | tcagccggga | caccatagac | 850 |
| tatttgcttt | caaagaatgg | gagtggcaat | gctatcatca | tcgtggtcgg | 900 |
| gggtgcggct | gagtctctga | ctccatgcc | tggcaagaat | gcagtcaccc | 950 |
| tgcggaaccg | caagggcttt | gtgaaactgg | ccctgcgtca | tggagctgac | 1000 |
| ctggttccca | tctactcctt | tggagagaat | gaagtgtaca | agcaggtgat | 1050 |
| cttcgaggag | ggctcctggg | gccgatgggt | ccagaagaag | ttccagaaat | 1100 |
| acattggttt | cgccccatgc | atcttccatg | gtcgaggccc | cttctcctcc | 1150 |
| gacacctggg | ggctggtgcc | ctactccaag | cccatcacca | ctgttgtggg | 1200 |
| agagcccatc | accatcccca | agctggagca | cccaacccag | caagacatcg | 1250 |
| acctgtacca | caccatgtac | atggaggccc | tggtgaagct | cttcgacaag | 1300 |
| cacaagacca | agttcggcct | cccggagact | gaggtcctgg | aggtgaactg | 1350 |
| agccagcctt | cggggccaat | tccctggagg | aaccagctgc | aaatcacttt | 1400 |

```
tttgctctgt aaatttggaa gtgtcatggg tgtctgtggg ttatttaaaa        1450
gaaattataa caattttgct aaaccaaaaa aaaaaaaaaa aaaaaaaaaa        1500
aaaaaaaaaa aaaaaaaaaa aaaaaaaaaa aaaaaaaaaa aaaaaaaaaa        1550
aaaaaaaaaa aaaaaaaaaa                                         1570
```

```
<210> SEQ ID NO 42
<211> LENGTH: 388
<212> TYPE: PRT
<213> ORGANISM: Homo sapiens

<400> SEQUENCE: 42

Met Lys Thr Leu Ile Ala Ala Tyr Ser Gly Val Leu Arg Gly Glu
 1               5                  10                  15

Arg Gln Ala Glu Ala Asp Arg Ser Gln Arg Ser His Gly Gly Pro
                20                  25                  30

Ala Leu Ser Arg Glu Gly Ser Gly Arg Trp Gly Thr Gly Ser Ser
                35                  40                  45

Ile Leu Ser Ala Leu Gln Asp Leu Phe Ser Val Thr Trp Leu Asn
                50                  55                  60

Arg Ser Lys Val Glu Lys Gln Leu Gln Val Ile Ser Val Leu Gln
                65                  70                  75

Trp Val Leu Ser Phe Leu Val Leu Gly Val Ala Cys Ser Ala Ile
                80                  85                  90

Leu Met Tyr Ile Phe Cys Thr Asp Cys Trp Leu Ile Ala Val Leu
                95                 100                 105

Tyr Phe Thr Trp Leu Val Phe Asp Trp Asn Thr Pro Lys Lys Gly
               110                 115                 120

Gly Arg Arg Ser Gln Trp Val Arg Asn Trp Ala Val Trp Arg Tyr
               125                 130                 135

Phe Arg Asp Tyr Phe Pro Ile Gln Leu Val Lys Thr His Asn Leu
               140                 145                 150

Leu Thr Thr Arg Asn Tyr Ile Phe Gly Tyr His Pro His Gly Ile
               155                 160                 165

Met Gly Leu Gly Ala Phe Cys Asn Phe Ser Thr Glu Ala Thr Glu
               170                 175                 180

Val Ser Lys Lys Phe Pro Gly Ile Arg Pro Tyr Leu Ala Thr Leu
               185                 190                 195

Ala Gly Asn Phe Arg Met Pro Val Leu Arg Glu Tyr Leu Met Ser
               200                 205                 210

Gly Gly Ile Cys Pro Val Ser Arg Asp Thr Ile Asp Tyr Leu Leu
               215                 220                 225

Ser Lys Asn Gly Ser Gly Asn Ala Ile Ile Val Val Gly Gly
               230                 235                 240

Ala Ala Glu Ser Leu Ser Ser Met Pro Gly Lys Asn Ala Val Thr
               245                 250                 255

Leu Arg Asn Arg Lys Gly Phe Val Lys Leu Ala Leu Arg His Gly
               260                 265                 270

Ala Asp Leu Val Pro Ile Tyr Ser Phe Gly Glu Asn Glu Val Tyr
               275                 280                 285

Lys Gln Val Ile Phe Glu Glu Gly Ser Trp Gly Arg Trp Val Gln
               290                 295                 300

Lys Lys Phe Gln Lys Tyr Ile Gly Phe Ala Pro Cys Ile Phe His
               305                 310                 315

Gly Arg Gly Leu Phe Ser Ser Asp Thr Trp Gly Leu Val Pro Tyr
```

```
                    320                 325                 330
Ser Lys Pro Ile Thr Thr Val Val Gly Glu Pro Ile Thr Ile Pro
                335                 340                 345

Lys Leu Glu His Pro Thr Gln Gln Asp Ile Asp Leu Tyr His Thr
                350                 355                 360

Met Tyr Met Glu Ala Leu Val Lys Leu Phe Asp Lys His Lys Thr
                365                 370                 375

Lys Phe Gly Leu Pro Glu Thr Glu Val Leu Glu Val Asn
                380                 385

<210> SEQ ID NO 43
<211> LENGTH: 535
<212> TYPE: DNA
<213> ORGANISM: Homo sapiens

<400> SEQUENCE: 43
agtgacaatc tcagagcagc ttctacacca cagccatttc cagcatgaag         50
atcactgggg gtctccttct gctctgtaca gtggtctatt tctgtagcag        100
ctcagaagct gctagtctgt ctccaaaaaa agtggactgc agcatttaca        150
agaagtatcc agtggtggcc atcccctgcc ccatcacata cctaccagtt        200
tgtggttctg actacatcac ctatgggaat gaatgtcact gtgtaccga         250 gagcttgaaa agtaatggaa gagttcagtt tcttcacgat ggaagttgct        300
aaattctcca tggacataga gagaaaggaa tgatattctc atcatcatct        350
tcatcatccc aggctctgac tgagtttctt tcagttttac tgatgttctg        400
ggtgggggac agagccagat tcagagtaat cttgactgaa tggagaaagt        450
ttctgtgcta cccctacaaa cccatgcctc actgacagac cagcattttt        500 ttttttaacac gtcaataaaa aaataatctc ccaga                       535

<210> SEQ ID NO 44
<211> LENGTH: 85
<212> TYPE: PRT
<213> ORGANISM: Homo sapiens

<400> SEQUENCE: 44

Met Lys Ile Thr Gly Gly Leu Leu Leu Cys Thr Val Val Tyr
 1               5                  10                  15

Phe Cys Ser Ser Ser Glu Ala Ala Ser Leu Ser Pro Lys Lys Val
                20                  25                  30

Asp Cys Ser Ile Tyr Lys Lys Tyr Pro Val Val Ala Ile Pro Cys
                35                  40                  45

Pro Ile Thr Tyr Leu Pro Val Cys Gly Ser Asp Tyr Ile Thr Tyr
                50                  55                  60

Gly Asn Glu Cys His Leu Cys Thr Glu Ser Leu Lys Ser Asn Gly
                65                  70                  75

Arg Val Gln Phe Leu His Asp Gly Ser Cys
                80                  85

<210> SEQ ID NO 45
<211> LENGTH: 1257
<212> TYPE: DNA
<213> ORGANISM: Homo sapiens

<400> SEQUENCE: 45
ggagagaggc gcgcgggtga aaggcgcatt gatgcagcct gcggcggcct         50
```

-continued

```
cggagcgcgg cggagccaga cgctgaccac gttcctctcc tcggtctcct      100
ccgcctccag ctccgcgctg cccggcagcc gggagccatg cgaccccagg      150
gccccgccgc ctccccgcag cggctccgcg gcctcctgct gctcctgctg      200
ctgcagctgc ccgcgccgtc gagcgcctct gagatcccca aggggaagca      250
aaaggcgcag ctccggcaga gggaggtggt ggacctgtat aatggaatgt      300
gcttacaagg gccagcagga gtgcctggtc gagacgggag ccctggggcc      350
aatgttattc cgggtacacc tgggatccca ggtcgggatg gattcaaagg      400
agaaaagggg gaatgtctga gggaaagctt tgaggagtcc tggacaccca      450
actacaagca gtgttcatgg agttcattga attatggcat agatcttggg      500
aaaattgcgg agtgtacatt tacaaagatg cgttcaaata gtgctctaag      550
agttttgttc agtggctcac ttcggctaaa atgcagaaat gcatgctgtc      600
agcgttggta tttcacattc aatggagctg aatgttcagg acctcttccc      650
attgaagcta taatttattt ggaccaagga agccctgaaa tgaattcaac      700
aattaatatt catcgcactt cttctgtgga aggactttgt gaaggaattg      750
gtgctggatt agtggatgtt gctatctggg ttggcacttg ttcagattac      800
ccaaaaggag atgcttctac tggatggaat tcagtttctc gcatcattat      850
tgaagaacta ccaaaataaa tgctttaatt ttcatttgct acctcttttt      900
ttattatgcc ttggaatggt tcacttaaat gacattttaa ataagtttat      950
gtatacatct gaatgaaaag caaagctaaa tatgtttaca gaccaaagtg     1000
tgatttcaca ctgttttttaa atctagcatt attcattttg cttcaatcaa     1050
aagtggtttc aatatttttt ttagttggtt agaatacttt cttcatagtc     1100
acattctctc aacctataat ttggaatatt gttgtggtct tttgttttt      1150 ctcttagtat agcattttta aaaaatata aaagctacca atctttgtac       1200
aatttgtaaa tgttaagaat ttttttata tctgttaaat aaaaattatt      1250
tccaaca                                                    1257
```

<210> SEQ ID NO 46
<211> LENGTH: 243
<212> TYPE: PRT
<213> ORGANISM: Homo sapiens

<400> SEQUENCE: 46

```
Met Arg Pro Gln Gly Pro Ala Ala Ser Pro Gln Arg Leu Arg Gly
 1               5                  10                  15

Leu Leu Leu Leu Leu Leu Leu Gln Leu Pro Ala Pro Ser Ser Ala
                20                  25                  30

Ser Glu Ile Pro Lys Gly Lys Gln Lys Ala Gln Leu Arg Gln Arg
                35                  40                  45

Glu Val Val Asp Leu Tyr Asn Gly Met Cys Leu Gln Gly Pro Ala
                50                  55                  60

Gly Val Pro Gly Arg Asp Gly Ser Pro Gly Ala Asn Val Ile Pro
                65                  70                  75

Gly Thr Pro Gly Ile Pro Gly Arg Asp Gly Phe Lys Gly Glu Lys
                80                  85                  90

Gly Glu Cys Leu Arg Glu Ser Phe Glu Glu Ser Trp Thr Pro Asn
                95                 100                 105

Tyr Lys Gln Cys Ser Trp Ser Ser Leu Asn Tyr Gly Ile Asp Leu
```

```
                110                 115                 120
Gly Lys Ile Ala Glu Cys Thr Phe Thr Lys Met Arg Ser Asn Ser
                125                 130                 135
Ala Leu Arg Val Leu Phe Ser Gly Ser Leu Arg Leu Lys Cys Arg
                140                 145                 150
Asn Ala Cys Cys Gln Arg Trp Tyr Phe Thr Phe Asn Gly Ala Glu
                155                 160                 165
Cys Ser Gly Pro Leu Pro Ile Glu Ala Ile Ile Tyr Leu Asp Gln
                170                 175                 180
Gly Ser Pro Glu Met Asn Ser Thr Ile Asn Ile His Arg Thr Ser
                185                 190                 195
Ser Val Glu Gly Leu Cys Glu Gly Ile Gly Ala Gly Leu Val Asp
                200                 205                 210
Val Ala Ile Trp Val Gly Thr Cys Ser Asp Tyr Pro Lys Gly Asp
                215                 220                 225
Ala Ser Thr Gly Trp Asn Ser Val Ser Arg Ile Ile Ile Glu Glu
                230                 235                 240
Leu Pro Lys

<210> SEQ ID NO 47
<211> LENGTH: 1174
<212> TYPE: DNA
<213> ORGANISM: Homo sapiens

<400> SEQUENCE: 47
gcggaactgg ctccggctgg cacctgagga gcggcgtgac cccgagggcc         50
cagggagctg cccggctggc ctaggcaggc agccgcacca tggccagcac        100
ggccgtgcag cttctgggct tcctgctcag cttcctgggc atggtgggca        150
cgttgatcac caccatcctg ccgcactggc ggaggacagc gcacgtgggc        200
accaacatcc tcacggccgt gtcctacctg aaagggctct ggatggagtg        250
tgtgtggcac agcacaggca tctaccagtc ccagatctac cgatccctgc        300
tggcgctgcc ccaagacctc caggctgccc gcgccctcat ggtcatctcc        350
tgcctgctct cgggcatagc ctgcgcctgc gccgtcatcg gatgaagtg         400 cacgcgctgc gccaagggca cccgccaa gaccacctt gccatcctcg            450 gcggcaccct cttcatcctg gccggcctcc tgtgcatggt ggccgtctcc        500
tggaccacca cgacgtggt gcagaacttc tacaacccgc tgctgcccag         550
cggcatgaag tttgagattg ccaggcccct gtacctgggc ttcatctcct        600
cgtccctctc gctcattggt ggcacccctgc tttgcctgtc ctgccaggac       650
gaggcaccct acaggcccta ccaggcccg cccagggcca ccacgaccac         700
tgcaaacacc gcacctgcct accagccacc agctgcctac aaagacaatc       750 gggcccctc agtgacctcg gccacgcaca gcgggtacag gctgaacgac         800
tacgtgtgag tccccacagc ctgcttctcc cctgggctgc tgtgggctgg       850
gtccccggcg ggactgtcaa tggaggcagg ggttccagca caaagtttac       900
ttctgggcaa ttttttgtatc caaggaaata atgtgaatgc gaggaaatgt      950
ctttagagca caggggacaga gggggaaata agaggaggag aaagctctct    1000
ataccaaaga ctgaaaaaaa aaatcctgtc tgttttttgta tttattatat    1050 atatttatgt gggtgatttg ataacaagtt taatataaag tgacttggga    1100
```

```
gtttggtcag tggggttggt ttgtgatcca ggaataaacc ttgcggatgt        1150
ggctgtttat gaaaaaaaaa aaaa                                    1174
```

<210> SEQ ID NO 48
<211> LENGTH: 239
<212> TYPE: PRT
<213> ORGANISM: Homo sapiens

<400> SEQUENCE: 48

```
Met Ala Ser Thr Ala Val Gln Leu Leu Gly Phe Leu Leu Ser Phe
 1               5                  10                  15

Leu Gly Met Val Gly Thr Leu Ile Thr Thr Ile Leu Pro His Trp
                20                  25                  30

Arg Arg Thr Ala His Val Gly Thr Asn Ile Leu Thr Ala Val Ser
            35                  40                  45

Tyr Leu Lys Gly Leu Trp Met Glu Cys Val Trp His Ser Thr Gly
        50                  55                  60

Ile Tyr Gln Cys Gln Ile Tyr Arg Ser Leu Leu Ala Leu Pro Gln
    65                  70                  75

Asp Leu Gln Ala Ala Arg Ala Leu Met Val Ile Ser Cys Leu Leu
80                  85                  90

Ser Gly Ile Ala Cys Ala Cys Ala Val Ile Gly Met Lys Cys Thr
            95                 100                 105

Arg Cys Ala Lys Gly Thr Pro Ala Lys Thr Thr Phe Ala Ile Leu
        110                 115                 120

Gly Gly Thr Leu Phe Ile Leu Ala Gly Leu Leu Cys Met Val Ala
    125                 130                 135

Val Ser Trp Thr Thr Asn Asp Val Val Gln Asn Phe Tyr Asn Pro
140                 145                 150

Leu Leu Pro Ser Gly Met Lys Phe Glu Ile Gly Gln Ala Leu Tyr
            155                 160                 165

Leu Gly Phe Ile Ser Ser Ser Leu Ser Leu Ile Gly Gly Thr Leu
        170                 175                 180

Leu Cys Leu Ser Cys Gln Asp Glu Ala Pro Tyr Arg Pro Tyr Gln
    185                 190                 195

Ala Pro Pro Arg Ala Thr Thr Thr Thr Ala Asn Thr Ala Pro Ala
200                 205                 210

Tyr Gln Pro Pro Ala Ala Tyr Lys Asp Asn Arg Ala Pro Ser Val
            215                 220                 225

Thr Ser Ala Thr His Ser Gly Tyr Arg Leu Asn Asp Tyr Val
        230                 235
```

<210> SEQ ID NO 49
<211> LENGTH: 2121
<212> TYPE: DNA
<213> ORGANISM: Homo sapiens

<400> SEQUENCE: 49

```
gagctcccct caggagcgcg ttagcttcac accttcggca gcaggagggc          50
ggcagcttct cgcaggcggc agggcgggcg gccaggatca tgtccaccac         100
cacatgccaa gtggtggcgt tcctcctgtc catcctgggg ctggccggct         150
gcatcgcggc caccgggatg gacatgtgga gcacccagga cctgtacgac         200
aaccccgtca cctccgtgtt ccagtacgaa gggctctgga ggagctgcgt         250
gaggcagagt tcaggcttca ccgaatgcag gccctatttc accatcctgg         300
```

```
gacttccagc catgctgcag gcagtgcgag ccctgatgat cgtaggcatc      350
gtcctgggtg ccattggcct cctggtatcc atctttgccc tgaaatgcat      400
ccgcattggc agcatggagg actctgccaa agccaacatg acactgacct      450
ccgggatcat gttcattgtc tcaggtcttt gtgcaattgc tggagtgtct      500
gtgtttgcca acatgctggt gactaacttc tggatgtcca cagctaacat      550
gtacaccggc atgggtggga tggtgcagac tgttcagacc aggtacacat      600
ttggtgcggc tctgttcgtg ggctgggtcg ctggaggcct cacactaatt      650
gggggtgtga tgatgtgcat cgcctgccgg ggcctggcac cagaagaaac      700
caactacaaa gccgtttctt atcatgcctc aggccacagt gttgcctaca      750
agcctggagg cttcaaggcc agcactggct ttgggtccaa caccaaaaac      800
aagaagatat acgatggagg tgcccgcaca gaggacgagg tacaatctta      850
tccttccaag cacgactatg tgtaatgctc taagacctct cagcacgggc      900
ggaagaaact cccggagagc tcacccaaaa acaaggaga tcccatctag       950 atttcttctt gcttttgact cacagctgga agttagaaaa gcctcgattt     1000
catctttgga gaggccaaat ggtcttagcc tcagtctctg tctctaaata     1050
ttccaccata aaacagctga gttatttatg aattagaggc tatagctcac     1100
attttcaatc ctctatttct tttttaaat ataactttct actctgatga      1150
gagaatgtgg ttttaatctc tctctcacat tttgatgatt tagacagact     1200 cccctcttc ctcctagtca ataaacccat tgatgatcta tttcccagct      1250
tatccccaag aaaacttttg aaggaaaga gtagacccaa agatgttatt      1300
ttctgctgtt tgaattttgt ctccccaccc ccaacttggc tagtaataaa     1350
cacttactga agaagaagca ataagagaaa gatatttgta atctctccag     1400
cccatgatct cggttttctt acactgtgat cttaaaagtt accaaaccaa     1450 agtcatttc agtttgaggc aaccaaacct ttctactgct gttgacatct      1500
tcttattaca gcaacaccat tctaggagtt tcctgagctc tccactggag     1550
tcctctttct gtcgcgggtc agaaattgtc cctagatgaa tgagaaaatt     1600 attttttta atttaagtcc taaatatagt taaaataaat aatgttttag      1650
taaaatgata cactatctct gtgaaatagc ctcacccta catgtggata      1700 gaaggaaatg aaaaaataat tgctttgaca ttgtctatat ggtactttgt     1750
aaagtcatgc ttaagtacaa attccatgaa aagctcacac ctgtaatcct     1800
agcactttgg gaggctgagg aggaaggatc acttgagccc agaagttcga     1850
gactagcctg gcaacatgg agaagccctg tctctacaaa atacagagag      1900
aaaaaatcag ccagtcatgg tggcatacac ctgtagtccc agcattccgg     1950
gaggctgagg tgggaggatc acttgagccc agggaggttg gggctgcagt     2000
gagccatgat cacaccactg cactccagcc aggtgacata gcgagatcct     2050
gtctaaaaaa ataaaaaata aataatggaa cacagcaagt cctaggaagt     2100
aggttaaaac taattctttta a                                   2121

<210> SEQ ID NO 50
<211> LENGTH: 261
<212> TYPE: PRT
<213> ORGANISM: Homo sapiens
```

<400> SEQUENCE: 50

```
Met Ser Thr Thr Thr Cys Gln Val Val Ala Phe Leu Leu Ser Ile
  1               5                  10                  15

Leu Gly Leu Ala Gly Cys Ile Ala Ala Thr Gly Met Asp Met Trp
                 20                  25                  30

Ser Thr Gln Asp Leu Tyr Asp Asn Pro Val Thr Ser Val Phe Gln
                 35                  40                  45

Tyr Glu Gly Leu Trp Arg Ser Cys Val Arg Gln Ser Ser Gly Phe
                 50                  55                  60

Thr Glu Cys Arg Pro Tyr Phe Thr Ile Leu Gly Leu Pro Ala Met
                 65                  70                  75

Leu Gln Ala Val Arg Ala Leu Met Ile Val Gly Ile Val Leu Gly
                 80                  85                  90

Ala Ile Gly Leu Leu Val Ser Ile Phe Ala Leu Lys Cys Ile Arg
                 95                 100                 105

Ile Gly Ser Met Glu Asp Ser Ala Lys Ala Asn Met Thr Leu Thr
                110                 115                 120

Ser Gly Ile Met Phe Ile Val Ser Gly Leu Cys Ala Ile Ala Gly
                125                 130                 135

Val Ser Val Phe Ala Asn Met Leu Val Thr Asn Phe Trp Met Ser
                140                 145                 150

Thr Ala Asn Met Tyr Thr Gly Met Gly Gly Met Val Gln Thr Val
                155                 160                 165

Gln Thr Arg Tyr Thr Phe Gly Ala Ala Leu Phe Val Gly Trp Val
                170                 175                 180

Ala Gly Gly Leu Thr Leu Ile Gly Gly Val Met Met Cys Ile Ala
                185                 190                 195

Cys Arg Gly Leu Ala Pro Glu Glu Thr Asn Tyr Lys Ala Val Ser
                200                 205                 210

Tyr His Ala Ser Gly His Ser Val Ala Tyr Lys Pro Gly Gly Phe
                215                 220                 225

Lys Ala Ser Thr Gly Phe Gly Ser Asn Thr Lys Asn Lys Lys Ile
                230                 235                 240

Tyr Asp Gly Gly Ala Arg Thr Glu Asp Glu Val Gln Ser Tyr Pro
                245                 250                 255

Ser Lys His Asp Tyr Val
                260
```

<210> SEQ ID NO 51
<211> LENGTH: 1706
<212> TYPE: DNA
<213> ORGANISM: Homo sapiens

<400> SEQUENCE: 51

```
ggagcgctgc tggaacccga gccggagccg gagccacagc ggggagggtg             50
gcctggcggc ctggagccgg acgtgtccgg ggcgtccccg cagaccgggg            100
cagcaggtcg tccgggggcc caccatgctg gtgactgcct accttgcttt            150
tgtaggcctc ctggcctcct gcctggggct ggaactgtca agatgccggg            200
ctaaaccccc tggaagggcc tgcagcaatc cctccttcct tcggtttcaa            250
ctggacttct atcaggtcta cttcctggcc ctggcagctg attggcttca            300 ggcccccctac ctctataaac tctaccagca ttactacttc ctggaaggtc           350
aaattgccat cctctatgtc tgtggccttg cctctacagt cctctttggc            400
```

```
ctagtggcct cctcccttgt ggattggctg ggtcgcaaga attcttgtgt        450
cctcttctcc ctgacttact cactatgctg cttaaccaaa ctctctcaag        500
actactttgt gctgctagtg gggcgagcac ttggtgggct gtccacagcc        550
ctgctcttct cagccttcga ggcctggtat atccatgagc acgtggaacg        600
gcatgacttc cctgctgagt ggatcccagc tacctttgct cgagctgcct        650
tctggaacca tgtgctggct gtagtggcag gtgtggcagc tgaggctgta        700
gccagctgga tagggctggg gcctgtagcg ccctttgtgg ctgccatccc        750
tctcctggct ctgcagggg ccttggccct tcgaaactgg ggggagaact         800
atgaccggca gcgtgccttc tcaaggacct gtgctggagg cctgcgctgc        850
ctcctgtcgg accgccgcgt gctgctgctg ggcaccatac aagctctatt        900
tgagagtgtc atcttcatct ttgtcttcct ctggacacct gtgctggacc        950
cacacggggc ccctctgggc attatcttct ccagcttcat ggcagccagc        1000
ctgcttggct cttccctgta ccgtatcgcc acctccaaga ggtaccacct        1050
tcagcccatg cacctgctgt cccttgctgt gctcatcgtc gtcttctctc        1100
tcttcatgtt gactttctct accagcccag gccaggagag tccggtggag        1150
tccttcatag cctttctact tattgagttg gcttgtggat tatactttcc        1200
cagcatgagc ttcctacgga gaaaggtgat ccctgagaca gagcaggctg        1250
gtgtactcaa ctggttccgg gtacctctgc actcactggc ttgcctaggg        1300
ctccttgtcc tccatgacag tgatcgaaaa acaggcactc ggaatatgtt        1350
cagcatttgc tctgctgtca tggtgatggc tctgctggca gtggtgggac        1400
tcttcaccgt ggtaaggcat gatgctgagc tgcgggtacc ttcacctact        1450
gaggagccct atgcccctga gctgtaaccc cactccagga caagatagct        1500
gggacagact cttgaattcc agctatccgg gattgtacag atctctctgt        1550
gactgacttt gtgactgtcc tgtggttct cctgccattg ctttgtgttt         1600
gggaggacat gatggggggtg atggactgga agaaggtgc caaaagttcc        1650
ctctgtgtta ctcccattta gaaataaac acttttaaat gatcaaaaaa         1700
aaaaaa                                                        1706
```

<210> SEQ ID NO 52
<211> LENGTH: 450
<212> TYPE: PRT
<213> ORGANISM: Homo sapiens

<400> SEQUENCE: 52

```
Met Leu Val Thr Ala Tyr Leu Ala Phe Val Gly Leu Leu Ala Ser
 1               5                  10                  15

Cys Leu Gly Leu Glu Leu Ser Arg Cys Arg Ala Lys Pro Pro Gly
                20                  25                  30

Arg Ala Cys Ser Asn Pro Ser Phe Leu Arg Phe Gln Leu Asp Phe
                35                  40                  45

Tyr Gln Val Tyr Phe Leu Ala Leu Ala Ala Asp Trp Leu Gln Ala
                50                  55                  60

Pro Tyr Leu Tyr Lys Leu Tyr Gln His Tyr Tyr Phe Leu Glu Gly
                65                  70                  75

Gln Ile Ala Ile Leu Tyr Val Cys Gly Leu Ala Ser Thr Val Leu
                80                  85                  90
```

```
Phe Gly Leu Val Ala Ser Ser Leu Val Asp Trp Gly Arg Lys
                 95                  100                 105

Asn Ser Cys Val Leu Phe Ser Leu Thr Tyr Ser Leu Cys Cys Leu
            110                 115                 120

Thr Lys Leu Ser Gln Asp Tyr Phe Val Leu Val Gly Arg Ala
            125                 130                 135

Leu Gly Gly Leu Ser Thr Ala Leu Leu Phe Ser Ala Phe Glu Ala
            140                 145                 150

Trp Tyr Ile His Glu His Val Glu Arg His Asp Phe Pro Ala Glu
            155                 160                 165

Trp Ile Pro Ala Thr Phe Ala Arg Ala Ala Phe Trp Asn His Val
            170                 175                 180

Leu Ala Val Val Ala Gly Val Ala Ala Glu Ala Val Ala Ser Trp
            185                 190                 195

Ile Gly Leu Gly Pro Val Ala Pro Phe Val Ala Ala Ile Pro Leu
            200                 205                 210

Leu Ala Leu Ala Gly Ala Leu Ala Leu Arg Asn Trp Gly Glu Asn
            215                 220                 225

Tyr Asp Arg Gln Arg Ala Phe Ser Arg Thr Cys Ala Gly Gly Leu
            230                 235                 240

Arg Cys Leu Leu Ser Asp Arg Arg Val Leu Leu Gly Thr Ile
            245                 250                 255

Gln Ala Leu Phe Glu Ser Val Ile Phe Ile Phe Val Phe Leu Trp
            260                 265                 270

Thr Pro Val Leu Asp Pro His Gly Ala Pro Leu Gly Ile Ile Phe
            275                 280                 285

Ser Ser Phe Met Ala Ala Ser Leu Leu Gly Ser Ser Leu Tyr Arg
            290                 295                 300

Ile Ala Thr Ser Lys Arg Tyr His Leu Gln Pro Met His Leu Leu
            305                 310                 315

Ser Leu Ala Val Leu Ile Val Val Phe Ser Leu Phe Met Leu Thr
            320                 325                 330

Phe Ser Thr Ser Pro Gly Gln Glu Ser Pro Val Glu Ser Phe Ile
            335                 340                 345

Ala Phe Leu Leu Ile Glu Leu Ala Cys Gly Leu Tyr Phe Pro Ser
            350                 355                 360

Met Ser Phe Leu Arg Arg Lys Val Ile Pro Glu Thr Glu Gln Ala
            365                 370                 375

Gly Val Leu Asn Trp Phe Arg Val Pro Leu His Ser Leu Ala Cys
            380                 385                 390

Leu Gly Leu Leu Val Leu His Asp Ser Asp Arg Lys Thr Gly Thr
            395                 400                 405

Arg Asn Met Phe Ser Ile Cys Ser Ala Val Met Val Met Ala Leu
            410                 415                 420

Leu Ala Val Val Gly Leu Phe Thr Val Arg His Asp Ala Glu
            425                 430                 435

Leu Arg Val Pro Ser Pro Thr Glu Glu Pro Tyr Ala Pro Glu Leu
            440                 445                 450

<210> SEQ ID NO 53
<211> LENGTH: 584
<212> TYPE: DNA
<213> ORGANISM: Homo sapiens

<400> SEQUENCE: 53
```

| | |
|---|---|
| cggaccacca gcaacagaca acatcttcat tcggctctcc ctgaagctgt | 50 |
| actgcctcgc tgagaggatg aaggtctccg aggctgccct gtctctcctt | 100 |
| gtcctcatcc ttatcattac ttcggcttct cgcagccagc caaaagttcc | 150 |
| tgagtgggtg aacaccccat ccacctgctg cctgaagtat tatgagaaag | 200 |
| tgttgccaag gagactagtg gtgggataca gaaaggccct caactgtcac | 250 |
| ctgccagcaa tcatcttcgt caccaagagg aaccgagaag tctgcaccaa | 300 |
| ccccaatgac gactgggtcc aagagtacat caaggatccc aacctaccct | 350 |
| tgctgcctac caggaacttg tccacggtta aaattattac agcaaagaat | 400 |
| ggtcaacccc agctcctcaa ctcccagtga tgaccaggct ttagtggaag | 450 |
| cccttgttta cagaagagag gggtaaacct atgaaaacag gggaagcctt | 500 |
| attaggctga aactagccag tcacattgag agaagcagaa caatgatcaa | 550 |
| aataaaggag aagtatttcg gaaaaaaaaa aaaa | 584 |

<210> SEQ ID NO 54
<211> LENGTH: 120
<212> TYPE: PRT
<213> ORGANISM: Homo sapiens

<400> SEQUENCE: 54

```
Met Lys Val Ser Glu Ala Ala Leu Ser Leu Leu Val Leu Ile Leu
 1               5                  10                  15
Ile Ile Thr Ser Ala Ser Arg Ser Gln Pro Lys Val Pro Glu Trp
                20                  25                  30
Val Asn Thr Pro Ser Thr Cys Cys Leu Lys Tyr Tyr Glu Lys Val
                35                  40                  45
Leu Pro Arg Arg Leu Val Val Gly Tyr Arg Lys Ala Leu Asn Cys
                50                  55                  60
His Leu Pro Ala Ile Ile Phe Val Thr Lys Arg Asn Arg Glu Val
                65                  70                  75
Cys Thr Asn Pro Asn Asp Asp Trp Val Gln Glu Tyr Ile Lys Asp
                80                  85                  90
Pro Asn Leu Pro Leu Leu Pro Thr Arg Asn Leu Ser Thr Val Lys
                95                 100                 105
Ile Ile Thr Ala Lys Asn Gly Gln Pro Gln Leu Leu Asn Ser Gln
               110                 115                 120
```

<210> SEQ ID NO 55
<211> LENGTH: 2036
<212> TYPE: DNA
<213> ORGANISM: Homo sapiens

<400> SEQUENCE: 55

| | |
|---|---|
| gccatggggc gctgggcctg ggtccccagc ccctggcccc caccggggct | 50 |
| gggccccttc ctcctcctcc tcctgctgct gctgctgctg ccacgggggt | 100 |
| tccagcccca gctggcggg aaccgtacgg agtccccaga acctaatgcc | 150 |
| acagcgaccc ctgcgatccc cactatcctg gtgacctctg tgacctctga | 200 |
| gaccccagca acaagtgctc cagaggcaga gggaccccaa agtgggggc | 250 |
| tcccgccccc gcccagggca gttccctcga gcagtagccc ccaggcccaa | 300 |
| gcactcaccg aggacgggag gccctgcagg ttccccttcc gctacggggg | 350 |
| ccgcatgctg catgcctgca cttcggaggg cagtgcacac aggaagtggt | 400 |

| | |
|---|---|
| gtgccacaac tcacaactac gaccgggaca gggcctgggg ctactgtgtg | 450 |
| gaggccaccc cgcctccagg gggcccagct gccctggatc cctgtgcctc | 500 |
| cggcccctgc tcaatggag gctcctgctc caatacccag gaccccagt | 550 |
| cctatcactg cagctgcccc cgggccttca ccggcaagga ctgcggcaca | 600 |
| gagaaatgct ttgatgagac ccgctacgag tacctggagg ggggcgaccg | 650 |
| ctgggcccgc gtgcgccagg gccacgtgga acagtgcgag tgcttcgggg | 700 |
| gccggacctg gtgcgaaggc acccgacata cagcttgtct gagcagccct | 750 |
| tgcctgaacg ggggcaccctg ccacctgatc gtggccaccg gaccaccgt | 800 |
| gtgtgcctgc ccaccaggct cgctggacg gctctgcaac atcgagcctg | 850 |
| atgagcgctg cttcttgggg aacggcactg ggtaccgtgg cgtggccagc | 900 |
| acctcagcct cgggcctcag ctgcctggcc tggaactccg atctgctcta | 950 |
| ccaggagctg cacgtggact ccgtgggcgc cgcggccctg ctgggcctgg | 1000 |
| gcccccatgc ctactgccgg aatccggaca atgacgagag gccctggtgc | 1050 |
| tacgtggtga aggacagcgc gctctcctgg gagtactgcc gcctggaggc | 1100 |
| ctgcgaatcc ctcaccagag tccaactgtc accggatctc ctggcgaccc | 1150 |
| tgcctgagcc agcctccccg gggcgccagg cctgcggcag gaggcacaag | 1200 |
| aagaggacgt tcctgcggcc acgtatcatc ggcggctcct cctcgctgcc | 1250 |
| cggctcgcac ccctggctgg ccgccatcta catcggggac agcttctgcg | 1300 |
| ccgggagcct ggtccacacc tgctgggtgg tgtcggccgc ccactgcttc | 1350 |
| tcccacagcc cccccaggga cagcgtctcc gtggtgctgg gccagcactt | 1400 |
| cttcaaccgc acgacggacg tgacgcagac cttcggcatc gagaagtaca | 1450 |
| tcccgtacac cctgtactcg gtgttcaacc ccagcgacca cgacctcgtc | 1500 |
| ctgatccggc tgaagaagaa aggggaccgc tgtgccacac gctcgcagtt | 1550 |
| cgtgcagccc atctgcctgc ccgagcccgg cagcaccttc cccgcaggac | 1600 |
| acaagtgcca gattgcgggc tggggccact ggatgagaa cgtgagcggc | 1650 |
| tactccagct ccctgcggga ggccctggtc ccctggtcg ccgaccacaa | 1700 |
| gtgcagcagc cctgaggtct acggcgccga catcagcccc aacatgctct | 1750 |
| gtgccggcta cttcgactgc aagtccgacg cctgccaggg ggactcaggg | 1800 |
| gggcccctgg cctgcgagaa gaacggcgtg gcttacctct acggcatcat | 1850 |
| cagctggggt gacggctgcg gcggctcca caagccgggg gtctacaccc | 1900 |
| gcgtggccaa ctatgtggac tggatcaacg accggatacg gcctcccagg | 1950 |
| cggcttgtgg ctccctcctg accctccagc gggacaccct ggttcccacc | 2000 |
| attccctgcc ttgctgacaa taaagatatt tccaag | 2036 |

<210> SEQ ID NO 56
<211> LENGTH: 655
<212> TYPE: PRT
<213> ORGANISM: Homo sapiens

<400> SEQUENCE: 56

Met Gly Arg Trp Ala Trp Val Pro Ser Pro Trp Pro Pro Pro Gly
1               5                   10                  15

Leu Gly Pro Phe Leu Leu Leu Leu Leu Leu Leu Leu Leu Pro
                20                  25                  30

-continued

Arg Gly Phe Gln Pro Gln Pro Gly Gly Asn Arg Thr Glu Ser Pro
        35                  40                  45

Glu Pro Asn Ala Thr Ala Thr Pro Ala Ile Pro Thr Ile Leu Val
        50                  55                  60

Thr Ser Val Thr Ser Glu Thr Pro Ala Thr Ser Ala Pro Glu Ala
        65                  70                  75

Glu Gly Pro Gln Ser Gly Gly Leu Pro Pro Pro Arg Ala Val
        80                  85                  90

Pro Ser Ser Ser Pro Gln Ala Gln Ala Leu Thr Glu Asp Gly
        95                  100                 105

Arg Pro Cys Arg Phe Pro Phe Arg Tyr Gly Gly Arg Met Leu His
        110                 115                 120

Ala Cys Thr Ser Glu Gly Ser Ala His Arg Lys Trp Cys Ala Thr
        125                 130                 135

Thr His Asn Tyr Asp Arg Asp Arg Ala Trp Gly Tyr Cys Val Glu
        140                 145                 150

Ala Thr Pro Pro Pro Gly Gly Pro Ala Leu Asp Pro Cys Ala
        155                 160                 165

Ser Gly Pro Cys Leu Asn Gly Gly Ser Cys Ser Asn Thr Gln Asp
        170                 175                 180

Pro Gln Ser Tyr His Cys Ser Cys Pro Arg Ala Phe Thr Gly Lys
        185                 190                 195

Asp Cys Gly Thr Glu Lys Cys Phe Asp Glu Thr Arg Tyr Glu Tyr
        200                 205                 210

Leu Glu Gly Gly Asp Arg Trp Ala Arg Val Arg Gln Gly His Val
        215                 220                 225

Glu Gln Cys Glu Cys Phe Gly Gly Arg Thr Trp Cys Glu Gly Thr
        230                 235                 240

Arg His Thr Ala Cys Leu Ser Ser Pro Cys Leu Asn Gly Gly Thr
        245                 250                 255

Cys His Leu Ile Val Ala Thr Gly Thr Thr Val Cys Ala Cys Pro
        260                 265                 270

Pro Gly Phe Ala Gly Arg Leu Cys Asn Ile Glu Pro Asp Glu Arg
        275                 280                 285

Cys Phe Leu Gly Asn Gly Thr Gly Tyr Arg Gly Val Ala Ser Thr
        290                 295                 300

Ser Ala Ser Gly Leu Ser Cys Leu Ala Trp Asn Ser Asp Leu Leu
        305                 310                 315

Tyr Gln Glu Leu His Val Asp Ser Val Gly Ala Ala Ala Leu Leu
        320                 325                 330

Gly Leu Gly Pro His Ala Tyr Cys Arg Asn Pro Asp Asn Asp Glu
        335                 340                 345

Arg Pro Trp Cys Tyr Val Val Lys Asp Ser Ala Leu Ser Trp Glu
        350                 355                 360

Tyr Cys Arg Leu Glu Ala Cys Glu Ser Leu Thr Arg Val Gln Leu
        365                 370                 375

Ser Pro Asp Leu Leu Ala Thr Leu Pro Glu Pro Ala Ser Pro Gly
        380                 385                 390

Arg Gln Ala Cys Gly Arg Arg His Lys Lys Arg Thr Phe Leu Arg
        395                 400                 405

Pro Arg Ile Ile Gly Gly Ser Ser Ser Leu Pro Gly Ser His Pro
        410                 415                 420

Trp Leu Ala Ala Ile Tyr Ile Gly Asp Ser Phe Cys Ala Gly Ser
        425                 430                 435

```
Leu Val His Thr Cys Trp Val Val Ser Ala Ala His Cys Phe Ser
                440                 445                 450

His Ser Pro Pro Arg Asp Ser Val Ser Val Val Leu Gly Gln His
                455                 460                 465

Phe Phe Asn Arg Thr Thr Asp Val Thr Gln Thr Phe Gly Ile Glu
                470                 475                 480

Lys Tyr Ile Pro Tyr Thr Leu Tyr Ser Val Phe Asn Pro Ser Asp
                485                 490                 495

His Asp Leu Val Leu Ile Arg Leu Lys Lys Lys Gly Asp Arg Cys
                500                 505                 510

Ala Thr Arg Ser Gln Phe Val Gln Pro Ile Cys Leu Pro Glu Pro
                515                 520                 525

Gly Ser Thr Phe Pro Ala Gly His Lys Cys Gln Ile Ala Gly Trp
                530                 535                 540

Gly His Leu Asp Glu Asn Val Ser Gly Tyr Ser Ser Ser Leu Arg
                545                 550                 555

Glu Ala Leu Val Pro Leu Val Ala Asp His Lys Cys Ser Ser Pro
                560                 565                 570

Glu Val Tyr Gly Ala Asp Ile Ser Pro Asn Met Leu Cys Ala Gly
                575                 580                 585

Tyr Phe Asp Cys Lys Ser Asp Ala Cys Gln Gly Asp Ser Gly Gly
                590                 595                 600

Pro Leu Ala Cys Glu Lys Asn Gly Val Ala Tyr Leu Tyr Gly Ile
                605                 610                 615

Ile Ser Trp Gly Asp Gly Cys Gly Arg Leu His Lys Pro Gly Val
                620                 625                 630

Tyr Thr Arg Val Ala Asn Tyr Val Asp Trp Ile Asn Asp Arg Ile
                635                 640                 645

Arg Pro Pro Arg Arg Leu Val Ala Pro Ser
                650                 655
```

<210> SEQ ID NO 57
<211> LENGTH: 2159
<212> TYPE: DNA
<213> ORGANISM: Homo sapiens

<400> SEQUENCE: 57

```
agggcccgcg ggtggagaga gcgacgcccg aggggatggc ggcagcgtcc         50
cggagcgcct ctggctgggc gctactgctg ctggtggcac tttggcagca        100
gcgcgcggcc ggctccggcg tcttccagct gcagctgcag gagttcatca        150
acgagcgcgg cgtactggcc agtgggcggc cttgcgagcc cggctgccgg        200
actttcttcc gcgtctgcct taagcacttc caggcggtcg tctcgcccgg        250
accctgcacc ttcgggaccg tctccacgcc ggtattgggc accaactcct        300
tcgctgtccg ggacgacagt agcggcgggg ggcgcaaccc tctccaactg        350
cccttcaatt tcacctggcc gggtaccttc tcgctcatca tcgaagcttg        400
gcacgcgcca ggagacgacc tgcggccaga ggccttgcca ccagatgcac        450
tcatcagcaa gatcgccatc cagggctccc tagctgtggg tcagaactgg        500
ttattggatg agcaaaccag caccctcaca aggctgcgct actcttaccg        550
ggtcatctgc agtgacaact actatggaga caactgctcc cgcctgtgca        600
agaagcgcaa tgaccacttc ggccactatg tgtgccagcc agatggcaac        650
```

```
ttgtcctgcc tgcccggttg gactggggaa tattgccaac agcctatctg      700
tctttcgggc tgtcatgaac agaatggcta ctgcagcaag ccagcagagt      750
gcctctgccg cccaggctgg cagggccggc tgtgtaacga atgcatcccc      800
cacaatggct gtcgccacgg cacctgcagc actccctggc aatgtacttg      850
tgatgagggc tggggaggcc tgttttgtga ccaagatctc aactactgca      900
cccaccactc cccatgcaag aatggggcaa cgtgctccaa cagtgggcag      950
cgaagctaca cctgcacctg tcgcccaggc tacactggtg tggactgtga     1000
gctggagctc agcgagtgtg acagcaaccc ctgtcgcaat ggaggcagct     1050
gtaaggacca ggaggatggc taccactgcc tgtgtcctcc gggctactat     1100
ggcctgcact gtgaacacag caccttgagc tgcgccgact cccccctgct     1150
caatgggggc tcctgccggg agcgcaacca ggggccaac tatgcttgtg      1200 aatgtccccc caacttcacc ggctccaact gcgagaagaa agtggacagg     1250
tgcaccagca cccctgtgc caacggggga cagtgcctga ccgaggtcc       1300 aagccgcatg tgccgctgcc gtcctggatt cacgggcacc tactgtgaac     1350
tccacgtcag cgactgtgcc cgtaaccctt gcgcccacgg tggcacttgc     1400
catgacctgg agaatgggct catgtgcacc tgccctgccg gcttctctgg     1450
ccgacgctgt gaggtgcgga catccatcga tgcctgtgcc tcgagtccct     1500
gcttcaacag ggccacctgc tacaccgacc tctccacaga cacctttgtg     1550
tgcaactgcc cttatggctt tgtgggcagc cgctgcgagt tccccgtggg     1600
cttgccgccc agcttcccct gggtggccgt ctcgctgggt gtggggctgg     1650
cagtgctgct ggtactgctg gcatggtgg cagtggctgt gcggcagctg      1700
cggcttcgac ggccggacga cggcagcagg gaagccatga caacttgtc      1750 ggacttccag aaggacaacc tgattcctgc cgcccagctt aaaaacacaa     1800
accagaagaa ggagctggaa gtggactgtg gcctggacaa gtccaactgt     1850
ggcaaacagc aaaaccacac attggactat aatctggccc cagggcccct     1900
ggggcggggg accatgccag gaaagtttcc ccacagtgac aagagcttag     1950
gagagaaggc gccactgcgg ttacacagtg aaaagccaga gtgtcggata     2000
tcagcgatat gctcccccag ggactccatg taccagtctg tgtgtttgat     2050
atcagaggag aggaatgaat gtgtcattgc cacggaggta taaggcagga     2100
gcctacctgg acatccctgc tcagccccgc ggctggacct tccttctgca     2150
ttgtttaca                                                  2159
```

<210> SEQ ID NO 58
<211> LENGTH: 685
<212> TYPE: PRT
<213> ORGANISM: Homo sapiens

<400> SEQUENCE: 58

```
Met Ala Ala Ala Ser Arg Ser Ala Ser Gly Trp Ala Leu Leu Leu
 1               5                  10                  15

Leu Val Ala Leu Trp Gln Gln Arg Ala Ala Gly Ser Gly Val Phe
                20                  25                  30

Gln Leu Gln Leu Gln Glu Phe Ile Asn Glu Arg Gly Val Leu Ala
                35                  40                  45

Ser Gly Arg Pro Cys Glu Pro Gly Cys Arg Thr Phe Phe Arg Val
```

```
            50                  55                  60
Cys Leu Lys His Phe Gln Ala Val Val Ser Pro Gly Pro Cys Thr
            65                  70                  75
Phe Gly Thr Val Ser Thr Pro Val Leu Gly Thr Asn Ser Phe Ala
            80                  85                  90
Val Arg Asp Asp Ser Ser Gly Gly Arg Asn Pro Leu Gln Leu
            95                 100                 105
Pro Phe Asn Phe Thr Trp Pro Gly Thr Phe Ser Leu Ile Ile Glu
           110                 115                 120
Ala Trp His Ala Pro Gly Asp Asp Leu Arg Pro Glu Ala Leu Pro
           125                 130                 135
Pro Asp Ala Leu Ile Ser Lys Ile Ala Ile Gln Gly Ser Leu Ala
           140                 145                 150
Val Gly Gln Asn Trp Leu Leu Asp Glu Gln Thr Ser Thr Leu Thr
           155                 160                 165
Arg Leu Arg Tyr Ser Tyr Arg Val Ile Cys Ser Asp Asn Tyr Tyr
           170                 175                 180
Gly Asp Asn Cys Ser Arg Leu Cys Lys Lys Arg Asn Asp His Phe
           185                 190                 195
Gly His Tyr Val Cys Gln Pro Asp Gly Asn Leu Ser Cys Leu Pro
           200                 205                 210
Gly Trp Thr Gly Glu Tyr Cys Gln Gln Pro Ile Cys Leu Ser Gly
           215                 220                 225
Cys His Glu Gln Asn Gly Tyr Cys Ser Lys Pro Ala Glu Cys Leu
           230                 235                 240
Cys Arg Pro Gly Trp Gln Gly Arg Leu Cys Asn Glu Cys Ile Pro
           245                 250                 255
His Asn Gly Cys Arg His Gly Thr Cys Ser Thr Pro Trp Gln Cys
           260                 265                 270
Thr Cys Asp Glu Gly Trp Gly Gly Leu Phe Cys Asp Gln Asp Leu
           275                 280                 285
Asn Tyr Cys Thr His His Ser Pro Cys Lys Asn Gly Ala Thr Cys
           290                 295                 300
Ser Asn Ser Gly Gln Arg Ser Tyr Thr Cys Thr Cys Arg Pro Gly
           305                 310                 315
Tyr Thr Gly Val Asp Cys Glu Leu Glu Leu Ser Glu Cys Asp Ser
           320                 325                 330
Asn Pro Cys Arg Asn Gly Gly Ser Cys Lys Asp Gln Glu Asp Gly
           335                 340                 345
Tyr His Cys Leu Cys Pro Pro Gly Tyr Tyr Gly Leu His Cys Glu
           350                 355                 360
His Ser Thr Leu Ser Cys Ala Asp Ser Pro Cys Phe Asn Gly Gly
           365                 370                 375
Ser Cys Arg Glu Arg Asn Gln Gly Ala Asn Tyr Ala Cys Glu Cys
           380                 385                 390
Pro Pro Asn Phe Thr Gly Ser Asn Cys Glu Lys Lys Val Asp Arg
           395                 400                 405
Cys Thr Ser Asn Pro Cys Ala Asn Gly Gly Gln Cys Leu Asn Arg
           410                 415                 420
Gly Pro Ser Arg Met Cys Arg Cys Arg Pro Gly Phe Thr Gly Thr
           425                 430                 435
Tyr Cys Glu Leu His Val Ser Asp Cys Ala Arg Asn Pro Cys Ala
           440                 445                 450
```

|     |     |     |     |     |     |     |     |     |     |
| --- | --- | --- | --- | --- | --- | --- | --- | --- | --- |
| His | Gly | Gly | Thr | Cys | His | Asp | Leu | Glu | Asn | Gly | Leu | Met | Cys | Thr |
|     |     |     |     | 455 |     |     |     |     | 460 |     |     |     |     | 465 |
| Cys | Pro | Ala | Gly | Phe | Ser | Gly | Arg | Arg | Cys | Glu | Val | Arg | Thr | Ser |
|     |     |     |     | 470 |     |     |     |     | 475 |     |     |     |     | 480 |
| Ile | Asp | Ala | Cys | Ala | Ser | Ser | Pro | Cys | Phe | Asn | Arg | Ala | Thr | Cys |
|     |     |     |     | 485 |     |     |     |     | 490 |     |     |     |     | 495 |
| Tyr | Thr | Asp | Leu | Ser | Thr | Asp | Thr | Phe | Val | Cys | Asn | Cys | Pro | Tyr |
|     |     |     |     | 500 |     |     |     |     | 505 |     |     |     |     | 510 |
| Gly | Phe | Val | Gly | Ser | Arg | Cys | Glu | Phe | Pro | Val | Gly | Leu | Pro | Pro |
|     |     |     |     | 515 |     |     |     |     | 520 |     |     |     |     | 525 |
| Ser | Phe | Pro | Trp | Val | Ala | Val | Ser | Leu | Gly | Val | Gly | Leu | Ala | Val |
|     |     |     |     | 530 |     |     |     |     | 535 |     |     |     |     | 540 |
| Leu | Leu | Val | Leu | Leu | Gly | Met | Val | Ala | Val | Ala | Val | Arg | Gln | Leu |
|     |     |     |     | 545 |     |     |     |     | 550 |     |     |     |     | 555 |
| Arg | Leu | Arg | Arg | Pro | Asp | Asp | Gly | Ser | Arg | Glu | Ala | Met | Asn | Asn |
|     |     |     |     | 560 |     |     |     |     | 565 |     |     |     |     | 570 |
| Leu | Ser | Asp | Phe | Gln | Lys | Asp | Asn | Leu | Ile | Pro | Ala | Ala | Gln | Leu |
|     |     |     |     | 575 |     |     |     |     | 580 |     |     |     |     | 585 |
| Lys | Asn | Thr | Asn | Gln | Lys | Lys | Glu | Leu | Glu | Val | Asp | Cys | Gly | Leu |
|     |     |     |     | 590 |     |     |     |     | 595 |     |     |     |     | 600 |
| Asp | Lys | Ser | Asn | Cys | Gly | Lys | Gln | Gln | Asn | His | Thr | Leu | Asp | Tyr |
|     |     |     |     | 605 |     |     |     |     | 610 |     |     |     |     | 615 |
| Asn | Leu | Ala | Pro | Gly | Pro | Leu | Gly | Arg | Gly | Thr | Met | Pro | Gly | Lys |
|     |     |     |     | 620 |     |     |     |     | 625 |     |     |     |     | 630 |
| Phe | Pro | His | Ser | Asp | Lys | Ser | Leu | Gly | Glu | Lys | Ala | Pro | Leu | Arg |
|     |     |     |     | 635 |     |     |     |     | 640 |     |     |     |     | 645 |
| Leu | His | Ser | Glu | Lys | Pro | Glu | Cys | Arg | Ile | Ser | Ala | Ile | Cys | Ser |
|     |     |     |     | 650 |     |     |     |     | 655 |     |     |     |     | 660 |
| Pro | Arg | Asp | Ser | Met | Tyr | Gln | Ser | Val | Cys | Leu | Ile | Ser | Glu | Glu |
|     |     |     |     | 665 |     |     |     |     | 670 |     |     |     |     | 675 |
| Arg | Asn | Glu | Cys | Val | Ile | Ala | Thr | Glu | Val |
|     |     |     |     | 680 |     |     |     |     | 685 |

```
<210> SEQ ID NO 59
<211> LENGTH: 1825
<212> TYPE: DNA
<213> ORGANISM: Homo sapiens

<400> SEQUENCE: 59
tgcaattaaa ggagtcgggt ctctaactgt tgatctgttt ttttcccttc          50
tgagcaatgg agcttaccat ctttatcctg agactggcca tttacatcct         100
gacatttccc ttgtacctgc tgaactttct gggcttgtgg agctggatat         150
gcaaaaaatg gttcccctac ttcttggtga ggttcactgt gatatacaac         200
gaacagatgg caagcaagaa gcgggagctc ttcagtaacc tgcaggagtt         250
tgcgggcccc tccgggaaac tctccctgct ggaagtgggc tgtggcacgg         300
gggccaactt caagttctac ccacctgggt gcagggtgac ctgtattgac         350
cccaacccca actttgagaa gttttttgatc aagagcattg cagagaaccg         400
acacctgcag tttgagcgct tgtggtagc tgccggggag aacatgcacc         450
aggtggctga tgctctgtg gatgtggtgg tctgcaccct ggtgctgtgc         500
tctgtgaaga accaggagcg gattctccgc gaggtgtgca gagtgctgag         550
accgggaggg gctttctatt tcatggagca tgtggcagct gagtgttcga         600
```

```
cttggaatta cttctggcaa caagtcctgg atcctgcctg gcaccttctg      650
tttgatgggt gcaacctgac cagagagagc tggaaggccc tggagcgggc      700
cagcttctct aagctgaagc tgcagcacat ccaggcccca ctgtcctggg      750
agttggtgcg ccctcatatc tatggatatg ctgtgaaata gtgtgagctg      800
gcagttaaga gctgaatggc tcaaagaatt taaagcttca gttttacatt      850
taaaatgcta agtgggagaa gagaaacctt ttttttgggg ggcggttttt      900
ttggtttgtt gttggttttt ttttttttttt tggcaggaga atctcttgaa      950
cccagaaggc gaaggttgca gtgaaccgag atcatgccat tgtactctag     1000
cctgggtgac aagagcaaga ctccgtctca aaaaaaaaaa aaaaaaaaa      1050 aagaagtaga gacagggaga cggggtctca ctgtgttgcc taggccggtc     1100
ttgaactcct gggctcaagt gattctccca ccttgacctc ctaaattgtt     1150
gggattacag gtgtgagaca gtgcacctgg ccgaaatagc tcaagtttct     1200
gaaaaacaaa tctgaatcta tttgttattc ttagcgtcac tggtctggct     1250
ttcagaatta acatacaagg ttgccacacc tagttctgcc cagctttatg     1300
tcttttattc cagtattcca ccaaagtttg ttttcctgca ttccagttct     1350
caagtcttaa gataaagatt gtacttgaca gtttagtata tccataaaac     1400
tatttgaggt ggttaaggtt cttgggttca ttttccttaa tactttgctg     1450
aatattgtag attgtaggca atgaaaaagt ctactaaatt aggaaaacct     1500
tgaataatta ggtatcctag gtaagagccc ctaaacatca agcaatctgt     1550
gagtctgtaa agaaataaat atttttttgga ttattcttat ctaattccac     1600
ccctgttgga agatgatttc tttgttcttt gcaactatgg aagctgtgaa     1650
aatcatcaca agtgcctctg aaagcgagtg ttaggttggt tagagggttt     1700
aatattttct gcaatggttt gtaggaattt taataaatgt agtatatttt     1750
ctgagatgat tttgtaaaag tactattta aatatcaaat caaccaataa     1800
attcacattt gtgttaggaa  caaaa                                1825
```

<210> SEQ ID NO 60
<211> LENGTH: 244
<212> TYPE: PRT
<213> ORGANISM: Homo sapiens

<400> SEQUENCE: 60

```
Met Glu Leu Thr Ile Phe Ile Leu Arg Leu Ala Ile Tyr Ile Leu
  1               5                  10                  15

Thr Phe Pro Leu Tyr Leu Leu Asn Phe Leu Gly Leu Trp Ser Trp
                 20                  25                  30

Ile Cys Lys Lys Trp Phe Pro Tyr Phe Leu Val Arg Phe Thr Val
                 35                  40                  45

Ile Tyr Asn Glu Gln Met Ala Ser Lys Lys Arg Glu Leu Phe Ser
                 50                  55                  60

Asn Leu Gln Glu Phe Ala Gly Pro Ser Gly Lys Leu Ser Leu Leu
                 65                  70                  75

Glu Val Gly Cys Gly Thr Gly Ala Asn Phe Lys Phe Tyr Pro Pro
                 80                  85                  90

Gly Cys Arg Val Thr Cys Ile Asp Pro Asn Pro Asn Phe Glu Lys
                 95                 100                 105

Phe Leu Ile Lys Ser Ile Ala Glu Asn Arg His Leu Gln Phe Glu
```

```
                    110                 115                 120
Arg Phe Val Val Ala Ala Gly Glu Asn Met His Gln Val Ala Asp
                125                 130                 135
Gly Ser Val Asp Val Val Cys Thr Leu Val Leu Cys Ser Val
            140                 145                 150
Lys Asn Gln Glu Arg Ile Leu Arg Glu Val Cys Arg Val Leu Arg
                155                 160                 165
Pro Gly Gly Ala Phe Tyr Phe Met Glu His Val Ala Ala Glu Cys
                170                 175                 180
Ser Thr Trp Asn Tyr Phe Trp Gln Gln Val Leu Asp Pro Ala Trp
                185                 190                 195
His Leu Leu Phe Asp Gly Cys Asn Leu Thr Arg Glu Ser Trp Lys
                200                 205                 210
Ala Leu Glu Arg Ala Ser Phe Ser Lys Leu Lys Leu Gln His Ile
                215                 220                 225
Gln Ala Pro Leu Ser Trp Glu Leu Val Arg Pro His Ile Tyr Gly
                230                 235                 240
Tyr Ala Val Lys

<210> SEQ ID NO 61
<211> LENGTH: 1786
<212> TYPE: DNA
<213> ORGANISM: Homo sapiens

<400> SEQUENCE: 61
ggcgtgtgca aggcggggtc cggcccgcgc aggtcgggta agcgcgtcta       50
gggcgctgcg cggcgcagcg aaaatggcgg cttccaggtg ggcgcgcaag      100
gccgtggtcc tgctttgtgc ctctgacctg ctgctgctgc tgctactgct      150
accaccgcct gggtcctgcg cggccgaagg ctcgcccggg acgcccgacg      200
agtctacccc acctccccgg aagaagaaga aggatattcg cgattacaat      250
gatgcagaca tggcgcgtct tctggagcaa tgggagaaag atgatgacat      300
tgaagaagga gatcttccag agcacaagag accttcagca cctgtcgact      350
tctcaaagat agacccaagc aagcctgaaa gcatattgaa aatgacgaaa      400
aaagggaaga ctctcatgat gtttgtcact gtatcaggaa gccctactga      450
gaaggagaca gaggaaatta cgagcctctg gcagggcagc cttttcaatg      500
ccaactatga cgtccagagg ttcattgtgg gatcagaccg tgctatcttc      550
atgcttcgcg atgggagcta cgcctggaga tcaaggact tttttggtcgg      600 tcaagacagg tgtgctgatg taactctgga gggccaggtg taccccggca      650
aaggaggagg aagcaaagag aaaaataaaa caaagcaaga caagggcaaa      700 aaaagaagg aaggagatct gaaatctcgg tcttccaagg aagaaaatcg      750
agctgggaat aaaagagaag acctgtgatg gggcagcagt gacgcgctgt      800 gggggggacag gtggacgtgg agagctcttt gcccagctcc tggggtggga      850
gtggtctcag gcaactgcac accggatgac attctagtgt cttctagaaa      900
gggtctgcca catgaccagt ttgtggtcaa agaattactg cttaataggc      950
ttcaagtaag aagacagatg tttttctaatt aatactggac actgacaaat     1000
tcatgtttac tataaaatct ccttacatgg aaatgtgact gtgttgcttt     1050
ttcccattta cacttggtga gtcatcaact ctactgagat tccactcccc     1100
```

| | |
|---|---|
| tccaagcacc tgctgtgatt gggtggcctg ctctgatcag atagcaaatt | 1150 |
| ctgatcagag aagactttaa aactcttgac ttaattgagt aaactcttca | 1200 |
| tgccatatac atcattttca ttatgttaaa ggtaaaatat gctttgtgaa | 1250 |
| ctcagatgtc tgtagccagg aagccagggt gtgtaaatcc aaaatctatg | 1300 |
| caggaaatgc ggagaataga aaatatgtca cttgaaatcc taagtagttt | 1350 |
| tgaatttctt tgacttgaat cttactcatc agtaagagaa ctcttggtgt | 1400 |
| ctgtcaggtt ttatgtggtc tgtaaagtta ggggttctgt tttgtttcct | 1450 |
| tatttaggaa agagtactgc tggtgtcgag gggttatatg ttccatttaa | 1500 |
| tgtgacagtt ttaaaggatt taagtaggga atcagagtcc tttgcagagt | 1550 |
| gtgacagacg actcaataac ctcatttgtt tctaaacatt tttctttgat | 1600 |
| aaagtgccta atctgtgct ttcgtataga gtaacatgat gtgctactgt | 1650 |
| tgatgtctga ttttgccgtt catgttagag cctactgtga ataagagtta | 1700 |
| gaacatttat atacagatgt catttctaag aactaaaatt ctttgggaaa | 1750 |
| aaccctcaaa aaaaaaaaaa aaaaaaaaaa aaaaaa | 1786 |

<210> SEQ ID NO 62
<211> LENGTH: 234
<212> TYPE: PRT
<213> ORGANISM: Homo sapiens

<400> SEQUENCE: 62

Met Ala Ala Ser Arg Trp Ala Arg Lys Ala Val Val Leu Leu Cys
 1               5                  10                  15

Ala Ser Asp Leu Leu Leu Leu Leu Leu Leu Pro Pro Pro Gly
            20                  25                  30

Ser Cys Ala Ala Glu Gly Ser Pro Gly Thr Pro Asp Glu Ser Thr
        35                  40                  45

Pro Pro Pro Arg Lys Lys Lys Asp Ile Arg Asp Tyr Asn Asp
        50                  55                  60

Ala Asp Met Ala Arg Leu Leu Glu Gln Trp Glu Lys Asp Asp
        65                  70                  75

Ile Glu Glu Gly Asp Leu Pro Glu His Lys Arg Pro Ser Ala Pro
        80                  85                  90

Val Asp Phe Ser Lys Ile Asp Pro Ser Lys Pro Glu Ser Ile Leu
        95                 100                 105

Lys Met Thr Lys Lys Gly Lys Thr Leu Met Met Phe Val Thr Val
       110                 115                 120

Ser Gly Ser Pro Thr Glu Lys Glu Thr Glu Glu Ile Thr Ser Leu
       125                 130                 135

Trp Gln Gly Ser Leu Phe Asn Ala Asn Tyr Asp Val Gln Arg Phe
       140                 145                 150

Ile Val Gly Ser Asp Arg Ala Ile Phe Met Leu Arg Asp Gly Ser
       155                 160                 165

Tyr Ala Trp Glu Ile Lys Asp Phe Leu Val Gly Gln Asp Arg Cys
       170                 175                 180

Ala Asp Val Thr Leu Glu Gly Gln Val Tyr Pro Gly Lys Gly Gly
       185                 190                 195

Gly Ser Lys Glu Lys Asn Lys Thr Lys Gln Asp Lys Gly Lys Lys
       200                 205                 210

Lys Lys Glu Gly Asp Leu Lys Ser Arg Ser Ser Lys Glu Glu Asn
       215                 220                 225

Arg Ala Gly Asn Lys Arg Glu Asp Leu
            230

<210> SEQ ID NO 63
<211> LENGTH: 755
<212> TYPE: DNA
<213> ORGANISM: Homo sapiens
<220> FEATURE:
<221> NAME/KEY: Unsure
<222> LOCATION: 67
<223> OTHER INFORMATION: Unknown base

<400> SEQUENCE: 63

| | | | | | |
|---|---|---|---|---|---|
| acgtcactgt | cttgaagcag | cagtagcctg | ggaagtgagg | caggaggaat | 50 |
| tgagaggcag | gaagggngct | ggagacacag | ctgagcctgg | aaatgagagt | 100 |
| gggcatcgcc | gtggtcatca | tgactcctct | gcggcgtggt | caccatgttg | 150 |
| gttcactgtg | ttgggctctt | attgacgggt | ctcctgctag | gcctgacctt | 200 |
| gggtgccgga | gccctgctgg | cttctgagcc | tatctaccaa | ccaccttcag | 250 |
| cctgggtgcc | agctgggggg | ctggtggggc | tggcgctgct | gggagccctg | 300 |
| ctcacacttc | ggtggccacg | tccattcaca | gttctgggca | caaccctgct | 350 |
| gggttctgca | gtgcttgtgg | cctgtgttga | ctacttcctg | gaggggctgg | 400 |
| cactggggag | ttggctgggc | caacgcctgc | agacacttcc | agccttgcct | 450 |
| tctctctgct | gatatagctg | ggtcttactg | gggatctggc | cagccttggg | 500 |
| ggcccttgga | gccctggccc | agtggaagct | cgtgcctgag | aacatggag | 550 |
| gccacgctaa | tgggtctgtt | cctggtttcc | cagatgcata | aaggaagaca | 600 |
| tatccctccc | ctgggcagca | aggctacaat | gggagggagg | gagaacatgg | 650 |
| gagcatgtga | ataaaatggc | attaaatact | gaaaaaaaaa | aaaaaaaaa | 700 |
| aaaaaaaaa | aaaaaaaaa | aaaaaaaaa | aaaaaaaaa | aaaaaaaaa | 750 |
| aaaaa | | | | | 755 |

<210> SEQ ID NO 64
<211> LENGTH: 105
<212> TYPE: PRT
<213> ORGANISM: Homo sapiens

<400> SEQUENCE: 64

Met Leu Val His Cys Val Gly Leu Leu Thr Gly Leu Leu Leu
  1               5                  10                  15

Gly Leu Thr Leu Gly Ala Gly Ala Leu Leu Ala Ser Glu Pro Ile
                 20                  25                  30

Tyr Gln Pro Pro Ser Ala Trp Val Pro Ala Gly Gly Leu Val Gly
                 35                  40                  45

Leu Ala Leu Leu Gly Ala Leu Leu Thr Leu Arg Trp Pro Arg Pro
                 50                  55                  60

Phe Thr Val Leu Gly Thr Thr Leu Leu Gly Ser Ala Val Leu Val
                 65                  70                  75

Ala Cys Val Asp Tyr Phe Leu Glu Gly Leu Ala Leu Gly Ser Trp
                 80                  85                  90

Leu Gly Gln Arg Leu Gln Thr Leu Pro Ala Leu Pro Ser Leu Cys
                 95                 100                 105

<210> SEQ ID NO 65
<211> LENGTH: 1226

<212> TYPE: DNA
<213> ORGANISM: Homo sapiens

<400> SEQUENCE: 65

| | |
|---|---:|
| atgaaagtga taatcaggca gcccaaatga ttgttaataa ggatcaaatg | 50 |
| agatcgtgta tgtgggtcca atcaattgat tctacacaaa ggagcctggg | 100 |
| gaggggccat ggtgccaatg cacttactgg ggagactgga gaagccgctt | 150 |
| ctcctcctgt gctgcgcctc cttcctactg gggctggctt tgctgggcat | 200 |
| aaagacggac atcaccccg ttgcttattt ctttctcaca ttgggtggct | 250 |
| tcttcttgtt tgcctatctc ctggtccggt ttctggaatg ggggcttcgg | 300 |
| tcccagctcc aatcaatgca gactgagagc ccagggccct caggcaatgc | 350 |
| acgggacaat gaagcctttg aagtgccagt ctatgaagag gccgtggtgg | 400 |
| gactagaatc ccagtgccgc cccaagagt tggaccaacc acccccctac | 450 |
| agcactgttg tgatacccc agcacctgag gaggaacaac ctagccatcc | 500 |
| agaggggtcc aggagagcca aactggaaca gaggcgaatg gcctcagagg | 550 |
| ggtccatggc ccaggaagga agccctggaa gagctccaat caaccttcgg | 600 |
| cttcggggac cacgggctgt gtccactgct cctgatctgc agagcttggc | 650 |
| ggcagtcccc acattagagc ctctgactcc acccccctgcc tatgatgtct | 700 |
| gctttggtca ccctgatgat gatagtgttt tttatgagga caactgggca | 750 |
| ccccttaaa tgactctccc aagatttctc ttctctccac accagacctc | 800 |
| gttcatttga ctaacatttt ccagcgccta ctatgtgtca gaaacaagtg | 850 |
| tttctgcctg acatcataa atggggactt ggaccctgag gagagtcagg | 900 |
| ccacggtaag cccttcccag ctgagatatg ggtggcataa tttgagtctt | 950 |
| ctggcaacat tggtgacct accccatatc caatatttcc agcgttagat | 1000 |
| tgaggatgag gtagggaggt gatccagaga aggcggagaa ggaagaagta | 1050 |
| acctctgagt ggcggctatt gcttctgttc caggtgctgt tcgagctgtt | 1100 |
| agaacccta ggcttgacag ctttgtgagt tattattgaa aaatgaggat | 1150 |
| tccaagagtc agaggagttt gataatgtgc acgagggcac actgctagta | 1200 |
| aataacatta aaataactgg aatgaa | 1226 |

<210> SEQ ID NO 66
<211> LENGTH: 216
<212> TYPE: PRT
<213> ORGANISM: Homo sapiens

<400> SEQUENCE: 66

Met Val Pro Met His Leu Leu Gly Arg Leu Glu Lys Pro Leu Leu
1               5                   10                  15

Leu Leu Cys Cys Ala Ser Phe Leu Leu Gly Leu Ala Leu Leu Gly
                20                  25                  30

Ile Lys Thr Asp Ile Thr Pro Val Ala Tyr Phe Phe Leu Thr Leu
            35                  40                  45

Gly Gly Phe Phe Leu Phe Ala Tyr Leu Leu Val Arg Phe Leu Glu
        50                  55                  60

Trp Gly Leu Arg Ser Gln Leu Gln Ser Met Gln Thr Glu Ser Pro
65                  70                  75

Gly Pro Ser Gly Asn Ala Arg Asp Asn Glu Ala Phe Glu Val Pro
            80                  85                  90

| | | | | | | | | | |
|---|---|---|---|---|---|---|---|---|---|
Val | Tyr | Glu | Glu | Ala | Val | Val | Gly | Leu | Glu | Ser | Gln | Cys | Arg | Pro
  |   | 95  |   |   |   |   | 100 |   |   |   |   | 105 |   |

Gln Glu Leu Asp Gln Pro Pro Pro Tyr Ser Thr Val Val Ile Pro
            110                 115                 120

Pro Ala Pro Glu Glu Gln Pro Ser His Pro Glu Gly Ser Arg
            125                 130                 135

Arg Ala Lys Leu Glu Gln Arg Arg Met Ala Ser Glu Gly Ser Met
            140                 145                 150

Ala Gln Glu Gly Ser Pro Gly Arg Ala Pro Ile Asn Leu Arg Leu
            155                 160                 165

Arg Gly Pro Arg Ala Val Ser Thr Ala Pro Asp Leu Gln Ser Leu
            170                 175                 180

Ala Ala Val Pro Thr Leu Glu Pro Leu Thr Pro Pro Ala Tyr
            185                 190                 195

Asp Val Cys Phe Gly His Pro Asp Asp Asp Ser Val Phe Tyr Glu
            200                 205                 210

Asp Asn Trp Ala Pro Pro
            215

<210> SEQ ID NO 67
<211> LENGTH: 999
<212> TYPE: DNA
<213> ORGANISM: Homo sapiens

<400> SEQUENCE: 67

```
gcgaggctgc accagcgcct ggcaccatga ggacgcctgg gcctctgccc           50
gtgctgctgc tgctcctggc gggagccccc gccgcgcggc ccactccccc          100
gacctgctac tcccgcatgc gggccctgag ccaggagatc acccgcgact          150
tcaacctcct gcaggtctcg gagccctcgg agccatgtgt gagataccTG          200
cccaggctgt acctggacat acacaattac tgtgtgctgg acaagctgcg          250
ggactttgtg gcctcgcccc cgtgttggaa agtggcccag gtagattcct          300
tgaaggacaa agcacggaag ctgtacacca tcatgaactc gttctgcagg          350
agagatttgg tattcctgtt ggatgactgc aatgccttgg aatacccaat          400
cccagtgact acggtcctgc cagatcgtca gcgctaaggg aactgagacc          450
agagaaagaa cccaagagaa ctaaagttat gtcagctacc agacttaat           500
gggccagagc catgacccTC acaggtcttg tgttagttgt atctgaaact          550
gttatgtatc tctctacctt ctggaaaaca gggctggtat tcctacccag          600
gaacctcctt tgagcataga gttagcaacc atgcttctca ttcccttgac          650
tcatgtcttg ccaggatggt tagatacaca gcatgttgat ttggtcacta          700
aaaagaagaa aaggactaac aagcttcact tttatgaaca actattttga          750
gaacatgcac aatagtatgt ttttattact ggtttaatgg agtaatggta          800
cttttattct ttcttgatag aaacctgctt acatttaacc aagcttctat          850
tatgcctttt tctaacacag actttcttca ctgtctttca tttaaaaaga          900
aattaatgct cttaagatat atattttacg tagtgctgac aggacccact          950
ctttcattga aggtgatga  aaatcaaata aagaatctct  tcacatgga           999
```

<210> SEQ ID NO 68
<211> LENGTH: 136
<212> TYPE: PRT

<213> ORGANISM: Homo sapiens

<400> SEQUENCE: 68

```
Met Arg Thr Pro Gly Pro Leu Pro Val Leu Leu Leu Leu Leu Ala
  1               5                  10                  15

Gly Ala Pro Ala Ala Arg Pro Thr Pro Thr Cys Tyr Ser Arg
             20                  25                  30

Met Arg Ala Leu Ser Gln Glu Ile Thr Arg Asp Phe Asn Leu Leu
             35                  40                  45

Gln Val Ser Glu Pro Ser Glu Pro Cys Val Arg Tyr Leu Pro Arg
             50                  55                  60

Leu Tyr Leu Asp Ile His Asn Tyr Cys Val Leu Asp Lys Leu Arg
             65                  70                  75

Asp Phe Val Ala Ser Pro Pro Cys Trp Lys Val Ala Gln Val Asp
             80                  85                  90

Ser Leu Lys Asp Lys Ala Arg Lys Leu Tyr Thr Ile Met Asn Ser
             95                 100                 105

Phe Cys Arg Arg Asp Leu Val Phe Leu Leu Asp Asp Cys Asn Ala
            110                 115                 120

Leu Glu Tyr Pro Ile Pro Val Thr Thr Val Leu Pro Asp Arg Gln
            125                 130                 135

Arg
```

<210> SEQ ID NO 69
<211> LENGTH: 3501
<212> TYPE: DNA
<213> ORGANISM: Homo sapiens
<220> FEATURE:
<221> NAME/KEY: Unsure
<222> LOCATION: 2762,2778
<223> OTHER INFORMATION: Unknown base

<400> SEQUENCE: 69

| | |
|---|---:|
| ggtgactgaa gcgagcctgg cctcttgcat cctccgcctg tgtacctccc | 50 |
| tcccctttt ttccgccttc tgccagcaga agcagcagcc gcagcacctg | 100 |
| agccgctact gccgctcact caggacaacg ctatggctga gcctgggcac | 150 |
| agccaccatc tctccgccag agtcaggaga agaactgaga ggcgcatacc | 200 |
| ccggctgtgg cggctgctgc tctgggctgg daccgccttc caggtgaccc | 250 |
| agggaacggg accggagctt catgcctgca aagagtctga gtaccactat | 300 |
| gagtacacgg cgtgtgacag cacgggttcc aggtggaggg tcgccgtgcc | 350 |
| gcataccccg ggcctgtgca ccagcctgtc tgacccccgtc aagggcaccg | 400 |
| agtgctcctt ctcctgcaac gccggggagt ttctggatat gaaggaccag | 450 |
| tcatgtaagc catgcgctga gggccgctac tccctcggca caggcattcg | 500 |
| gtttgatgag tgggatgagc tgccccatgg ctttgccagc ctctcagcca | 550 |
| acatggagct ggatgacagt gctgctgagt ccaccgggaa ctgtacttcg | 600 |
| tccaagtggg ttccccgggg cgactacatc gcctccaaca cggacgaatg | 650 |
| cacagccaca ctgatgtacg ccgtcaacct gaagcaatct ggcaccgtta | 700 |
| acttcgaata ctactatcca gactccagca tcatctttga gtttttcgtt | 750 |
| cagaatgacc agtgccagcc caatgcagat gactccaggt ggatgaagac | 800 |
| cacagagaaa ggatgggaat tccacagtgt ggagctaaat cgaggcaata | 850 |
| atgtcctcta ttggagaacc acagccttct cagtatggac caaagtaccc | 900 |

```
aagcctgtgc tggtgagaaa cattgccata acaggggtgg cctacacttc         950
agaatgcttc ccctgcaaac ctggcacgta tgcagacaag cagggctcct        1000
ctttctgcaa actttgccca gccaactctt attcaaataa aggagaaact        1050
tcttgccacc agtgtgaccc tgacaaatac tcagagaaag gatcttcttc        1100
ctgtaacgtg cgcccagctt gcacagacaa agattatttc tacacacaca        1150
cggcctgcga tgccaacgga gagacacaac tcatgtacaa atgggccaag        1200
ccgaaaatct gtagcgagga ccttgagggg gcagtgaagc tgcctgcctc        1250
tggtgtgaag acccactgcc caccctgcaa cccaggcttc ttcaaaacca        1300
acaacagcac ctgccagccc tgcccatatg gttcctactc caatggctca        1350
gactgtaccc gctgccctgc agggactgaa cctgctgtgg gatttgaata        1400
caaatggtgg aacacgctgc ccacaaacat ggaaacgacc gttctcagtg        1450
ggatcaactt cgagtacaag ggcatgcaga gctgggaggt ggctggtgat        1500
cacatttaca cagctgctgg agcctcagac aatgacttca tgattctcac        1550
tctggttgtg ccaggattta gacctccgca gtcggtgatg gcagacacag        1600
agaataaaga ggtggccaga atcacatttg tctttgagac cctctgttct        1650
gtgaactgtg agctctactt catggtgggt gtgaattcta ggaccaacac        1700
tcctgtggag acgtggaaag gttccaaagg caaacagtcc tatacctaca        1750
tcattgagga gaacactacc acgagcttca cctgggcctt ccagaggacc        1800
acttttcatg aggcaagcag gaagtacacc aatgacgttg ccaagatcta        1850
ctccatcaat gtcaccaatg ttatgaatgg cgtggcctcc tactgccgtc        1900
cctgtgccct agaagcctct gatgtgggct cctcctgcac ctcttgtcct        1950
gctggttact atattgaccg agattcagga acctgccact cctgcccccc        2000
taacacaatt ctgaaagccc accagcctta tggtgtccag gcctgtgtgc        2050
cctgtggtcc agggaccaag aacaacaaga tccactctct gtgctacaat        2100
gattgcacct tctcacgcaa cactccaacc aggactttca actacaactt        2150
ctccgctttg gcaaacaccg tcactcttgc tggagggcca agcttcactt        2200
ccaaagggtt gaaatacttc catcacttta ccctcagtct ctgtggaaac        2250
cagggtagga aaatgtctgt gtgcaccgac aatgtcactg acctccggat        2300
tcctgagggt gagtcagggt tctccaaatc tatcacagcc tacgtctgcc        2350
aggcagtcat catccccccca gaggtgacag gctacaaggc cggggtttcc        2400
tcacagcctg tcagccttgc tgatcgactt attggggtga caacagatat        2450
gactctggat ggaatcacct ccccagctga acttttccac ctggagtcct        2500
tgggaatacc ggacgtgatc ttcttttata ggtccaatga tgtgacccag        2550
tcctgcagtt ctgggagatc aaccaccatc cgcgtcaggt gcagtccaca        2600
gaaaactgtc cctggaagtt tgctgctgcc aggaacgtgc tcagatggga        2650
cctgtgatgg ctgcaacttc cacttcctgt gggagagcgc ggctgcttgc        2700
ccgctctgct cagtggctga ctaccatgct atcgtcagca gctgtgtggc        2750
tgggatccag angactactt acgtgtgncg agaacccaag ctatgctctg        2800
gtggcatttc tctgcctgag cagagagtca ccatctgcaa aaccatagat        2850
ttctggctga aagtgggcat ctctgcaggc acctgtactg ccatcctgct        2900
```

```
caccgtcttg acctgctact tttggaaaaa gaatcaaaaa ctagagtaca        2950
agtactccaa gctggtgatg aatgctactc tcaaggactg tgacctgcca        3000
gcagctgaca gctgcgccat catggaaggc gaggatgtag aggacgacct        3050
catctttacc agcaagaagt cacttttggg gaagatcaaa tcatttacct        3100
ccaagaggac tcctgatgga tttgactcag tgccgctgaa gacatcctca        3150
ggaggcccag acatggacct gtgagaggca ctgcctgcct cacctgcctc        3200
ctcaccttgc atagcacctt tgcaagcctg cggcgatttg ggtgccagca        3250
tcctgcaaca cccactgctg gaaatctctt cattgtggcc ttatcagatg        3300
tttgaatttc agatctttt ttatagagta cccaaacct cctttctgct          3350
tgcctcaaac ctgccaaata tacccacatt tttttttaaa aaaaaaaaa         3400
aaaaaaaaaa aaaaaaaaaa aaaaaaaaaa aaaaaaaaaa aaaaaaaaaa        3450
aaaaaaaaaa aaaaaaaaaa aaaaaaaaaa aaaaaaaaaa aaaaaaaaaa        3500
a                                                            3501
```

<210> SEQ ID NO 70
<211> LENGTH: 1013
<212> TYPE: PRT
<213> ORGANISM: Homo sapiens
<220> FEATURE:
<221> NAME/KEY: Unsure
<222> LOCATION: 877, 882
<223> OTHER INFORMATION: Unknown amino acid

<400> SEQUENCE: 70

```
Met Ala Glu Pro Gly His Ser His His Leu Ser Ala Arg Val Arg
 1               5                  10                  15

Arg Arg Thr Glu Arg Arg Ile Pro Arg Leu Trp Arg Leu Leu Leu
                20                  25                  30

Trp Ala Gly Thr Ala Phe Gln Val Thr Gln Gly Thr Gly Pro Glu
                35                  40                  45

Leu His Ala Cys Lys Glu Ser Glu Tyr His Tyr Glu Tyr Thr Ala
                50                  55                  60

Cys Asp Ser Thr Gly Ser Arg Trp Arg Val Ala Val Pro His Thr
            65                  70                  75

Pro Gly Leu Cys Thr Ser Leu Ser Asp Pro Val Lys Gly Thr Glu
            80                  85                  90

Cys Ser Phe Ser Cys Asn Ala Gly Glu Phe Leu Asp Met Lys Asp
                95                 100                 105

Gln Ser Cys Lys Pro Cys Ala Glu Gly Arg Tyr Ser Leu Gly Thr
                110                 115                 120

Gly Ile Arg Phe Asp Glu Trp Asp Glu Leu Pro His Gly Phe Ala
                125                 130                 135

Ser Leu Ser Ala Asn Met Glu Leu Asp Asp Ser Ala Ala Glu Ser
                140                 145                 150

Thr Gly Asn Cys Thr Ser Ser Lys Trp Val Pro Arg Gly Asp Tyr
                155                 160                 165

Ile Ala Ser Asn Thr Asp Glu Cys Thr Ala Thr Leu Met Tyr Ala
                170                 175                 180

Val Asn Leu Lys Gln Ser Gly Thr Val Asn Phe Glu Tyr Tyr Tyr
                185                 190                 195

Pro Asp Ser Ser Ile Ile Phe Glu Phe Phe Val Gln Asn Asp Gln
                200                 205                 210
```

-continued

```
Cys Gln Pro Asn Ala Asp Asp Ser Arg Trp Met Lys Thr Thr Glu
                215                 220                 225

Lys Gly Trp Glu Phe His Ser Val Glu Leu Asn Arg Gly Asn Asn
            230                 235                 240

Val Leu Tyr Trp Arg Thr Thr Ala Phe Ser Val Trp Thr Lys Val
            245                 250                 255

Pro Lys Pro Val Leu Val Arg Asn Ile Ala Ile Thr Gly Val Ala
            260                 265                 270

Tyr Thr Ser Glu Cys Phe Pro Cys Lys Pro Gly Thr Tyr Ala Asp
            275                 280                 285

Lys Gln Gly Ser Ser Phe Cys Lys Leu Cys Pro Ala Asn Ser Tyr
            290                 295                 300

Ser Asn Lys Gly Glu Thr Ser Cys His Gln Cys Asp Pro Asp Lys
            305                 310                 315

Tyr Ser Glu Lys Gly Ser Ser Cys Asn Val Arg Pro Ala Cys
            320                 325                 330

Thr Asp Lys Asp Tyr Phe Tyr Thr His Thr Ala Cys Asp Ala Asn
            335                 340                 345

Gly Glu Thr Gln Leu Met Tyr Lys Trp Ala Lys Pro Lys Ile Cys
            350                 355                 360

Ser Glu Asp Leu Glu Gly Ala Val Lys Leu Pro Ala Ser Gly Val
            365                 370                 375

Lys Thr His Cys Pro Pro Cys Asn Pro Gly Phe Phe Lys Thr Asn
            380                 385                 390

Asn Ser Thr Cys Gln Pro Cys Pro Tyr Gly Ser Tyr Ser Asn Gly
            395                 400                 405

Ser Asp Cys Thr Arg Cys Pro Ala Gly Thr Glu Pro Ala Val Gly
            410                 415                 420

Phe Glu Tyr Lys Trp Trp Asn Thr Leu Pro Thr Asn Met Glu Thr
            425                 430                 435

Thr Val Leu Ser Gly Ile Asn Phe Glu Tyr Lys Gly Met Thr Gly
            440                 445                 450

Trp Glu Val Ala Gly Asp His Ile Tyr Thr Ala Ala Gly Ala Ser
            455                 460                 465

Asp Asn Asp Phe Met Ile Leu Thr Leu Val Val Pro Gly Phe Arg
            470                 475                 480

Pro Pro Gln Ser Val Met Ala Asp Thr Glu Asn Lys Glu Val Ala
            485                 490                 495

Arg Ile Thr Phe Val Phe Glu Thr Leu Cys Ser Val Asn Cys Glu
            500                 505                 510

Leu Tyr Phe Met Val Gly Val Asn Ser Arg Thr Asn Thr Pro Val
            515                 520                 525

Glu Thr Trp Lys Gly Ser Lys Gly Lys Gln Ser Tyr Thr Tyr Ile
            530                 535                 540

Ile Glu Glu Asn Thr Thr Thr Ser Phe Thr Trp Ala Phe Gln Arg
            545                 550                 555

Thr Thr Phe His Glu Ala Ser Arg Lys Tyr Thr Asn Asp Val Ala
            560                 565                 570

Lys Ile Tyr Ser Ile Asn Val Thr Asn Val Met Asn Gly Val Ala
            575                 580                 585

Ser Tyr Cys Arg Pro Cys Ala Leu Glu Ala Ser Asp Val Gly Ser
            590                 595                 600

Ser Cys Thr Ser Cys Pro Ala Gly Tyr Tyr Ile Asp Arg Asp Ser
```

```
                      605                 610                 615
Gly Thr Cys His Ser Cys Pro Pro Asn Thr Ile Leu Lys Ala His
                620                 625                 630
Gln Pro Tyr Gly Val Gln Ala Cys Val Pro Cys Gly Pro Gly Thr
                635                 640                 645
Lys Asn Asn Lys Ile His Ser Leu Cys Tyr Asn Asp Cys Thr Phe
                650                 655                 660
Ser Arg Asn Thr Pro Thr Arg Thr Phe Asn Tyr Asn Phe Ser Ala
                665                 670                 675
Leu Ala Asn Thr Val Thr Leu Ala Gly Gly Pro Ser Phe Thr Ser
                680                 685                 690
Lys Gly Leu Lys Tyr Phe His His Phe Thr Leu Ser Leu Cys Gly
                695                 700                 705
Asn Gln Gly Arg Lys Met Ser Val Cys Thr Asp Asn Val Thr Asp
                710                 715                 720
Leu Arg Ile Pro Glu Gly Glu Ser Gly Phe Ser Lys Ser Ile Thr
                725                 730                 735
Ala Tyr Val Cys Gln Ala Val Ile Ile Pro Pro Glu Val Thr Gly
                740                 745                 750
Tyr Lys Ala Gly Val Ser Ser Gln Pro Val Ser Leu Ala Asp Arg
                755                 760                 765
Leu Ile Gly Val Thr Thr Asp Met Thr Leu Asp Gly Ile Thr Ser
                770                 775                 780
Pro Ala Glu Leu Phe His Leu Glu Ser Leu Gly Ile Pro Asp Val
                785                 790                 795
Ile Phe Phe Tyr Arg Ser Asn Asp Val Thr Gln Ser Cys Ser Ser
                800                 805                 810
Gly Arg Ser Thr Thr Ile Arg Val Arg Cys Ser Pro Gln Lys Thr
                815                 820                 825
Val Pro Gly Ser Leu Leu Leu Pro Gly Thr Cys Ser Asp Gly Thr
                830                 835                 840
Cys Asp Gly Cys Asn Phe His Phe Leu Trp Glu Ser Ala Ala Ala
                845                 850                 855
Cys Pro Leu Cys Ser Val Ala Asp Tyr His Ala Ile Val Ser Ser
                860                 865                 870
Cys Val Ala Gly Ile Gln Xaa Thr Thr Tyr Val Xaa Arg Glu Pro
                875                 880                 885
Lys Leu Cys Ser Gly Gly Ile Ser Leu Pro Glu Gln Arg Val Thr
                890                 895                 900
Ile Cys Lys Thr Ile Asp Phe Trp Leu Lys Val Gly Ile Ser Ala
                905                 910                 915
Gly Thr Cys Thr Ala Ile Leu Leu Thr Val Leu Thr Cys Tyr Phe
                920                 925                 930
Trp Lys Lys Asn Gln Lys Leu Glu Tyr Lys Tyr Ser Lys Leu Val
                935                 940                 945
Met Asn Ala Thr Leu Lys Asp Cys Asp Leu Pro Ala Ala Asp Ser
                950                 955                 960
Cys Ala Ile Met Glu Gly Glu Asp Val Glu Asp Asp Leu Ile Phe
                965                 970                 975
Thr Ser Lys Lys Ser Leu Phe Gly Lys Ile Lys Ser Phe Thr Ser
                980                 985                 990
Lys Arg Thr Pro Asp Gly Phe Asp Ser Val Pro Leu Lys Thr Ser
                995                 1000                1005
```

Ser Gly Gly Pro Asp Met Asp Leu
            1010

<210> SEQ ID NO 71
<211> LENGTH: 3192
<212> TYPE: DNA
<213> ORGANISM: Homo sapiens
<220> FEATURE:
<221> NAME/KEY: Unsure
<222> LOCATION: 1428,1431
<223> OTHER INFORMATION: Unknown base

<400> SEQUENCE: 71

| | | |
|---|---|---|
| gcttgcacac atggctccgg aggctccggt tgcccatccg agcccctgcc | 50 | |
| aggctctaac gttcccaact gacaacacca gtaactaaat ataggagcag | 100 | |
| atggtgggga cgggctgtcg cagcggctcc tttgcagagg tctccggact | 150 | |
| gcagataagg ctcaggccct tttgtgagaa gcagaccagc ctggggggctg | 200 | |
| gcggcaggac acctgtgtct gcatgctgaa gaagatgggg gaggccgtgg | 250 | |
| ccagagtagc aaggaaggtc aacgagacgg tggagagcgg ctctgacact | 300 | |
| ctggacctgg ccgagtgcaa gctggtctcc tttcccattg gcatctacaa | 350 | |
| ggtcctgcgg aatgtctctg ccagatcca cctcatcacc ctggctaaca | 400 | |
| acgagcttaa gtccctcacc agcaagttca tgaccacatt cagtcagctc | 450 | |
| cgagagctcc acctggaggg gaacttccta caccgcctcc ccagcgaggt | 500 | |
| cagtgccctg cagcacctca aggccattga cctgtcccgg aaccagttcc | 550 | |
| aggacttccc tgagcagctt accgccctgc cggcgctgga gaccatcaac | 600 | |
| ctggaggaga cgagatcgt agatgtgccc gtggagaagc tggccgccat | 650 | |
| gccagccttg cgcagcatca acctccgctt caacccactc aacgccgagg | 700 | |
| tgcgcgtgat cgccccgccg ctcatcaagt ttgacatgct catgtctccg | 750 | |
| gaaggcgcaa gagcccccct accttaggcc accctcctca tgcccaccca | 800 | |
| gcaagggaca gaggccacag gcctggaacc ctggaaggga gggaggccca | 850 | |
| tgggaggcca agcctggggg ctgggggcgg gtgggccgag cagcacgtgg | 900 | |
| tgggtggggt gcagctggtc tggatagata gcttacagca gtagtgggct | 950 | |
| ctggaatgcc caagggaaga ggcaaggtgg ggcctgcagc ctggactcgg | 1000 | |
| cactcacagc tgctgtgcaa actcaggcag atctcctgcc ctctctgagc | 1050 | |
| cttgtcactt gaaaaaaaca ggacccttc cctcctttgg gctccctgga | 1100 | |
| ggttttaag cagtacgtgc ctccaagtta cctccagatc agcaggcaca | 1150 | |
| ggtgggcatt gccaggtatt ttctgagccc ctgcgggttt gaggccttgt | 1200 | |
| ttttagtgct gagagccagt tgctgccctg agaagagaag acaacctcca | 1250 | |
| tctatttatt gcttcctgag aactgacctg gatgcggccc tctgcagggc | 1300 | |
| ccagtcttca gtcctgtggt ccctggactg gtgggaacct gaactaggag | 1350 | |
| tcctgggaga gctgtggtgg gaatatgggc tggcactgct gcagggcaag | 1400 | |
| aacattcatg taggagcccg aggaccanca ngctgggaat ggggagcaag | 1450 | |
| tcacgtcagc tctgtcattc cccacagtta acaaattggc ggggtgggaa | 1500 | |
| gtcctgagtg ctccgtccct ctagcatcac tcctgagctg cgggagaggt | 1550 | |
| ggcccagaga acagcagagt cagttacacc tgcagctctt gtctaaagtg | 1600 | |
| attagatggc caccctcacc actgtccagt ccagcagcag cctggctgcc | 1650 | |

| | |
|---|---|
| ttgtcatggc ctcctggggg cagaaggcga tgtggaccac gggatttgta | 1700 |
| gccagccagc tcccaggcca acgcccaaag ccctgatgac ctggttcttc | 1750 |
| tgaggccctc aacctggcat cttagggtat ggtcaggcaa cagggtgacc | 1800 |
| agctgtcctg gtttcccagg acatggaact ttcaatgcta aaactgggac | 1850 |
| attacccagc aagtggggat ggttggtccc ctaccaggag agggcctggg | 1900 |
| gctcttgctt cccgagaacg cctgtggctt gaagaacctt gactgcttgg | 1950 |
| tcctcaggta tctacctccc accttctcct catctgtgga gcaagccaac | 2000 |
| tcagtgcccc agaccccacc tgatctgcat ctttgtttgc tccagagaca | 2050 |
| cctgaggccc cagagcttga ggcaaagcca ggccgtccaa atcctgtgtg | 2100 |
| ccgtggacga gtggccactt tactactcct aaggctaaga tgttgagagc | 2150 |
| tcagaccact gctcagagca gtaatccctg ctcagaatgc tcccagttcc | 2200 |
| ctcgtccctg cccaggtctc ttgtctcttg ggaaggaact gataggtcgg | 2250 |
| gccattgttg ggccatcact gagcgctcag tatctcaaga gactctgttc | 2300 |
| attctgctcg tatcccaagg cctggttggt caaactctgg gcaaagggtt | 2350 |
| ttcaggatga ggaggtcaag acaggatgtc cagagctacc gagttcatct | 2400 |
| gtgggtgttg ggggcaagtg ggggctgaag tcctgtgcag gctgcgctgg | 2450 |
| ccccacctgc cttgtgccct ggagtggggt ttctccttgt tgaagaagag | 2500 |
| gcatccttct ctgatgtgca caaacacaat gtatgaccag agccttgcaa | 2550 |
| ctcaaagtgt ggtctgtgga ccagcagcgg cagtgacacc tgggagcttg | 2600 |
| ttaggaatgc agagtctagg cctcacccta tacctcccga ctcagaccct | 2650 |
| gcattttagc aagaccccca gctgattcct ataagcactt tagagtttga | 2700 |
| gaagcaagga cctaggctgg ggatgtcctc cgagcagagg gtgaagtttc | 2750 |
| tctcagttct ctccctgcca cttccaggga tctgagcctg tgttcagcct | 2800 |
| cctccctaac ccaccctggg agacacttgg cctgttagat tgttccagag | 2850 |
| tctgcatggc actcctgaag aagggagtgt gacctgcagt caccaggaga | 2900 |
| tgagggttag gtgtgcccag ccctccagac ccggcctttc tggttaaccc | 2950 |
| ctgcatgcca agctgcctgc tgccccaggt cctcacctca ggccttgaa | 3000 |
| ggggcagctt ctggaagttg ttttctcctc tgcttggaga gtttgcccct | 3050 |
| gtctgtcttg gaaagtgtgg gcagccacag atgcccccaa atcagagctc | 3100 |
| acagtgagtg agcccctaag cttcagtctg caataaagaa tgcattggtt | 3150 |
| tcaaaaaaaa aaaaaaaaa aaaaaaaaa aaaaaaaaa aa | 3192 |

<210> SEQ ID NO 72
<211> LENGTH: 184
<212> TYPE: PRT
<213> ORGANISM: Homo sapiens

<400> SEQUENCE: 72

Met Leu Lys Lys Met Gly Glu Ala Val Ala Arg Val Ala Arg Lys
1               5                   10                  15

Val Asn Glu Thr Val Glu Ser Gly Ser Asp Thr Leu Asp Leu Ala
                20                  25                  30

Glu Cys Lys Leu Val Ser Phe Pro Ile Gly Ile Tyr Lys Val Leu
                35                  40                  45

-continued

```
Arg Asn Val Ser Gly Gln Ile His Leu Ile Thr Leu Ala Asn Asn
             50                  55                  60
Glu Leu Lys Ser Leu Thr Ser Lys Phe Met Thr Thr Phe Ser Gln
         65                  70                  75
Leu Arg Glu Leu His Leu Glu Gly Asn Phe Leu His Arg Leu Pro
     80                  85                  90
Ser Glu Val Ser Ala Leu Gln His Leu Lys Ala Ile Asp Leu Ser
 95                 100                 105
Arg Asn Gln Phe Gln Asp Phe Pro Glu Gln Leu Thr Ala Leu Pro
        110                 115                 120
Ala Leu Glu Thr Ile Asn Leu Glu Glu Asn Ile Val Asp Val
        125                 130                 135
Pro Val Glu Lys Leu Ala Ala Met Pro Ala Leu Arg Ser Ile Asn
        140                 145                 150
Leu Arg Phe Asn Pro Leu Asn Ala Glu Val Arg Val Ile Ala Pro
        155                 160                 165
Pro Leu Ile Lys Phe Asp Met Leu Met Ser Pro Glu Gly Ala Arg
        170                 175                 180
Ala Pro Leu Pro
```

<210> SEQ ID NO 73
<211> LENGTH: 1321
<212> TYPE: DNA
<213> ORGANISM: Homo sapiens

<400> SEQUENCE: 73

```
gtcgacccac gcgtccgaag ctgctggagc cacgattcag tccccctggac        50
tgtagataaa gaccctttct tgccaggtgc tgagacaacc acactatgag        100
aggcactcca ggagacgctg atggtggagg aagggccgtc tatcaatcaa        150
tcactgttgc tgttatcaca tgcaagtatc cagaggctct tgagcaaggc        200
agagggatc ccatttattt gggaatccag aatccagaaa tgtgtttgta         250
ttgtgagaag gttggagaac agcccacatt gcagctaaaa gagcagaaga        300
tcatggatct gtatggccaa cccgagcccg tgaaaccctt ccttttctac        350
cgtgccaaga ctggtaggac ctccacccct gagtctgtgg ccttcccgga        400
ctggttcatt gcctcctcca agagagacca gcccatcatt ctgacttcag        450
aacttgggaa gtcatacaac actgcctttg aattaaatat aaatgactga        500
actcagccta gaggtggcag cttggtcttt gtcttaaagt ttctggttcc        550
caatgtgttt tcgtctacat tttcttagtg tcattttcac gctggtgctg        600
agacaggagc aaggctgctg ttatcatctc attttataat gaagaagaag        650
caattacttc atagcaactg aagaacagga tgtggcctca gaagcaggag        700
agctgggtgg tataaggctg tcctctcaag ctggtgctgt gtaggccaca        750
aggcatctgc atgagtgact ttaagactca aagaccaaac actgagcttt        800
cttctagggg tgggtatgaa gatgcttcag agctcatgcg cgttacccac        850
gatggcatga ctagcacaga gctgatctct gtttctgttt tgctttattc        900
cctcttggga tgatatcatc cagtctttat atgttgccaa tacctcat          950
tgtgtgtaat agaaccttct tagcattaag accttgtaaa caaaaataat        1000
tcttggggtg ggtatgaaga tgcttcgaga ctcatgcgcg ttacccacga        1050
tggcatgact agcacagagc tgatctctgt ttctgttttg ctttattccc        1100
```

```
tcttgggatg atatcatcca gtctttatat gttgccaata tacctcattg        1150
tgtgtaatag aaccttctta gcattaagac cttgtaaaca aaataattc         1200 ttgtgttaag ttaaatcatt tttgtcctaa ttgtaatgtg taatcttaaa        1250
gttaaataaa ctttgtgtat ttatataata ataaagctaa aactgatata        1300
aaataaagaa agagtaaact g                                       1321
```

```
<210> SEQ ID NO 74
<211> LENGTH: 134
<212> TYPE: PRT
<213> ORGANISM: Homo sapiens

<400> SEQUENCE: 74
```

```
Met Arg Gly Thr Pro Gly Asp Ala Asp Gly Gly Arg Ala Val
 1               5                  10                  15

Tyr Gln Ser Ile Thr Val Ala Val Ile Thr Cys Lys Tyr Pro Glu
                20                  25                  30

Ala Leu Glu Gln Gly Arg Gly Asp Pro Ile Tyr Leu Gly Ile Gln
                35                  40                  45

Asn Pro Glu Met Cys Leu Tyr Cys Glu Lys Val Gly Glu Gln Pro
                50                  55                  60

Thr Leu Gln Leu Lys Glu Gln Lys Ile Met Asp Leu Tyr Gly Gln
            65                  70                  75

Pro Glu Pro Val Lys Pro Phe Leu Phe Tyr Arg Ala Lys Thr Gly
                80                  85                  90

Arg Thr Ser Thr Leu Glu Ser Val Ala Phe Pro Asp Trp Phe Ile
                95                  100                 105

Ala Ser Ser Lys Arg Asp Gln Pro Ile Ile Leu Thr Ser Glu Leu
                110                 115                 120

Gly Lys Ser Tyr Asn Thr Ala Phe Glu Leu Asn Ile Asn Asp
                125                 130
```

```
<210> SEQ ID NO 75
<211> LENGTH: 520
<212> TYPE: DNA
<213> ORGANISM: Homo sapiens

<400> SEQUENCE: 75
cgggtcatgc gccgccgcct gtggctgggc ctggcctggc tgctgctggc        50
gcgggcgccg gacgccgcgg gaaccccgag cgcgtcgcgg ggaccgcgca        100
gctacccgca cctggagggc gacgtgcgct ggcggcgcct cttctcctcc        150
actcacttct tcctgcgcgt ggatcccggc ggccgcgtgc agggcacccg        200
ctggcgccac ggccaggaca gcatcctgga gatccgctct gtacacgtgg        250
gcgtcgtggt catcaaagca gtgtcctcag gcttctacgt ggccatgaac        300
cgccggggcc gcctctacgg gtcgcgactc tacaccgtgg actgcaggtt        350 ccggagcgc atcgaagaga acggccacaa cacctacgcc tcacagcgct         400
ggcgccgccg cggccagccc atgttcctgg cgctggacag gaggggggg         450 cccggccag gcggcggac gcggcggtac cacctgtccg cccacttcct         500
gcccgtcctg gtctcctgag                                         520
```

```
<210> SEQ ID NO 76
<211> LENGTH: 170
<212> TYPE: PRT
```

<213> ORGANISM: Homo sapiens

<400> SEQUENCE: 76

```
Met Arg Arg Arg Leu Trp Leu Gly Leu Ala Trp Leu Leu Leu Ala
 1               5                  10                  15
Arg Ala Pro Asp Ala Ala Gly Thr Pro Ser Ala Ser Arg Gly Pro
                20                  25                  30
Arg Ser Tyr Pro His Leu Glu Gly Asp Val Arg Trp Arg Arg Leu
                35                  40                  45
Phe Ser Ser Thr His Phe Phe Leu Arg Val Asp Pro Gly Gly Arg
                50                  55                  60
Val Gln Gly Thr Arg Trp Arg His Gly Gln Asp Ser Ile Leu Glu
 65                  70                  75
Ile Arg Ser Val His Val Gly Val Val Ile Lys Ala Val Ser
                80                  85                  90
Ser Gly Phe Tyr Val Ala Met Asn Arg Arg Gly Arg Leu Tyr Gly
                95                  100                 105
Ser Arg Leu Tyr Thr Val Asp Cys Arg Phe Arg Glu Arg Ile Glu
                110                 115                 120
Glu Asn Gly His Asn Thr Tyr Ala Ser Gln Arg Trp Arg Arg Arg
                125                 130                 135
Gly Gln Pro Met Phe Leu Ala Leu Asp Arg Gly Gly Pro Arg
                140                 145                 150
Pro Gly Gly Arg Thr Arg Arg Tyr His Leu Ser Ala His Phe Leu
                155                 160                 165
Pro Val Leu Val Ser
                170
```

<210> SEQ ID NO 77
<211> LENGTH: 1971
<212> TYPE: DNA
<213> ORGANISM: Homo sapiens

<400> SEQUENCE: 77

| | |
|---|---|
| ggaaggcgct caaggtgcgc ggcccggggc gcgctactgg gggcgccctc | 50 |
| cgcggtgggc agcgcgccag ggatcggcct gggcagccgc ggggcgcgcg | 100 |
| aaggctgcgc tttccctacg gcccccctcg cttcctccgg cacggcggca | 150 |
| acggagattt cctctcgggg aaactacgcg gatccttttc ggggatcctc | 200 |
| gccccgcccc agttctccgc cccctcccct ttgctgggc gcctgggctg | 250 |
| gcccgcgcag gggaggaggc tctggcagcc tgggcaggga ggcggcgggg | 300 |
| ggccgcggag ccgctggcca tcgattctcc ccgccatgtg acgccgtcct | 350 |
| tagccctgcg accccagcg cgtcccgggc ctgcgcctcc gccccgccgc | 400 |
| gcagcgcacg atgcttctgc cgggacgcgc acgccaaccg ccgacgcccc | 450 |
| agcccgtgca gcatcccggc ctccgccggc aggtagagcc gccggggcag | 500 |
| ctcctgcgcc tcttctactg cactgtcctg gtctgctcca agagatctc | 550 |
| agcgctcacc gacttctctg gttacctaac caaactcctg caaaaccaca | 600 |
| ccacctatgc ctgtgatggg gactatttga atctacagtg ccctcggcat | 650 |
| tctacgataa gtgtccaatc ggcatttat gggcaagatt accaaatgtg | 700 |
| tagttcccag aagcctgcct cccagaggga agacagctta acctgtgtgg | 750 |
| cagccaccac cttccagaag gtgctggacg aatgccagaa ccagcggggcc | 800 |

| | |
|---|---|
| tgccacctcc tggtcaatag ccgtgttttt ggacctgacc tttgtccagg | 850 |
| aagcagtaaa tacctcctgg tctcctttaa atgccaacct aatgaattaa | 900 |
| aaaacaaaac cgtgtgtgaa gaccaggagc tgaaactgca ctgccatgaa | 950 |
| tccaagttcc tcaacatcta ctctgcgacc tacggcagga ggacccagga | 1000 |
| aagggacatc tgctcctcca aggcagagcg gctccccccct ttcgattgct | 1050 |
| tgtcttactc agctttgcaa gtcctatccc gaaggtgcta tgggaagcag | 1100 |
| agatgcaaaa tcatcgtcaa caatcaccat tttggaagcc ctgtttgcc | 1150 |
| aggcgtgaaa aaatacctca ctgtgaccta cgcatgtgtt cccaagaaca | 1200 |
| tactcacagc gattgatcca gccattgcta atctaaaacc ttctttgaag | 1250 |
| cagaaagatg gtgaatatgg tataaacttc gacccaagcg gatcgaaggt | 1300 |
| tctgaggaaa gatggaattc ttgttagcaa ctctctggca gcctttgctt | 1350 |
| acattagagc ccacccagag agagctgccc tgctgttcgt gtccagtgtc | 1400 |
| tgcatcggcc tggccctcac actgtgcgcc ctggtcatca gagagtcctg | 1450 |
| tgccaaggac ttccgcgact tgcagctggg gagggagcag ctggtgccag | 1500 |
| gaagtgacaa ggtcgaggag gacagcgagg atgaagaaga ggaggaggac | 1550 |
| ccctctgagt ctgatttccc agggggaactg tcggggttct gtaggacttc | 1600 |
| atatcctata tacagttcca tagaagctgc agagctcgca gaaaggattg | 1650 |
| agcgcaggga gcaaatcatt caggaaatat ggatgaacag tggtttggac | 1700 |
| acctcgctcc caagaaacat gggccagttc tactgaaaac cacatgcatc | 1750 |
| ttgatgcgat cgcactttct gaagaaggaa ggatcccaaa tgcccctcca | 1800 |
| gttctggttc acctgtacct tctatgaagg agaattcgtc atgtcattca | 1850 |
| acactcgtga ggccaggaag ctattaaagg gatgtttcaa gctgtttcta | 1900 |
| gcacattcca aaataaatga ggagggagga aaaaaaaaaa aaaaaaaaa | 1950 |
| aaaaaaaaaa aaaaaaaaaa a | 1971 |

<210> SEQ ID NO 78
<211> LENGTH: 441
<212> TYPE: PRT
<213> ORGANISM: Homo sapiens

<400> SEQUENCE: 78

Met Leu Leu Pro Gly Arg Ala Arg Gln Pro Thr Pro Gln Pro
1               5                   10                  15

Val Gln His Pro Gly Leu Arg Arg Gln Val Glu Pro Pro Gly Gln
            20                  25                  30

Leu Leu Arg Leu Phe Tyr Cys Thr Val Leu Val Cys Ser Lys Glu
            35                  40                  45

Ile Ser Ala Leu Thr Asp Phe Ser Gly Tyr Leu Thr Lys Leu Leu
            50                  55                  60

Gln Asn His Thr Thr Tyr Ala Cys Asp Gly Asp Tyr Leu Asn Leu
            65                  70                  75

Gln Cys Pro Arg His Ser Thr Ile Ser Val Gln Ser Ala Phe Tyr
            80                  85                  90

Gly Gln Asp Tyr Gln Met Cys Ser Ser Gln Lys Pro Ala Ser Gln
            95                  100                 105

Arg Glu Asp Ser Leu Thr Cys Val Ala Ala Thr Thr Phe Gln Lys
            110                 115                 120

```
Val Leu Asp Glu Cys Gln Asn Gln Arg Ala Cys His Leu Leu Val
            125                 130                 135

Asn Ser Arg Val Phe Gly Pro Asp Leu Cys Pro Gly Ser Ser Lys
            140                 145                 150

Tyr Leu Leu Val Ser Phe Lys Cys Gln Pro Asn Glu Leu Lys Asn
            155                 160                 165

Lys Thr Val Cys Glu Asp Gln Glu Leu Lys Leu His Cys His Glu
            170                 175                 180

Ser Lys Phe Leu Asn Ile Tyr Ser Ala Thr Tyr Gly Arg Arg Thr
            185                 190                 195

Gln Glu Arg Asp Ile Cys Ser Ser Lys Ala Glu Arg Leu Pro Pro
            200                 205                 210

Phe Asp Cys Leu Ser Tyr Ser Ala Leu Gln Val Leu Ser Arg Arg
            215                 220                 225

Cys Tyr Gly Lys Gln Arg Cys Lys Ile Ile Val Asn Asn His His
            230                 235                 240

Phe Gly Ser Pro Cys Leu Pro Gly Val Lys Lys Tyr Leu Thr Val
            245                 250                 255

Thr Tyr Ala Cys Val Pro Lys Asn Ile Leu Thr Ala Ile Asp Pro
            260                 265                 270

Ala Ile Ala Asn Leu Lys Pro Ser Leu Lys Gln Lys Asp Gly Glu
            275                 280                 285

Tyr Gly Ile Asn Phe Asp Pro Ser Gly Ser Lys Val Leu Arg Lys
            290                 295                 300

Asp Gly Ile Leu Val Ser Asn Ser Leu Ala Ala Phe Ala Tyr Ile
            305                 310                 315

Arg Ala His Pro Glu Arg Ala Ala Leu Leu Phe Val Ser Ser Val
            320                 325                 330

Cys Ile Gly Leu Ala Leu Thr Leu Cys Ala Leu Val Ile Arg Glu
            335                 340                 345

Ser Cys Ala Lys Asp Phe Arg Asp Leu Gln Leu Gly Arg Glu Gln
            350                 355                 360

Leu Val Pro Gly Ser Asp Lys Val Glu Glu Asp Ser Glu Asp Glu
            365                 370                 375

Glu Glu Glu Glu Asp Pro Ser Glu Ser Asp Phe Pro Gly Glu Leu
            380                 385                 390

Ser Gly Phe Cys Arg Thr Ser Tyr Pro Ile Tyr Ser Ser Ile Glu
            395                 400                 405

Ala Ala Glu Leu Ala Glu Arg Ile Glu Arg Arg Glu Gln Ile Ile
            410                 415                 420

Gln Glu Ile Trp Met Asn Ser Gly Leu Asp Thr Ser Leu Pro Arg
            425                 430                 435

Asn Met Gly Gln Phe Tyr
            440

<210> SEQ ID NO 79
<211> LENGTH: 3322
<212> TYPE: DNA
<213> ORGANISM: Homo sapiens

<400> SEQUENCE: 79
cagcagccga  dacagcagct  gagacggcag  cggcagcttc  tcagggccgg         50
agccagttct  tggaggagac  tctgcacagg  gcatggatca  ctgtggtgcc        100
cttttcctgt  gcctgtgcct  tctgactttg  cagaatgcaa  caacagagac        150
```

```
atgggaagaa ctcctgagct acatggagaa tatgcaggtg tccaggggcc        200
ggagctcagt ttttcctct cgtcaactcc accagctgga gcagatgcta         250
ctgaacacca gcttcccagg ctacaacctg accttgcaga cacccaccat        300
ccagtctctg gccttcaagc tgagctgtga cttctctggc ctctcgctga        350
ccagtgccac tctgaagcgg gtgccccagg caggaggtca gcatgcccgg        400
ggtcagcacg ccatgcagtt ccccgccgag ctgacccggg acgcctgcaa        450
gacccgcccc agggagctgc ggctcatctg tatctacttc tccaacaccc        500 acttttcaa ggatgaaaac aactcatctc tgctgaataa ctacgtcctg         550
ggggcccagc tgagtcatgg gcacgtgaac aacctcaggg atcctgtgaa        600
catcagcttc tggcacaacc aaagcctgga aggctacacc ctgacctgtg        650
tcttctggaa ggagggagcc aggaaacagc cctgggggg ctggagccct         700 gagggctgtc gtacagagca gccctcccac tctcaggtgc tctgccgctg        750
caaccacctc acctactttg ctgttctcat gcaactctcc ccagccctgg        800
tccctgcaga gttgctggca cctcttacgt acatctccct cgtgggctgc        850
agcatctcca tcgtggcctc gctgatcaca gtcctgctgc acttccattt        900
caggaagcag agtgactcct taacacgtat ccacatgaac ctgcatgcct        950
ccgtgctgct cctgaacatc gccttcctgc tgagccccgc attcgcaatg       1000
tctcctgtgc ccgggtcagc atgcacggct ctggccgctg ccctgcacta       1050
cgcgctgctc agctgcctca cctggatggc catcgagggc ttcaacctct       1100
acctcctcct cgggcgtgtc tacaacatct acatccgcag atatgtgttc       1150
aagcttggtg tgctaggctg gggggcccca gccctcctgg tgctgctttc       1200
cctctctgtc aagagctcgg tatacggacc ctgcacaatc cccgtcttcg       1250
acagctggga gaatggcaca ggcttccaga acatgtccat atgctgggtg       1300
cggagccccg tggtgcacag tgtcctggtc atgggctacg gcggcctcac       1350
gtccctcttc aacctggtgg tgctggcctg gcgctgtgg accctgcgca        1400 ggctgcggga gcgggcggat gcaccaagtg tcagggcctg ccatgacact       1450
gtcactgtgc tgggcctcac cgtgctgctg gaaccacct gggccttggc        1500 cttctttct tttggcgtct tcctgctgcc ccagctgttc ctcttcacca        1550
tcttaaactc gctgtacggt ttcttccttt tcctgtggtt ctgctcccag       1600
cggtgccgct cagaagcaga ggccaaggca cagatagagg ccttcagctc       1650
ctcccaaaca acacagtagt ccgggcctcc tggcctggaa tcctcagcct       1700
ctctggccgc cagtagcctg aggctacggc tcctgctaga gagggtggca       1750
ggcctgctgc tggaccccag aggccactgt gaccgccaag ggccttttc        1800 cacttccacg gcctctccag gcactgaggg gaaggcattg ctctacctct       1850
ccctgacatt ttgctccggg gcagatccaa ccttacctgg ggcagcaaac       1900
tttgtcctgg tacctgggcc cagctcgcca gggatgtggg cagagcacca       1950
gcctgggcat caggaagcca agtttcaagg actgtctttg agtctgtctg       2000
tatgaccttg ggcctgccac ttctcacaga ccctaggtat ccacagctgt       2050
gacatggggg caagcagctt tgtttcagcc taacccagga gcttagtaaa       2100
aattgcataa gaccagggg aagagtgtca gcgtggggtg ggaattcccg        2150
```

```
cggcctccac ctgcttgcta ggggcaggat ctcattcagg ctgccctgga       2200
agcacctgct tggccctgcc accttcctcc aggggagggc cagatggcat       2250
cctggcttgg ggcgggtggg acctacccag gctctgagac tttactggcc       2300
tatgcctgag gcctcttttc ctttaactcc ctaaattatg atgactccaa       2350
gtccaagccc accctcccaa agattgggaa ggttccgccg ttcccagagg       2400
ctcctcctgc ggtgctccca agacttccat agaccatctg gaccagtagc       2450
ccatcccgca gttttcttgg gggcagagga aaacgcttct ttctcctcca       2500
gctgaatcag ctggatccca gtgtcctggc tgtttggtga ttgggcaaga       2550
ttgaatttgc ccaggtaggc gtgagagtgt gggttttaaa ttcgaagctc       2600
aggccatagt ttcagagaat caccccttacc ccagaccttc atgagacagt       2650
gctcatgaag ccagtgcgtt tcccagaacg aacactaggc ggcaccgttg       2700
gtccacactc agaggccctt ggcgccaaga ctgcatctag aatcgctcaa       2750
acacctgttt gcagacccca tgcaccagct ggaggggccg taactgcagg       2800
actgcgccta ctgagtgacc catttcctcc aggaggaaag gcaagacacg       2850
cttacacggc catttgtctc ttttcccaat gcggcggtgc actttcgctc       2900 ttggggggctg caccccagac atagctggca ccagagcagg gtgctcaggt      2950
ggtgggtgct cagggccctg ccccaggcca ctgggccgtt ttgatgacct       3000
caaaggtcac aggcagaaaa taggagcagg atttcccctg ggaaaagtt        3050 atcctgggac atcttctgct cttctgtaca tttctagatg caaataactc       3100
cttcaccagg cagtgagtgg cgtaggctct ggagccaggc tgcctgggct       3150
ccaatgccag ctctgccact tgctagctgt gagactgtgg acaaaccact       3200
cagcctctgt gtgcctcagt tttcctattt gtaaaataga gaccatagtg       3250
gtacctattt tgaagactaa gtaaaagaat tcaaataaag agacttggca       3300
cagagtaagt gctcagtaaa aa                                     3322
```

<210> SEQ ID NO 80
<211> LENGTH: 528
<212> TYPE: PRT
<213> ORGANISM: Homo sapiens

<400> SEQUENCE: 80

```
Met Asp His Cys Gly Ala Leu Phe Leu Cys Leu Cys Leu Leu Thr
  1               5                  10                  15

Leu Gln Asn Ala Thr Thr Glu Thr Trp Glu Glu Leu Leu Ser Tyr
                 20                  25                  30

Met Glu Asn Met Gln Val Ser Arg Gly Arg Ser Ser Val Phe Ser
                 35                  40                  45

Ser Arg Gln Leu His Gln Leu Glu Gln Met Leu Leu Asn Thr Ser
                 50                  55                  60

Phe Pro Gly Tyr Asn Leu Thr Leu Gln Thr Pro Thr Ile Gln Ser
                 65                  70                  75

Leu Ala Phe Lys Leu Ser Cys Asp Phe Ser Gly Leu Ser Leu Thr
                 80                  85                  90

Ser Ala Thr Leu Lys Arg Val Pro Gln Ala Gly Gly Gln His Ala
                 95                 100                 105

Arg Gly Gln His Ala Met Gln Phe Pro Ala Glu Leu Thr Arg Asp
                110                 115                 120
```

```
Ala Cys Lys Thr Arg Pro Arg Glu Leu Arg Leu Ile Cys Ile Tyr
            125                 130                 135

Phe Ser Asn Thr His Phe Phe Lys Asp Glu Asn Asn Ser Ser Leu
            140                 145                 150

Leu Asn Asn Tyr Val Leu Gly Ala Gln Leu Ser His Gly His Val
            155                 160                 165

Asn Asn Leu Arg Asp Pro Val Asn Ile Ser Phe Trp His Asn Gln
            170                 175                 180

Ser Leu Glu Gly Tyr Thr Leu Thr Cys Val Phe Trp Lys Glu Gly
            185                 190                 195

Ala Arg Lys Gln Pro Trp Gly Gly Trp Ser Pro Glu Gly Cys Arg
            200                 205                 210

Thr Glu Gln Pro Ser His Ser Gln Val Leu Cys Arg Cys Asn His
            215                 220                 225

Leu Thr Tyr Phe Ala Val Leu Met Gln Leu Ser Pro Ala Leu Val
            230                 235                 240

Pro Ala Glu Leu Leu Ala Pro Leu Thr Tyr Ile Ser Leu Val Gly
            245                 250                 255

Cys Ser Ile Ser Ile Val Ala Ser Leu Ile Thr Val Leu Leu His
            260                 265                 270

Phe His Phe Arg Lys Gln Ser Asp Ser Leu Thr Arg Ile His Met
            275                 280                 285

Asn Leu His Ala Ser Val Leu Leu Asn Ile Ala Phe Leu Leu
            290                 295                 300

Ser Pro Ala Phe Ala Met Ser Pro Val Pro Gly Ser Ala Cys Thr
            305                 310                 315

Ala Leu Ala Ala Ala Leu His Tyr Ala Leu Leu Ser Cys Leu Thr
            320                 325                 330

Trp Met Ala Ile Glu Gly Phe Asn Leu Tyr Leu Leu Leu Gly Arg
            335                 340                 345

Val Tyr Asn Ile Tyr Ile Arg Arg Tyr Val Phe Lys Leu Gly Val
            350                 355                 360

Leu Gly Trp Gly Ala Pro Ala Leu Leu Val Leu Leu Ser Leu Ser
            365                 370                 375

Val Lys Ser Ser Val Tyr Gly Pro Cys Thr Ile Pro Val Phe Asp
            380                 385                 390

Ser Trp Glu Asn Gly Thr Gly Phe Gln Asn Met Ser Ile Cys Trp
            395                 400                 405

Val Arg Ser Pro Val Val His Ser Val Leu Val Met Gly Tyr Gly
            410                 415                 420

Gly Leu Thr Ser Leu Phe Asn Leu Val Val Leu Ala Trp Ala Leu
            425                 430                 435

Trp Thr Leu Arg Arg Leu Arg Glu Arg Ala Asp Ala Pro Ser Val
            440                 445                 450

Arg Ala Cys His Asp Thr Val Thr Val Leu Gly Leu Thr Val Leu
            455                 460                 465

Leu Gly Thr Thr Trp Ala Leu Ala Phe Phe Ser Phe Gly Val Phe
            470                 475                 480

Leu Leu Pro Gln Leu Phe Leu Phe Thr Ile Leu Asn Ser Leu Tyr
            485                 490                 495

Gly Phe Phe Leu Phe Leu Trp Phe Cys Ser Gln Arg Cys Arg Ser
            500                 505                 510

Glu Ala Glu Ala Lys Ala Gln Ile Glu Ala Phe Ser Ser Ser Gln
            515                 520                 525
```

Thr Thr Gln

<210> SEQ ID NO 81
<211> LENGTH: 1759
<212> TYPE: DNA
<213> ORGANISM: Homo sapiens

<400> SEQUENCE: 81

```
cgatgccggc ggtcagtggt ccaggtccct tattctgcct tctcctcctg        50
ctcctggacc cccacagccc tgagacgggg tgtcctcctc tacgcaggtt       100
tgagtacaag ctcagcttca aaggcccaag gctggcattg cctggggctg       150
gaatacccct ctggagccat catggagacg ccatcctggg cctggaggaa       200
gtgcggctga cgccatccat gaggaaccgg agtggcgccg tgtggagcag       250
ggcctctgtc cccttctctg cctgggaagt agaggtgcag atgagggtga       300
cgggactggg gcgccgggga gcccagggca tggccgtgtg gtacacccgg       350
ggcaggggcc atgtaggctc tgtccttggg gggctggctt cgtgggacgg       400
catcgggatc ttctttgact ctccggcaga ggatactcag acagtcctg        450
ccatccgtgt gctggccagc gacgggcaca tccctctga gcagcctggg        500
gatgagcta gccaagggct gggctcctgt cattgggact tccggaaccg        550
gccacactcc ttcagagcac ggatcaccta ctggggcag aggctgcgca        600
tgtccttgaa cagtgcctc actcccagtg atccaggtga gttctgtgtg        650
gatgtggggc ccctgctttt ggtccctgga ggtttctttg gggtctcagc       700
agccaccggc accctggcag gtgaggatcc cactggacag gttcccctc        750
agcccttcct ggagatgcag cagctccgcc tggcgaggca gctggaaggg       800
ctgtgggcaa ggctgggctt gggcaccagg gaggatgtaa ctccaaaatc       850
agactctgaa gctcaaggag aaggggaaag gctctttgac ctggaggaga       900
cgctgggcag acaccgccgg atcctgcagg ctctgcgggg tctctccaag       950
cagctggccc aggctgagag acaatggaag aagcagctgg ggccccagg       1000
ccaagccagg cctgacggag gctgggccct ggatgcttcc tgccagattc       1050
catccacccc agggaggggt ggccacctct ccatgtcact caataaggac       1100
tctgccaagg tcggtgccct gctccatgga cagtggactc tgctccaggc       1150
cctgcaagag atgagggatg cagctgtccg catggctgca gaagcccagg       1200
tctcctacct gcctgtgggc attgagcatc atttcttaga gctggaccac       1250
atcctgggcc tcctgcagga ggagcttcgg ggcccggcga aggcagcagc       1300
caaggccccc cgcccacctg gccagccccc aagggcctcc tcgtgcctgc       1350
agcctggcat cttcctgttc tacctcctca ttcagactgt aggcttcttc       1400
ggctacgtgc acttcaggca ggagctgaac aagagccttc aggagtgtct       1450
gtccacaggc agccttcctc tgggtcctgc accacacacc cccagggccc       1500
tgggggattct gaggaggcag cctccccctg ccagcatgcc tgcctgaccc       1550
acctcagagc ctgctttgca tcactgggaa gcaggcagtg tcttgggtgg       1600
gggcttggtc agtatcctct ccgtctgggt gcccagctcc cacgcacacc       1650
tgagctttcg gcatgctccc acctcgttaa aggtgatttc cctctccca       1700
aaaaaaaaaa aaaaaaaaaa aaaaaaaaaa aaaaaaaaaa aaaaaaaaaa       1750
```

-continued aaaaaaaaa                                                              1759

<210> SEQ ID NO 82
<211> LENGTH: 514
<212> TYPE: PRT
<213> ORGANISM: Homo sapiens

<400> SEQUENCE: 82

Met Pro Ala Val Ser Gly Pro Gly Pro Leu Phe Cys Leu Leu Leu
  1               5                  10                  15

Leu Leu Leu Asp Pro His Ser Pro Glu Thr Gly Cys Pro Pro Leu
                 20                  25                  30

Arg Arg Phe Glu Tyr Lys Leu Ser Phe Lys Gly Pro Arg Leu Ala
                 35                  40                  45

Leu Pro Gly Ala Gly Ile Pro Phe Trp Ser His His Gly Asp Ala
                 50                  55                  60

Ile Leu Gly Leu Glu Glu Val Arg Leu Thr Pro Ser Met Arg Asn
                 65                  70                  75

Arg Ser Gly Ala Val Trp Ser Arg Ala Ser Val Pro Phe Ser Ala
                 80                  85                  90

Trp Glu Val Glu Val Gln Met Arg Val Thr Gly Leu Gly Arg Arg
                 95                 100                 105

Gly Ala Gln Gly Met Ala Val Trp Tyr Thr Arg Gly Arg Gly His
                110                 115                 120

Val Gly Ser Val Leu Gly Gly Leu Ala Ser Trp Asp Gly Ile Gly
                125                 130                 135

Ile Phe Phe Asp Ser Pro Ala Glu Asp Thr Gln Asp Ser Pro Ala
                140                 145                 150

Ile Arg Val Leu Ala Ser Asp Gly His Ile Pro Ser Glu Gln Pro
                155                 160                 165

Gly Asp Gly Ala Ser Gln Gly Leu Gly Ser Cys His Trp Asp Phe
                170                 175                 180

Arg Asn Arg Pro His Ser Phe Arg Ala Arg Ile Thr Tyr Trp Gly
                185                 190                 195

Gln Arg Leu Arg Met Ser Leu Asn Ser Gly Leu Thr Pro Ser Asp
                200                 205                 210

Pro Gly Glu Phe Cys Val Asp Val Gly Pro Leu Leu Leu Val Pro
                215                 220                 225

Gly Gly Phe Phe Gly Val Ser Ala Ala Thr Gly Thr Leu Ala Gly
                230                 235                 240

Glu Asp Pro Thr Gly Gln Val Pro Pro Gln Pro Phe Leu Glu Met
                245                 250                 255

Gln Gln Leu Arg Leu Ala Arg Gln Leu Glu Gly Leu Trp Ala Arg
                260                 265                 270

Leu Gly Leu Gly Thr Arg Glu Asp Val Thr Pro Lys Ser Asp Ser
                275                 280                 285

Glu Ala Gln Gly Glu Gly Glu Arg Leu Phe Asp Leu Glu Glu Thr
                290                 295                 300

Leu Gly Arg His Arg Arg Ile Leu Gln Ala Leu Arg Gly Leu Ser
                305                 310                 315

Lys Gln Leu Ala Gln Ala Glu Arg Gln Trp Lys Lys Gln Leu Gly
                320                 325                 330

Pro Pro Gly Gln Ala Arg Pro Asp Gly Gly Trp Ala Leu Asp Ala
                335                 340                 345

```
Ser Cys Gln Ile Pro Ser Thr Pro Gly Arg Gly Gly His Leu Ser
            350                 355                 360

Met Ser Leu Asn Lys Asp Ser Ala Lys Val Gly Ala Leu Leu His
            365                 370                 375

Gly Gln Trp Thr Leu Leu Gln Ala Leu Gln Glu Met Arg Asp Ala
            380                 385                 390

Ala Val Arg Met Ala Ala Glu Ala Gln Val Ser Tyr Leu Pro Val
            395                 400                 405

Gly Ile Glu His His Phe Leu Glu Leu Asp His Ile Leu Gly Leu
            410                 415                 420

Leu Gln Glu Glu Leu Arg Gly Pro Ala Lys Ala Ala Lys Ala
            425                 430                 435

Pro Arg Pro Pro Gly Gln Pro Pro Arg Ala Ser Ser Cys Leu Gln
            440                 445                 450

Pro Gly Ile Phe Leu Phe Tyr Leu Leu Ile Gln Thr Val Gly Phe
            455                 460                 465

Phe Gly Tyr Val His Phe Arg Gln Glu Leu Asn Lys Ser Leu Gln
            470                 475                 480

Glu Cys Leu Ser Thr Gly Ser Leu Pro Leu Gly Pro Ala Pro His
            485                 490                 495

Thr Pro Arg Ala Leu Gly Ile Leu Arg Arg Gln Pro Leu Pro Ala
            500                 505                 510

Ser Met Pro Ala

<210> SEQ ID NO 83
<211> LENGTH: 3244
<212> TYPE: DNA
<213> ORGANISM: Homo sapiens

<400> SEQUENCE: 83
gtagagagtg aagcagcaag actgcagagc ctcatcaaga agtgtggagt              50
gaagggaagg cttcagatgg acaatttgtg tgctggggaa aaaatggaat             100
gtgctgcaaa ttcccctgtg gataagggtg acggctgct ctgtcaactt              150 tgaccatttt cagattctgc gggccattgg taaagggagt tttggaaagg             200
tatgcatcgt gcagaagcga gacactaaga aaatgtatgc aatgaagtac             250
atgaacaagc agaagtgcat cgagagggat gaggttcgga atgttttccg             300
ggagctgcag atcatgcaag gctggagca cccccttcctg gtcaatctgt             350 ggtactcctt ccaggatgag gaggacatgt tcatggtggt ggacctgctc             400
ctgggaggcg acctgcgcta ccatctgcag cagaatgtgc atttcacaga             450
ggggactgtg aaactctaca tctgtgagct ggcactggcc ctggagtatc             500
ttcagaggta ccacatcatc cacagagaca tcaagccaga caatatcctg             550
ctggatgaac acggacatgt tcacattaca gacttcaaca tagcgacggt             600
agtgaaagga gcagaaaggg cttcctccat ggctggcacc aagccctaca             650
tggctccaga agtattccag gtgtacatgg acagaggccc cggatactcg             700
taccctgtcg actggtggtc cctgggcatc acagcctatg agctgctgcg             750
gggctggagg ccgtacgaaa tccactcggt cacgcccatc gatgaaatcc             800
ttaacatgtt caaggtggag cgtgtccact actcctccac gtggtgcaag             850
gggatggtgg ccctgctgag gaagctcctg accaaggatc tgagagccg              900 cgtgtccagc cttcatgaca tacagagcgt gccctacttg gccgacatga             950
```

```
actgggacgc ggtgttcaag aaggcactga tgcccggctt tgtgcccaat      1000
aaagggaggt tgaactgcga tcccacattt gagcttgaag agatgattct      1050
agaatccaag ccacttcaca aaagaagaa gcgattggca agaacagat        1100 ccagggatgg cacaaaggac agctgcccgc tgaatggaca cctgcagcac      1150
tgtttggaga ctgtccggga ggaattcatc atattcaaca gagagaagct      1200
caggaggcag cagggacagg gcagccagct cttggacacc gacagccgag      1250
ggggaggcca ggcccaaagc aagctccagg acgggtgcaa caacaacctc      1300
ctcacccaca cctgcacccg tggctgcagc agctgagccc acacttgttg      1350
ctgctcaaca ggactgcact cgtctctgcc ctgcccaccc agagcccctc      1400
tttgtgccct gatggtccct gtctcacccc tgaaaacatc agatgcagaa      1450
aaagccctgg acttggagct gggaagcctg ggttctggtc ccatctccat      1500
gactgattca cgtgtgacct cagacaagtc acgccctctc tgtgcctccg      1550
ttttctgcat ctgccaaagg ggttaaacac ttctgcccca cttcaaatta      1600
caagattatg gggagaaccc aattaggtag gaaacatgaa aaacctttga      1650
tatttataaa atcattttta cgtgcaaaat ataaccttaa tatttgaagt      1700 gaccccccatt ccccaaagca atcaaaccgt catgactttg caatttggca     1750
catcctagct tgttagaggg cacttccgaa aaacacagcc ctgacagcaa      1800
aataaaggtc tgatatgttg gccccttcta tggaaacaac gctgccaaat      1850
cctggagcaa aacctgaagt gtcttcatgt gcattctctg gcaggccaca      1900
gtccttctga gcttgtaaga tggtgcagca tgcagaccag acttgtcccc      1950
aaggtctcag cgctgcggtc tcactcctcc cctcatttaa gaagactatc      2000 cttaccttt agtttcagca gtcctcacca ccaccatatc cccagtgctg       2050
ggatggcaca caggtgtcca ttcagatgag agttgggtcg ctgagcattg      2100
gttactcctg cagagtgtaa tcagcacccc atccaactgg cccgaaagcc      2150
cagacctgca gcagaactct ccaactctct atcagctttc agggttttct     2200
ctcctgggaa gggtgtaaaa tcagcttgtc agattcttct tacagagagt      2250
atccaatcgg tattggtgga gcggctccct atttatacaa taggaagcat      2300
gggtgcttag aaagtttatt tcaggaggaa aatgggttca cacaaaaagc      2350
aaactacatt ctgatctgct cagggagaag cttgcctttg aactggaaga      2400
tgttgggatg agcagggaaa gcttagactt tggagtcagg tttgtgttca      2450
gaatccagcc ctgctggcta ctaactaact gggagacctt aggcaaagca      2500
tgcaatcgct ctgaatggca gtttcctcat ttttaaacag ggataataaa      2550
actaatattg caggggagtt acagggttaa ataagatcct gtgtgtaacc      2600
ccaagcattg gatgactcat agaatggcct tttttgtcag cataatcgtc      2650
atcattattt agatactttc ttccttcact cacccagcag gtcagttttc      2700
tgtgcaaaca aacctgttta ggattcttcc aaatgttctt cctggggtct      2750
ttgatatttg tttgttacat cctgctgaag ttcgactgtg ttttatttt      2800 ttcatccaac ttccattttt cacttttttac atgattactc aatccttggg     2850
gctgtccatg tcatctctta gatttcttaa aagcattttt aatgtatggt      2900
taggttttat attttatttt tttaaaaaag aaatagtcag tgtttccctc      2950
```

-continued

```
ctttcaaccg agactatttc tggattgtgt gctcctcgtc agttgacttg        3000
ttttgcacac ttttctttac ttcatgtccc catcaacaac cgtcctgctc        3050
cccacctccc ccaggaaata aggggcctgc tcctctccct actgtgaccc        3100
tggaggctct taagatgatg atggttttt ttattgggct gagttcacga         3150
attaggggca ggagctggaa gtcgccctag aacaccaga tttcctggtt         3200 ctgttcaagt tggcatttct tgtttggaat aaactatttc  ttgg             3244
```

<210> SEQ ID NO 84
<211> LENGTH: 364
<212> TYPE: PRT
<213> ORGANISM: Homo sapiens

<400> SEQUENCE: 84

```
Met Lys Tyr Met Asn Lys Gln Lys Cys Ile Glu Arg Asp Glu Val
 1               5                  10                  15

Arg Asn Val Phe Arg Glu Leu Gln Ile Met Gln Gly Leu Glu His
                20                  25                  30

Pro Phe Leu Val Asn Leu Trp Tyr Ser Phe Gln Asp Glu Glu Asp
                35                  40                  45

Met Phe Met Val Val Asp Leu Leu Leu Gly Gly Asp Leu Arg Tyr
                50                  55                  60

His Leu Gln Gln Asn Val His Phe Thr Glu Gly Thr Val Lys Leu
                65                  70                  75

Tyr Ile Cys Glu Leu Ala Leu Ala Leu Glu Tyr Leu Gln Arg Tyr
                80                  85                  90

His Ile Ile His Arg Asp Ile Lys Pro Asp Asn Ile Leu Leu Asp
                95                 100                 105

Glu His Gly His Val His Ile Thr Asp Phe Asn Ile Ala Thr Val
               110                 115                 120

Val Lys Gly Ala Glu Arg Ala Ser Ser Met Ala Gly Thr Lys Pro
               125                 130                 135

Tyr Met Ala Pro Glu Val Phe Gln Val Tyr Met Asp Arg Gly Pro
               140                 145                 150

Gly Tyr Ser Tyr Pro Val Asp Trp Trp Ser Leu Gly Ile Thr Ala
               155                 160                 165

Tyr Glu Leu Leu Arg Gly Trp Arg Pro Tyr Glu Ile His Ser Val
               170                 175                 180

Thr Pro Ile Asp Glu Ile Leu Asn Met Phe Lys Val Glu Arg Val
               185                 190                 195

His Tyr Ser Ser Thr Trp Cys Lys Gly Met Val Ala Leu Leu Arg
               200                 205                 210

Lys Leu Leu Thr Lys Asp Pro Glu Ser Arg Val Ser Ser Leu His
               215                 220                 225

Asp Ile Gln Ser Val Pro Tyr Leu Ala Asp Met Asn Trp Asp Ala
               230                 235                 240

Val Phe Lys Lys Ala Leu Met Pro Gly Phe Val Pro Asn Lys Gly
               245                 250                 255

Arg Leu Asn Cys Asp Pro Thr Phe Glu Leu Glu Glu Met Ile Leu
               260                 265                 270

Glu Ser Lys Pro Leu His Lys Lys Lys Arg Leu Ala Lys Asn
               275                 280                 285

Arg Ser Arg Asp Gly Thr Lys Asp Ser Cys Pro Leu Asn Gly His
               290                 295                 300
```

```
Leu Gln His Cys Leu Glu Thr Val Arg Glu Glu Phe Ile Ile Phe
            305                 310                 315

Asn Arg Glu Lys Leu Arg Arg Gln Gln Gly Gln Gly Ser Gln Leu
            320                 325                 330

Leu Asp Thr Asp Ser Arg Gly Gly Gly Gln Ala Gln Ser Lys Leu
            335                 340                 345

Gln Asp Gly Cys Asn Asn Asn Leu Leu Thr His Thr Cys Thr Arg
            350                 355                 360

Gly Cys Ser Ser

<210> SEQ ID NO 85
<211> LENGTH: 3501
<212> TYPE: DNA
<213> ORGANISM: Homo sapiens

<400> SEQUENCE: 85
```

| | | | | |
|---|---|---|---|---|
| ctgagctccc | gggctccggc | agcgcgctgg | cggggcgccg | cattgcacac | 50 |
| tctgggggcg | ccgcagtgtt | cgtgggatgg | ggcagcgggc | tgcagctggc | 100 |
| ggccggaatc | cgcgcgcagc | ccgggtgcaa | gttctctcct | gttgccctga | 150 |
| gtgcccactc | ccaggccctc | tgtatgagtg | acacttcagt | ctgccatgga | 200 |
| acctggccct | gctctggcct | ggctcctgct | cctgagcctg | ctggcggatt | 250 |
| gtctgaaagc | tgctcagtcc | cgagacttca | cagtgaaaga | cattatctac | 300 |
| ctccatcctt | caaccacacc | atatcctggt | ggatttaaat | gtttcacctg | 350 |
| tgaaaaggca | gcagacaatt | atgagtgcaa | ccgatgggct | ccagacatct | 400 |
| actgccctcg | agagaccaga | tactgctaca | ctcagcacac | aatggaagtc | 450 |
| acaggaaaca | gtatctcagt | caccaaacgc | tgtgtcccac | tggaagagtg | 500 |
| cttatccact | ggctgcagag | actccgagca | tgaaggccac | aaggtctgca | 550 |
| cttcttgttg | tgaaggaaat | atctgtaact | tgccactgcc | ccgaaatgaa | 600 |
| actgatgcca | catttgccac | gacgtcacct | ataaatcaga | caaatgggca | 650 |
| cccacgctgt | atgtcagtga | tagtgtcctg | cttgtggttg | tggttagggc | 700 |
| tcatgttata | gtggctcagt | ggctccatgt | gttaatagcg | atccatgggg | 750 |
| atctcgatgg | tccacagacc | tgcatgagtc | attggcctga | cagtaattac | 800 |
| acatgtgaga | cacaacactc | ttggaggtca | tcacagccaa | gcattgccac | 850 |
| ttaccatgag | gaataaatgt | tgcttcattg | tagccatttt | gagtctaacc | 900 |
| gagactcatc | aaagccttct | gtcagtacag | cccaagttcc | ataccataaa | 950 |
| cgtttgtttt | cattccaaga | agtagttctg | catttatcga | gatctggggt | 1000 |
| tcttaatttg | gaagaataca | tgcatgagat | gcagtaggtc | ctgagactgt | 1050 |
| aagatattag | gagtatgtta | tagggcatg | tatagatgtg | ggcttttcag | 1100 |
| gagaaaagta | accattggtt | taaatataat | catgagttca | tttgtagctt | 1150 |
| tagaatttta | aaacattgac | tccaaactga | atggactatt | tccttggaaa | 1200 |
| ttctgactga | gtccctggaa | gagtagtaat | tccaacaatt | ccagccattt | 1250 |
| gttcaattaa | ttttcccaac | attcttctcc | cagtgctggg | aatcacattt | 1300 |
| cctctgttct | gtgcagaaga | caaaaaggca | atcataaaag | tttgttatat | 1350 |
| ttgtgggggt | gcctggagga | ggattttcct | caacttaatg | gagccactgt | 1400 |
| ccataaagtg | gctgttatcc | cttcatataa | ttggtgagat | cagccttctc | 1450 |

| | |
|---|---|
| cttgacttgg cacctaatta tgcttcatga gatcctagat tccacctgag | 1500 |
| tcaattgtgt ccagagcccc aaaccaggat ggagttgttt tccccagata | 1550 |
| tggggttcta ttcagccata gataatctag acagaggatt tcagaatgaa | 1600 |
| aggaaaaatg tgtggagatt agtcctagtt cattctgagg gccgactaag | 1650 |
| tggctcagcc agcttcttac tccatctgca gttcatactg ccaaagagct | 1700 |
| cccacttcca aatccccagt gactttatgg agaagattct gcattaaatt | 1750 |
| gtctttcgaa tgatggggaa gcaaggcata atatgcgatg atgaggagaa | 1800 |
| agtagaccag tgaggtgatt gcaagactaa caaggagact caatgggaag | 1850 |
| tttttctttc ttttagatat tgcttttgaa gtagatggta aaattttgt | 1900 |
| catccttctt gtatttttg taccccaagt tacaattttt cttcttcctt | 1950 |
| gtaaataatt taaacagtat ttattttgt aaggcataac tagaaactaa | 2000 |
| aatatattct aaaaaattca ttattctgaa caaagtgatc aaattagaat | 2050 |
| acatatttt caacagtggt agagctttta atatatgttt attgaaagtt | 2100 |
| atctataata cttgcaccag tgttgaaaaa agttaacatg taggcaagag | 2150 |
| caatatgttt gtctcaagga ttttccatg gtttcctcag tgatggtgtc | 2200 |
| ctggaattat tcaggtggtg accatcactg gtctaagttt gtgtgcaggg | 2250 |
| ttttcagacg tgttttgtg aaacttggta gaaccatggc taataaagag | 2300 |
| gacagtgttg tcagggtcca tctgccctcc atagaaaaat gtctctggct | 2350 |
| cataaaatga gactccctca gggactaaat atgaactgac agcagtaact | 2400 |
| ctgatacaga ataatctaaa ttgcatcaaa tggccttaat tcagagtttg | 2450 |
| ttaggcttat cagtatgttg cttttaattg gggtgggaaa gtagagggag | 2500 |
| agaaagcaag acatttatta agcacctcgt atgtgccagg cactatgcta | 2550 |
| agcactttac ataagttagg attaatccct gcaagaatcc tataaagaat | 2600 |
| gttactagca tttacacttc ccaaatgaag gtaccaaagc tcaaacgcaa | 2650 |
| tgttgtgaag ctgtttcctt cagatttagg ttatgtggga tgatgtggga | 2700 |
| ttgaagagga aagaaaggtg ggattatccc cctaggaaga ctttcaggcc | 2750 |
| tgacttcata ggaattcatc catcttatca tgtggagttt atctcaccct | 2800 |
| gctgttgcag gatgctattt gcatgtgtcc ccaggtgatg tttttctt | 2850 |
| ggggagtagg ggtttggctt cctcattcat ccctcttgct aaaagaggag | 2900 |
| atagttgatg ttgcatctaa agatgctata agacaatgaa agtttgatgt | 2950 |
| tgtacatacc tacaagtacc atttttgtgc atgattacac tccactgaca | 3000 |
| tcttccaagt actacatgtg attgaataag aaacaagaaa gtgaccacac | 3050 |
| caaagcctcc ctggctggtg tacagggatc aggtccacag tggtgcagat | 3100 |
| tcaaccacca cccagggagt gcttgcagac tctgcataga tgttgctgca | 3150 |
| tgcgtcccat gtgcctgtca gaatggcagt gtttaattct cttgaaagaa | 3200 |
| agttatttgc tcactatccc cagcctcaag gagccaagga agagtcattc | 3250 |
| acatggaagg tccgggactg gtcagccact ctgacttttc taccacatta | 3300 |
| aattctccat tacatctcac tattggtaat ggcttaagtg taaagagcca | 3350 |
| tgatgtgtat attaagctat gtgccacata tttattttta gactctccac | 3400 |
| agcattcatg tcaatatggg attaatgcct aaactttgta aatattgtac | 3450 |

```
agtttgtaaa tcaatgaata aaggttttga gtgtaaaaaa aaaaaaaaaa         3500
a                                                              3501
```

<210> SEQ ID NO 86
<211> LENGTH: 171
<212> TYPE: PRT
<213> ORGANISM: Homo sapiens

<400> SEQUENCE: 86

```
Met Glu Pro Gly Pro Ala Leu Ala Trp Leu Leu Leu Leu Ser Leu
 1               5                  10                  15

Leu Ala Asp Cys Leu Lys Ala Ala Gln Ser Arg Asp Phe Thr Val
                20                  25                  30

Lys Asp Ile Ile Tyr Leu His Pro Ser Thr Thr Pro Tyr Pro Gly
                35                  40                  45

Gly Phe Lys Cys Phe Thr Cys Glu Lys Ala Ala Asp Asn Tyr Glu
                50                  55                  60

Cys Asn Arg Trp Ala Pro Asp Ile Tyr Cys Pro Arg Glu Thr Arg
                65                  70                  75

Tyr Cys Tyr Thr Gln His Thr Met Glu Val Thr Gly Asn Ser Ile
                80                  85                  90

Ser Val Thr Lys Arg Cys Val Pro Leu Glu Glu Cys Leu Ser Thr
                95                 100                 105

Gly Cys Arg Asp Ser Glu His Glu Gly His Lys Val Cys Thr Ser
               110                 115                 120

Cys Cys Glu Gly Asn Ile Cys Asn Leu Pro Leu Pro Arg Asn Glu
               125                 130                 135

Thr Asp Ala Thr Phe Ala Thr Thr Ser Pro Ile Asn Gln Thr Asn
               140                 145                 150

Gly His Pro Arg Cys Met Ser Val Ile Val Ser Cys Leu Trp Leu
               155                 160                 165

Trp Leu Gly Leu Met Leu
               170
```

<210> SEQ ID NO 87
<211> LENGTH: 3151
<212> TYPE: DNA
<213> ORGANISM: Homo sapiens

<400> SEQUENCE: 87

```
atggcccgcg ggacaacatg gctgcgcccg cactagggct ggtgtgtgga         50
cgttgccctg agctgggtct cgtcctcttg ctgctgctgc tctcgctgct        100
gtgtggagcg gcagggagcc aggaggccgg gaccggtgcg ggcgcggggt        150
cccttgcggg ttcttgcggc tgcggcacgc cccagcggcc tggcgcccat        200
ggcaattcgg cagccgctca ccgatactcg cgggaggcta acgctccggg        250
ccccgtaccc ggagagcggc aactcgcgca ctcaaagatg gtccccatcc        300
ctgctggagt atttacaatg gcacagatg atcctcagat aaagcaggat         350
ggggaagcac ctgcgaggag agttactatt gatgcctttt acatggatgc        400
ctatgaagtc agtaatactg aatttgagaa gtttgtgaac tcaactggct        450
atttgacaga ggctgagaag tttggcgact cctttgtctt tgaaggcatg        500
ttgagtgagc aagtgaagac caatattcaa caggcagttg cagctgctcc        550
ctggtggtta cctgtgaaag gcgctaactg gagacaccca gaagggcctg        600
```

```
actctactat tctgcacagg ccggatcatc cagttctcca tgtgtcctgg       650
aatgatgcgg ttgcctactg cacttgggca gggaagcggc tgcccacgga       700
agctgagtgg gaatacagct gtcgaggagg cctgcataat agacttttcc       750
cctggggcaa caaactgcag cccaaaggcc agcattatgc caacatttgg       800
cagggcgagt ttccggtgac caacactggt gaggatggct tccaaggaac       850
tgcgcctgtt gatgccttcc ctcccaatgg ttatggctta taacacatag       900
tggggaacgc atgggaatgg acttcagact ggtggactgt tcatcattct       950
gttgaagaaa cgcttaaccc aaaaggtccc ccttctggga agaccgagt        1000 gaagaaaggt ggatcctaca tgtgccatag gtcccaagag tactatgatc       1050
cctattttca agatgtggca tctgagatgt tgagaagaca cacagccagc       1100
aggtggaagg ccttctcatc tctagaacca tgctgctcaa tacgtaggca       1150
tcagcaatat gcagctattg aacgtttgac atgtggcaag tttgaattga       1200
gatgtgctag tttaagaaaa atagattgcc tcaacaccaa cattgcctgt       1250
agctactcca tgaggcaaca tggacccaga ctccactgtg tggactgacc       1300
tcccagaagg atcctcctgt ccctgaaggc cactctgcct tcagctacag       1350
gccccagtgc tgattgtgat acttaacaag ggctttcaga tgtctgaaac       1400
aagagtatag cataaagtta agaatgcggc ttctggagag acagacttgg       1450
tttcaaattc agctctgtga ccttgggtgc acagcaaagt cttcttctcc       1500
ccccgatgaa agaatgggaa ggactcagga aggctcaact tgcaaactcc       1550
ccagtatcaa gtggctgcct tcaaaatcca acccttctct tcccagctca       1600
tttccagtat gtattttcaa aggccatgtc attttttgaag tgcctgagaa       1650 gaaaacagaa ctgccagcag actatgggac aaacgactaa atgccctcca       1700
gacgttccag agtcctctgc ctctcaggct tcagttcttc ctgaaggaat       1750
ctggagctgg aaagcaggaa gcaatttgct gtggaatttt ttccatcaca       1800
gactccaagt tcctcagcct ttggactctt gaacttacac cagtgttttg       1850
gcaggagcgc tcgggccttt ggccacagac tgaaggctgc attgtcagct       1900
ttcctacttt tgaggttttg ggactcagac tgatccacca ctggcttcct       1950
tgctcttcaa cttgaagacg gcctatcgtg agactttacc tcgtgattat       2000
gtgagtcaat tctcctaata aactcccctt cgtatgtaca tatacccctat      2050 tacttctgtc cctttagaga accctgacta atacagtaga gattgcctgg       2100
acttattaat aataatgact ctgtttagtt aatgtaacag acagataaag       2150
acaaatgagt gacacccatg caattaatat aattttggtg gggagtgaga       2200
ggagttggtt ctccactcac agtggaaagt tttagcgtat actgctgcac       2250
atgacatggg agtattttgc acttccactg gaaaaaagta aggggaataa       2300 aaaccctgg attctacttg ctgacttgag agtgactaaa gcgatttatc        2350
tgaaggttcc ccagggtgga ttcatagtgg actcaggcca gattctctgc       2400
tgatgctttg aacttatgtc cagagcatca tctccaccac aaaagagctt       2450
gcctgctctg tgtcctggcc aaagagatgc acgtgctcta tcactgggtt       2500
gtggctcttg agtaactcct ggaattaccc agctggaatt tctattcctt       2550
tggaccacaa atttcatatc ttcacctgct gcctatatca tgctaaaaga       2600
```

-continued

```
tggaaatgtc tcaactaaac catgtaggtg gactagcctc attaacaaga            2650
taagcaatgg gccatttct  cactggttat taactatgta cattatctat            2700 gaataacat  atctggtcat ggttactact ctattctgta gggtggaata            2750 gaaaaggta  gaggatatat atttcagttg cattttaaa  attgtttatt            2800 ttgttttta  attgacaaat aatattaggt tggtgcaaaa gtaattgcag            2850
tttttgccat taaaggtaga caaggctggg cacggtggct cagcacgctt            2900
gtaatcccag cactttggga ggcagaggcg ggcagatcac aaggtcagga            2950
gaccgagacc atcctggcta acacggtgaa accccatctc tactaaaaat            3000
acaaaaaatt agccgggtgt ggtggtgggc acctgtagtc ccagctactc            3050
gggaggctga ggcaggagaa tggcgtgaac ctgggaggtg gagcttgtag            3100
tgagctgcac cactgcactc cagcctgggc aacagagcaa gaccccatat            3150
c                                                                 3151
```

<210> SEQ ID NO 88
<211> LENGTH: 426
<212> TYPE: PRT
<213> ORGANISM: Homo sapiens

<400> SEQUENCE: 88

```
Met Ala Ala Pro Ala Leu Gly Leu Val Cys Gly Arg Cys Pro Glu
 1               5                  10                  15

Leu Gly Leu Val Leu Leu Leu Leu Leu Ser Leu Leu Cys Gly
            20                  25                  30

Ala Ala Gly Ser Gln Glu Ala Gly Thr Gly Ala Gly Ala Gly Ser
            35                  40                  45

Leu Ala Gly Ser Cys Gly Cys Gly Thr Pro Gln Arg Pro Gly Ala
            50                  55                  60

His Gly Asn Ser Ala Ala Ala His Arg Tyr Ser Arg Glu Ala Asn
            65                  70                  75

Ala Pro Gly Pro Val Pro Gly Glu Arg Gln Leu Ala His Ser Lys
            80                  85                  90

Met Val Pro Ile Pro Ala Gly Val Phe Thr Met Gly Thr Asp Asp
            95                 100                 105

Pro Gln Ile Lys Gln Asp Gly Glu Ala Pro Ala Arg Arg Val Thr
           110                 115                 120

Ile Asp Ala Phe Tyr Met Asp Ala Tyr Glu Val Ser Asn Thr Glu
           125                 130                 135

Phe Glu Lys Phe Val Asn Ser Thr Gly Tyr Leu Thr Glu Ala Glu
           140                 145                 150

Lys Phe Gly Asp Ser Phe Val Phe Glu Gly Met Leu Ser Glu Gln
           155                 160                 165

Val Lys Thr Asn Ile Gln Gln Ala Val Ala Ala Pro Trp Trp
           170                 175                 180

Leu Pro Val Lys Gly Ala Asn Trp Arg His Pro Glu Gly Pro Asp
           185                 190                 195

Ser Thr Ile Leu His Arg Pro Asp His Pro Val Leu His Val Ser
           200                 205                 210

Trp Asn Asp Ala Val Ala Tyr Cys Thr Trp Ala Gly Lys Arg Leu
           215                 220                 225

Pro Thr Glu Ala Glu Trp Glu Tyr Ser Cys Arg Gly Gly Leu His
           230                 235                 240
```

```
Asn Arg Leu Phe Pro Trp Gly Asn Lys Leu Gln Pro Lys Gln
            245                 250                 255

His Tyr Ala Asn Ile Trp Gln Gly Glu Phe Pro Val Thr Asn Thr
            260                 265                 270

Gly Glu Asp Gly Phe Gln Gly Thr Ala Pro Val Asp Ala Phe Pro
            275                 280                 285

Pro Asn Gly Tyr Gly Leu Tyr Asn Ile Val Gly Asn Ala Trp Glu
            290                 295                 300

Trp Thr Ser Asp Trp Trp Thr Val His His Ser Val Glu Glu Thr
            305                 310                 315

Leu Asn Pro Lys Gly Pro Ser Gly Lys Asp Arg Val Lys Lys
            320                 325                 330

Gly Gly Ser Tyr Met Cys His Arg Ser Gln Glu Tyr Tyr Asp Pro
            335                 340                 345

Tyr Phe Gln Asp Val Ala Ser Glu Met Leu Arg Arg His Thr Ala
            350                 355                 360

Ser Arg Trp Lys Ala Phe Ser Ser Leu Glu Pro Cys Cys Ser Ile
            365                 370                 375

Arg Arg His Gln Gln Tyr Ala Ala Ile Glu Arg Leu Thr Cys Gly
            380                 385                 390

Lys Phe Glu Leu Arg Cys Ala Ser Leu Arg Lys Ile Asp Cys Leu
            395                 400                 405

Asn Thr Asn Ile Ala Cys Ser Tyr Ser Met Arg Gln His Gly Pro
            410                 415                 420

Arg Leu His Cys Val Asp
            425

<210> SEQ ID NO 89
<211> LENGTH: 521
<212> TYPE: DNA
<213> ORGANISM: Homo sapiens

<400> SEQUENCE: 89
ttccagtcag agttaagtta aaacagaaaa aaggaagatg gcaagaatat          50
tgttactttt cctcccgggt cttgtggctg tatgtgctgt gcatggaata         100
tttatggacc gtctagcttc caagaagctc tgtgcagatg atgagtgtgt         150
ctatactatt tctctggcta gtgctcaaga agattataat gccccggact         200
gtagattcat taacgttaaa aagggcagc agatctatgt gtactcaaag          250
ctggtaaaag aaaatggagc tggagaattt tgggctggca gtgtttatgg         300
tgatggccag gacgagatgg gagtcgtggg ttatttcccc aggaacttgg         350
tcaaggaaca gcgtgtgtac caggaagcta ccaaggaagt tcccaccacg         400
gatattgact tcttctgcga gtaataaatt agttaaaact gcaaatagaa         450
agaaaacacc aaaaataaag aaaagagcaa aagtggccaa aaaatgcatg         500
tctgtaattt tggactgacg t                                        521

<210> SEQ ID NO 90
<211> LENGTH: 128
<212> TYPE: PRT
<213> ORGANISM: Homo sapiens

<400> SEQUENCE: 90

Met Ala Arg Ile Leu Leu Leu Phe Leu Pro Gly Leu Val Ala Val
 1               5                   10                  15
```

```
Cys Ala Val His Gly Ile Phe Met Asp Arg Leu Ala Ser Lys Lys
             20                  25                  30

Leu Cys Ala Asp Asp Glu Cys Val Tyr Thr Ile Ser Leu Ala Ser
         35                  40                  45

Ala Gln Glu Asp Tyr Asn Ala Pro Asp Cys Arg Phe Ile Asn Val
     50                  55                  60

Lys Lys Gly Gln Gln Ile Tyr Val Tyr Ser Lys Leu Val Lys Glu
 65                  70                  75

Asn Gly Ala Gly Glu Phe Trp Ala Gly Ser Val Tyr Gly Asp Gly
             80                  85                  90

Gln Asp Glu Met Gly Val Val Gly Tyr Phe Pro Arg Asn Leu Val
         95                 100                 105

Lys Glu Gln Arg Val Tyr Gln Glu Ala Thr Lys Glu Val Pro Thr
    110                 115                 120

Thr Asp Ile Asp Phe Phe Cys Glu
            125
```

<210> SEQ ID NO 91
<211> LENGTH: 939
<212> TYPE: DNA
<213> ORGANISM: Homo sapiens

<400> SEQUENCE: 91

| | |
|---|---|
| ctgtcagctg aggatccagc cgaaagagga gccaggcact caggccacct | 50 |
| gagtctactc acctggacaa ctggaatctg caccaattc taaaccactc | 100 |
| agcttctccg agctcacacc ccggagatca cctgaggacc cgagccattg | 150 |
| atggactcgg acgagaccgg gttcgagcac tcaggactgt gggtttctgt | 200 |
| gctggctggt ctgctgggag cctgccaggc acccccatc cctgactcca | 250 |
| gtcctctcct gcaattcggg ggccaagtcc ggcagcggta cctctacaca | 300 |
| gatgatgccc agcagacaga agcccacctg agatcaggg aggatgggac | 350 |
| ggtgggggc gctgctgacc agagccccga agtctcctg cagctgaaag | 400 |
| ccttgaagcc gggagttatt caaatcttgg gagtcaagac atccaggttc | 450 |
| ctgtgccagc ggccagatgg ggccctgtat ggatcgctcc actttgaccc | 500 |
| tgaggcctgc agcttccggg agctgcttct tgaggacgga tacaatgttt | 550 |
| accagtccga agcccacggc ctcccgctgc acctgccagg gaacaagtcc | 600 |
| ccacaccggg accctgcacc ccgaggacca gctcgcttcc tgccactacc | 650 |
| aggcctgccc ccgcactcc cggagccacc cggaatcctg ccccccagc | 700 |
| cccccgatgt gggctcctcg accctctga gcatggtggg accttcccag | 750 |
| ggccgaagcc ccagctacgc ttcctgaagc cagaggctgt ttactatgac | 800 |
| atctcctctt tatttattag gttatttatc ttatttattt ttttattttt | 850 |
| cttacttgag ataataaaga gttccagagg agaaaaaaaa aaaaaaaaa | 900 |
| aaaaaaaaaa aaaaaaaaa aaaaaaaaa aaaaaaaag | 939 |

<210> SEQ ID NO 92
<211> LENGTH: 208
<212> TYPE: PRT
<213> ORGANISM: Homo sapiens

<400> SEQUENCE: 92

Met Asp Ser Asp Glu Thr Gly Phe Glu His Ser Gly Leu Trp Val

```
             1               5                  10                 15
Ser Val Leu Ala Gly Leu Leu Gly Ala Cys Gln Ala His Pro Ile
            20                 25                 30
Pro Asp Ser Ser Pro Leu Leu Gln Phe Gly Gly Gln Val Arg Gln
            35                 40                 45
Arg Tyr Leu Tyr Thr Asp Asp Ala Gln Gln Thr Glu Ala His Leu
            50                 55                 60
Glu Ile Arg Glu Asp Gly Thr Val Gly Gly Ala Ala Asp Gln Ser
            65                 70                 75
Pro Glu Ser Leu Leu Gln Leu Lys Ala Leu Lys Pro Gly Val Ile
            80                 85                 90
Gln Ile Leu Gly Val Lys Thr Ser Arg Phe Leu Cys Gln Arg Pro
            95                100                105
Asp Gly Ala Leu Tyr Gly Ser Leu His Phe Asp Pro Glu Ala Cys
           110                115                120
Ser Phe Arg Glu Leu Leu Leu Glu Asp Gly Tyr Asn Val Tyr Gln
           125                130                135
Ser Glu Ala His Gly Leu Pro Leu His Leu Pro Gly Asn Lys Ser
           140                145                150
Pro His Arg Asp Pro Ala Pro Arg Gly Pro Ala Arg Phe Leu Pro
           155                160                165
Leu Pro Gly Leu Pro Pro Ala Leu Pro Glu Pro Gly Ile Leu
           170                175                180
Ala Pro Gln Pro Pro Asp Val Gly Ser Ser Asp Pro Leu Ser Met
           185                190                195
Val Gly Pro Ser Gln Gly Arg Ser Pro Ser Tyr Ala Ser
           200                205

<210> SEQ ID NO 93
<211> LENGTH: 1589
<212> TYPE: DNA
<213> ORGANISM: Homo sapiens

<400> SEQUENCE: 93
catctaaagc ctcctcagcc ttctgagtca gcctgaaagg aacaggccga          50
actgctgtat gggctctact gccagtgtga cctcaccctc tccagtcacc         100
cctcctcagt tccagctatg agttcctgca acttcacaca tgccaccttt         150
gtgcttattg gtatcccagg attagagaaa gcccatttct gggttggctt         200
cccccctcct tccatgtatg tagtggcaat gtttggaaac tgcatcgtgg         250
tcttcatcgt aaggacggaa cgcagcctgc acgctccgat gtacctcttt         300
ctctgcatgc ttgcagccat tgacctggcc ttatccacat ccaccatgcc         350
taagatcctt gccctttttct ggtttgattc ccgagagatt agctttgagg        400
cctgtcttac ccagatgttc tttattcatg ccctctcagc cattgaatcc         450
accatcctgc tggccatggc ctttgaccgt tatgtggcca tctgccaccc         500
actgcgccat gctgcagtgc tcaacaatac agtaacagcc cagattggca         550
tcgtggctgt ggtccgcgga tccctctttt ttttcccact gcctctgctg         600
atcaagcggc tggccttctg ccactccaat gtcctctcgc actcctattg         650
tgtccaccag gatgtaatga agttggccta tgcagacact ttgcccaatg         700
tggtatatgg tcttactgcc attctgctgg tcatgggcgt ggacgtaatg         750
ttcatctcct tgtcctattt tctgataata cgaacggttc tgcaactgcc         800
```

-continued

```
ttccaagtca gagcgggcca aggcctttgg aacctgtgtg tcacacattg          850
gtgtggtact cgccttctat gtgccactta ttggcctctc agttgtacac          900
cgctttggaa acagccttca tcccattgtg cgtgttgtca tgggtgacat          950
ctacctgctg ctgcctcctg tcatcaatcc catcatctat ggtgccaaaa         1000
ccaaacagat cagaacacgg gtgctggcta tgttcaagat cagctgtgac         1050
aaggacttgc aggctgtggg aggcaagtga cccttaacac tacacttctc         1100
cttatcttta ttggcttgat aaacataatt atttctaaca ctagcttatt         1150
tccagttgcc cataagcaca tcagtacttt tctctggctg gaatagtaaa         1200
ctaaagtatg gtacatctac ctaaaggact attatgtgga ataatacata         1250
ctaatgaagt attacatgat ttaaagacta caataaaacc aaacatgctt         1300
ataacattaa gaaaaacaat aaagatacat gattgaaacc aagttgaaaa         1350
atagcatatg ccttggagga aatgtgctca aattactaat gatttagtgt         1400
tgtccctact ttctctctct tttttctttc tttttttttt attatggtta         1450
gctgtcacat acaactttt tttttttga gatggggtct ccagcctggg           1500
caacagagca agaccctgtc tcaaagcata aaatggaata acatatcaaa         1550
tgaaacaggg aaaatgaagc tgacaattta  tgggagcca                    1589
```

<210> SEQ ID NO 94
<211> LENGTH: 320
<212> TYPE: PRT
<213> ORGANISM: Homo sapiens

<400> SEQUENCE: 94

```
Met Ser Ser Cys Asn Phe Thr His Ala Thr Phe Val Leu Ile Gly
 1               5                  10                  15

Ile Pro Gly Leu Glu Lys Ala His Phe Trp Val Gly Phe Pro Leu
                20                  25                  30

Leu Ser Met Tyr Val Val Ala Met Phe Gly Asn Cys Ile Val Val
                35                  40                  45

Phe Ile Val Arg Thr Glu Arg Ser Leu His Ala Pro Met Tyr Leu
                50                  55                  60

Phe Leu Cys Met Leu Ala Ala Ile Asp Leu Ala Leu Ser Thr Ser
                65                  70                  75

Thr Met Pro Lys Ile Leu Ala Leu Phe Trp Phe Asp Ser Arg Glu
                80                  85                  90

Ile Ser Phe Glu Ala Cys Leu Thr Gln Met Phe Phe Ile His Ala
                95                 100                 105

Leu Ser Ala Ile Glu Ser Thr Ile Leu Leu Ala Met Ala Phe Asp
               110                 115                 120

Arg Tyr Val Ala Ile Cys His Pro Leu Arg His Ala Ala Val Leu
               125                 130                 135

Asn Asn Thr Val Thr Ala Gln Ile Gly Ile Val Ala Val Val Arg
               140                 145                 150

Gly Ser Leu Phe Phe Phe Pro Leu Pro Leu Leu Ile Lys Arg Leu
               155                 160                 165

Ala Phe Cys His Ser Asn Val Leu Ser His Ser Tyr Cys Val His
               170                 175                 180

Gln Asp Val Met Lys Leu Ala Tyr Ala Asp Thr Leu Pro Asn Val
               185                 190                 195
```

```
Val Tyr Gly Leu Thr Ala Ile Leu Leu Val Met Gly Val Asp Val
                200                 205                 210

Met Phe Ile Ser Leu Ser Tyr Phe Leu Ile Ile Arg Thr Val Leu
                215                 220                 225

Gln Leu Pro Ser Lys Ser Glu Arg Ala Lys Ala Phe Gly Thr Cys
                230                 235                 240

Val Ser His Ile Gly Val Val Leu Ala Phe Tyr Val Pro Leu Ile
                245                 250                 255

Gly Leu Ser Val Val His Arg Phe Gly Asn Ser Leu His Pro Ile
                260                 265                 270

Val Arg Val Val Met Gly Asp Ile Tyr Leu Leu Leu Pro Pro Val
                275                 280                 285

Ile Asn Pro Ile Ile Tyr Gly Ala Lys Thr Lys Gln Ile Arg Thr
                290                 295                 300

Arg Val Leu Ala Met Phe Lys Ile Ser Cys Asp Lys Asp Leu Gln
                305                 310                 315

Ala Val Gly Gly Lys
                320

<210> SEQ ID NO 95
<211> LENGTH: 2795
<212> TYPE: DNA
<213> ORGANISM: Homo sapiens

<400> SEQUENCE: 95
gggagggctc tgtgccagcc ccgatgagga cgctgctgac catcttgact         50
gtgggatccc tggctgctca cgcccctgag accccctcgg atctgctcca         100
gcacgtgaaa ttccagtcca gcaactttga aaacatcctg acgtgggaca         150
gcgggccaga gggcacccca gacacggtct acagcatcga gtataagacg         200
tacggagaga gggactgggt ggcaaagaag ggctgtcagc ggatcacccg         250
gaagtcctgc aacctgacgg tggagacggg caacctcacg gagctctact         300
atgccagggt caccgctgtc agtgcgggag gccggtcagc caccaagatg         350
actgacaggt tcagctctct gcagcacact accctcaagc cacctgatgt         400
gacctgtatc tccaaagtga gatcgattca gatgattgtt catcctaccc         450
ccacgccaat ccgtgcaggc gatggccacc ggctaaccct ggaagacatc         500
ttccatgacc tgttctacca cttagagctc caggtcaacc gcacctacca         550
aatgcacctt ggagggaagc agagagaata tgagttcttc ggcctgaccc         600
ctgacacaga gttccttggc accatcatga tttgcgttcc cacctgggcc         650
aaggagagtg cccctacat gtgccgagtg aagacactgc cagaccggac         700
atggacctac tccttctccg gagccttcct gttctccatg gcttcctcg         750 tcgcagtact ctgctacctg agctacagat atgtcaccaa gccgcctgca         800
cctcccaact ccctgaacgt ccagcgagtc ctgactttcc agccgctgcg         850
cttcatccag gagcacgtcc tgatccctgt ctttgacctc agcggcccca         900
gcagtctggc ccagcctgtc cagtactccc agatcagggt gtctggaccc         950
agggagcccg caggagctcc acagcggcat agcctgtccg agatcaccta         1000
cttagggcag ccagacatct ccatcctcca gccctccaac gtgccacctc         1050
cccagatcct ctcccactg tcctatgccc caaacgctgc ccctgaggtc         1100
gggcccccat cctatgcacc tcaggtgacc cccgaagctc aattcccatt         1150
```

-continued

```
ctacgcccca caggccatct ctaaggtcca gccttcctcc tatgcccctc      1200
aagccactcc ggacagctgg cctccctcct atggggtatg catggaaggt      1250
tctggcaaag actccccac tgggacactt tctagtccta aacaccttag       1300
gcctaaaggt cagcttcaga aagagccacc agctggaagc tgcatgttag      1350
gtggcctttc tctgcaggag gtgacctcct tggctatgga ggaatcccaa      1400
gaagcaaaat cattgcacca gccctgggg atttgcacag acagaacatc       1450
tgacccaaat gtgctacaca gtggggagga agggacacca cagtacctaa      1500
agggccagct ccccctcctc tcctcagtcc agatcgaggg ccaccccatg      1550
tccctccctt tgcaacctcc ttccggtcca tgttcccct cggaccaagg       1600 tccaagtccc tggggcctgc tggagtccct tgtgtgtccc aaggatgaag      1650
ccaagagccc agcccctgag acctcagacc tggagcagcc cacagaactg      1700
gattctcttt tcagaggcct ggccctgact gtgcagtggg agtcctgagg      1750
ggaatgggaa aggcttggtg cttcctccct gtccctaccc agtgtcacat      1800
ccttggctgt caatcccatg cctgcccatg ccacacactc tgcgatctgg      1850
cctcagacgg gtgcccttga gagaagcaga gggagtggca tgcagggccc      1900
ctgccatggg tgcgctcctc accggaacaa agcagcatga taaggactgc      1950
agcgggggag ctctggggag cagcttgtgt agacaagcgc gtgctcgctg      2000
agccctgcaa ggcagaaatg acagtgcaag gaggaaatgc agggaaactc      2050
ccgaggtcca gagccccacc tcctaacacc atggattcaa agtgctcagg      2100
gaatttgcct ctccttgccc cattcctggc cagtttcaca atctagctcg      2150
acagagcatg aggcccctgc ctcttctgtc attgttcaaa ggtgggaaga      2200
gagcctggaa aagaaccagg cctggaaaag aaccagaagg aggctgggca      2250
gaaccagaac aacctgcact ctgccaaggg ccagggccag caggacggca      2300
ggactctagg gaggggtgtg gcctgcagct cattcccagc cagggcaact      2350
gcctgacgtt gcacgatttc agcttcattc ctctgataga acaaagcgaa      2400
atgcaggtcc accagggagg gagacacaca agccttttct gcaggcagga      2450
gtttcagacc ctatcctgag aatggggttt gaaaggaagg tgagggctgt      2500
ggcccctgga cgggtacaat aacacactgt actgatgtca caactttgca      2550
agctctgcct tgggttcagc ccatctgggc tcaaattcca gcctcaccac      2600
tcacaagctg tgtgacttca aacaaatgaa atcagtgccc agaacctcgg      2650
tttcctcatc tgtaatgtgg ggatcataac acctacctca tggagttgtg      2700
gtgaagatga aatgaagtca tgtctttaaa gtgcttaata gtgcctggta      2750
catgggcagt gcccaataaa cggtagctat ttaaaaaaaa aaaaa          2795
```

<210> SEQ ID NO 96
<211> LENGTH: 574
<212> TYPE: PRT
<213> ORGANISM: Homo sapiens

<400> SEQUENCE: 96

```
Met Arg Thr Leu Leu Thr Ile Leu Thr Val Gly Ser Leu Ala Ala
 1               5                  10                  15

His Ala Pro Glu Asp Pro Ser Asp Leu Leu Gln His Val Lys Phe
                20                  25                  30
```

```
Gln Ser Ser Asn Phe Glu Asn Ile Leu Thr Trp Asp Ser Gly Pro
                35                  40                  45
Glu Gly Thr Pro Asp Thr Val Tyr Ser Ile Glu Tyr Lys Thr Tyr
        50                  55                  60
Gly Glu Arg Asp Trp Val Ala Lys Lys Gly Cys Gln Arg Ile Thr
    65                  70                  75
Arg Lys Ser Cys Asn Leu Thr Val Glu Thr Gly Asn Leu Thr Glu
80                  85                  90
Leu Tyr Tyr Ala Arg Val Thr Ala Val Ser Ala Gly Gly Arg Ser
                95                 100                 105
Ala Thr Lys Met Thr Asp Arg Phe Ser Ser Leu Gln His Thr Thr
            110                 115                 120
Leu Lys Pro Pro Asp Val Thr Cys Ile Ser Lys Val Arg Ser Ile
        125                 130                 135
Gln Met Ile Val His Pro Thr Pro Thr Pro Ile Arg Ala Gly Asp
    140                 145                 150
Gly His Arg Leu Thr Leu Glu Asp Ile Phe His Asp Leu Phe Tyr
155                 160                 165
His Leu Glu Leu Gln Val Asn Arg Thr Tyr Gln Met His Leu Gly
                170                 175                 180
Gly Lys Gln Arg Glu Tyr Glu Phe Phe Gly Leu Thr Pro Asp Thr
            185                 190                 195
Glu Phe Leu Gly Thr Ile Met Ile Cys Val Pro Thr Trp Ala Lys
        200                 205                 210
Glu Ser Ala Pro Tyr Met Cys Arg Val Lys Thr Leu Pro Asp Arg
    215                 220                 225
Thr Trp Thr Tyr Ser Phe Ser Gly Ala Phe Leu Phe Ser Met Gly
230                 235                 240
Phe Leu Val Ala Val Leu Cys Tyr Leu Ser Tyr Arg Tyr Val Thr
                245                 250                 255
Lys Pro Pro Ala Pro Pro Asn Ser Leu Asn Val Gln Arg Val Leu
            260                 265                 270
Thr Phe Gln Pro Leu Arg Phe Ile Gln Glu His Val Leu Ile Pro
        275                 280                 285
Val Phe Asp Leu Ser Gly Pro Ser Ser Leu Ala Gln Pro Val Gln
    290                 295                 300
Tyr Ser Gln Ile Arg Val Ser Gly Pro Arg Glu Pro Ala Gly Ala
305                 310                 315
Pro Gln Arg His Ser Leu Ser Glu Ile Thr Tyr Leu Gly Gln Pro
                320                 325                 330
Asp Ile Ser Ile Leu Gln Pro Ser Asn Val Pro Pro Pro Gln Ile
            335                 340                 345
Leu Ser Pro Leu Ser Tyr Ala Pro Asn Ala Ala Pro Glu Val Gly
        350                 355                 360
Pro Pro Ser Tyr Ala Pro Gln Val Thr Pro Glu Ala Gln Phe Pro
    365                 370                 375
Phe Tyr Ala Pro Gln Ala Ile Ser Lys Val Gln Pro Ser Ser Tyr
380                 385                 390
Ala Pro Gln Ala Thr Pro Asp Ser Trp Pro Pro Ser Tyr Gly Val
                395                 400                 405
Cys Met Glu Gly Ser Gly Lys Asp Ser Pro Thr Gly Thr Leu Ser
            410                 415                 420
Ser Pro Lys His Leu Arg Pro Lys Gly Gln Leu Gln Lys Glu Pro
```

```
                    425                 430                 435
Pro Ala Gly Ser Cys Met Leu Gly Gly Leu Ser Leu Gln Glu Val
            440                 445                 450
Thr Ser Leu Ala Met Glu Glu Ser Gln Glu Ala Lys Ser Leu His
            455                 460                 465
Gln Pro Leu Gly Ile Cys Thr Asp Arg Thr Ser Asp Pro Asn Val
            470                 475                 480
Leu His Ser Gly Glu Glu Gly Thr Pro Gln Tyr Leu Lys Gly Gln
            485                 490                 495
Leu Pro Leu Leu Ser Ser Val Gln Ile Glu Gly His Pro Met Ser
            500                 505                 510
Leu Pro Leu Gln Pro Pro Ser Gly Pro Cys Ser Pro Ser Asp Gln
            515                 520                 525
Gly Pro Ser Pro Trp Gly Leu Leu Glu Ser Leu Val Cys Pro Lys
            530                 535                 540
Asp Glu Ala Lys Ser Pro Ala Pro Glu Thr Ser Asp Leu Glu Gln
            545                 550                 555
Pro Thr Glu Leu Asp Ser Leu Phe Arg Gly Leu Ala Leu Thr Val
            560                 565                 570
Gln Trp Glu Ser

<210> SEQ ID NO 97
<211> LENGTH: 1398
<212> TYPE: DNA
<213> ORGANISM: Homo sapiens

<400> SEQUENCE: 97
gccaacactg gccaaagagc tgcgagcttg agcggcgcga ggagatgcta         50
gagggcgcag cgccgccagc accatgcgcc cccgcccgc gctggccctg         100 gccgggctct gcctgctggc gctgcccgcc gccgccgcct cctacttcgg         150
cctgaccggg cgggaagtcc tgacgccctt ccaggattg ggcactgcgg          200 cagccccggc acagggcggg gcccacctga agcagtgtga cctgctgaag         250
ctgtcccggc ggcagaagca gctctgccgg agggagcccg gcctggctga         300
gaccctgagg gatgctgcgc acctcggcct gcttgagtgc cagtttcagt         350
tccggcatga gcgctggaac tgtagcctgg agggcaggat gggcctgctc         400
aagagaggct tcaaagagac agcttttcctg tacgcggtgt cctctgccgc         450
cctcacccac accctggccc gggcctgcag cgctgggcgc atggagcgct         500
gcacctgtga tgactctccg gggctggaga ccggcaggc ctggcagtgg          550 ggcgtgtgcg gtgacaacct caagtacagc accaagtttc tgagcaactt         600
cctggggtcc aagagaggaa caaggacct gcgggcacgg gcagacgccc          650 acaatacccca cgtgggcatc aaggctgtga agagtggcct caggaccacg        700
tgtaagtgcc atggcgtatc aggctcctgt gccgtgcgca cctgctggaa         750
gcagctctcc ccgttccgtg agacgggcca ggtgctgaaa ctgcgctatg         800
actcggctgt caaggtgtcc agtgccacca atgaggcctt gggccgccta         850
gagctgtggg ccctgccag caggcagca ctcaccaaag gcctggcccc           900
aaggtctggg gacctggtgt acatggagga ctcacccagc ttctgccggc         950
ccagcaagta ctcacctggc acagcaggta gggtgtgctc ccgggaggcc         1000
agctgcagca gcctgtgctg cgggcggggc tatgacaccc agagccgcct         1050
```

-continued

```
ggtggccttc tcctgccact gccaggtgca gtggtgctgc tacgtggagt          1100
gccagcaatg tgtgcaggag gagcttgtgt acacctgcaa gcactaggcc          1150
tactgcccag caagccagtc tggcactgcc aggacctcct gtggcaccct          1200
tcaagctgcc cagccggccc tctgggcaga ctgtcatcac atgcatgcat          1250
aaaccggcat gtgtgccaat gcacacgagt gtgccactca ccaccattcc          1300
ttggccagcc ttttgcctcc ctcgatactc aacaaagaga agcaaagcct          1350
cctcccttaa cccaagcatc cccaaccttg ttgaggactt  ggagagaa           1398
```

<210> SEQ ID NO 98
<211> LENGTH: 357
<212> TYPE: PRT
<213> ORGANISM: Homo sapiens

<400> SEQUENCE: 98

```
Met Arg Pro Pro Ala Leu Ala Leu Ala Gly Leu Cys Leu Leu
  1               5                  10                  15

Ala Leu Pro Ala Ala Ala Ser Tyr Phe Gly Leu Thr Gly Arg
                 20                  25                  30

Glu Val Leu Thr Pro Phe Pro Gly Leu Gly Thr Ala Ala Pro
                 35                  40                  45

Ala Gln Gly Gly Ala His Leu Lys Gln Cys Asp Leu Leu Lys Leu
         50                  55                  60

Ser Arg Arg Gln Lys Gln Leu Cys Arg Arg Glu Pro Gly Leu Ala
         65                  70                  75

Glu Thr Leu Arg Asp Ala Ala His Leu Gly Leu Leu Glu Cys Gln
         80                  85                  90

Phe Gln Phe Arg His Glu Arg Trp Asn Cys Ser Leu Glu Gly Arg
         95                  100                 105

Met Gly Leu Leu Lys Arg Gly Phe Lys Glu Thr Ala Phe Leu Tyr
        110                  115                 120

Ala Val Ser Ser Ala Ala Leu Thr His Thr Leu Ala Arg Ala Cys
        125                  130                 135

Ser Ala Gly Arg Met Glu Arg Cys Thr Cys Asp Asp Ser Pro Gly
        140                  145                 150

Leu Glu Ser Arg Gln Ala Trp Gln Trp Gly Val Cys Gly Asp Asn
        155                  160                 165

Leu Lys Tyr Ser Thr Lys Phe Leu Ser Asn Phe Leu Gly Ser Lys
        170                  175                 180

Arg Gly Asn Lys Asp Leu Arg Ala Arg Ala Asp Ala His Asn Thr
        185                  190                 195

His Val Gly Ile Lys Ala Val Lys Ser Gly Leu Arg Thr Thr Cys
        200                  205                 210

Lys Cys His Gly Val Ser Gly Ser Cys Ala Val Arg Thr Cys Trp
        215                  220                 225

Lys Gln Leu Ser Pro Phe Arg Glu Thr Gly Gln Val Leu Lys Leu
        230                  235                 240

Arg Tyr Asp Ser Ala Val Lys Val Ser Ala Thr Asn Glu Ala
        245                  250                 255

Leu Gly Arg Leu Glu Leu Trp Ala Pro Ala Arg Gln Gly Ser Leu
        260                  265                 270

Thr Lys Gly Leu Ala Pro Arg Ser Gly Asp Leu Val Tyr Met Glu
        275                  280                 285
```

```
Asp Ser Pro Ser Phe Cys Arg Pro Ser Lys Tyr Ser Pro Gly Thr
                290                 295                 300
Ala Gly Arg Val Cys Ser Arg Glu Ala Ser Cys Ser Ser Leu Cys
            305                 310                 315
Cys Gly Arg Gly Tyr Asp Thr Gln Ser Arg Leu Val Ala Phe Ser
            320                 325                 330
Cys His Cys Gln Val Gln Trp Cys Tyr Val Glu Cys Gln Gln
            335                 340                 345
Cys Val Gln Glu Glu Leu Val Tyr Thr Cys Lys His
            350                 355
```

<210> SEQ ID NO 99
<211> LENGTH: 1352
<212> TYPE: DNA
<213> ORGANISM: Homo sapiens

<400> SEQUENCE: 99

| | |
|---|---:|
| tcgcccttcg agcaaatggg tctggccatg gagcacggag ggtcctacgc | 50 |
| tcgggcgggg ggcagctctc ggggctgctg gtattacctg cgctacttct | 100 |
| tcctcttcgt ctccctcatc caattcctca tcatcctggg gctcgtgctc | 150 |
| ttcatggtct atggcaacgt gcacgtgagc acagagtcca acctgcaggc | 200 |
| caccgagcgc cgagccgagg gcctatacag tcagctccta gggctcacgg | 250 |
| cctcccagtc caacttgacc aaggagctca acttcaccac ccgcgccaag | 300 |
| gatgccatca tgcagatgtg gctgaatgct cgccgcgacc tggaccgcat | 350 |
| caatgccagc ttccgccagt gccagggtga ccgggtcatc tacacgaaca | 400 |
| atcagaggta catggctgcc atcatcttga gtgagaagca atgcagagat | 450 |
| caattcaagg acatgaacaa gagctgcgat gccttgctct tcatgctgaa | 500 |
| tcagaaggtg aagacgctgg aggtggagat agccaaggag aagaccattt | 550 |
| gcactaagga taaggaaagc gtgctgctga caaacgcgt ggcggaggaa | 600 |
| cagctggttg aatgcgtgaa acccgggag ctgcagcacc aagagcgcca | 650 |
| gctggccaag gagcaactgc aaaaggtgca agccctctgc ctgcccctgg | 700 |
| acaaggacaa gtttgagatg gaccttcgta acctgtggag ggactccatt | 750 |
| atcccacgca gcctggacaa cctgggttac aacctctacc atccctggg | 800 |
| ctcggaattg gcctccatcc gcagagcctg cgaccacatg cccagcctca | 850 |
| tgagctccaa ggtggaggag ctggcccgga gcctccgggc ggatatcgaa | 900 |
| cgcgtggccc gcgagaactc agacctccaa cgccagaagc tggaagccca | 950 |
| gcagggcctg cgggccagtc aggaggcgaa acagaaggtg gagaaggagg | 1000 |
| ctcaggcccg ggaggccaag ctccaagctg aatgctcccg gcagacccag | 1050 |
| ctagcgctgg aggagaaggc ggtgctgcgg aaggaacgag acaacctggc | 1100 |
| caaggagctg gaagagaaga gaggggaggc ggagcagctc aggatggagc | 1150 |
| tggccatcag aaactcagcc ctggacacct gcatcaagac caagtcgcag | 1200 |
| ccgatgatgc cagtgtcaag gcccatgggc cctgtcccca accccagcc | 1250 |
| catcgaccca gctagcctgg aggagttcaa gaggaagatc ctggagtccc | 1300 |
| agaggccccc tgcaggcatc cctgtagccc catccagtgg ctgagaaggg | 1350 |
| cg | 1352 |

<210> SEQ ID NO 100
<211> LENGTH: 442
<212> TYPE: PRT
<213> ORGANISM: Homo sapiens

<400> SEQUENCE: 100

Met Gly Leu Ala Met Glu His Gly Gly Ser Tyr Ala Arg Ala Gly
1               5                   10                  15

Gly Ser Ser Arg Gly Cys Trp Tyr Tyr Leu Arg Tyr Phe Phe Leu
            20                  25                  30

Phe Val Ser Leu Ile Gln Phe Leu Ile Ile Leu Gly Leu Val Leu
            35                  40                  45

Phe Met Val Tyr Gly Asn Val His Val Ser Thr Glu Ser Asn Leu
            50                  55                  60

Gln Ala Thr Glu Arg Arg Ala Glu Gly Leu Tyr Ser Gln Leu Leu
            65                  70                  75

Gly Leu Thr Ala Ser Gln Ser Asn Leu Thr Lys Glu Leu Asn Phe
            80                  85                  90

Thr Thr Arg Ala Lys Asp Ala Ile Met Gln Met Trp Leu Asn Ala
            95                  100                 105

Arg Arg Asp Leu Asp Arg Ile Asn Ala Ser Phe Arg Gln Cys Gln
            110                 115                 120

Gly Asp Arg Val Ile Tyr Thr Asn Asn Gln Arg Tyr Met Ala Ala
            125                 130                 135

Ile Ile Leu Ser Glu Lys Gln Cys Arg Asp Gln Phe Lys Asp Met
            140                 145                 150

Asn Lys Ser Cys Asp Ala Leu Leu Phe Met Leu Asn Gln Lys Val
            155                 160                 165

Lys Thr Leu Glu Val Glu Ile Ala Lys Glu Lys Thr Ile Cys Thr
            170                 175                 180

Lys Asp Lys Glu Ser Val Leu Leu Asn Lys Arg Val Ala Glu Glu
            185                 190                 195

Gln Leu Val Glu Cys Val Lys Thr Arg Glu Leu Gln His Gln Glu
            200                 205                 210

Arg Gln Leu Ala Lys Glu Gln Leu Gln Lys Val Gln Ala Leu Cys
            215                 220                 225

Leu Pro Leu Asp Lys Asp Lys Phe Glu Met Asp Leu Arg Asn Leu
            230                 235                 240

Trp Arg Asp Ser Ile Ile Pro Arg Ser Leu Asp Asn Leu Gly Tyr
            245                 250                 255

Asn Leu Tyr His Pro Leu Gly Ser Glu Leu Ala Ser Ile Arg Arg
            260                 265                 270

Ala Cys Asp His Met Pro Ser Leu Met Ser Ser Lys Val Glu Glu
            275                 280                 285

Leu Ala Arg Ser Leu Arg Ala Asp Ile Glu Arg Val Ala Arg Glu
            290                 295                 300

Asn Ser Asp Leu Gln Arg Gln Lys Leu Glu Ala Gln Gln Gly Leu
            305                 310                 315

Arg Ala Ser Gln Glu Ala Lys Gln Lys Val Glu Lys Glu Ala Gln
            320                 325                 330

Ala Arg Glu Ala Lys Leu Gln Ala Glu Cys Ser Arg Gln Thr Gln
            335                 340                 345

Leu Ala Leu Glu Glu Lys Ala Val Leu Arg Lys Glu Arg Asp Asn
            350                 355                 360

Leu Ala Lys Glu Leu Glu Glu Lys Lys Arg Glu Ala Glu Gln Leu

```
                365                 370                 375
Arg Met Glu Leu Ala Ile Arg Asn Ser Ala Leu Asp Thr Cys Ile
            380                 385                 390

Lys Thr Lys Ser Gln Pro Met Met Pro Val Ser Arg Pro Met Gly
            395                 400                 405

Pro Val Pro Asn Pro Gln Pro Ile Asp Pro Ala Ser Leu Glu Glu
            410                 415                 420

Phe Lys Arg Lys Ile Leu Glu Ser Gln Arg Pro Pro Ala Gly Ile
            425                 430                 435

Pro Val Ala Pro Ser Ser Gly
            440

<210> SEQ ID NO 101
<211> LENGTH: 1289
<212> TYPE: DNA
<213> ORGANISM: Homo sapiens

<400> SEQUENCE: 101
agaaaccgtt gatgggactg agaaaccaga gttaaaacct ctttggagct         50
tctgaggact cagctggaac caacgggcac agttggcaac accatcatga        100
catcacaacc tgttcccaat gagaccatca tagtgctccc atcaaatgtc        150
atcaacttct cccaagcaga gaaacccgaa cccaccaacc aggggcagga        200
tagcctgaag aaacatctac acgcagaaat caaagttatt ggactatcc         250 agatcttgtg tggcatgatg gtattgagct tggggatcat tttggcatct        300
gcttccttct ctccaaattt tacccaagtg acttctacac tgttgaactc        350
tgcttaccca ttcataggac cctttttttt tatcatctct ggctctctat        400
caatcgccac agagaaaagg ttgaccaagc ttttggtgca tagcagcctg        450
gttggaagca ttctgagtgc tctgtctgcc ctggtgggtt tcattatcct        500
gtctgtcaaa caggccacct taaatcctgc ctcactgcag tgtgagttgg        550
acaaaaataa ataccaaca agaagttatg tttcttactt ttatcatgat         600
tcactttata ccacggactg ctatacagcc aaagccagtc tggctggatc        650
tctctctctg atgctgattt gcactctgct ggaattctgc ctagctgtgc        700
tcactgctgt gctgcggtgg aaacaggctt actctgactt ccctggggtg        750
agtgtgctgg ccggcttcac ttaaccttgc ctagtgtatc ttatccctgc        800
actgtgttga gtatgtcacc aagagtggta gaaggaacaa ccagccaatc        850
acgagatcac atgggagggc atttgcattg tgatggaaga cagagaagaa        900
aagcagatgg caattgagta gctgataagc tgaaaattca ctggatatga        950
aaatagttaa tcatgagaaa tcaactgatt caatcttcct attttgtcag       1000
cgaagggaat gagactctgg gaagttaaat gactggcctg gcattatgct       1050
atgagtttgt gcctttgctg aggacactag aacctggctt gcctccctta       1100
taagcagaaa caatttctgc cacaaccact agtctcttta atagtattga       1150
cttggtaaag ggcatttaca cacgtaactg gatccagtga atgtcttatg       1200
ctctgcattt gccctggtg atcttaaaat tcgtttgcct ttttaaagct        1250
atattaaaaa tgtattgttg aatcaaaaaa  aaaaaaaaa                  1289

<210> SEQ ID NO 102
<211> LENGTH: 225
```

```
<212> TYPE: PRT
<213> ORGANISM: Homo sapiens

<400> SEQUENCE: 102

Met Thr Ser Gln Pro Val Pro Asn Glu Thr Ile Ile Val Leu Pro
 1               5                  10                  15

Ser Asn Val Ile Asn Phe Ser Gln Ala Glu Lys Pro Glu Pro Thr
                20                  25                  30

Asn Gln Gly Gln Asp Ser Leu Lys Lys His Leu His Ala Glu Ile
                35                  40                  45

Lys Val Ile Gly Thr Ile Gln Ile Leu Cys Gly Met Met Val Leu
                50                  55                  60

Ser Leu Gly Ile Ile Leu Ala Ser Ala Ser Phe Ser Pro Asn Phe
                65                  70                  75

Thr Gln Val Thr Ser Thr Leu Leu Asn Ser Ala Tyr Pro Phe Ile
                80                  85                  90

Gly Pro Phe Phe Phe Ile Ile Ser Gly Ser Leu Ser Ile Ala Thr
                95                 100                 105

Glu Lys Arg Leu Thr Lys Leu Leu Val His Ser Ser Leu Val Gly
               110                 115                 120

Ser Ile Leu Ser Ala Leu Ser Ala Leu Val Gly Phe Ile Ile Leu
               125                 130                 135

Ser Val Lys Gln Ala Thr Leu Asn Pro Ala Ser Leu Gln Cys Glu
               140                 145                 150

Leu Asp Lys Asn Asn Ile Pro Thr Arg Ser Tyr Val Ser Tyr Phe
               155                 160                 165

Tyr His Asp Ser Leu Tyr Thr Thr Asp Cys Tyr Thr Ala Lys Ala
               170                 175                 180

Ser Leu Ala Gly Ser Leu Ser Leu Met Leu Ile Cys Thr Leu Leu
               185                 190                 195

Glu Phe Cys Leu Ala Val Leu Thr Ala Val Leu Arg Trp Lys Gln
               200                 205                 210

Ala Tyr Ser Asp Phe Pro Gly Val Ser Val Leu Ala Gly Phe Thr
               215                 220                 225

<210> SEQ ID NO 103
<211> LENGTH: 3557
<212> TYPE: DNA
<213> ORGANISM: Homo sapiens

<400> SEQUENCE: 103
gagagggtcc ttcagggtct gcttatgccc ttgttcaaga acaccagtgt         50
cagctctctg tactctggtt gcagactgac cttgctcagg cctgagaagg        100
atggggcagc caccagagtg gatgctgtct gcacccatcg tcctgacccc        150
aaaagccctg gactgacag agagcggctg tactggaagc tgagccagct         200
gacccacggc atcactgagc tgggccccta caccctggac aggcacagtc        250
tctatgtcaa tggtttcacc atcagagct ctatgacgac caccagaact         300
cctgatacct ccacaatgca cctggcaacc tcgagaactc cagcctccct        350
gtctggacct acgaccgcca gccctctcct ggtgctattc acaattaact        400
tcaccatcac taacctgcgg tatgaggaga acatgcatca ccctggctct        450
agaaagttta acaccacgga gagagtcctt cagggtctgc tcaggcctgt        500
gttcaagaac accagtgttg ccctctctgta ctctggctgc agactgacct      550
```

-continued

```
tgctcaggcc caagaaggat ggggcagcca ccaaagtgga tgccatctgc      600
acctaccgcc ctgatcccaa aagccctgga ctggacagag agcagctata      650
ctgggagctg agccagctaa cccacagcat cactgagctg ggcccctaca      700
ccctggacag ggacagtctc tatgtcaatg gtttcacaca gcggagctct      750
gtgcccacca ctagcattcc tgggaccccc acagtggacc tgggaacatc      800
tgggactcca gtttctaaac ctggtccctc ggctgccagc cctctcctgg      850
tgctattcac tctcaacttc accatcacca acctgcggta tgaggagaac      900
atgcagcacc ctggctccag gaagttcaac accacgagag ggtccttca      950 gggcctgctc aggtccctgt tcaagagcac cagtgttggc cctctgtact     1000
ctggctgcag actgactttg ctcaggcctg aaaaggatgg gacagccact     1050
ggagtggatg ccatctgcac ccaccaccct gaccccaaaa gccctaggct     1100
ggacagagag cagctgtatt gggagctgag ccagctgacc cacaatatca     1150
ctgagctggg ccactatgcc ctggacaacg acagcctctt tgtcaatggt     1200
ttcactcatc ggagctctgt gtccaccacc agcactcctg gaccccac       1250 agtgtatctg ggagcatcta agactccagc ctcgatattt ggcccttcag     1300
ctgccagcca tctcctgata ctattcaccc tcaacttcac catcactaac     1350
ctgcggtatg aggagaacat gtggcctggc tccaggaagt caacactac      1400 agagagggtc cttcagggcc tgctaaggcc cttgttcaag aacaccagtg     1450
ttggccctct gtactctggc tccaggctga ccttgctcag gccagagaaa     1500
gatggggaag ccaccggagt ggatgccatc tgcacccacc gccctgaccc     1550
cacaggccct gggctggaca gagagcagct gtatttggag ctgagccagc     1600
tgacccacag catcactgag ctgggcccct acacactgga cagggacagt     1650
ctctatgtca atggtttcac ccatcggagc tctgtaccca ccaccagcac     1700
cggggtggtc agcgaggagc cattcacact gaacttcacc atcaacaacc     1750
tgcgctacat ggcggacatg ggccaacccg gctccctcaa gttcaacatc     1800
acagacaacg tcatgaagca cctgctcagt cctttgttcc agaggagcag     1850
cctgggtgca cggtacacag gctgcagggt catcgcacta aggtctgtga     1900
agaacggtgc tgagacacgg gtggacctcc tctgcaccta cctgcagccc     1950
ctcagcggcc caggtctgcc tatcaagcag gtgttccatg agctgagcca     2000
gcagacccat ggcatcaccc ggctgggccc ctactctctg gacaaagaca     2050
gcctctacct taacggttac aatgaacctg gtctagatga gcctcctaca     2100
actcccaagc cagccaccac attcctgcct cctctgtcag aagccacaac     2150
agccatgggg taccacctga agaccctcac actcaacttc accatctcca     2200
atctccagta ttcaccagat atgggcaagg gctcagctac attcaactcc     2250
accgaggggg tccttcagca cctgctcaga cccttgttcc agaagagcag     2300
catgggcccc ttctacttgg gttgccaact gatctccctc aggcctgaga     2350 aggatgggc agccactggt gtggacacca cctgcaccta ccccctgac       2400 cctgtgggcc ccgggctgga catacagcag ctttactggg agctgagtca     2450
gctgacccat ggtgtcaccc aactgggctt ctatgtcctg acagggata      2500 gcctcttcat caatggctat gcaccccaga atttatcaat ccggggcgag     2550
```

-continued

| | |
|---|---|
| taccagataaa atttccacat tgtcaactgg aacctcagta atccagaccc | 2600 |
| cacatcctca gagtacatca ccctgctgag ggacatccag gacaaggtca | 2650 |
| ccacactcta caaaggcagt caactacatg acacattccg cttctgcctg | 2700 |
| gtcaccaact tgacgatgga ctccgtgttg gtcactgtca aggcattgtt | 2750 |
| ctcctccaat ttggacccca gcctggtgga gcaagtcttt ctagataaga | 2800 |
| ccctgaatgc ctcattccat tggctgggct ccacctacca gttggtggac | 2850 |
| atccatgtga cagaaatgga gtcatcagtt tatcaaccaa caagcagctc | 2900 |
| cagcacccag cacttctacc cgaatttcac catcaccaac ctaccatatt | 2950 |
| cccaggacaa agcccagcca ggcaccacca attaccagag gaacaaaagg | 3000 |
| aatattgagg atgcgctcaa ccaactcttc cgaaacagca gcatcaagag | 3050 |
| ttattttcct gactgtcaag tttcaacatt caggtctgtc cccaacaggc | 3100 |
| accacaccgg ggtggactcc ctgtgtaact tctcgccact ggctcggaga | 3150 |
| gtagacagag ttgccatcta tgaggaattt ctgcggatga cccggaatgg | 3200 |
| tacccagctg cagaacttca ccctggacag gagcagtgtc cttgtggatg | 3250 |
| ggtattctcc caacagaaat gagcccttaa ctgggaattc tgaccttccc | 3300 |
| ttctgggctg tcatcttcat cggcttggca ggactcctgg gactcatcac | 3350 |
| atgcctgatc tgcggtgtcc tggtgaccac ccgccggcgg aagaaggaag | 3400 |
| gagaatacaa cgtccagcaa cagtgcccag gctactacca gtcacaccta | 3450 |
| gacctggagg atctgcaatg actggaactt gccggtgcct ggggtgcctt | 3500 |
| tcccccagcc agggtccaaa gaagcttggc tggggcagaa ataaaccata | 3550 |
| ttggtcg | 3557 |

<210> SEQ ID NO 104
<211> LENGTH: 1148
<212> TYPE: PRT
<213> ORGANISM: Homo sapiens

<400> SEQUENCE: 104

Met Pro Leu Phe Lys Asn Thr Ser Val Ser Ser Leu Tyr Ser Gly
1               5                   10                  15

Cys Arg Leu Thr Leu Leu Arg Pro Glu Lys Asp Gly Ala Ala Thr
                20                  25                  30

Arg Val Asp Ala Val Cys Thr His Arg Pro Asp Pro Lys Ser Pro
                35                  40                  45

Gly Leu Asp Arg Glu Arg Leu Tyr Trp Lys Leu Ser Gln Leu Thr
                50                  55                  60

His Gly Ile Thr Glu Leu Gly Pro Tyr Thr Leu Asp Arg His Ser
                65                  70                  75

Leu Tyr Val Asn Gly Phe Thr His Gln Ser Ser Met Thr Thr Thr
                80                  85                  90

Arg Thr Pro Asp Thr Ser Thr Met His Leu Ala Thr Ser Arg Thr
                95                  100                 105

Pro Ala Ser Leu Ser Gly Pro Thr Thr Ala Ser Pro Leu Leu Val
                110                 115                 120

Leu Phe Thr Ile Asn Phe Thr Ile Thr Asn Leu Arg Tyr Glu Glu
                125                 130                 135

Asn Met His His Pro Gly Ser Arg Lys Phe Asn Thr Thr Glu Arg
                140                 145                 150

-continued

```
Val Leu Gln Gly Leu Leu Arg Pro Val Phe Lys Asn Thr Ser Val
            155                 160                 165
Gly Pro Leu Tyr Ser Gly Cys Arg Leu Thr Leu Leu Arg Pro Lys
            170                 175                 180
Lys Asp Gly Ala Ala Thr Lys Val Asp Ala Ile Cys Thr Tyr Arg
            185                 190                 195
Pro Asp Pro Lys Ser Pro Gly Leu Asp Arg Glu Gln Leu Tyr Trp
            200                 205                 210
Glu Leu Ser Gln Leu Thr His Ser Ile Thr Glu Leu Gly Pro Tyr
            215                 220                 225
Thr Leu Asp Arg Asp Ser Leu Tyr Val Asn Gly Phe Thr Gln Arg
            230                 235                 240
Ser Ser Val Pro Thr Thr Ser Ile Pro Gly Thr Pro Thr Val Asp
            245                 250                 255
Leu Gly Thr Ser Gly Thr Pro Val Ser Lys Pro Gly Pro Ser Ala
            260                 265                 270
Ala Ser Pro Leu Leu Val Leu Phe Thr Leu Asn Phe Thr Ile Thr
            275                 280                 285
Asn Leu Arg Tyr Glu Glu Asn Met Gln His Pro Gly Ser Arg Lys
            290                 295                 300
Phe Asn Thr Thr Glu Arg Val Leu Gln Gly Leu Leu Arg Ser Leu
            305                 310                 315
Phe Lys Ser Thr Ser Val Gly Pro Leu Tyr Ser Gly Cys Arg Leu
            320                 325                 330
Thr Leu Leu Arg Pro Glu Lys Asp Gly Thr Ala Thr Gly Val Asp
            335                 340                 345
Ala Ile Cys Thr His His Pro Asp Pro Lys Ser Pro Arg Leu Asp
            350                 355                 360
Arg Glu Gln Leu Tyr Trp Glu Leu Ser Gln Leu Thr His Asn Ile
            365                 370                 375
Thr Glu Leu Gly His Tyr Ala Leu Asp Asn Asp Ser Leu Phe Val
            380                 385                 390
Asn Gly Phe Thr His Arg Ser Ser Val Ser Thr Thr Ser Thr Pro
            395                 400                 405
Gly Thr Pro Thr Val Tyr Leu Gly Ala Ser Lys Thr Pro Ala Ser
            410                 415                 420
Ile Phe Gly Pro Ser Ala Ala Ser His Leu Leu Ile Leu Phe Thr
            425                 430                 435
Leu Asn Phe Thr Ile Thr Asn Leu Arg Tyr Glu Glu Asn Met Trp
            440                 445                 450
Pro Gly Ser Arg Lys Phe Asn Thr Thr Glu Arg Val Leu Gln Gly
            455                 460                 465
Leu Leu Arg Pro Leu Phe Lys Asn Thr Ser Val Gly Pro Leu Tyr
            470                 475                 480
Ser Gly Ser Arg Leu Thr Leu Leu Arg Pro Glu Lys Asp Gly Glu
            485                 490                 495
Ala Thr Gly Val Asp Ala Ile Cys Thr His Arg Pro Asp Pro Thr
            500                 505                 510
Gly Pro Gly Leu Asp Arg Glu Gln Leu Tyr Leu Glu Leu Ser Gln
            515                 520                 525
Leu Thr His Ser Ile Thr Glu Leu Gly Pro Tyr Thr Leu Asp Arg
            530                 535                 540
Asp Ser Leu Tyr Val Asn Gly Phe Thr His Arg Ser Ser Val Pro
            545                 550                 555
```

```
Thr Thr Ser Thr Gly Val Val Ser Glu Glu Pro Phe Thr Leu Asn
            560                 565                 570

Phe Thr Ile Asn Asn Leu Arg Tyr Met Ala Asp Met Gly Gln Pro
            575                 580                 585

Gly Ser Leu Lys Phe Asn Ile Thr Asp Asn Val Met Lys His Leu
            590                 595                 600

Leu Ser Pro Leu Phe Gln Arg Ser Ser Leu Gly Ala Arg Tyr Thr
            605                 610                 615

Gly Cys Arg Val Ile Ala Leu Arg Ser Val Lys Asn Gly Ala Glu
            620                 625                 630

Thr Arg Val Asp Leu Leu Cys Thr Tyr Leu Gln Pro Leu Ser Gly
            635                 640                 645

Pro Gly Leu Pro Ile Lys Gln Val Phe His Glu Leu Ser Gln Gln
            650                 655                 660

Thr His Gly Ile Thr Arg Leu Gly Pro Tyr Ser Leu Asp Lys Asp
            665                 670                 675

Ser Leu Tyr Leu Asn Gly Tyr Asn Glu Pro Gly Leu Asp Glu Pro
            680                 685                 690

Pro Thr Thr Pro Lys Pro Ala Thr Thr Phe Leu Pro Pro Leu Ser
            695                 700                 705

Glu Ala Thr Thr Ala Met Gly Tyr His Leu Lys Thr Leu Thr Leu
            710                 715                 720

Asn Phe Thr Ile Ser Asn Leu Gln Tyr Ser Pro Asp Met Gly Lys
            725                 730                 735

Gly Ser Ala Thr Phe Asn Ser Thr Glu Gly Val Leu Gln His Leu
            740                 745                 750

Leu Arg Pro Leu Phe Gln Lys Ser Ser Met Gly Pro Phe Tyr Leu
            755                 760                 765

Gly Cys Gln Leu Ile Ser Leu Arg Pro Glu Lys Asp Gly Ala Ala
            770                 775                 780

Thr Gly Val Asp Thr Thr Cys Thr Tyr His Pro Asp Pro Val Gly
            785                 790                 795

Pro Gly Leu Asp Ile Gln Gln Leu Tyr Trp Glu Leu Ser Gln Leu
            800                 805                 810

Thr His Gly Val Thr Gln Leu Gly Phe Tyr Val Leu Asp Arg Asp
            815                 820                 825

Ser Leu Phe Ile Asn Gly Tyr Ala Pro Gln Asn Leu Ser Ile Arg
            830                 835                 840

Gly Glu Tyr Gln Ile Asn Phe His Ile Val Asn Trp Asn Leu Ser
            845                 850                 855

Asn Pro Asp Pro Thr Ser Ser Glu Tyr Ile Thr Leu Leu Arg Asp
            860                 865                 870

Ile Gln Asp Lys Val Thr Thr Leu Tyr Lys Gly Ser Gln Leu His
            875                 880                 885

Asp Thr Phe Arg Phe Cys Leu Val Thr Asn Leu Thr Met Asp Ser
            890                 895                 900

Val Leu Val Thr Val Lys Ala Leu Phe Ser Ser Asn Leu Asp Pro
            905                 910                 915

Ser Leu Val Glu Gln Val Phe Leu Asp Lys Thr Leu Asn Ala Ser
            920                 925                 930

Phe His Trp Leu Gly Ser Thr Tyr Gln Leu Val Asp Ile His Val
            935                 940                 945

Thr Glu Met Glu Ser Ser Val Tyr Gln Pro Thr Ser Ser Ser Ser
```

```
                      950                 955                 960
Thr Gln His Phe Tyr Pro Asn Phe Thr Ile Thr Asn Leu Pro Tyr
                  965                 970                 975
Ser Gln Asp Lys Ala Gln Pro Gly Thr Thr Asn Tyr Gln Arg Asn
                  980                 985                 990
Lys Arg Asn Ile Glu Asp Ala Leu Asn Gln Leu Phe Arg Asn Ser
                  995                1000                1005
Ser Ile Lys Ser Tyr Phe Ser Asp Cys Gln Val Ser Thr Phe Arg
                 1010                1015                1020
Ser Val Pro Asn Arg His His Thr Gly Val Asp Ser Leu Cys Asn
                 1025                1030                1035
Phe Ser Pro Leu Ala Arg Arg Val Asp Arg Val Ala Ile Tyr Glu
                 1040                1045                1050
Glu Phe Leu Arg Met Thr Arg Asn Gly Thr Gln Leu Gln Asn Phe
                 1055                1060                1065
Thr Leu Asp Arg Ser Ser Val Leu Val Asp Gly Tyr Ser Pro Asn
                 1070                1075                1080
Arg Asn Glu Pro Leu Thr Gly Asn Ser Asp Leu Pro Phe Trp Ala
                 1085                1090                1095
Val Ile Phe Ile Gly Leu Ala Gly Leu Leu Gly Leu Ile Thr Cys
                 1100                1105                1110
Leu Ile Cys Gly Val Leu Val Thr Thr Arg Arg Arg Lys Lys Glu
                 1115                1120                1125
Gly Glu Tyr Asn Val Gln Gln Gln Cys Pro Gly Tyr Tyr Gln Ser
                 1130                1135                1140
His Leu Asp Leu Glu Asp Leu Gln
                 1145

<210> SEQ ID NO 105
<211> LENGTH: 1071
<212> TYPE: DNA
<213> ORGANISM: Homo sapiens

<400> SEQUENCE: 105
gttggcattc ggtggtcctg gcagttagct gagcacgccc tctgagccgc            50
tcggtggaca ccaggcactc tagtaggcct ggcctaccca gaaacagcag           100
gagagagaag aaacaggcca gctgtgagaa gccaaggaca ccgagtcagt           150
catggcacct aaggcggcaa aggggggccaa gccagagcca gcaccagctc          200
cacctccacc cggggccaaa cccgaggaag acaagaagga cggtaaggag           250
ccatcggaca aacctcaaaa ggcggtgcag gaccataagg agccatcgga           300
caaacctcaa aaggcggtgc agcccaagca cgaagtgggc acgaggaggg           350
ggtgtcgccg ctaccggtgg gaattaaaag acagcaataa agagttctgg           400
ctcttggggc acgctgagat caagattcgg agtttgggct gcctaatagc           450
tgcaatgata ctgttgtcct cactcaccgt gcaccccatc ttgaggctta           500
tcatcaccat ggagatatcc ttcttcagct tcttcatctt actgtacagc           550
tttgccattc atagatacat acccttcatc ctgtggccca tttctgacct           600
cttcaacgac ctgattgctt gtgcgttcct tgtgggagcc gtggtctttg           650
ctgtgagaag tcggcgatcc atgaatctcc actacttact tgctgtgatc           700
cttattggtg cggctggagt ttttgctttt atcgatgtgt gtcttcaaag           750
aaaccacttc agaggcaaga aggccaaaaa gcatatgctg gttcctcctc           800
```

```
caggaaagga aaaaggaccc cagcagggca agggaccaga acccgccaag         850
ccaccagaac ctggcaagcc accagggcca gcaaagggaa agaaatgact         900
tggaggaggc tcctggtgtc tgaaacggca gtgtatttta cagcaatatg         950
tttccactct cttccttgtc ttctttctgg aatggttttc ttttccattt        1000
tcattaccac ctttgcttgg aaaagaatgg attaatggat tctaaaagcc        1050
taaaaaaaaa aaaaaaaaa  a                                       1071
```

<210> SEQ ID NO 106
<211> LENGTH: 248
<212> TYPE: PRT
<213> ORGANISM: Homo sapiens

<400> SEQUENCE: 106

```
Met Ala Pro Lys Ala Ala Lys Gly Ala Lys Pro Glu Pro Ala Pro
 1               5                  10                  15

Ala Pro Pro Pro Gly Ala Lys Pro Glu Asp Lys Lys Asp
                20                  25                  30

Gly Lys Glu Pro Ser Asp Lys Pro Gln Lys Ala Val Gln Asp His
            35                  40                  45

Lys Glu Pro Ser Asp Lys Pro Gln Lys Ala Val Gln Pro Lys His
        50                  55                  60

Glu Val Gly Thr Arg Arg Gly Cys Arg Arg Tyr Arg Trp Glu Leu
65                  70                  75

Lys Asp Ser Asn Lys Glu Phe Trp Leu Leu Gly His Ala Glu Ile
                80                  85                  90

Lys Ile Arg Ser Leu Gly Cys Leu Ile Ala Ala Met Ile Leu Leu
            95                 100                 105

Ser Ser Leu Thr Val His Pro Ile Leu Arg Leu Ile Ile Thr Met
        110                 115                 120

Glu Ile Ser Phe Phe Ser Phe Ile Leu Leu Tyr Ser Phe Ala
    125                 130                 135

Ile His Arg Tyr Ile Pro Phe Ile Leu Trp Pro Ile Ser Asp Leu
            140                 145                 150

Phe Asn Asp Leu Ile Ala Cys Ala Phe Leu Val Gly Ala Val Val
        155                 160                 165

Phe Ala Val Arg Ser Arg Arg Ser Met Asn Leu His Tyr Leu Leu
    170                 175                 180

Ala Val Ile Leu Ile Gly Ala Ala Gly Val Phe Ala Phe Ile Asp
            185                 190                 195

Val Cys Leu Gln Arg Asn His Phe Arg Gly Lys Lys Ala Lys Lys
        200                 205                 210

His Met Leu Val Pro Pro Gly Lys Glu Lys Gly Pro Gln Gln
    215                 220                 225

Gly Lys Gly Pro Glu Pro Ala Lys Pro Pro Glu Pro Gly Lys Pro
            230                 235                 240

Pro Gly Pro Ala Lys Gly Lys Lys
        245
```

<210> SEQ ID NO 107
<211> LENGTH: 43
<212> TYPE: DNA
<213> ORGANISM: Artificial sequence
<220> FEATURE:
<223> OTHER INFORMATION: Oligonucleotide Probe

```
<400> SEQUENCE: 107
tgtaaaacga cggccagtta aatagacctg caattattaa tct                      43

<210> SEQ ID NO 108
<211> LENGTH: 41
<212> TYPE: DNA
<213> ORGANISM: Artificial sequence
<220> FEATURE:
<223> OTHER INFORMATION: Oligonucleotide Probe

<400> SEQUENCE: 108
caggaaacag ctatgaccac ctgcacacct gcaaatccat t                        41

<210> SEQ ID NO 109
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 109
attctgcgtg aacactgagg gc                                             22

<210> SEQ ID NO 110
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 110
atctgcttgt agccctcggc ac                                             22

<210> SEQ ID NO 111
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 111
cctggctatc agcaggtggg ctccaagtgt ctcgatgtgg atgagtgtga               50

<210> SEQ ID NO 112
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 112
tctctattcc aaactgtggc g                                              21

<210> SEQ ID NO 113
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 113
tttgatgacg attcgaaggt gg                                             22

<210> SEQ ID NO 114
<211> LENGTH: 47
<212> TYPE: DNA
```

-continued

<213> ORGANISM: Artificial sequence
<220> FEATURE:
<223> OTHER INFORMATION: Oligonucleotide probe

<400> SEQUENCE: 114
ggaaggatcc ttcaccagcc ccaattaccc aaagccgcat cctgagc                    47

<210> SEQ ID NO 115
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 115
tgaggtgggc aagcggcgaa atg                                              23

<210> SEQ ID NO 116
<211> LENGTH: 20
<212> TYPE: DNA
<213> ORGANISM: Artificial sequence
<220> FEATURE:
<223> OTHER INFORMATION: Oligonucleotide Probe

<400> SEQUENCE: 116
tatgtggatc aggacgtgcc                                                  20

<210> SEQ ID NO 117
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 117
tgcagggttc agtctagatt g                                                21

<210> SEQ ID NO 118
<211> LENGTH: 25
<212> TYPE: DNA
<213> ORGANISM: Artificial sequence
<220> FEATURE:
<223> OTHER INFORMATION: Oligonucleotide Probe

<400> SEQUENCE: 118
ttgaaggaca aaggcaatct gccac                                            25

<210> SEQ ID NO 119
<211> LENGTH: 45
<212> TYPE: DNA
<213> ORGANISM: Artificial sequence
<220> FEATURE:
<223> OTHER INFORMATION: Oligonucleotide Probe

<400> SEQUENCE: 119
ggagtcttgc agttcccctg gcagtcctgg tgctgttgct ttggg                      45

<210> SEQ ID NO 120
<211> LENGTH: 43
<212> TYPE: DNA
<213> ORGANISM: Artificial sequence
<220> FEATURE:
<223> OTHER INFORMATION: Oligonucleotide Probe

<400> SEQUENCE: 120
tgactgcact accccgtggc aagctgttga gccagctcag ctg                        43

<210> SEQ ID NO 121
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 121
ccagtgcaca gcaggcaacg aagc                                            24

<210> SEQ ID NO 122
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 122
actaggctgt atgcctgggt gggc                                            24

<210> SEQ ID NO 123
<211> LENGTH: 43
<212> TYPE: DNA
<213> ORGANISM: Artificial sequence
<220> FEATURE:
<223> OTHER INFORMATION: Oligonucleotide Probe

<400> SEQUENCE: 123
gtatgtacaa agcatcggca tggttgcagg agcagtgaca ggc                       43

<210> SEQ ID NO 124
<211> LENGTH: 20
<212> TYPE: DNA
<213> ORGANISM: Artificial sequence
<220> FEATURE:
<223> OTHER INFORMATION: Oligonucleotide Probe

<400> SEQUENCE: 124
aatgtgacca ctggactccc                                                 20

<210> SEQ ID NO 125
<211> LENGTH: 18
<212> TYPE: DNA
<213> ORGANISM: Artificial sequence
<220> FEATURE:
<223> OTHER INFORMATION: Oligonucleotide Probe

<400> SEQUENCE: 125
aggcttggaa ctcccttc                                                   18

<210> SEQ ID NO 126
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 126
aagattcttg agcgattcca gctg                                            24

<210> SEQ ID NO 127
<211> LENGTH: 47
<212> TYPE: DNA
<213> ORGANISM: Artificial sequence
<220> FEATURE:
<223> OTHER INFORMATION: Oligonucleotide Probe

<400> SEQUENCE: 127
aatccctgct cttcatggtg acctatgacg acggaagcac aagactg　　　　　　　47

<210> SEQ ID NO 128
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 128
tgacatcgcc cttatgaagc tggc　　　　　　　24

<210> SEQ ID NO 129
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 129
tacacgtccc tgtggttgca gatc　　　　　　　24

<210> SEQ ID NO 130
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 130
cgttcaatgc agaaatgatc cagcctgtgt gcctgcccaa ctctgaagag　　　　　　　50

<210> SEQ ID NO 131
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 131
aagcgtgaca gcgggcacgt c　　　　　　　21

<210> SEQ ID NO 132
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 132
tgcacagtct ctgcagtgcc cagg　　　　　　　24

<210> SEQ ID NO 133
<211> LENGTH: 40
<212> TYPE: DNA
<213> ORGANISM: Artificial sequence
<220> FEATURE:
<223> OTHER INFORMATION: Oligonucleotide Probe

<400> SEQUENCE: 133
gaatgctgga acgggcacag caaagccaga tacttgcctg　　　　　　　40

<210> SEQ ID NO 134
<211> LENGTH: 24
<212> TYPE: DNA

```
<213> ORGANISM: Artificial sequence
<220> FEATURE:
<223> OTHER INFORMATION: Oligonucleotide Probe

<400> SEQUENCE: 134
tggaaggctg ccgcaacgac aatc                                          24

<210> SEQ ID NO 135
<211> LENGTH: 20
<212> TYPE: DNA
<213> ORGANISM: Artificial sequence
<220> FEATURE:
<223> OTHER INFORMATION: Oligonucleotide Probe

<400> SEQUENCE: 135
ctgatgtggc cgatgttctg                                               20

<210> SEQ ID NO 136
<211> LENGTH: 20
<212> TYPE: DNA
<213> ORGANISM: Artificial sequence
<220> FEATURE:
<223> OTHER INFORMATION: Oligonucleotide Probe

<400> SEQUENCE: 136
atggctcagt gtgcagacag                                               20

<210> SEQ ID NO 137
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 137
gcatgctgct ccgtgaagta gtcc                                          24

<210> SEQ ID NO 138
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 138
atgcatggga aagaaggcct gccc                                          24

<210> SEQ ID NO 139
<211> LENGTH: 47
<212> TYPE: DNA
<213> ORGANISM: Artificial sequence
<220> FEATURE:
<223> OTHER INFORMATION: Oligonucleotide Probe

<400> SEQUENCE: 139
tgcactggtg accacgaggg ggtgcactat agccatctgg agctgag                 47

<210> SEQ ID NO 140
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 140
caatatgcat cttgcacgtc tgg                                           23
```

<210> SEQ ID NO 141
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 141
aagcttctct gcttcctttc ctgc                                          24

<210> SEQ ID NO 142
<211> LENGTH: 43
<212> TYPE: DNA
<213> ORGANISM: Artificial sequence
<220> FEATURE:
<223> OTHER INFORMATION: Oligonucleotide Probe

<400> SEQUENCE: 142 tgacccatt gagaaggtca ttgaagggat caaccgaggg ctg                       43

<210> SEQ ID NO 143
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 143
tggacaccgt accctggtat ctgc                                          24

<210> SEQ ID NO 144
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 144
ccaactctga ggagagcaag tggc                                          24

<210> SEQ ID NO 145
<211> LENGTH: 44
<212> TYPE: DNA
<213> ORGANISM: Artificial sequence
<220> FEATURE:
<223> OTHER INFORMATION: Oligonucleotide Probe

<400> SEQUENCE: 145
tgtatgtgca caccctcacc atcacctcca agggcaagga gaac                    44

<210> SEQ ID NO 146
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 146
ttttgcggtc accattgtct gc                                            22

<210> SEQ ID NO 147
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 147
cgtaggtgac acagaagccc agg　　　　　　　　　　　　　　　　23

<210> SEQ ID NO 148
<211> LENGTH: 49
<212> TYPE: DNA
<213> ORGANISM: Artificial sequence
<220> FEATURE:
<223> OTHER INFORMATION: Oligonucleotide Probe

<400> SEQUENCE: 148
tacggcatga ccggctcctt tcctatgagg aactcccagg cactgatat　　49

<210> SEQ ID NO 149
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 149
gctgacctgg ttcccatcta ctcc　　　　　　　　　　　　　24

<210> SEQ ID NO 150
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 150
cccacagaca cccatgacac ttcc　　　　　　　　　　　　　24

<210> SEQ ID NO 151
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 151
aagaatgaat tgtacaaagc aggtgatctt cgaggagggc tcctgggcc　　50

<210> SEQ ID NO 152
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 152
ttctctggcc gacgctgtga gg　　　　　　　　　　　　　　22

<210> SEQ ID NO 153
<211> LENGTH: 25
<212> TYPE: DNA
<213> ORGANISM: Artificial sequence
<220> FEATURE:
<223> OTHER INFORMATION: Oligonucleotide Probe

<400> SEQUENCE: 153
gccataaggg cattgcacac aaagg　　　　　　　　　　　　25

<210> SEQ ID NO 154
<211> LENGTH: 43
<212> TYPE: DNA

<213> ORGANISM: Artificial sequence
<220> FEATURE:
<223> OTHER INFORMATION: Oligonucleotide Probe

<400> SEQUENCE: 154
agtccctgct tcaacagggc cacctgctac ccgacctctc    cac                43

<210> SEQ ID NO 155
<211> LENGTH: 25
<212> TYPE: DNA
<213> ORGANISM: Artificial sequence
<220> FEATURE:
<223> OTHER INFORMATION: Oligonucleotide Probe

<400> SEQUENCE: 155
tgtcctctat tggagaacca    cagcc                                     25

<210> SEQ ID NO 156
<211> LENGTH: 25
<212> TYPE: DNA
<213> ORGANISM: Artificial sequence
<220> FEATURE:
<223> OTHER INFORMATION: Oligonucleotide Probe

<400> SEQUENCE: 156
taaaagttgg ctgggcaaag    tttgc                                     25

<210> SEQ ID NO 157
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 157
ctcagtatgg accaaagtac ccaagcctgt gctggtgaga aacattggca              50

<210> SEQ ID NO 158
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 158
caaggtcctg cggaatgtct    ctgg                                      24

<210> SEQ ID NO 159
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 159
gggaagtcct ggaactggtt    ccgg                                      24

<210> SEQ ID NO 160
<211> LENGTH: 46
<212> TYPE: DNA
<213> ORGANISM: Artificial sequence
<220> FEATURE:
<223> OTHER INFORMATION: Oligonucleotide Probe

<400> SEQUENCE: 160
cctcatcacc ctggctaaca acgagcttaa gtccctcacc    agcaag              46

<210> SEQ ID NO 161
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 161
cagcgaaccg ggtgccgggt c                                    21

<210> SEQ ID NO 162
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 162
gagcgacgag cgcgcagcga ac                                   22

<210> SEQ ID NO 163
<211> LENGTH: 43
<212> TYPE: DNA
<213> ORGANISM: Artificial sequence
<220> FEATURE:
<223> OTHER INFORMATION: Oligonucleotide Probe

<400> SEQUENCE: 163
atactgcgat cgctaaacca ccatgcgccg ccgcctgtgg ctg            43

<210> SEQ ID NO 164
<211> LENGTH: 21
<212> TYPE: DNA
<213> ORGANISM: Artificial sequence
<220> FEATURE:
<223> OTHER INFORMATION: Oligonucleotide Probe

<400> SEQUENCE: 164
gccggcctct cagggcctca g                                    21

<210> SEQ ID NO 165
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 165
cccacgtgta cagagcggat ctc                                  23

<210> SEQ ID NO 166
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 166
gagaccagga cgggcaggaa gtg                                  23

<210> SEQ ID NO 167
<211> LENGTH: 21
<212> TYPE: DNA
<213> ORGANISM: Artificial sequence
<220> FEATURE:
<223> OTHER INFORMATION: Oligonucleotide Probe

```
<400> SEQUENCE: 167
caggcacctt ggggagccgc c                                              21

<210> SEQ ID NO 168
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 168
cccacgtgta cagagcggat ctc                                            23

<210> SEQ ID NO 169
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 169
gagaccagga cgggcaggaa gtg                                            23

<210> SEQ ID NO 170
<211> LENGTH: 44
<212> TYPE: DNA
<213> ORGANISM: Artificial sequence
<220> FEATURE:
<223> OTHER INFORMATION: Oligonucleotide Probe

<400> SEQUENCE: 170
ctctacgggt actgcaggtt ccgggagcgc atcgaagaga acgg                     44

<210> SEQ ID NO 171
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 171
cgacccaagc ggatcgaagg ttc                                            23

<210> SEQ ID NO 172
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 172
gtcacttcct ggcaccagct gctc                                           24

<210> SEQ ID NO 173
<211> LENGTH: 45
<212> TYPE: DNA
<213> ORGANISM: Artificial sequence
<220> FEATURE:
<223> OTHER INFORMATION: Oligonucleotide Probe

<400> SEQUENCE: 173
gttagcaact ctctggcagc ctttgcttac attagagacc acccg                    45

<210> SEQ ID NO 174
<211> LENGTH: 21
<212> TYPE: DNA
```

```
<213> ORGANISM: Artificial sequence
<220> FEATURE:
<223> OTHER INFORMATION: Oligonucleotide Probe

<400> SEQUENCE: 174
cgatactcgc gggaggctaa  c                                              21

<210> SEQ ID NO 175
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 175
ccttctgggt gtctccagtt  agcg                                           24

<210> SEQ ID NO 176
<211> LENGTH: 37
<212> TYPE: DNA
<213> ORGANISM: Artificial sequence
<220> FEATURE:
<223> OTHER INFORMATION: Oligonucleotide Probe

<400> SEQUENCE: 176
caactcgcgc actcaaagat ggtccccatc  cctgctg                             37

<210> SEQ ID NO 177
<211> LENGTH: 22
<212> TYPE: DNA
<213> ORGANISM: Artificial sequence
<220> FEATURE:
<223> OTHER INFORMATION: Oligonucleotide Probe

<400> SEQUENCE: 177
cagaaaaaag gaagatggca  ag                                             22

<210> SEQ ID NO 178
<211> LENGTH: 28
<212> TYPE: DNA
<213> ORGANISM: Artificial sequence
<220> FEATURE:
<223> OTHER INFORMATION: Oligonucleotide Probe

<400> SEQUENCE: 178
ggcaagaata ttgttacttt  tcctcccg                                       28

<210> SEQ ID NO 179
<211> LENGTH: 24
<212> TYPE: DNA
<213> ORGANISM: Artificial sequence
<220> FEATURE:
<223> OTHER INFORMATION: Oligonucleotide Probe

<400> SEQUENCE: 179
ttaccagctt tgagtacaca  taga                                           24

<210> SEQ ID NO 180
<211> LENGTH: 27
<212> TYPE: DNA
<213> ORGANISM: Artificial sequence
<220> FEATURE:
<223> OTHER INFORMATION: Oligonucleotide Probe

<400> SEQUENCE: 180
aacgttaatg aatctacagt  ccggggc                                        27
```

```
<210> SEQ ID NO 181
<211> LENGTH: 50
<212> TYPE: DNA
<213> ORGANISM: Artificial sequence
<220> FEATURE:
<223> OTHER INFORMATION: Oligonucleotide Probe

<400> SEQUENCE: 181
ggtccataaa tattccatgc acagcacata cagccacaag acccgggagg              50

<210> SEQ ID NO 182
<211> LENGTH: 40
<212> TYPE: DNA
<213> ORGANISM: Artificial sequence
<220> FEATURE:
<223> OTHER INFORMATION: Oligonucleotide Probe

<400> SEQUENCE: 182
tgtgcatgga atatttatgg accgtctagc ttccaagaag                         40

<210> SEQ ID NO 183
<211> LENGTH: 28
<212> TYPE: DNA
<213> ORGANISM: Artificial sequence
<220> FEATURE:
<223> OTHER INFORMATION: Oligonucleotide Probe

<400> SEQUENCE: 183
acagcaccaa gtttctgagc  aacttcct                                     28

<210> SEQ ID NO 184
<211> LENGTH: 23
<212> TYPE: DNA
<213> ORGANISM: Artificial sequence
<220> FEATURE:
<223> OTHER INFORMATION: Oligonucleotide Probe

<400> SEQUENCE: 184
acttgaggtt gtcaccgcac  acg                                          23

<210> SEQ ID NO 185
<211> LENGTH: 36
<212> TYPE: DNA
<213> ORGANISM: Artificial sequence
<220> FEATURE:
<223> OTHER INFORMATION: Oligonucleotide Probe

<400> SEQUENCE: 185
agagaggaaa caaggacctg cgggcacggg  cagacg                            36
```